(12) United States Patent
Mun et al.

(10) Patent No.: US 10,700,285 B2
(45) Date of Patent: Jun. 30, 2020

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si, Chungcheongnam-do (KR)

(72) Inventors: Soung Yun Mun, Cheonan-si (KR); Sun-Hee Lee, Cheonan-si (KR); Jung Cheol Park, Suwon-si (KR); DaeSung Kim, Yongin-si (KR); Bum Sung Lee, Cheonan-si (KR); Seok hyun Kim, Seongnam-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 323 days.

(21) Appl. No.: 15/120,330

(22) PCT Filed: Feb. 11, 2015

(86) PCT No.: PCT/KR2015/001362
§ 371 (c)(1),
(2) Date: Aug. 19, 2016

(87) PCT Pub. No.: WO2015/126090
PCT Pub. Date: Aug. 27, 2015

(65) Prior Publication Data
US 2017/0062728 A1    Mar. 2, 2017

(30) Foreign Application Priority Data

Feb. 19, 2014 (KR) .......... 10-2014-0018889
Jun. 13, 2014 (KR) .......... 10-2014-0072377

(51) Int. Cl.
*H01L 51/00* (2006.01)
*C07D 209/86* (2006.01)
(Continued)

(52) U.S. Cl.
CPC ........ *H01L 51/0061* (2013.01); *C07D 209/86* (2013.01); *C07D 401/10* (2013.01);
(Continued)

(58) Field of Classification Search
CPC . C07D 209/82; H01L 51/0072; H01L 51/006; H01L 51/5056
See application file for complete search history.

(56) References Cited

U.S. PATENT DOCUMENTS

2008/0124572 A1*  5/2008 Mizuki ................ C07C 211/54
                                                                428/690
2015/0236267 A1*  8/2015 Hiroaki ............... H01L 51/0061
                                                                257/40

FOREIGN PATENT DOCUMENTS

JP    10-316658 A    12/1998
JP    2004-103467 A   4/2004
(Continued)

OTHER PUBLICATIONS

The International Search Report for PCT Application No. PCT/KR2015/001362, dated Jun. 5, 2015, three pages; with English translation, two pages.
(Continued)

*Primary Examiner* — Jeinnifer A Chriss
*Assistant Examiner* — Sean M DeGuire
(74) *Attorney, Agent, or Firm* — Vorys, Sater, Seymour & Pease LLP; Mih Suhn Koh

(57) ABSTRACT

Provided are a compound of Formula 1 and an organic electric element including a first electrode, a second electrode, and an organic material layer between the first electrode and the second electrode and comprising the compound, the element showing improved luminous efficiency, stability, and life span.

14 Claims, 1 Drawing Sheet

(51) Int. Cl.
    *C07D 409/12*     (2006.01)
    *C07D 403/10*     (2006.01)
    *C09K 11/06*      (2006.01)
    *C07D 403/12*     (2006.01)
    *C07D 405/12*     (2006.01)
    *C07D 403/04*     (2006.01)
    *C07D 409/04*     (2006.01)
    *C07D 405/04*     (2006.01)
    *C07D 401/10*     (2006.01)
    *H01L 51/50*      (2006.01)

(52) U.S. Cl.
    CPC ......... *C07D 403/04* (2013.01); *C07D 403/10* (2013.01); *C07D 403/12* (2013.01); *C07D 405/04* (2013.01); *C07D 405/12* (2013.01); *C07D 409/04* (2013.01); *C07D 409/12* (2013.01); *C09K 11/06* (2013.01); *H01L 51/0072* (2013.01); *H01L 51/0074* (2013.01); *H01L 51/006* (2013.01); *H01L 51/0058* (2013.01); *H01L 51/50* (2013.01); *H01L 51/5016* (2013.01); *H01L 51/5056* (2013.01); *H01L 51/5096* (2013.01); *Y02E 10/549* (2013.01)

(56) References Cited

FOREIGN PATENT DOCUMENTS

KR        10-1188280 B1     9/2012
KR        10-2013-0096334 A     8/2013

OTHER PUBLICATIONS

Korean Notice of Allowance for Korean Application No. 10-2014-0072377, dated May 26, 2016, two pages.
Korean Office Action for Korean Application No. 10-2014-0072377, dated Nov. 11, 2015, six pages.

* cited by examiner

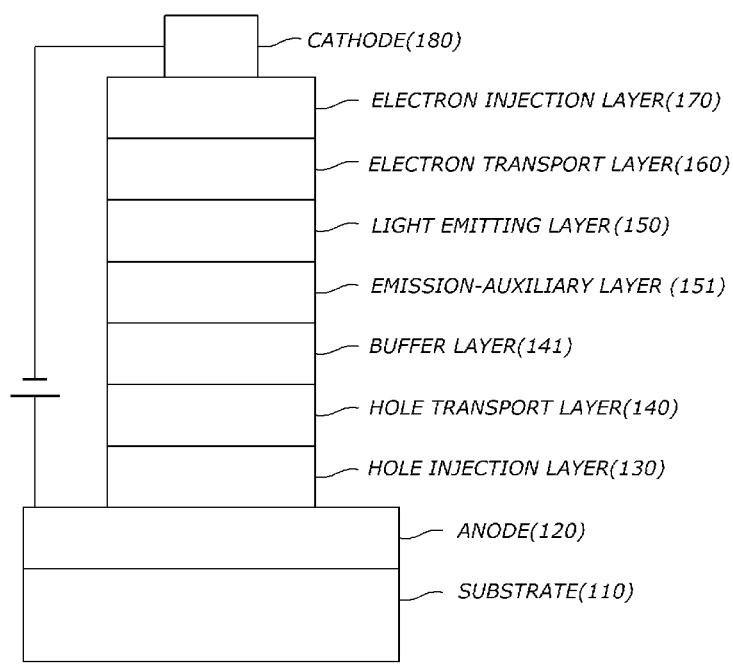

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims benefit under 35 U.S.C. 119(e), 120, 121, or 365(c), and is a National Stage entry from International Application No. PCT/KR2015/001362, filed Feb. 11, 2015, which claims priority to Korean Patent Application No. 10-2014-0018889 filed on Feb. 19, 2014, and Korean Patent Application No. 10-2014-0072377 filed on Jun. 13, 2014, the contents of which are hereby incorporated by reference for all purposes as if fully set forth herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given. Therefore it is required to develop a light emitting material that has high thermal stability and can achieve efficiently a charge balance in the light-emitting layer.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton. However, since a material used in a hole transporting layer should have a low HOMO value, it mainly has a low T1 value.

However, since a material used in a hole transporting layer should have a low HOMO value, it mainly has a low T1 value. Due to this, excitons generated from a light emitting layer are transported to the hole transporting layer, resulting in a charge unbalance in the light emitting layer. Thus, light emission occurs in the hole transporting layer or at an interface of the hole transporting layer so that the organic electroluminescent device is reduced in color purity, efficiency, and lifespan.

Also, when using a material having rapid hole mobility for reducing a driving voltage, this is tend to decrease the efficiency. In an OLEDs, a charge unbalance in the light emitting layer is caused because of that hole mobility is faster than electron mobility, and reduced efficiency and lifespan is happened.

Therefore, an emitting auxiliary layer must be formed by a material what can solve the problems of an hole transport layer, having hole mobility (within the driving voltage range of the blue element of full device) to give the suitable driving voltage, high T1 energy value (electron block) and wide band gap. These requirements are not satisfied only by structural characteristics about a core of the emitting auxiliary layer's material. Therefore, it is necessary to develop of the material for the emitting auxiliary layer having high T1 energy value and wide band gap, to improve efficiency and lifespan of the organic electric element as combined core of material and characteristics of sub substituents appropriately.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

In order to solve one or more of the above-mentioned problems occurring in the prior art, an aspect of the present invention is to provide a compound which allows an organic electric element to be improved in luminescence efficiency, stability and lifespan, an organic electric element containing the same, and an electronic device including the organic electric element.

In accordance with an aspect of the present invention, the compound represented by the following Formula is provided.

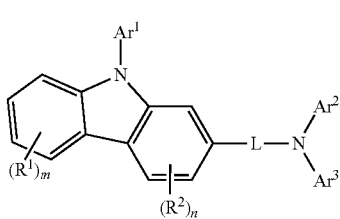

In another aspect of the present invention, organic electric elements containing the compound represented by the formula above and electronic devices including the organic electric element are provided.

By employing the compound of the present invention that has wide band gap and high T1 energy value due to the non-linear linker (L) attached to the carbazole core, the organic electric element according to one or more embodiments of the present invention can have not only high luminescence efficiency and high heat-resistance, but also significantly improved color purity and lifespan.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component. In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), an alkyl group substituted with a cycloalkyl, or an cycloalkyl substituted with a alkyl group.

Unless otherwise stated, the term "haloalkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "alkenoxyl group", "alkenoxy group", "alkenyloxyl group" or "alkenyloxy group" as used herein means an oxygen radical attached to an alkyl group, but not limited to, and has 2 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, or a spirofluorene group.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the "heteroaryl group" or "heteroarylene group" as used herein means, but not limited to, a ring containing one or more heteroatoms, and having 2 to 60 carbon atoms. They include at least one monocyclic or polycyclic ring, and may be linked together to form a fused ring.

Unless otherwise stated, the term "heterocyclic group" as used herein means, but not limited to, a ring containing one or more heteroatoms, and having 2 to 60 carbon atoms. They include at least one monocyclic or polycyclic ring, and may be linked together to form a fused ring.

Unless otherwise stated, the term "heteroatom" as used herein represents at least one of N, O, S, P, and Si.

Also, the term "heterocyclic group" may include $SO_2$ instead of carbon consisting of cycle. For example, "heterocyclic group" includes compound below.

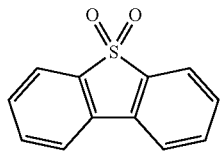

Unless otherwise stated, the term "aliphatic" as used herein means aliphatic hydrocarbon, having 1 to 60 carbon atoms. The term "aliphatic ring" means aliphatic hydrocarbon ring, having 1 to 60 carbon.

Unless otherwise stated, the term "ring" as used herein means aliphatic ring having 3 to 60 carbon or aromatic ring having 6 to 60 carbon, or heterocyclic ring having 2 to 60 carbon or a fused ring formed by combinations thereof, includes saturated or unsaturated ring.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

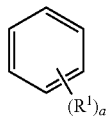

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

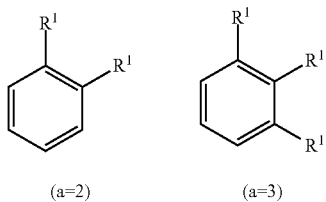

(a=2)   (a=3)

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a light emitting layer and/or an emission-auxiliary layer by using the compound represented by Formula 1, and thus the life span and efficiency of the organic electric element can be improved at the same time.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer

151 may be comprised between the hole transport layer 140 and the light emitting layer 150.

And also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

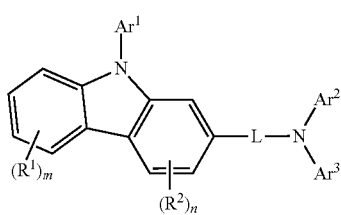

[Formula 1]

In Formula 1 above, L may be

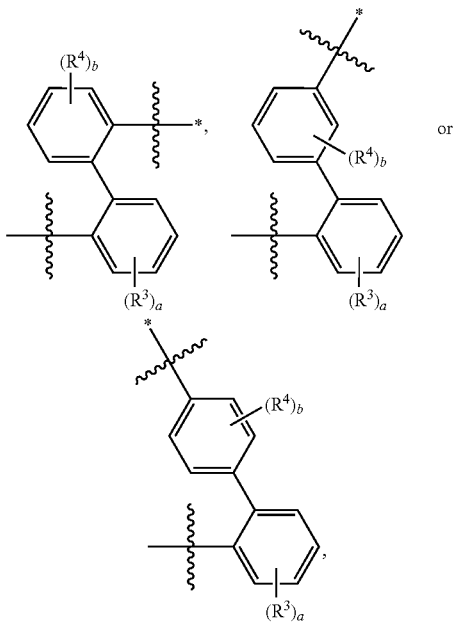

wherein * indicates the position to which the nitrogen atom (N) of the amine group in Formula 1 is linked.

a and b are each an integer of 0 to 4. $R^3$ and $R^4$ are each independently selected from the group consisting of i) deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -Ly-N($R^a$)($R^b$); or ii) adjacent groups, namely, adjacent $R^3$s, adjacent $R^4$s and/or adjacent $R^3$ and $R^4$, may be linked together to form at least one ring, and wherein the group(s) of $R^3$ and $R^4$ not forming a ring is(are) the same as defined in above i). The ring formed by linking between the adjacent groups may be a mono or poly cyclic ring, including a $C_6$-$C_{60}$ aromatic ring, a $C_2$-$C_{60}$ hetero cyclic ring, a $C_3$-$C_{60}$ aliphatic ring, or a fused ring formed by combination thereof. The fused ring may be a saturated or unsaturated ring.

$R^3$s may be same or different each other when a is 2 or more, $R^4$s may be same or different each other when b is 2 or more.

Preferably, both $R^3$ and $R^4$ may be hydrogen, a $C_6$-$C_{16}$ aryl group, a $C_5$-$C_9$ heterocyclic group, more preferably a $C_6$, $C_{10}$, $C_{12}$ or $C_{16}$ aryl group, or a $C_5$, $C_8$ or $C_9$ heterocyclic group.

More preferably, $R^3$ and $R^4$ may be each independently selected from the following structures:

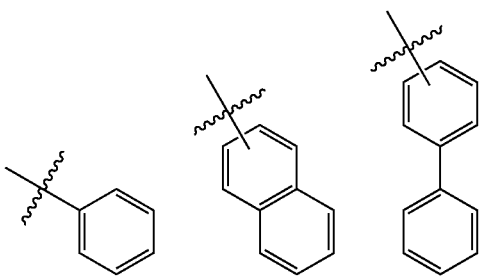

-continued

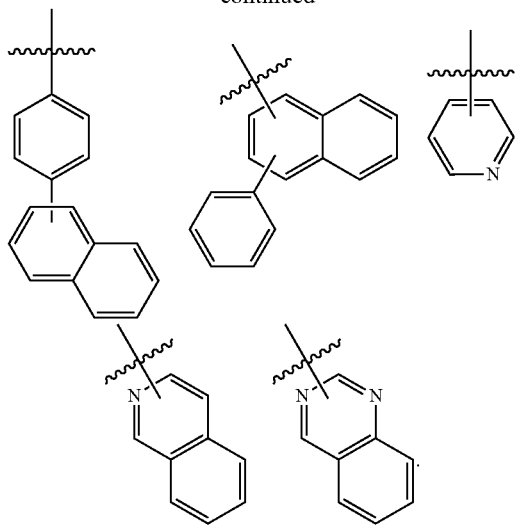

Meanwhile, $R^3$, $R^4$ and/or the ring formed by any two adjacent groups thereof may be optionally substituted with one or more substituents selected from the group consisting of deuterium, halogen, a silane group, a siloxane group, a boron group, a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

In Formula 1 above, $Ar^1$ to $Ar^3$ may be each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group.

Preferably, $Ar^1$ may be any one of the following structures:

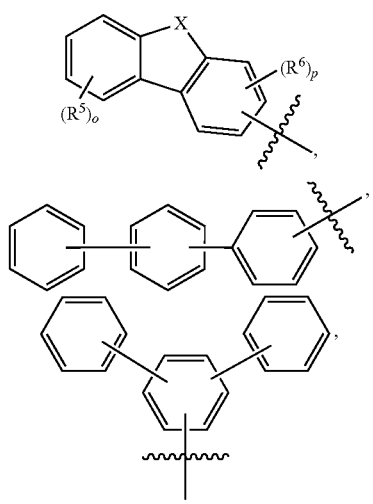

wherein, X may be O, S or C(R')(R''), R' and R'' may be each independently selected from the group consisting of hydrogen; deuterium; tritium; a $C_6$-$C_{20}$ aryl group; a $C_1$-$C_{20}$ alkyl group; and a $C_2$-$C_{20}$ alkenyl group, and R' and R'' may be linked together to form a spiro-compound with the carbon to which they are attached.

Preferably, $Ar^1$ may be

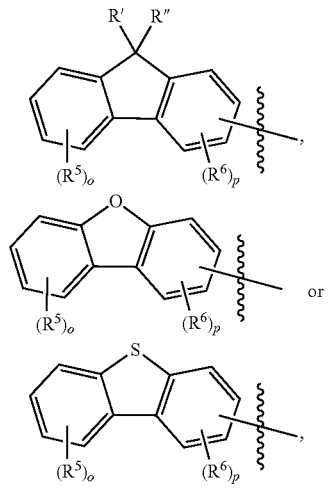

wherein the symbols of R', R'', o, p and the like may be the same as defined above.

$R^5$ and $R^6$ in the above structure may be each independently selected from the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; or ii) any adjacent groups may be optionally linked together to form at least one ring, and the group(s) not forming a ring among $R^5$ and $R^6$ may be the same as defined in the above i).

For example, when both o and p are 2, any two adjacent $R^5$s may be linked together to form a ring, but even if $R^6$s are adjacent group, $R^6$s may be each independently an aryl group or a heterocyclic group. Where o is 2 or more, plural $R^5$s may be same or different each other, some of the adjacent groups may be linked together to form a ring, and the other groups not forming a ring may be selected from the substituent group defined above. The same applies to plural $R^6$s where p is 2 or more.

Preferably, $Ar^1$ may be a $C_6$-$C_{25}$ aryl group, more preferably a $C_6$-$C_{18}$ aryl group, more preferably a $C_6$, $C_{10}$, $C_{12}$, $C_{18}$ aryl group, each of which may be substituted with at least one deuterium. For example, $Ar^1$ may be phenyl, naphthyl, biphenyl, terphenyl, or phenyl substituted with biphenyl and they may be each substituted with at least one deuterium.

Also, preferably $Ar^1$ may be a fluorenyl group, for example, 9,9-diphenyl-9H-fluorenyl group or 7,7-dimethyl-7H-benzo[c] fluorenyl group.

Also, $Ar^1$ may be preferably a $C_3$-$C_{12}$ heterocyclic group, more preferably a $C_{12}$ heterocyclic group, for example, dibenzothienyl or dibenzofuryl.

Preferably, $Ar^2$ and $Ar^3$ may be each independently a $C_6$-$C_{25}$ aryl, more preferably a $C_6$-$C_{18}$ aryl group, more preferably a $C_6$, $C_{10}$, $C_{12}$, $C_{18}$ aryl group. For example $Ar^2$ and $Ar^3$ may be each independently phenyl, naphthyl, biphenyl or terphenyl(including p-terphenyl or m-terphenyl), and phenyl may be further substituted by deuterium, methyl, methoxy, or t-butyl.

Also, preferably $Ar^2$ and $Ar^3$ may be each independently, for example, 9,9-dimethyl-9H-fluorenyl, 9,9-diphenyl-9H-fluorenyl or 9,9'-spirobifluorenyl.

Also, preferably $Ar^2$ and $Ar^3$ may be each independently a $C_3$-$C_{12}$ heterocyclic group, for example, pyrimidyl substituted or unsubstituted with phenyl, dibenzothienyl or dibenzofuryl.

Also, preferably, $Ar^2$ and $Ar^3$ may be each independently selected from the following structures:

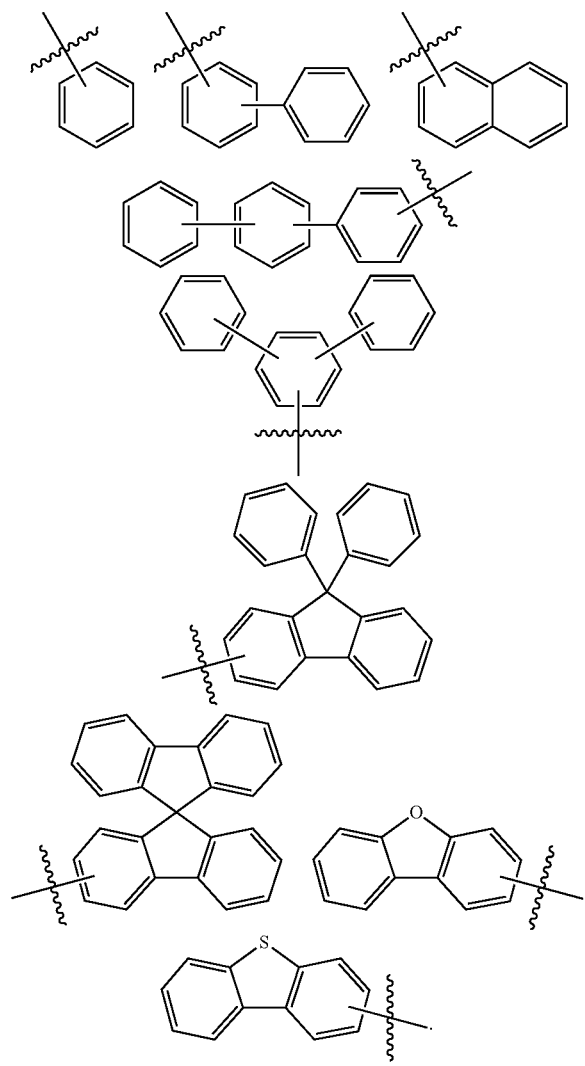

Preferably, $Ar^1$ to $Ar^3$ may be optionally substituted with one or more substituents selected from the group consisting of deuterium, halogen, a silane group, a siloxane group, a boron group, a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

In Formula 1 above, $R^1$ and $R^2$ may be each independently selected from the group consisting of i) deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-$N(R^a)(R^b)$); or ii) any adjacent groups, that is, adjacent $R^1$s, adjacent $R^2$s and/or adjacent $R^1$ and $R^2$, may be optionally linked together to form at least one ring, and the group(s) of $R^1$ and $R^2$ not forming a ring may be the same as defined in the above i). The ring formed by linking between the adjacent groups may be a $C_6$-$C_{60}$ aromatic ring, a $C_2$-$C_{60}$ heterocyclic ring, a $C_3$-$C_{60}$ aliphatic ring, or a fused ring formed by combination thereof, and the formed ring may be a mono cyclic or poly cyclic ring, and/or a saturated or unsaturated ring.

In Formula 1, m may be an integer of 0 to 4, and n may be an integer of 0 to 3, wherein plural R's may be same or different each other when m is an integer of 2 or more, and plural $R^2$s may be same or different each other when n is 2 or more.

Preferably, $R^1$ may be hydrogen, a $C_6$-$C_{18}$ aryl group, a $C_3$-$C_{10}$ heterocyclic group, or a $C_2$-$C_5$ alkenyl group, more preferably $C_6$ aryl, $C_3$, $C_8$, $C_9$, or $C_{10}$ heterocyclic group or $C_3$ alkenyl group, for example, phenyl, dibenzothienyl, triazinyl, quinolyl, quinazolyl substituted or unsubstituted with phenyl, propenyl.

Also, preferably adjacent R's may be linked together to form one or two benzene ring, and the ring formed by adjacent R's together with the benzene ring to which R's are attached may be naphthalene or phenanthrene, and so on.

Also, preferably adjacent $R^2$s may be linked together to form one or two benzene ring, and the ring formed by adjacent $R^2$s together with the benzene ring to which R's are attached may be naphthalene or phenanthrene, and so on.

Meanwhile, $R^1$ and $R^2$ may be optionally substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

In -L'-$N(R^a)(R^b)$ of $R^1$ to $R^4$ above, L' may be selected from the group consisting of a single bond; a $C_6$-$C_{60}$ arylene group; a fluorenylene group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, and $R^a$ and $R^b$ may be each independently selected from the group consisting of a $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P.

In Formula 1 above, when adjacent R's and/or adjacent $R^2$s may be linked together to form a ring, Formula 1 may be represented any one of Formula 2 to Formula 10 below. Formula 2 to Formula 5 below may be examples of when adjacent R's may be linked together to form a benzene ring, Formula 6 to Formula 9 below may be examples of when both adjacent R's and adjacent $R^2$s may be linked together to form benzene rings, Formula 10 may be an example of when adjacent $R^2$s may be linked together to form a benzene ring.

[Formula 2]

[Formula 3]

[Formula 4]

[Formula 5]

[Formula 6]

[Formula 7]

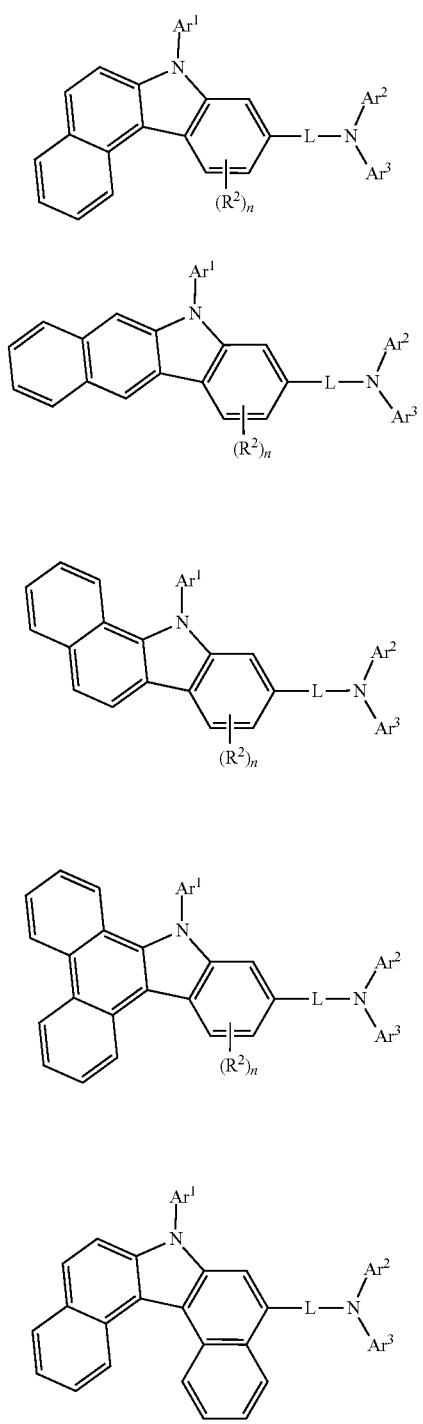
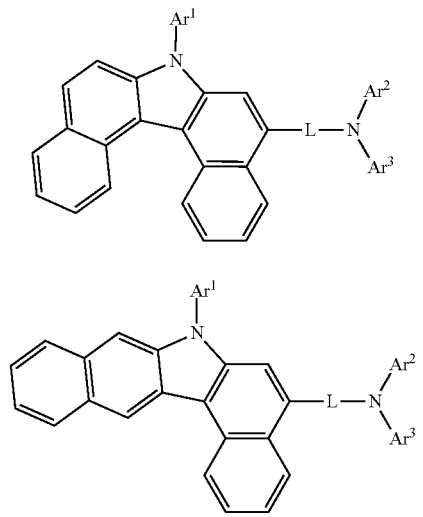

[Formula 8]

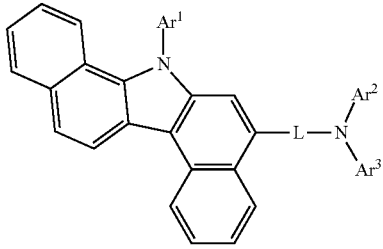

[Formula 9]

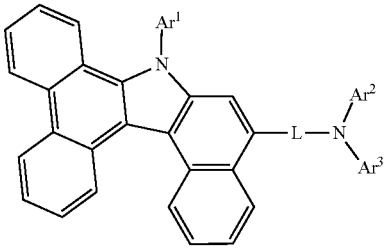

[Formula 10]

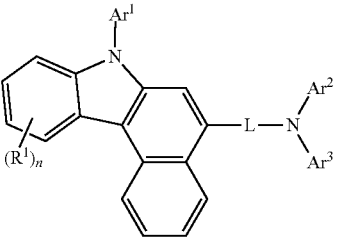

In the Formula 2 to Formula 10 above, Ar¹ to Ar$^a$, L, R¹, R², m and n may be the same as defined in the above Formula 1.

Preferably, in Formula 1 above, when Ar¹ is

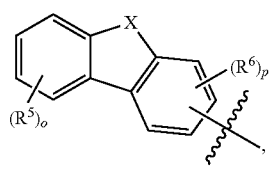

Formula 1 may be represented by any one of Formula 11 to 20 below. Formula 12 to Formula 15 below may be examples of when adjacent R¹'s may be linked together to form a benzene ring, Formula 16 to Formula 19 below may be examples of when both adjacent R¹s and adjacent R²s may be linked together to form benzene rings, Formula 20 below may be an example of when adjacent R²s may be linked together to form benzene rings.

[Formula 11]
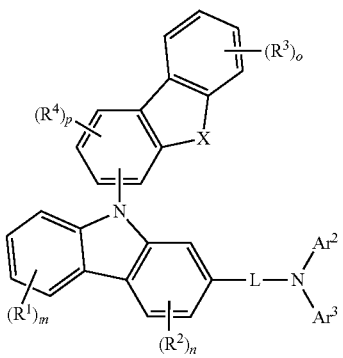
[Formula 12]
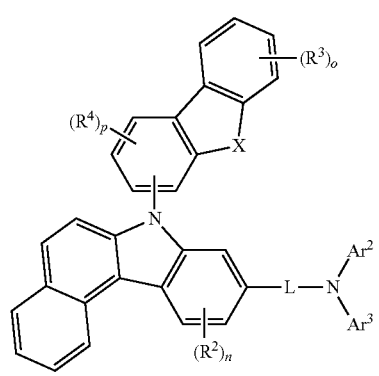
[Formula 13]
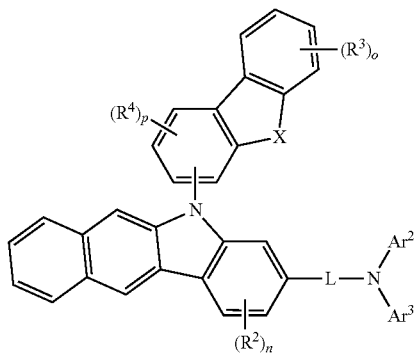
[Formula 14]
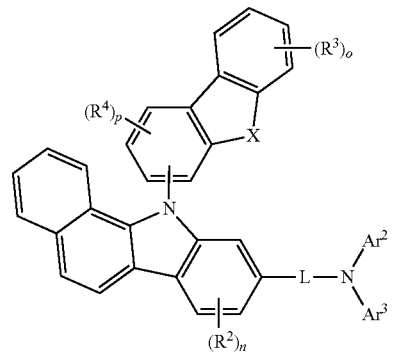
[Formula 15]
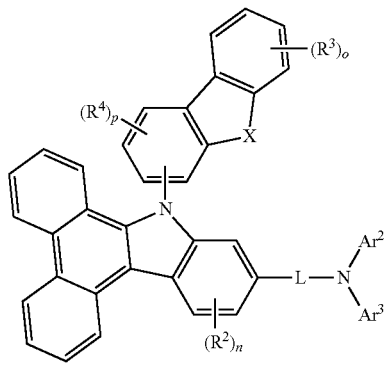
[Formula 16]
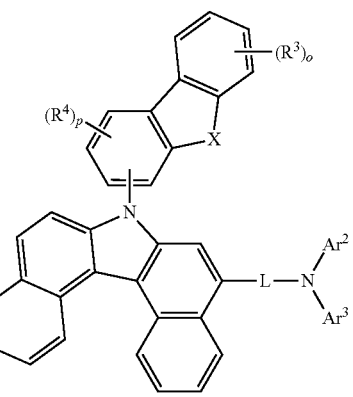
[Formula 17]
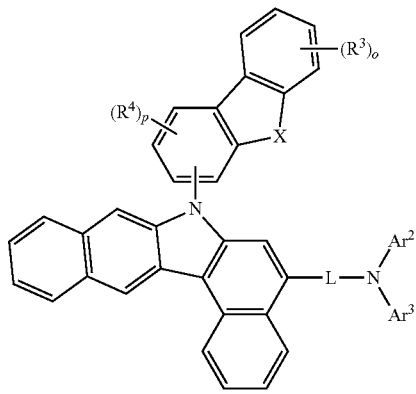
[Formula 18]
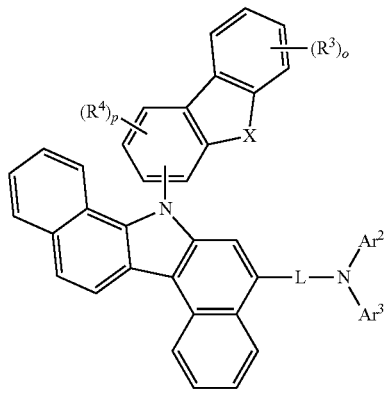

17
-continued

[Formula 19]
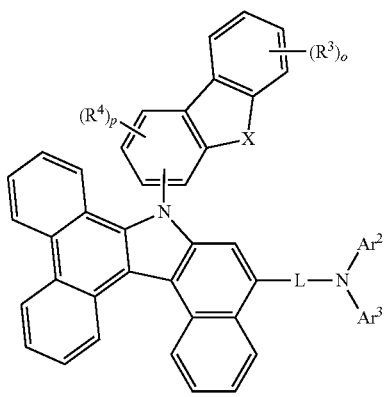

[Formula 20]
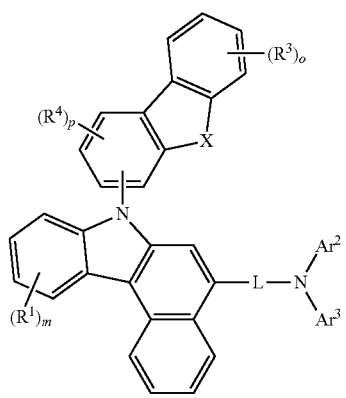

In Formula 11 to Formula 20 above, $Ar^2$, $Ar^3$, L, $R^1$, $R^2$, m, n and the like may be the same as defined in Formula 1.

X may be O, S or C(R')(R"), wherein R' and R" may be each independently selected from the group consisting of hydrogen; deuterium; tritium; a $C_6$-$C_{20}$ aryl group; and a $C_1$-$C_{20}$ alkyl group; and a $C_2$-$C_{20}$ alkenyl group, R' and R" may be linked together to form a spiro compound with the carbon to which they are attached.

o may be an integer of 0 to 4, p may be an integer of 0 to 3, and $R^5$ and $R^6$ may be each independently selected from the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group; or ii) any adjacent groups may be optionally linked together to form at least one ring, and the group(s) of $R^5$ and $R^6$ not forming a ring may be the same as defined in i) above More specifically, the compound represented by Formula 1 to Formula 20 above may be any one of the following compounds.

P1-1
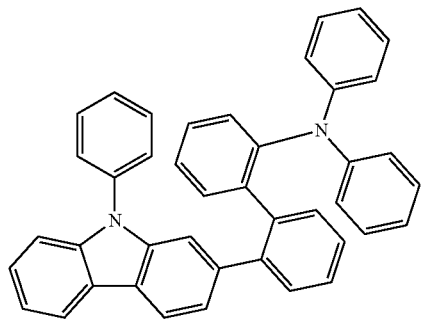

P1-2
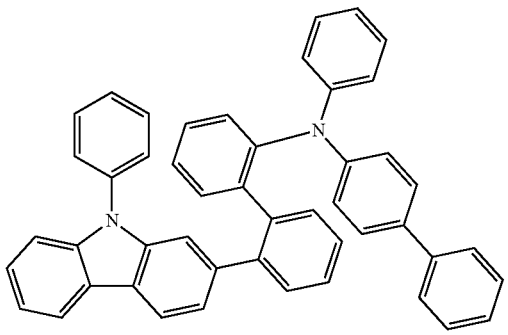

P1-3
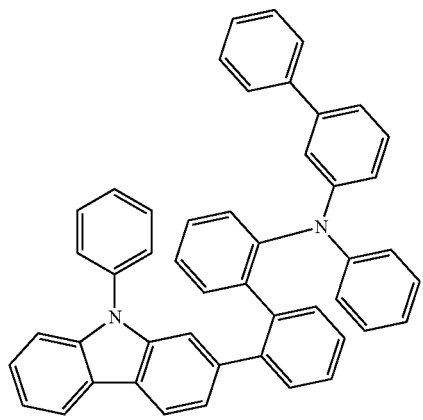

P1-4
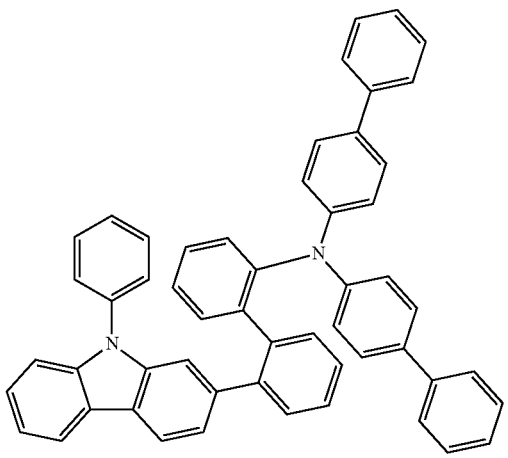

P1-5
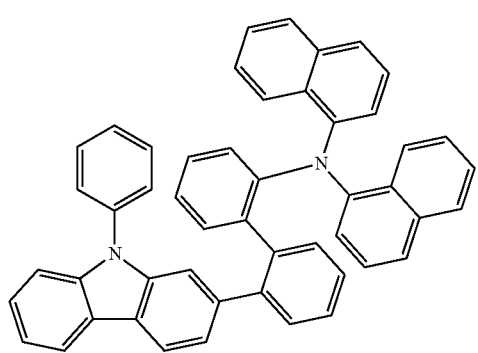
P1-6
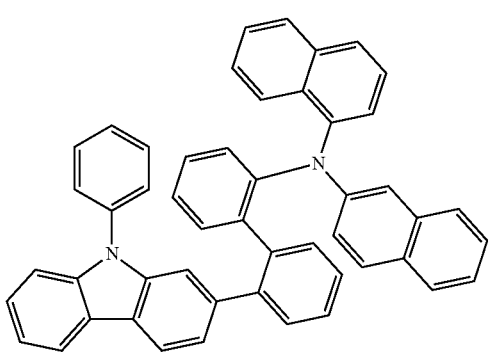
P1-7
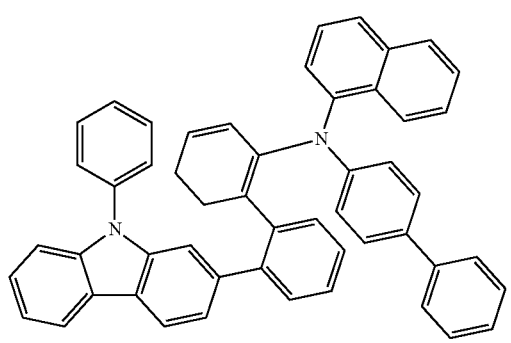
P1-8
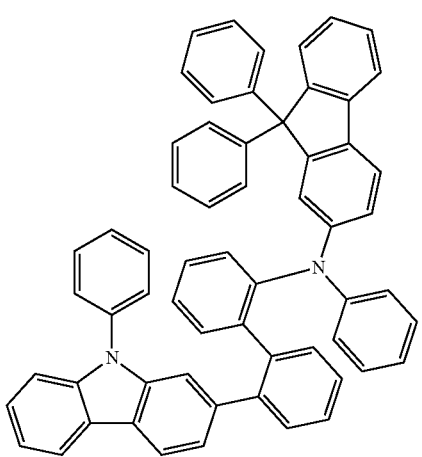
P1-9
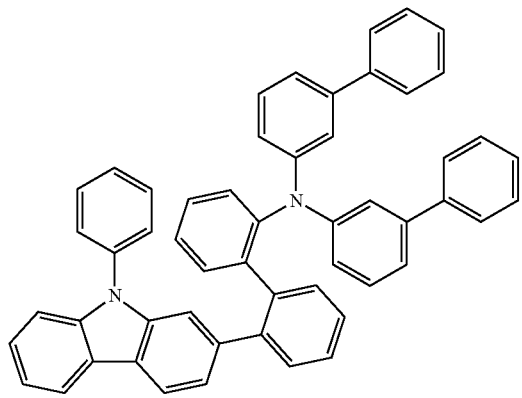
P1-10
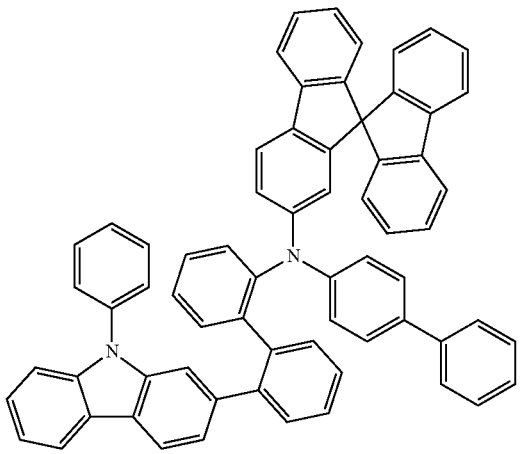

-continued
P1-11
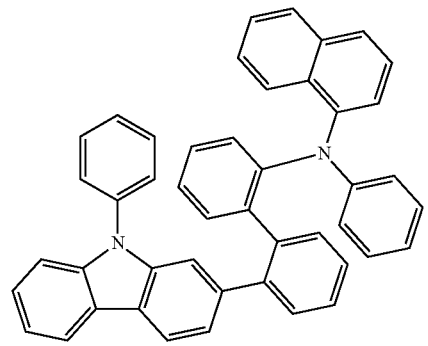
P1-12
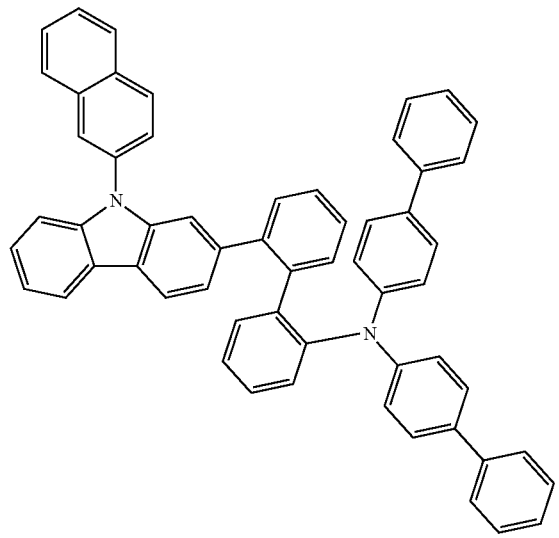
P1-13
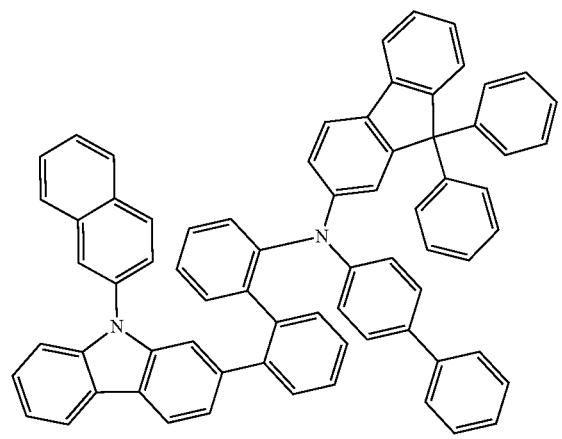
P1-14
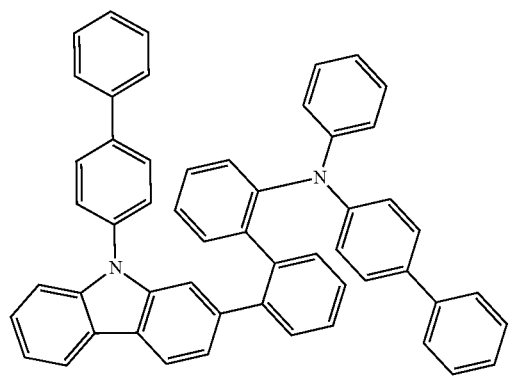
P1-15
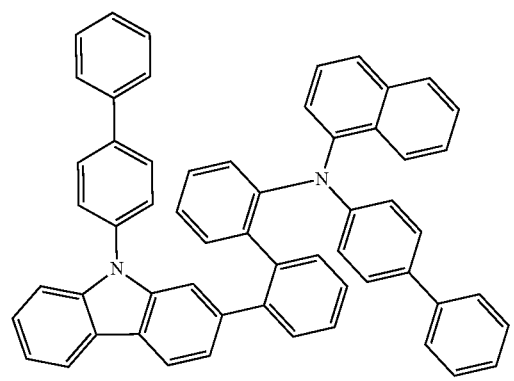
P1-16
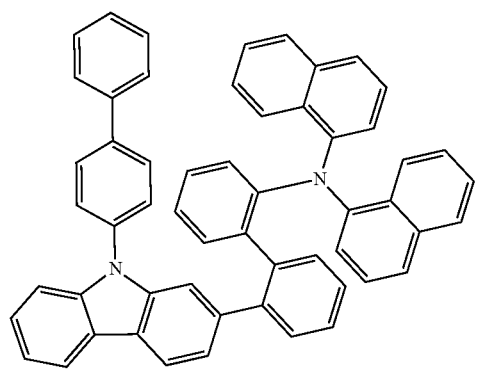

-continued
P1-17
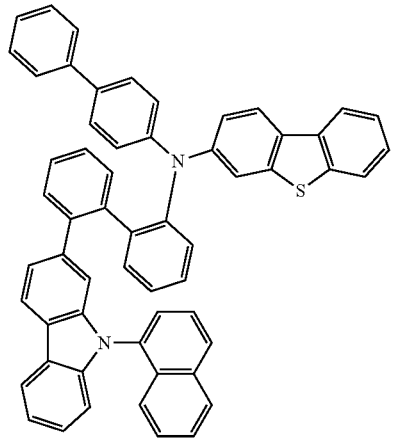
P1-18
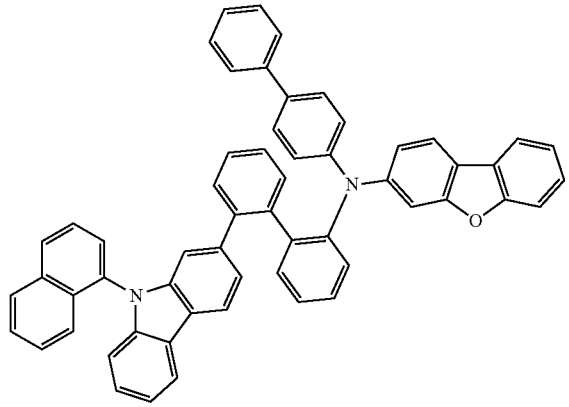
P1-19
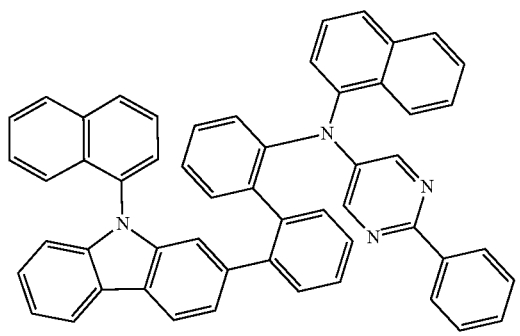
P1-20
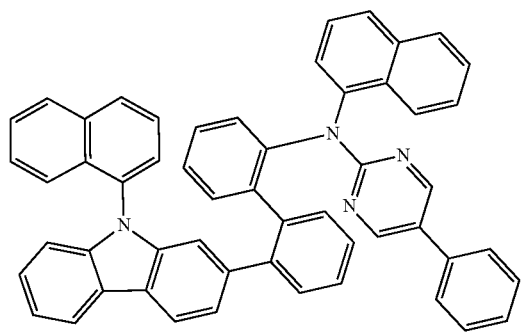
P1-21
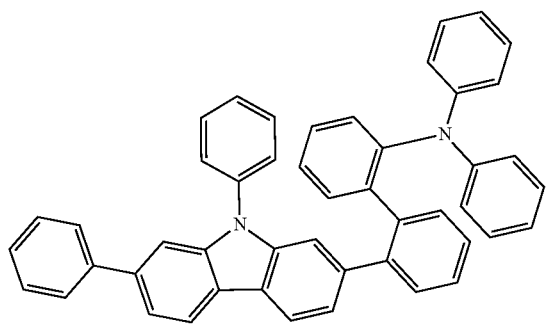
P1-22
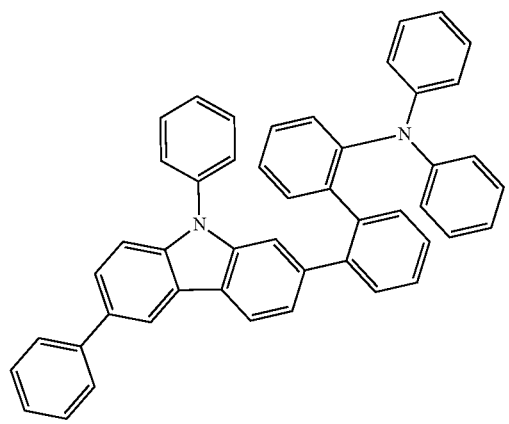

-continued
P1-23
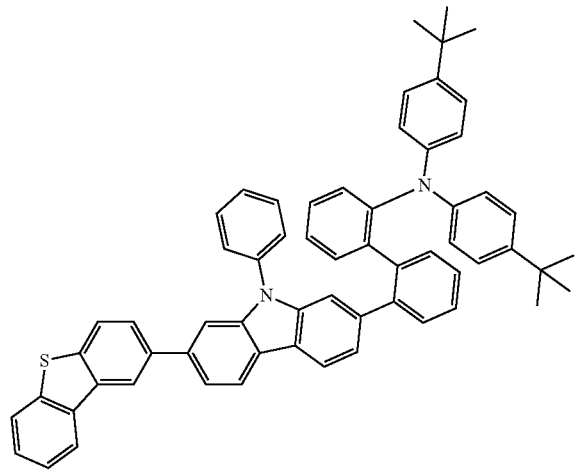
P1-24
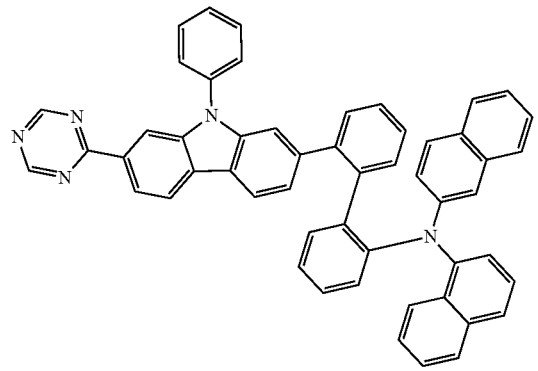
P1-25
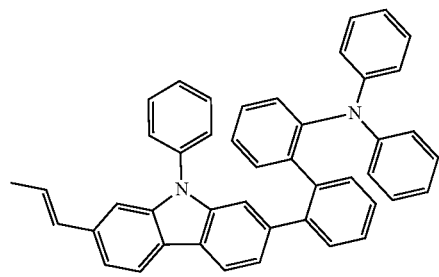
P1-26
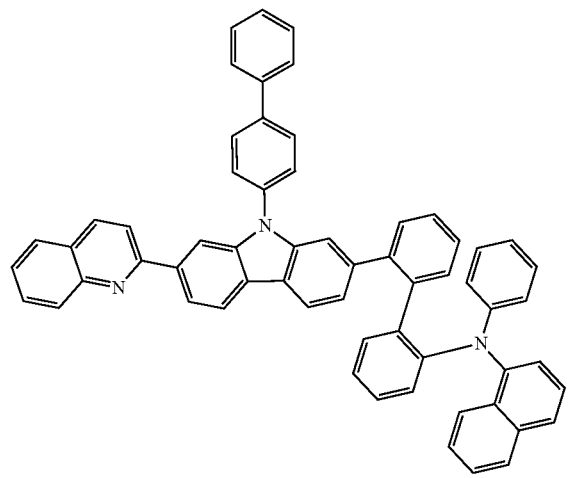
P1-27
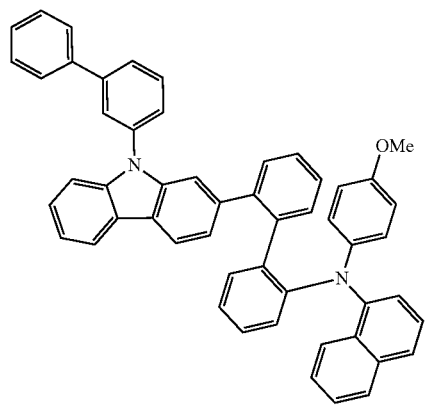
P1-28
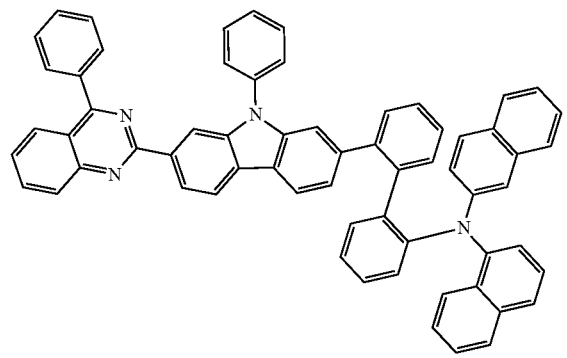

-continued
P1-29
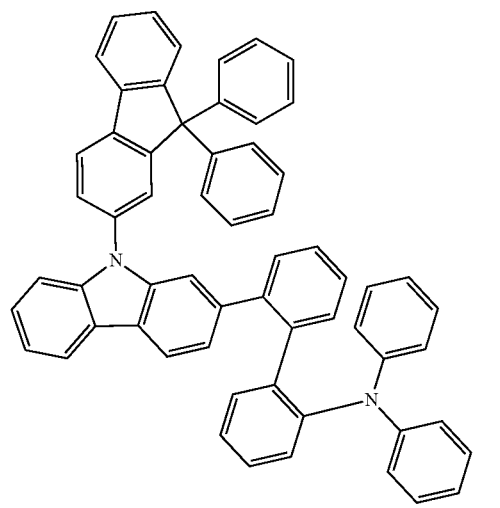
P1-30
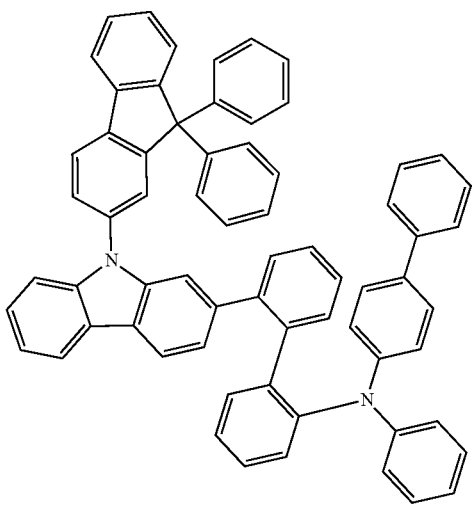
P1-31
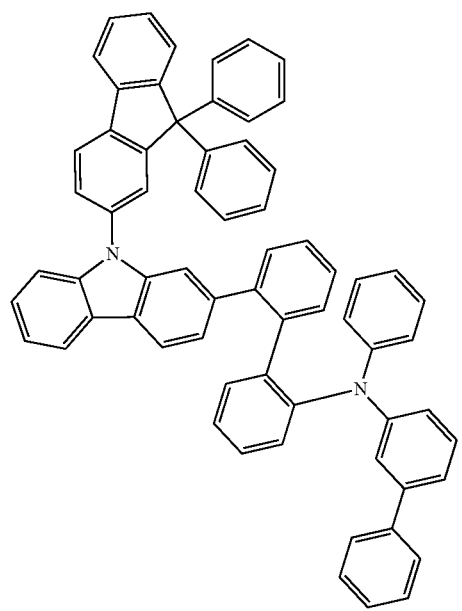
P1-32
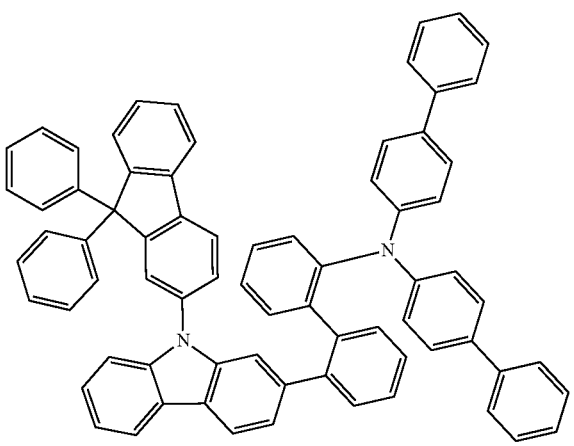
P1-33
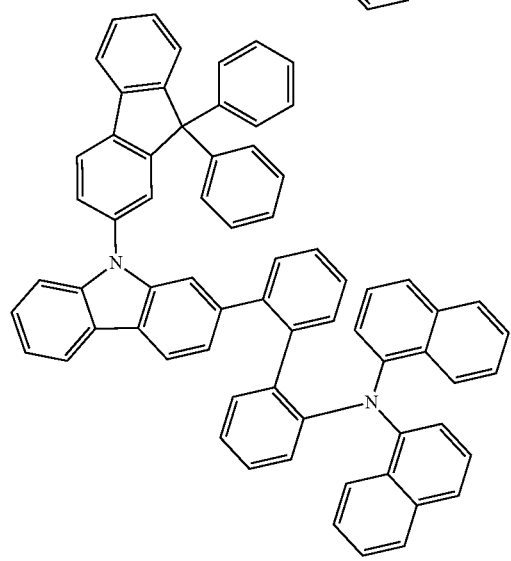
P1-34
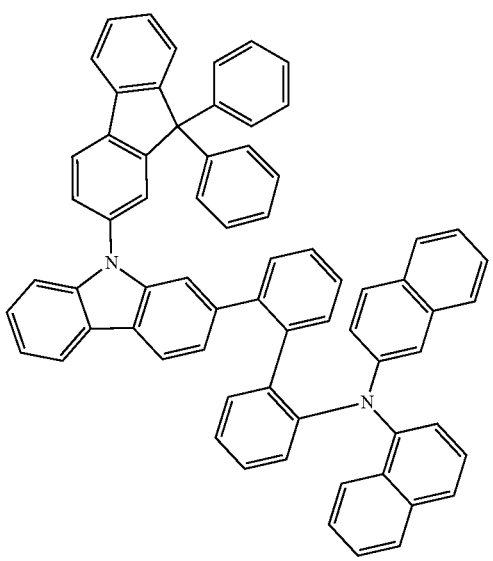

-continued
P1-35
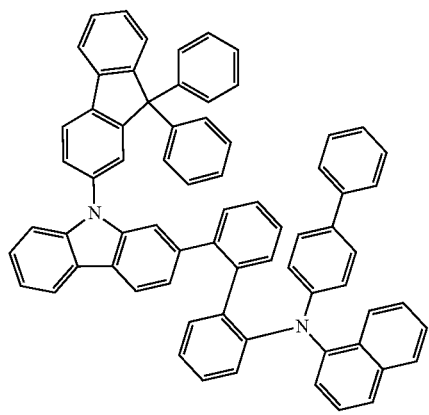
P1-36
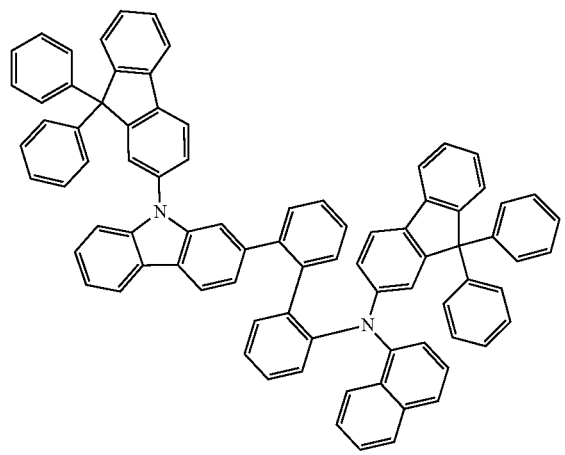
P1-37
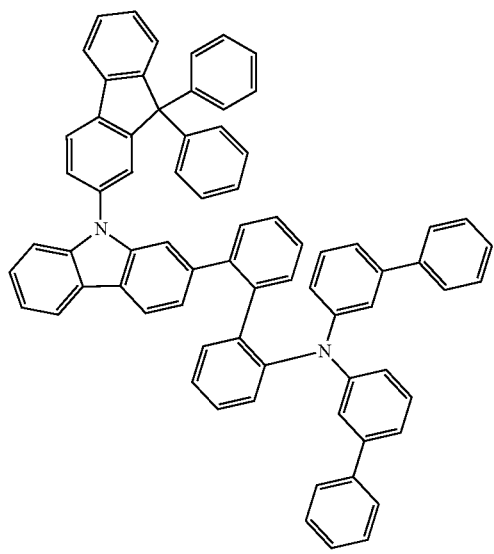
P1-38
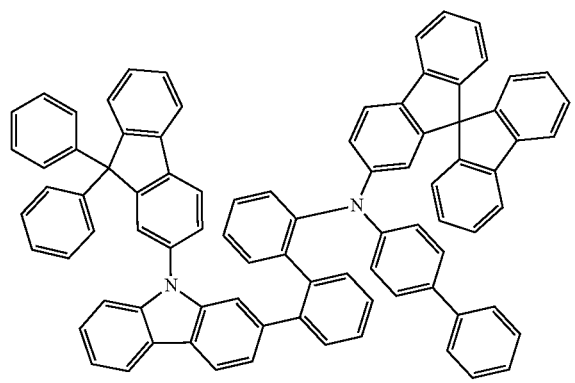
P1-39
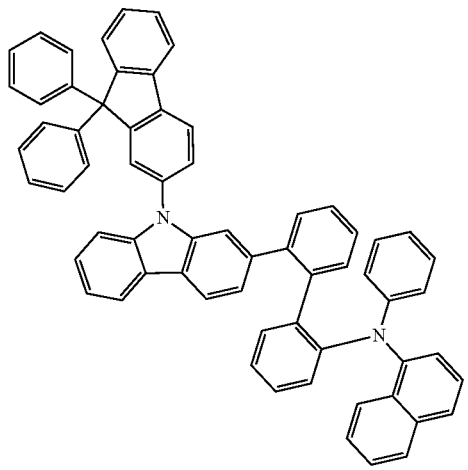
P1-40
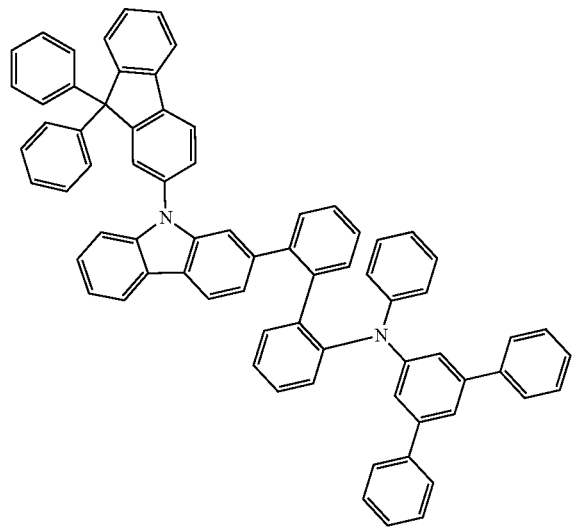

-continued
P1-41
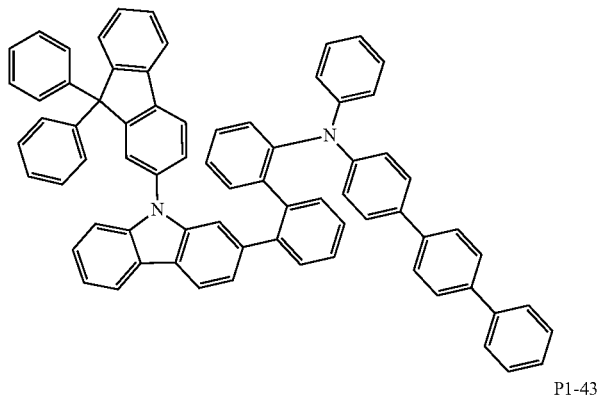
P1-42
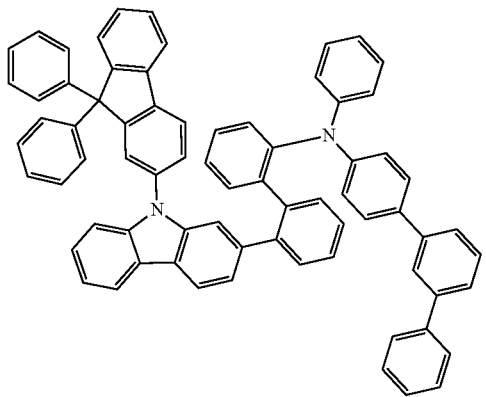
P1-43
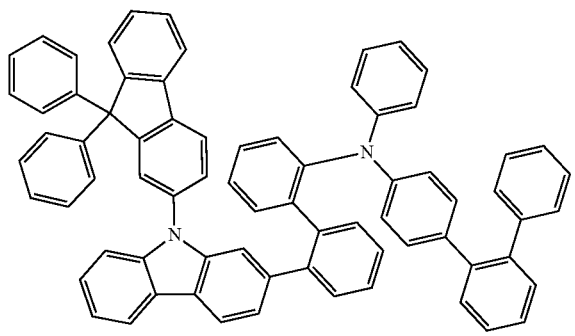
P1-44
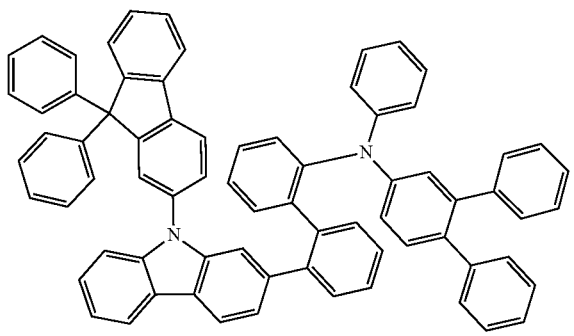
P1-45
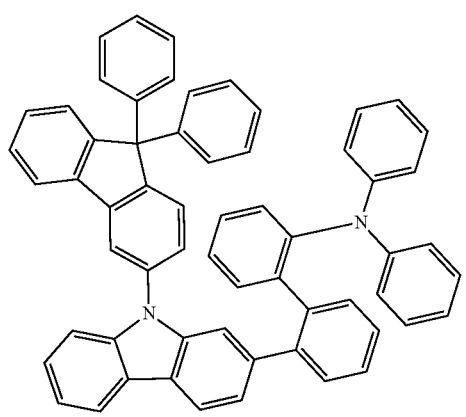
P1-46
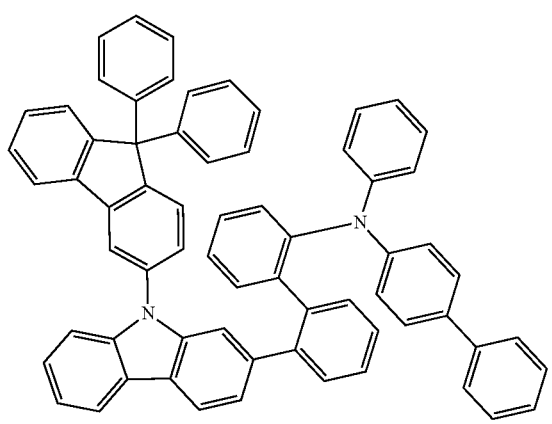
P1-47
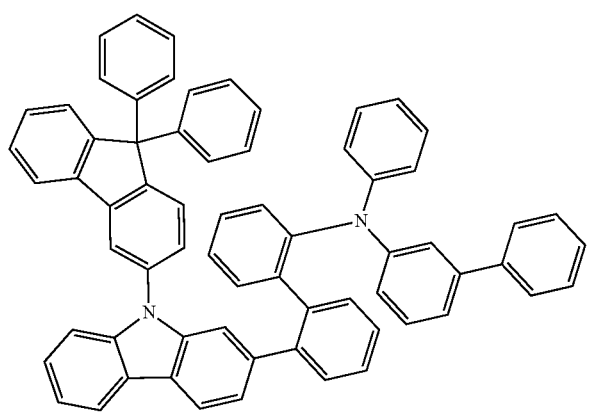
P1-48
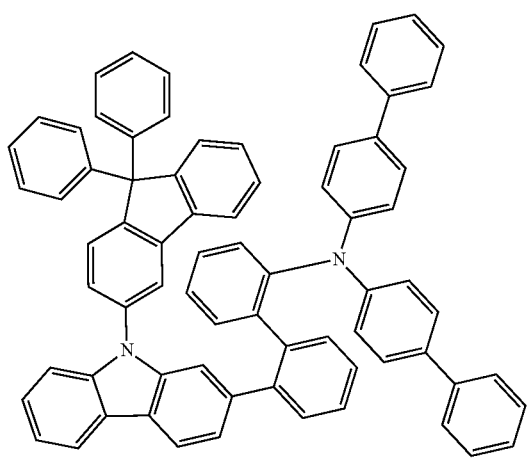

-continued
P1-49
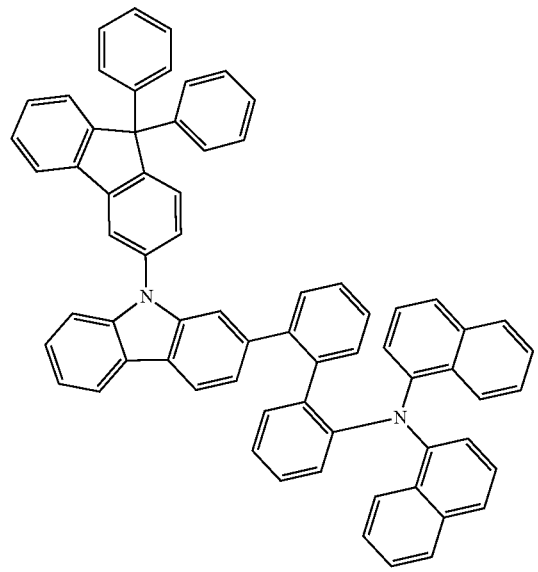
P1-50
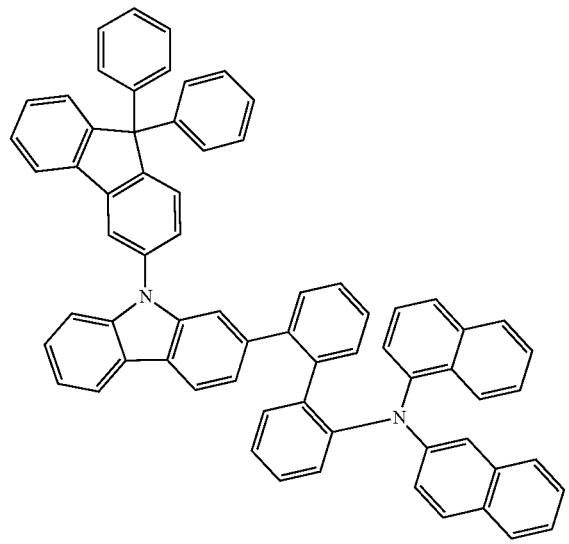
P1-51
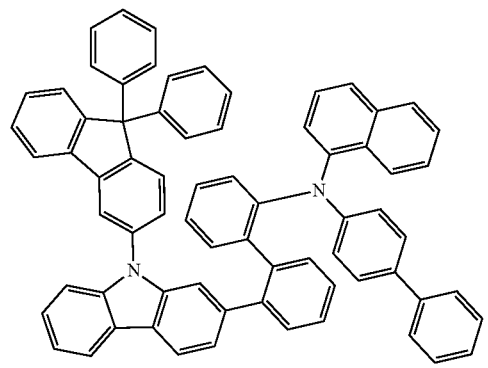
P1-52
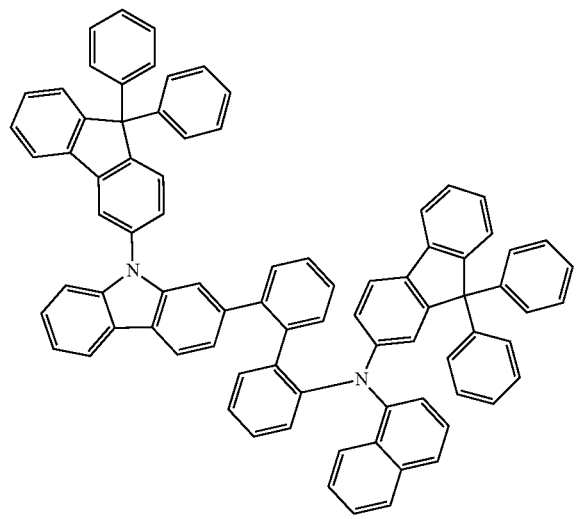
P1-53
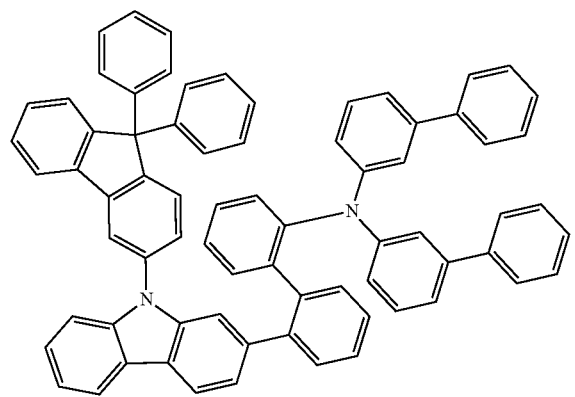
P1-54
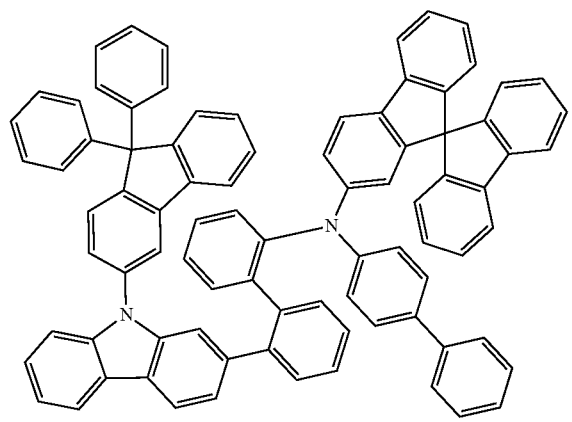

-continued
P1-55
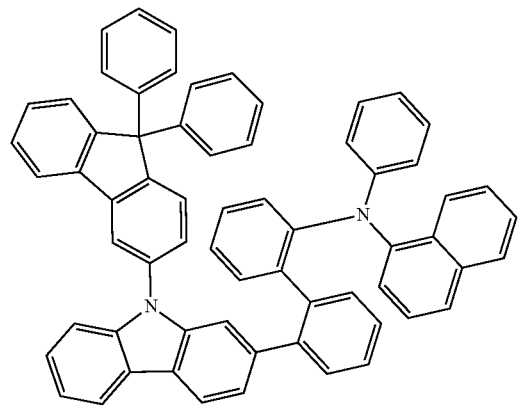
P1-56
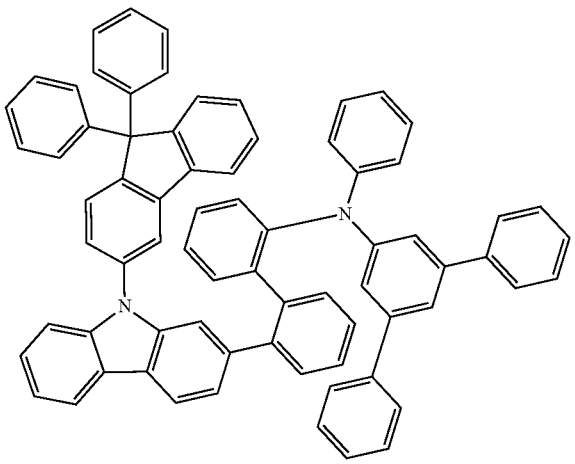
P1-57
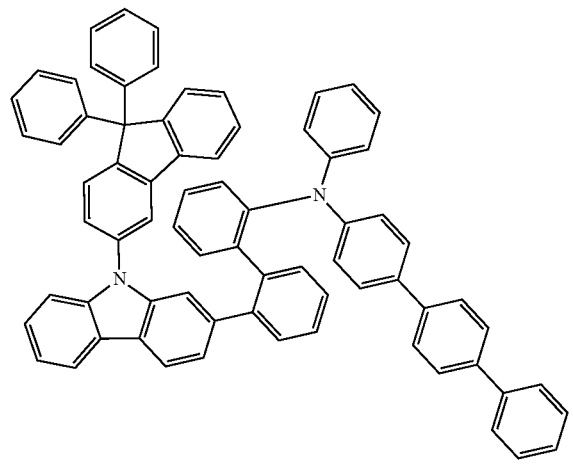
P1-58
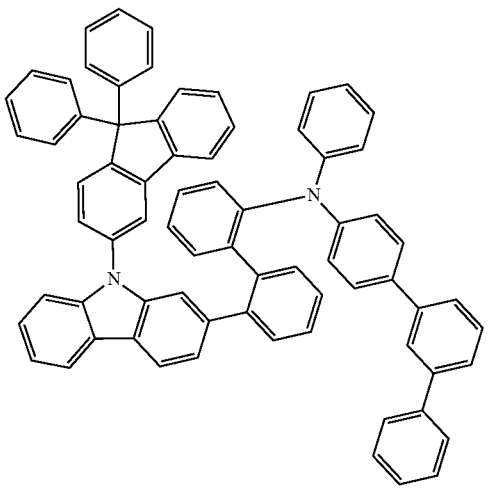
P1-59
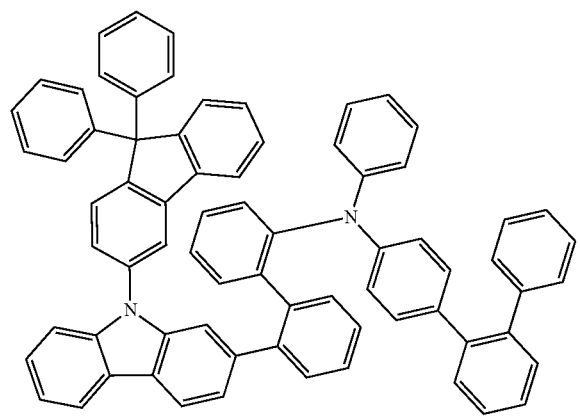
P1-60
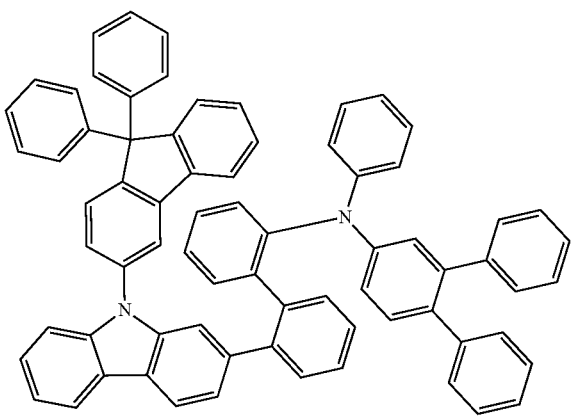

-continued
P1-61
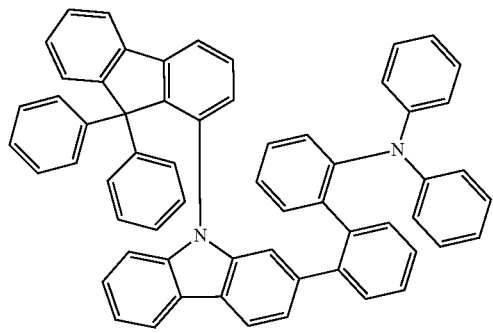
P1-62
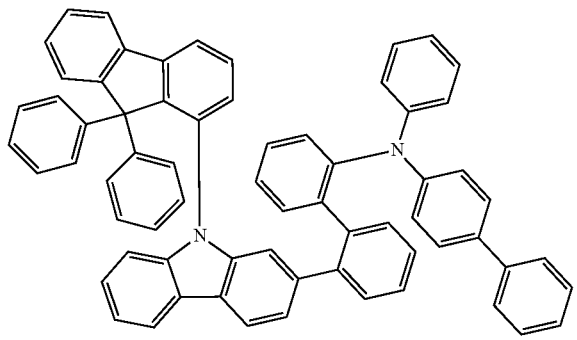
P1-63
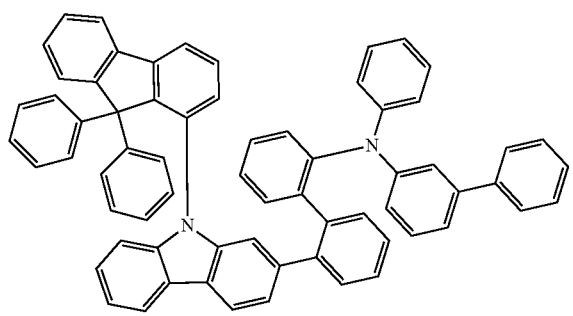
P1-64
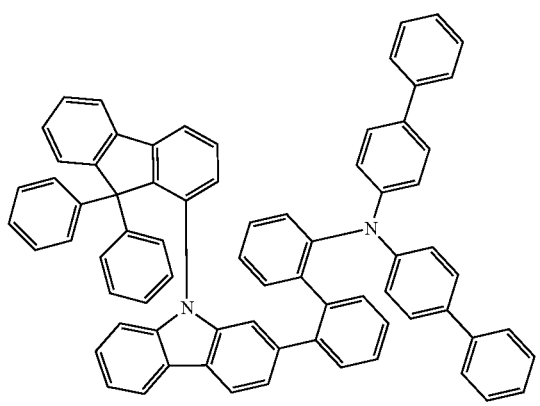
P1-65
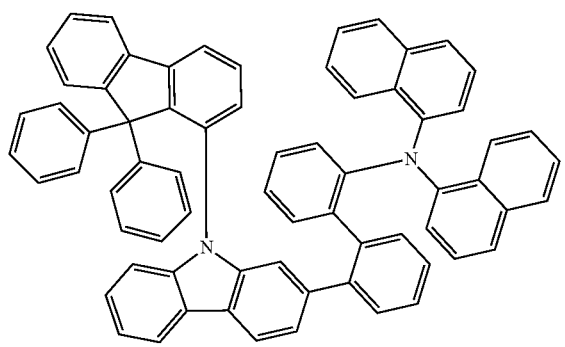
P1-66
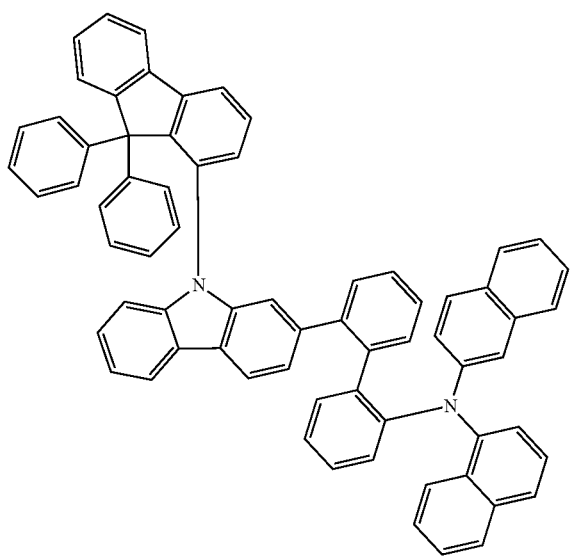

-continued
P1-67
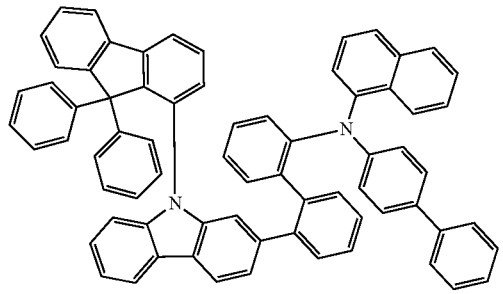
P1-68
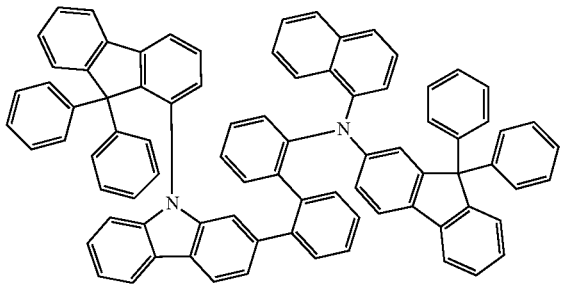
P1-69
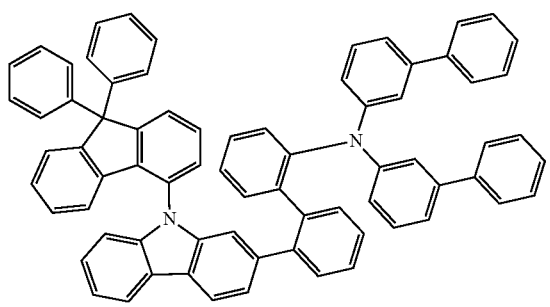
P1-70
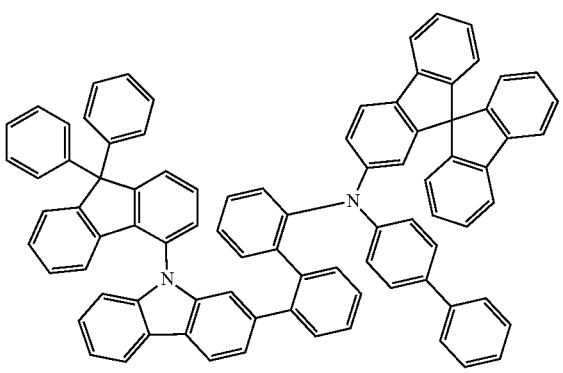
P1-71
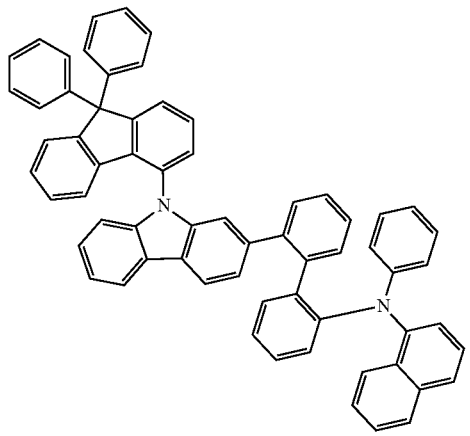
P1-72
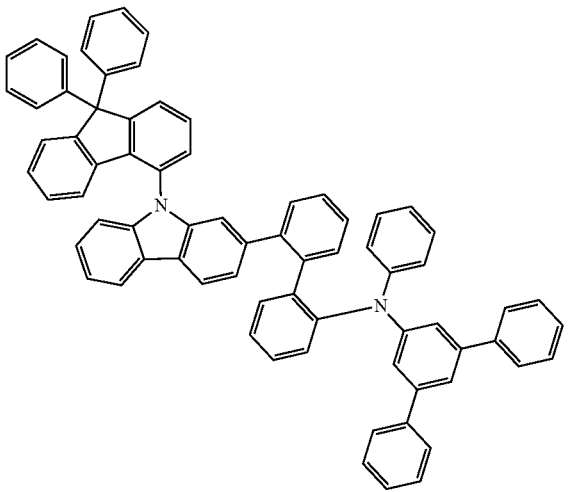
P1-73
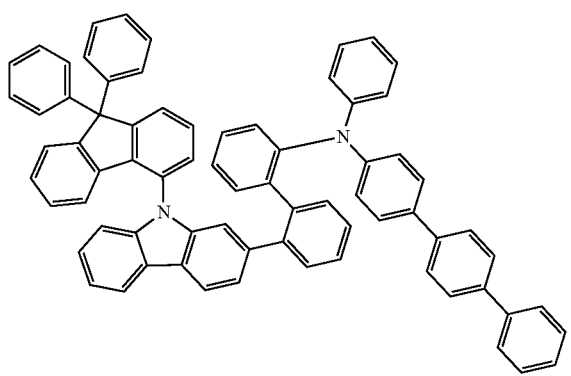
P1-74
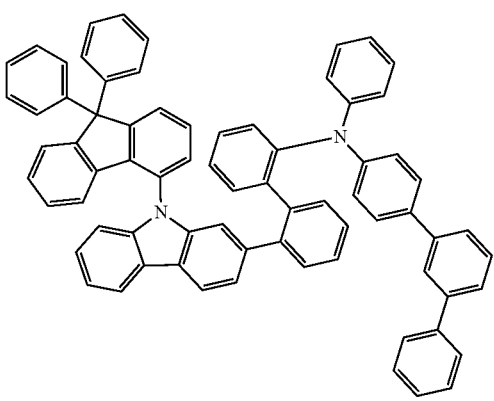

-continued
P1-75
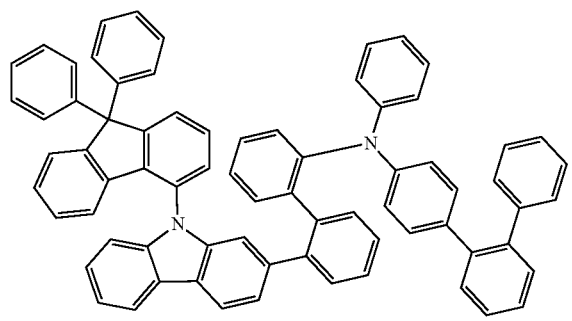
P1-76
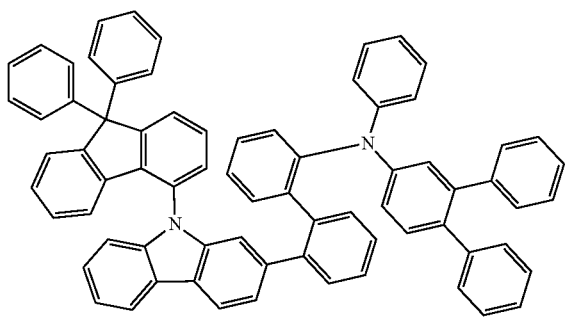
P1-77
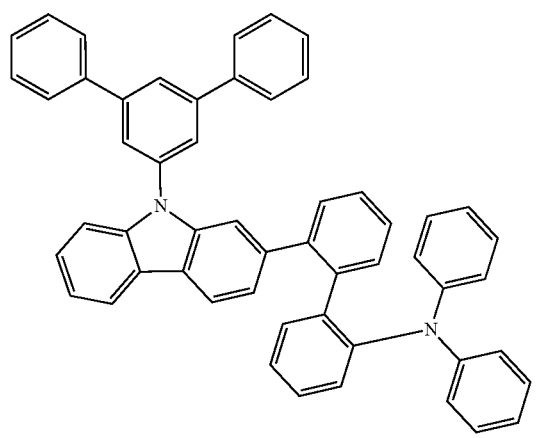
P1-78
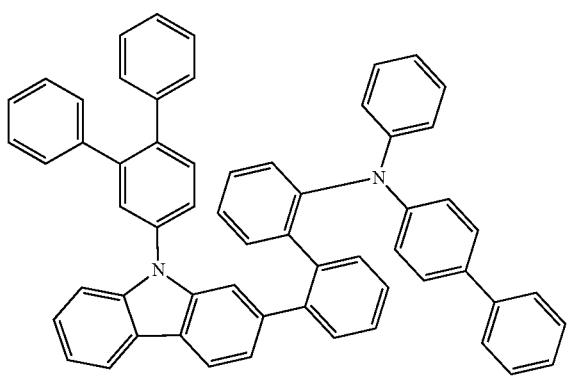
P1-79
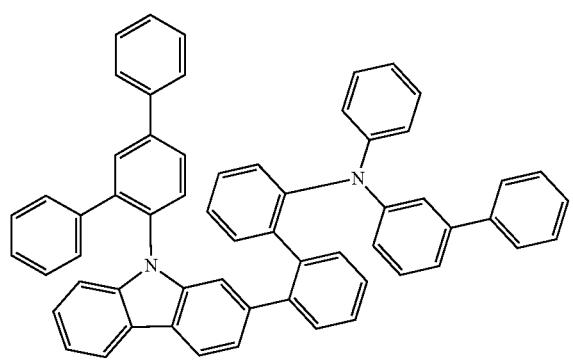
P1-80
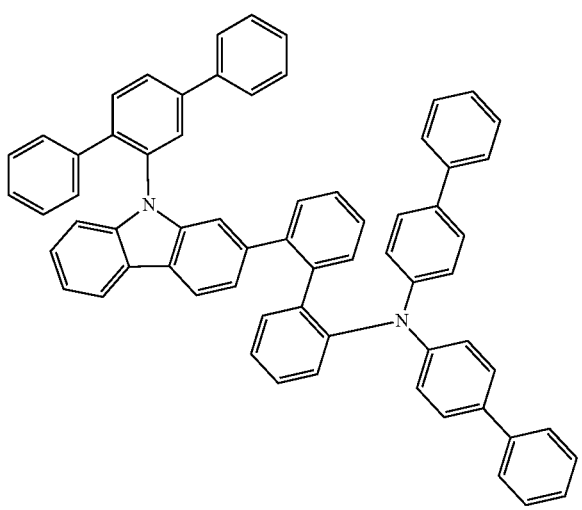

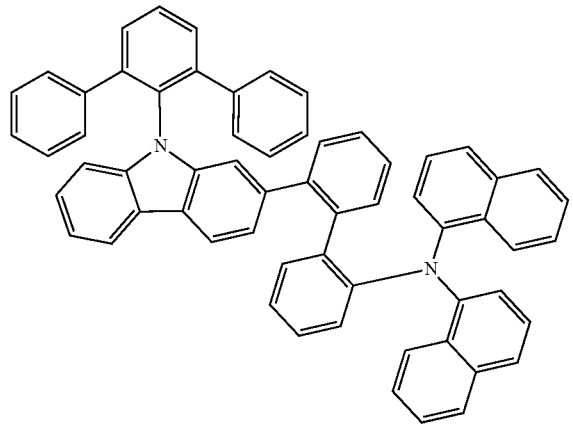
P1-81
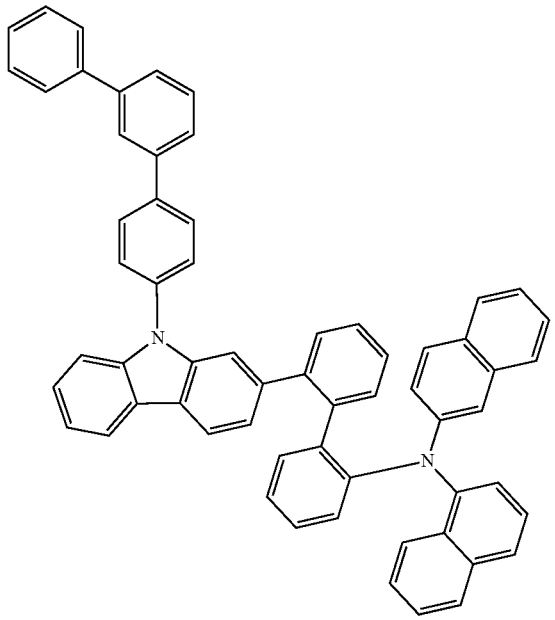
P1-82
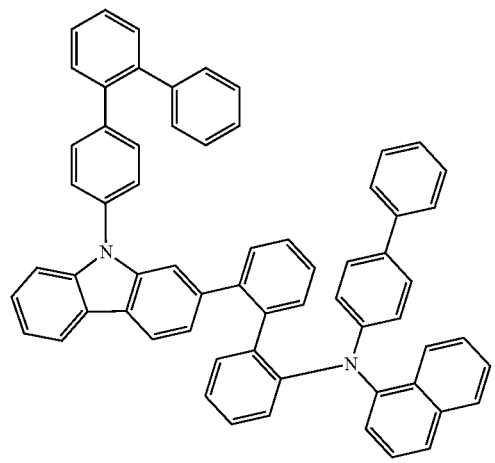
P1-83
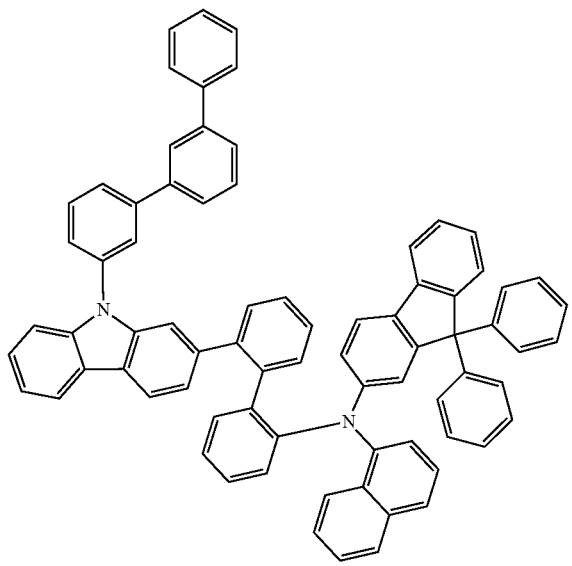
P1-84

-continued
P1-85
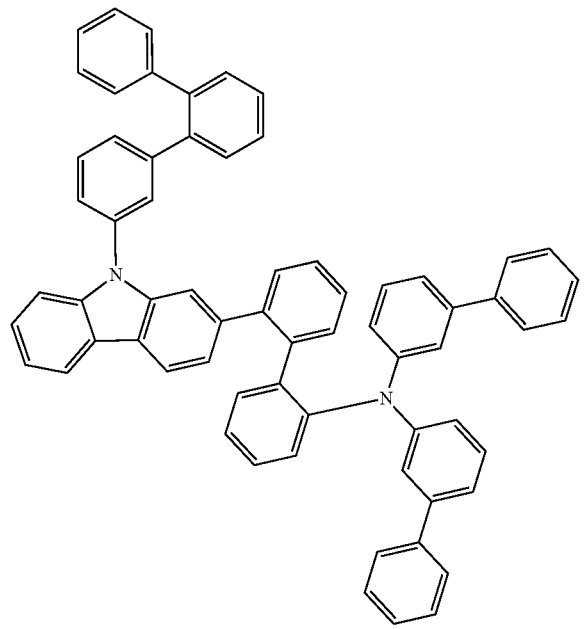
P1-86
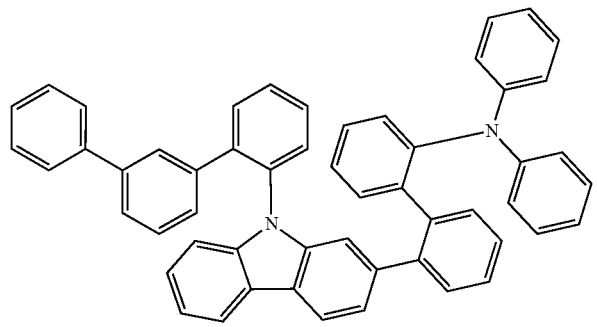
P1-87
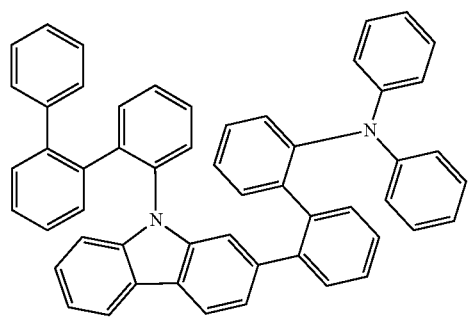
P1-88
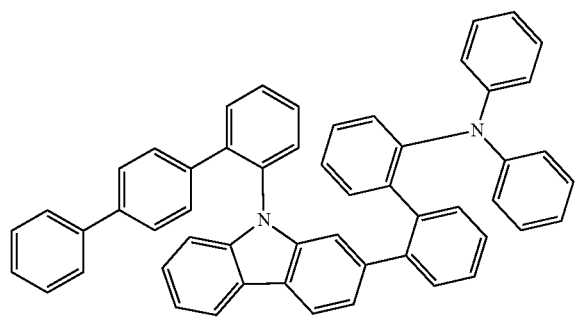
P1-89
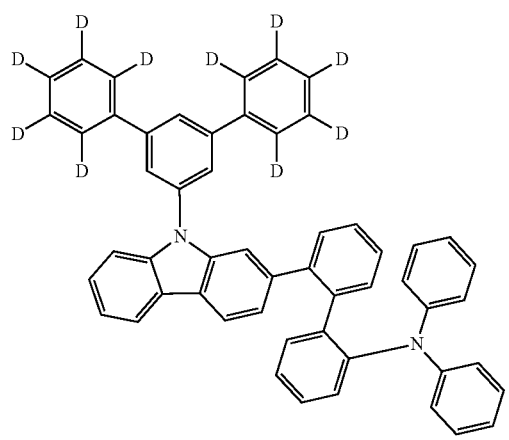
P1-90
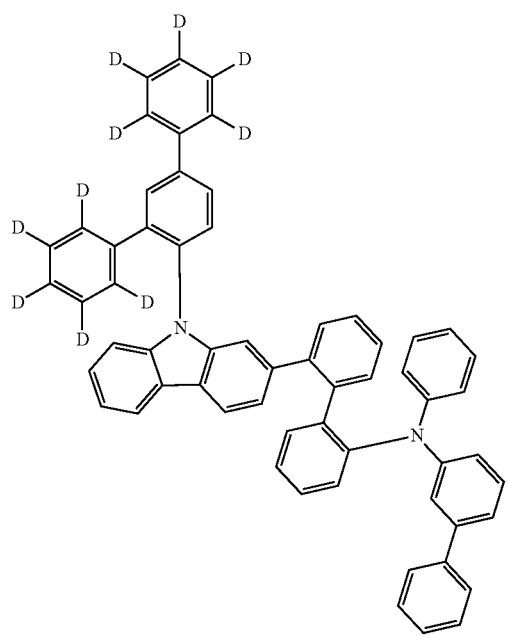

-continued
P1-91
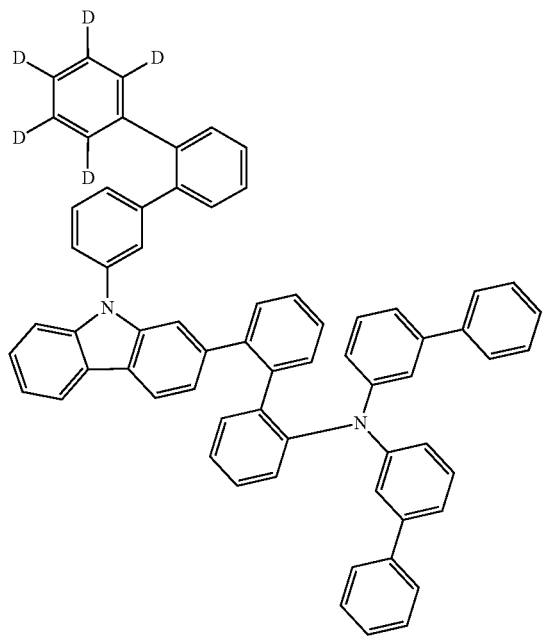
P1-92
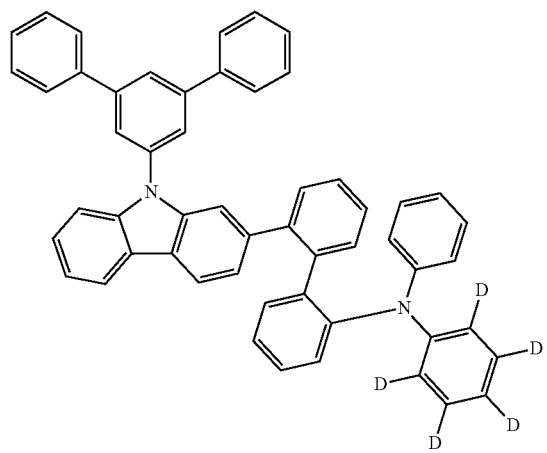
P1-93
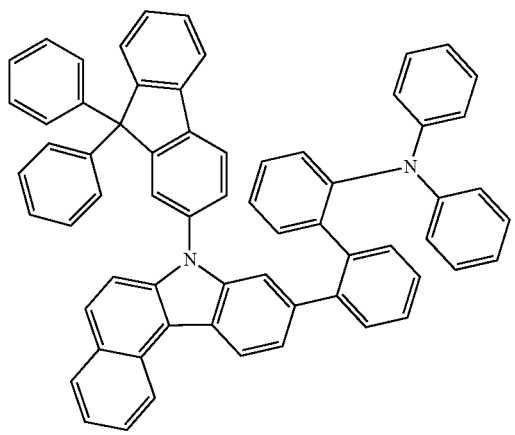
P1-94
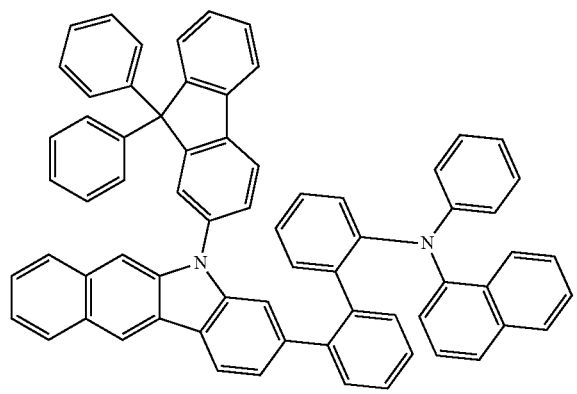
P1-95
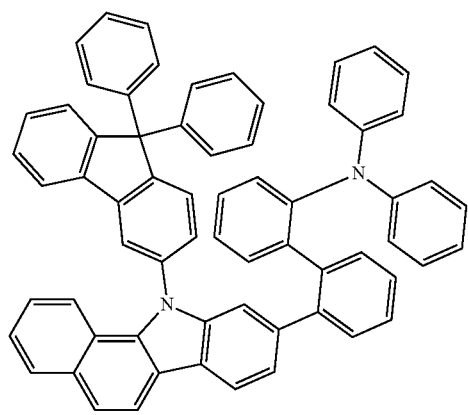
P1-96
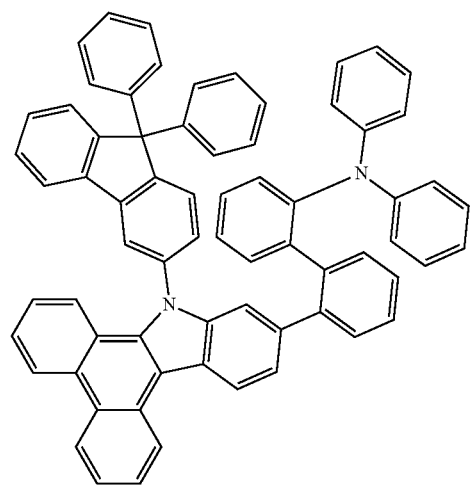

-continued
P1-97
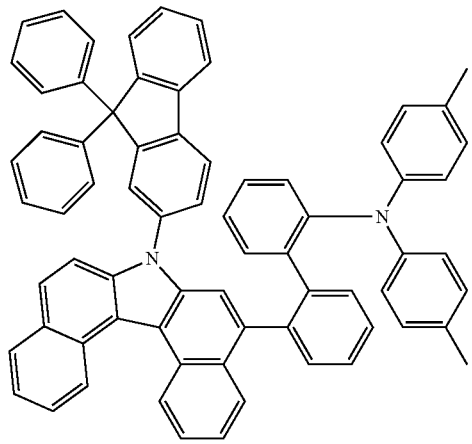
P1-98
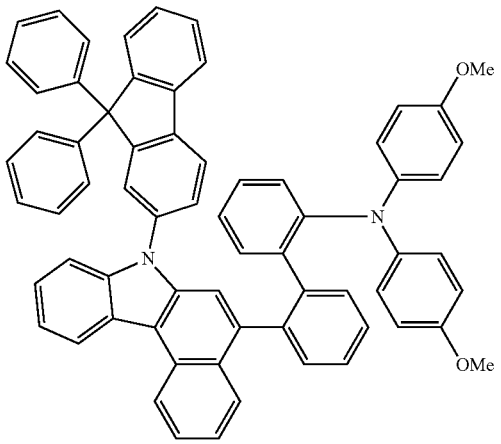
P1-99
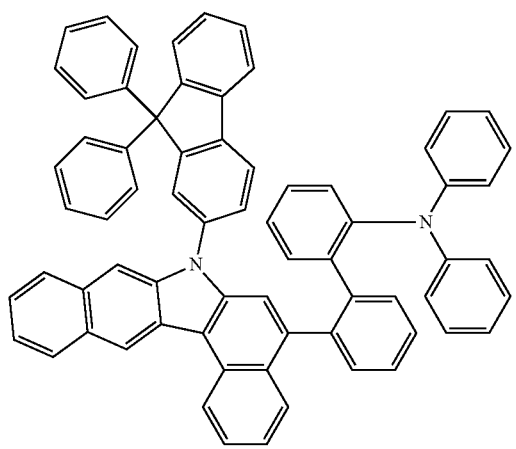
P1-100
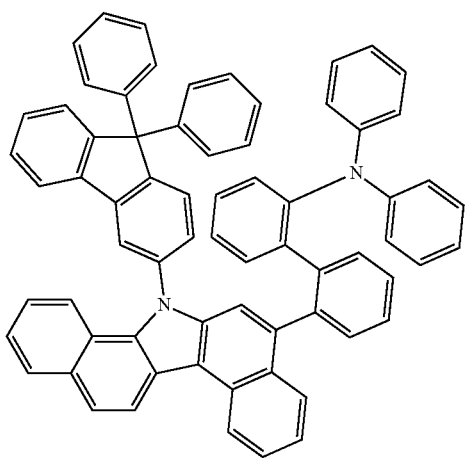
P1-101
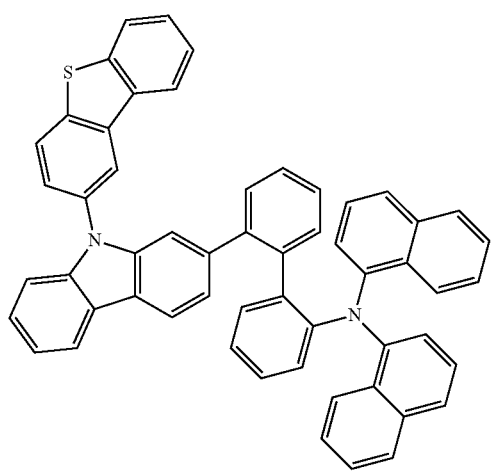
P1-102
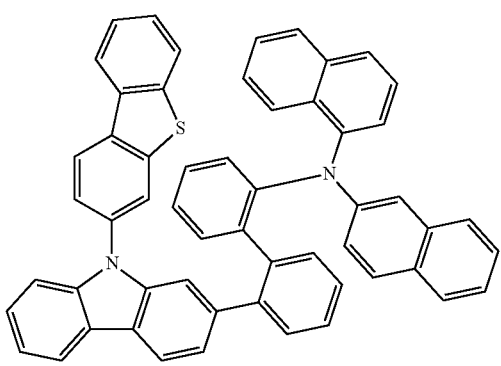

-continued
P1-103
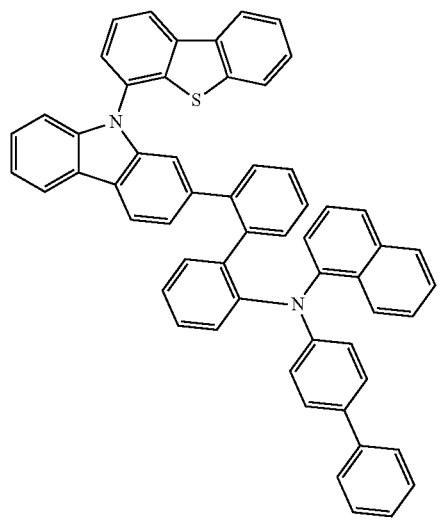
P1-104
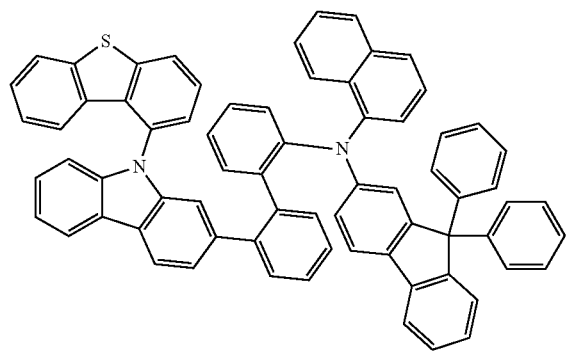
P1-105
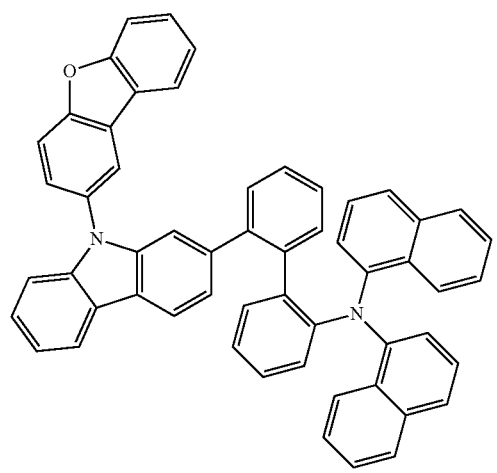
P1-106
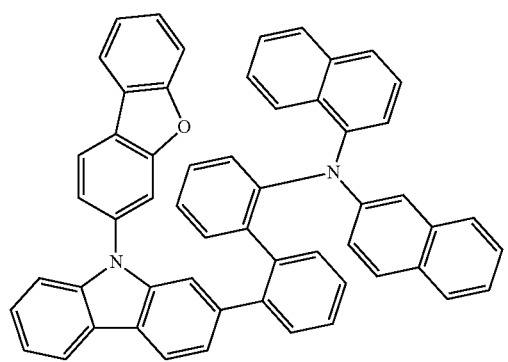
P1-107
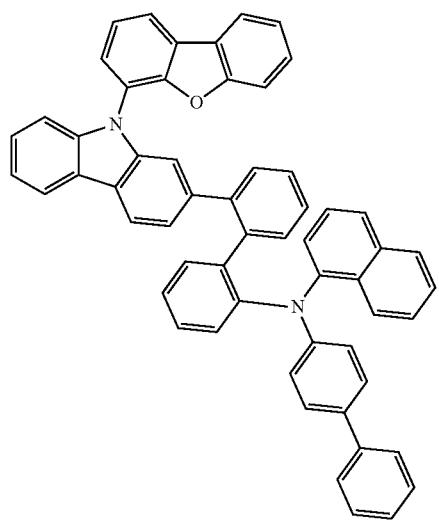
P1-108
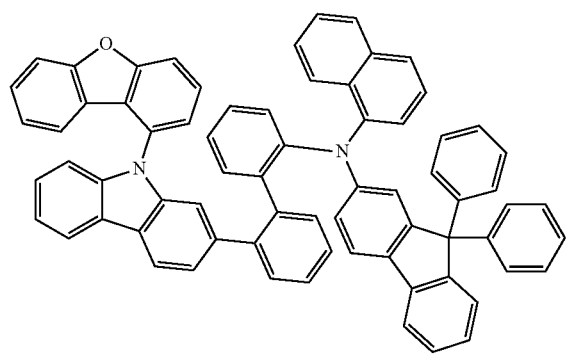

-continued
P1-109
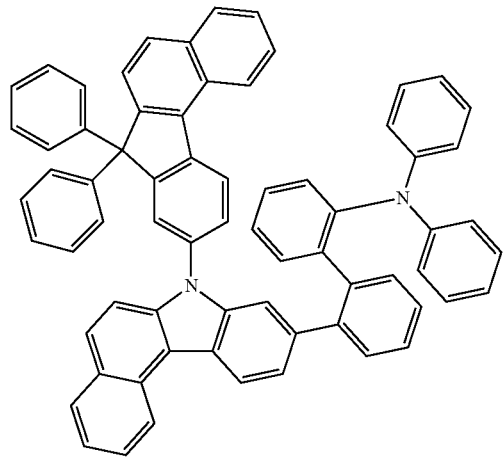
P1-110
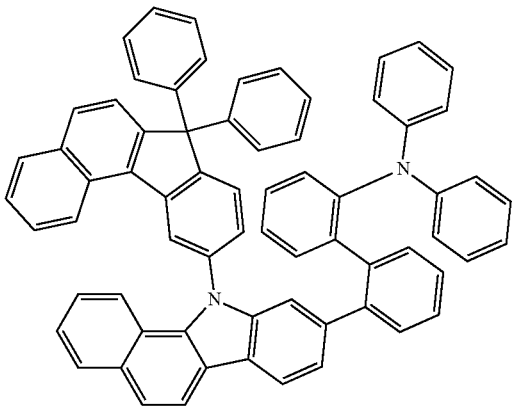
P1-111
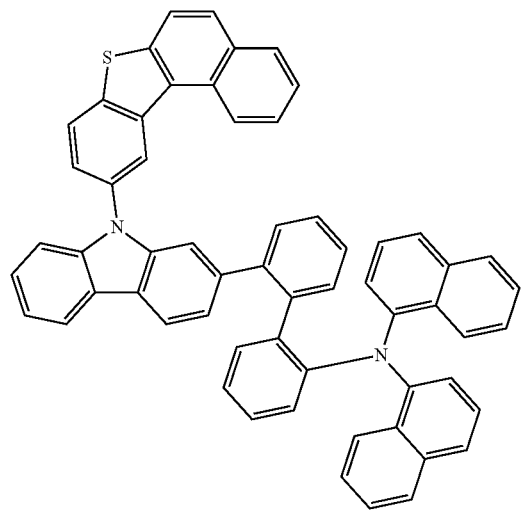
P1-112
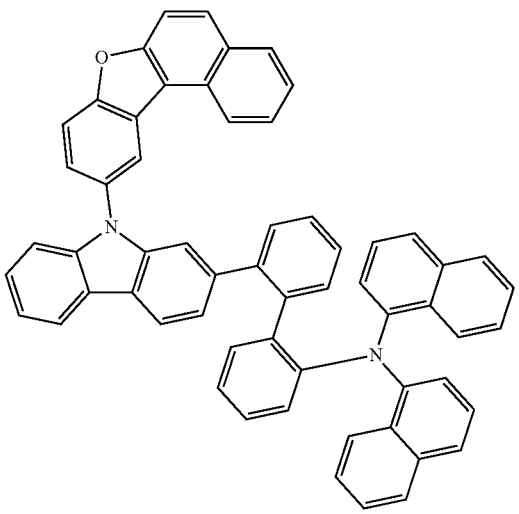
P2-1
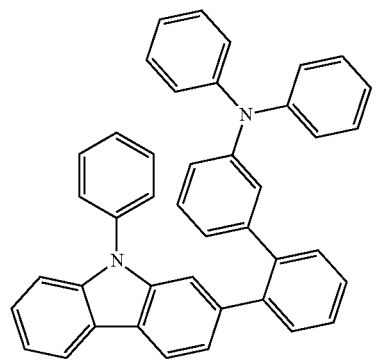
P2-2
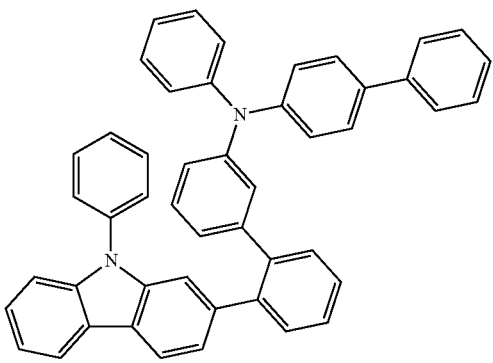

P2-3
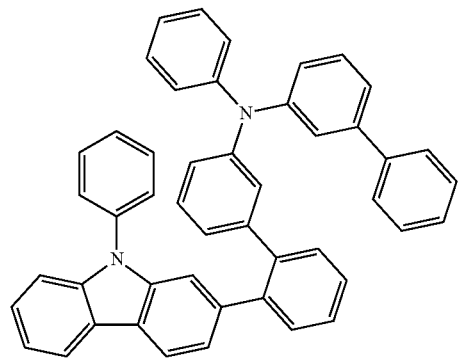
P2-4
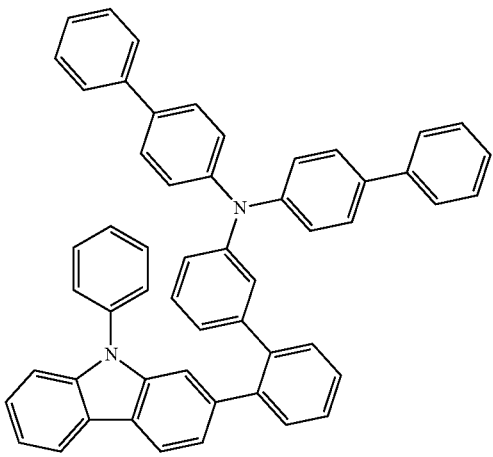
P2-5
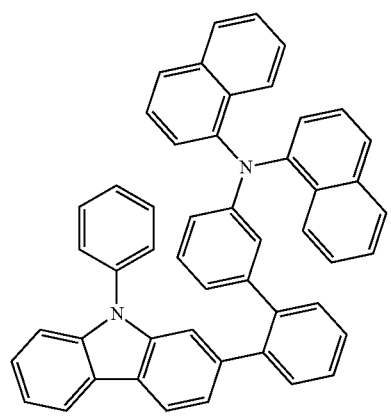
P2-6
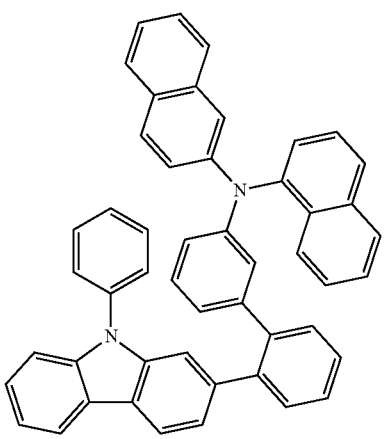
P2-7
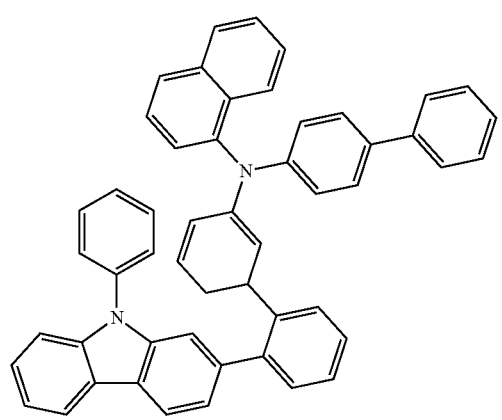
P2-8
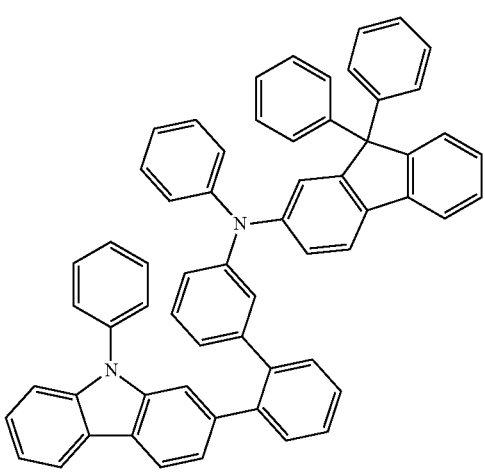

-continued
P2-9
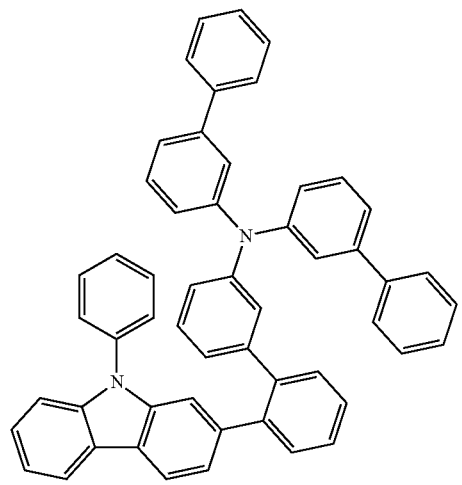
P2-10
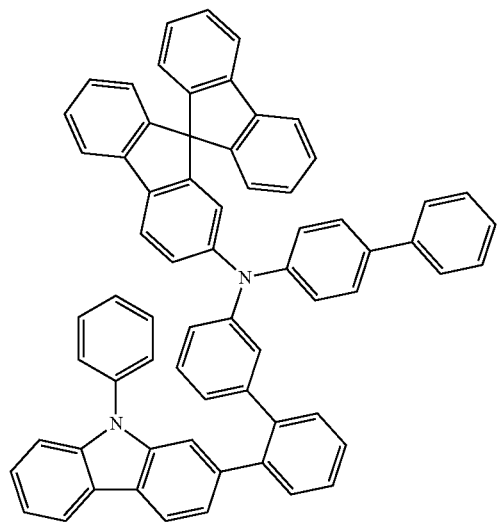
P2-11
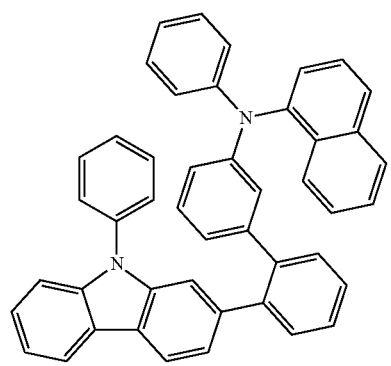
P2-12
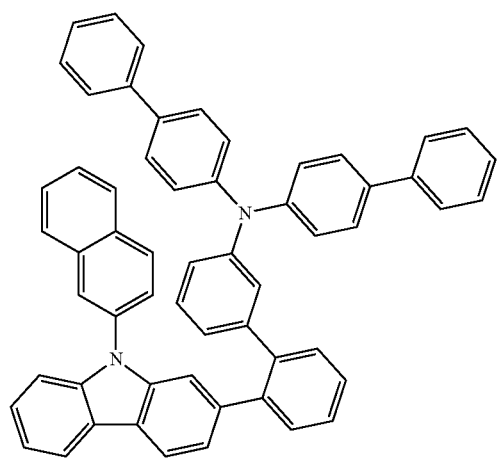
P2-13
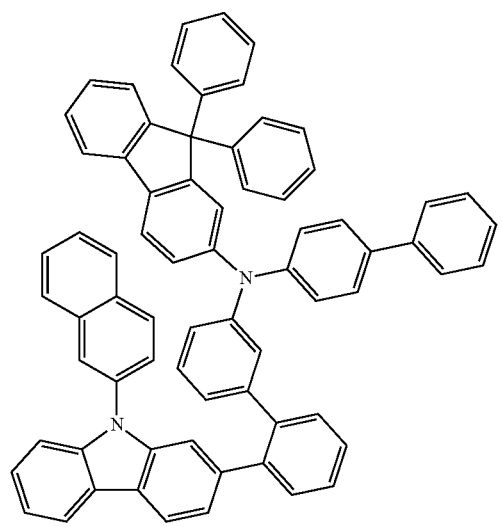
P2-14
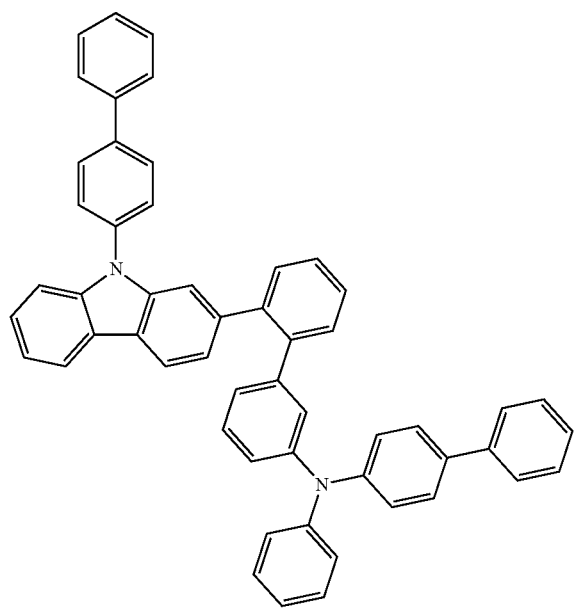

-continued
P2-15
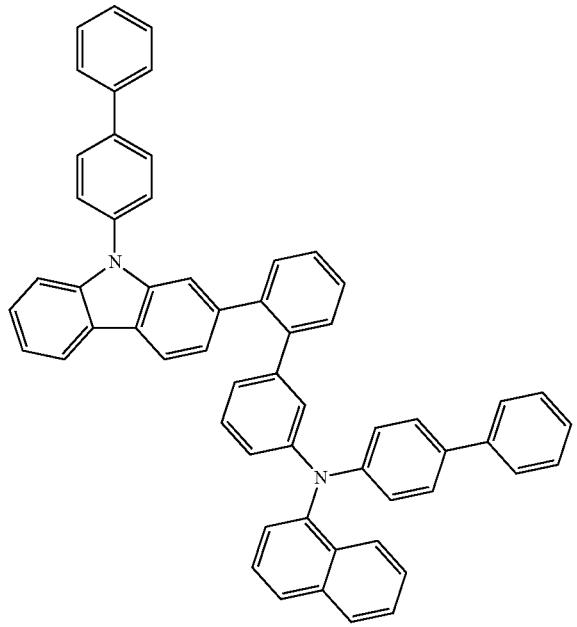
P2-16
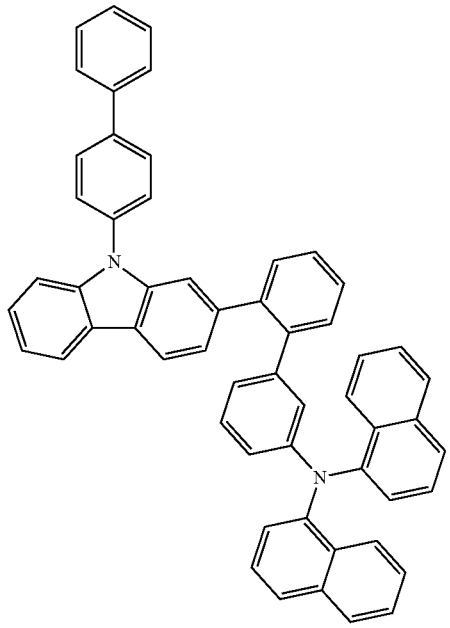
P2-17
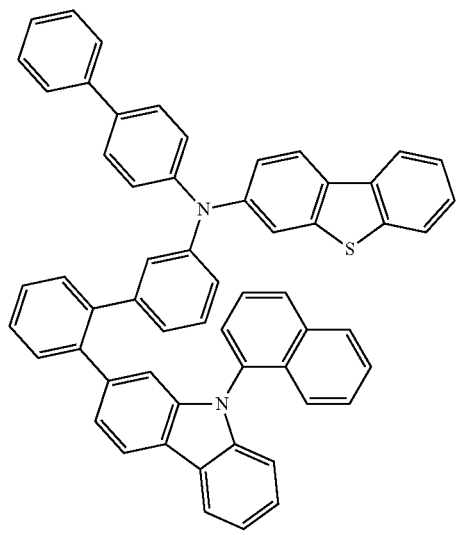
P2-18
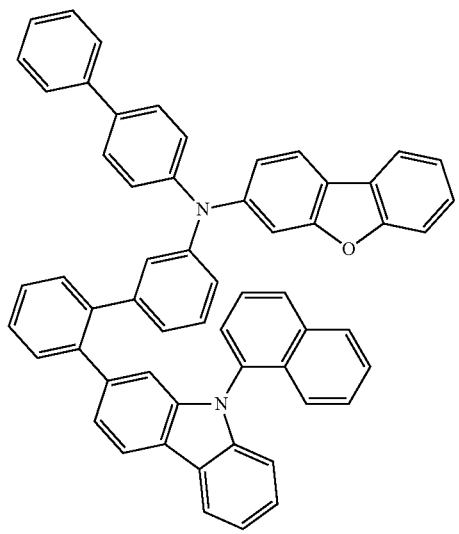
P2-19
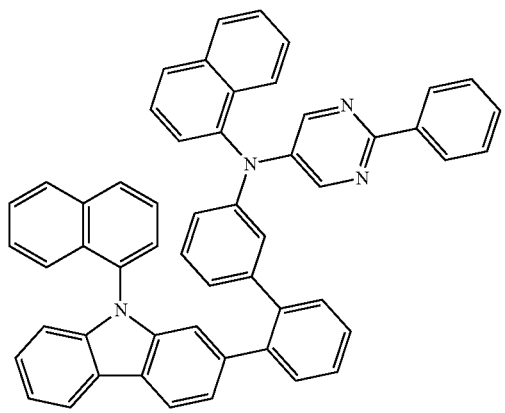
P2-20
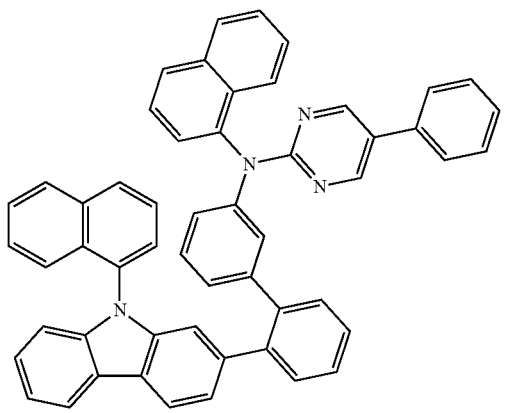

P2-21 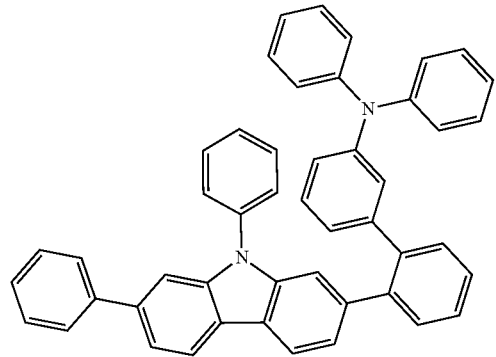
P2-22 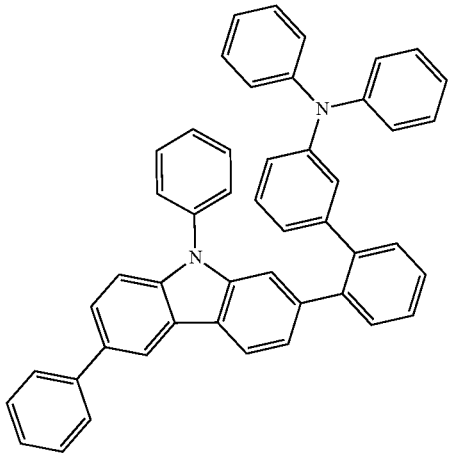
P2-23 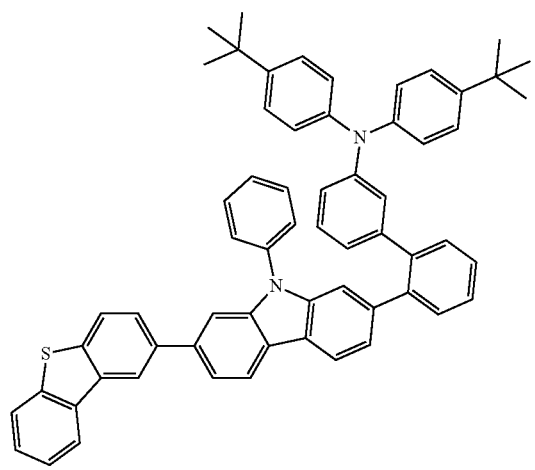
P2-24 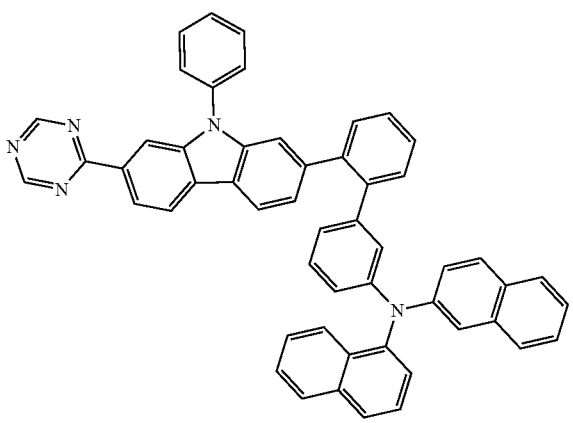
P2-25 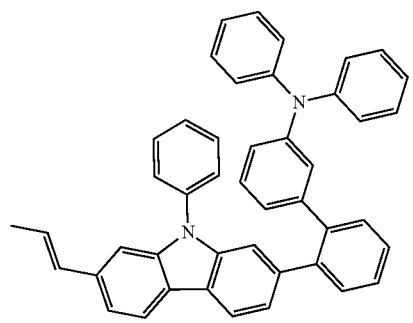
P2-26 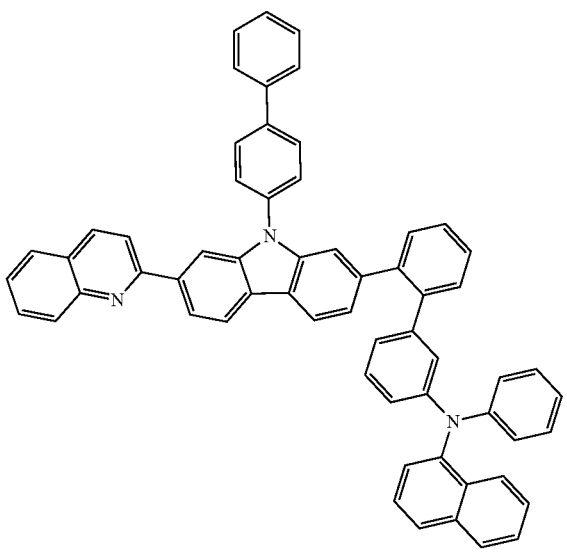

-continued
P2-27
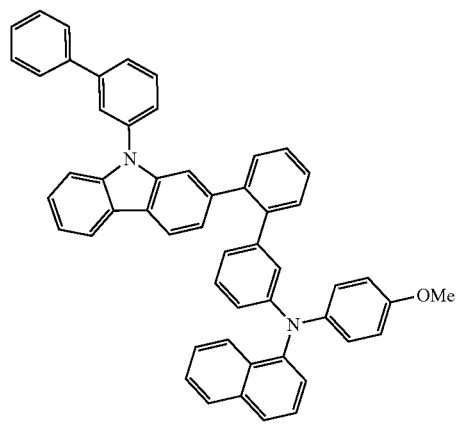
P2-28
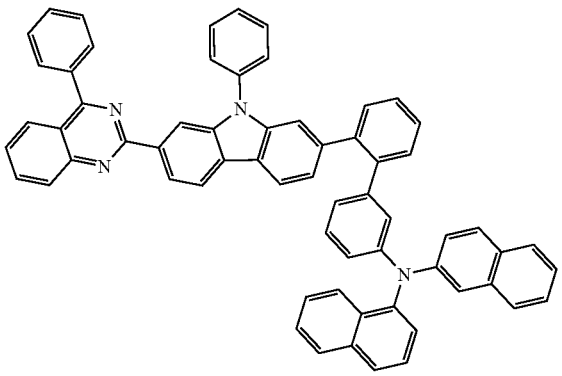
P2-29
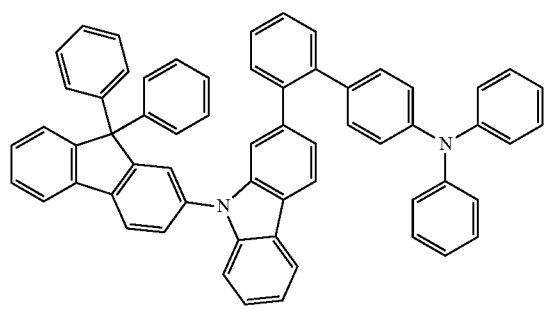
P2-30
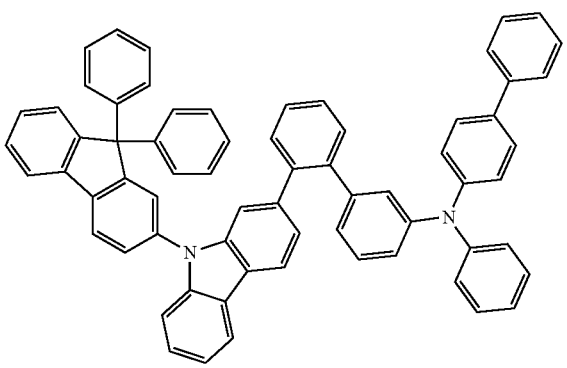
P2-31
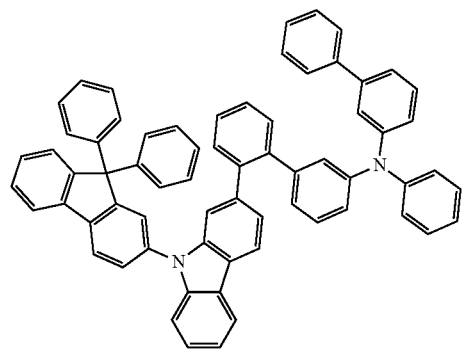
P2-32
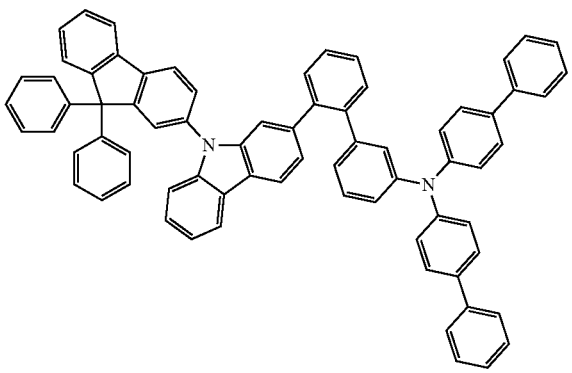
P2-33
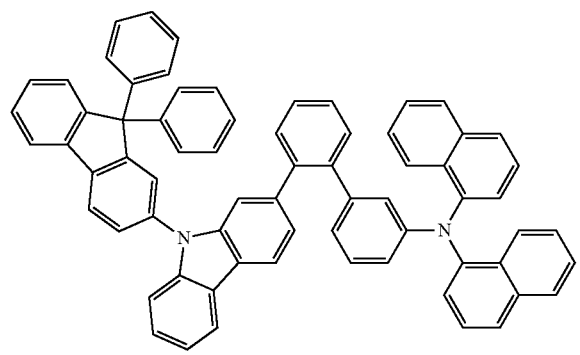
P2-34
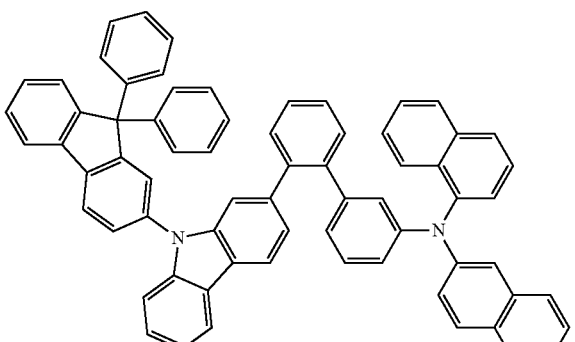

-continued
P2-35
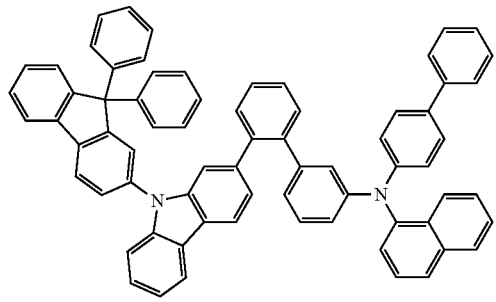
P2-36
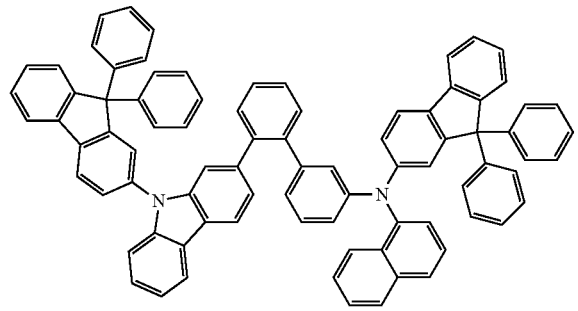
P2-37
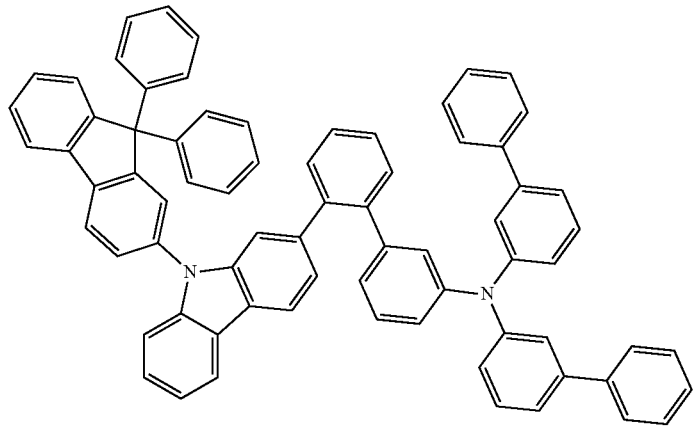
P2-38
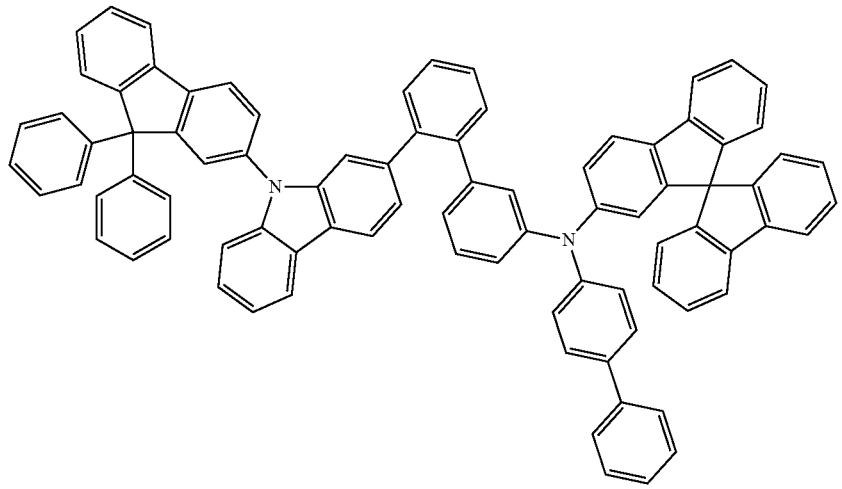
P2-39
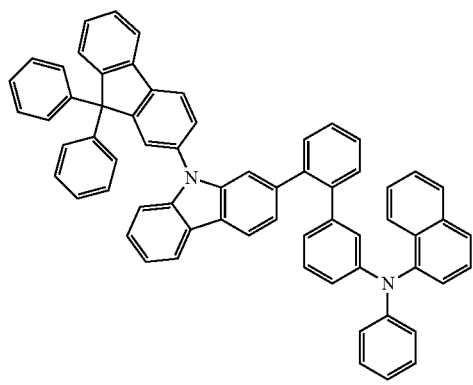
P2-40
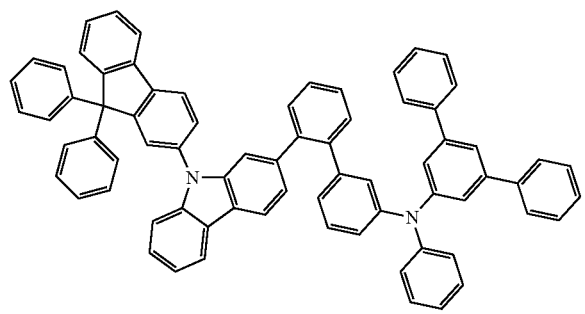

-continued
P2-41
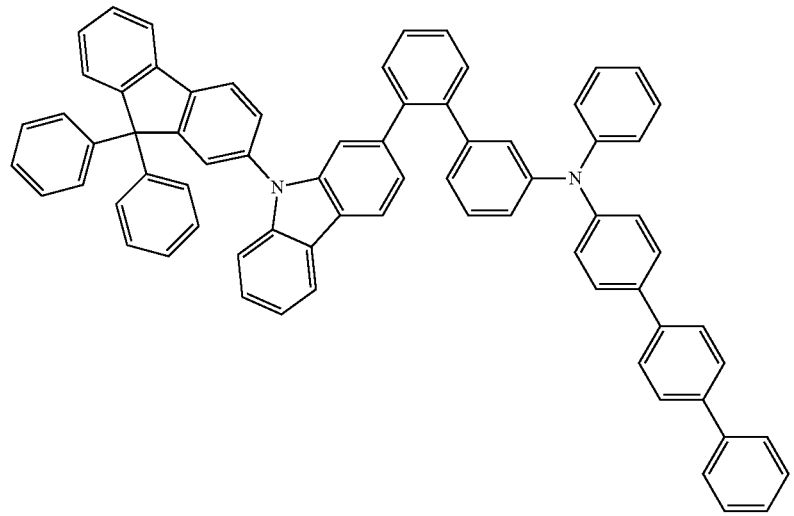
P2-42 P2-43
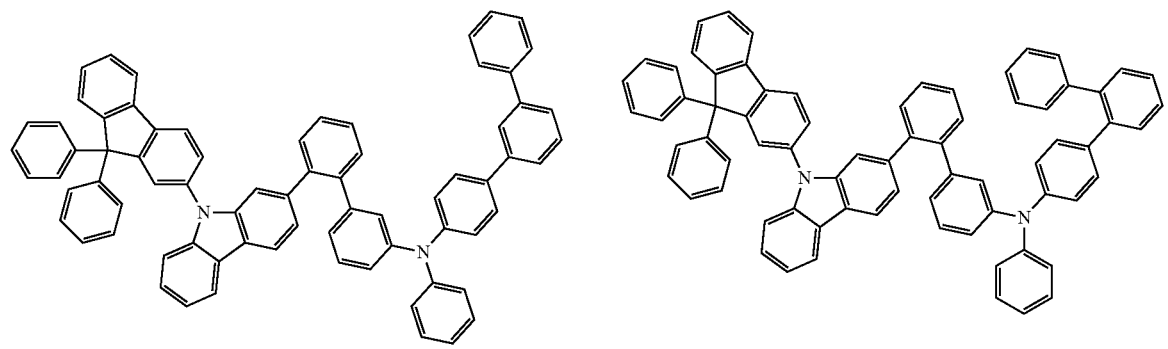
P2-44
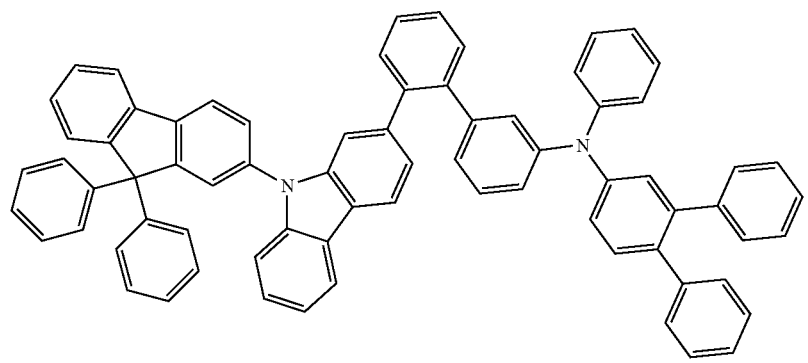

-continued
P2-45 P2-46
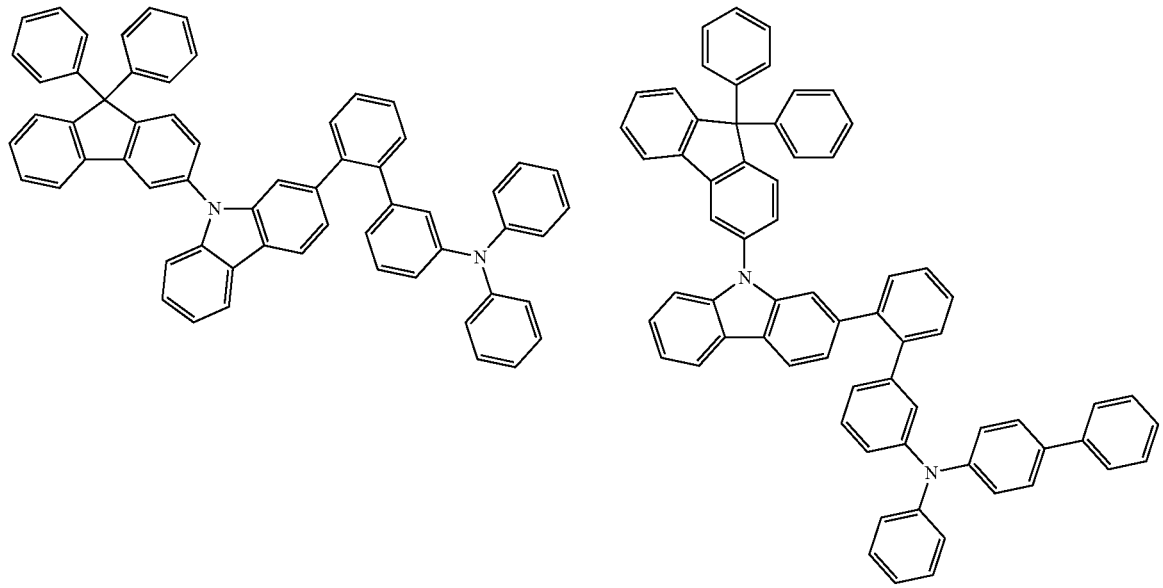
P2-47 P2-48
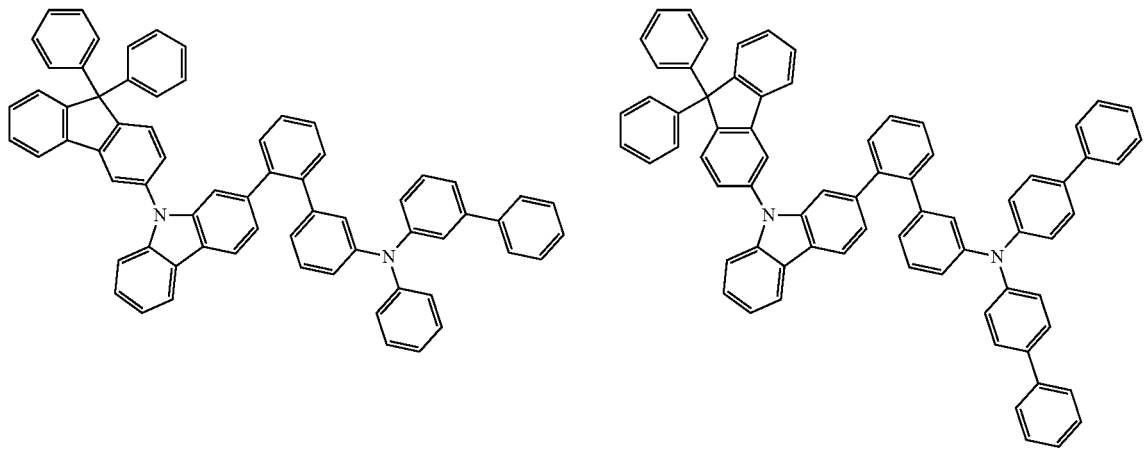
P2-49 P2-50
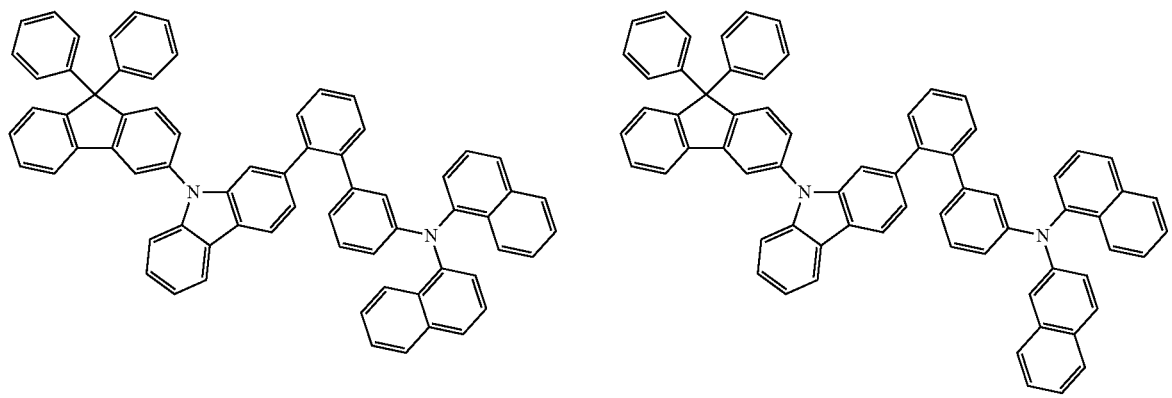

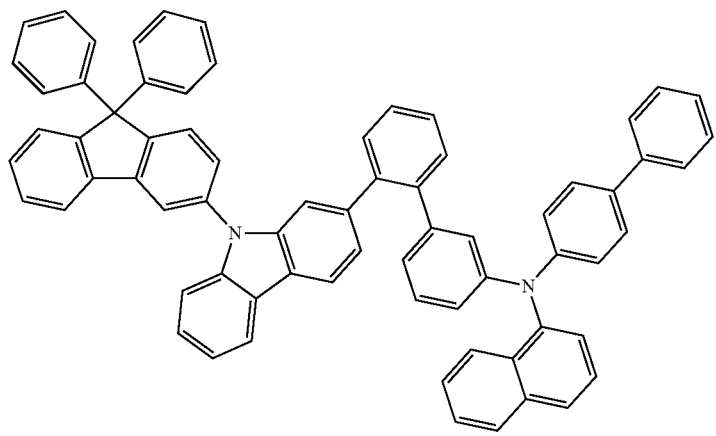
P2-51
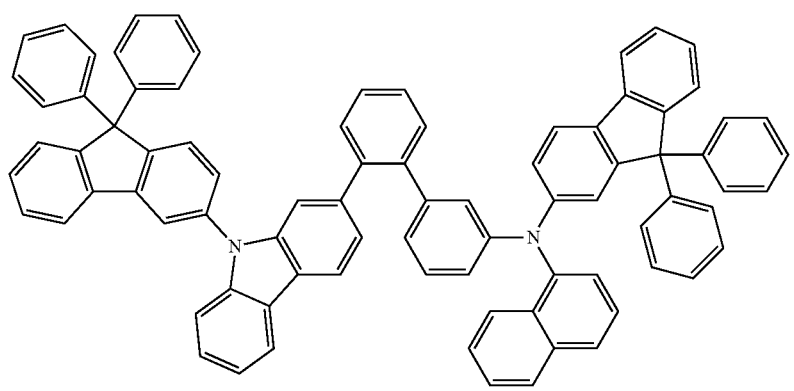
P2-52
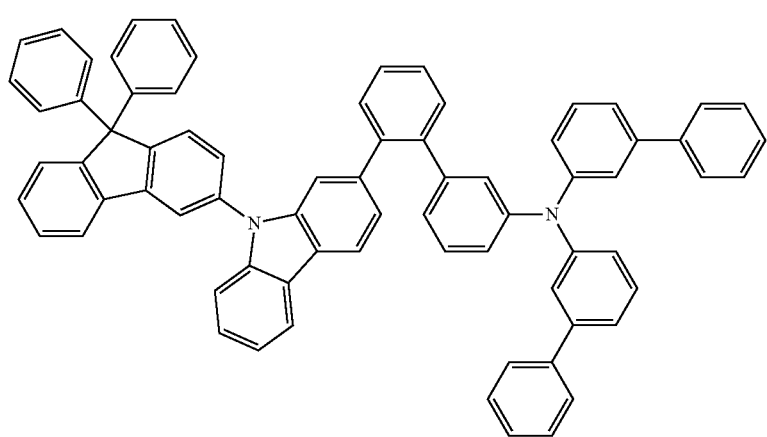
P2-53

-continued
P2-54
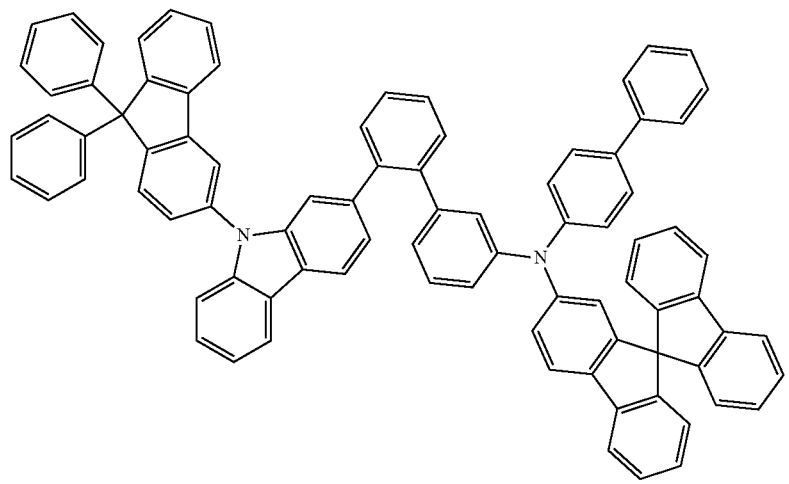
P2-55
P2-56
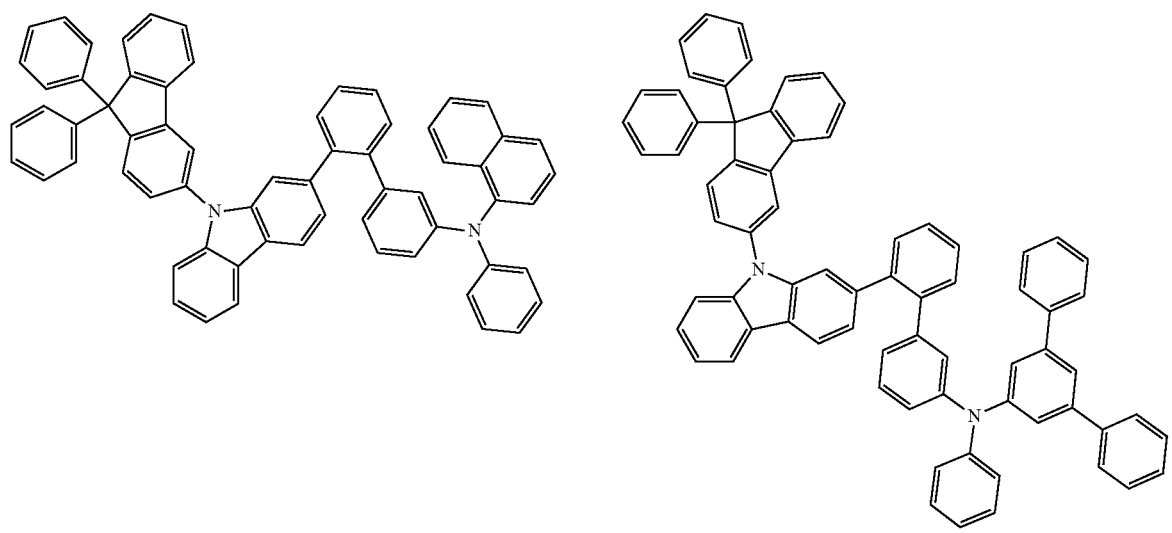
P2-57
P2-58
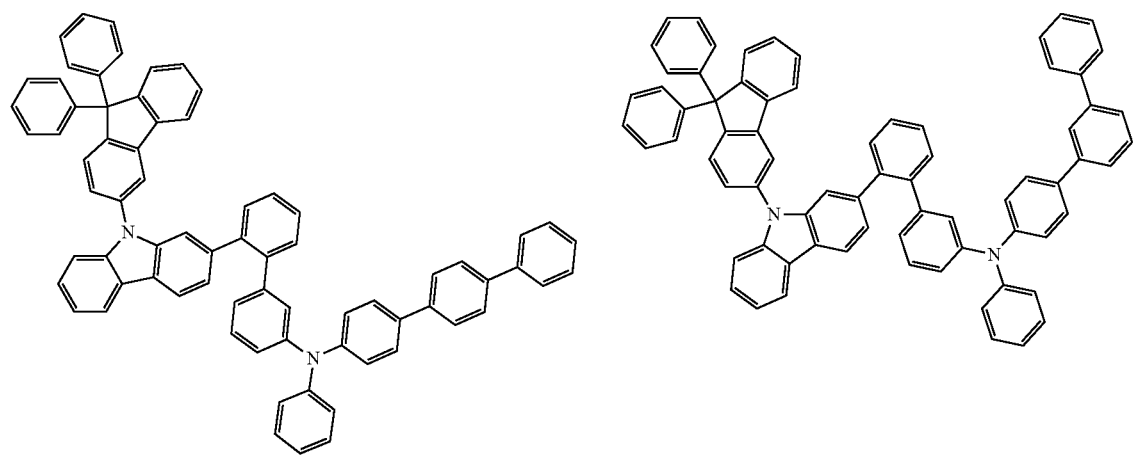

-continued
P2-59
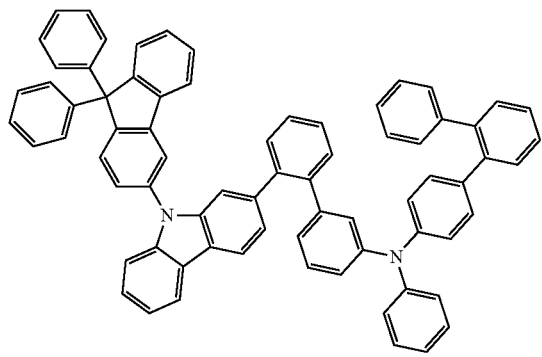
P2-60
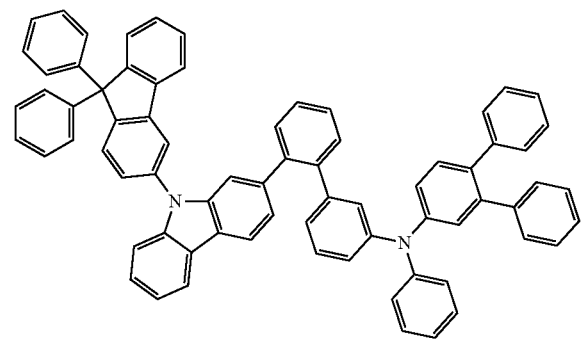
P2-61
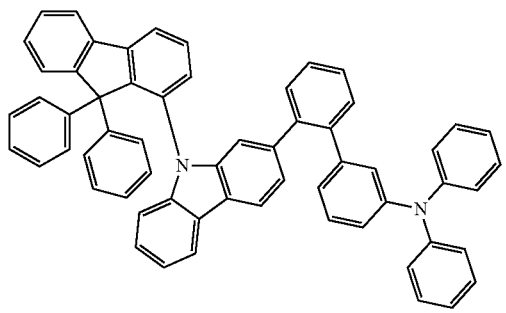
P2-62
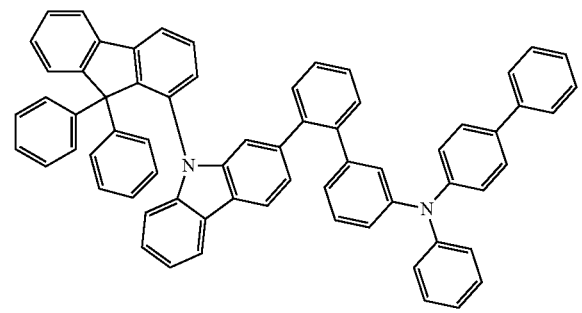
P2-63
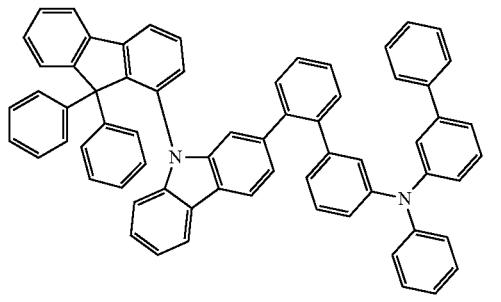
P2-64
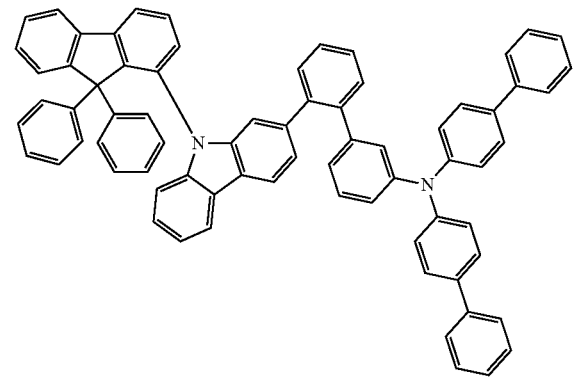
P2-65
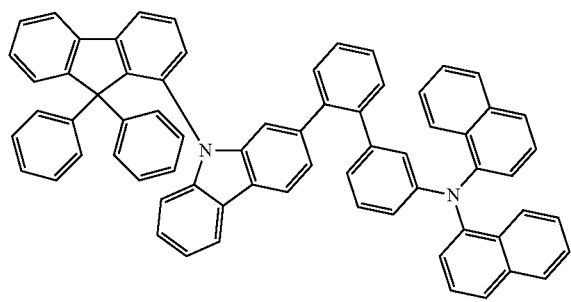
P2-66
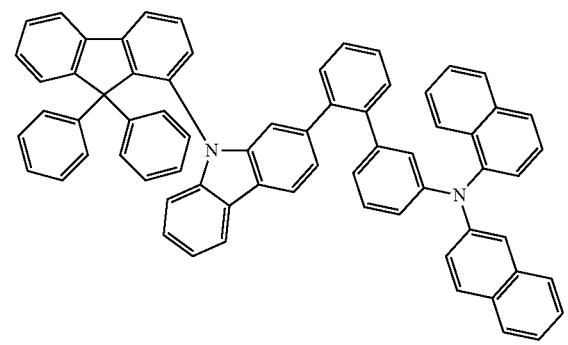

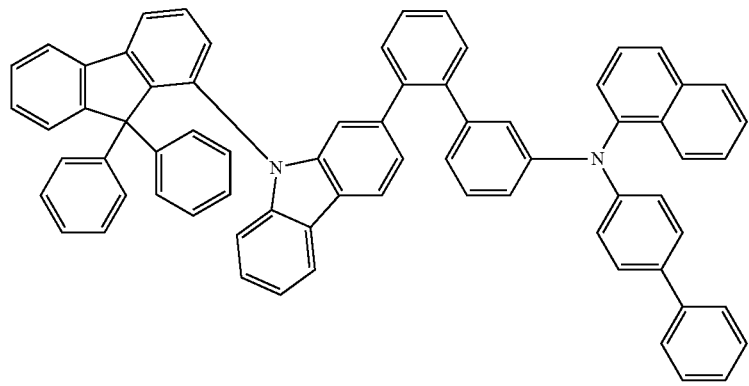
P2-67
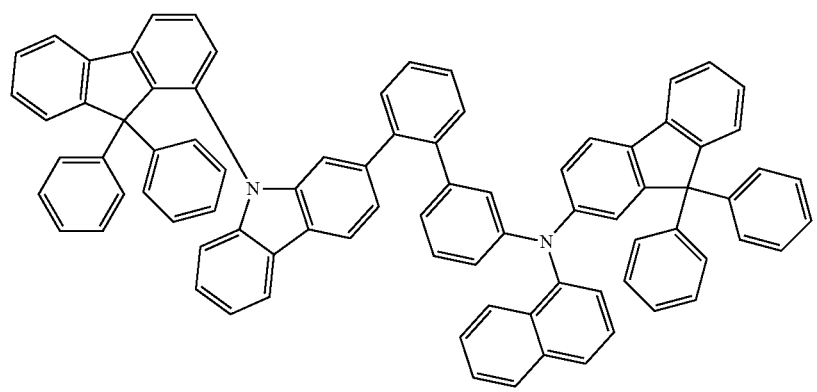
P2-68
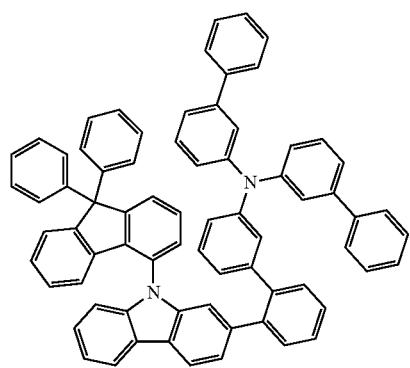
P2-69
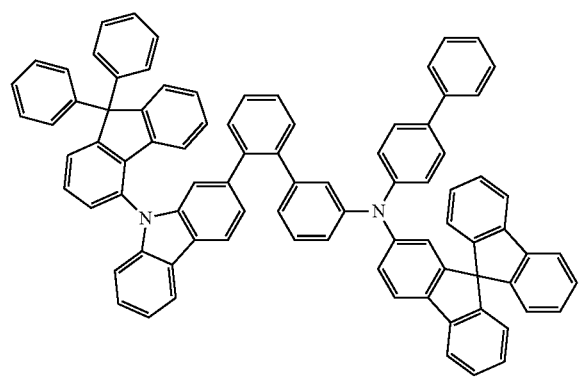
P2-70

-continued
P2-71
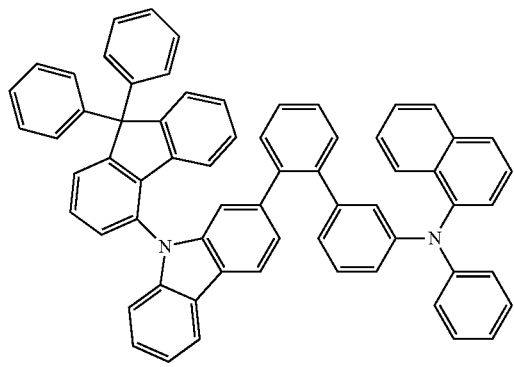
P2-72
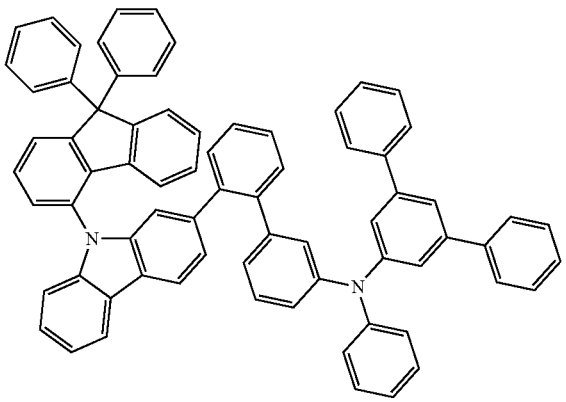
P2-73
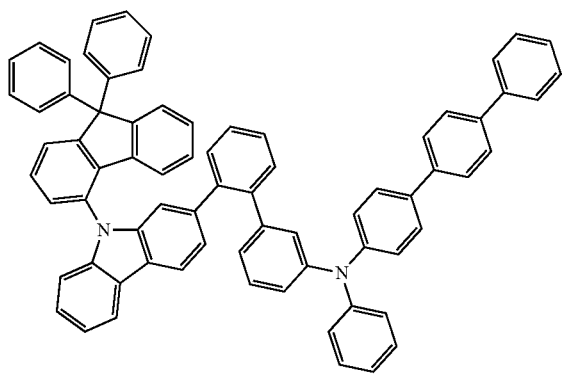
P2-74
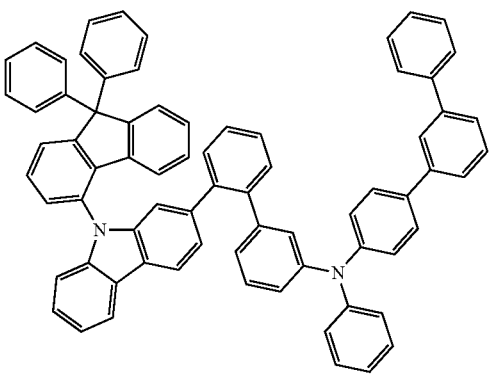
P2-75
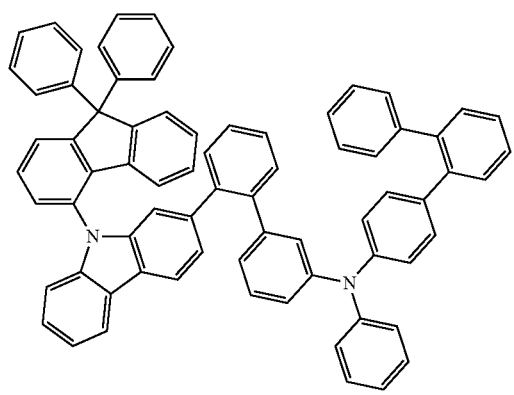
P2-76
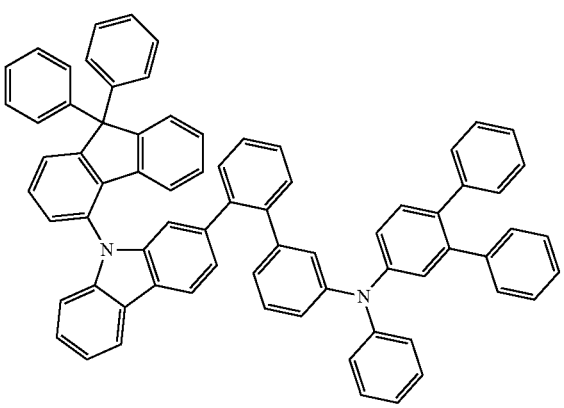
P2-77
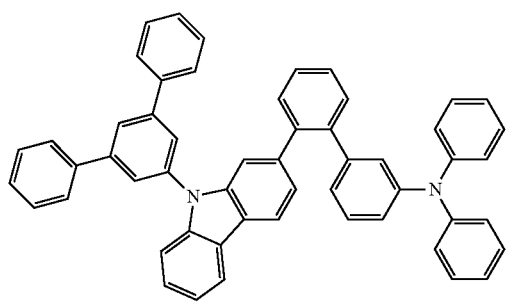
P2-78
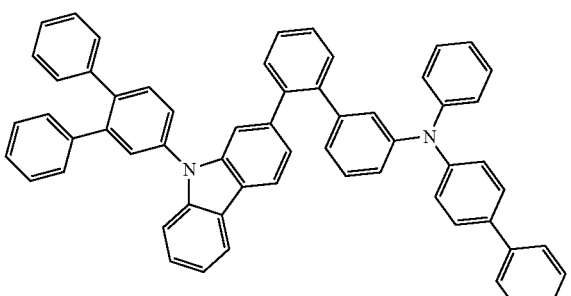

-continued
P2-79
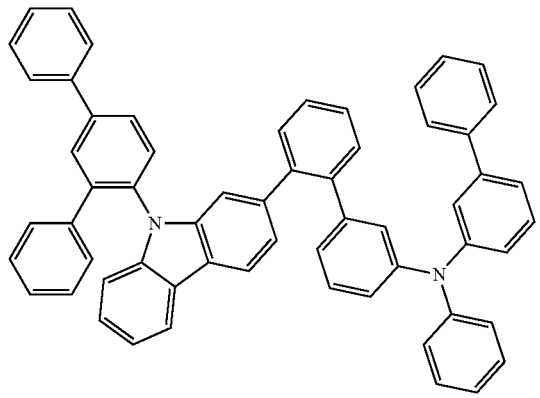
P2-80
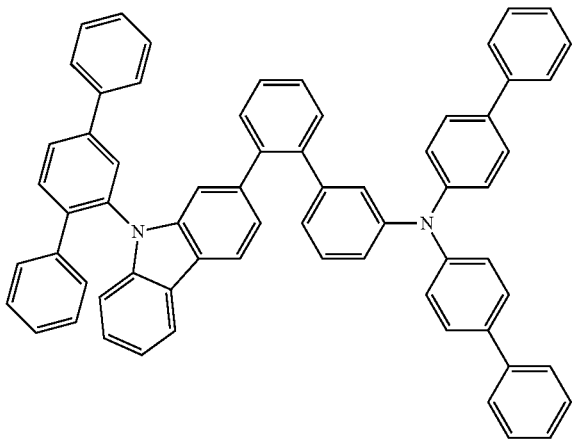
P2-81
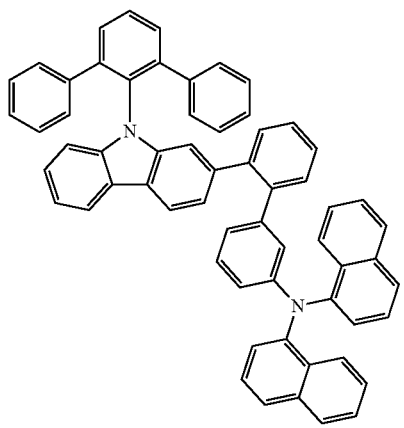
P2-82
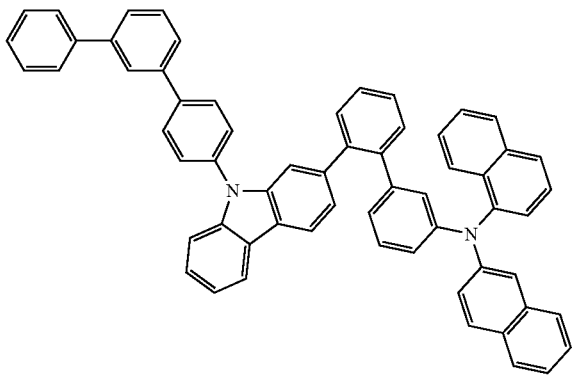
P2-83
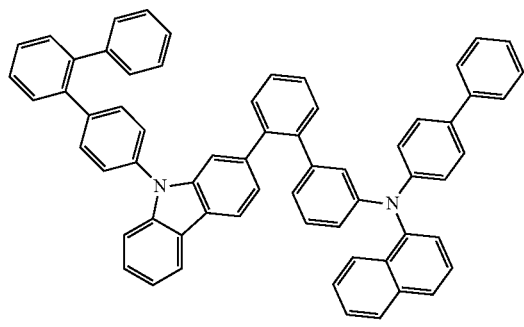
P2-84
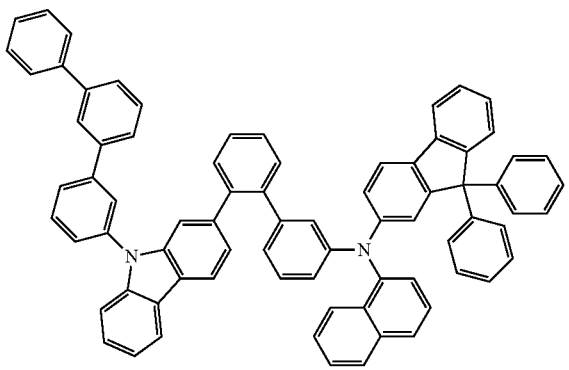

P2-85
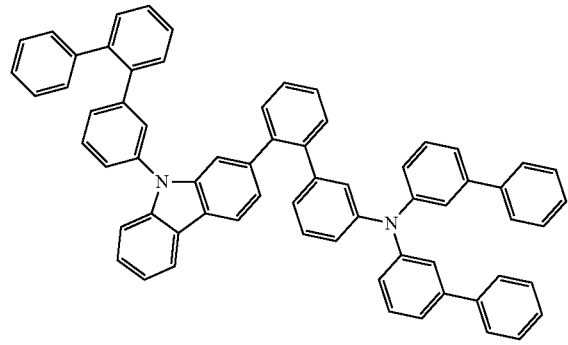
P2-86
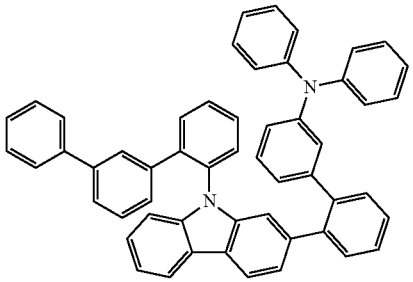
P2-87
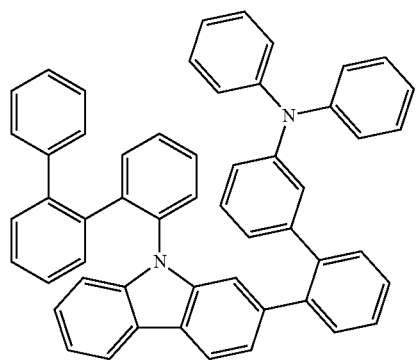
P2-88
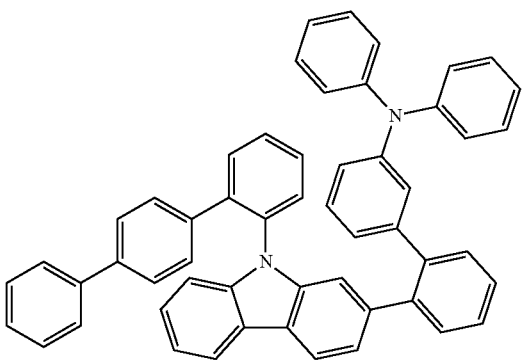
P2-89
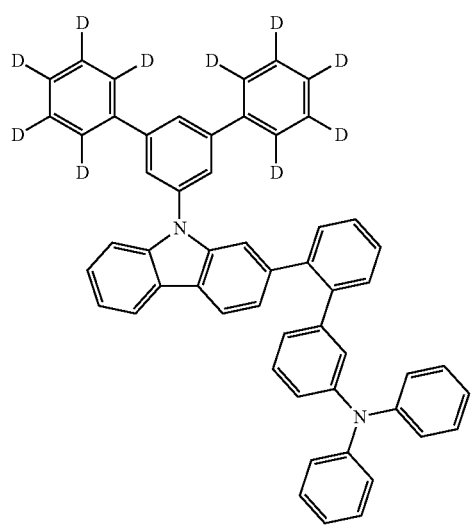
P2-90
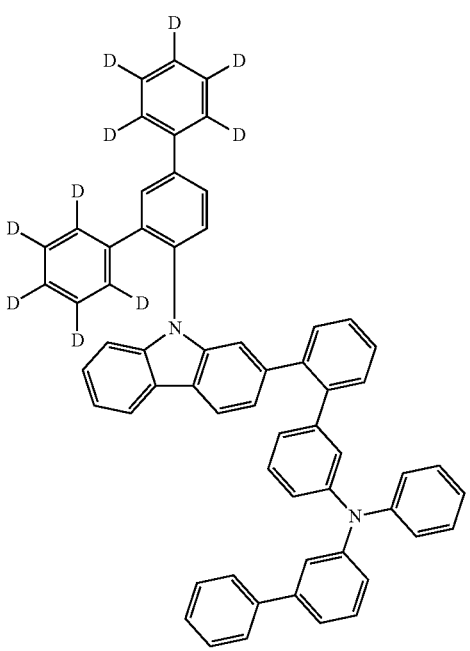

-continued
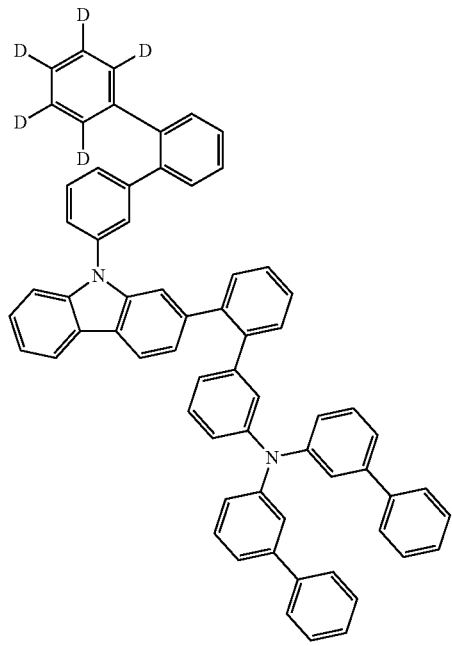
P2-91
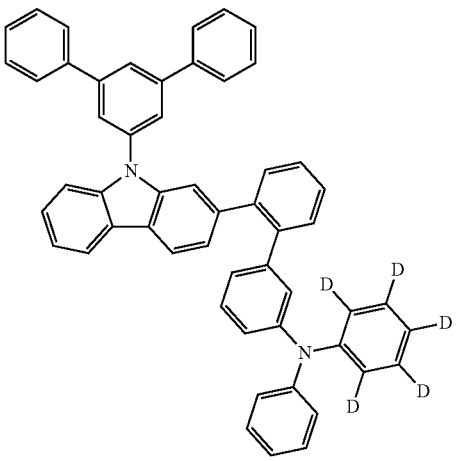
P2-92
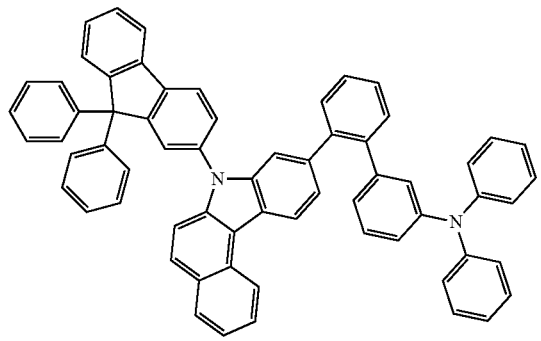
P2-93
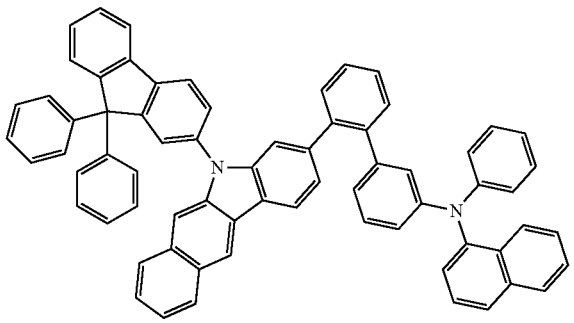
P2-94
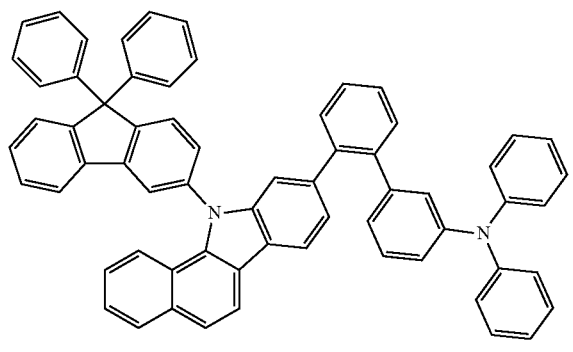
P2-95
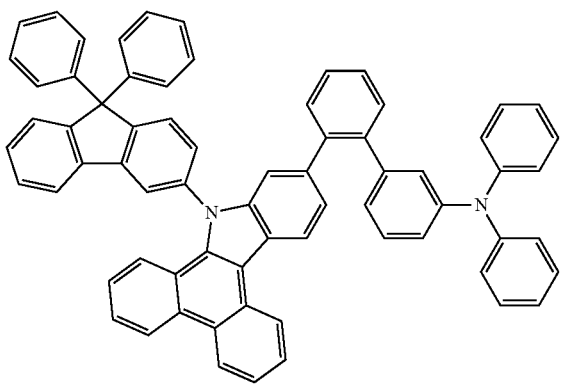
P2-96

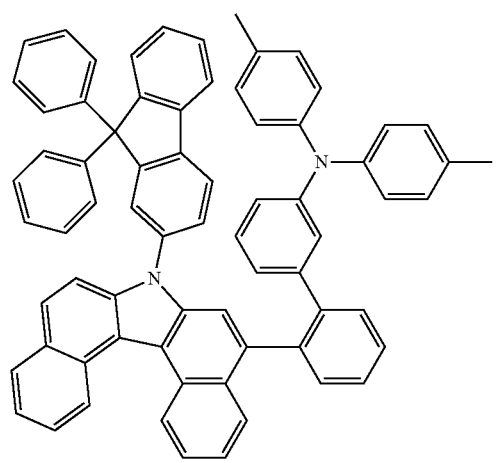 P2-97
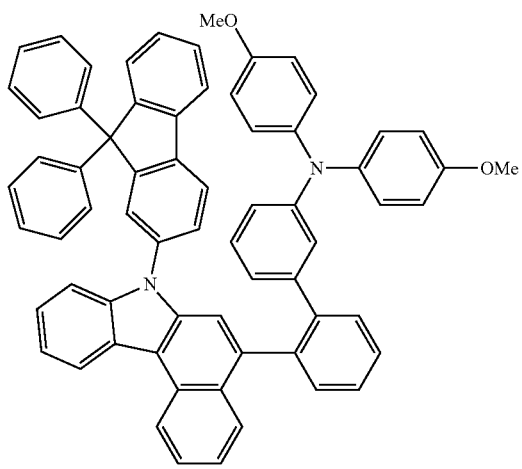 P2-98
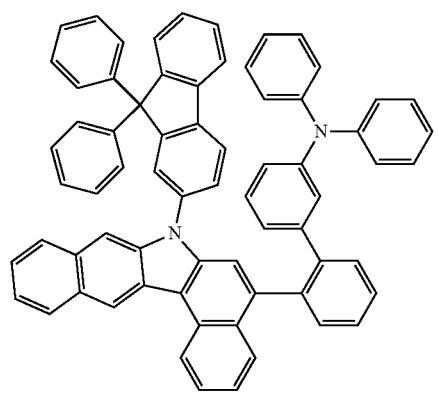 P2-99
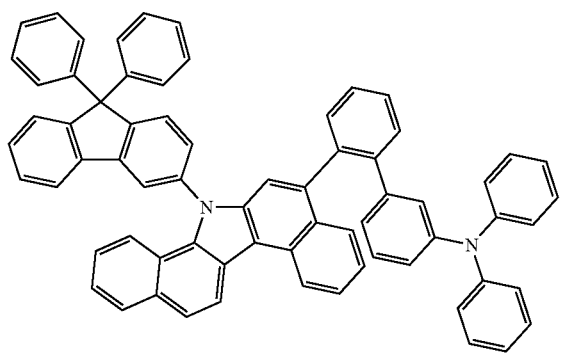 P2-100
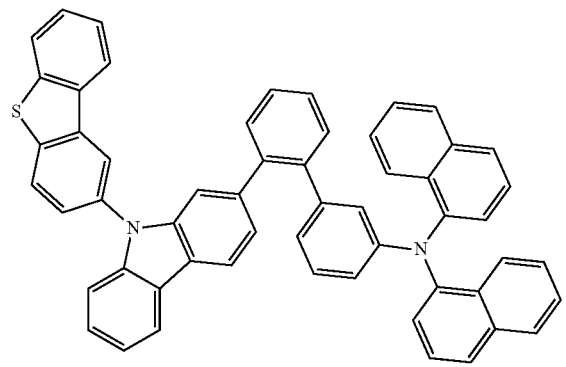 P2-101
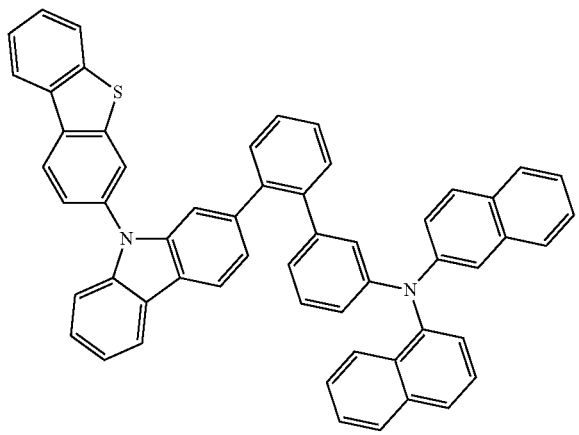 P2-102

-continued
P2-103
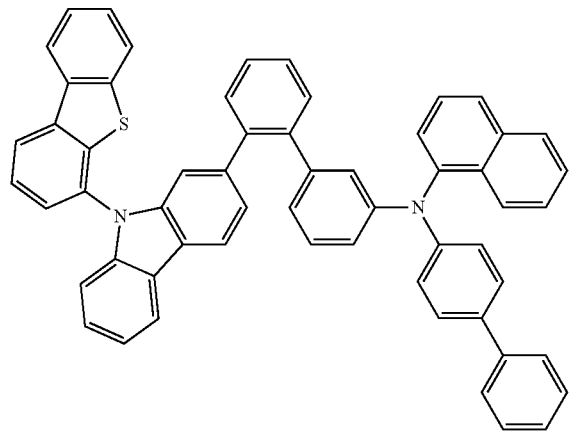
P2-104
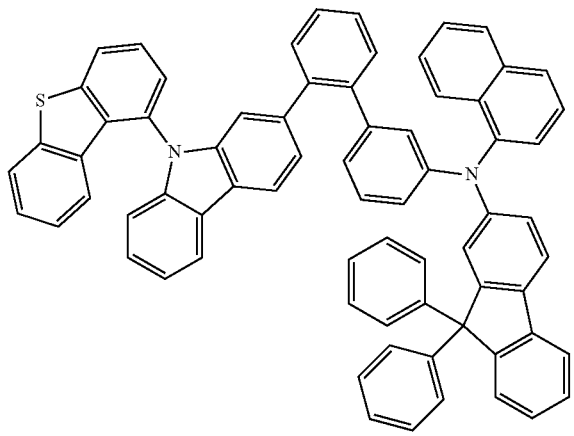
P2-105
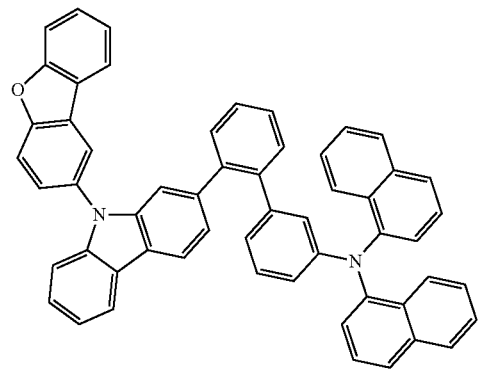
P2-106
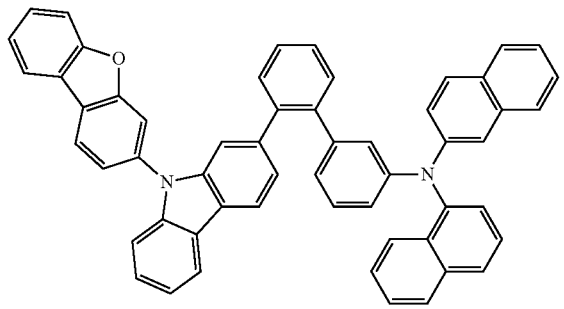
P2-107
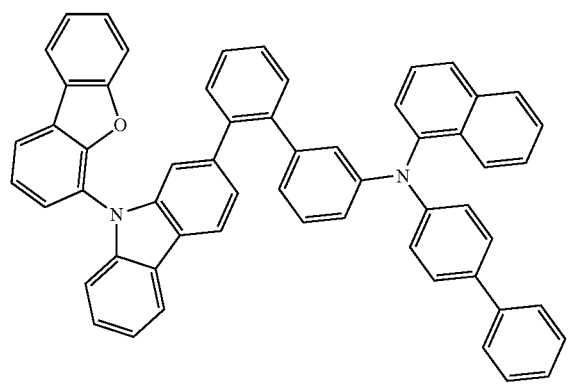
P2-108
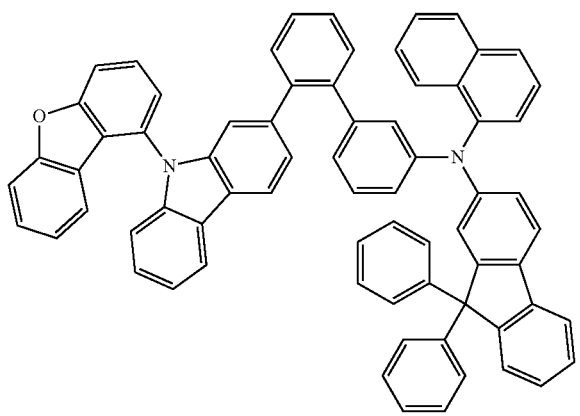

-continued
P2-109
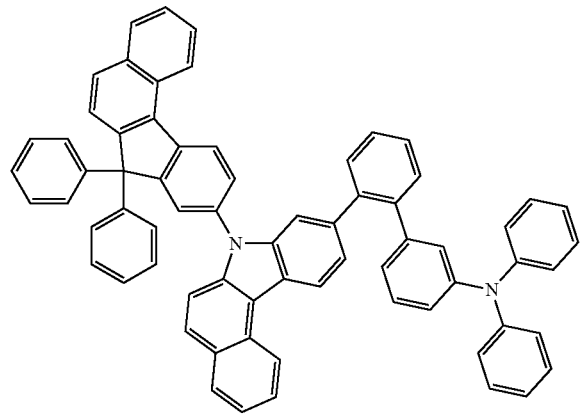
P2-110
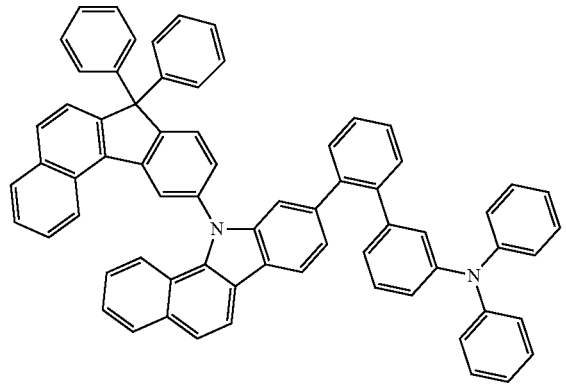
P2-111
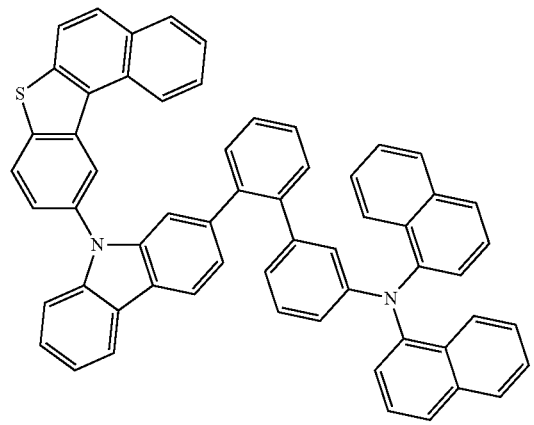
P2-112
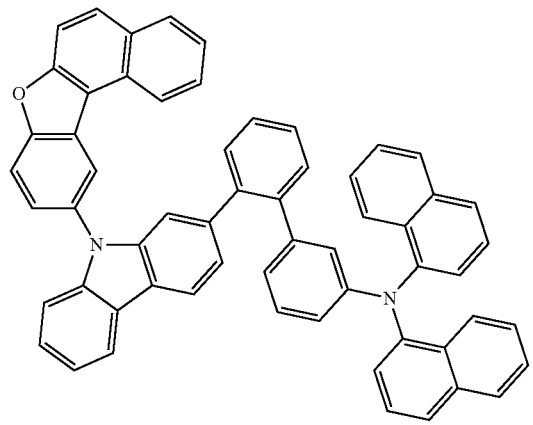
P3-1
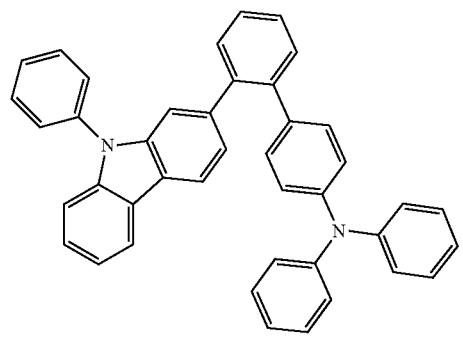
P3-2
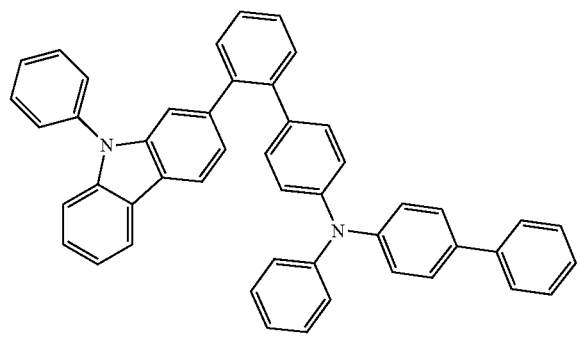

-continued
P3-3
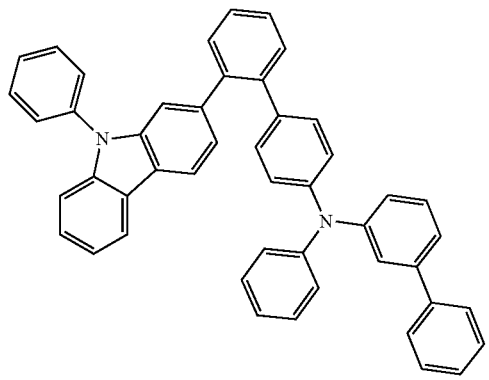
P3-4
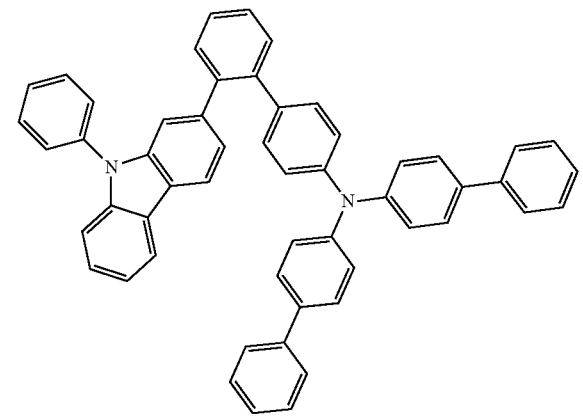
P3-5
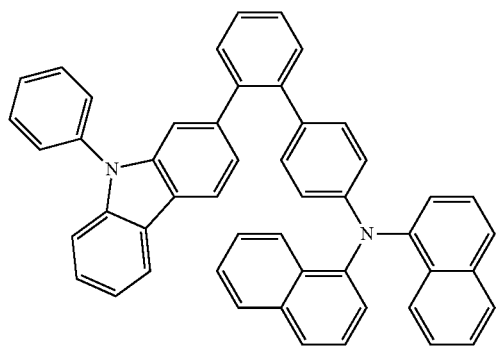
P3-6
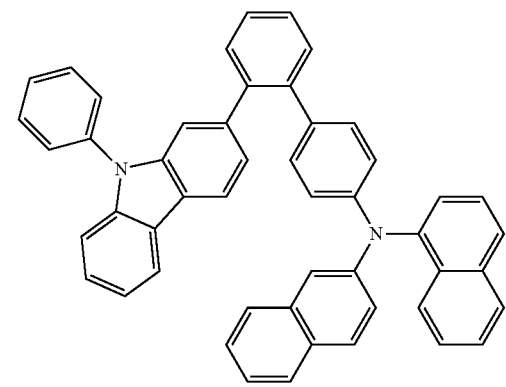
P3-7
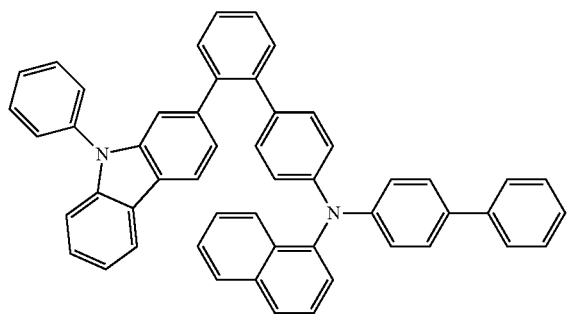
P3-8
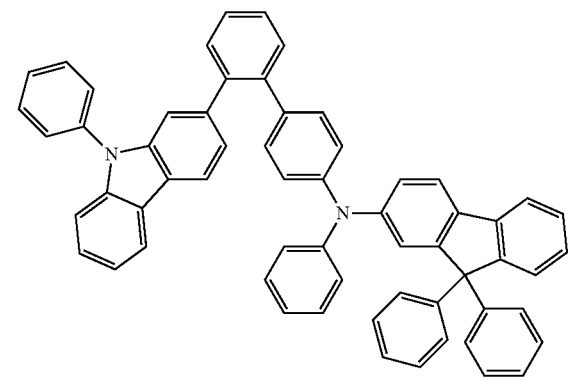
P3-9
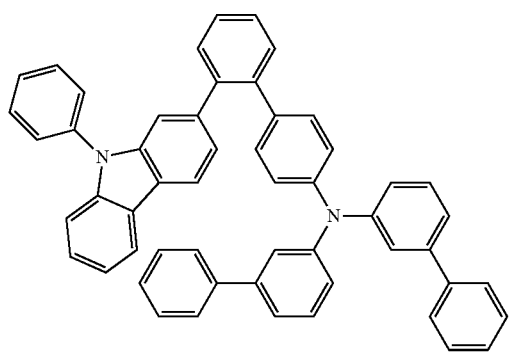
P3-10
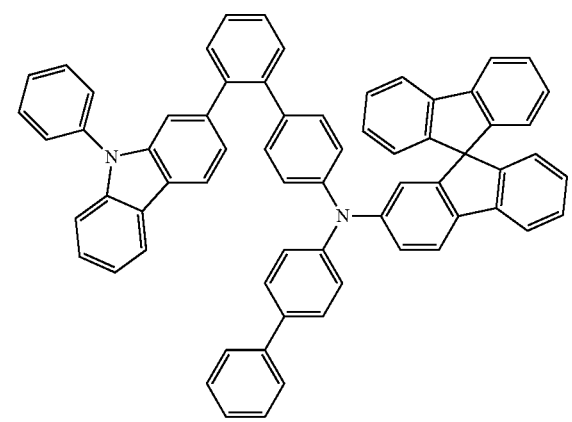

-continued
P311
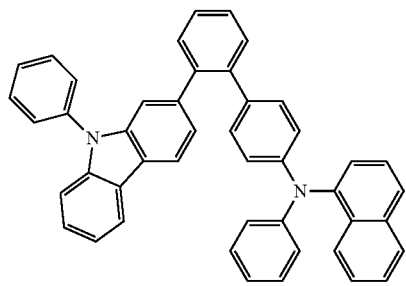
P3-12
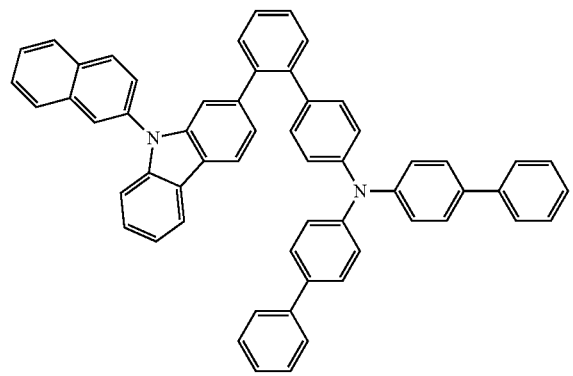
P3-13
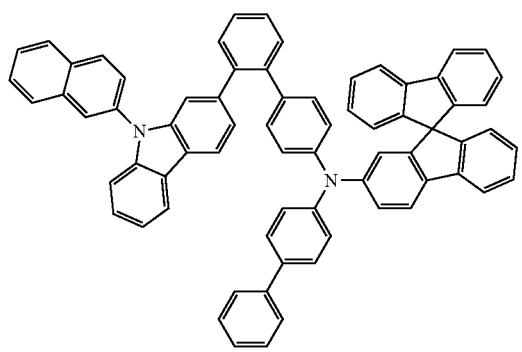
P3-14
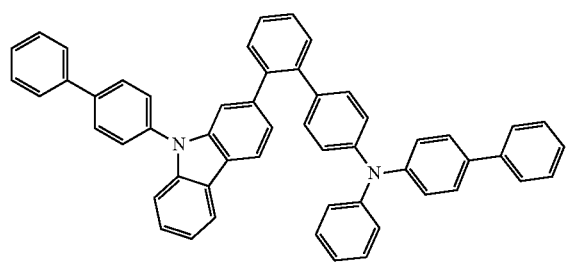
P3-15
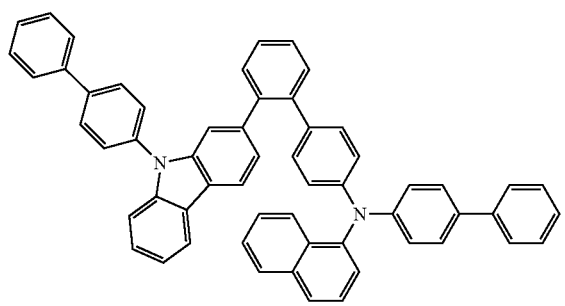
P3-16
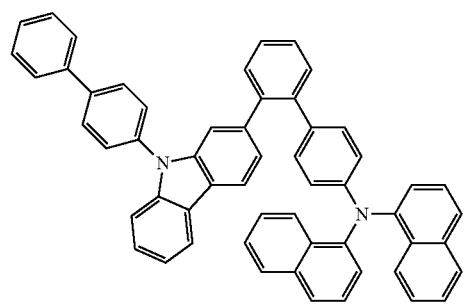
P3-17
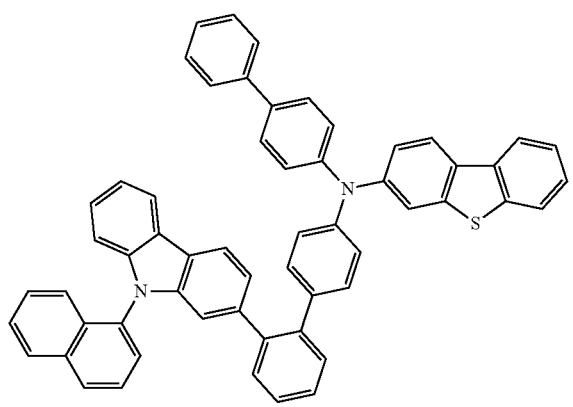
P3-18
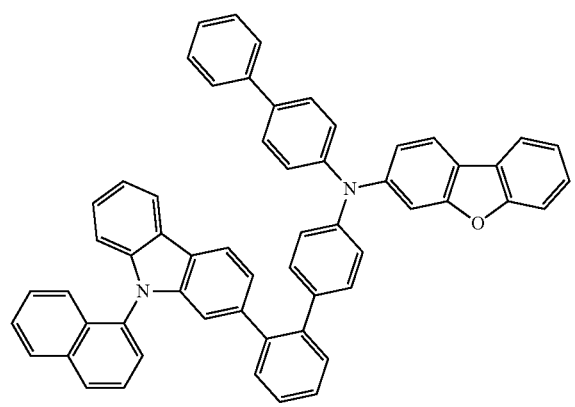

-continued
P3-19
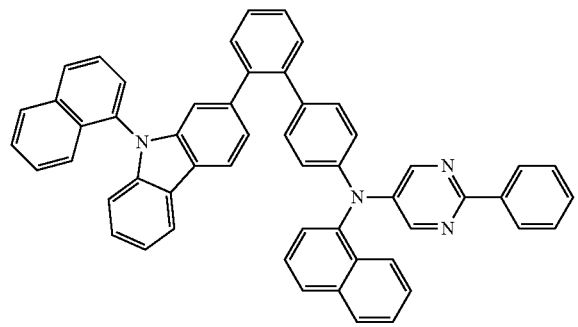
P3-20
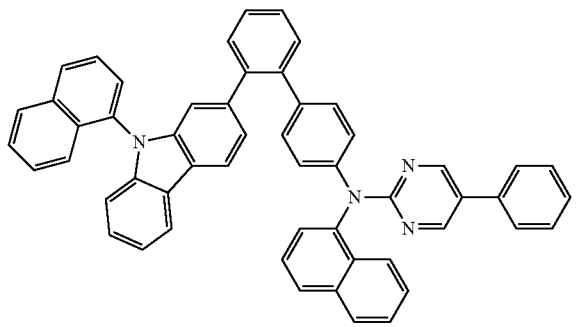
P3-21
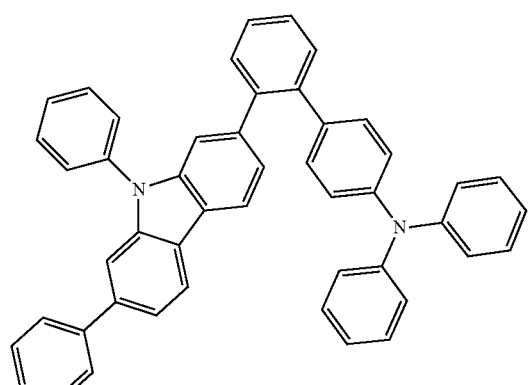
P3-22
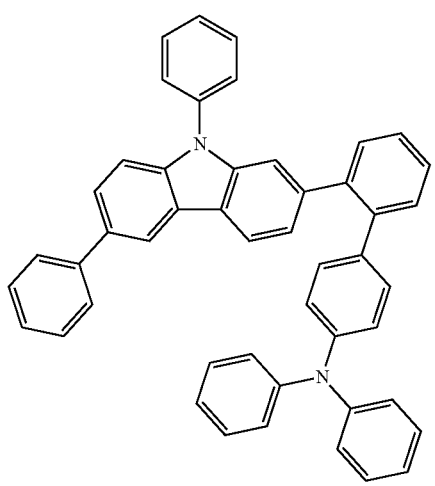
P3-23
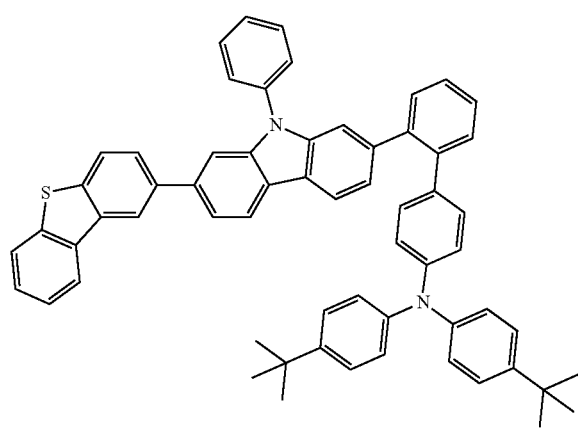
P3-24
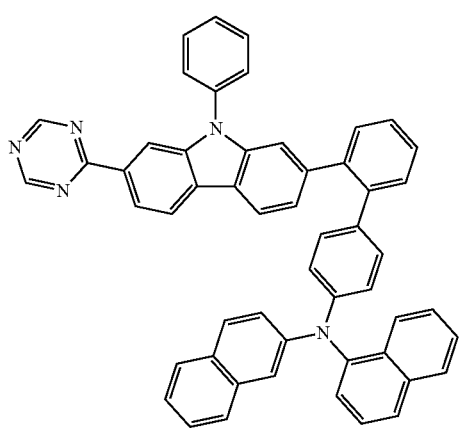

P3-25
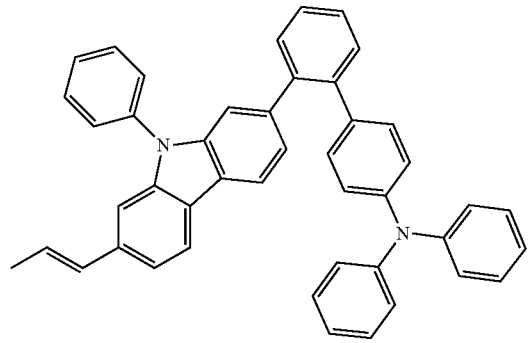
P3-26
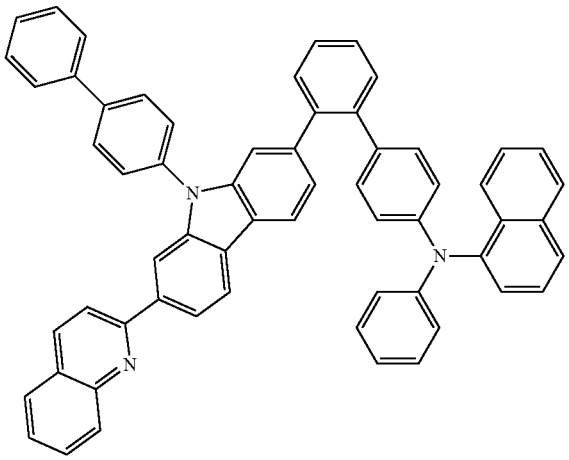
P3-27
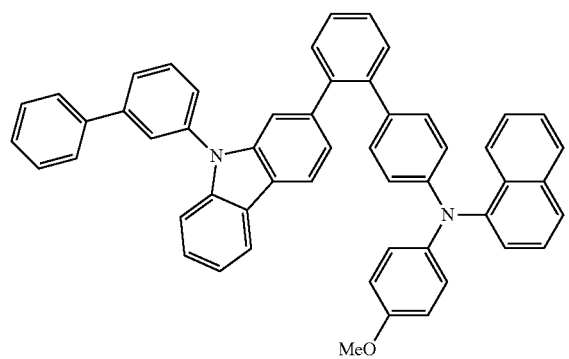
P3-28
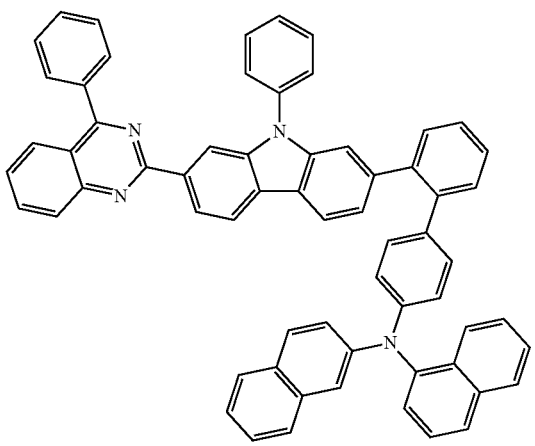
P3-29
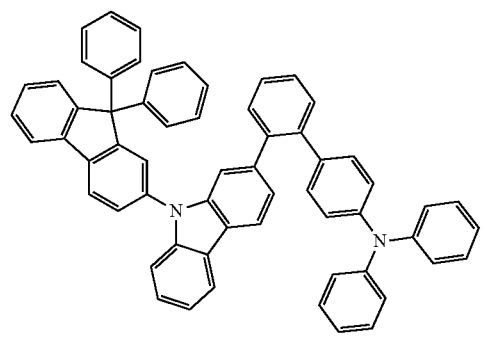
P3-30
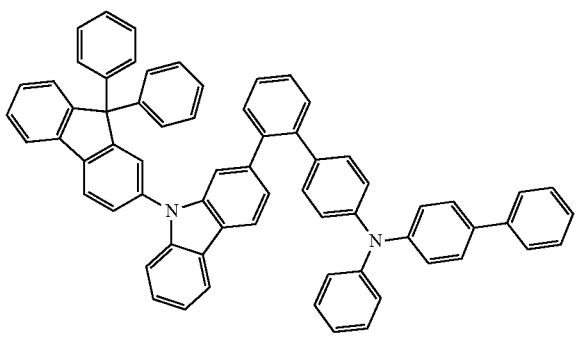

-continued
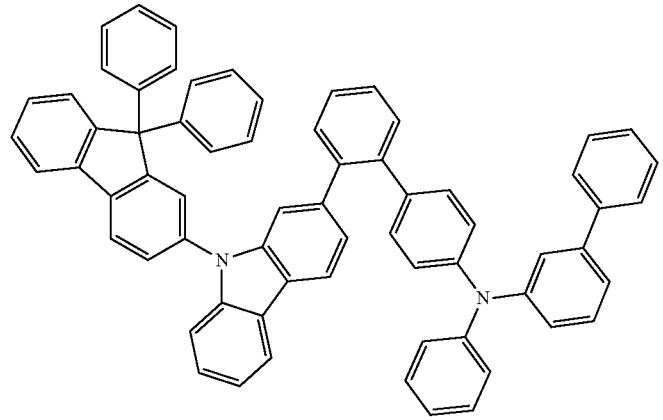
P3-31
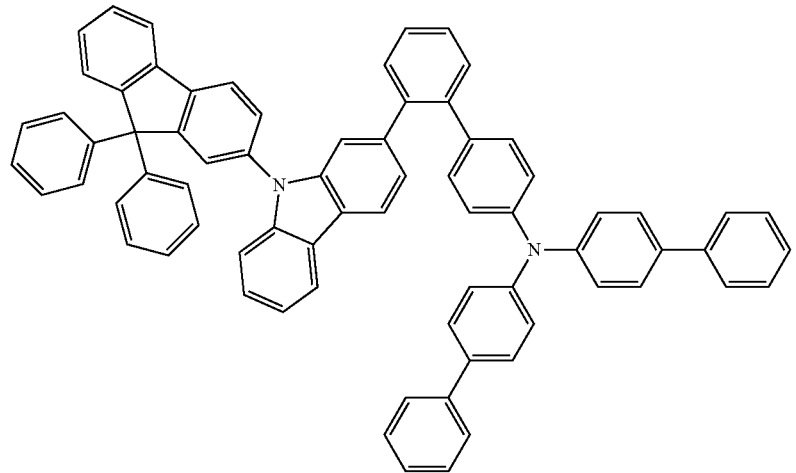
P3-32
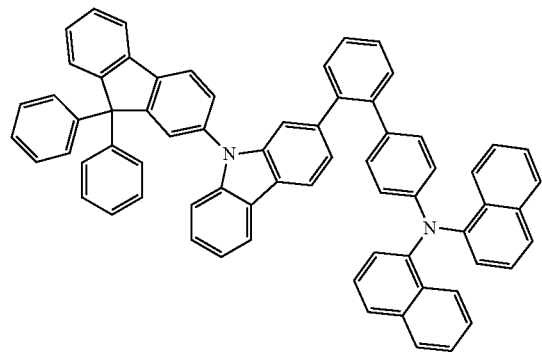
P3-33
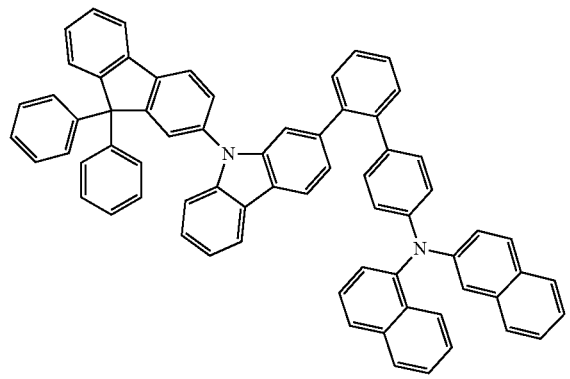
P3-34

-continued
P3-35
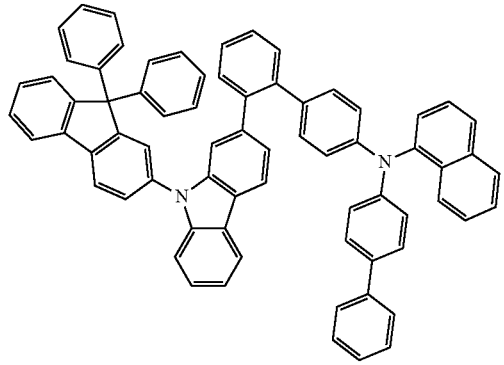
P3-36
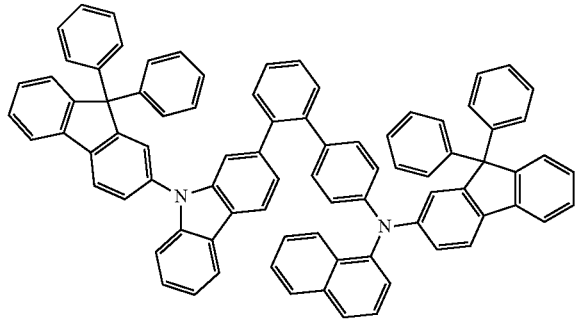
P3-37
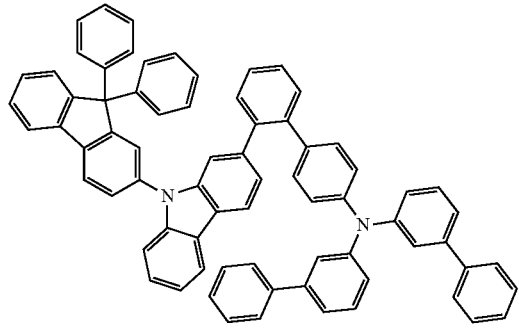
P3-38
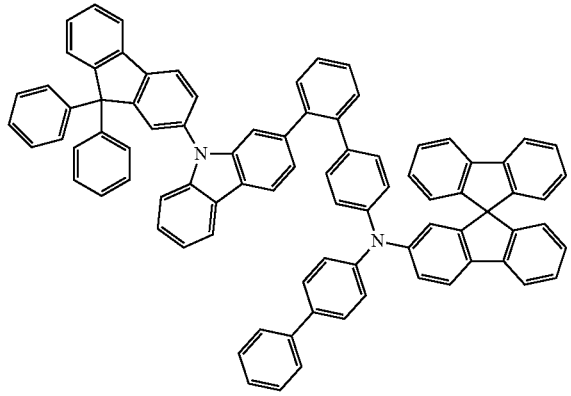
P3-39
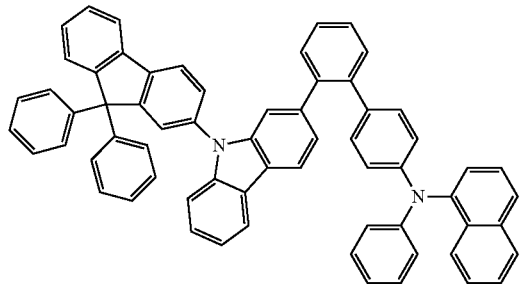
P3-40
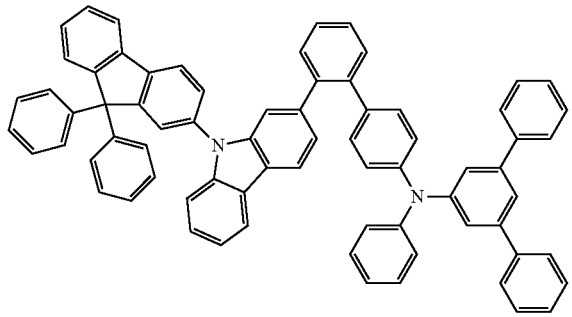
P3-41
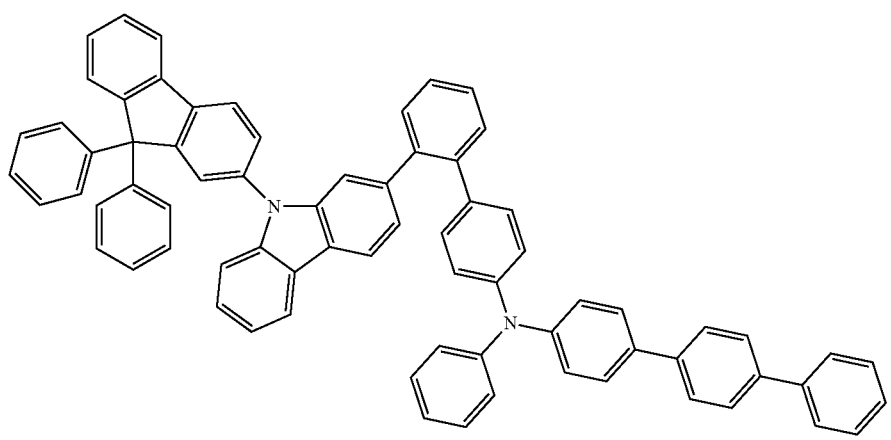

P3-42
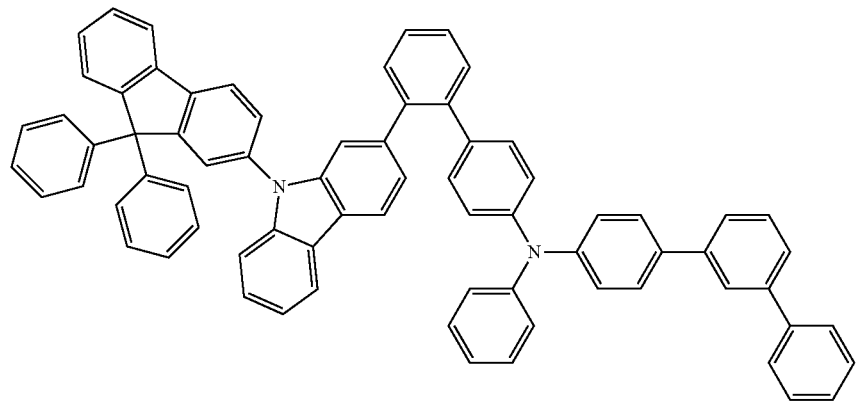
P3-43
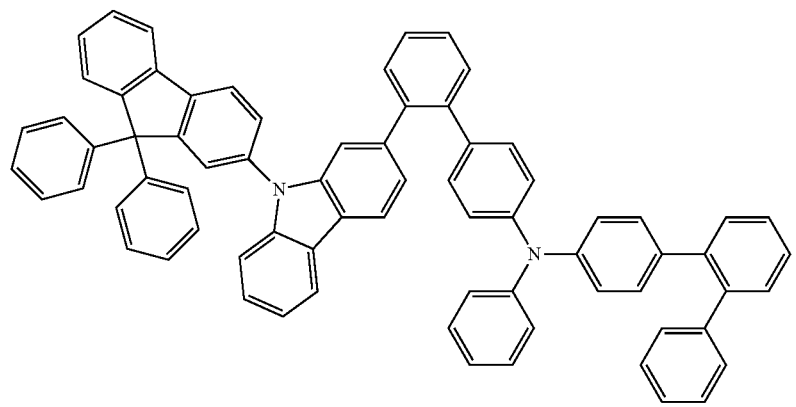
P#-44
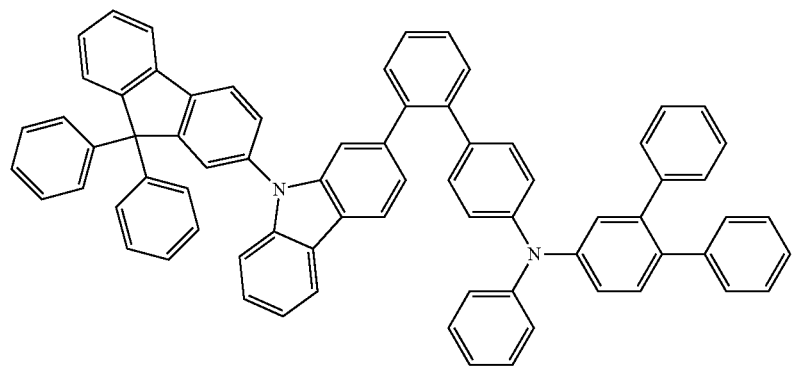
P3-45
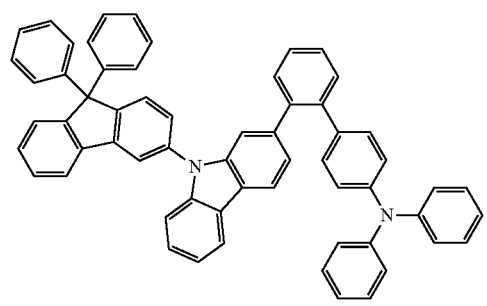
P3-46
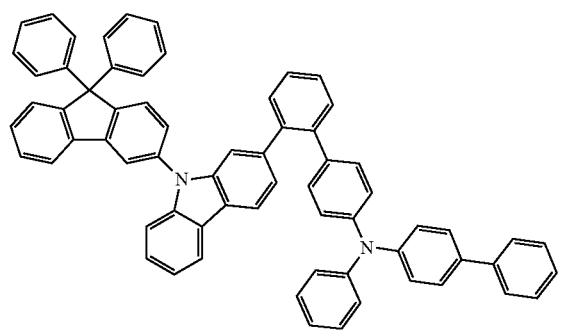

-continued
P3-47
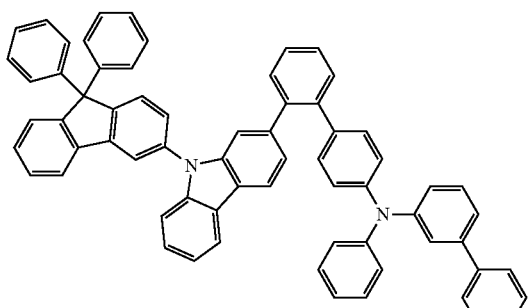
P3-48
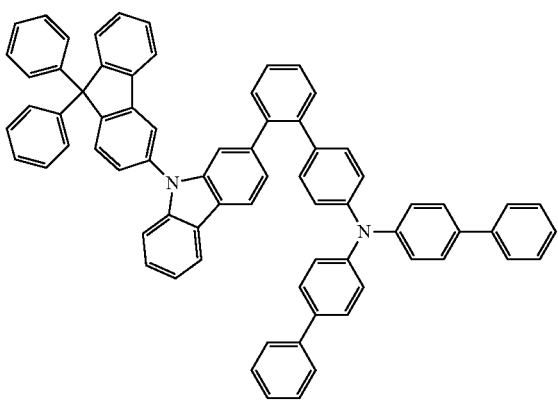
P3-49
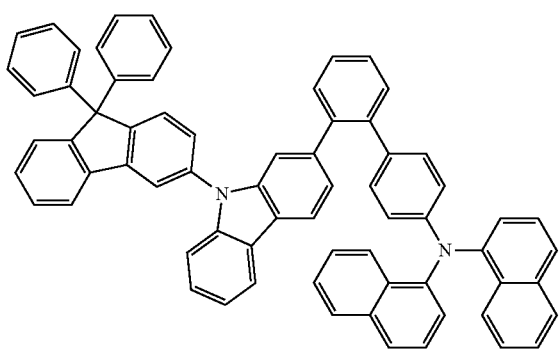
P3-50
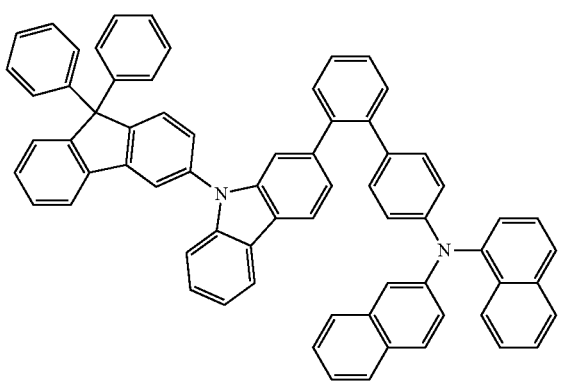
P3-51
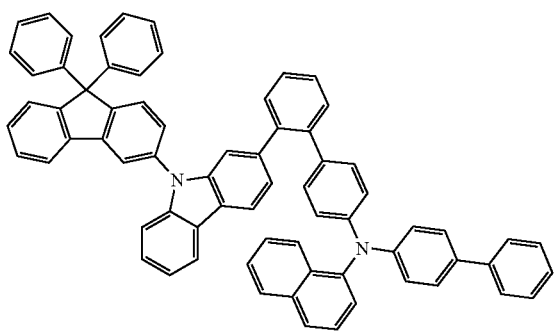
P3-52
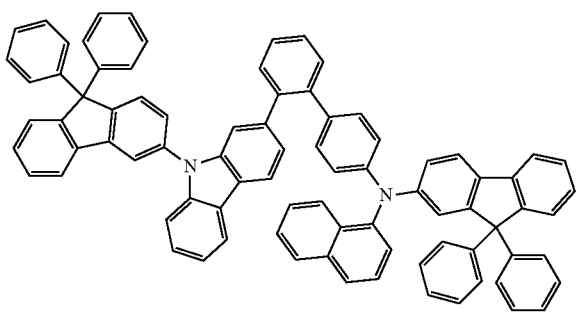
P3-53
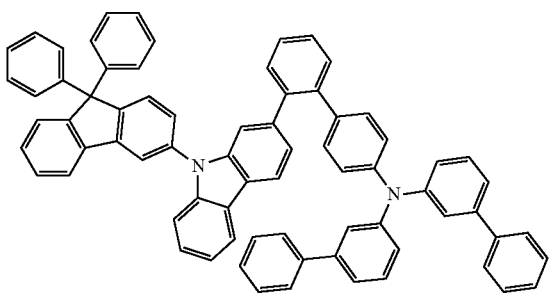
P3-54
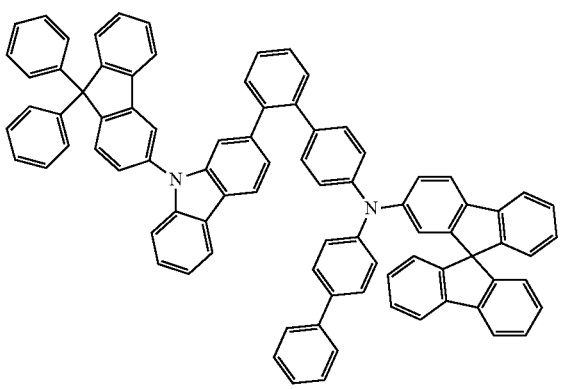

-continued
P3-55
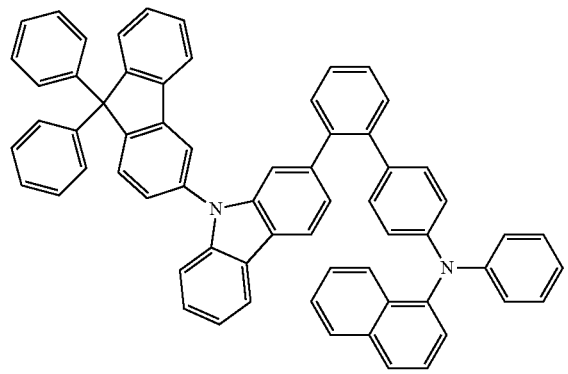
P3-56
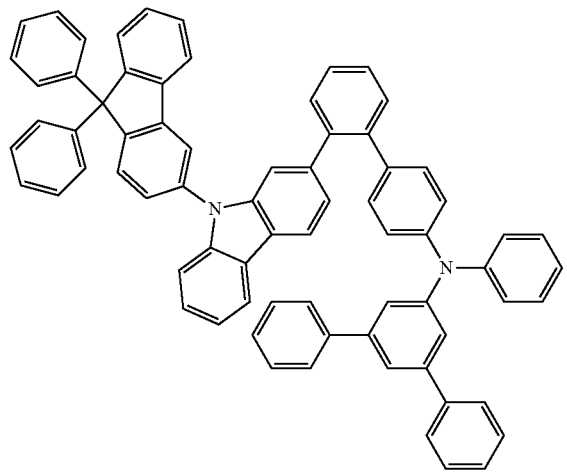
P3-57
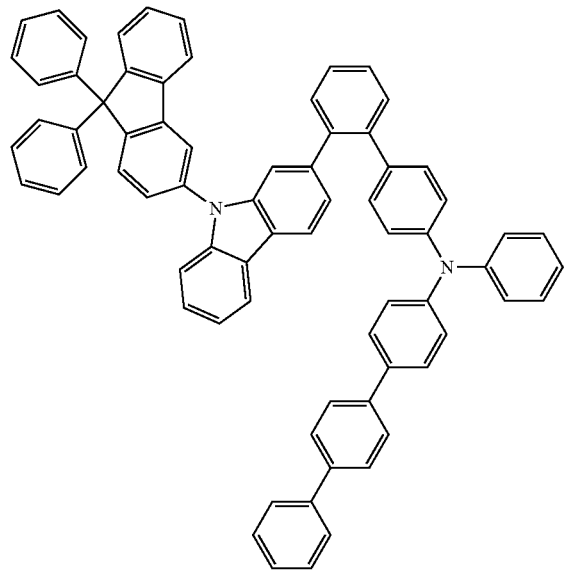
P3-58
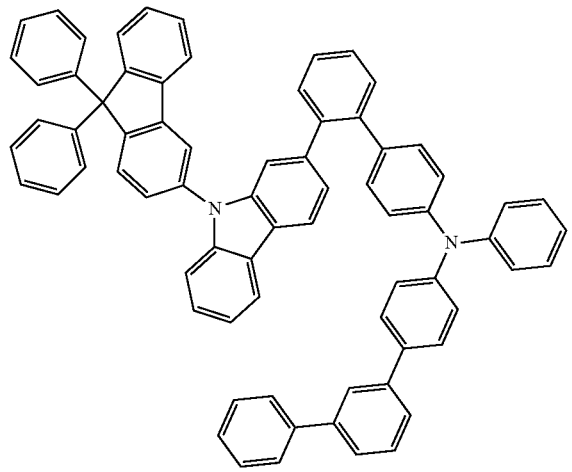
P3-59
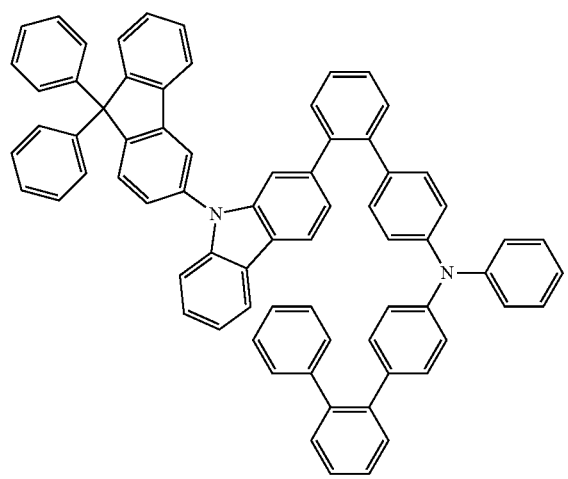
P3-60
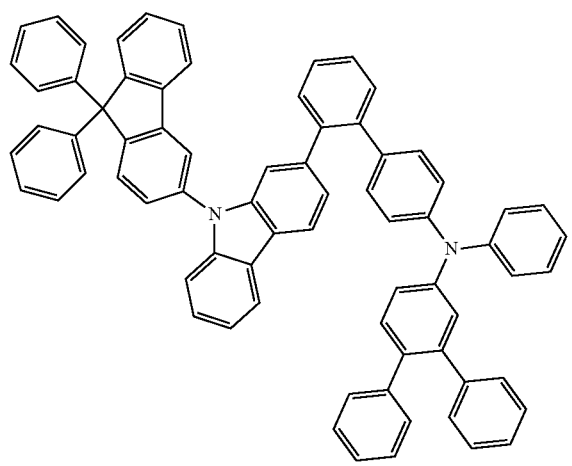

-continued
P3-61
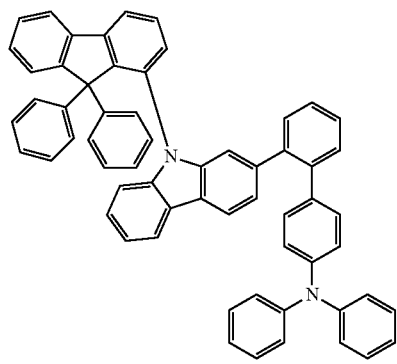
P3-62
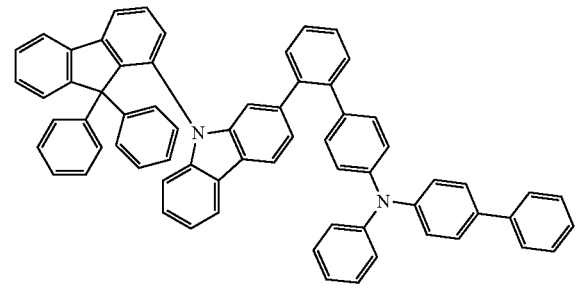
P3-63
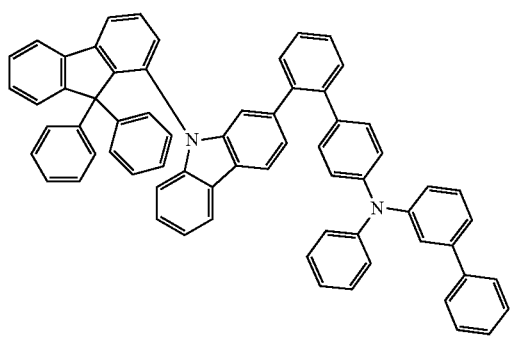
P3-64
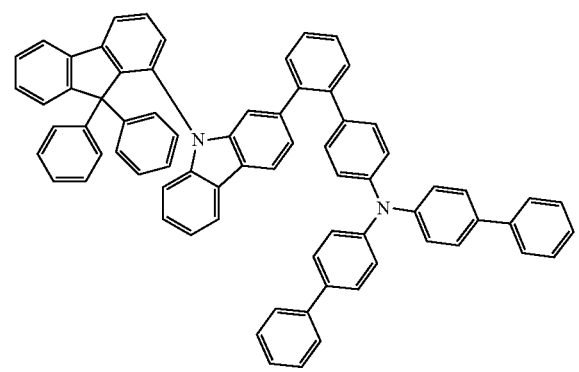
P3-65
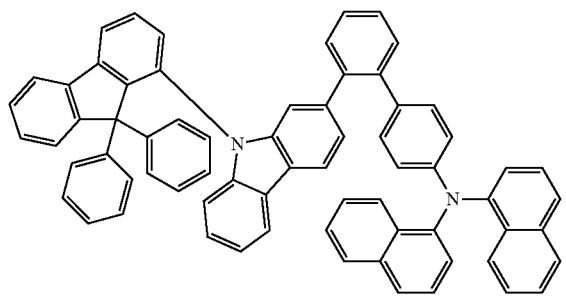
P3-66
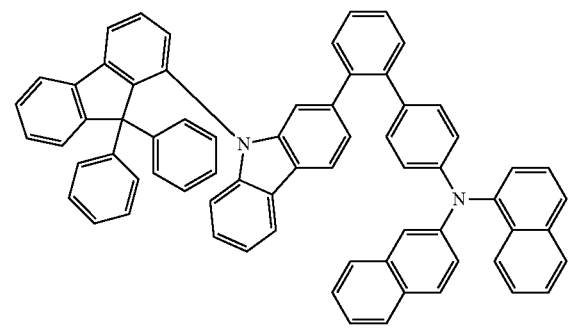
P3-67
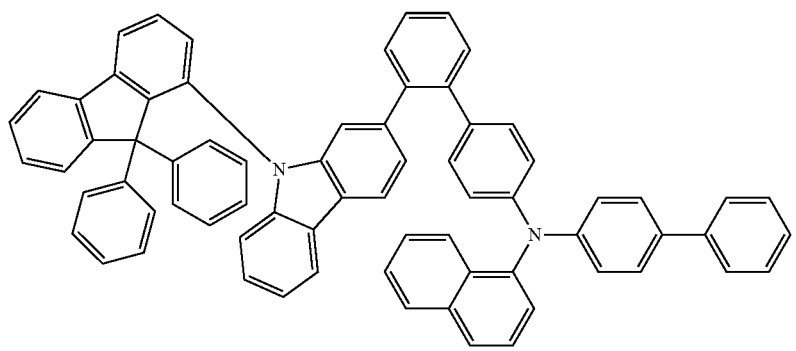

P3-68
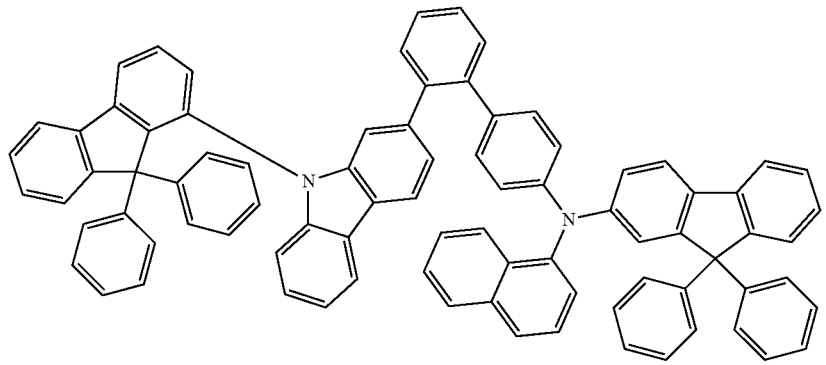
P3-69
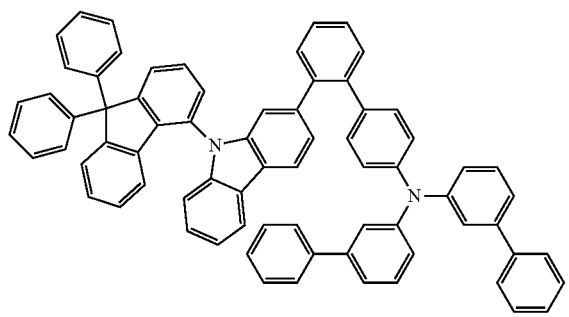
P3-70
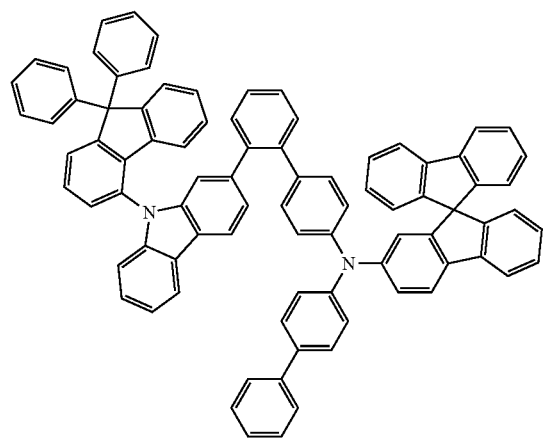
P3-71
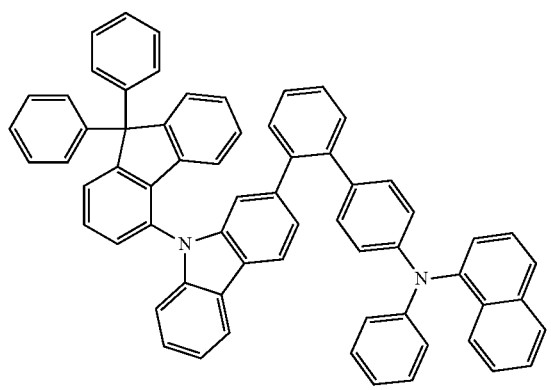
P3-72
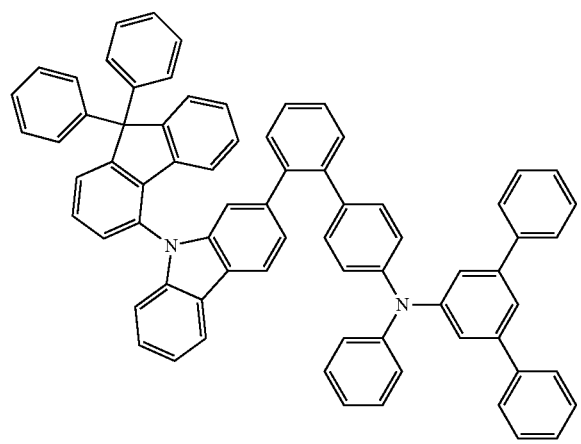

P3-73
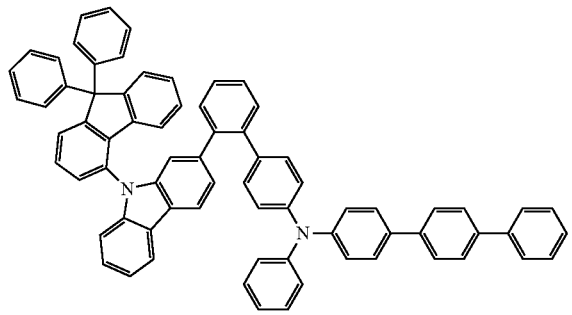
P3-74
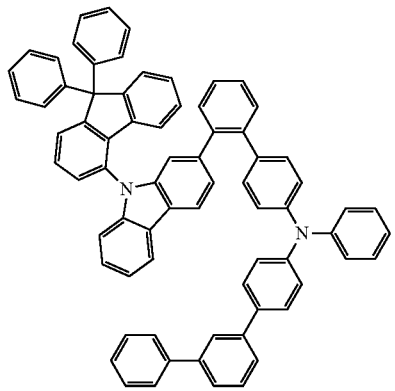
P3-75
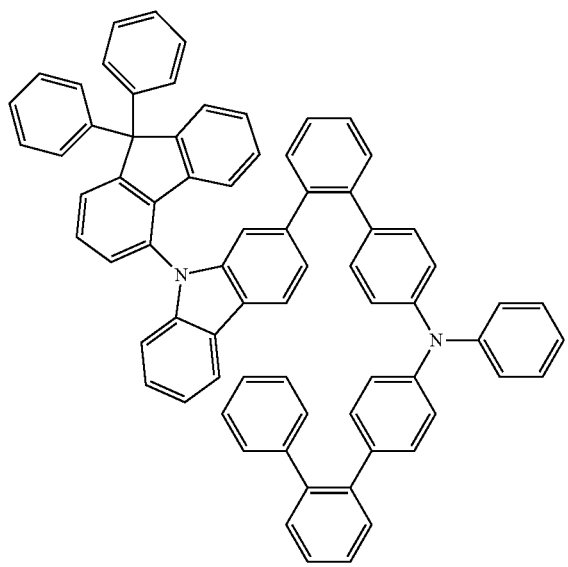
P3-76
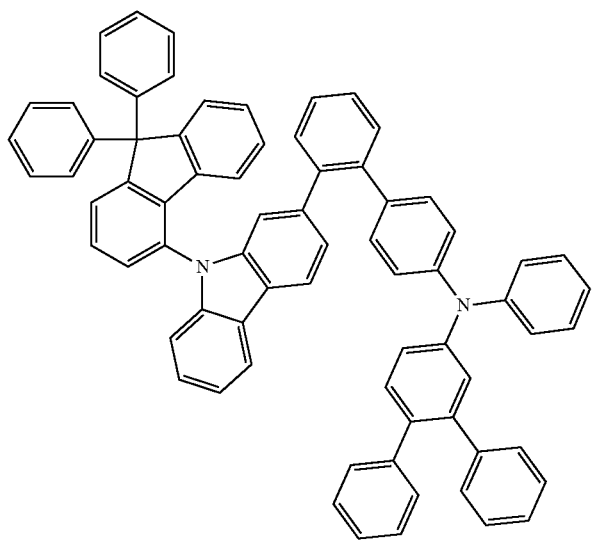
P3-77
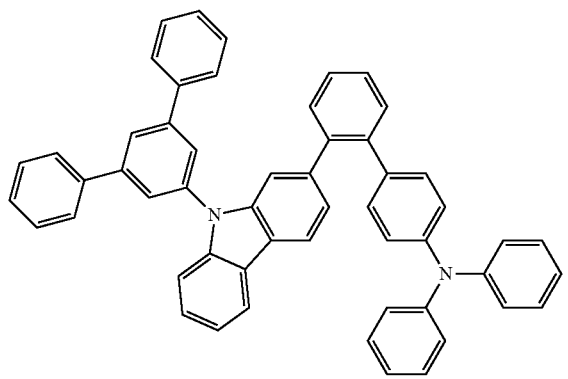
P3-78
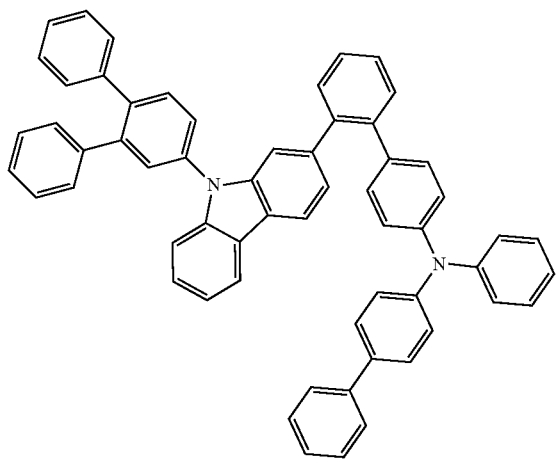

-continued
P3-79
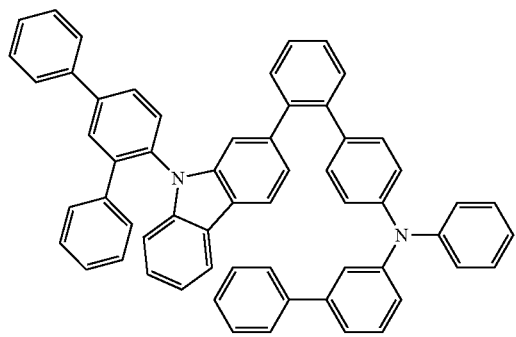
P3-80
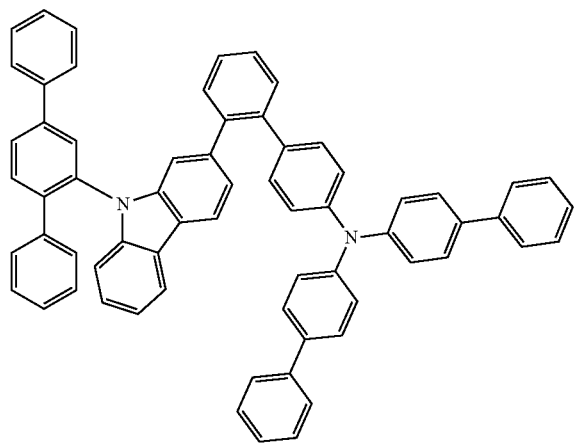
P3-81
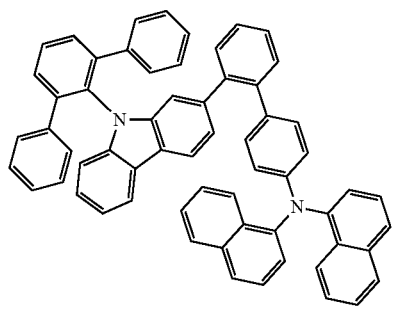
P3-82
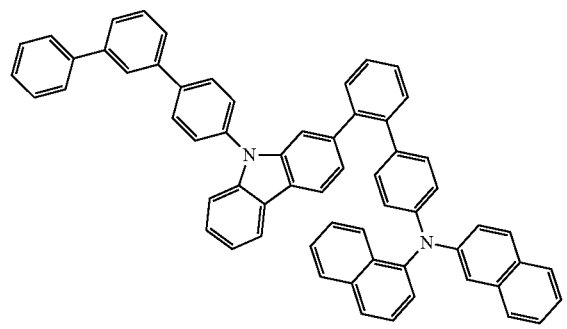
P3-83
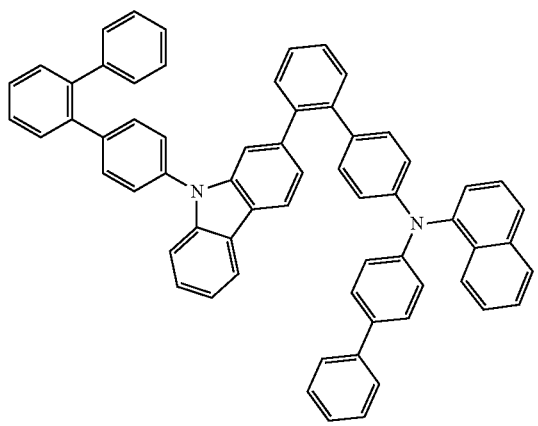
P3-84
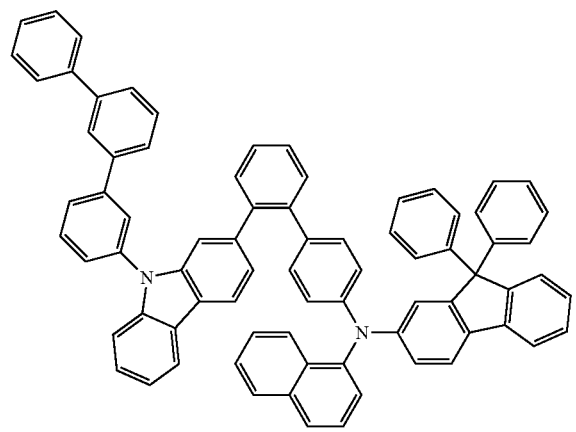
P3-85
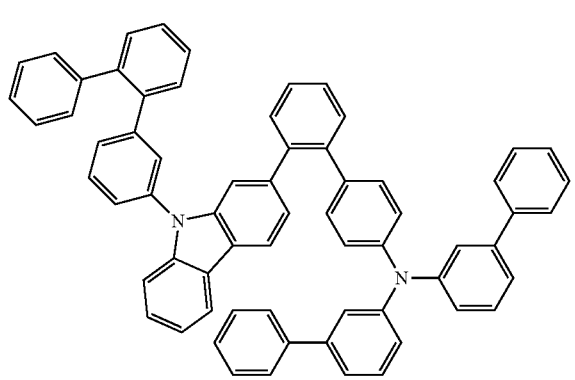
P3-86
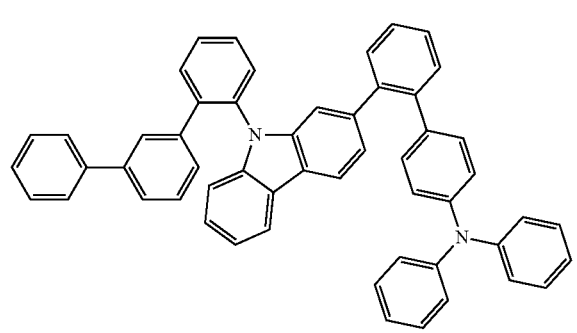

-continued
P3-87
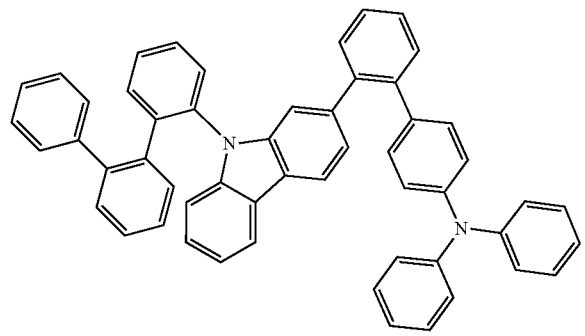
P3-88
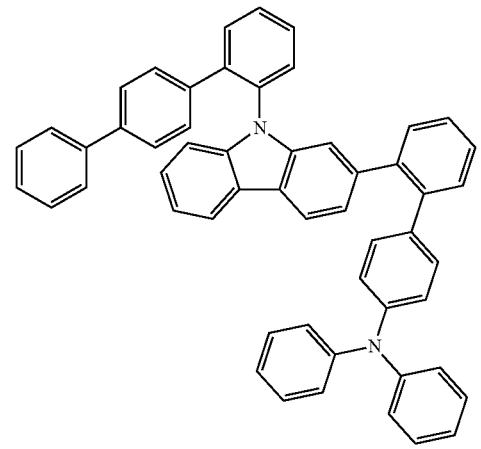
P3-89
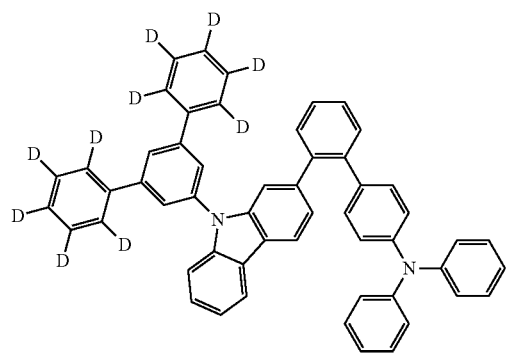
P3-90
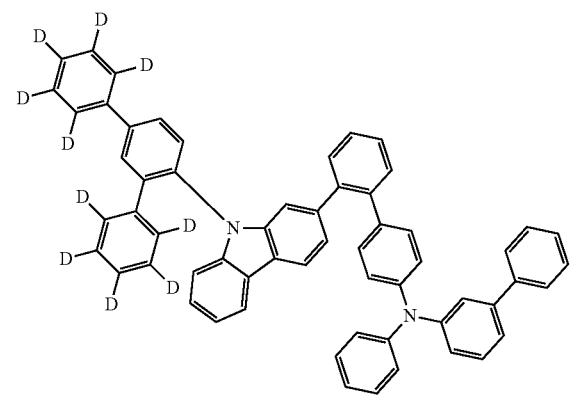
P3-91
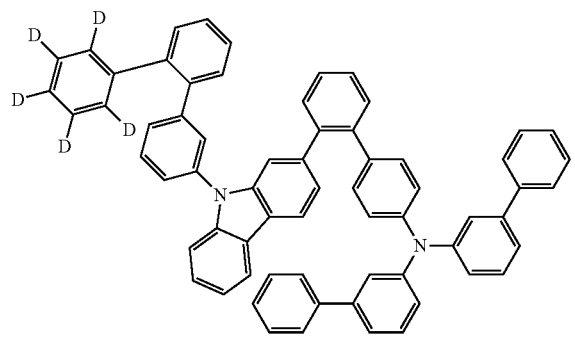
P3-92
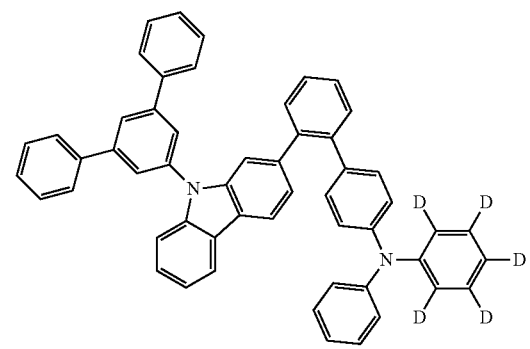
P3-93
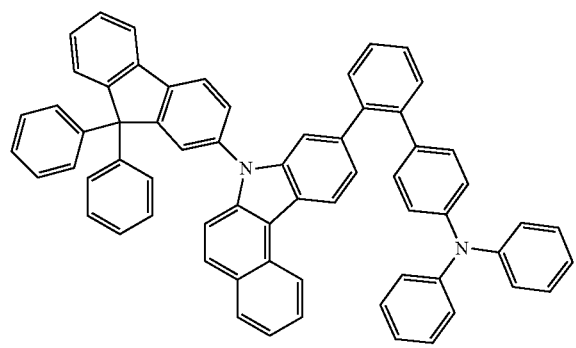
P3-94
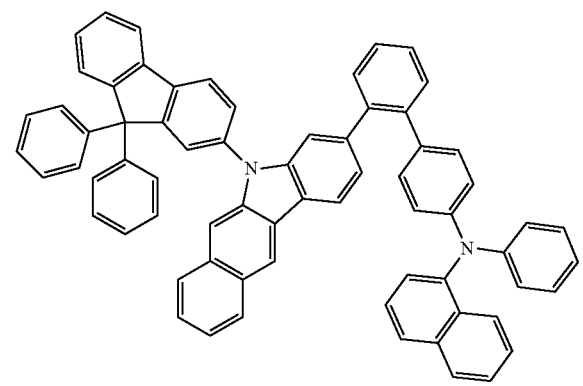

-continued
P3-95
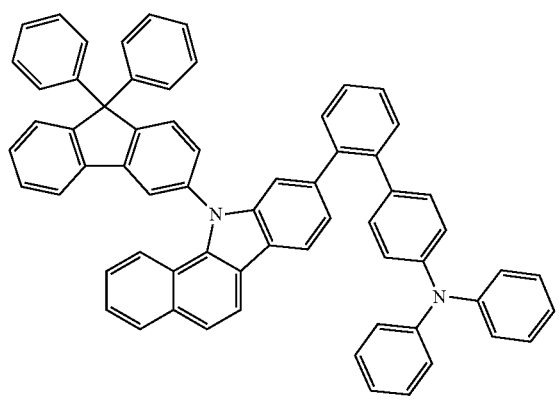
P3-96
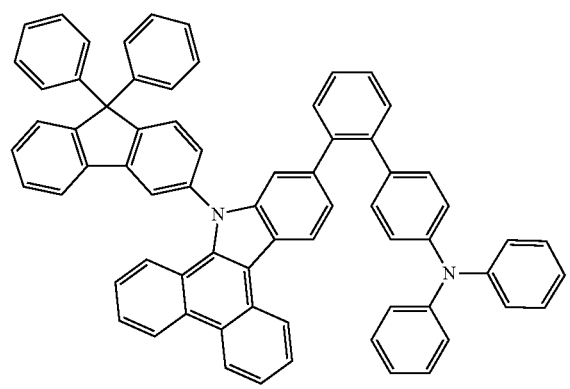
P3-97
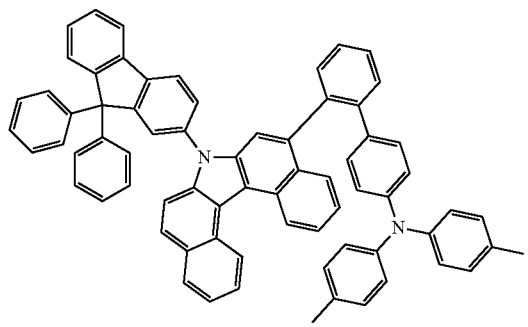
P3-98
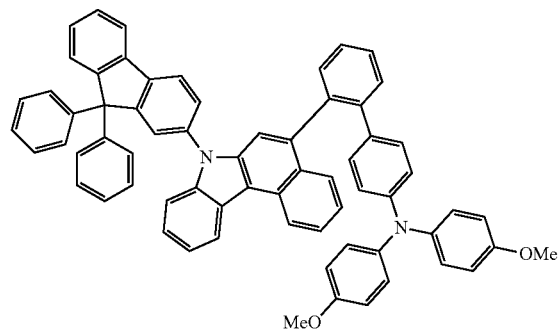
P3-99
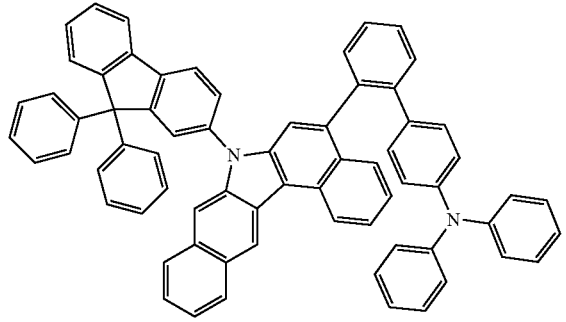
P3-100
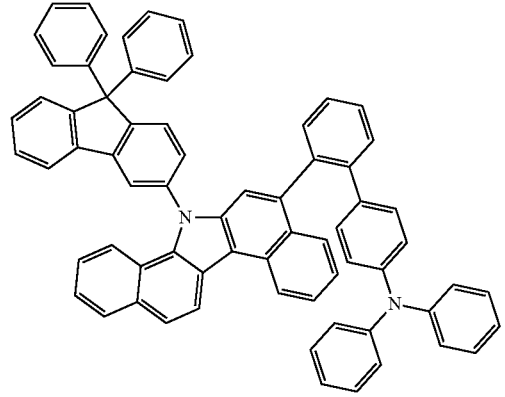
P3-101
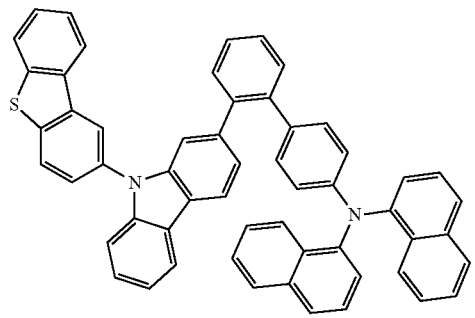
P3-102
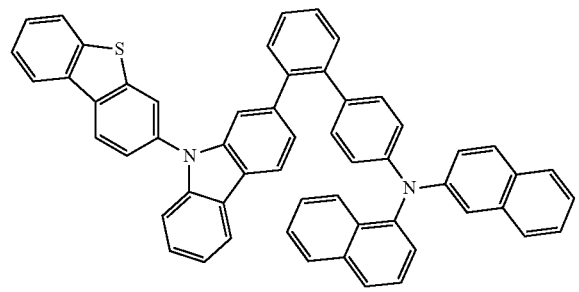

-continued
P3-103
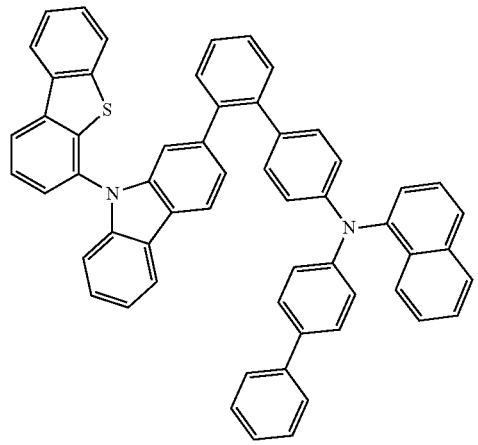
P3-104
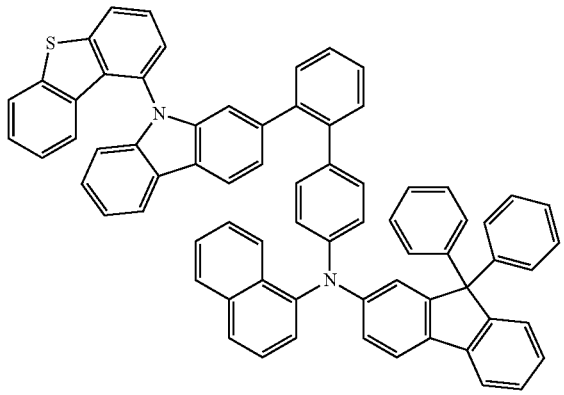
P3-105
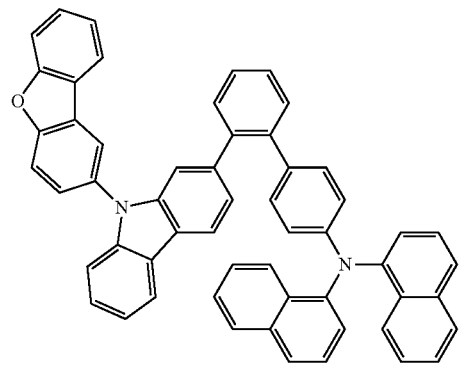
P3-106
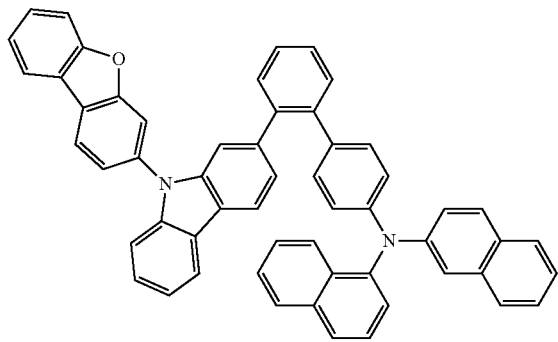
P3-107
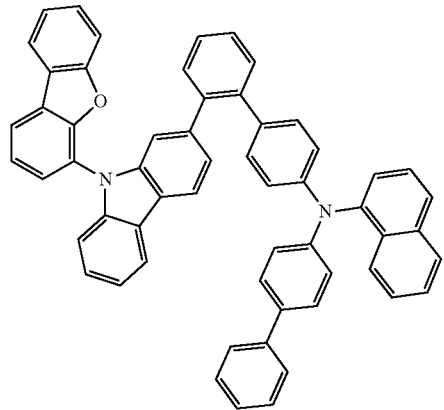
P3-108
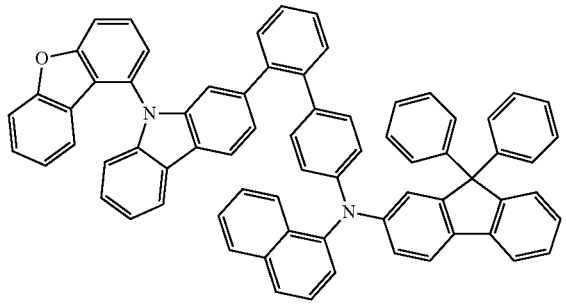
P3-109
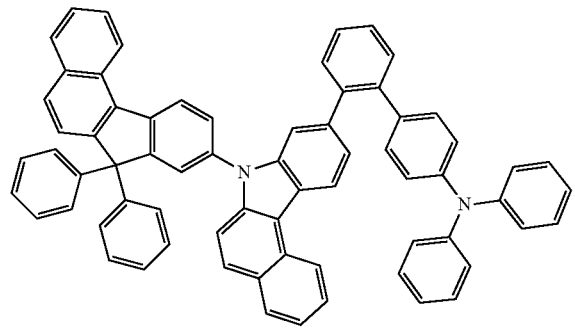
P3-110
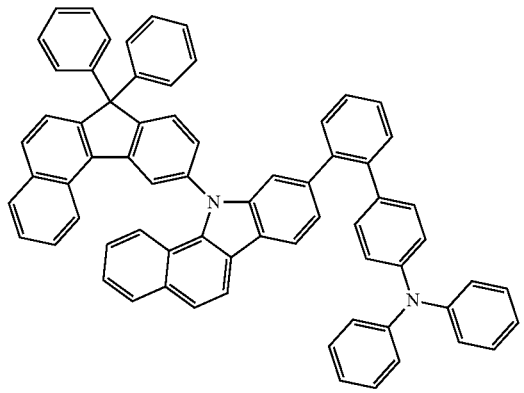

-continued
P3-111
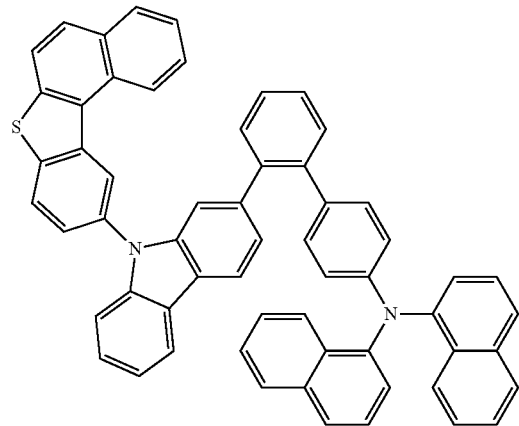
P3-112
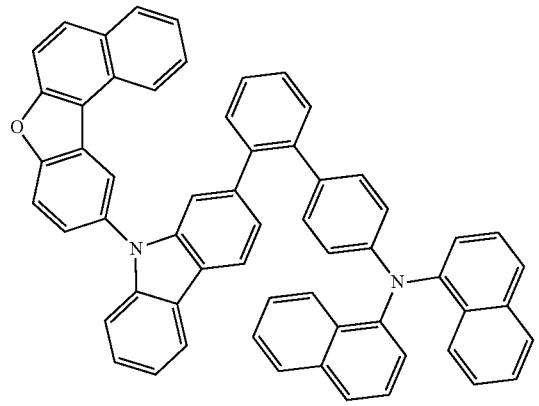
P4-1
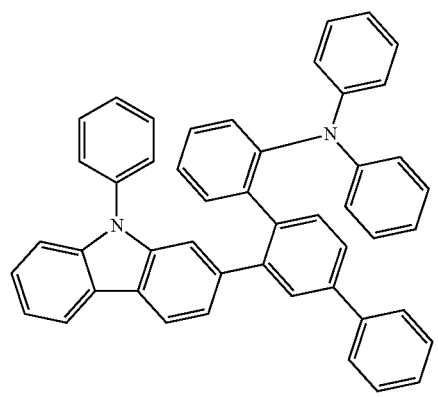
P4-2
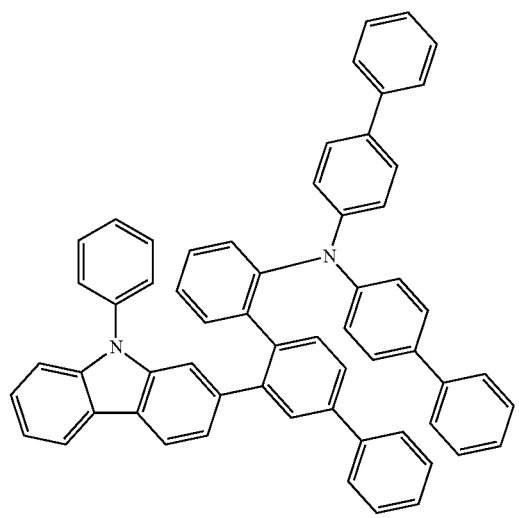
P4-3
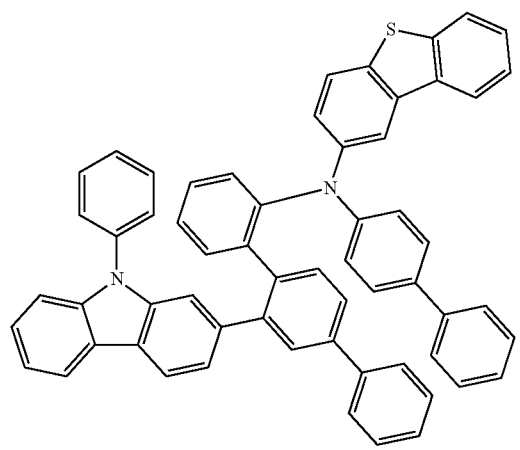
P4-4
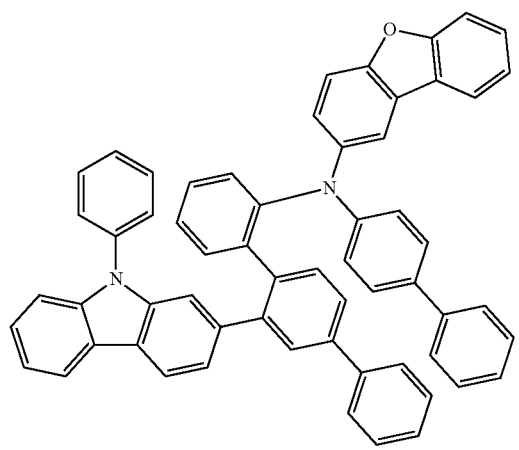

-continued
P4-5
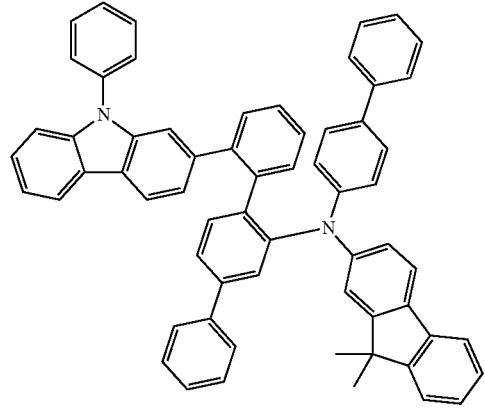
P4-6
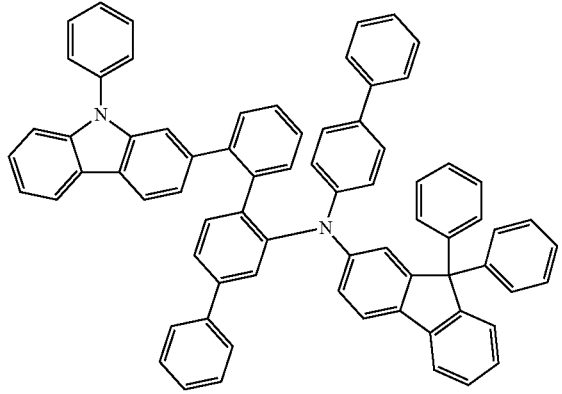
P4-7
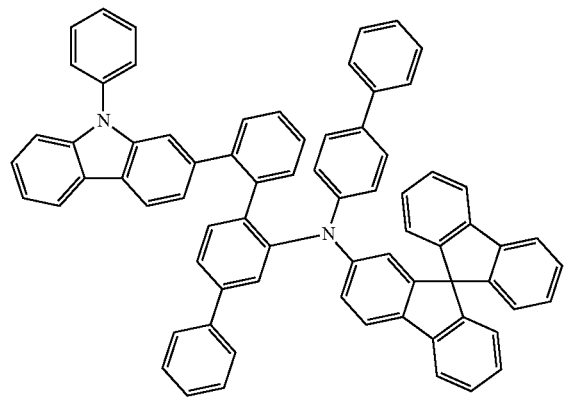
P4-8
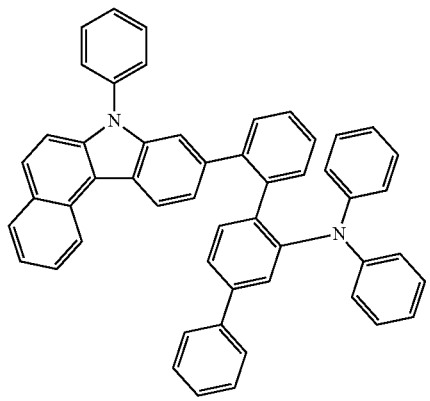
P4-9
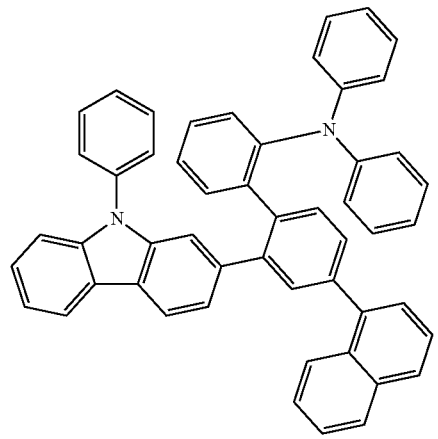
P4-10
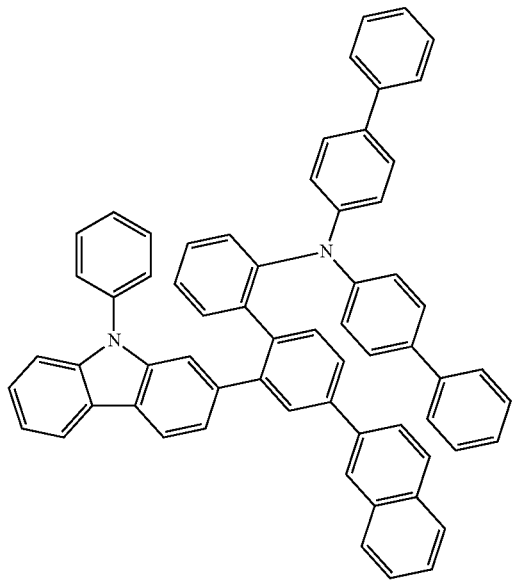

-continued
P4-11
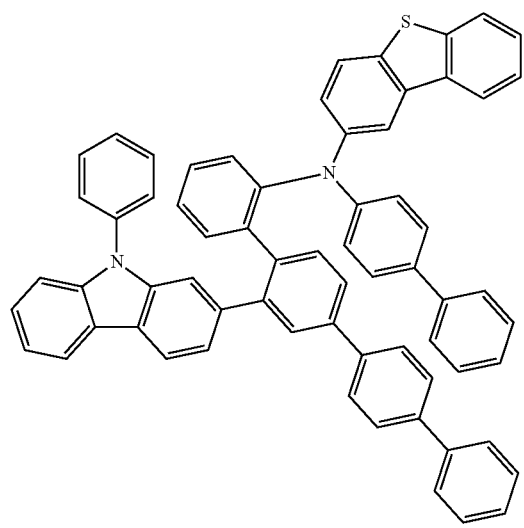
P4-12
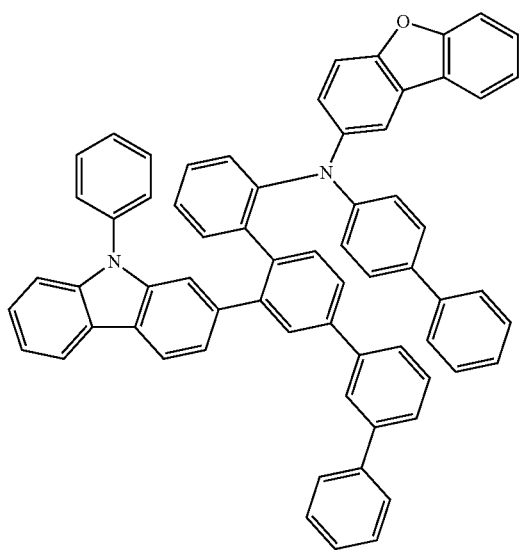
P4-13
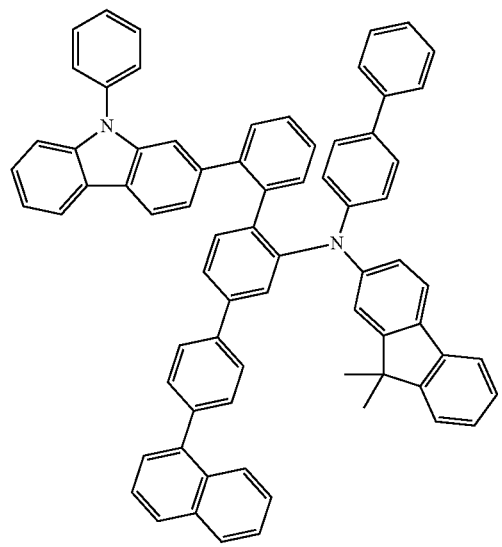
P4-14
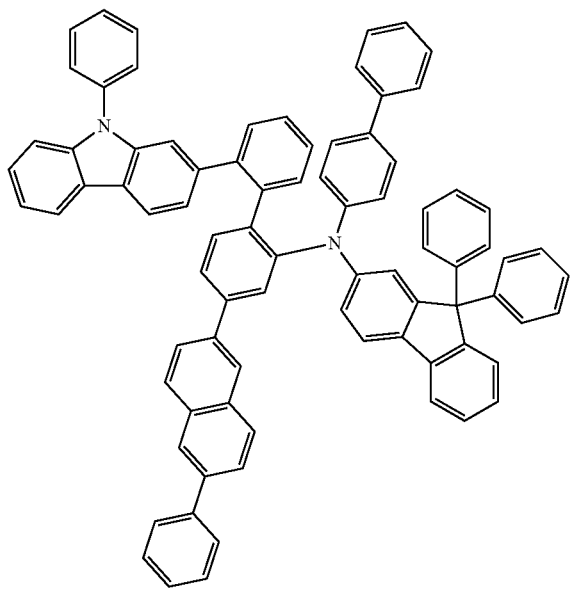
P4-15
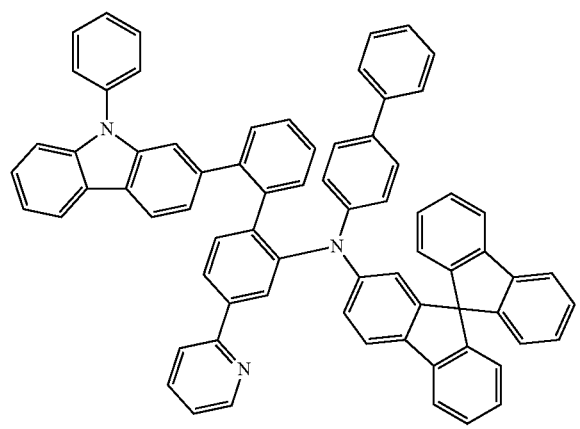
P4-16
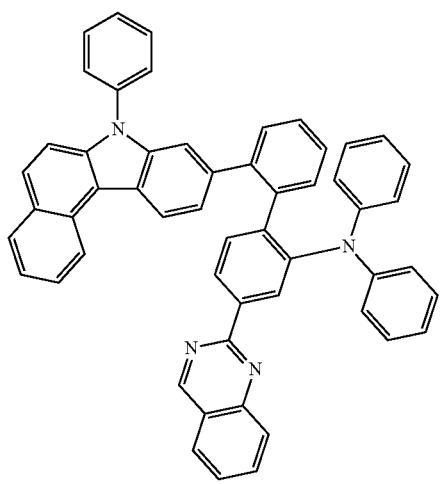

-continued
P4-17
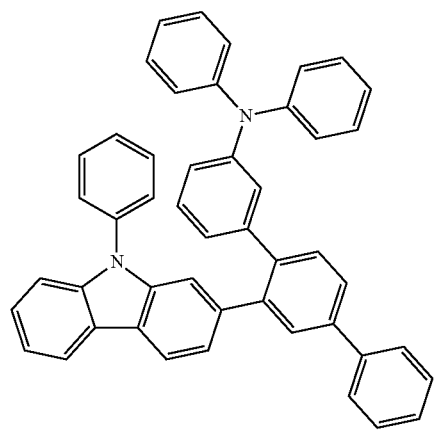
P4-18
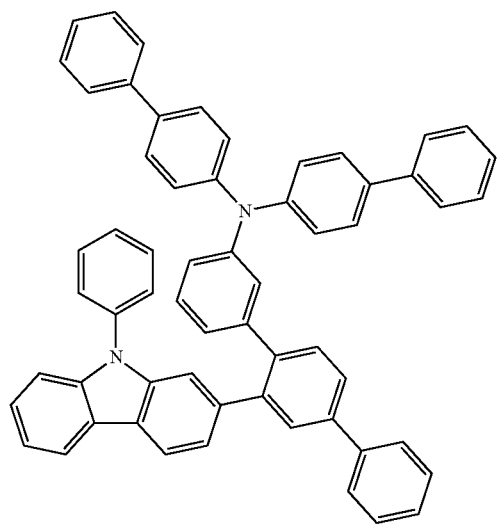
P4-19
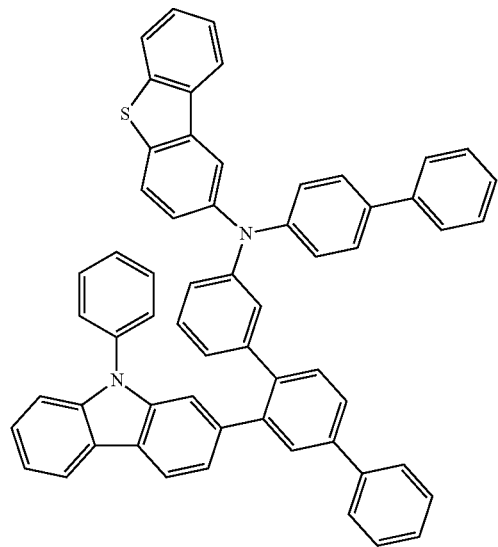
P4-20
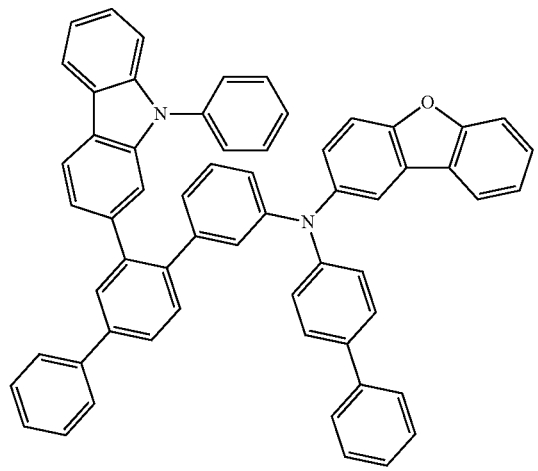
P4-21
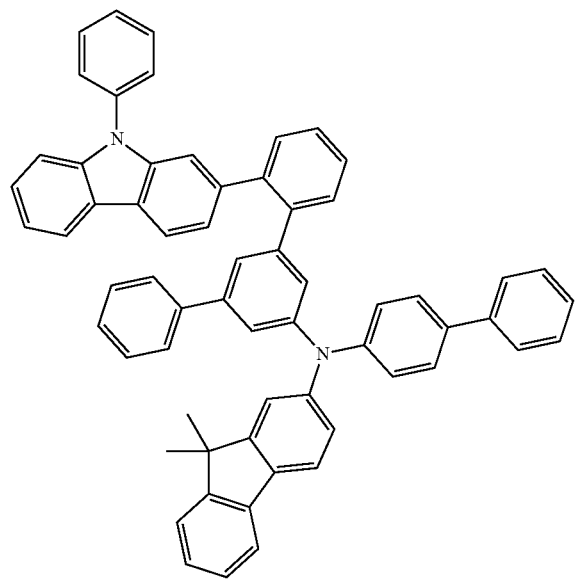
P4-22
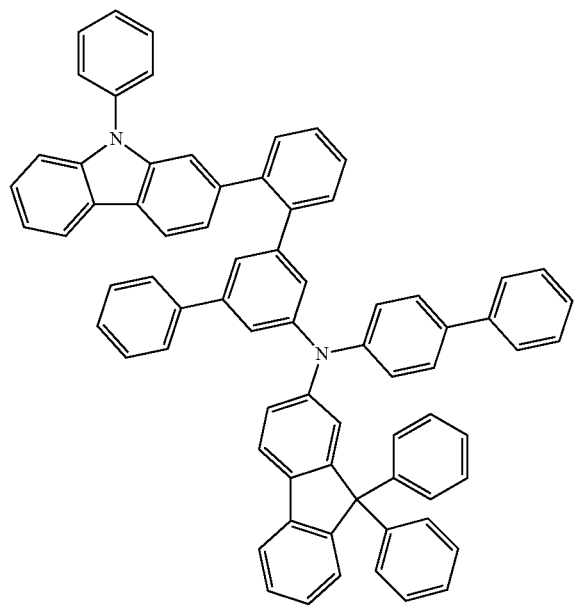

P4-23
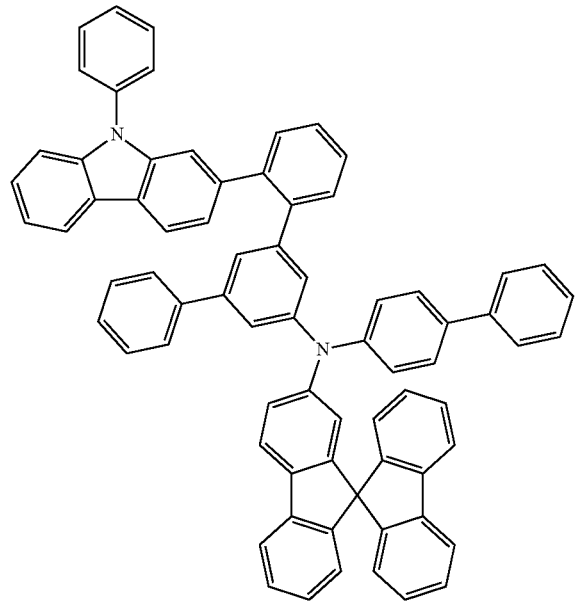
P4-24
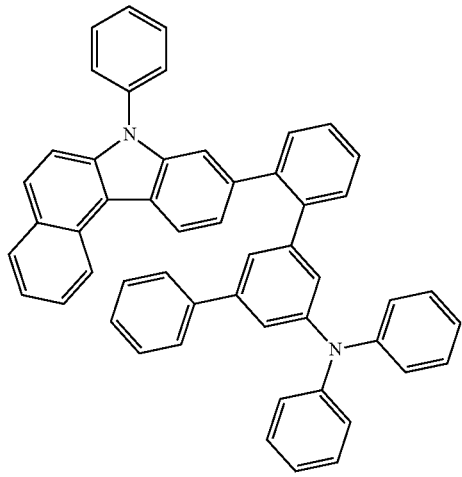
P4-25
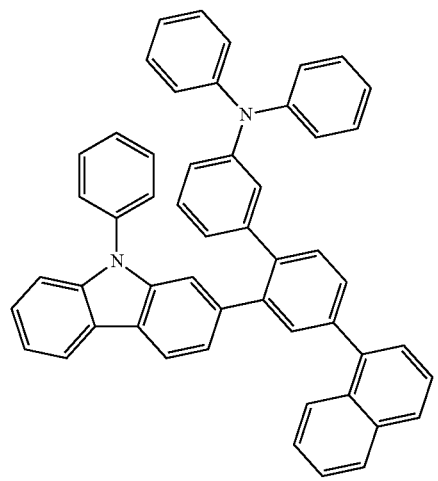
P4-26
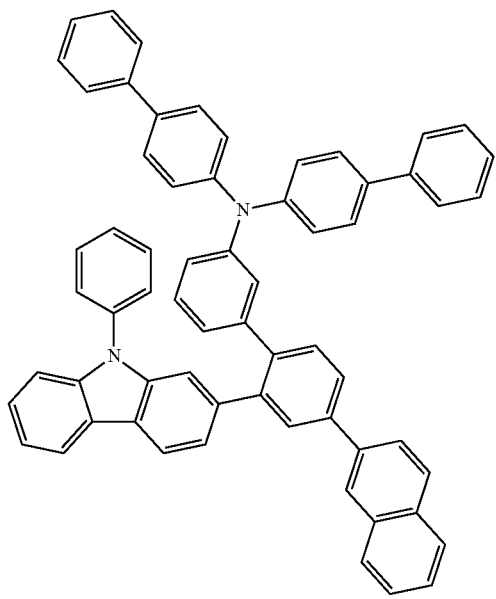

P4-27
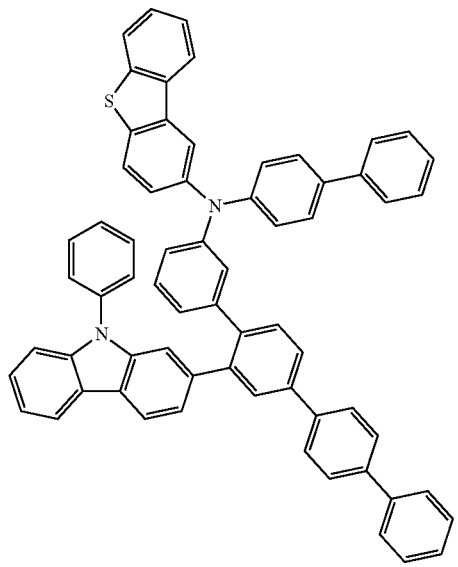
P4-28
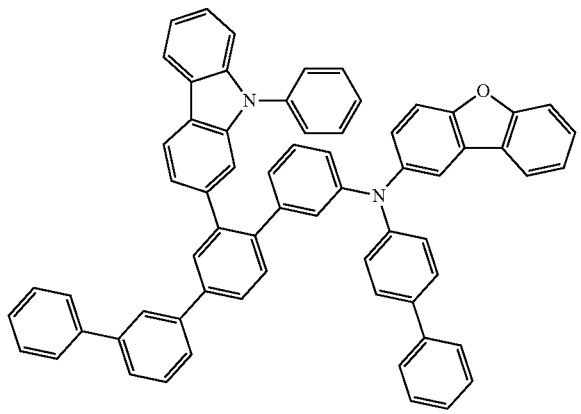
P4-29
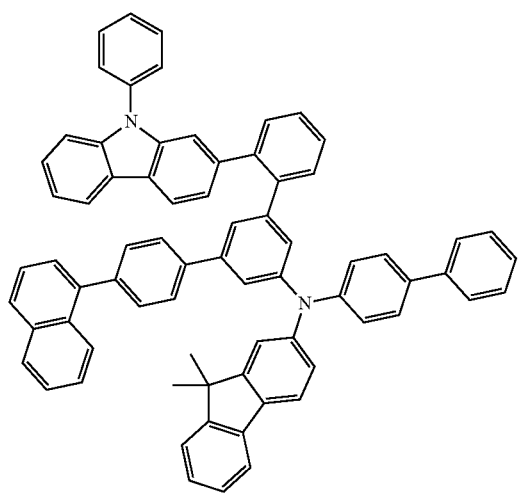
P4-30
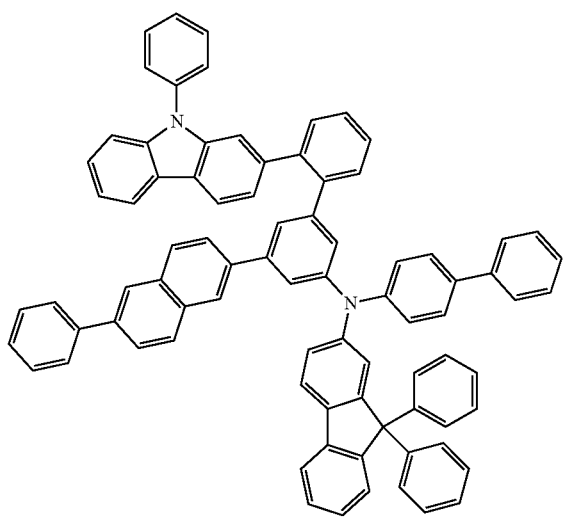

P4-31
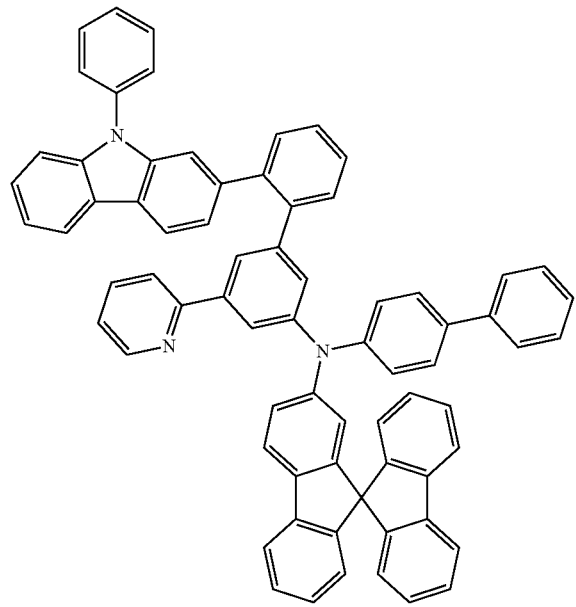
P4-32
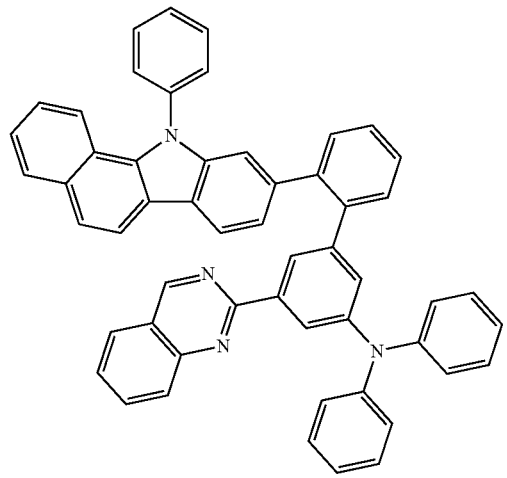
P4-33
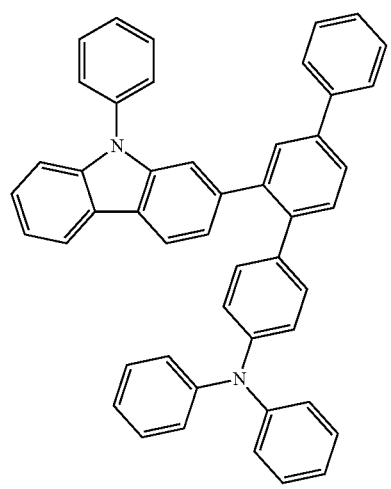
P4-34
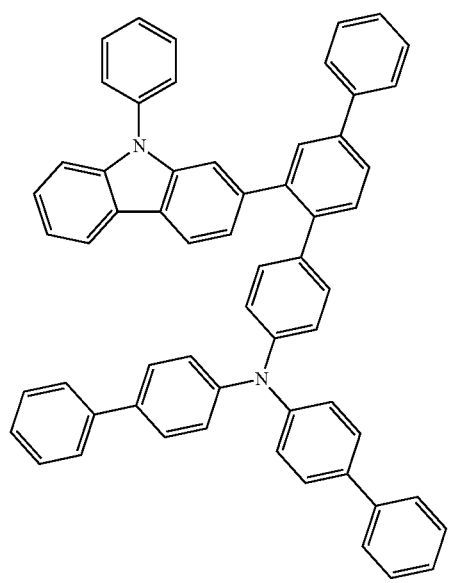

P4-35
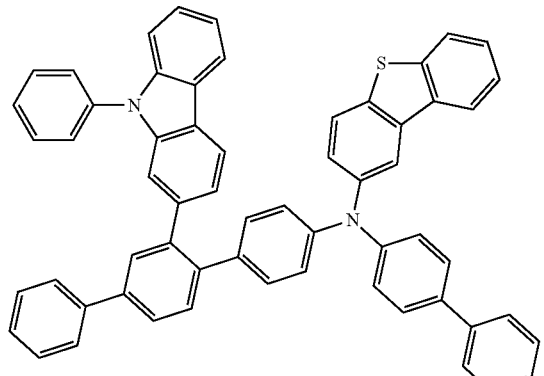
P4-36
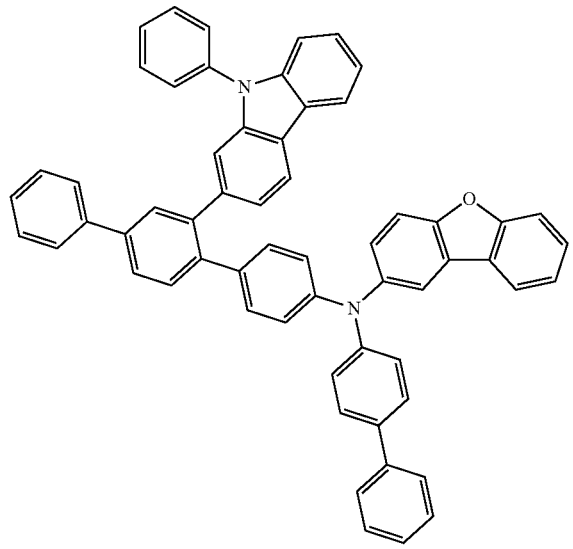
P4-37
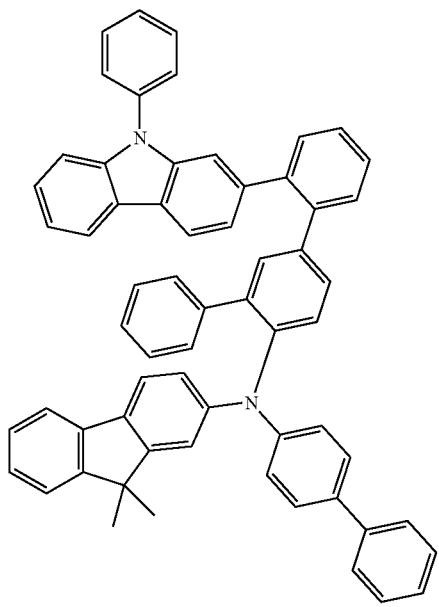
P4-38
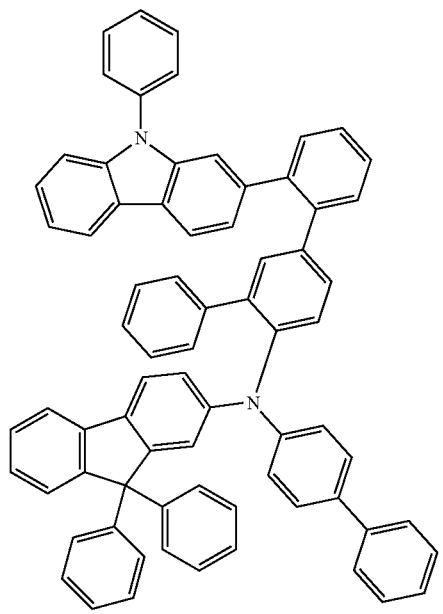

-continued
P4-39
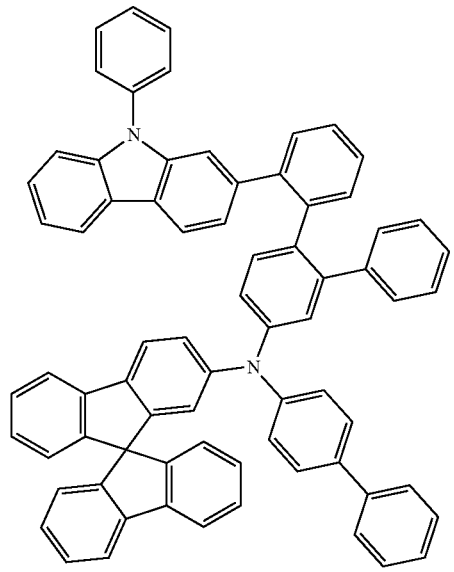
P4-40
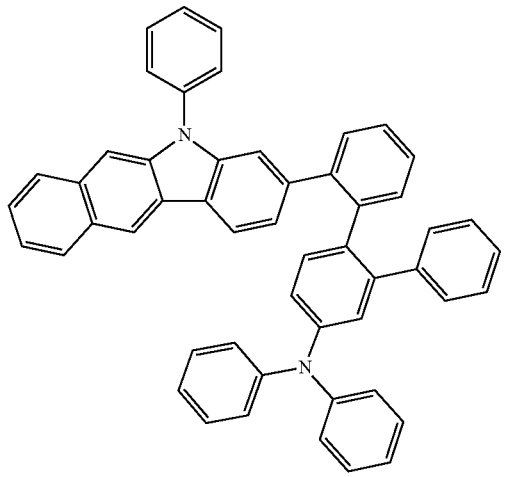
P4-41
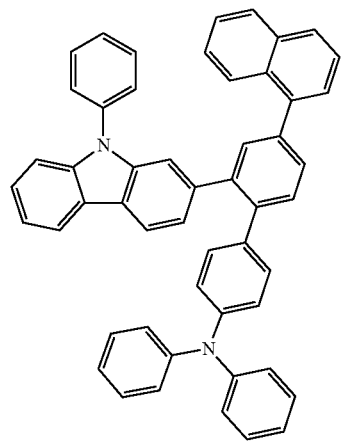
P4-42
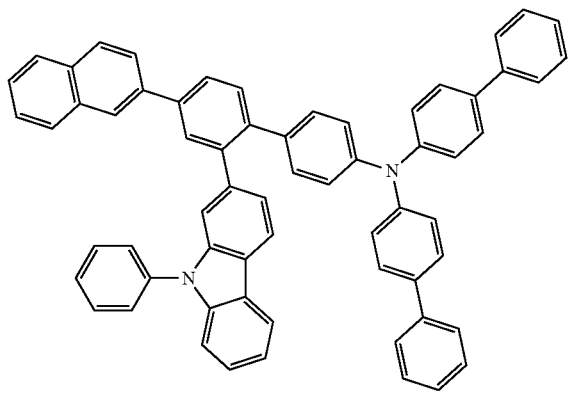
P4-43
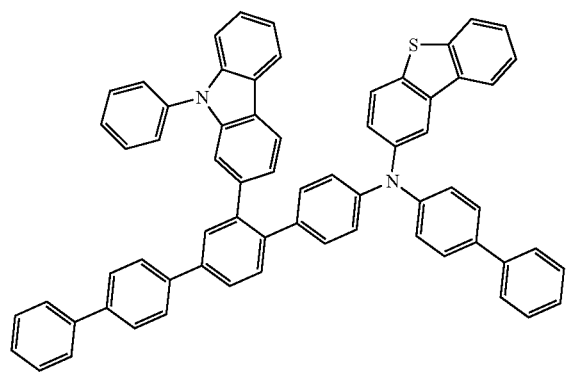
P4-44
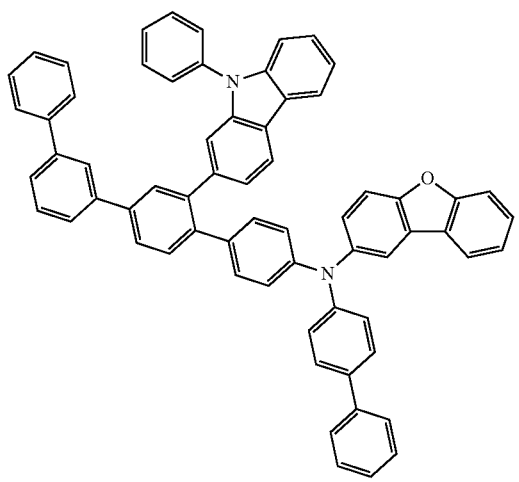

-continued

P4-45

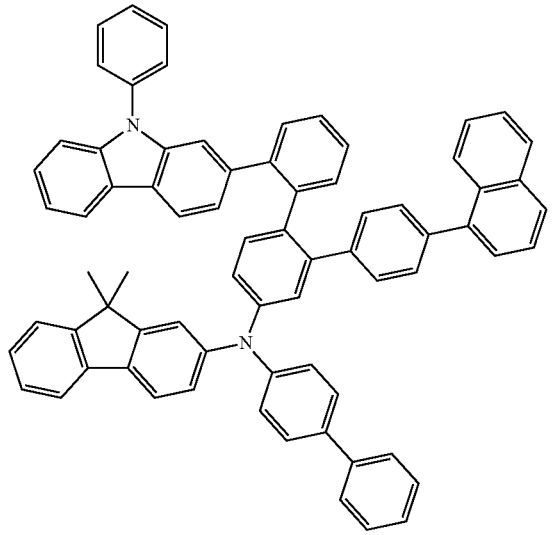

P4-46

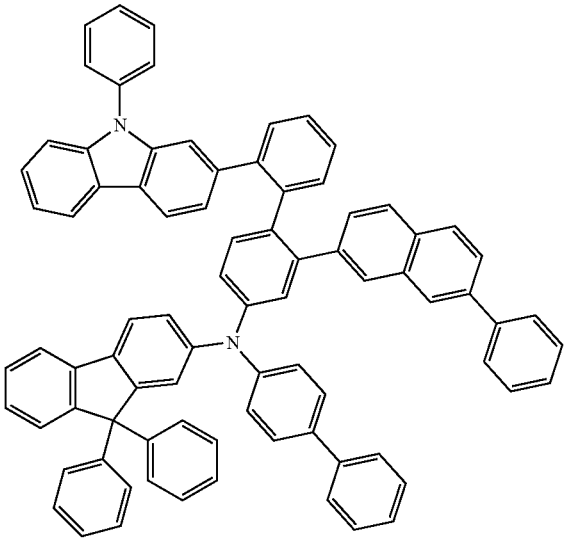

P4-47

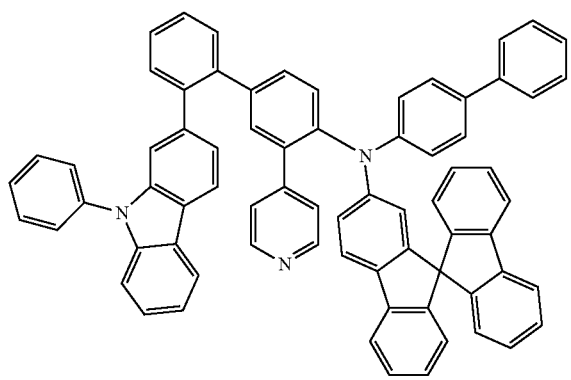

P4-48

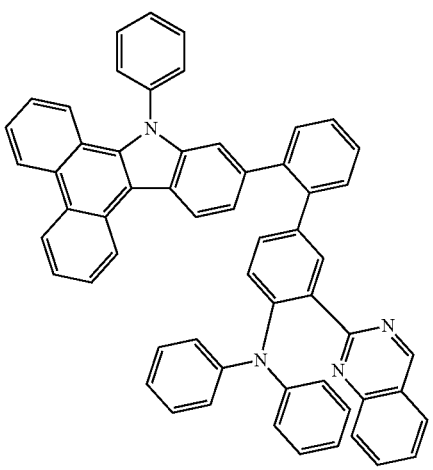

In another aspect of the present invention, a compound for an organic electric element represented by Formula 1 above is provided.

In another aspect of the present invention, an organic electric element comprising the compound represented by Formula 1 above is provided.

The organic electric element comprise a first electrode, a second electrode, and an organic material layer disposed between the first electrode and the second electrode. The organic material layer comprise the compound represented by Formula 1, and the compound represented by Formula 1 is contained in at least one layer of a hole injection layer, a hole transport layer, an emission-auxiliary layer and a light emitting layer of the organic material layer. That is, the compound represented by Formula 1 may be used as material of the hole injection layer, the hole transport layer, the emission-auxiliary layer, or a the light emitting layer.

Specifically, the organic electric element of which the organic material layer comprises at least one of the compounds represented by Formula 2 to 10 is provided, and more specifically the organic electric element of which the organic material layer comprises at least one of the compounds represented by Formula 11 to 20 is provided, more specially, the organic electric element of which the organic material layer comprises at least one of the compounds P1-1 to P1-112, P2-1 to P2-112, P3-1 to P3-32 and P4-1 to P4-48 is provided. That is, the compounds which are comprised in the organic material layer or by which the organic material layer is formed may be one kind or two or more different kinds of the compounds represented by Formula 1 above.

In another aspect of the present invention, the present invention provides an organic electric element further including a layer to improve a luminescence efficiency which is formed on at least one of the sides the first and second electrodes, which is opposite to the organic material layer.

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

Synthesis Example

The final product of the present invention represented by Formula 1 can be synthesized by reaction of Sub 1 and Sub 2 as illustrated in the following Reaction Scheme 1, but the present invention is not limited to the following examples.

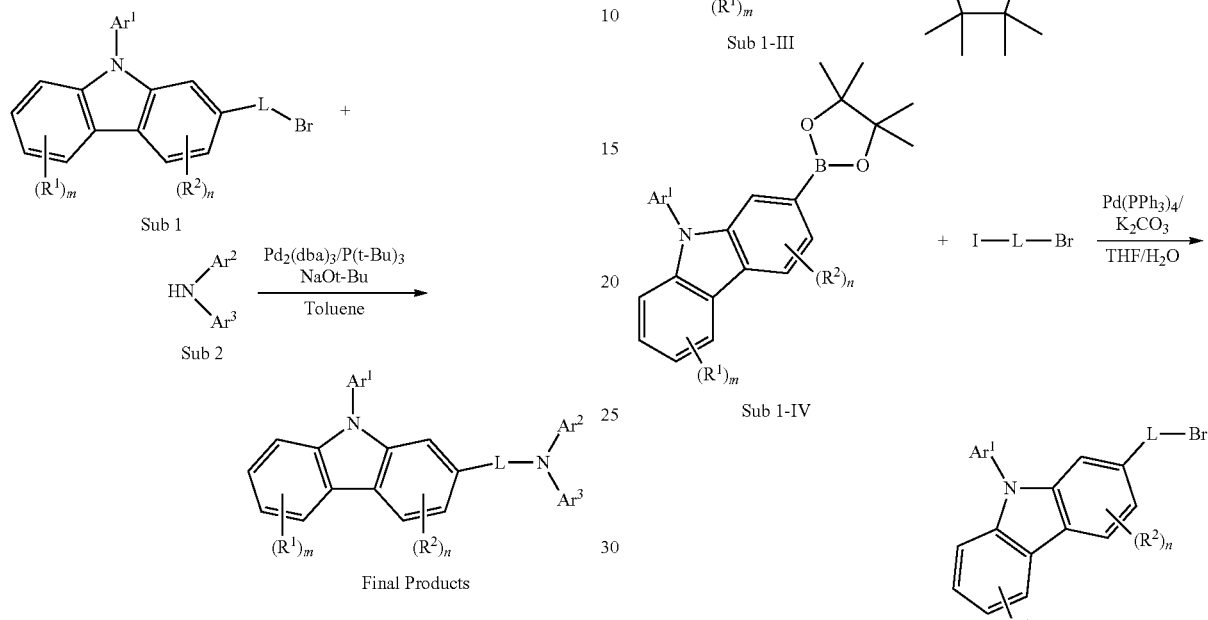

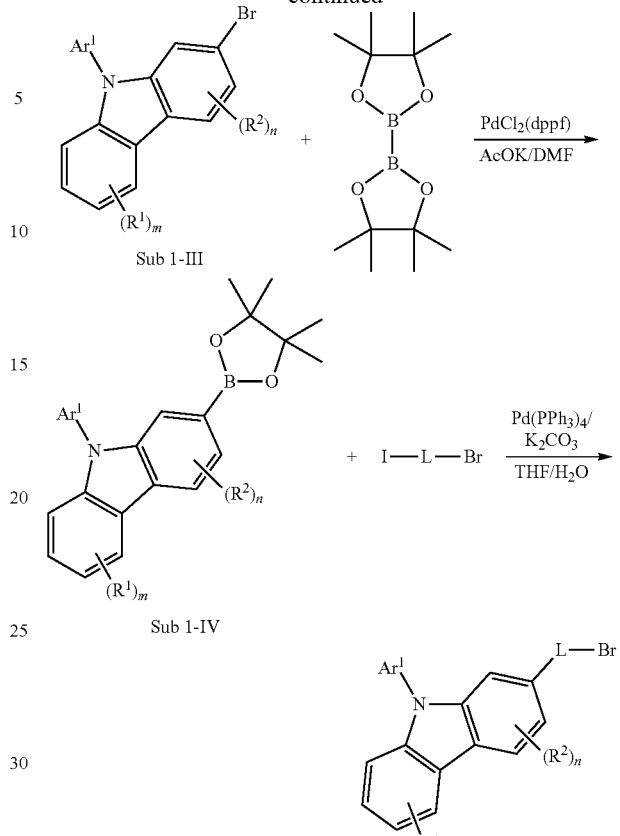

I. Synthesis Example of Sub 1

Sub 1 of the Reaction Scheme 1 can be synthesized according to the following Reaction Scheme 2.

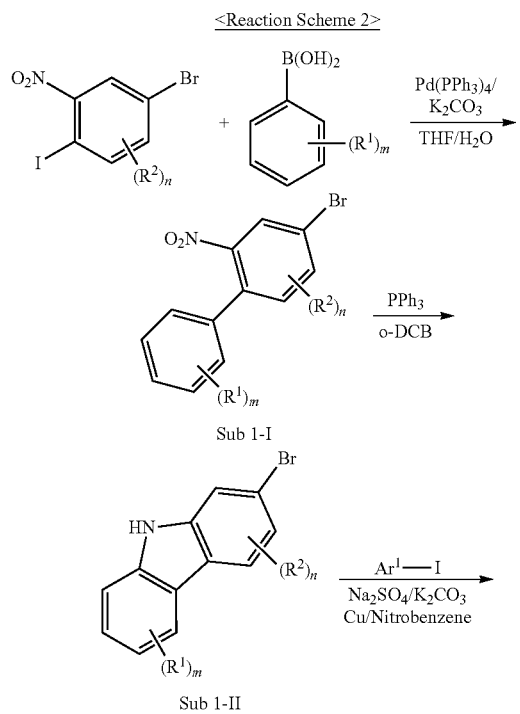

1. Synthesis Example of Sub 1-1

(1) Synthesis of Sub 1-I-1

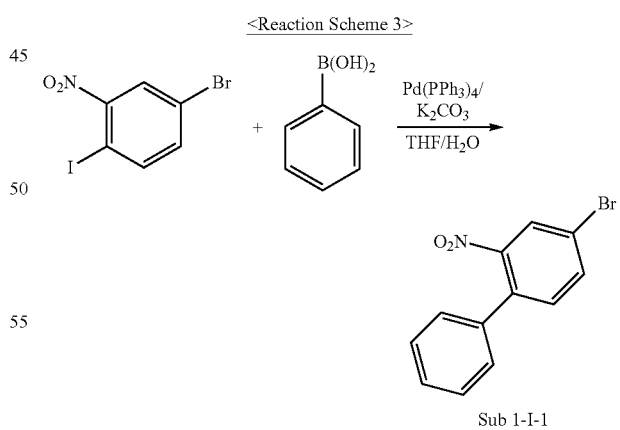

Phenylboronic acid (76.84 g, 630.2 mmol) was dissolved in THF (2780 ml) in a round bottom flask. Then, 4-bromo-1-iodo-2-nitrobenzene (309.96 g, 945.3 mmol), Pd(PPh$_3$)$_4$ (36.41 g, 31.5 mmol), K$_2$CO$_3$ (261.3 g, 1890.6 mmol) and water (1390 ml) were added into the round bottom flask, and the mixture was stirred at 80° C. After the completion of the reaction, the reaction product was extracted with CH$_2$Cl$_2$ and water. The extracted organic layer was dried over MgSO$_4$ and concentrated. The concentrated resultant was separated by silica gel column chromatography, and was then recrystallized, whereby a compound Sub 1-I-1 was obtained in an amount of 122.68 g in 70% yield.

(2) Synthesis of Sub 1-II-1

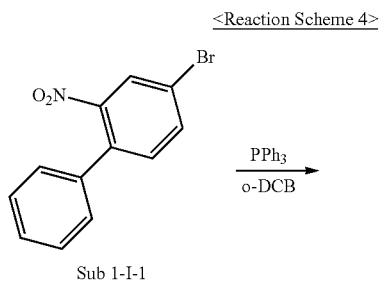

The compound Sub 1-I-1 (122.68 g, 441.1 mmol) obtained above was dissolved in o-dichlorobenzene (1810 ml) in a round bottom flask. Then, triphenylphosphine (289.26 g, 1102.8 mmol) was added into the round bottom flask, and the mixture was stirred at 200° C. After the completion of the reaction, o-dichlorobenzene from the reaction product was removed by distillation and the reaction product was extracted with CH$_2$Cl$_2$ and water. The extracted organic layer was dried over MgSO$_4$ and concentrated. The concentrated resultant was separated by silica gel column chromatography, and was then recrystallized, whereby a compound Sub 1-II-1 was obtained in an amount of 80.34 g in 74% yield.

(3) Synthesis of Sub 1-III-1

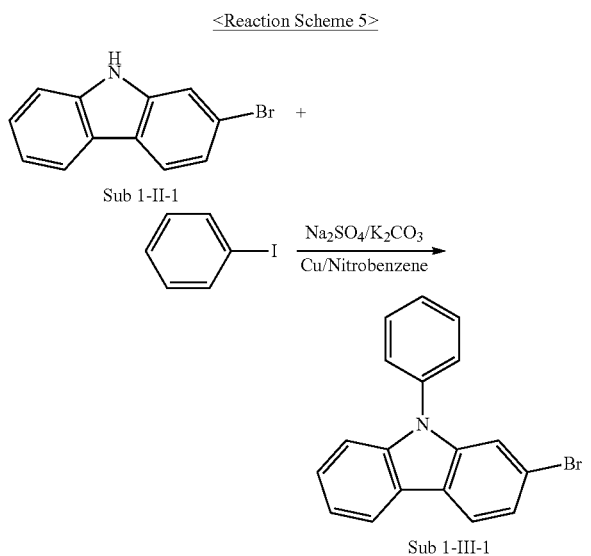

The compound Sub 1-II-1 (80.34 g, 326.5 mmol) obtained above was dissolved in nitrobenzene (653 ml) in a round bottom flask. Then, iodobenzene (99.9 g, 489.7 mmol), Na$_2$SO$_4$ (46.37 g, 326.5 mmol), K$_2$CO$_3$ (45.12 g, 326.5 mmol) and Cu (6.22 g, 97.9 mmol) were added into the round bottom flask, and the mixture was stirred at 200° C. After the completion of the reaction, nitrobenzene from the reaction product was removed by distillation and the reaction product was extracted with CH$_2$Cl$_2$ and water. The extracted organic layer was dried over MgSO$_4$ and concentrated. The concentrated resultant was separated by silica gel column chromatography, and was then recrystallized, whereby a compound Sub 1-III-1 was obtained in an amount of 76.78 g in 73% yield.

(4) Synthesis of Sub 1-IV-1

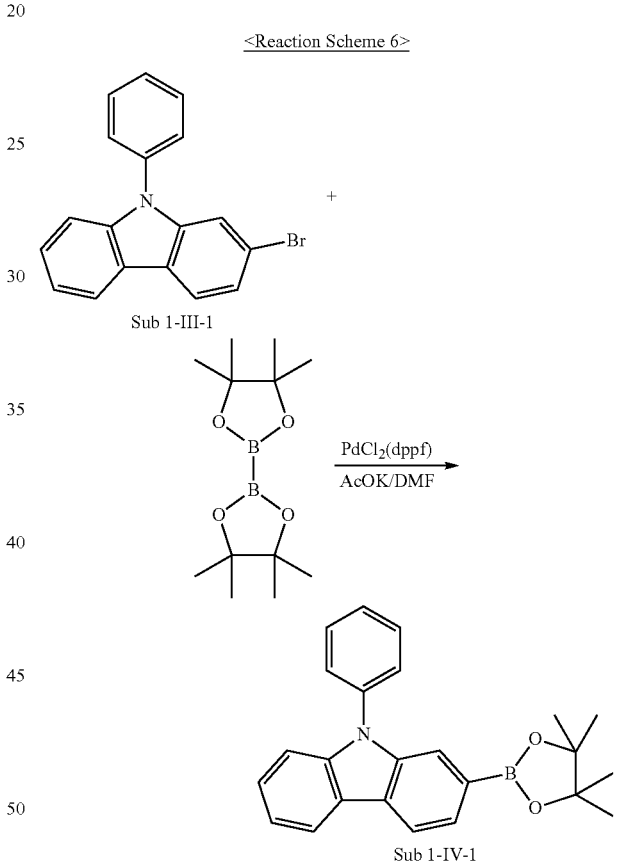

The compound Sub 11-III-1 (76.78 g, 238.3 mmol) obtained above was dissolved in DMF in a round bottom flask. Then, Bis(pinacolato)diboron (66.57 g, 262.1 mmol), Pd(dppf)Cl2 (5.84 g, 7.1 mmol) and KOAc (70.16 g, 714.9 mmol) were added into the round bottom flask, and the mixture was stirred at 90° C. After the completion of the reaction, DMF from the reaction product was removed by distillation and the reaction product was extracted with CH$_2$Cl$_2$ and water. The extracted organic layer was dried over MgSO$_4$ and concentrated. The concentrated resultant was separated by silica gel column chromatography, and was then recrystallized, whereby a compound Sub 1-IV-1 was obtained in an amount of 73.92 g in 84% yield.

(5) Synthesis of Sub 1-1

<Reaction Scheme 7>

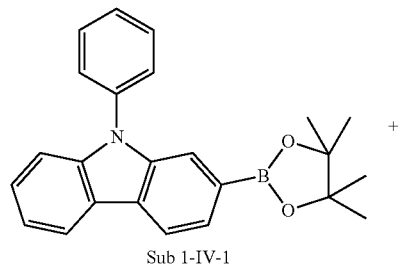

Sub 1-IV-1

+

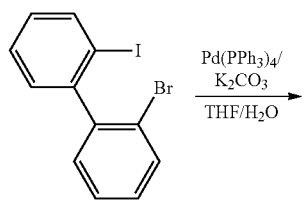

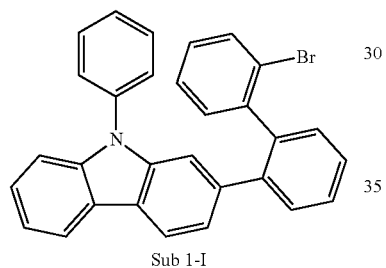

Sub 1-I

The compound Sub 1-IV-1 (73.92 g, 200.2 mmol) obtained above was dissolved in THF (880 ml) in a round bottom flask. Then, 2-bromo-2'-iodo-1,1'-biphenyl (108 g, 300.3 mmol), Pd(PPh$_3$)$_4$ (11.6 g, 10 mmol), K$_2$CO$_3$ (83 g, 600.6 mmol) and water (440 mL) were added into the round bottom flask, and the mixture was stirred at 80° C. After the completion of the reaction, the reaction product was extracted with CH$_2$Cl$_2$ and water. The extracted organic layer was dried over MgSO$_4$ and concentrated. The concentrated resultant was separated by silica gel column chromatography, and was then recrystallized, whereby a compound Sub 1-1 was obtained in an amount of 63.6 g in 67% yield.

2. Synthesis Examples of Sub 1-7

(1) Synthesis of Sub 1-I-7

<Reaction Scheme 8>

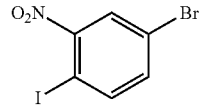

+

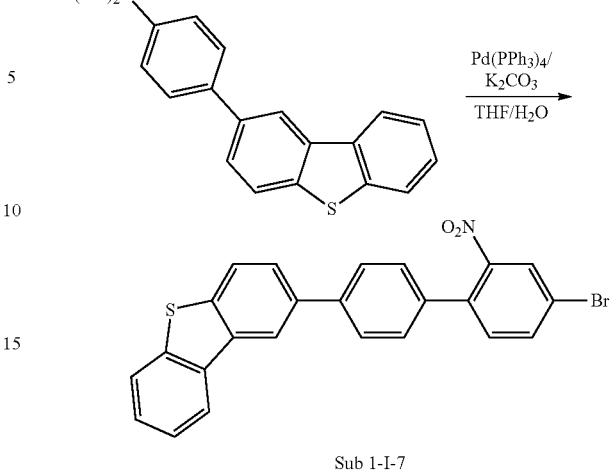

Sub 1-I-7

The compound Sub 1-I-7 was synthesized by using (4-(dibenzo[b,d]thiophen-2-yl)phenyl)boronic acid (95.8 g, 315.1 mmol), THF (1390 ml), 4-bromo-1-iodo-2-nitrobenzene (155 g, 472.7 mmol), Pd(PPh$_3$)$_4$ (18.2 g, 15.8 mmol), K$_2$CO$_3$ (130.7 g, 945.3 mmol) and water (695 ml) in the same manner as described in the synthesis method of the compound Sub 1-I-1 above, whereby a compound Sub 1-I-7 was obtained in an amount of 103 g in 71% yield.

(2) Synthesis of Sub 1-II-7

<Reaction Scheme 9>

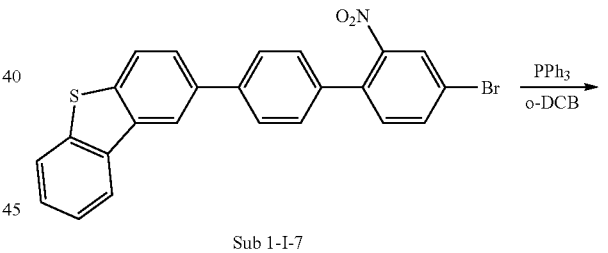

Sub 1-I-7

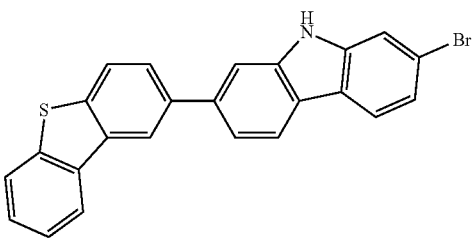

Sub 1-II-7

The compound Sub 1-II-7 was synthesized by using Sub 1-I-7 (103 g, 223.7 mmol), o-dichlorobenzene (917 ml), and triphenylphosphine (146.7 g, 559.3 mmol) in the same manner as described in the synthesis method of the compound Sub 1-II-1 above, whereby a compound Sub 1-II-7 was obtained in an amount of 69 g in 72% yield.

(3) Synthesis of Sub 1-III-7

<Reaction Scheme 10>

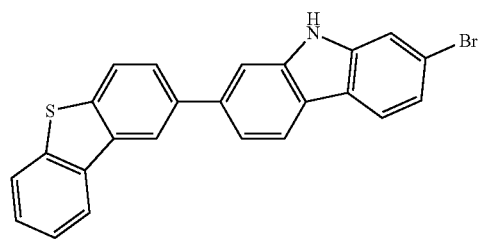

Sub 1-II-7

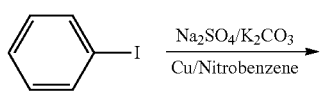

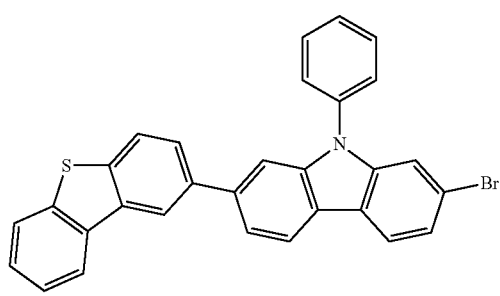

Sub 1-III-7

The compound Sub 1-III-7 was synthesized by using Sub 1-II-7 (69 g, 161.1 mmol), nitrobenzene (322 ml), iodobenzene (49.4 g, 242 mmol), Na$_2$SO$_4$ (22.9 g, 161.1 mmol), K$_2$CO$_3$ (22.3 g, 161.1 mmol) and Cu (3.1 g, 48.3 mmol) in the same manner as described in the synthesis method of the compound Sub 1-III-1 above, whereby a compound Sub 1-III-7 was obtained in an amount of 57 g in 70% yield.

(4) Synthesis of Sub 1-IV-7

<Reaction Scheme 11>

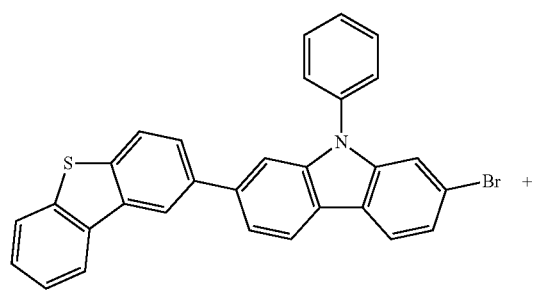

Sub 1-III-7

-continued

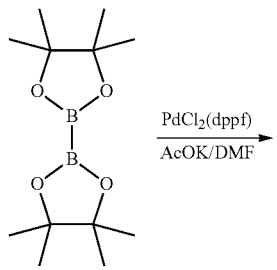

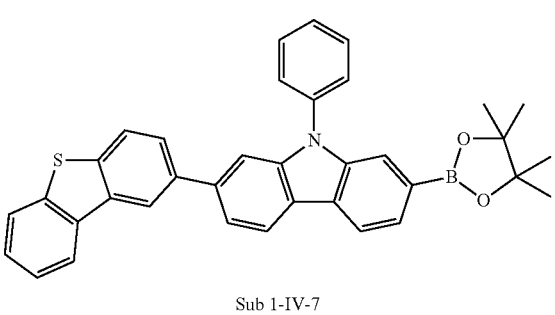

Sub 1-IV-7

The compound Sub 1-IV-7 was synthesized by using Sub 1-III-7 (57 g, 113 mmol), DMF (712 ml), Bis(pinacolato)diboron (31.6 g, 124.3 mmol), Pd(dppf)Cl$_2$ (2.8 g, 3.4 mmol) and KOAc (33.3 g, 339 mmol) in the same manner as described in the synthesis method of the compound Sub 1-IV-1 above, whereby a compound Sub 1-IV-7 was obtained in an amount of 49.2 g in 79% yield.

(5) Synthesis of Sub 1-7

<Reaction Scheme 12>

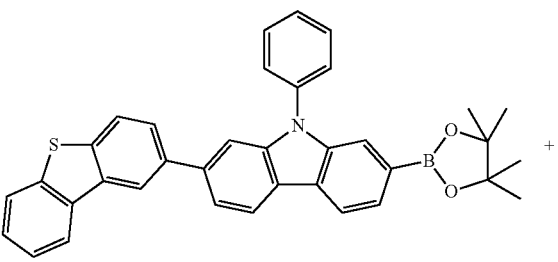

Sub 1-IV-7

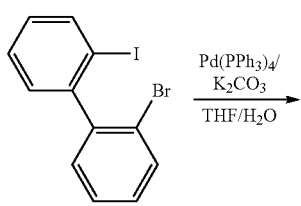

-continued

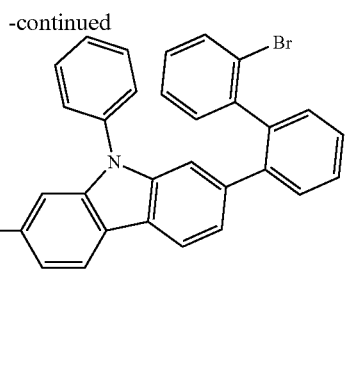

Sub 1-7

The compound Sub 1-7 was synthesized by using Sub 1-IV-7 (49.2 g, 89.2 mmol), 2-bromo-2'-iodo-1,1'-biphenyl (48.1 g, 134 mmol), Pd(PPh$_3$)$_4$ (5.2 g, 4.5 mmol), K$_2$CO$_3$ (37 g, 268 mmol), THF (392 ml) and water (196 ml) in the same manner as described in the synthesis method of the compound Sub 1-1 above, whereby a compound Sub 1-7 was obtained in an amount of 40.4 g in 69% yield.

3. Synthesis Examples of Sub 1-13

(1) Synthesis of Sub 1-III-13

<Reaction Scheme 13>

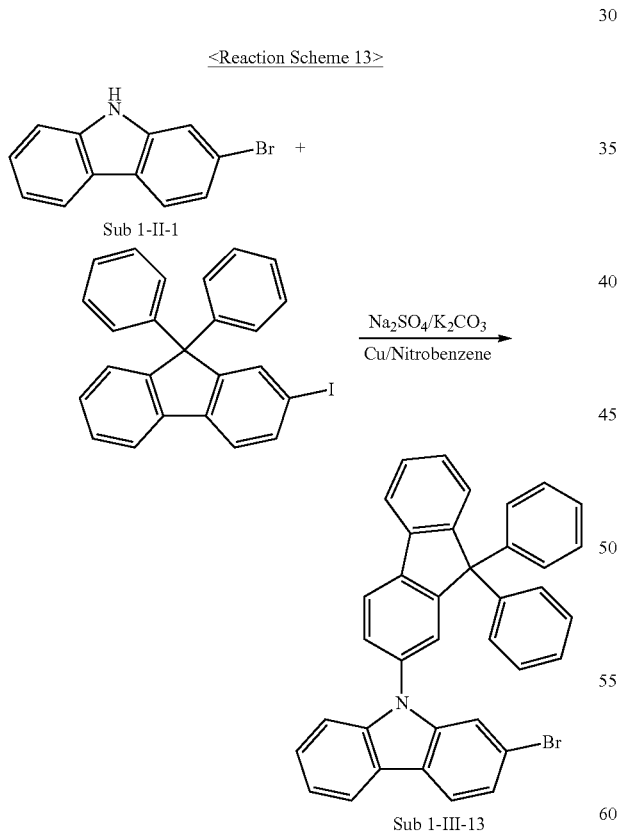

Sub 1-III-13

The compound Sub 1-III-13 was synthesized by using Sub 1-II-1 (70 g, 284.4 mmol), nitrobenzene (570 ml), 2-iodo-9,9-diphenyl-9H-fluorene (189.6 g, 426.7 mmol), Na$_2$SO$_4$ (40.4 g, 284.4 mmol), K$_2$CO$_3$ (39.3 g, 284.4 mmol) and Cu (5.42 g, 85.3 mmol) in the same manner as described in the synthesis method of the compound Sub 1-III-1 above, whereby a compound Sub 1-III-13 was obtained in an amount of 108.8 g in 68% yield.

(2) Synthesis of Sub 1-IV-13

<Reaction Scheme 14>

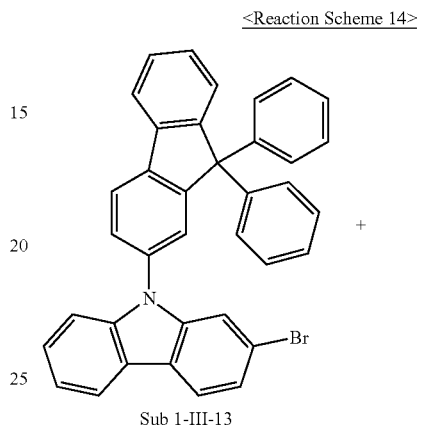

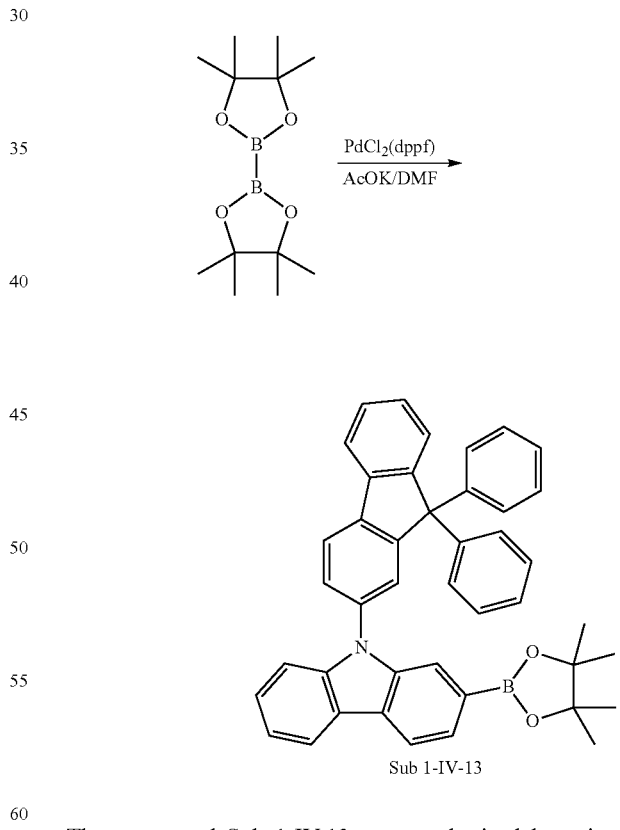

Sub 1-IV-13

The compound Sub 1-IV-13 was synthesized by using (108.8 g, 193.4 mmol), DMF (1220 ml), Bis(pinacolato)diboron (54.0 g, 212.76 mmol), Pd(dppf)Cl$_2$ (4.73 g, 5.8 mmol) and KOAc (56.94 g, 580.3 mmol) in the same manner as described in the synthesis method of the compound Sub 1-IV-1 above, whereby a compound Sub 1-IV-13 was obtained in an amount of 86.1 g in 73% yield.

(3) Synthesis of Sub 1-13

<Reaction Scheme 15>

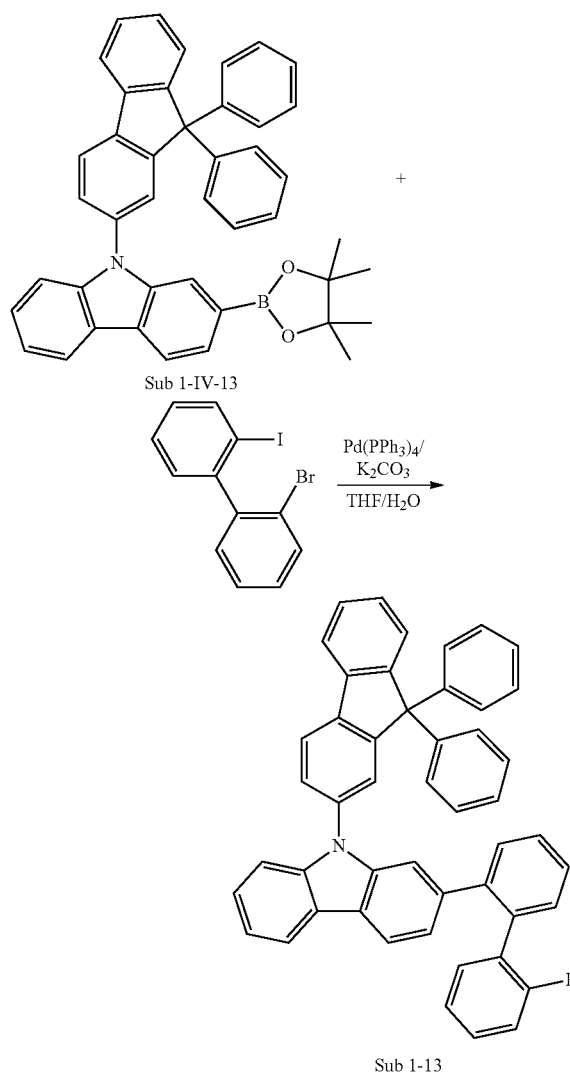

The compound Sub 1-13 was synthesized by using Sub 1-IV-13 (86.1 g, 141.2 mmol), THF (620 ml), 2-bromo-2'-iodo-1,1'-biphenyl (76.1 g, 211.9 mmol), Pd(PPh$_3$)$_4$ (8.2 g, 7.06 mmol), K$_2$CO$_3$ (58.6 g, 423.7 mmol) and water (310 ml) in the same manner as described in the synthesis method of the compound Sub 1-1 above, whereby a compound Sub 1-13 was obtained in an amount of 68.6 g in 68% yield.

4. Synthesis of Sub 1-14

(1) Synthesis of Sub 1-III-14

<Reaction Scheme 16>

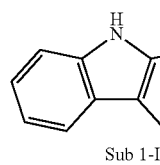

Sub 1-II-1

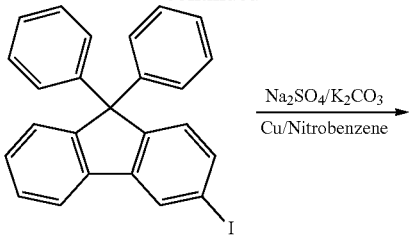

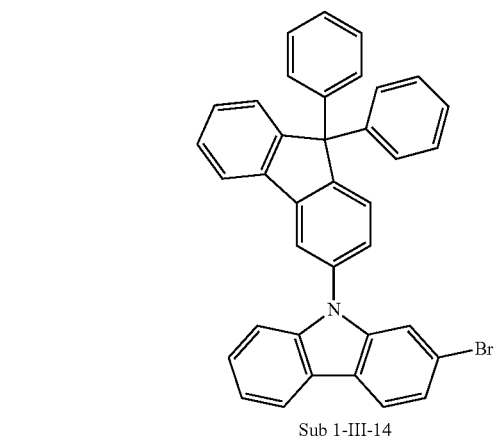

Sub 1-III-14

The compound Sub 1-III-14 was synthesized by using Sub 1-II-1 (63 g, 255.9 mmol), nitrobenzene (512 ml), 3-iodo-9,9-diphenyl-9H-fluorene (170.6 g, 383.9 mmol), Na$_2$SO$_4$ (36.4 g, 256 mmol), K$_2$CO$_3$ (35.4 g, 256 mmol) and Cu (4.88 g, 76.8 mmol) in the same manner as described in the synthesis method of the compound Sub 1-III-1 above, whereby a compound Sub 1-III-14 was obtained in an amount of 99.3 g in 69% yield.

(2) Synthesis of Sub 1-IV-14

<Reaction Scheme 17>

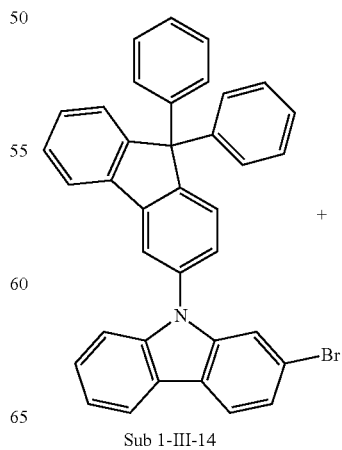

Sub 1-III-14

-continued

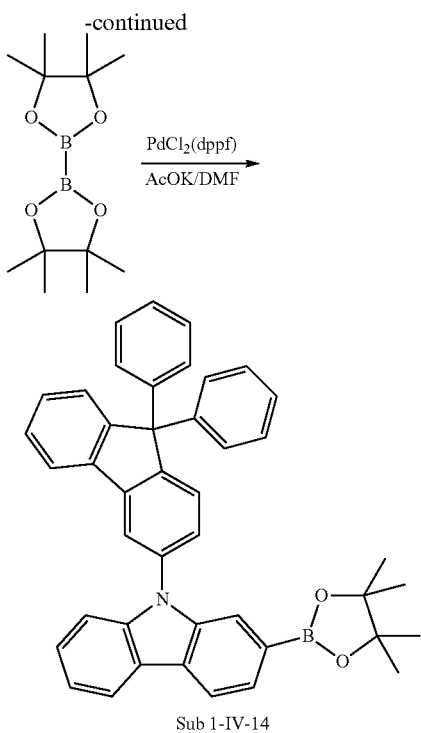

Sub 1-IV-14

The compound Sub 1-IV-14 was synthesized by using Sub 1-III-14 (99.3 g, 193.4 mmol), DMF (1110 ml), Bis(pinacolato)diboron (49.3 g, 194.2 mmol), Pd(dppf)Cl₂ (4.32 g, 5.3 mmol) and KOAc (52 g, 529.6 mmol) in the same manner as described in the synthesis method of the compound Sub 1-IV-1 above, whereby a compound Sub 1-IV-14 was obtained in an amount of 80.7 g in 75% yield.

(3) Synthesis of Sub 1-14

<Reaction Scheme 18>

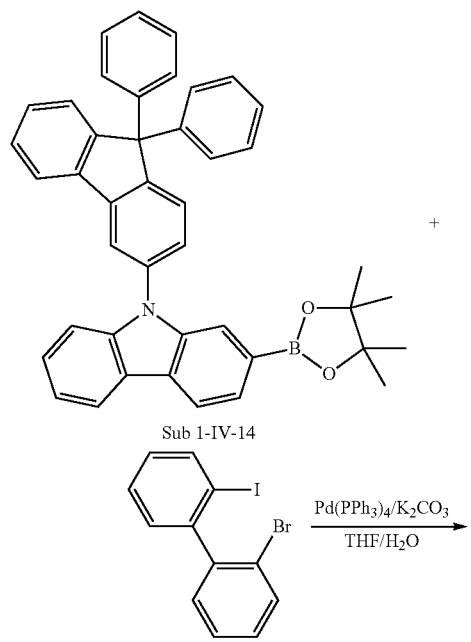

-continued

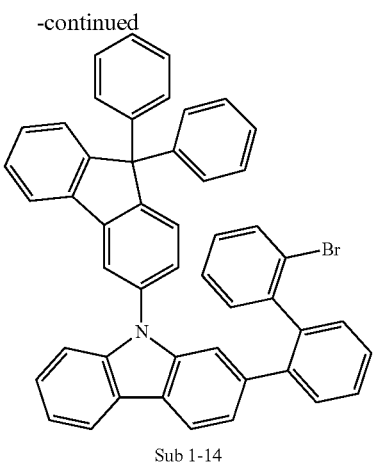

Sub 1-14

The compound Sub 1-14 was synthesized by using Sub 1-IV-14 (80.7 g, 132.3 mmol), THF (582 ml), 2-bromo-2'-iodo-1,1'-biphenyl (71.3 g, 198.6 mmol), Pd(PPh₃)₄ (7.65 g, 6.62 mmol), K₂CO₃ (54.9 g, 397.2 mmol) and water (291 ml) in the same manner as described in the synthesis method of the compound Sub 1-1 above, whereby a compound Sub 1-14 was obtained in an amount of 62.4 g in 66% yield.

5. Synthesis of Sub 1-17

(1) Synthesis of Sub 1-III-17

<Reaction Scheme 19>

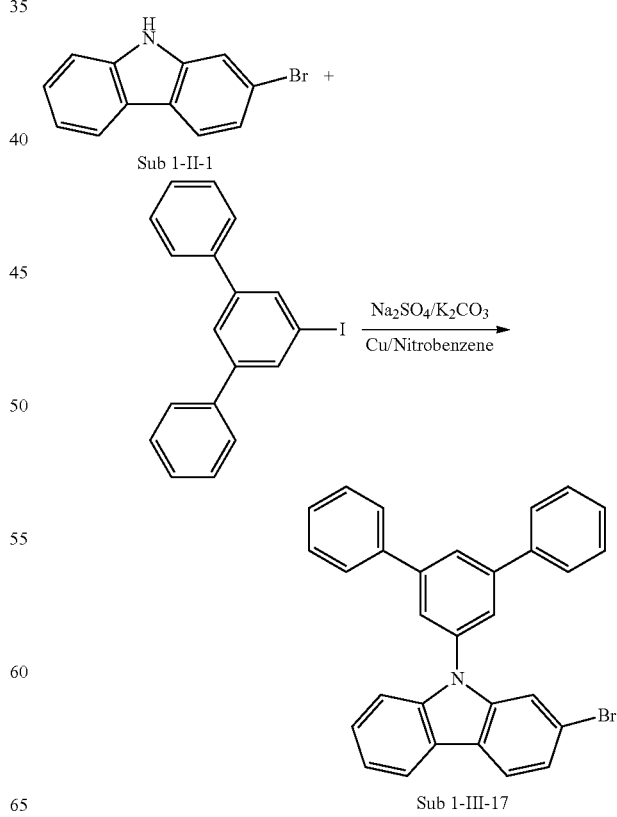

The compound Sub 1-III-17 was synthesized by using Sub 1-II-1 (60 g, 244 mmol), nitrobenzene (487 ml), 5'-iodo-1,1':3',1''-terphenyl (130.3 g, 365.7 mmol), Na₂SO₄ (34.6 g, 244 mmol), K₂CO₃ (33.7 g, 244 mmol) and Cu (4.65 g, 73.1 mmol) in the same manner as described in the synthesis method of the compound Sub 1-III-1 above, whereby a compound Sub 1-III-17 was obtained in an amount of 82.1 g in 71% yield.

(2) Synthesis of Sub 1-IV-17

<Reaction Scheme 20>

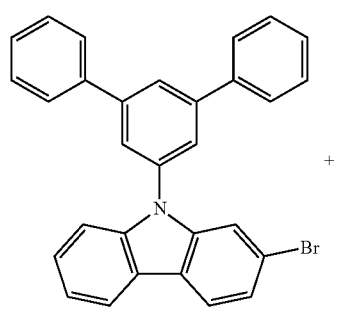

Sub 1-III-17

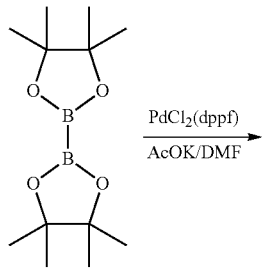

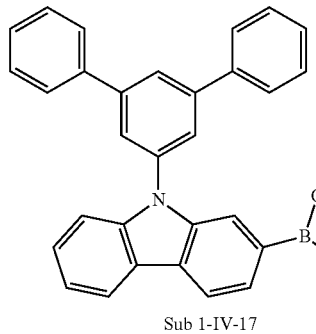

Sub 1-IV-17

The compound Sub 1-IV-17 was synthesized by using Sub 1-III-17 (82.1 g, 173.1 mmol), DMF (1090 ml), Bis(pinacolato)diboron (48.3 g, 190.4 mmol), Pd(dppf)Cl₂ (4.24 g, 5.2 mmol) and KOAc (51 g, 519.2 mmol) in the same manner as described in the synthesis method of the compound Sub 1-IV-1 above, whereby a compound Sub 1-IV-17 was obtained in an amount of 65.9 g in 73% yield.

(3) Synthesis of Sub 1-17

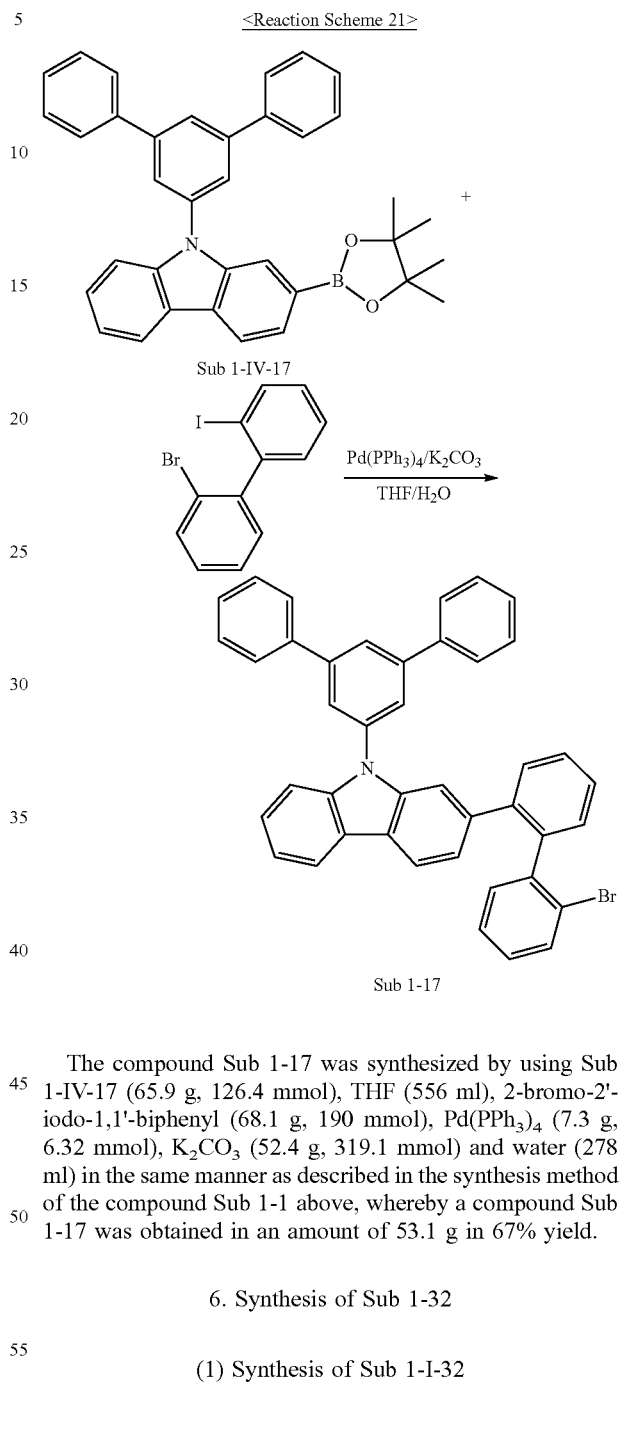

The compound Sub 1-17 was synthesized by using Sub 1-IV-17 (65.9 g, 126.4 mmol), THF (556 ml), 2-bromo-2'-iodo-1,1'-biphenyl (68.1 g, 190 mmol), Pd(PPh₃)₄ (7.3 g, 6.32 mmol), K₂CO₃ (52.4 g, 319.1 mmol) and water (278 ml) in the same manner as described in the synthesis method of the compound Sub 1-1 above, whereby a compound Sub 1-17 was obtained in an amount of 53.1 g in 67% yield.

6. Synthesis of Sub 1-32

(1) Synthesis of Sub 1-I-32

<Reaction Scheme 22>

(3) Synthesis of Sub 1-III-32

<Reaction Scheme 24>

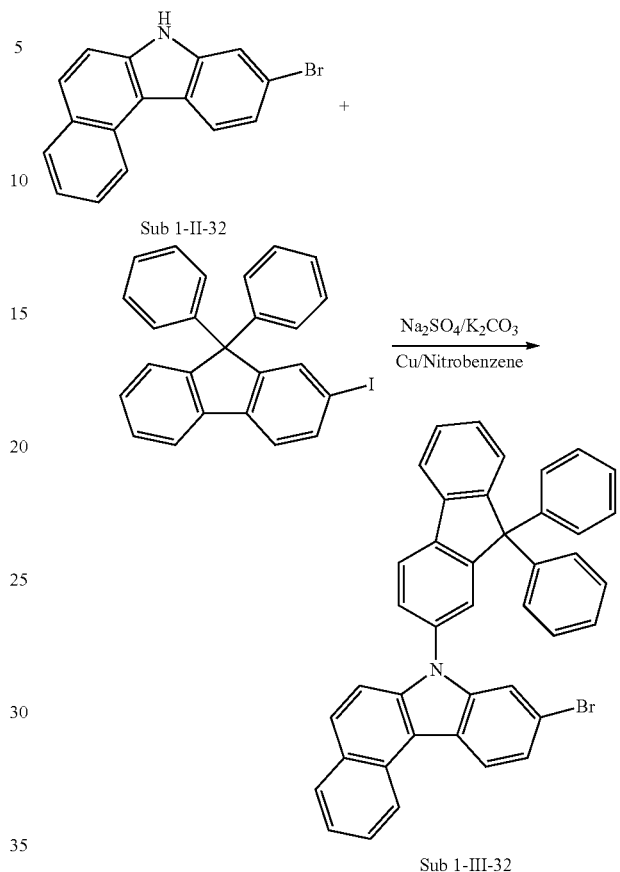

The compound Sub 1-III-32 was synthesized by using Sub 1-II-32 (61.2 g, 206.6 mmol), nitrobenzene (413 ml), 2-iodo-9,9-diphenyl-9H-fluorene (137.7 g, 310 mmol), Na$_2$SO$_4$ (29.35 g, 206.6 mmol), K$_2$CO$_3$ (28.6 g, 206.6 mmol) and Cu (3.9 g, 62 mmol) in the same manner as described in the synthesis method of the compound Sub 1-III-1 above, whereby a compound Sub 1-III-32 was obtained in an amount of 89.86 g in 71% yield.

(4) Synthesis of Sub 1-IV-32

<Reaction Scheme 25>

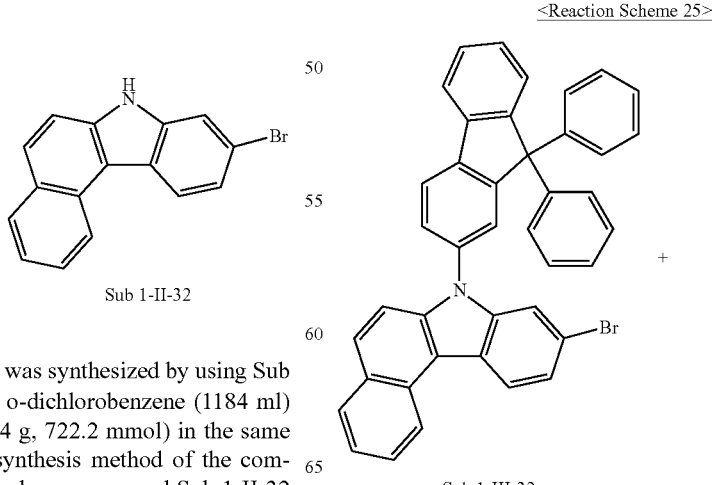

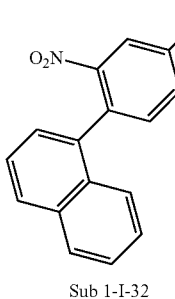

Sub 1-I-32

The compound Sub 1-I-32 was synthesized by using naphthalen-1-ylboronic acid (70 g, 407 mmol), THF (1790 ml), 4-bromo-1-iodo-2-nitrobenzene (200 g, 610.5 mmol), Pd(PPh$_3$)$_4$ (23.5 g, 20.35 mmol), K$_2$CO$_3$ (168.8 g, 1221 mmol) and water (895 ml) in the same manner as described in the synthesis method of the compound Sub 1-I-1 above, whereby a compound Sub 1-I-32 was obtained in an amount of 94.8 g in 71% yield.

(2) Synthesis of Sub 1-II-32

<Reaction Scheme 23>

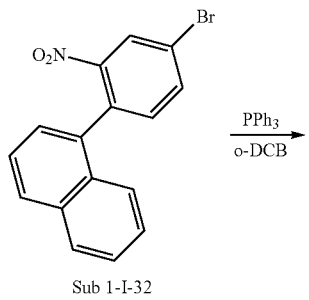

The compound Sub 1-II-32 was synthesized by using Sub 1-I-32 (94.8 g, 288.9 mmol), o-dichlorobenzene (1184 ml) and triphenylphosphine (189.4 g, 722.2 mmol) in the same manner as described in the synthesis method of the compound Sub 1-II-1 above, whereby a compound Sub 1-II-32 was obtained in an amount of 61.2 g in 75% yield.

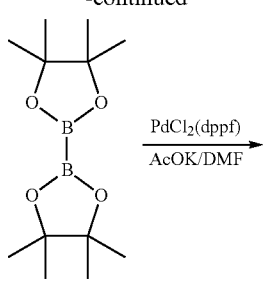

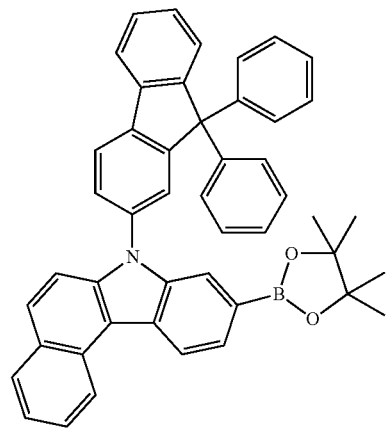

Sub 1-IV-32

The compound Sub 1-IV-32 was synthesized by using Sub 1-III-32 (89.86 g, 146.7 mmol), DMF (924 ml), Bis(pinacolato)diboron (41 g, 161.4 mmol), Pd(dppf)Cl$_2$ (3.59 g, 4.4 mmol) and KOAc (43.2 g, 440.1 mmol) in the same manner as described in the synthesis method of the compound Sub 1-IV-1 above, whereby a compound Sub 1-IV-32 was obtained in an amount of 74.5 g in 77% yield.

(5) Synthesis of Sub 1-32

<Reaction Scheme 26>

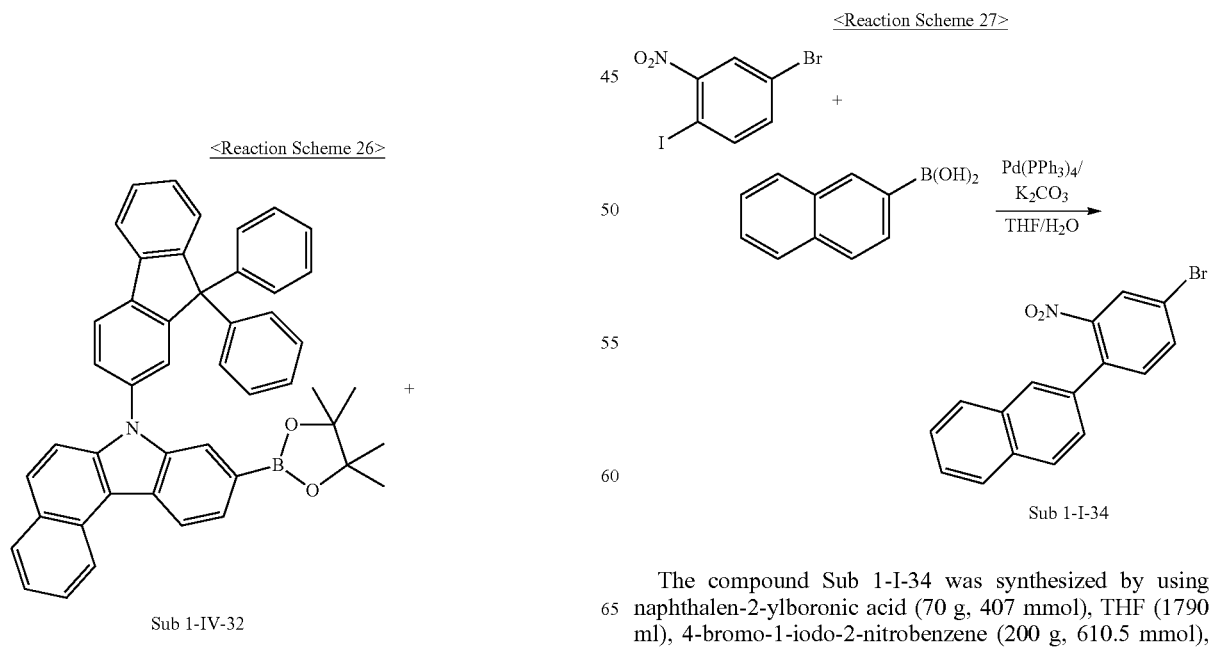

Sub 1-IV-32

Sub 1-32

The compound Sub 1-32 was synthesized by using Sub 1-IV-32 (74.5 g, 112.9 mmol), THF (496 ml), 2-bromo-2'-iodo-1,1'-biphenyl (60.8 g, 169.4 mmol), Pd(PPh$_3$)$_4$ (6.53 g, 5.65 mmol), K$_2$CO$_3$ (46.8 g, 338.8 mmol) and water (248 ml) in the same manner as described in the synthesis method of the compound Sub 1-1 above, whereby a compound Sub 1-32 was obtained in an amount of 59.6 g in 69% yield.

7. Synthesis of 1-34

(1) Synthesis of Sub 1-I-34

<Reaction Scheme 27>

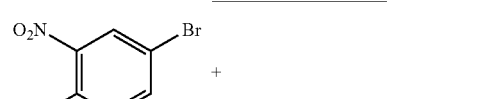

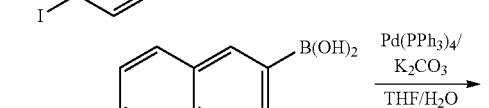

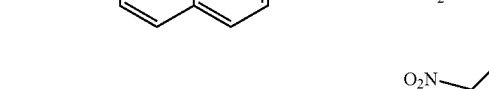

Sub 1-I-34

The compound Sub 1-I-34 was synthesized by using naphthalen-2-ylboronic acid (70 g, 407 mmol), THF (1790 ml), 4-bromo-1-iodo-2-nitrobenzene (200 g, 610.5 mmol), Pd(PPh$_3$)$_4$ (23.5 g, 20.35 mmol), K$_2$CO$_3$ (168.8 g, 1221 mmol) and water (895 ml) in the same manner as described in the synthesis method of the compound Sub 1-I-1 above, whereby a compound Sub 1-I-34 was obtained in an amount of 97.5 g in 73% yield.

(2) Synthesis of Sub 1-II-34

<Reaction Scheme 28>

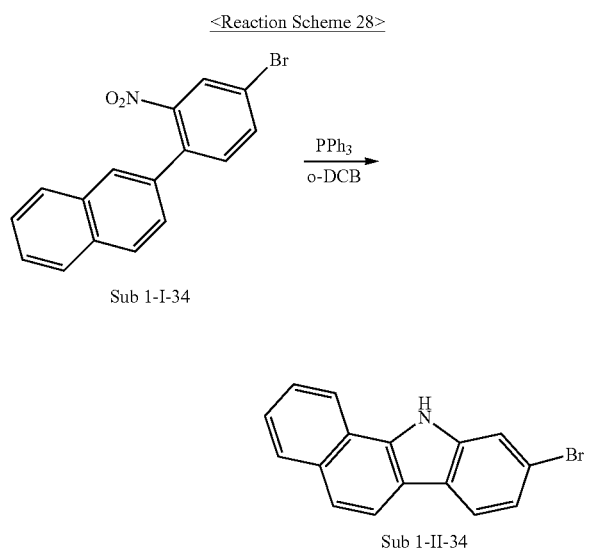

Sub 1-I-34

Sub 1-II-34

The compound Sub 1-II-34 was synthesized by using Sub 1-I-34 (97.5 g, 297.1 mmol), o-dichlorobenzene (1220 ml) and triphenylphosphine (194.8 g, 742.8 mmol) in the same manner as described in the synthesis method of the compound Sub 1-II-1 above, whereby a compound Sub 1-II-34 was obtained in an amount of 65.1 g in 74% yield.

(3) Synthesis of Sub 1-III-34

<Reaction Scheme 29>

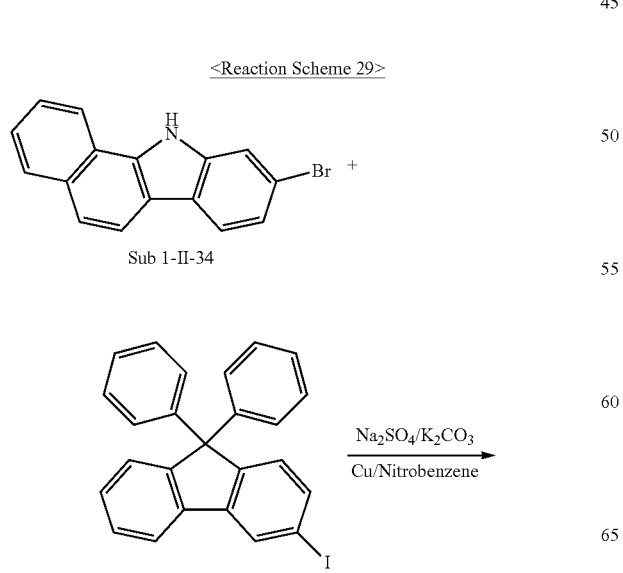

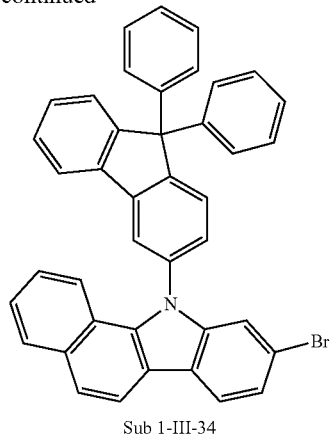

Sub 1-III-34

The compound Sub 1-III-34 was synthesized by using Sub 1-II-34 (65.1 g, 220 mmol), nitrobenzene (440 ml), 3-iodo-9,9-diphenyl-9H-fluorene (146.5 g, 330 mmol), Na$_2$SO$_4$ (31.2 g, 220 mmol), K$_2$CO$_3$ (30.4 g, 220 mmol) and Cu (4.2 g, 66 mmol) in the same manner as described in the synthesis method of the compound Sub 1-III-1 above, whereby a compound Sub 1-III-34 was obtained in an amount of 95.6 g in 71% yield.

(4) Synthesis of Sub 1-IV-34

<Reaction Scheme 30>

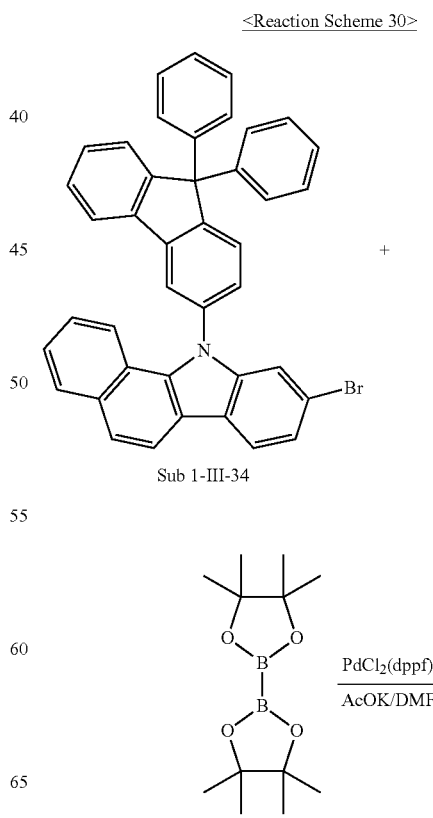

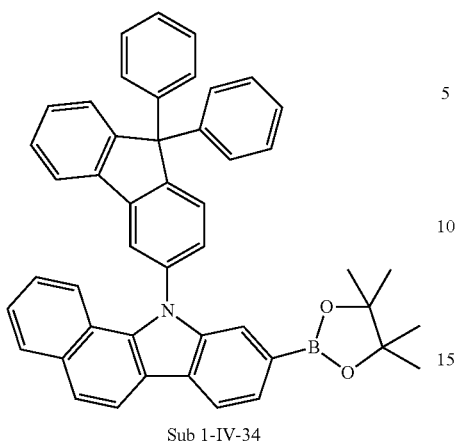

Sub 1-IV-34

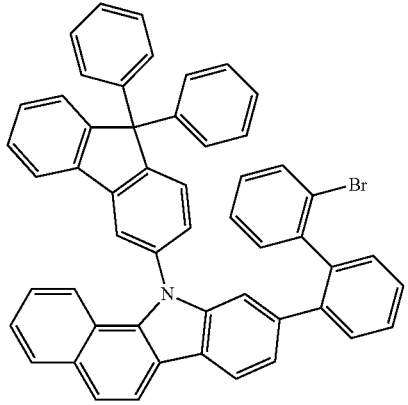

Sub 1-34

The compound Sub 1-IV-34 was synthesized by using Sub 1-III-34 (95.6 g, 156.1 mmol), DMF (980 ml)-Bis(pinacolato)diboron (43.6 g, 171.7 mmol), Pd(dppf)Cl$_2$ (3.82 g, 4.7 mmol) and KOAc (46 g, 468.2 mmol) in the same manner as described in the synthesis method of the compound Sub 1-IV-1 above, whereby a compound Sub 1-IV-34 was obtained in an amount of 77.2 g in 75% yield.

(5) Synthesis of Sub 1-34

The compound Sub 1-34 was synthesized by using Sub 1-IV-34 (77.2 g, 117 mmol), THF (510 ml), 2-bromo-2'-iodo-1,1'-biphenyl (63 g, 175.6 mmol), Pd(PPh$_3$)$_4$ (6.76 g, 5.85 mmol), K$_2$CO$_3$ (48.5 g, 351 mmol) and water (255 ml) in the same manner as described in the synthesis method of the compound Sub 1-1 above, whereby a compound Sub 1-34 was obtained in an amount of 58.2 g in 65% yield.

8. Synthesis of 1-35

(1) Synthesis of Sub 1-I-35

<Reaction Scheme 31>

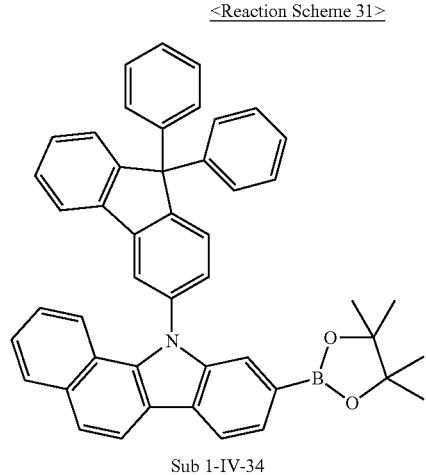

Sub 1-IV-34

+

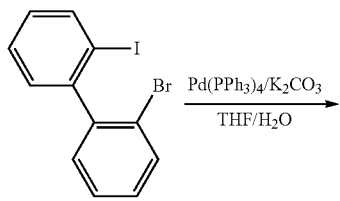

<Reaction Scheme 32>

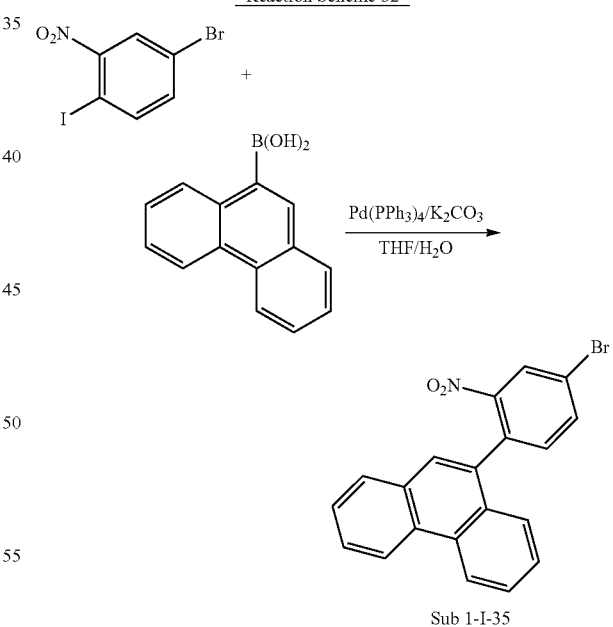

Sub 1-I-35

The compound Sub 1-I-35 was synthesized by using phenanthren-9-ylboronic acid (70 g, 315.2 mmol), THF (1388 ml), 4-bromo-1-iodo-2-nitrobenzene (155.1 g, 472.9 mmol), Pd(PPh$_3$)$_4$ (18.2 g, 15.8 mmol), K$_2$CO$_3$ (130.7 g, 945.7 mmol) and water (694 ml) in the same manner as described in the synthesis method of the compound Sub 1-I-1 above, whereby a compound Sub 1-I-35 was obtained in an amount of 85.8 g in 72% yield.

(2) Synthesis of Sub 1-II-35

<Reaction Scheme 33>

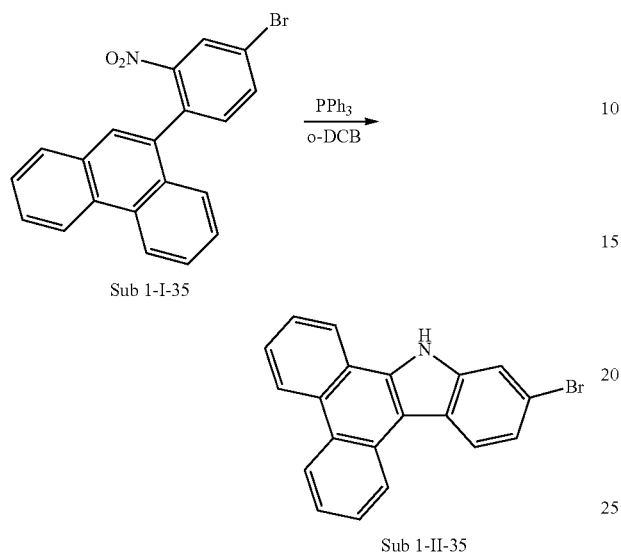

The compound Sub 1-II-35 was synthesized by using Sub 1-I-35 (85.8 g, 226.9 mmol), o-dichlorobenzene (930 ml) and triphenylphosphine (148.8 g, 567.1 mmol) in the same manner as described in the synthesis method of the compound Sub 1-II-1 above, whereby a compound Sub 1-II-35 was obtained in an amount of 60.5 g in 77% yield.

(3) Synthesis of Sub 1-III-35

<Reaction Scheme 34>

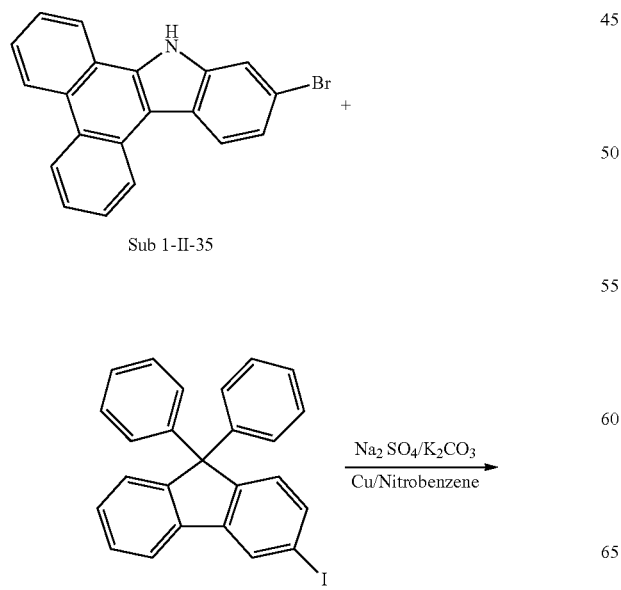

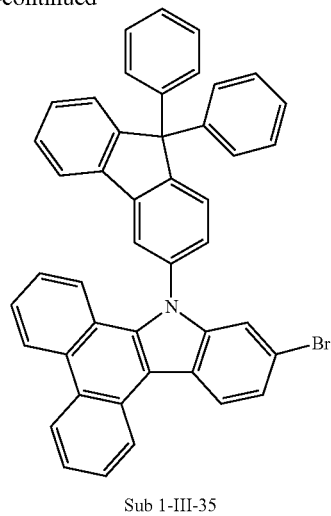

The compound Sub 1-III-35 was synthesized by using Sub 1-II-35 (60.5 g, 174.7 mmol), nitrobenzene (350 ml), 3-iodo-9,9-diphenyl-9H-fluorene (116.5 g, 262.1 mmol), $Na_2SO_4$ (24.8 g, 174.7 mmol), $K_2CO_3$ (24.2 g, 174.7 mmol) and Cu (3.33 g, 52.4 mmol) in the same manner as described in the synthesis method of the compound Sub 1-III-1 above, whereby a compound Sub 1-III-35 was obtained in an amount of 84.5 g in 73% yield.

(4) Synthesis of Sub 1-IV-35

<Reaction Scheme 35>

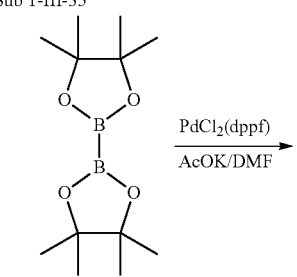

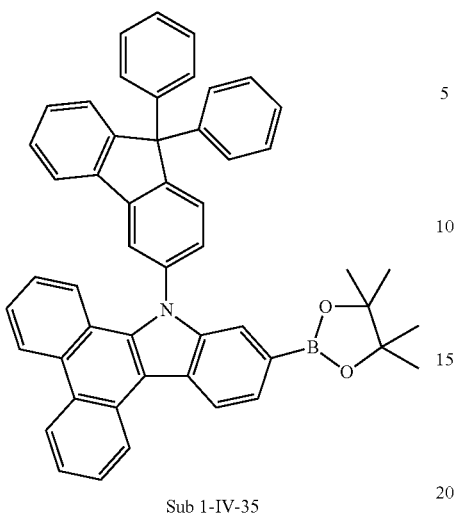

Sub 1-IV-35

The compound Sub 1-IV-35 was synthesized by using Sub 1-III-35 (84.5 g, 127.5 mmol), DMF (854 ml), Bis(pinacolato)diboron (35.6 g, 140.3 mmol), Pd(dppf)Cl₂ (3.12 g, 3.82 mmol) and KOAc (37.5 g, 382.5 mmol) in the same manner as described in the synthesis method of the compound Sub 1-IV-1 above, whereby a compound Sub 1-IV-35 was obtained in an amount of 70.6 g in 78% yield.

(5) Synthesis of Sub 1-35

<Reaction Scheme 36>

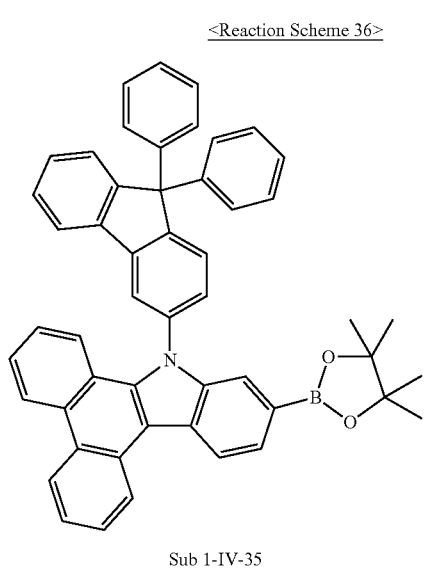

Sub 1-IV-35

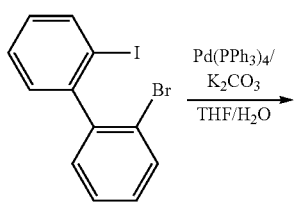

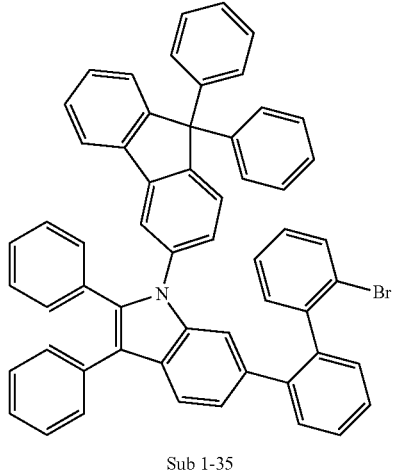

Sub 1-35

The compound Sub 1-35 was synthesized by using Sub 1-IV-35 (70.6 g, 99.5 mmol), THF (438 ml), 2-bromo-2'-iodo-1,1'-biphenyl (53.6 g, 149.2 mmol), Pd(PPh₃)₄ (5.75 g, 4.97 mmol), K₂CO₃ (41.2 g, 298.4 mmol) and water (219 ml) in the same manner as described in the synthesis method of the compound Sub 1-1 above, whereby a compound Sub 1-35 was obtained in an amount of 55.1 g in 68% yield.

9. Synthesis of Sub 1-44

(1) Synthesis of Sub 1-III-44

<Reaction Scheme 37>

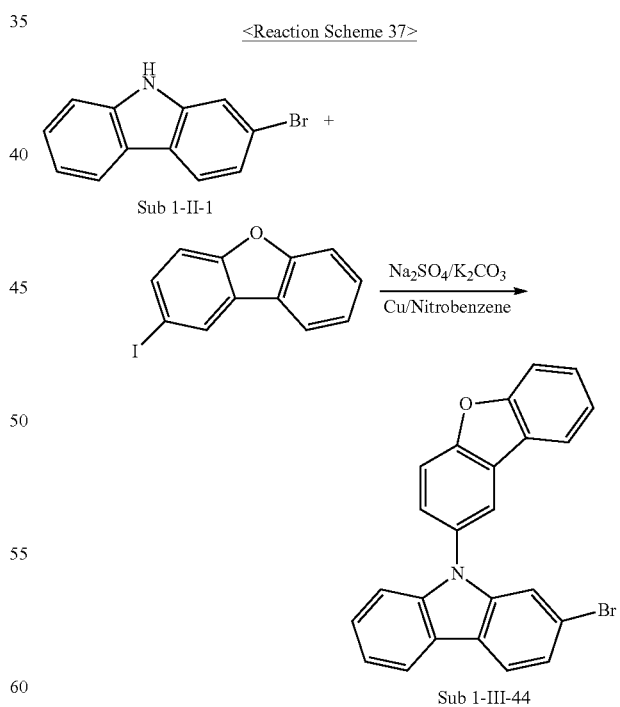

Sub 1-III-44

The compound Sub 1-III-44 was synthesized by using Sub 1-II-1 (60 g, 244 mmol), nitrobenzene (487 ml), 2-iododibenzo[b,d]furan (107.6 g, 365.7 mmol), Na₂SO₄ (34.6 g, 244 mmol), K₂CO₃ (33.7 g, 244 mmol) and Cu (4.65 g, 73.1 mmol) in the same manner as described in the synthesis method of the compound Sub 1-III-1 above, whereby a compound Sub 1-III-44 was obtained in an amount of 68.4 g in 68% yield.

(2) Synthesis of Sub 1-IV-44

<Reaction Scheme 38>

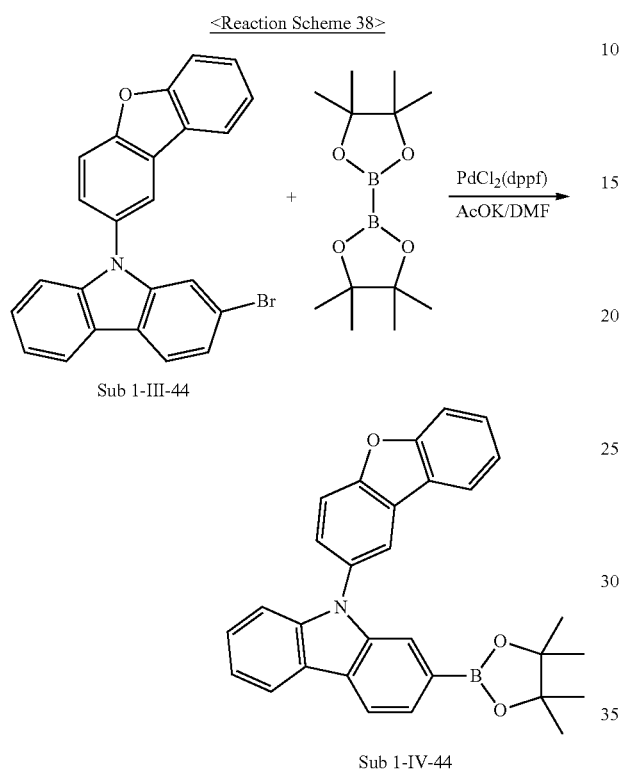

Sub 1-III-44

Sub 1-IV-44

The compound Sub 1-IV-44 was synthesized by using Sub 1-III-44 (68.4 g, 166 mmol), DMF (1045 ml), Bis(pinacolato)diboron (46.3 g, 182.5 mmol), Pd(dppf)Cl₂ (4.06 g, 5 mmol) and KOAc (48.8 g, 497.7 mmol) in the same manner as described in the synthesis method of the compound Sub 1-IV-1 above, whereby a compound Sub 1-IV-44 was obtained in an amount of 56.4 g in 74% yield.

(3) Synthesis of Sub 1-44

<Reaction Scheme 39>

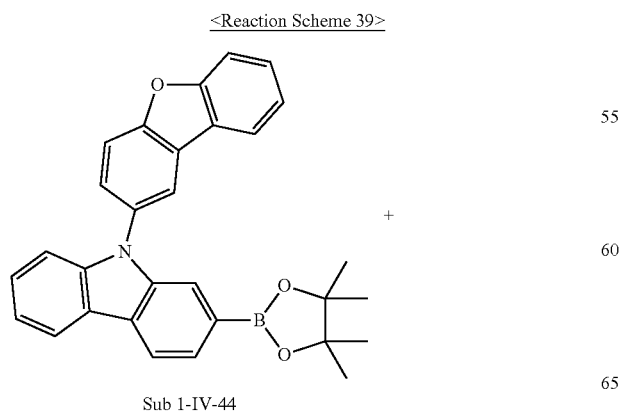

Sub 1-IV-44

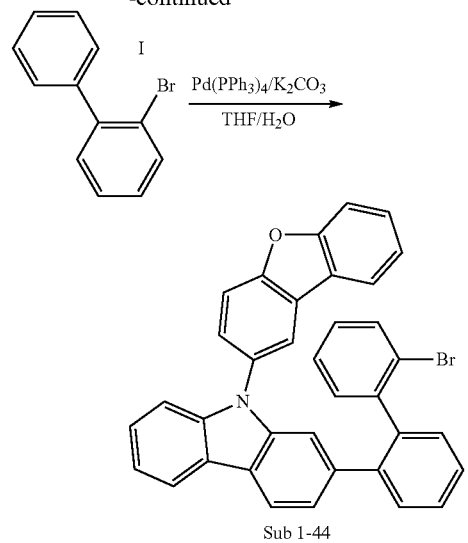

Sub 1-44

The compound Sub 1-44 was synthesized by using Sub 1-IV-44 (56.4 g, 122.8 mmol), THF (540 ml), 2-bromo-2'-iodo-1,1'-biphenyl (66.1 g, 184 mmol), Pd(PPh₃)₄ (7.1 g, 6.14 mmol), K₂CO₃ (50.9 g, 368.4 mmol) and water (270 ml) in the same manner as described in the synthesis method of the compound Sub 1-1 above, whereby a compound Sub 1-44 was obtained in an amount of 47.8 g in 69% yield.

10. Synthesis of Sub 1-54

(1) Synthesis of Sub 1-III-54

<Reaction Scheme 40>

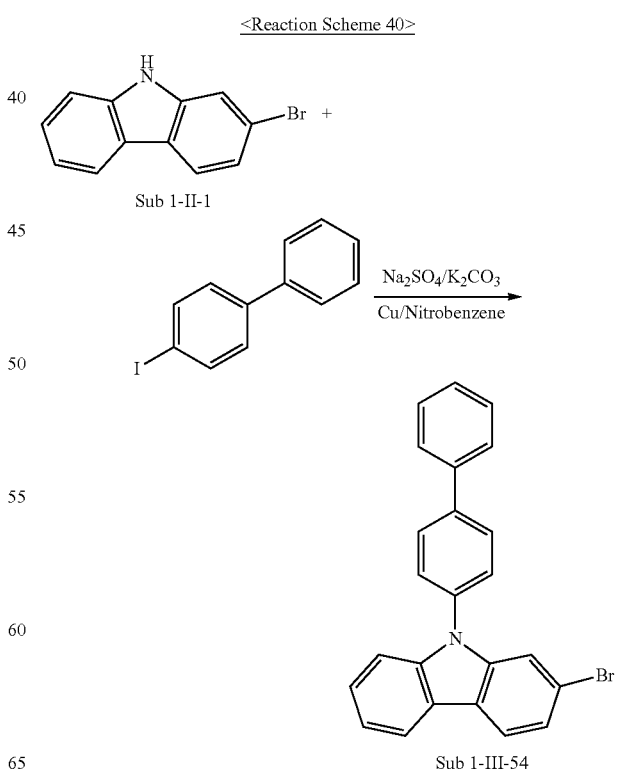

Sub 1-II-1

Sub 1-III-54

The compound Sub 1-III-54 was synthesized by using Sub 1-II-1 (50 g, 203.2 mmol), nitrobenzene (406 ml), 4-iodo-1,1'-biphenyl(85.4 g, 304.7 mmol), Na₂SO₄ (28.9 g, 203.2 mmol), K₂CO₃ (28.1 g, 203.2 mmol) and Cu (3.87 g, 61 mmol) in the same manner as described in the synthesis method of the compound Sub 1-III-1 above, whereby a compound Sub 1-III-54 was obtained in an amount of 54.2 g in 68% yield.

(2) Synthesis of Sub 1-IV-54

<Reaction Scheme 41>

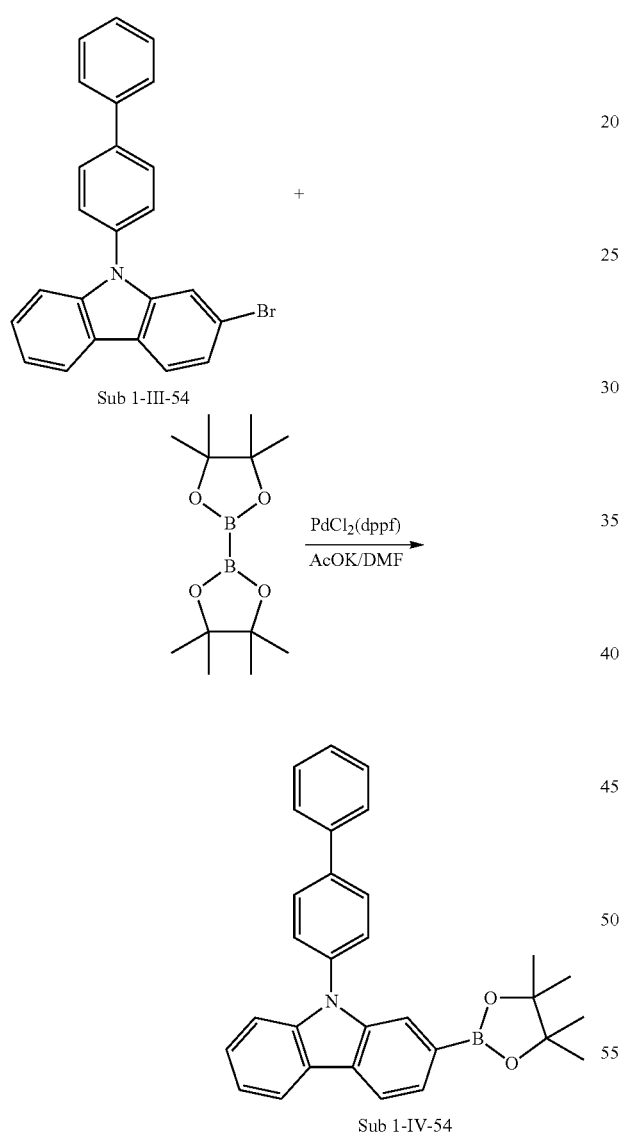

The compound Sub 1-IV-54 was synthesized by using Sub 1-III-54 (54.2 g, 136.1 mmol), DMF (857 ml), Bis(pinacolato)diboron (38.0 g, 150 mmol), Pd(dppf)Cl₂ (3.33 g, 4.1 mmol) and KOAc (40.1 g, 408 mmol) in the same manner as described in the synthesis method of the compound Sub 1-IV-1 above, whereby a compound Sub 1-IV-54 was obtained in an amount of 42.4 g in 70% yield.

(3) Synthesis of Sub 1-54

<Reaction Scheme 42>

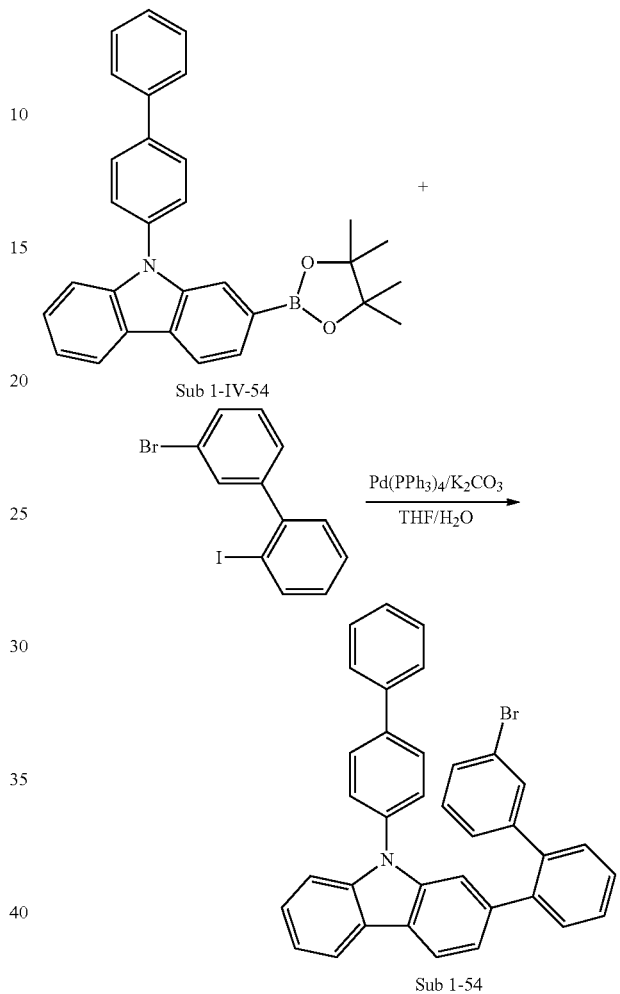

The compound Sub 1-54 was synthesized by using Sub 1-IV-54 (42.4 g, 95.2 mmol), THF (418 ml), 3'-bromo-2-iodo-1,1'-biphenyl (51.3 g, 142.8 mmol), Pd(PPh₃)₄ (5.5 g, 4.76 mmol), K₂CO₃ (39.5 g, 285.6 mmol) and water (209 ml) in the same manner as described in the synthesis method of the compound Sub 1-1 above, whereby a compound Sub 1-54 was obtained in an amount of 34.1 g in 65% yield.

11. Synthesis of Sub 1-117

(1) Synthesis of Sub 1-III-117

<Reaction Scheme 43>

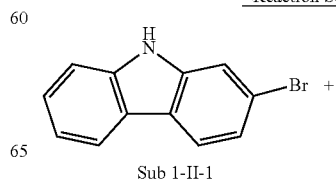

Sub 1-II-1

-continued

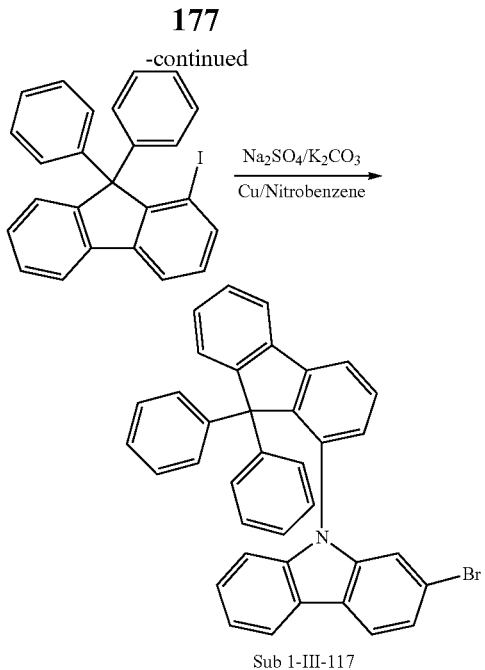

Sub 1-III-117

The compound Sub 1-III-117 was synthesized by using Sub 1-II-1 (50 g, 203.2 mmol), nitrobenzene (406 ml), 1-iodo-9,9-diphenyl-9H-fluorene (135.4 g, 305 mmol), Na$_2$SO$_4$ (28.9 g, 203.2 mmol), K$_2$CO$_3$ (28.1 g, 203.2 mmol) and Cu (3.87 g, 61 mmol) in the same manner as described in the synthesis method of the compound Sub 1-III-1 above, whereby a compound Sub 1-III-117 was obtained in an amount of 70.9 g in 62% yield.

(2) Synthesis of Sub 1-IV-117

-continued

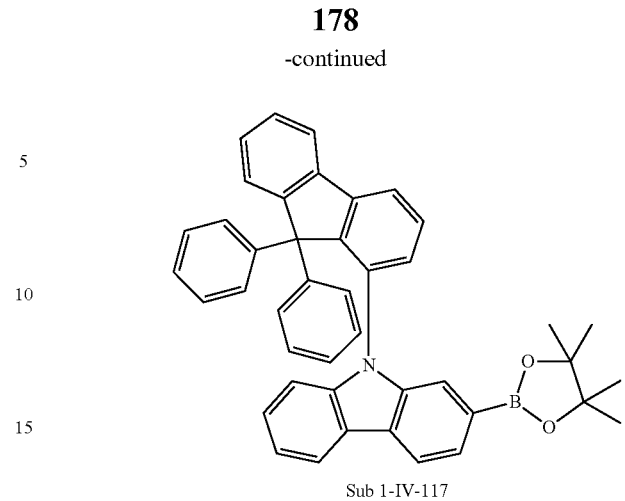

Sub 1-IV-117

The compound Sub 1-IV-117 was synthesized by using Sub 1-III-117 (70.9 g, 126 mmol), DMF (794 ml), Bis(pinacolato)diboron (35.2 g, 138.7 mmol), Pd(dppf)Cl$_2$ (3.09 g, 3.78 mmol) and KOAc (37.11 g, 378.1 mmol) in the same manner as described in the synthesis method of the compound Sub 1-IV-1 above, whereby a compound Sub 1-IV-117 was obtained in an amount of 51.5 g in 67% yield.

(3) Synthesis of Sub 1-117

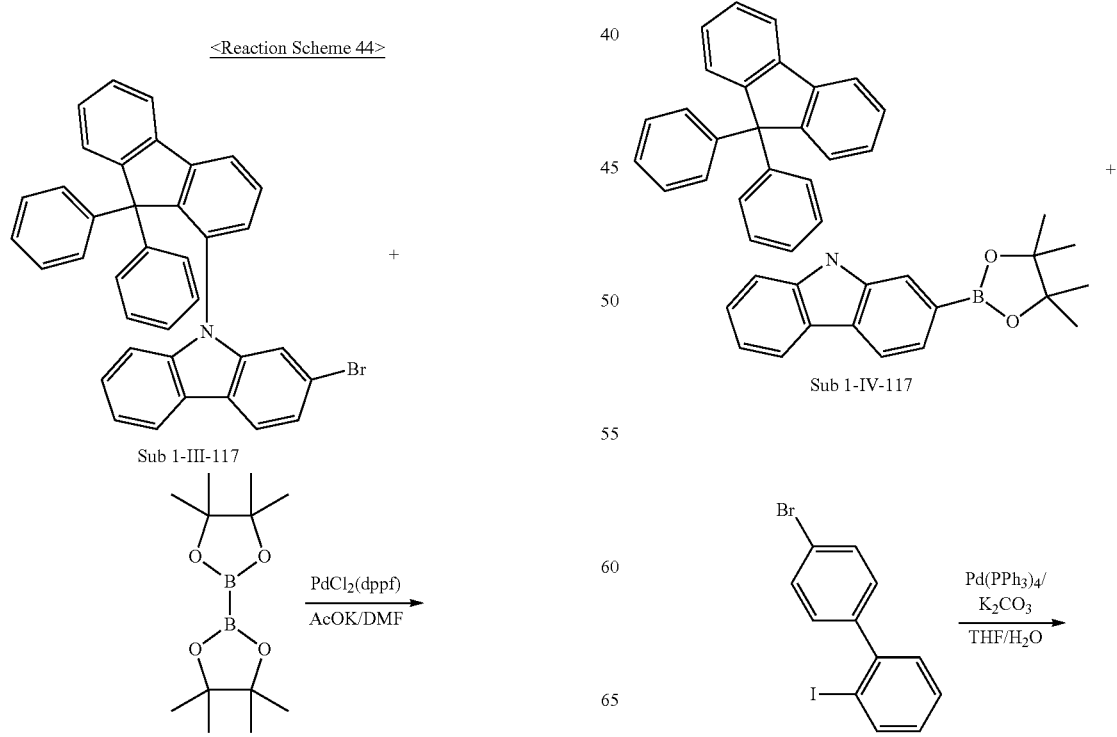

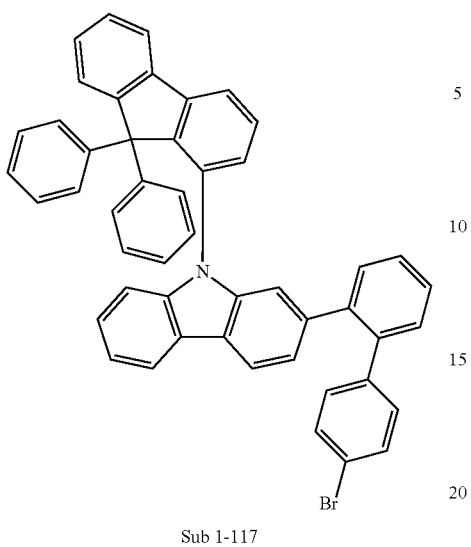

Sub 1-117

The compound Sub 1-117 was synthesized by using Sub 1-IV-117 (51.5 g, 84.5 mmol), THF (370 ml), 2-bromo-4'-iodo-1,1'-biphenyl (45.5 g, 126.7 mmol), Pd(PPh₃)₄ (4.88 g, 4.22 mmol), K₂CO₃ (35.03 g, 253.5 mmol) and water (185 ml) in the same manner as described in the synthesis method of the compound Sub 1-1 above, whereby a compound Sub 1-117 was obtained in an amount of 36.2 g in 60% yield.

(4) Synthesis of Sub 1-148

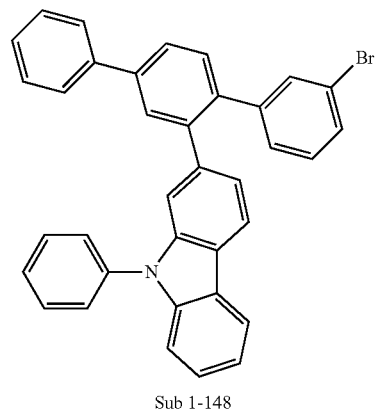

Sub 1-148

The compound Sub 1-148 was synthesized by using Sub 1-IV-1 (31.2 g, 84.5 mmol), THF 370 mL, 3-bromo-2'-iodo-1,1': 4',1''-terphenyl(55.1 g, 126.7 mmol), P$_d$(PPh₃)₄(4.88 g, 4.22 mmol), K₂CO₃ (35.03 g, 253.5 mmol) and water (185 mL) in the same manner as described in the synthesis method of the compound Sub 1-1 above, whereby a compound Sub 1-148 was obtained in an amount of 31.6 g in 68% yield.

Examples of Sub 1 compounds include, but are not limited to, the following compounds, and FD-MS (Field Desorption-Mass Spectrometry) data of the compounds are given in Table 1 below.

<Reaction Scheme 46>

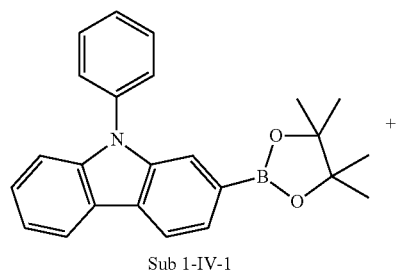

Sub 1-IV-1

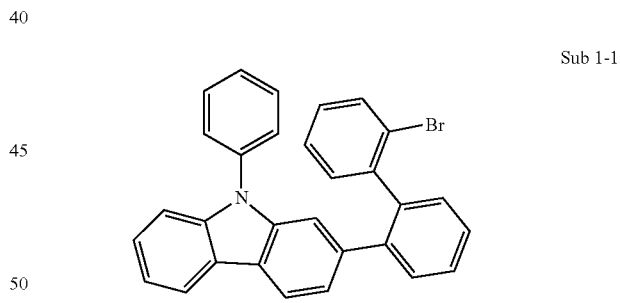

Sub 1-1

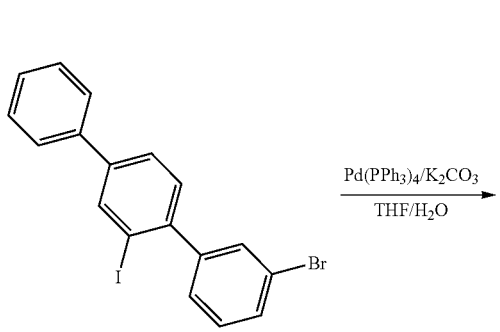

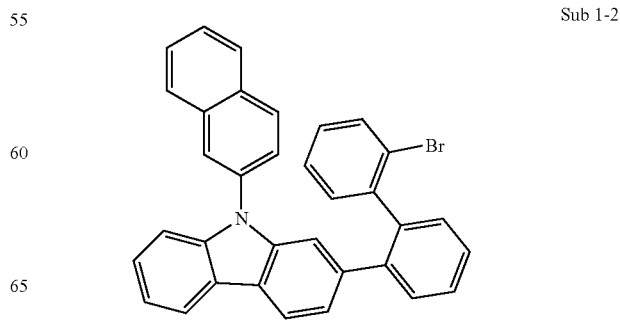

Sub 1-2

-continued
Sub 1-3
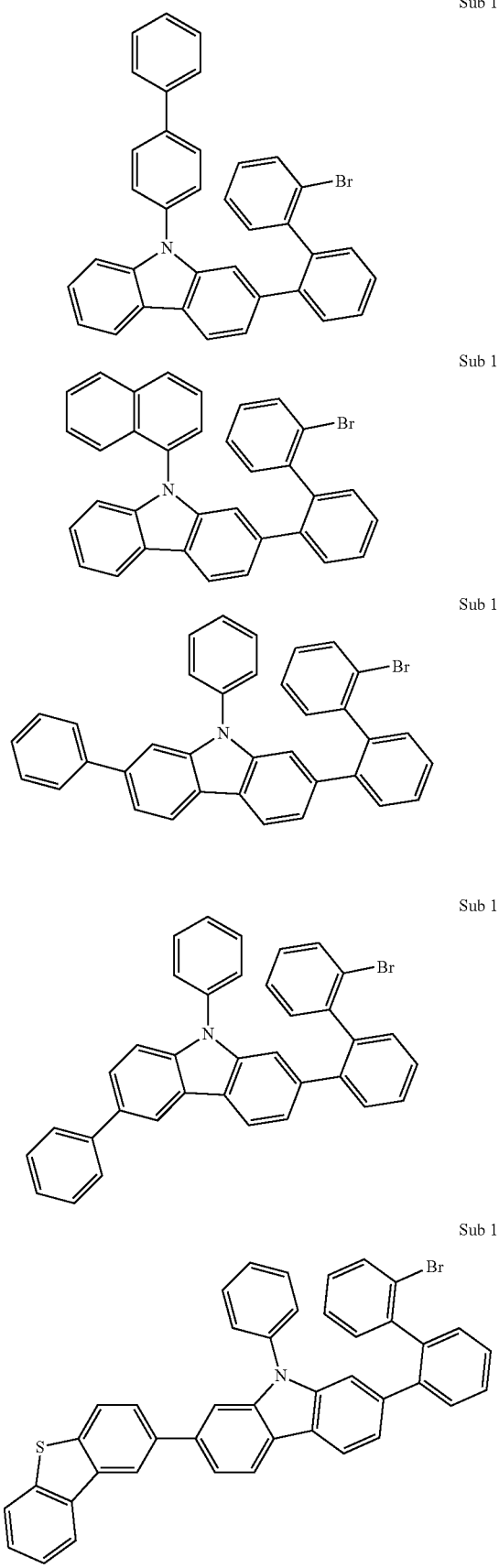
Sub 1-4
Sub 1-5
Sub 1-6
Sub 1-7
Sub 1-8
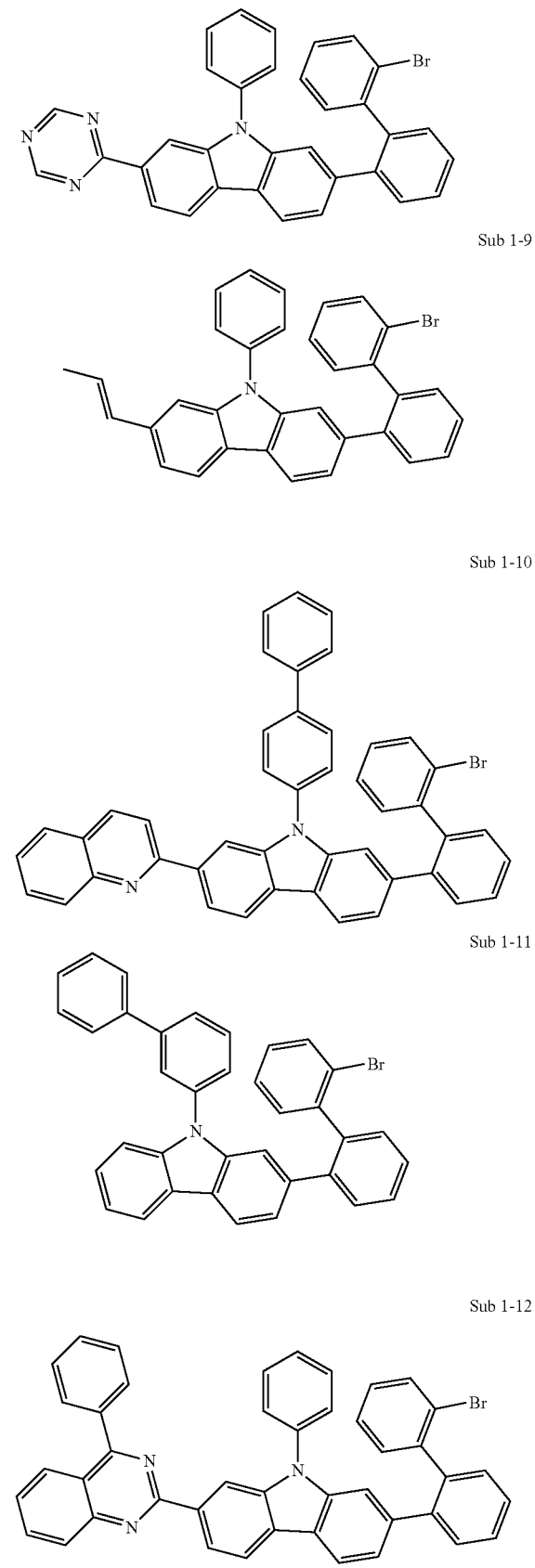
Sub 1-9
Sub 1-10
Sub 1-11
Sub 1-12

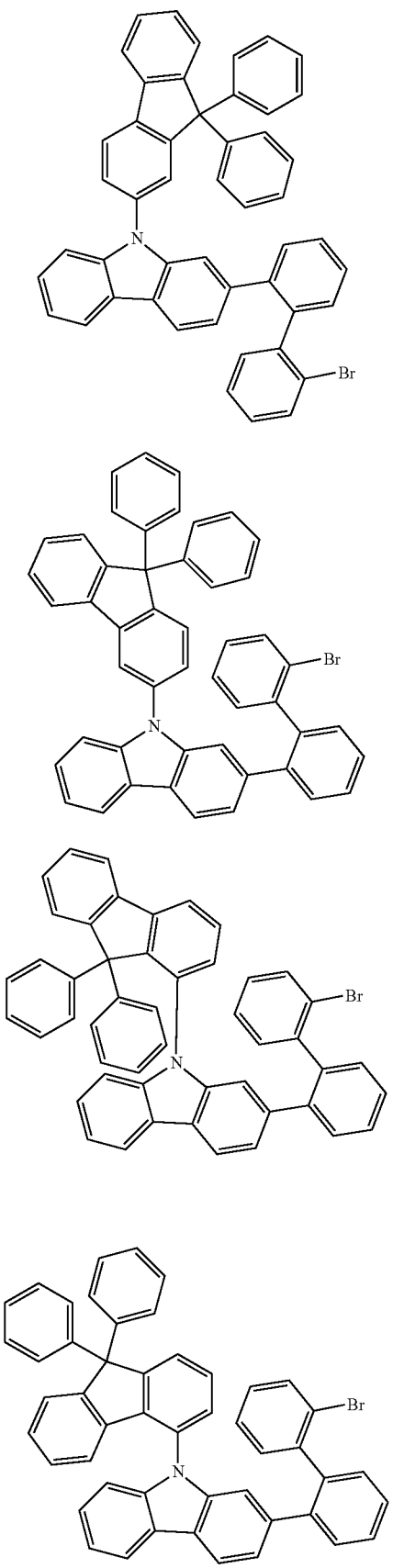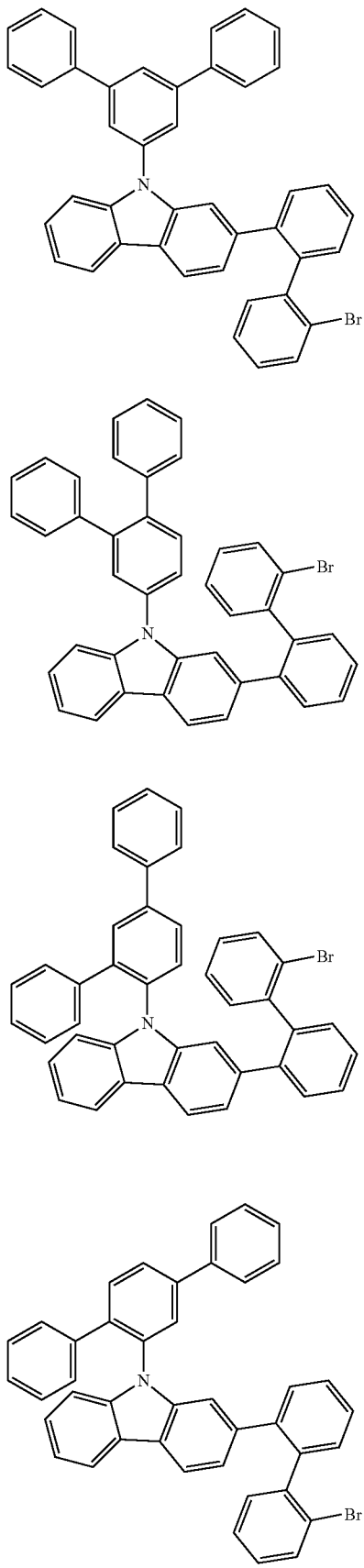

Sub 1-21
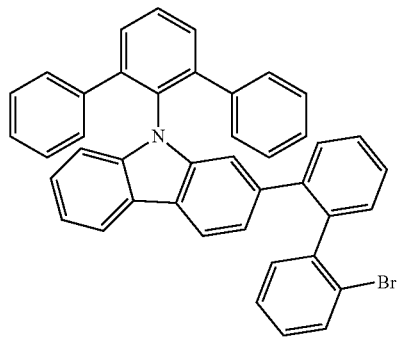
Sub 1-22
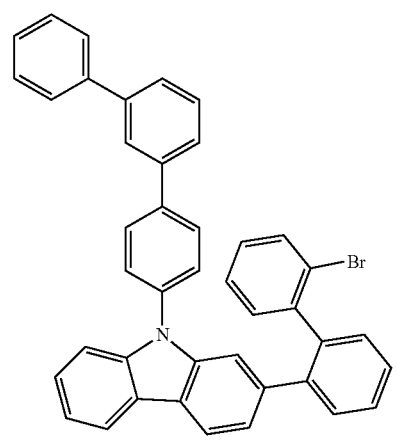
Sub 1-23
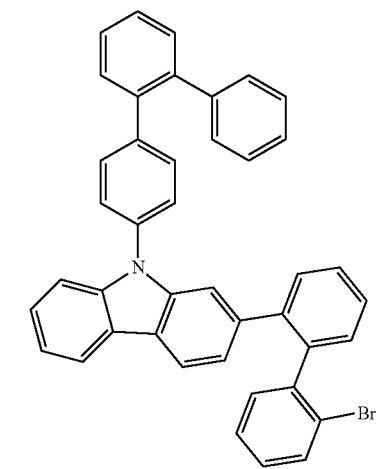
Sub 1-24
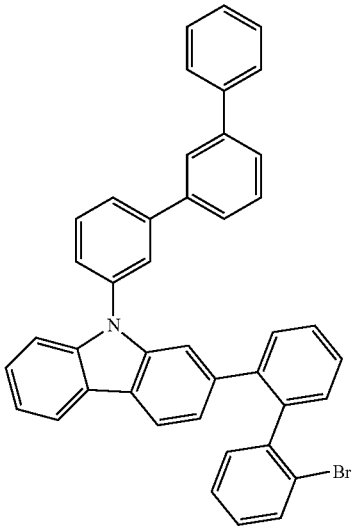
Sub 1-25
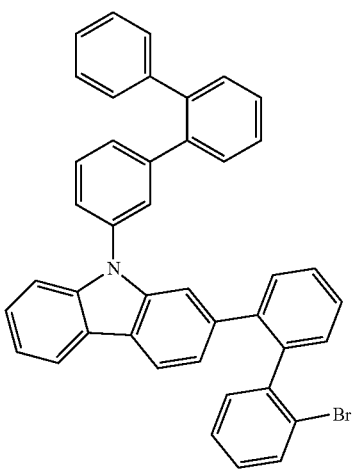
Sub 1-26
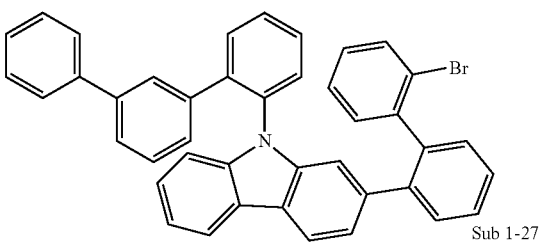
Sub 1-27
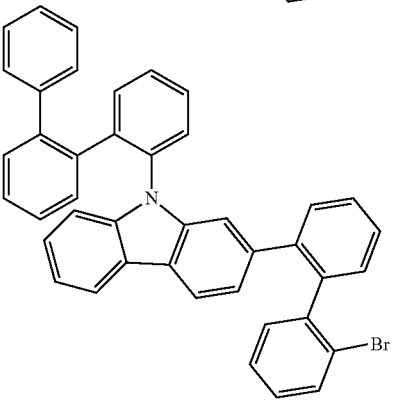

Sub 1-28
Sub 1-29
Sub 1-30
Sub 1-31
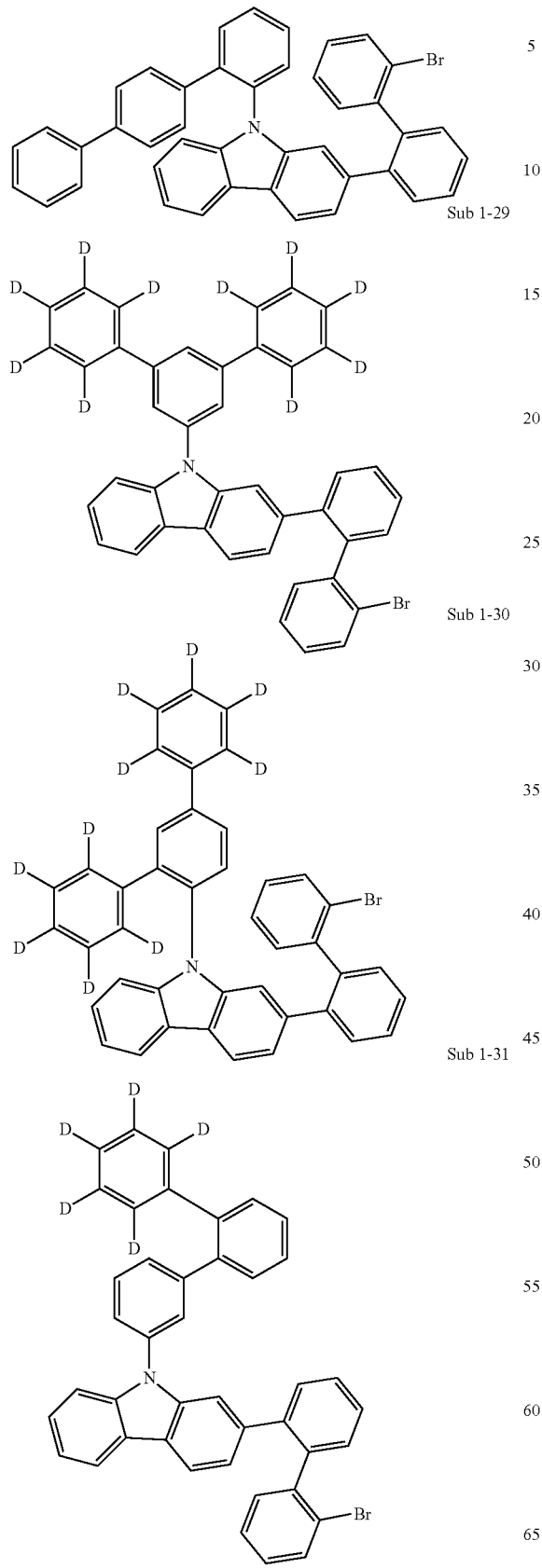
Sub 1-32
Sub 1-33
Sub 1-34
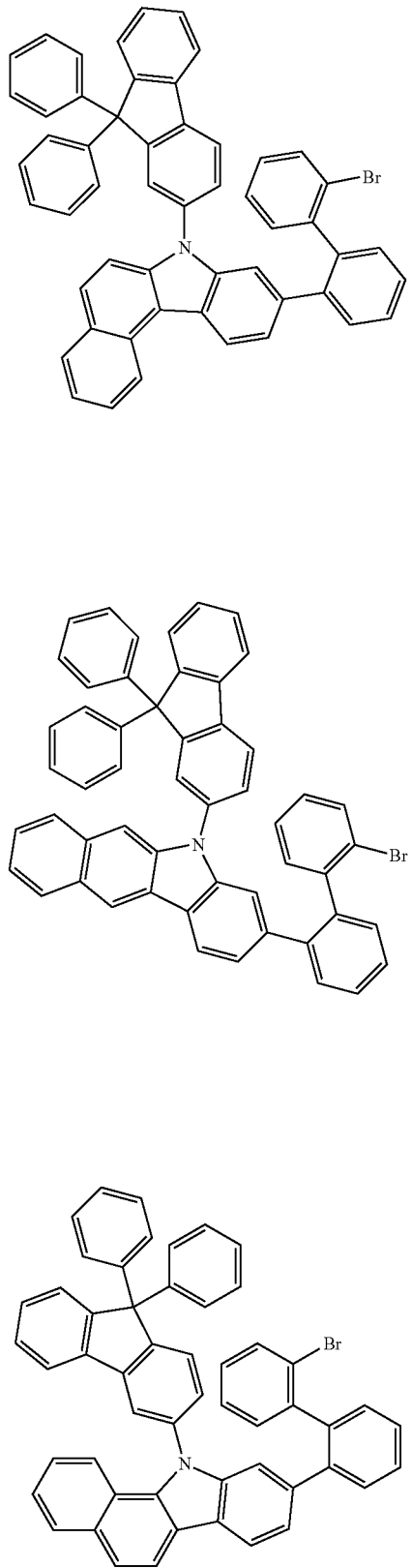

Sub 1-35
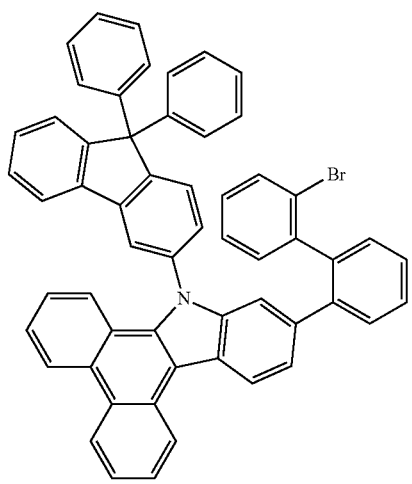
Sub 1-36
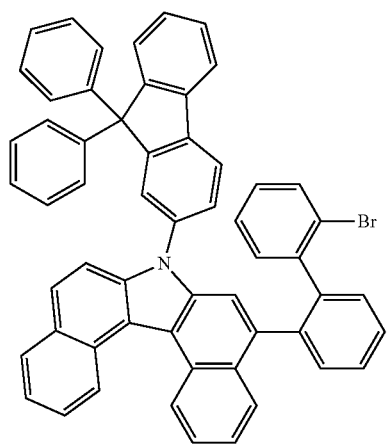
Sub 1-37
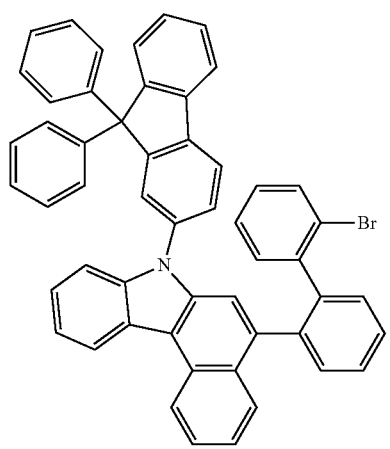
Sub 1-38
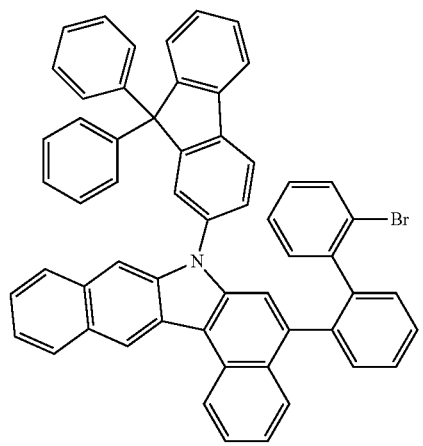
Sub 1-39
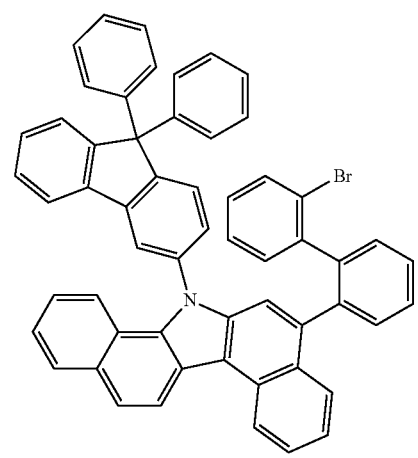
Sub 1-40
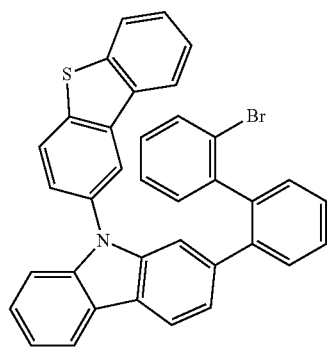

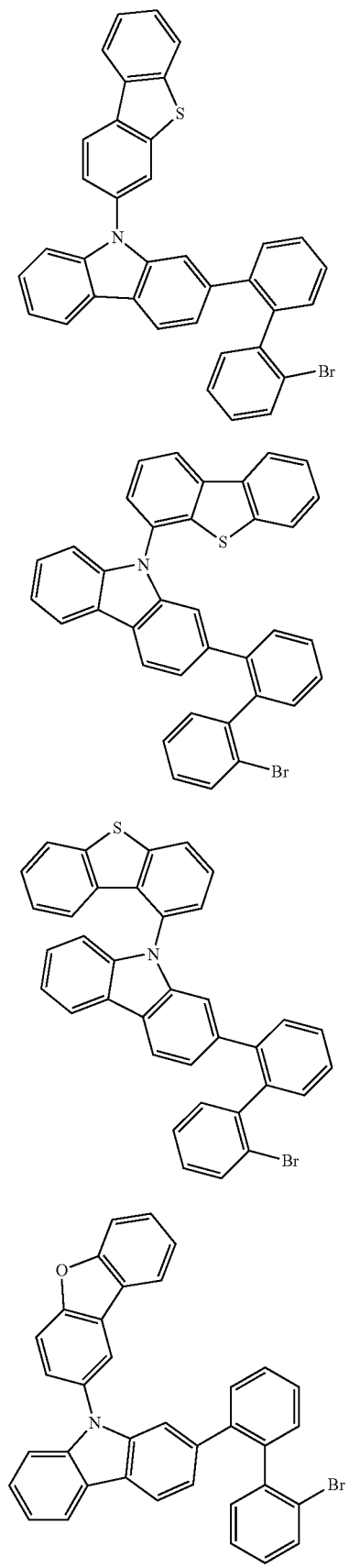
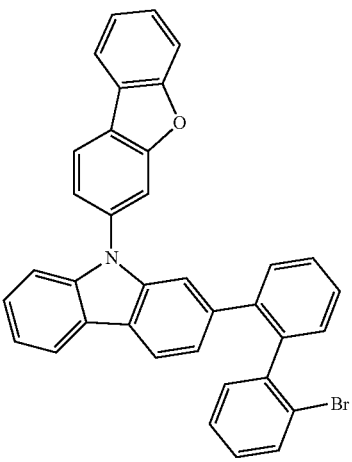
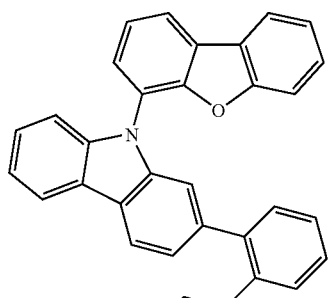
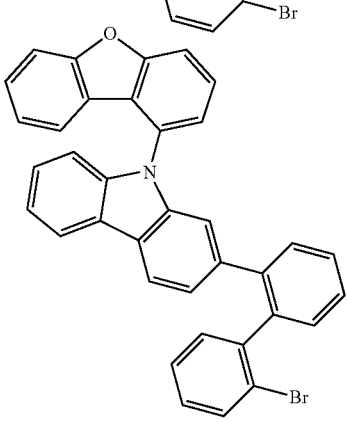
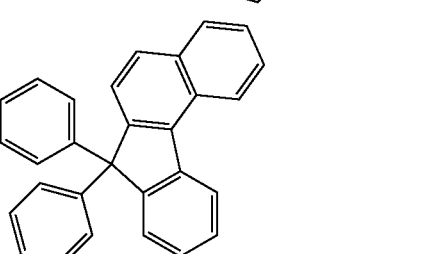
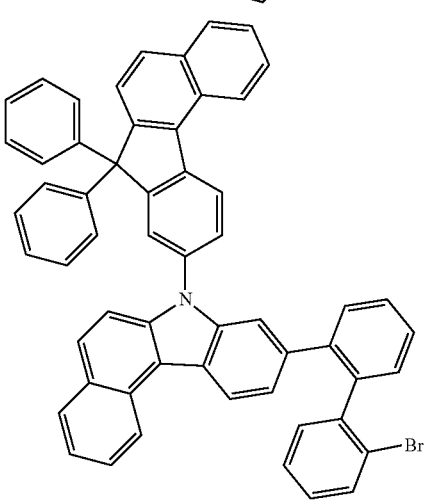
Sub 1-41
Sub 1-42
Sub 1-43
Sub 1-44
Sub 1-45
Sub 1-46
Sub 1-47
Sub 1-48

Sub 1-49
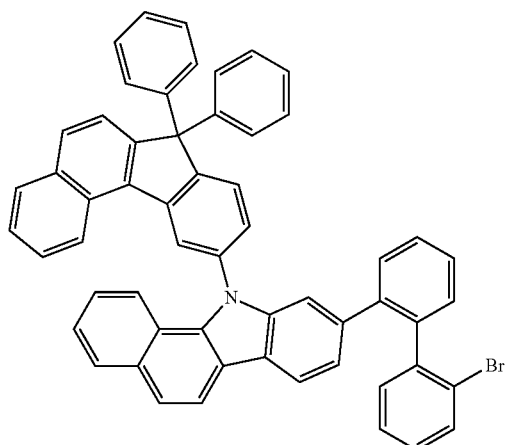
Sub 1-50
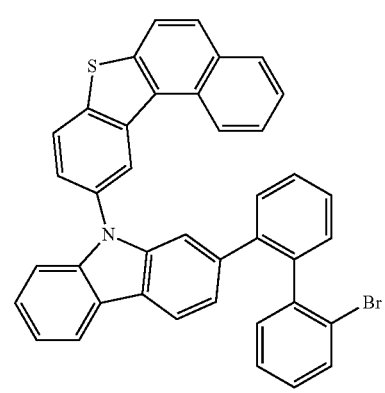
Sub 1-51
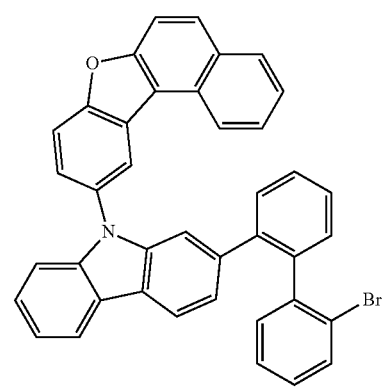
Sub 1-52
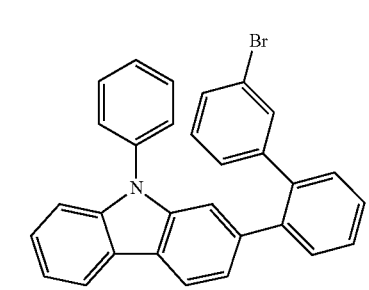
Sub 1-53
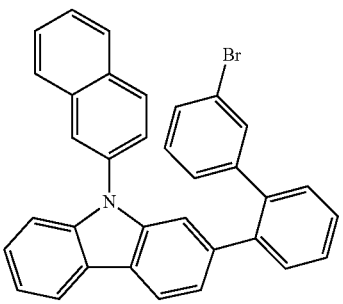
Sub 1-54
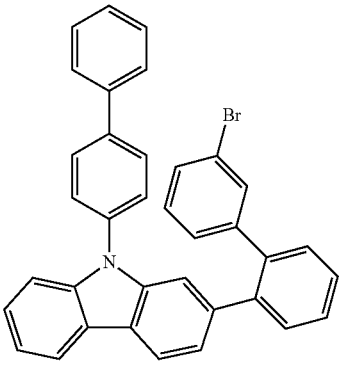
Sub 1-55
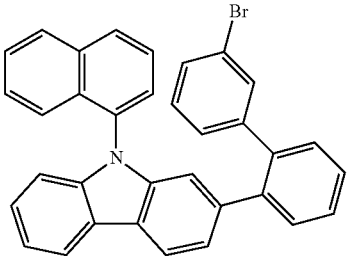
Sub 1-56
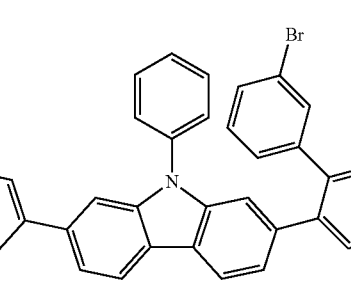
Sub 1-57
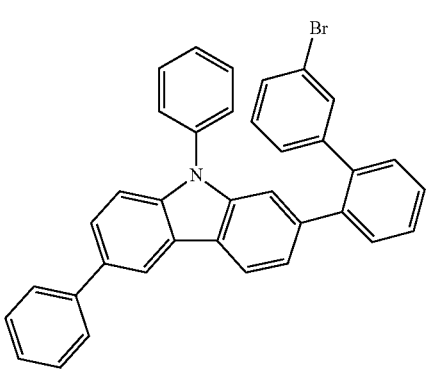

-continued
Sub 1-58
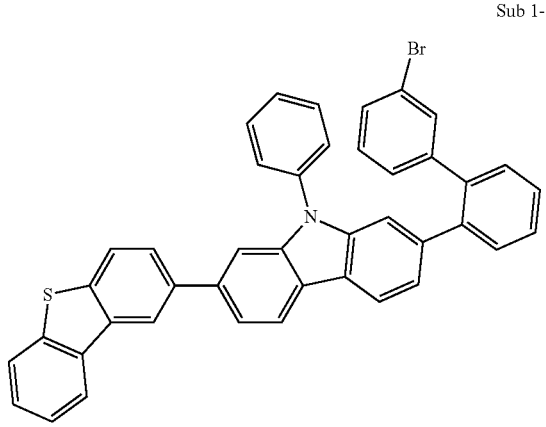
Sub 1-59
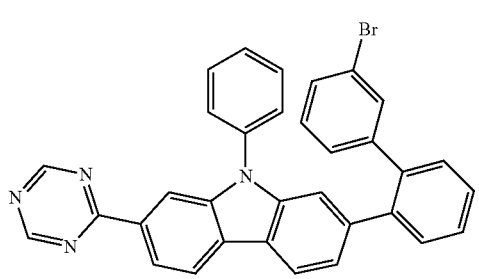
Sub 1-60
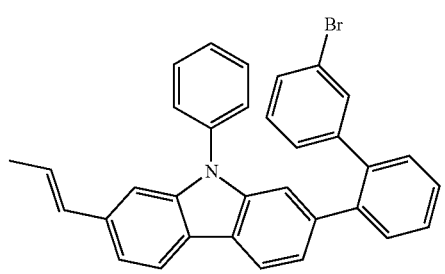
Sub 1-61
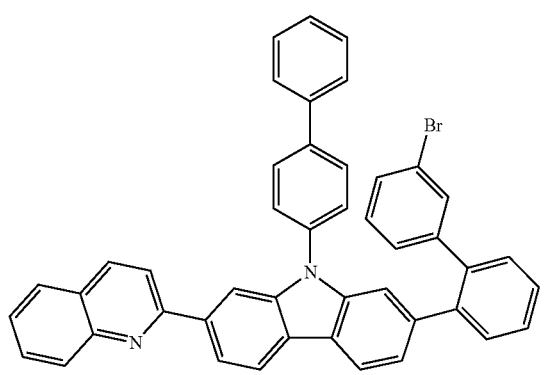
-continued
Sub 1-62
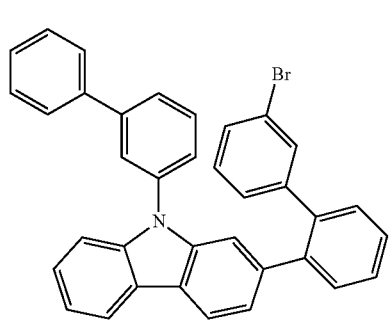
Sub 1-63
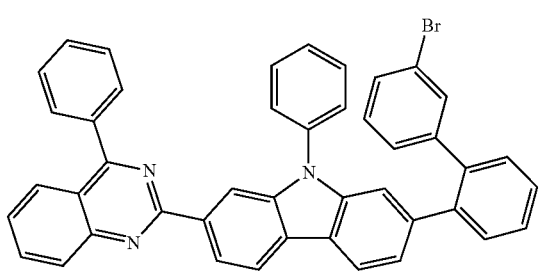
Sub 1-64
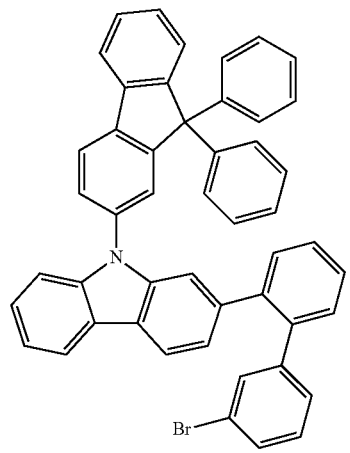
Sub 1-65
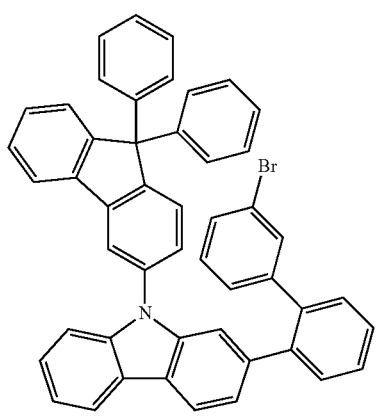

Sub 1-66
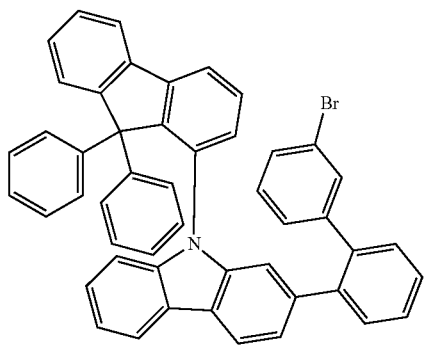
Sub 1-67
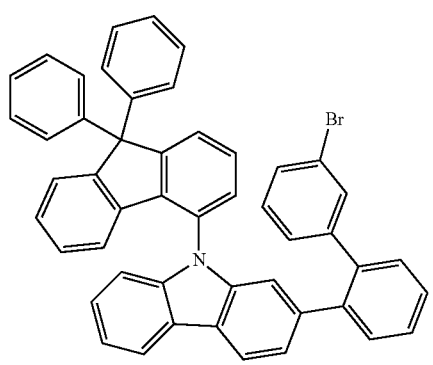
Sub 1-68
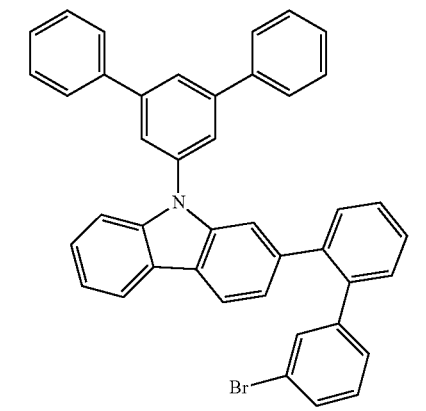
Sub 1-69
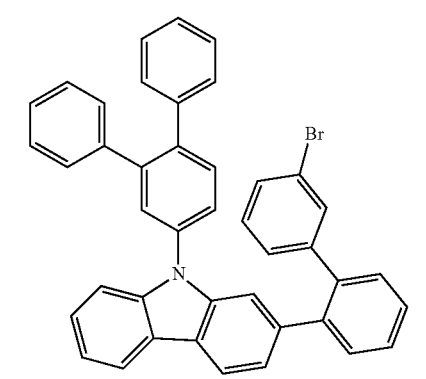
Sub 1-70
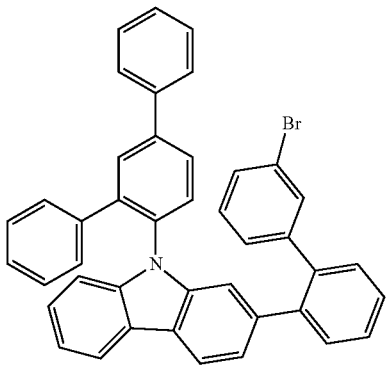
Sub 1-71
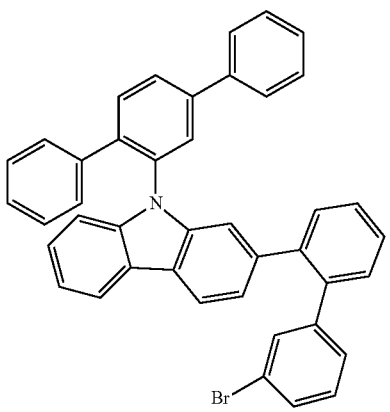
Sub 1-72
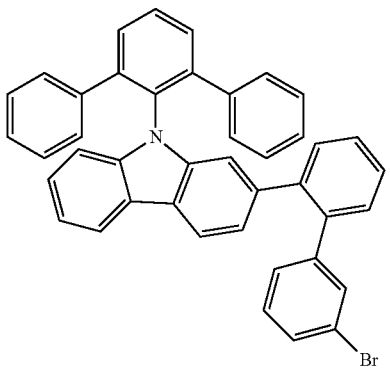
Sub 1-73
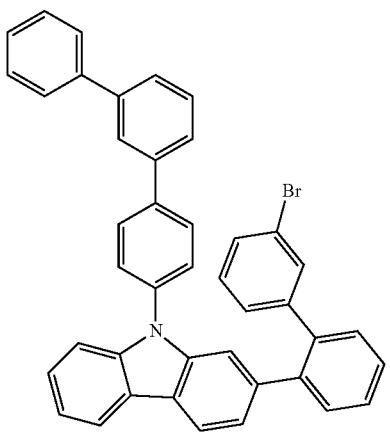

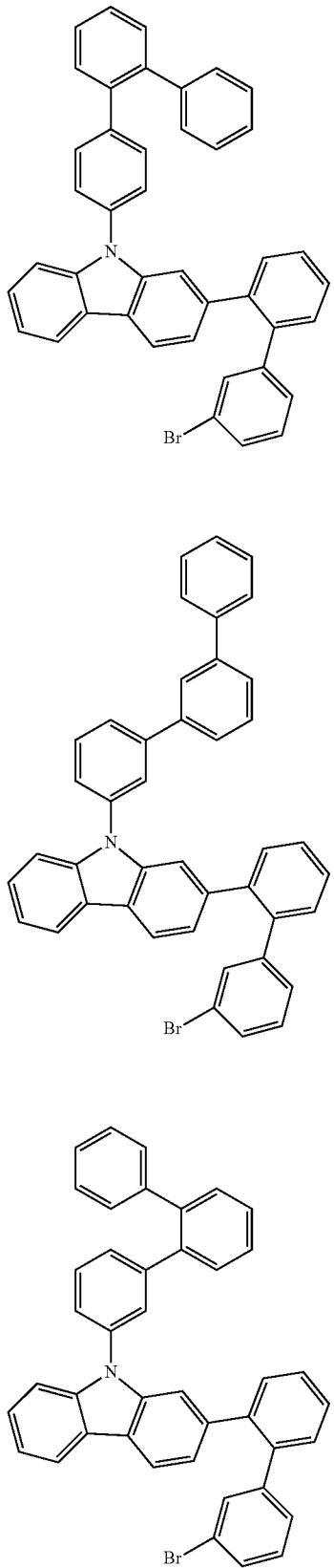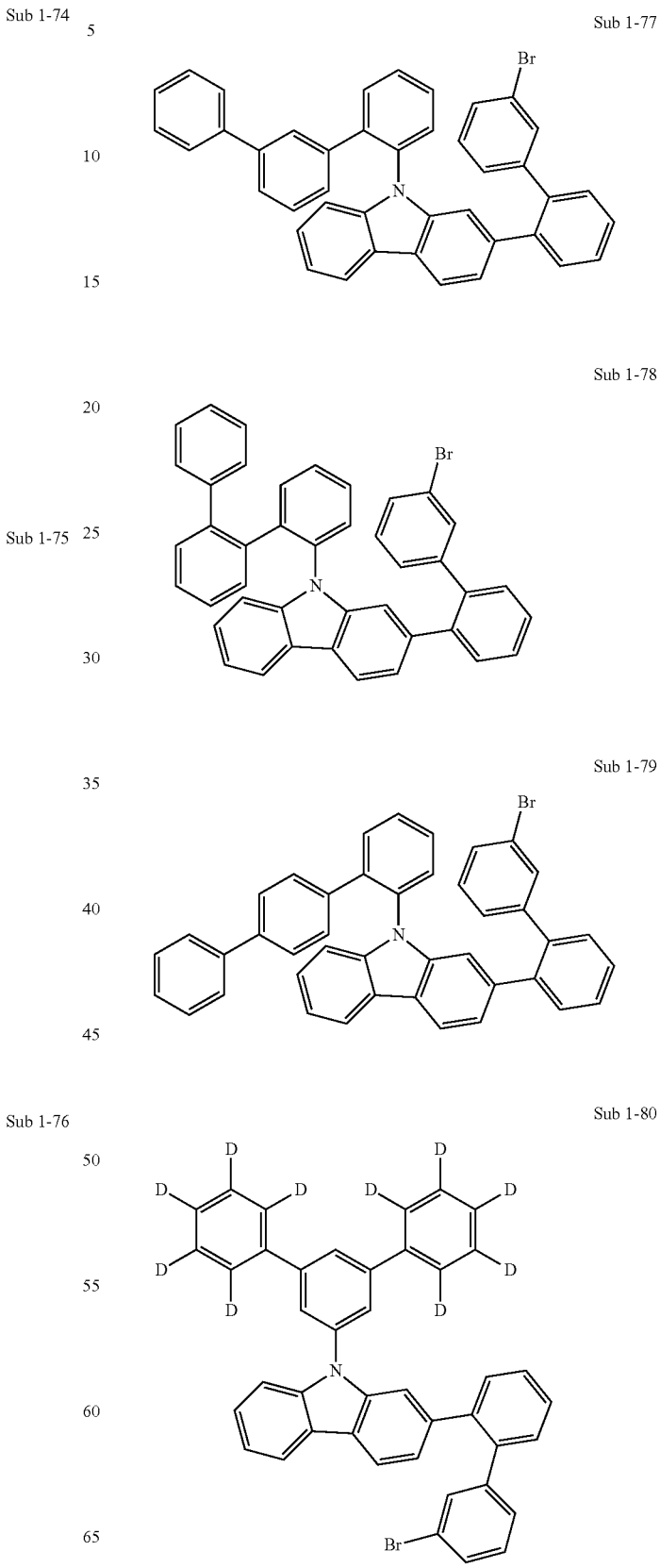

Sub 1-81
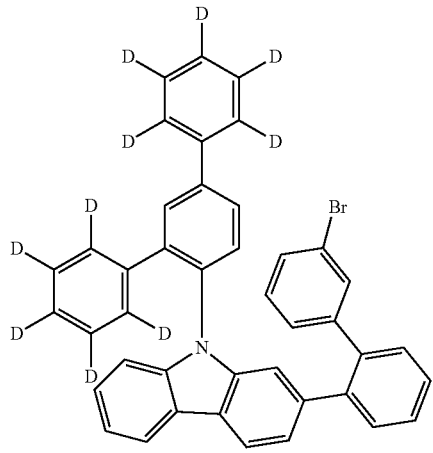
Sub 1-82
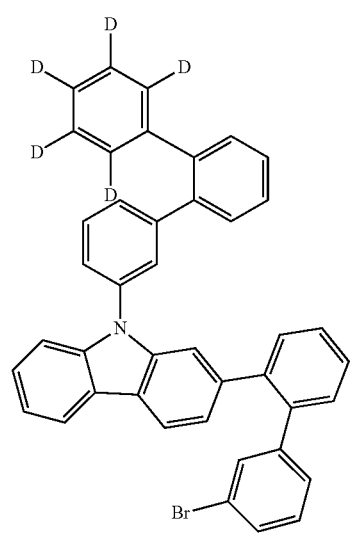
Sub 1-83
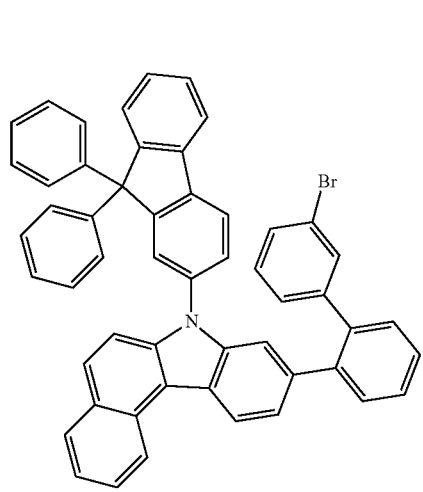
Sub 1-84
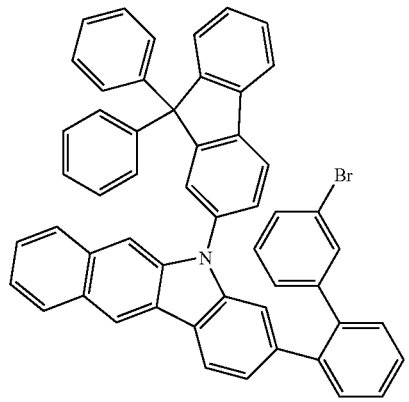
Sub 1-85
Sub 1-86
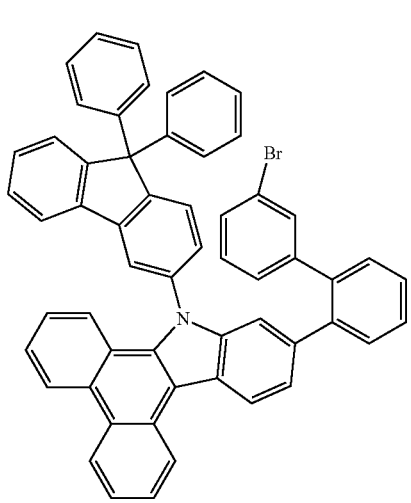

Sub 1-87
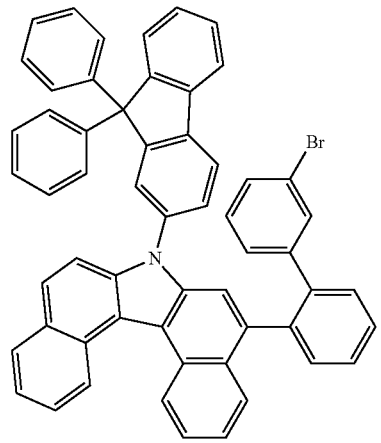
Sub 1-88
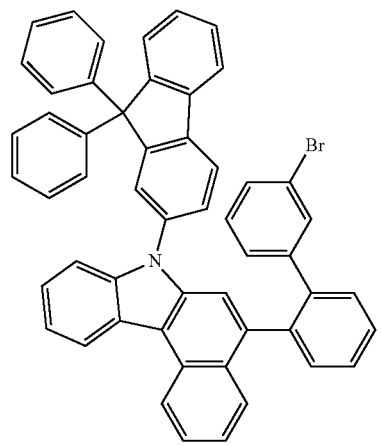
Sub 1-89
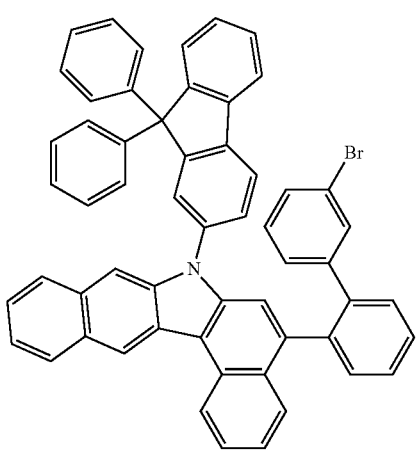
Sub 1-90
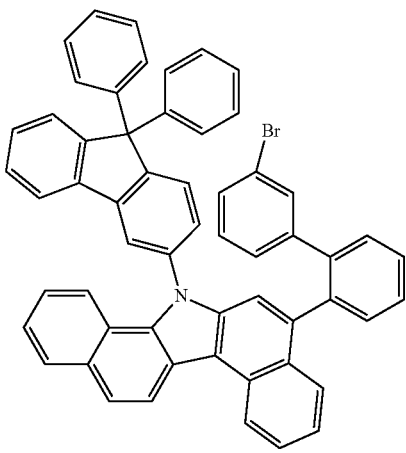
Sub 1-91
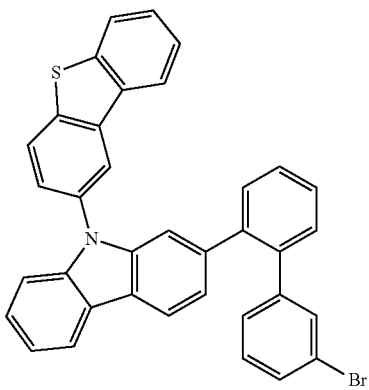
Sub 1-92
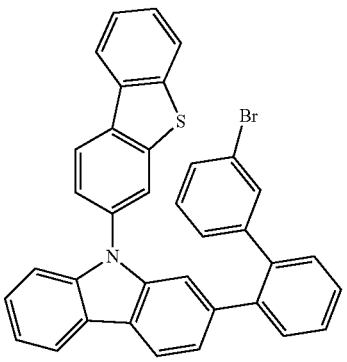
Sub 1-93
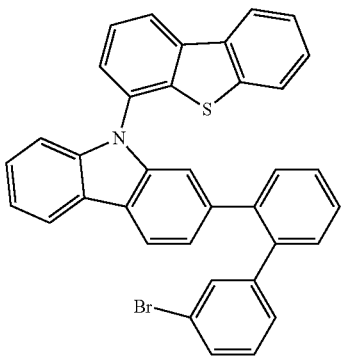

Sub 1-94
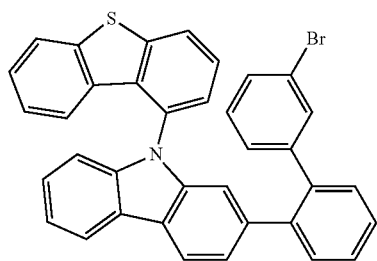
Sub 1-95
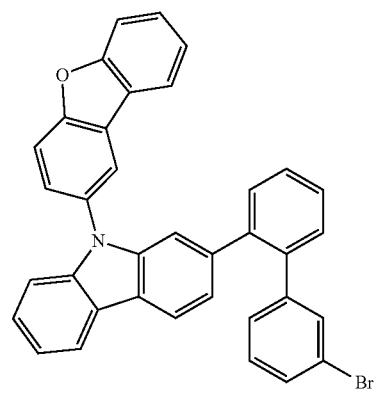
Sub 1-96
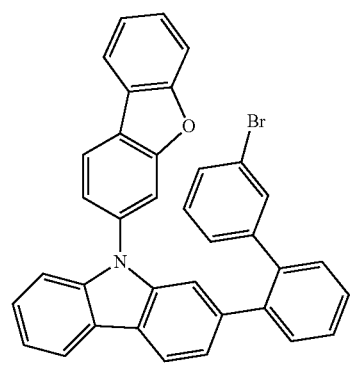
Sub 1-97
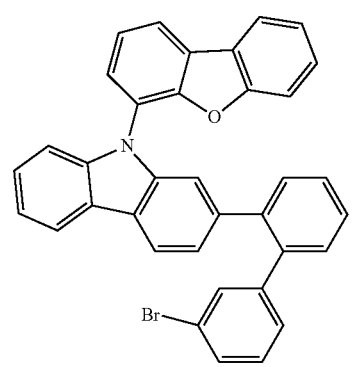
Sub 1-98
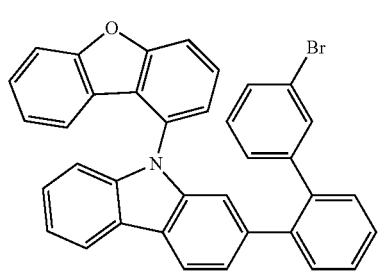
Sub 1-99
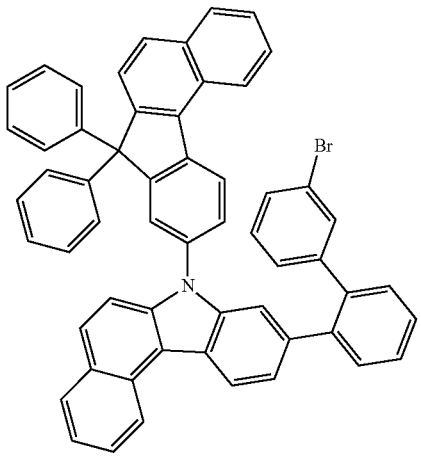
Sub 1-100
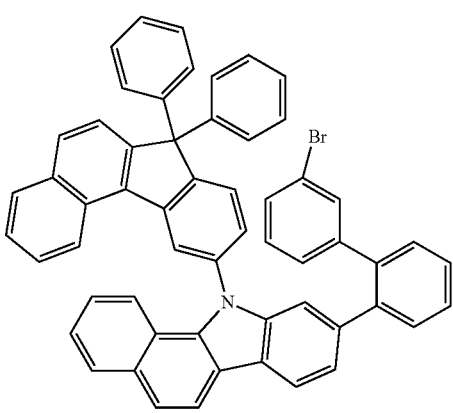
Sub 1-101
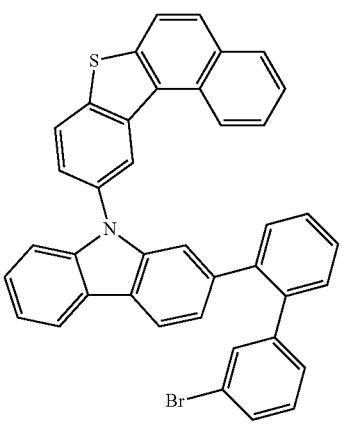

US 10,700,285 B2
207
-continued
208
-continued
Sub 1-102
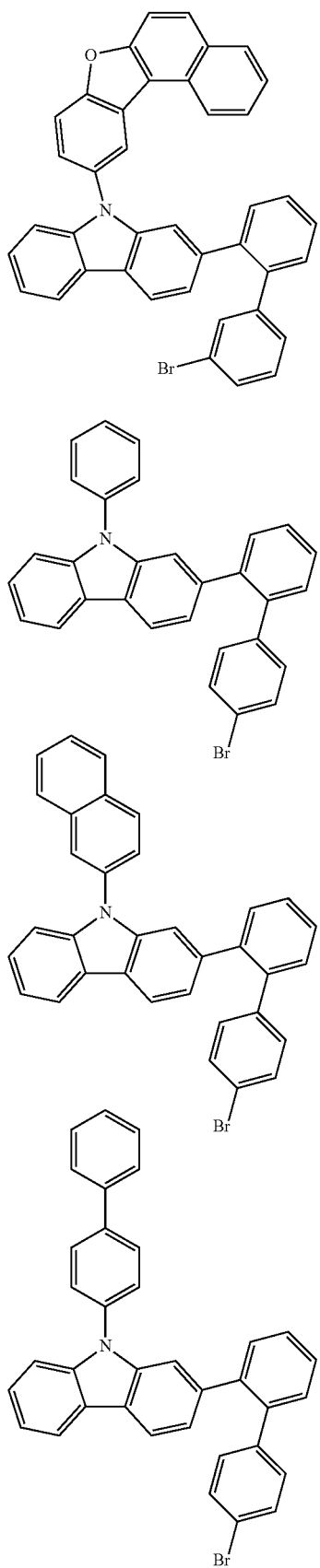
Sub 1-106
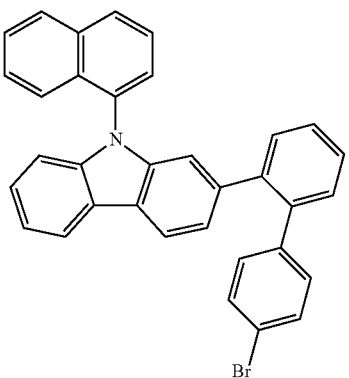
Sub 1-103
Sub 1-107
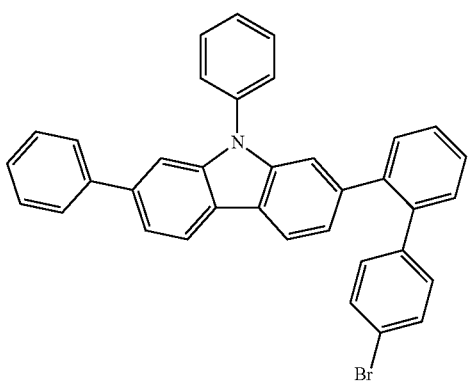
Sub 1-104
Sub 1-108
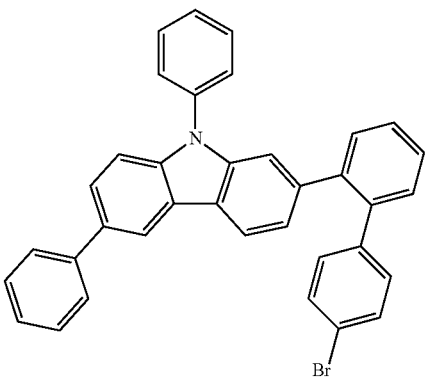
Sub 1-105
Sub 1-109
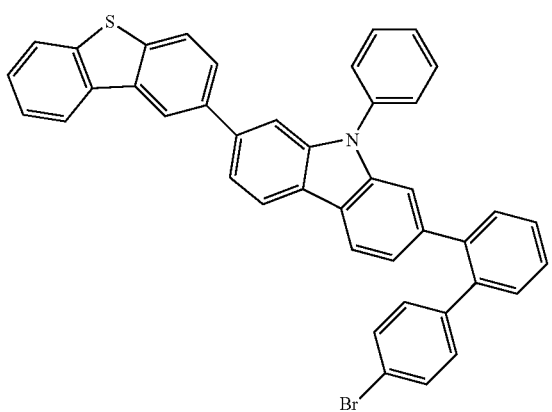

Sub 1-110
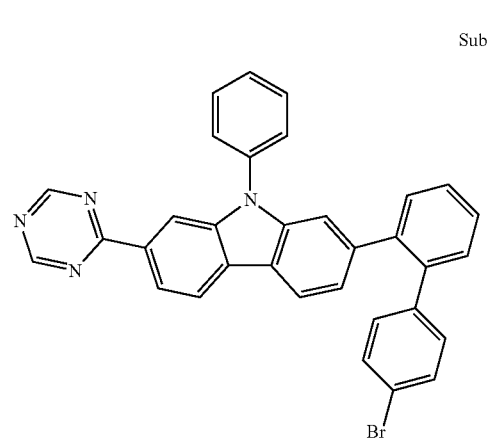
Sub 1-113
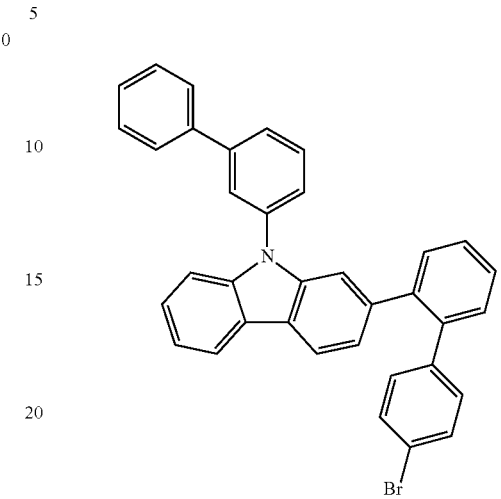
Sub 1-111
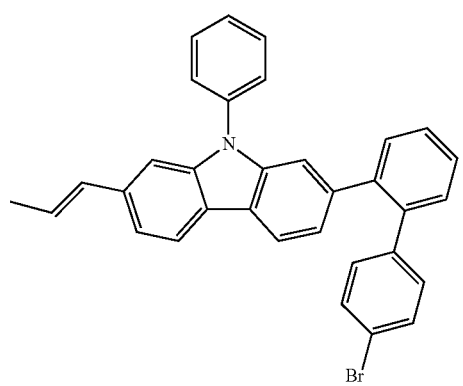
Sub 1-114
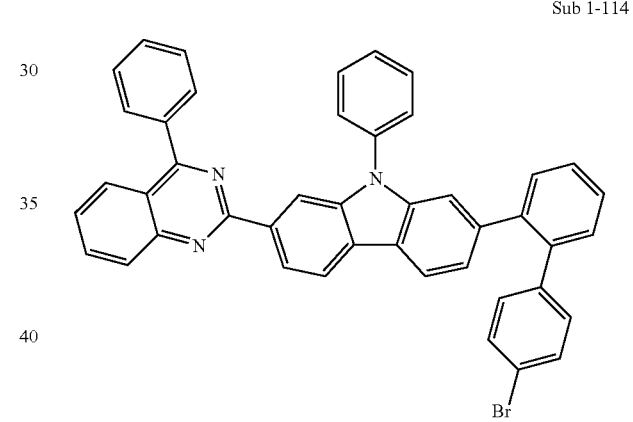
Sub 1-112
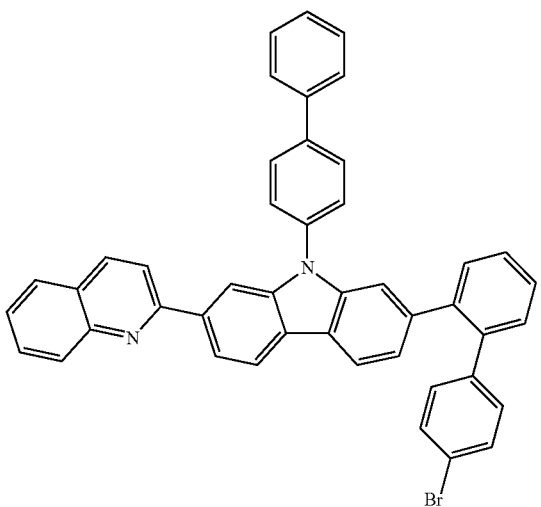
Sub 1-115
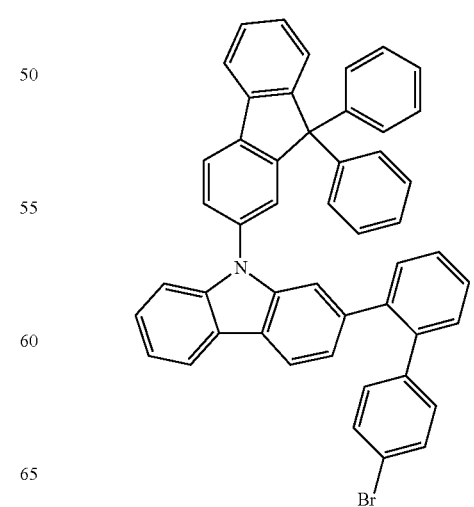

Sub 1-116
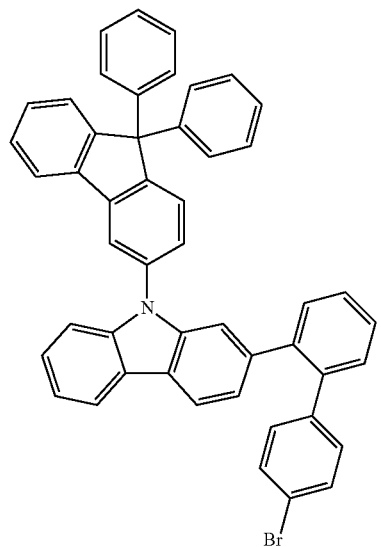
Sub 1-119
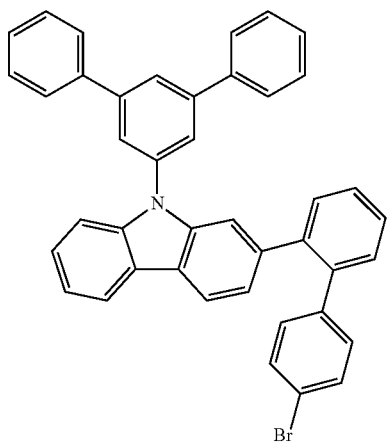
Sub 1-117
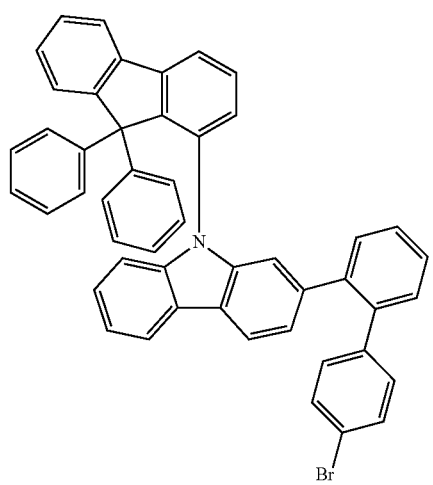
Sub 1-120
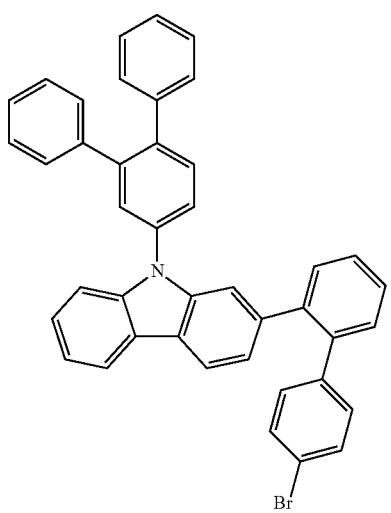
Sub 1-118
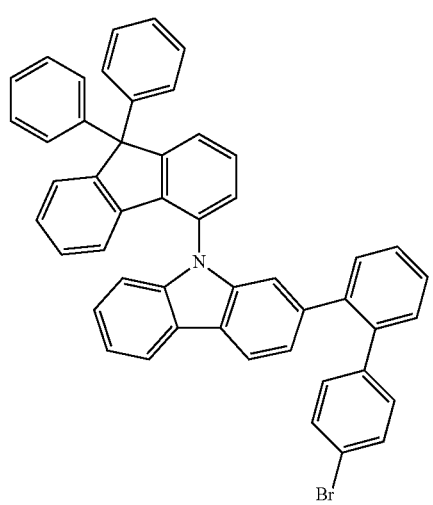
Sub 1-121
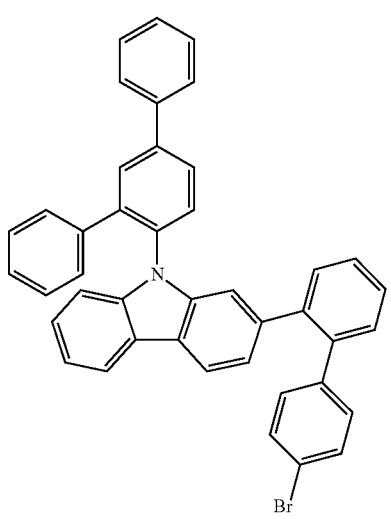

Sub 1-122
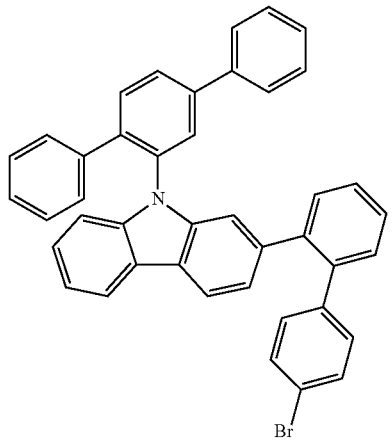
Sub 1-125
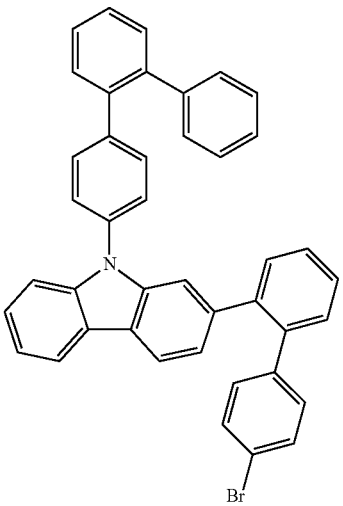
Sub 1-123
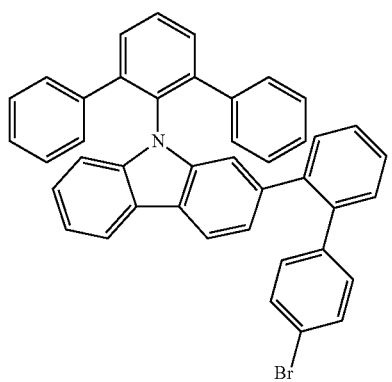
Sub 1-126
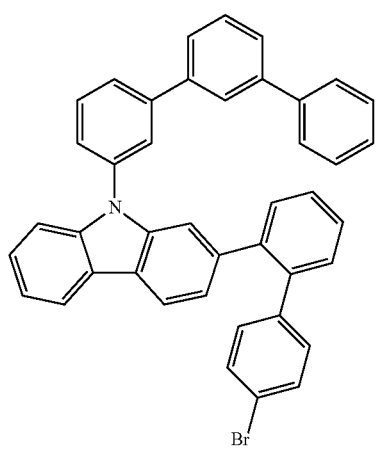
Sub 1-124
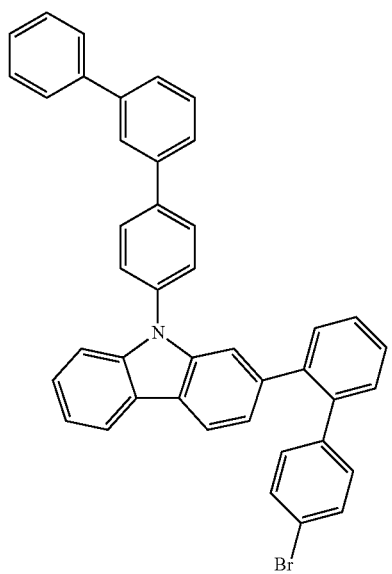
Sub 1-127
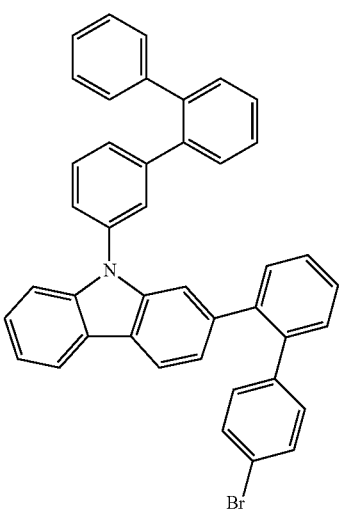

Sub 1-128
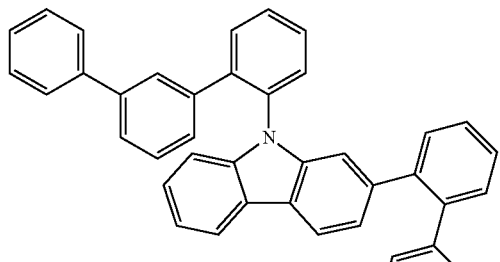
Sub 1-129
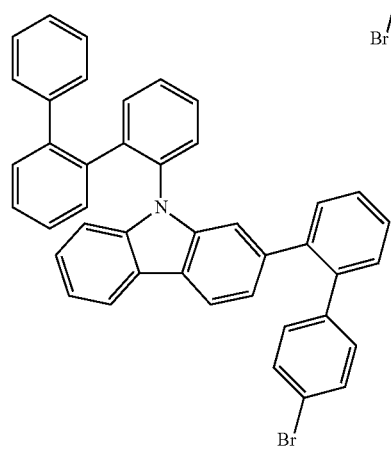
Sub 1-130
Sub 1-131
Sub 1-132
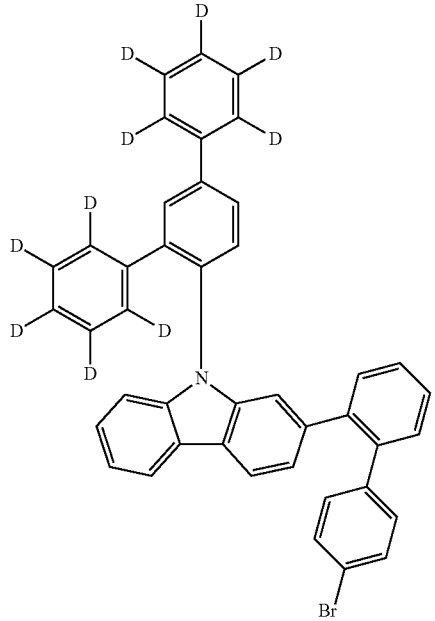
Sub 1-133
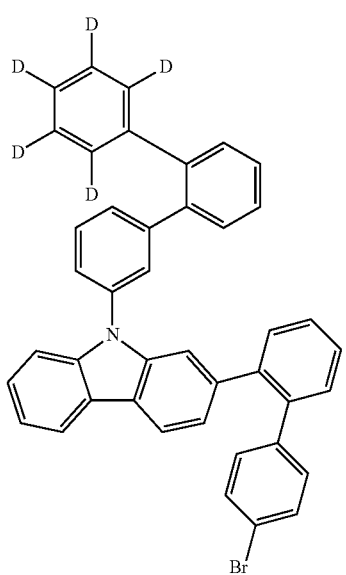
Sub 1-134
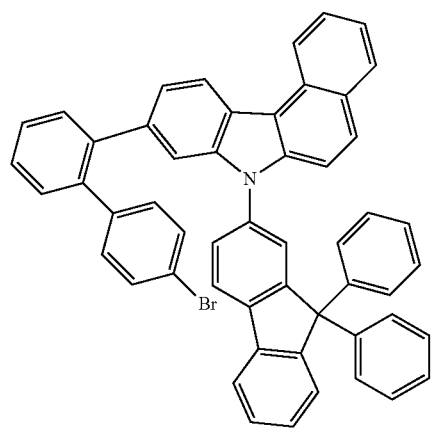

Sub 1-135
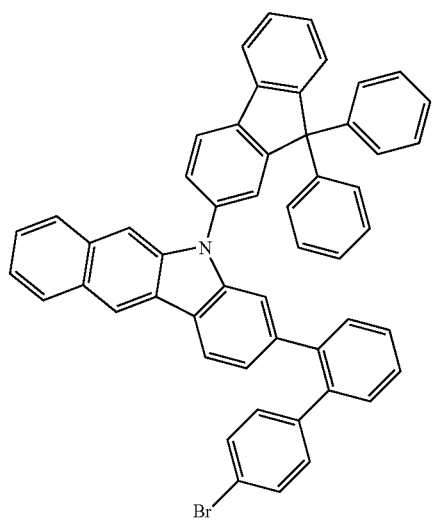
Sub 1-138
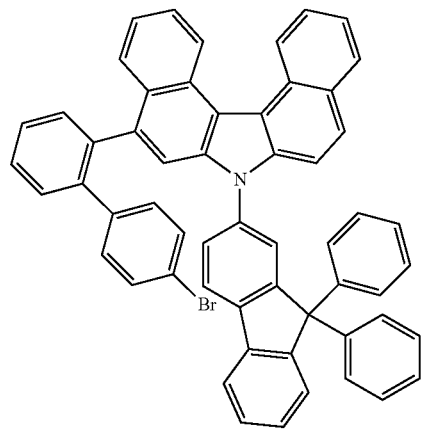
Sub 1-136
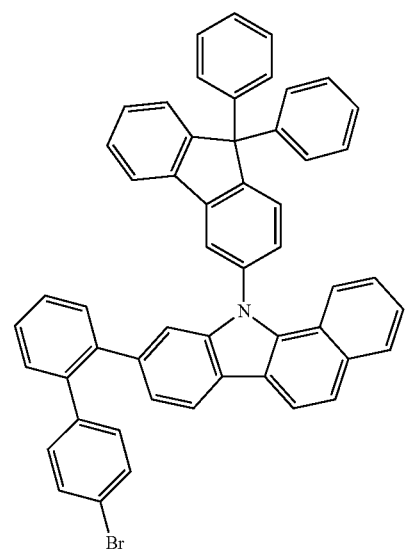
Sub 1-139
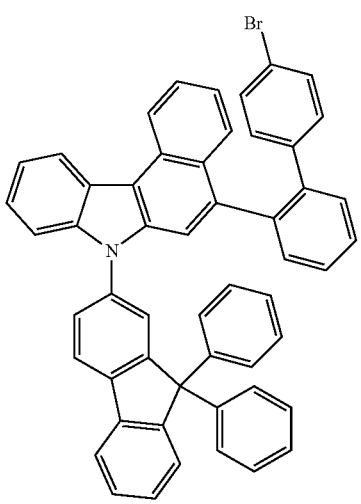
Sub 1-137
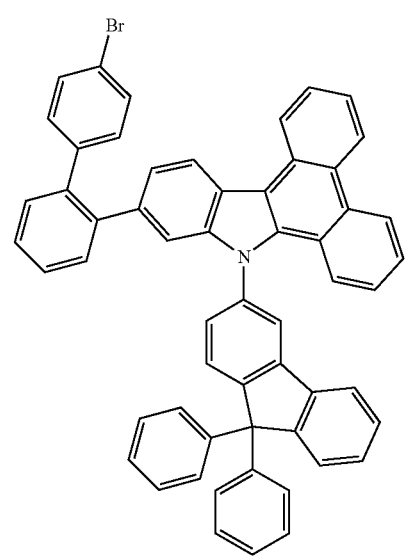
Sub 1-140
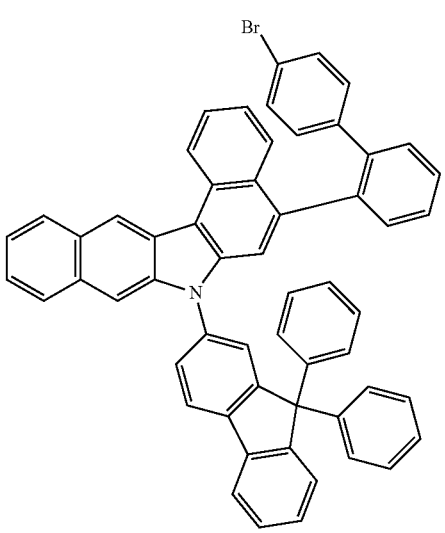

-continued
Sub 1-141
Sub 1-142
Sub 1-143
Sub 1-144
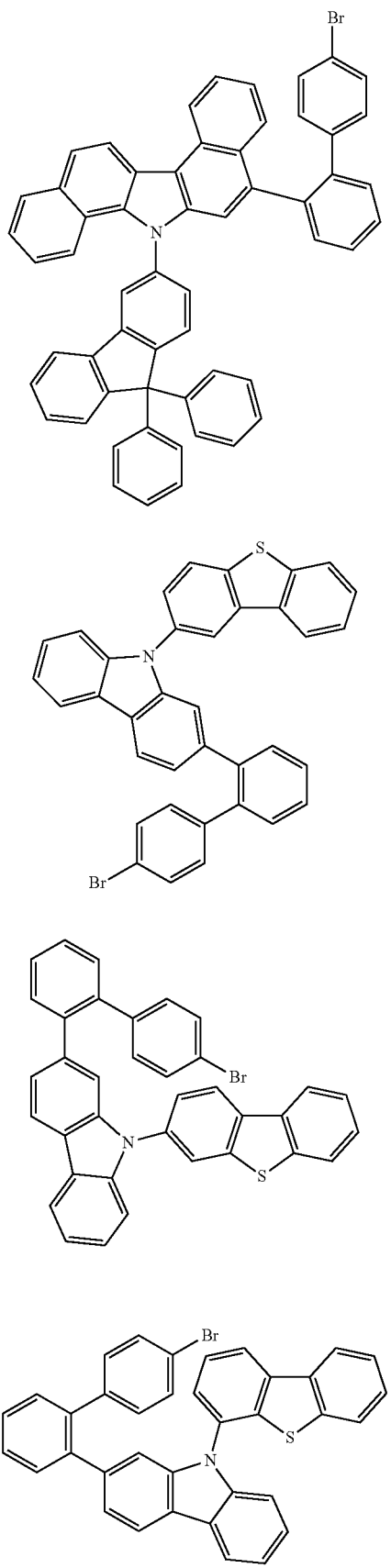
-continued
Sub 1-145
Sub 1-146
Sub 1-147
Sub 1-148
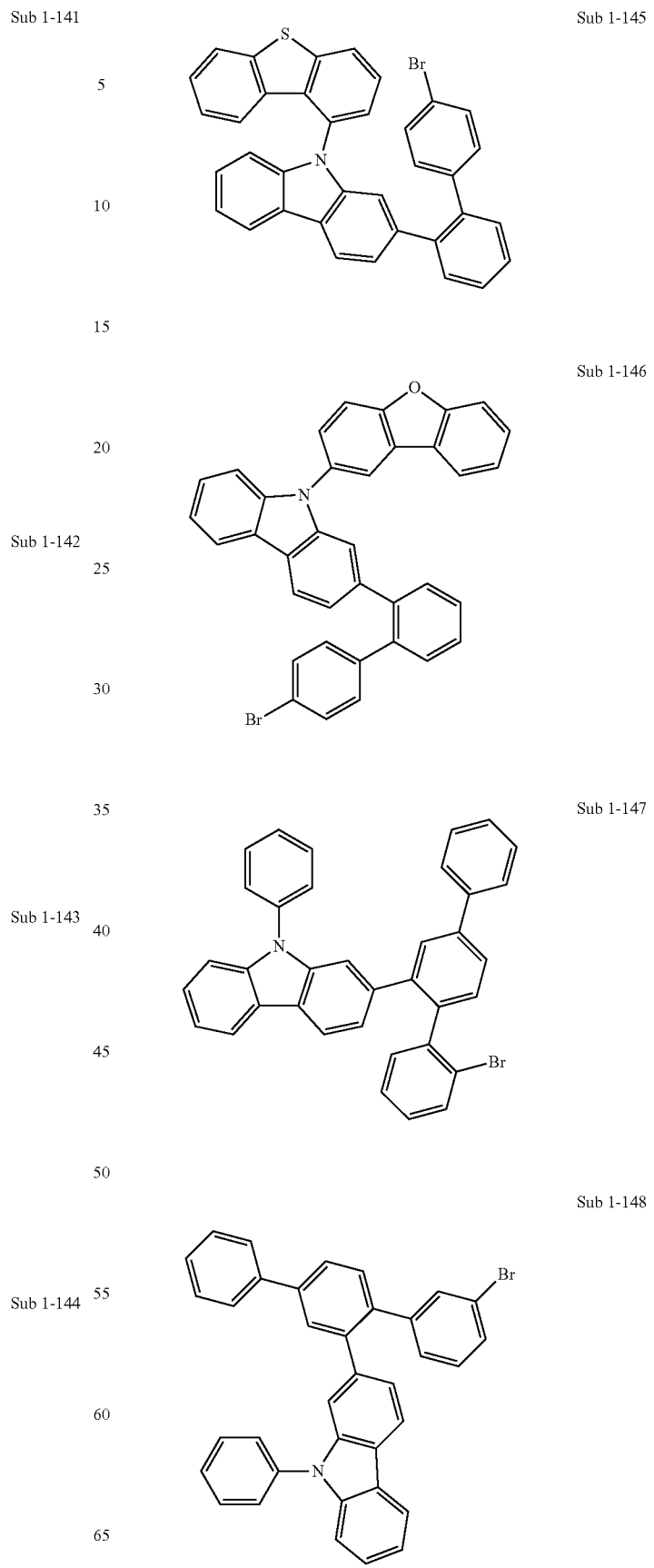

Sub 1-149
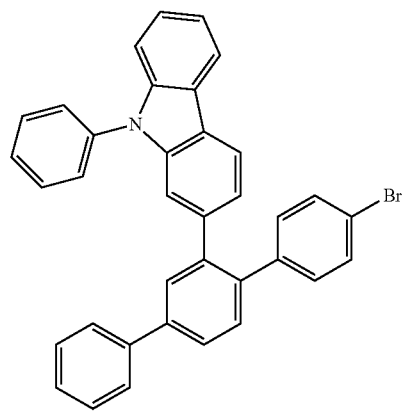
Sub 1-152
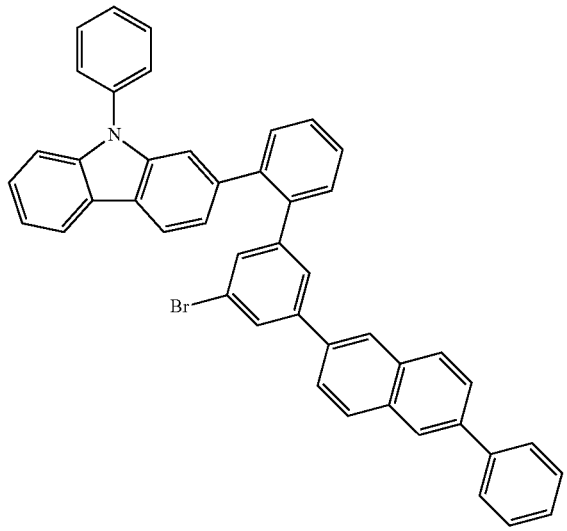
Sub 1-150
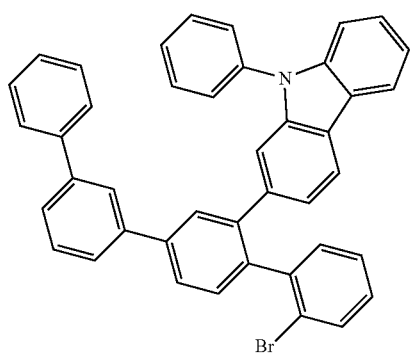
Sub 1-153
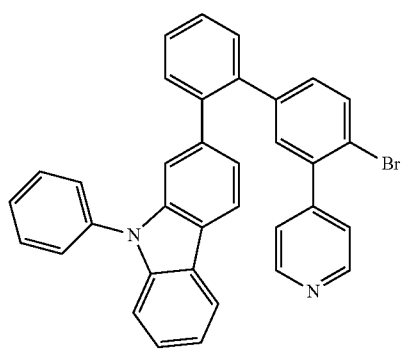
Sub 1-151
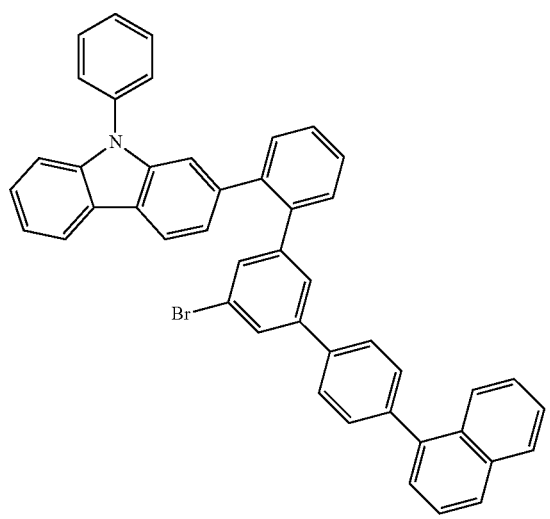
Sub 1-154
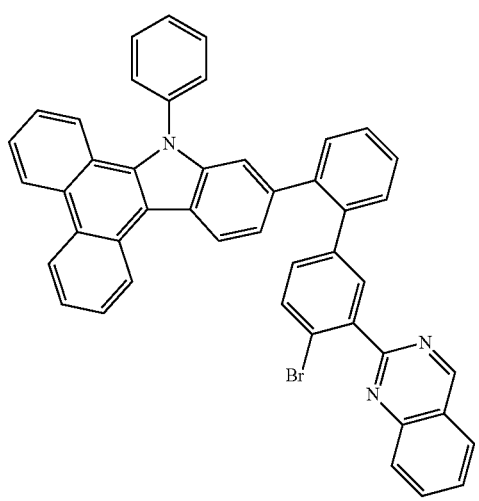

-continued

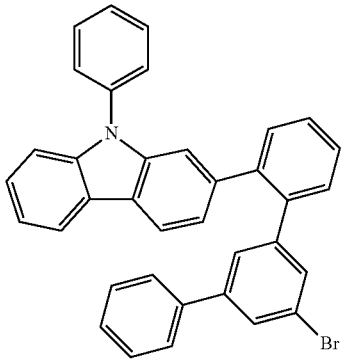

Sub 1-155

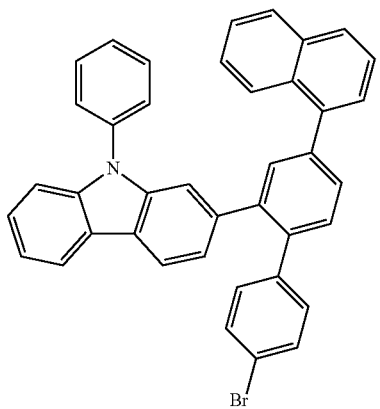

Sub 1-156

TABLE 1

| Compound | FD-MS | Compound | FD-MS |
|---|---|---|---|
| Sub 1-1 | m/z = 473.08 ($C_{30}H_{20}BrN$ = 474.39) | Sub 1-2 | m/z = 523.09 ($C_{34}H_{22}BrN$ = 524.45) |
| Sub 1-3 | m/z = 549.11 ($C_{36}H_{24}BrN$ = 550.49) | Sub 1-4 | m/z = 523.09 ($C_{34}H_{22}BrN$ = 524.45) |
| Sub 1-5 | m/z = 549.11 ($C_{36}H_{24}BrN$ = 550.49) | Sub 1-6 | m/z = 549.11 ($C_{36}H_{24}BrN$ = 550.49) |
| Sub 1-7 | m/z = 655.10 ($C_{42}H_{26}BrNS$ = 656.63) | Sub 1-8 | m/z = 552.09 ($C_{33}H_{21}BrN_4$ = 553.45) |
| Sub 1-A9 | m/z = 513.11 ($C_{33}H_{24}BrN$ = 514.45) | Sub 1-10 | m/z = 676.15 ($C_{45}H_{29}BrN_2$ = 677.63) |
| Sub 1-11 | m/z = 549.11 ($C_{36}H_{24}BrN$ = 550.49) | Sub 1-12 | m/z = 677.15 ($C_{44}H_{29}BrN_3$ = 678.62) |
| Sub 1-13 | m/z = 713.17 ($C_{49}H_{32}BrN$ = 714.69) | Sub 1-14 | m/z = 713.17 ($C_{49}H_{32}BrN$ = 714.69) |
| Sub 1-15 | m/z = 713.17 ($C_{49}H_{32}BrN$ = 714.69) | Sub 1-16 | m/z = 713.17 ($C_{49}H_{32}BrN$ = 714.69) |
| Sub 1-17 | m/z = 625.14 ($C_{42}H_{28}BrN$ = 626.58) | Sub 1-18 | m/z = 625.14 ($C_{42}H_{28}BrN$ = 626.58) |
| Sub 1-19 | m/z = 625.14 ($C_{42}H_{28}BrN$ = 626.58) | Sub 1-20 | m/z = 625.14 ($C_{42}H_{28}BrN$ = 626.58) |
| Sub 1-21 | m/z = 625.14 ($C_{42}H_{28}BrN$ = 626.58) | Sub 1-22 | m/z = 625.14 ($C_{42}H_{28}BrN$ = 626.58) |
| Sub 1-23 | m/z = 625.14 ($C_{42}H_{28}BrN$ = 626.58) | Sub 1-24 | m/z = 625.14 ($C_{42}H_{28}BrN$ = 626.58) |
| Sub 1-25 | m/z = 625.14 ($C_{42}H_{28}BrN$ = 626.58) | Sub 1-26 | m/z = 625.14 ($C_{42}H_{28}BrN$ = 626.58) |
| Sub 1-27 | m/z = 625.14 ($C_{42}H_{28}BrN$ = 626.58) | Sub 1-28 | m/z = 625.14 ($C_{42}H_{28}BrN$ = 626.58) |
| Sub 1-29 | m/z = 635.20 ($C_{42}H_{18}D_{10}BrN$ = 636.64.) | Sub 1-30 | m/z = 635.20 ($C_{42}H_{18}D_{10}BrN$ = 636.64) |
| Sub 1-31 | m/z = 630.17 ($C_{42}H_{23}D_5BrN$ = 631.6) | Sub 1-32 | m/z = 763.19 ($C_{53}H_{34}BrN$ = 764.75) |
| Sub 1-33 | m/z = 763.19 ($C_{53}H_{34}BrN$ = 764.75) | Sub 1-34 | m/z = 763.19 ($C_{53}H_{34}BrN$ = 764.75) |
| Sub 1-35 | m/z = 813.20 ($C_{57}H_{36}BrN$ = 814.81) | Sub 1-36 | m/z = 813.20 ($C_{57}H_{36}BrN$ = 814.81) |
| Sub 1-37 | m/z = 763.19 ($C_{53}H_{34}BrN$ = 764.75) | Sub 1-38 | m/z = 813.20 ($C_{57}H_{36}BrN$ = 814.81) |
| Sub 1-39 | m/z = 813.20 ($C_{57}H_{36}BrN$ = 814.81) | Sub 1-40 | m/z = 579.07 ($C_{36}H_{22}BrNS$ = 580.54) |
| Sub 1-41 | m/z = 579.07 ($C_{36}H_{22}BrNS$ = 580.54) | Sub 1-42 | m/z = 579.07 ($C_{36}H_{22}BrNS$ = 580.54) |
| Sub 1-43 | m/z = 579.07 ($C_{36}H_{22}BrNS$ = 580.54) | Sub 1-44 | m/z = 563.09 ($C_{36}H_{22}BrNO$ = 564.47) |
| Sub 1-45 | m/z = 563.1 ($C_{36}H_{22}BrNO$ = 564.47) | Sub 1-46 | m/z = 563.09 ($C_{36}H_{22}BrNO$ = 564.47) |
| Sub 1-47 | m/z = 563.1 ($C_{36}H_{22}BrNO$ = 564.47) | Sub 1-48 | m/z = 813.20 ($C_{57}H_{36}BrN$ = 814.81) |
| Sub 1-49 | m/z = 813.20 ($C_{57}H_{36}BrN$ = 814.81) | Sub 1-50 | m/z = 629.08 ($C_{40}H_{24}BrNS$ = 630.59) |
| Sub 1-51 | m/z = 613.10 ($C_{40}H_{24}BrNO$ = 614.53) | Sub 1-52 | m/z = 523.09 ($C_{34}H_{22}BrN$ = 524.45) |
| Sub 1-53 | m/z = 473.08 ($C_{30}H_{20}BrN$ = 474.39) | Sub 1-54 | m/z = 523.09 ($C_{34}H_{22}BrN$ = 524.45) |
| Sub 1-55 | m/z = 549.11 ($C_{36}H_{24}BrN$ = 550.49) | Sub 1-56 | m/z = 549.11 ($C_{36}H_{24}BrN$ = 550.49) |
| Sub 1-57 | m/z = 549.11 ($C_{36}H_{24}BrN$ = 550.49) | Sub 1-58 | m/z = 552.09 ($C_{33}H_{21}BrN_4$ = 553.45) |
| Sub 1-59 | m/z = 655.10 ($C_{42}H_{26}BrNS$ = 656.63) | Sub 1-60 | m/z = 676.15 ($C_{45}H_{29}BrN_2$ = 677.63) |
| Sub 1-61 | m/z = 513.11 ($C_{33}H_{24}BrN$ = 514.45) | Sub 1-62 | m/z = 677.15 ($C_{44}H_{29}BrN_3$ = 678.62) |
| Sub 1-63 | m/z = 549.11 ($C_{36}H_{24}BrN$ = 550.49) | Sub 1-64 | m/z = 713.17 ($C_{49}H_{32}BrN$ = 714.69) |
| Sub 1-65 | m/z = 713.17 ($C_{49}H_{32}BrN$ = 714.69) | Sub 1-66 | m/z = 713.17 ($C_{49}H_{32}BrN$ = 714.69) |
| Sub 1-67 | m/z = 713.17 ($C_{49}H_{32}BrN$ = 714.69) | Sub 1-68 | m/z = 625.14 ($C_{42}H_{28}BrN$ = 626.58) |
| Sub 1-69 | m/z = 625.14 ($C_{42}H_{28}BrN$ = 626.58) | Sub 1-70 | m/z = 625.14 ($C_{42}H_{28}BrN$ = 626.58) |
| Sub 1-71 | m/z = 625.14 ($C_{42}H_{28}BrN$ = 626.58) | Sub 1-72 | m/z = 625.14 ($C_{42}H_{28}BrN$ = 626.58) |
| Sub 1-73 | m/z = 625.14 ($C_{42}H_{28}BrN$ = 626.58) | Sub 1-74 | m/z = 625.14 ($C_{42}H_{28}BrN$ = 626.58) |
| Sub 1-75 | m/z = 625.14 ($C_{42}H_{28}BrN$ = 626.58) | Sub 1-76 | m/z = 625.14 ($C_{42}H_{28}BrN$ = 626.58) |
| Sub 1-77 | m/z = 625.14 ($C_{42}H_{28}BrN$ = 626.58) | Sub 1-78 | m/z = 625.14 ($C_{42}H_{28}BrN$ = 626.58) |
| Sub 1-79 | m/z = 625.14 ($C_{42}H_{28}BrN$ = 626.58) | Sub 1-80 | m/z = 635.20 ($C_{42}H_{18}D_{10}BrN$ = 636.64) |
| Sub 1-81 | m/z = 635.20 ($C_{42}H_{18}D_{10}BrN$ = 636.) | Sub 1-82 | m/z = 763.19 ($C_{53}H_{34}BrN$ = 764.75) |
| Sub 1-83 | m/z = 630.17($C_{42}H_{23}D_5BrN$ = 631.6) | Sub 1-84 | m/z = 763.19 ($C_{53}H_{34}BrN$ = 764.75) |
| Sub 1-85 | m/z = 763.19 ($C_{53}H_{34}BrN$ = 764.75) | Sub 1-86 | m/z = 813.20 ($C_{57}H_{36}BrN$ = 814.81) |
| Sub 1-87 | m/z = 813.20 ($C_{57}H_{36}BrN$ = 814.81) | Sub 1-88 | m/z = 813.20 ($C_{57}H_{36}BrN$ = 814.81) |
| Sub 1-89 | m/z = 763.19 ($C_{53}H_{34}BrN$ = 764.75) | Sub 1-90 | m/z = 579.07 ($C_{36}H_{22}BrNS$ = 580.54) |
| Sub 1-91 | m/z = 813.20 ($C_{57}H_{36}BrN$ = 814.81) | Sub 1-92 | m/z = 579.07 ($C_{36}H_{22}BrNS$ = 580.54) |
| Sub 1-93 | m/z = 579.07 ($C_{36}H_{22}BrNS$ = 580.54) | Sub 1-94 | m/z = 563.09 ($C_{36}H_{22}BrNO$ = 564.47) |
| Sub 1-95 | m/z = 579.07 ($C_{36}H_{22}BrNS$ = 580.54) | Sub 1-96 | m/z = 563.09 ($C_{36}H_{22}BrNO$ = 564.47) |
| Sub 1-97 | m/z = 563.1 ($C_{36}H_{22}BrNO$ = 564.47) | Sub 1-98 | m/z = 813.20 ($C_{57}H_{36}BrN$ = 814.81) |
| Sub 1-99 | m/z = 563.1 ($C_{36}H_{22}BrNO$ = 564.47) | Sub 1-100 | m/z = 629.08 ($C_{40}H_{24}BrNS$ = 630.59) |
| Sub 1-101 | m/z = 813.20 ($C_{57}H_{36}BrN$ = 814.81) | Sub 1-102 | m/z = 523.09($C_{34}H_{22}BrN$ = 524.45) |
| Sub 1-103 | m/z = 613.10 ($C_{40}H_{24}BrNO$ = 614.53) | Sub 1-104 | m/z = 523.09 ($C_{34}H_{22}BrN$ = 524.45) |
| Sub 1-105 | m/z = 473.08 ($C_{30}H_{20}BrN$ = 474.39) | Sub 1-106 | m/z = 549.11 ($C_{36}H_{24}BrN$ = 550.49) |

TABLE 1-continued

| Compound | FD-MS | Compound | FD-MS |
|---|---|---|---|
| Sub 1-107 | m/z = 549.11 ($C_{36}H_{24}BrN$ = 550.49) | Sub 1-108 | m/z = 552.09 ($C_{33}H_{21}BrN_4$ = 553.45) |
| Sub 1-109 | m/z = 549.11($C_{36}H_{24}BrN$ = 550.49) | Sub 1-110 | m/z = 676.15 ($C_{45}H_{29}BrN_2$ = 677.63) |
| Sub 1-111 | m/z = 655.10 ($C_{42}H_{26}BrNS$ = 656.63) | Sub 1-112 | m/z = 677.15 ($C_{44}H_{28}BrN_3$ = 678.62) |
| Sub 1-113 | m/z = 513.11($C_{33}H_{24}BrN$ = 514.45) | Sub 1-114 | m/z = 713.17 ($C_{49}H_{32}BrN$ = 714.69) |
| Sub 1-115 | m/z = 549.11 ($C_{36}H_{24}BrN$ = 550.49) | Sub 1-116 | m/z = 713.17 ($C_{49}H_{32}BrN$ = 714.69) |
| Sub 1-117 | m/z = 713.17 ($C_{49}H_{32}BrN$ = 714.69) | Sub 1-118 | m/z = 625.14 ($C_{42}H_{28}BrN$ = 626.58) |
| Sub 1-119 | m/z = 713.17 ($C_{49}H_{32}BrN$ = 714.69) | Sub 1-120 | m/z = 625.14 ($C_{42}H_{28}BrN$ = 626.58) |
| Sub 1-121 | m/z = 625.14 ($C_{42}H_{28}BrN$ = 626.58) | Sub 1-122 | m/z = 625.14 ($C_{42}H_{28}BrN$ = 626.58) |
| Sub 1-123 | m/z = 625.14 ($C_{42}H_{28}BrN$ = 626.58) | Sub 1-124 | m/z = 625.14 ($C_{42}H_{28}BrN$ = 626.58) |
| Sub 1-125 | m/z = 625.14 ($C_{42}H_{28}BrN$ = 626.58) | Sub 1-126 | m/z = 625.14 ($C_{42}H_{28}BrN$ = 626.58) |
| Sub 1-127 | m/z = 625.14 ($C_{42}H_{28}BrN$ = 626.58) | Sub 1-128 | m/z = 625.14 ($C_{42}H_{28}BrN$ = 626.58) |
| Sub 1-129 | m/z = 625.14 ($C_{42}H_{28}BrN$ = 626.58) | Sub 1-130 | m/z = 635.20 ($C_{42}H_{18}D_{10}BrN$ = 636.64) |
| Sub 1-131 | m/z = 625.14 ($C_{42}H_{28}BrN$ = 626.58) | Sub 1-132 | m/z = 763.19 ($C_{53}H_{34}BrN$ = 764.75) |
| Sub 1-133 | m/z = 635.20 ($C_{42}H_{18}D_{10}BrN$ = 636.) | Sub 1-134 | m/z = 763.19 ($C_{53}H_{34}BrN$ = 764.75) |
| Sub 1-135 | m/z = 630.17 ($C_{42}H_{23}D_{5}BrN$ = 631.6) | Sub 1-136 | m/z = 813.20 ($C_{57}H_{36}BrN$ = 814.81) |
| Sub 1-137 | m/z = 763.19 ($C_{53}H_{34}BrN$ = 764.75) | Sub 1-138 | m/z = 813.20 ($C_{57}H_{36}BrN$ = 814.81) |
| Sub 1-139 | m/z = 813.20 ($C_{57}H_{36}BrN$ = 814.81) | Sub 1-140 | m/z = 579.07 ($C_{36}H_{22}BrNS$ = 580.54) |
| Sub 1-141 | m/z = 763.19 ($C_{53}H_{34}BrN$ = 764.75) | Sub 1-142 | m/z = 579.07 ($C_{36}H_{22}BrNS$ = 580.54) |
| Sub 1-143 | m/z = 813.20 ($C_{57}H_{36}BrN$ = 814.81) | Sub 1-144 | m/z = 563.09 ($C_{36}H_{22}BrNO$ = 564.47) |
| Sub 1-145 | m/z = 579.07 ($C_{36}H_{22}BrNS$ = 580.54) | Sub 1-146 | m/z = 563.09 ($C_{36}H_{22}BrNO$ = 564.47) |
| Sub 1-147 | m/z = 549.11 ($C_{36}H_{24}BrN$ = 550.49) | Sub 1-148 | m/z = 549.11 ($C_{36}H_{24}BrN$ = 550.49) |
| Sub 1-149 | m/z = 549.11 ($C_{36}H_{24}BrN$ = 550.49) | Sub 1-150 | m/z = 625.14 ($C_{42}H_{28}BrN$ = 626.58) |
| Sub 1-151 | m/z = 675.16 ($C_{46}H_{30}BrN$ = 646.64) | Sub 1-152 | m/z = 675.16 ($C_{46}H_{30}BrN$ = 646.64) |
| Sub 1-153 | m/z = 550.10 ($C_{35}H_{23}BrN_2$ = 551.47) | Sub 1-154 | m/z = 701.15 ($C_{46}H_{28}BrN_3$ = 702.64) |
| Sub 1-155 | m/z = 549.11 ($C_{36}H_{24}BrN$ = 550.49) | Sub 1-156 | m/z = 599.12 ($C_{40}H_{26}BrN$ = 600.55) |

II. Synthesis Examples of Sub 2

Sub 2 of the Reaction Scheme 1 can be synthesized according to, but not limited to, the following Reaction Scheme 47.

<Reaction Scheme 47>

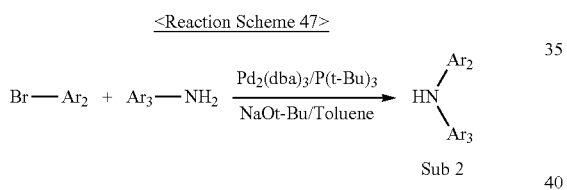

2. Synthesis of Sub 2-1

<Reaction Scheme 48>

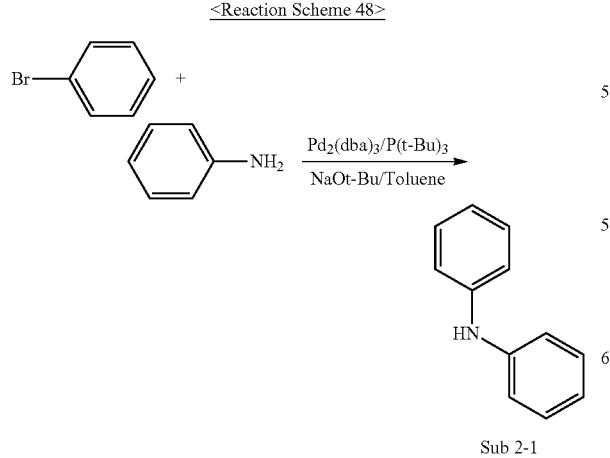

Bromobenzene (37.1 g, 236.2 mmol) was dissolved in toluene (2200 ml) in a round bottom flask. Then, aniline (20 g, 214.8 mmol), Pd$_2$(dba)$_3$ (9.83 g, 10.7 mmol), P(t-Bu)$_3$ (4.34 g, 21.5 mmol) and NaOt-Bu (62 g, 644.3 mmol) were added into the round bottom flask, and the mixture was stirred 100° C. After the completion of the reaction, the reaction product was extracted with ether and water. The extracted organic layer was dried over MgSO$_4$ and concentrated. The concentrated resultant was separated by silica gel column chromatography, and was then recrystallized, whereby a compound Sub 2-1 was obtained in an amount of 28 g in 77% yield.

2. Synthesis of Sub 2-3

<Reaction Scheme 49>

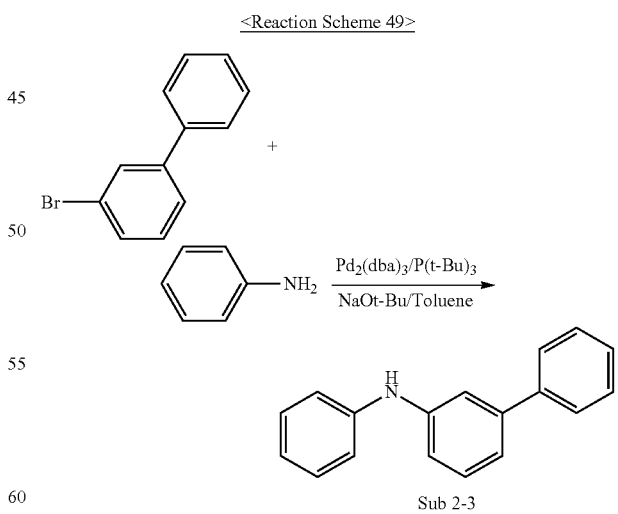

The compound Sub 2-3 was synthesized by using 3-bromo-1,1'-biphenyl (55.1 g, 236.2 mmol), aniline (20 g, 214.8 mmol), Pd$_2$(dba)$_3$ (9.83 g, 10.7 mmol), P(t-Bu)$_3$ (4.34 g, 21.5 mmol), NaOt-Bu (62 g, 644.3 mmol) and toluene (2200 ml) in the same manner as described in the synthesis method of the compound Sub 2-1 above, whereby a compound Sub 2-3 was obtained in an amount of 41.1 g in 78% yield.

3. Synthesis of Sub 2-4

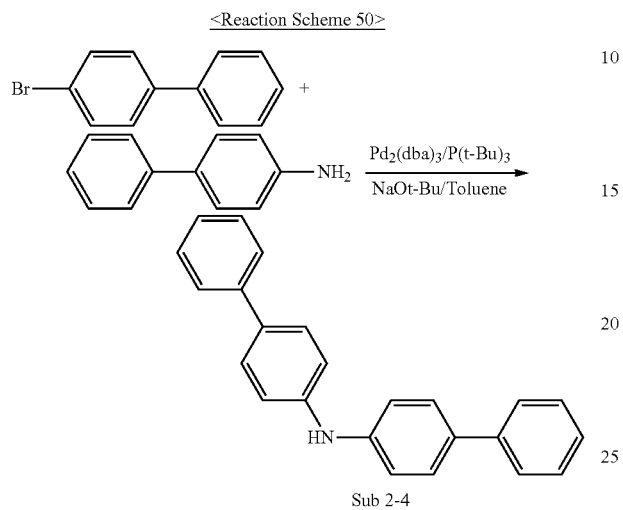

<Reaction Scheme 50>

Sub 2-4

The compound Sub 2-4 was synthesized by using 4-bromo-1,1'-biphenyl (37.88 g, 162.5 mmol), [1,1'-biphenyl]-4-amine (25 g, 147.7 mmol), Pd$_2$(dba)$_3$ (6.76 g, 7.4 mmol), P(t-Bu)$_3$ (3 g, 14.8 mmol) and NaOt-Bu (66.62 g, 693.2 mmol) in the same manner as described in the synthesis method of the compound Sub 2-1 above, whereby a compound Sub 2-4 was obtained in an amount of 35.6 g in 75% yield.

4. Synthesis of Sub 2-7

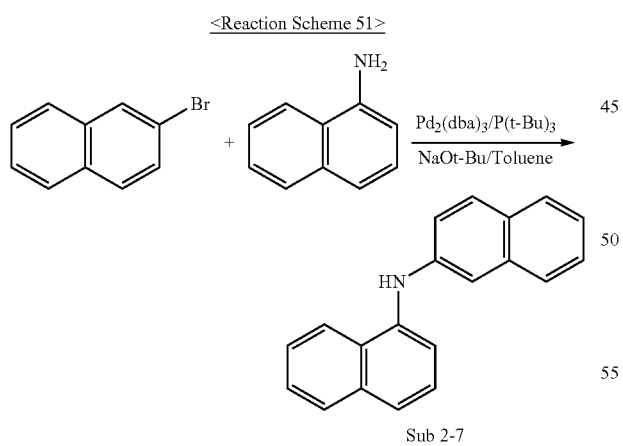

<Reaction Scheme 51>

Sub 2-7

The compound Sub 2-7 was synthesized by using 2-bromonaphthalene (39.8 g, 192.1 mmol), naphthalen-1-amine (25 g, 174.6 mmol), Pd$_2$(dba)$_3$ (8.0 g, 8.73 mmol), P(t-Bu)$_3$ (3.53 g, 17.5 mmol), NaOt-Bu (50.3 g, 523.8 mmol) and toluene (1800 ml) in the same manner as described in the synthesis method of the compound Sub 2-1 above, whereby a compound Sub 2-7 was obtained in an amount of 36.2 g in 77% yield.

5. Synthesis of Sub 2-9

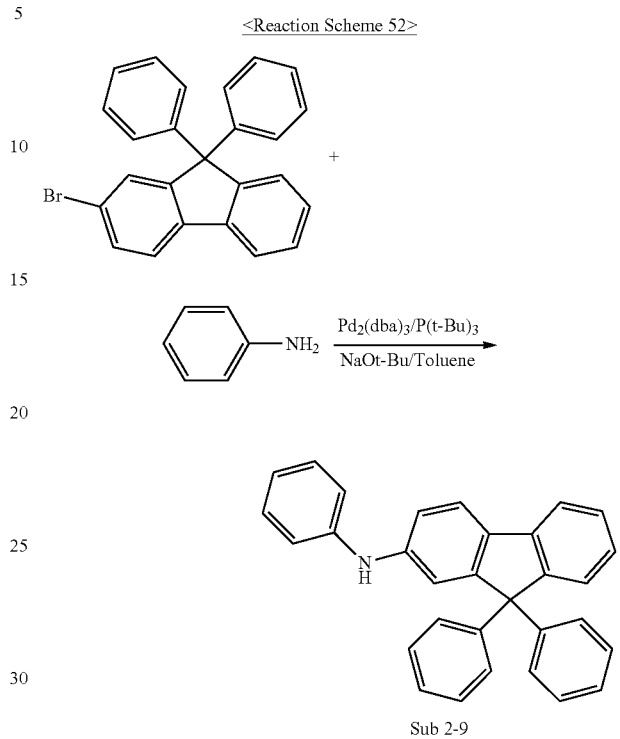

<Reaction Scheme 52>

Sub 2-9

The compound Sub 2-9 was synthesized by using 2-bromo-9,9-diphenyl-9H-fluorene (93.9 g, 236.2 mmol), toluene (2250 ml), aniline (20 g, 214.8 mmol), Pd$_2$(dba)$_3$ (9.83 g, 10.7 mmol), P(t-Bu)$_3$ (4.34 g, 21.5 mmol) and NaOt-Bu (62 g, 644.3 mmol) in the same manner as described in the synthesis method of the compound Sub 2-1 above, whereby a compound Sub 2-9 was obtained in an amount of 63.3 g in 72% yield.

6. Synthesis of Sub 2-12

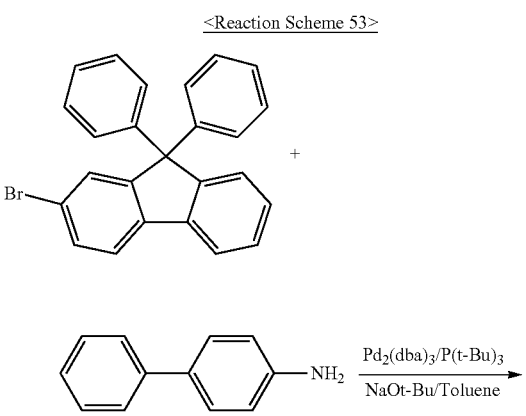

<Reaction Scheme 53>

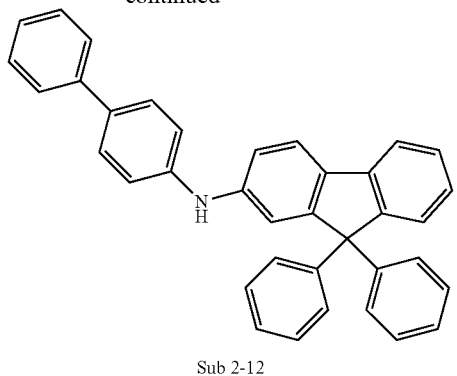

Sub 2-12

The compound Sub 2-12 was synthesized by using 2-bromo-9,9-diphenyl-9H-fluorene (64.6 g, 162.5 mmol), toluene (1550 ml), [1,1'-biphenyl]-4-amine (25 g, 147.7 mmol), Pd$_2$(dba)$_3$ (6.76 g, 162.5 mmol), P(t-Bu)$_3$ (3 g, 14.8 mmol) and NaOt-Bu (42.6 g, 443.2 mmol) in the same manner as described in the synthesis method of the compound Sub 2-1 above, whereby a compound Sub 2-12 was obtained in an amount of 53.8 g in 75% yield.

7. Synthesis of Sub 2-13

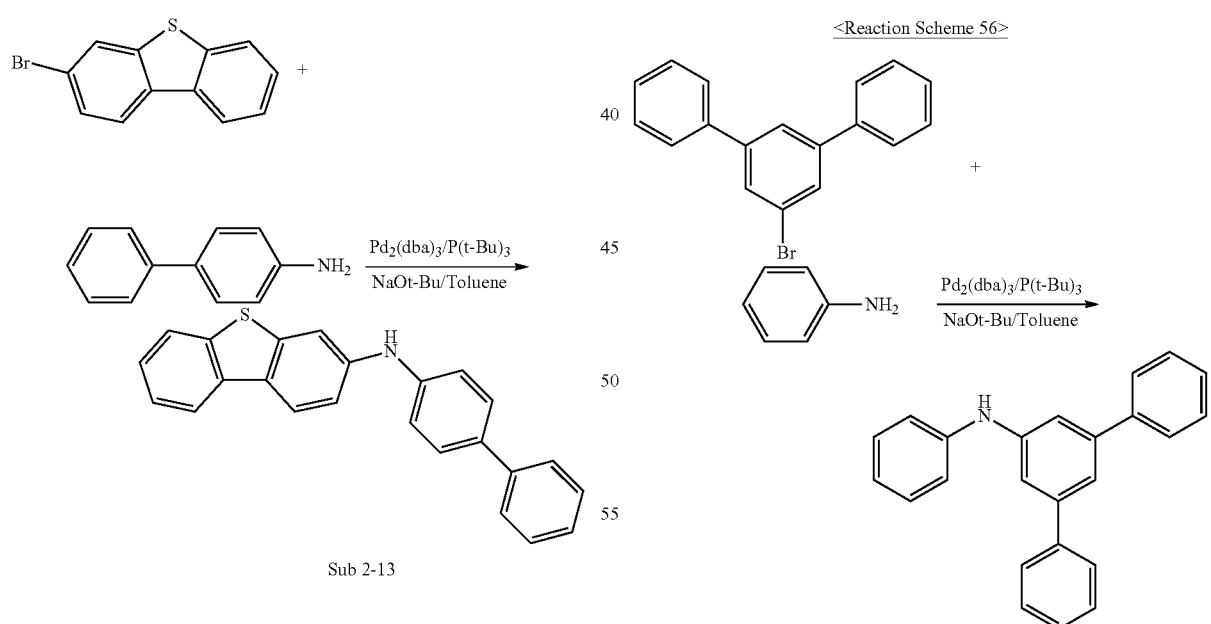

Sub 2-13

The compound Sub 2-13 was synthesized by using 3-bromodibenzo[b,d]thiophene (42.8 g, 162.5 mmol), toluene (1550 ml), [1,1'-biphenyl]-4-amine (25 g, 147.7 mmol), Pd$_2$(dba)$_3$ (6.76 g, 162.5 mmol), P(t-Bu)$_3$ (3 g, 14.8 mmol) and NaOt-Bu (42.6 g, 443.2 mmol) in the same manner as described in the synthesis method of the compound Sub 2-1 above, whereby a compound Sub 2-13 was obtained in an amount of 37.9 g in 73% yield.

8. Synthesis of Sub 2-17

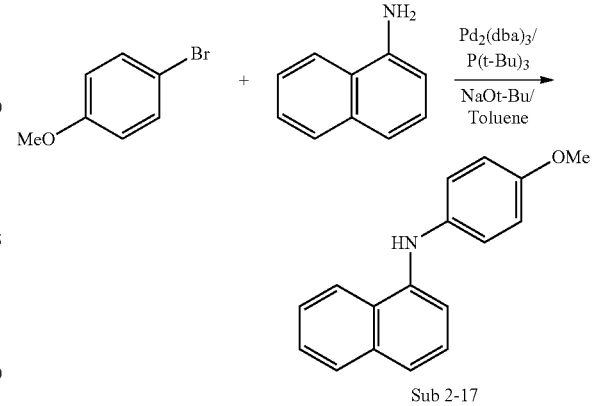

Sub 2-17

The compound Sub 2-17 was synthesized by using 1-bromo-4-methoxybenzene (36 g, 192.1 mmol), naphthalen-1-amine (25 g, 174.6 mmol), Pd$_2$(dba)$_3$ (8.0 g, 8.73 mmol), P(t-Bu)$_3$ (3.53 g, 17.5 mmol), NaOt-Bu (50.3 g, 523.8 mmol) and toluene (1800 ml) in the same manner as described in the synthesis method of the compound Sub 2-1 above, whereby a compound Sub 2-17 was obtained in an amount of 32.2 g in 74% yield.

9. Synthesis of Sub 2-26

<Reaction Scheme 56>

Sub 2-26

The compound Sub 2-26 was synthesized by using 5'-bromo-1,1':3',1''-terphenyl (73.04 g, 236.2 mmol), amine (20 g, 214.8 mmol), Pd$_2$(dba)$_3$ (9.83 g, 10.7 mmol), P(t-Bu)$_3$ (4.34 g, 21.5 mmol), NaOt-Bu (62 g, 644.3 mmol) and toluene (2250 ml) in the same manner as described in the synthesis method of the compound Sub 2-1 above, whereby a compound Sub 2-26 was obtained in an amount of 49 g in 71% yield.
Examples of Sub 2 compounds include, but are not limited to, the following compounds, and FD-MS data of the compounds are given in Table 2 below.
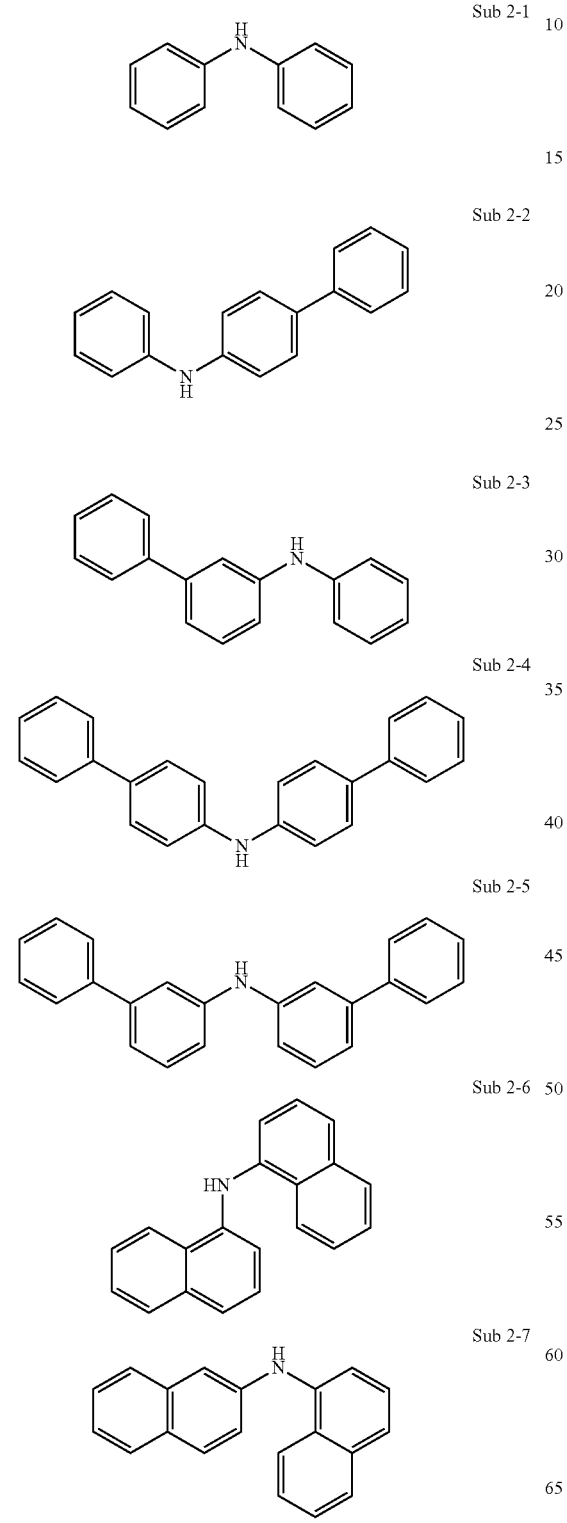
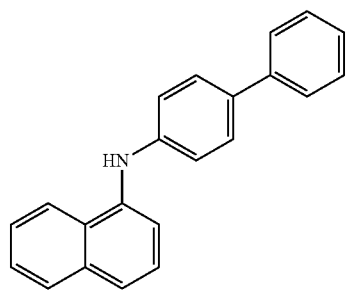
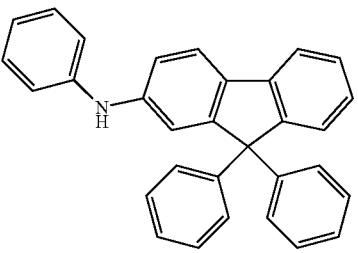
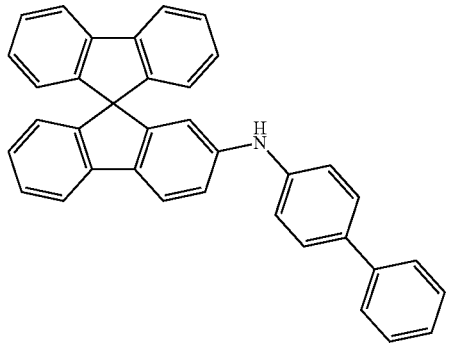
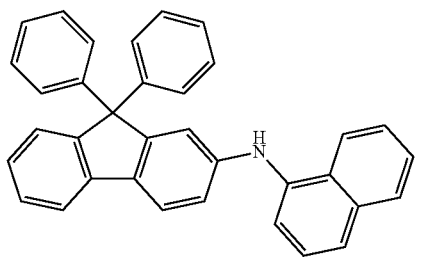
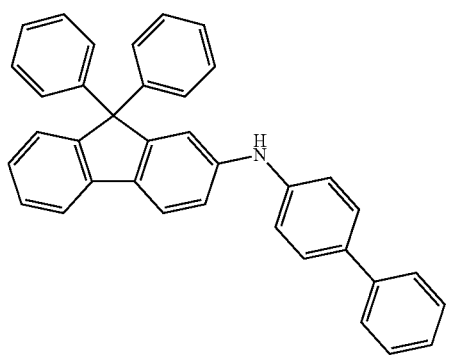

Sub 2-13
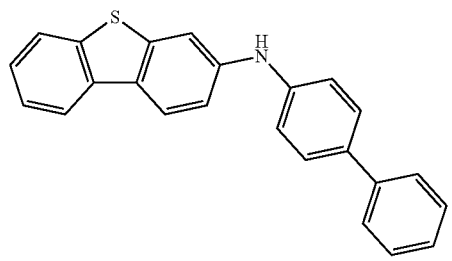
Sub 2-14
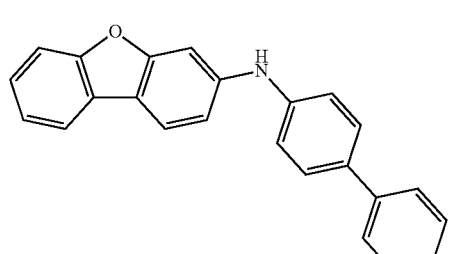
Sub 2-15
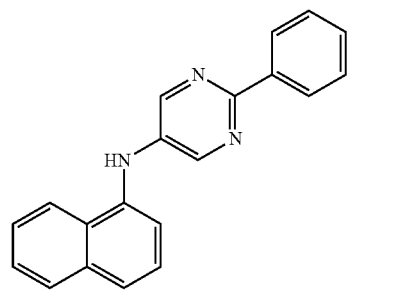
Sub 2-16
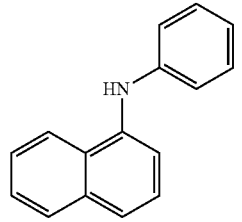
Sub 2-17
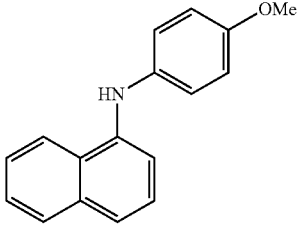
Sub 2-18
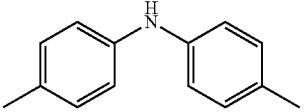
Sub 2-19
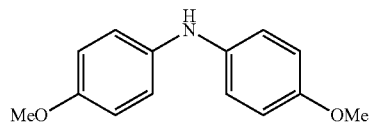
Sub 2-20
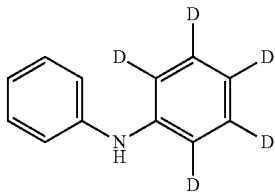
Sub 2-21
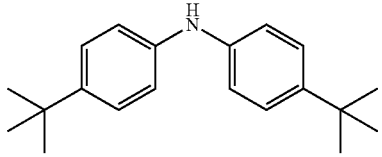
Sub 2-22
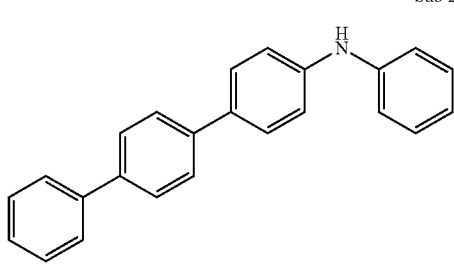
Sub 2-23
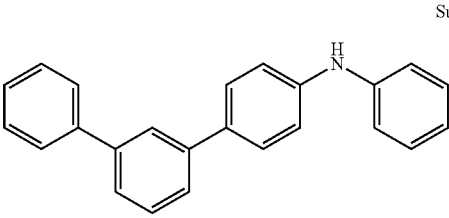
Sub 2-24
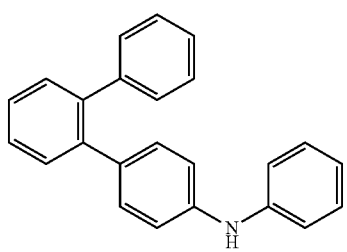
Sub 2-25
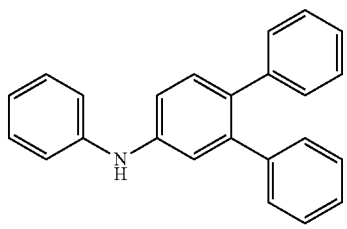
Sub 2-26
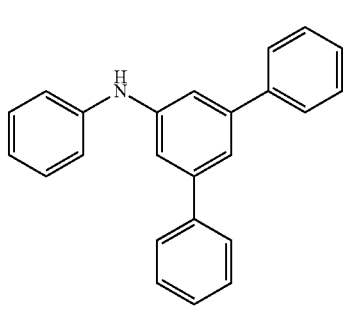

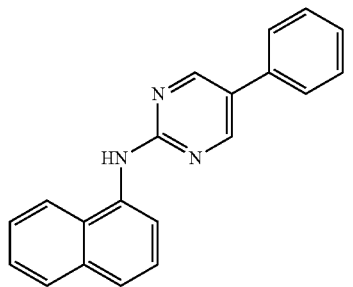

Sub 2-27

TABLE 2

| Compound | FD-MS | Compound | FD-MS |
|---|---|---|---|
| Sub 2-1 | m/z = 169.09 ($C_{12}H_{11}N$ = 169.22) | Sub 2-2 | m/z = 245.12 ($C_{18}H_{15}N$ = 245.32) |
| Sub 2-3 | m/z = 245.12 ($C_{18}H_{15}N$ = 245.32) | Sub 2-4 | m/z = 321.15 ($C_{24}H_{19}N$ = 321.41) |
| Sub 2-5 | m/z = 321.15 ($C_{24}H_{19}N$ = 321.41) | Sub 2-6 | m/z = 269.12 ($C_{20}H_{15}N$ = 269.34) |
| Sub 2-7 | m/z = 269.12 ($C_{20}H_{15}N$ = 269.34) | Sub 2-8 | m/z = 295.14 ($C_{22}H_{17}N$ = 295.38) |
| Sub 2-9 | m/z = 409.18 ($C_{31}H_{23}N$ = 409.52) | Sub 2-10 | m/z = 483.20 ($C_{37}H_{25}N$ = 483.60) |
| Sub 2-11 | m/z = 459.20 ($C_{35}H_{25}N$ = 459.58) | Sub 2-12 | m/z = 485.21 ($C_{37}H_{27}N$ = 485.62) |
| Sub 2-13 | m/z = 351.11 ($C_{34}H_{17}NS$ = 351.46) | Sub 2-14 | m/z = 335.13 ($C_{24}H_{17}NO$ = 335.40) |
| Sub 2-15 | m/z = 297.13 ($C_{20}H_{15}N_3$ = 297.35) | Sub 2-16 | m/z = 219.10 ($C_{16}H_{13}N$ = 219.28) |
| Sub 2-17 | m/z = 249.12 ($C_{17}H_{15}NO$ = 249.31) | Sub 2-18 | m/z = 197.12 ($C_{14}H_{15}N$ = 197.28) |
| Sub 2-19 | m/z = 229.11 ($C_{14}H_{15}NO_2$ = 229.27) | Sub 2-20 | m/z = 174.12 ($C_{12}H_6D_5N$ = 174.25) |
| Sub 2-21 | m/z = 281.21 ($C_{20}H_{27}N$ = 281.44) | Sub 2-22 | m/z = 321.15 ($C_{24}H_{19}N$ = 321.41) |
| Sub 2-23 | m/z = 321.15 ($C_{24}H_{19}N$ = 321.41) | Sub 2-24 | m/z = 321.15 ($C_{24}H_{19}N$ = 321.41) |
| Sub 2-25 | m/z = 321.15 ($C_{24}H_{19}N$ = 321.41) | Sub 2-26 | m/z = 321.15 ($C_{24}H_{19}N$ = 321.41) |
| Sub 2-27 | m/z = 297.13 ($C_{20}H_{15}N_3$ = 297.35) | | |

III. Synthesis Examples of Final Products

Sub 2 (1 eq) was dissolved in toluene in a round bottom flask. Then, 1 (1.1 eq), $Pd_2(dba)_3$ (0.05 eq), P(t-Bu)$_3$ (0.1 eq) and NaOt-Bu (3 eq) were added into the round bottom flask, and the mixture was stirred 100° C. After the completion of the reaction, the reaction product was extracted with $CH_2Cl_2$ and water. The extracted organic layer was dried over $MgSO_4$ and concentrated. The concentrated resultant was separated by silica gel column chromatography, and was then recrystallized, whereby Final products was obtained.

1. Synthesis of Product P1-1

<Reaction Scheme 57>

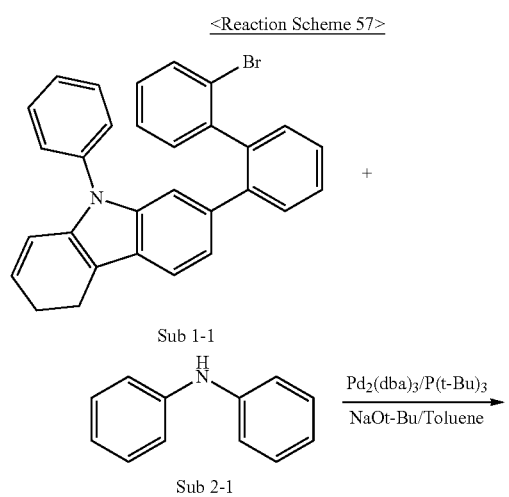

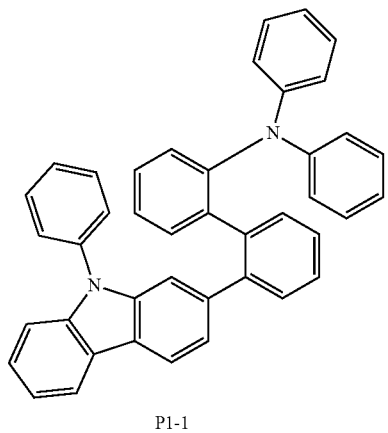

P1-1

Sub 2-1 (8 g, 47.3 mmol) was dissolved in in toluene (500 ml) in a round bottom flask. Then, Sub 1-1 (24.7 g, 52.0 mmol), $Pd_2(dba)_3$ (2.2 g, 2.4 mmol), P(t-Bu)$_3$ (1 g, 4.73 mmol) and NaOt-Bu (13.6 g, 141.8 mmol) were added into the round bottom flask, and the mixture was stirred at 100° C. After the completion of the reaction, the reaction product was extracted with $CH_2Cl_2$ and water. The extracted organic layer was dried over $MgSO_4$ and concentrated. The concentrated resultant was separated by silica gel column chromatography, and was then recrystallized, whereby a compound P1-1 was obtained in an amount of 20.2 g in 76% yield.

2. Synthesis of Product P1-4

<Reaction Scheme 58>

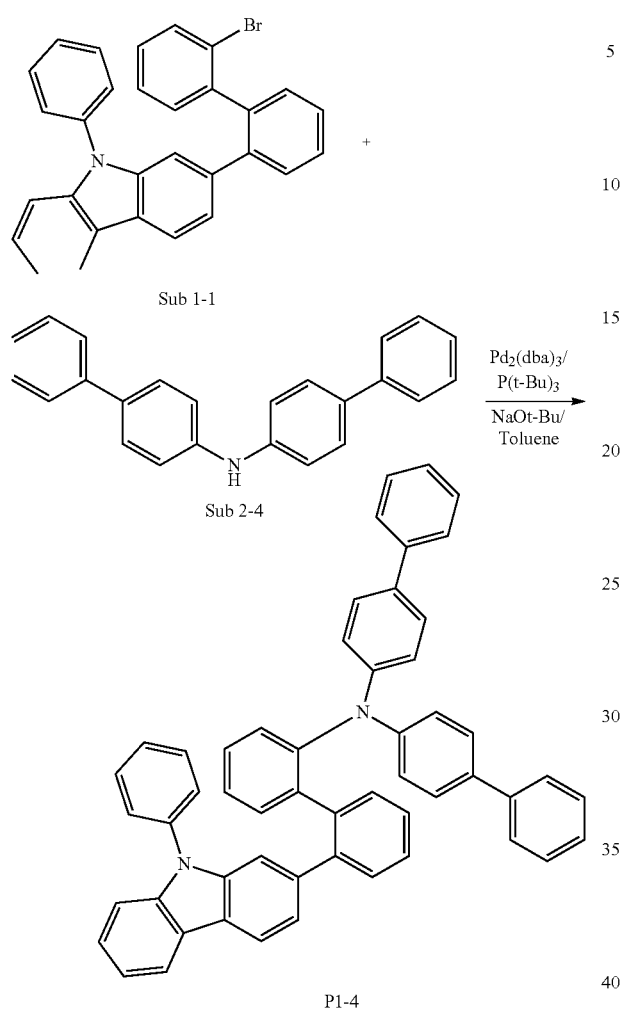

P1-4

The compound P1-4 was synthesized by using Sub 2-4 (8 g, 24.9 mmol), Sub 1-1 (13 g, 27.4 mmol), Pd$_2$(dba)$_3$ (1.14 g, 1.24 mmol), P(t-Bu)$_3$ (0.5 g, 2.49 mmol), NaOt-Bu (7.17 g, 74.7 mmol) and toluene (265 ml) in the same manner as described in the synthesis method of the compound Product P1-1 above, whereby a compound P1-4 was obtained in an amount of 13 g in 73% yield.

3. Synthesis of Product P1-8

<Reaction Scheme 59>

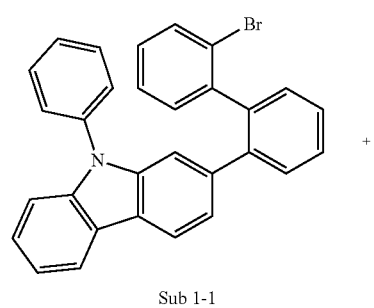

Sub 1-1

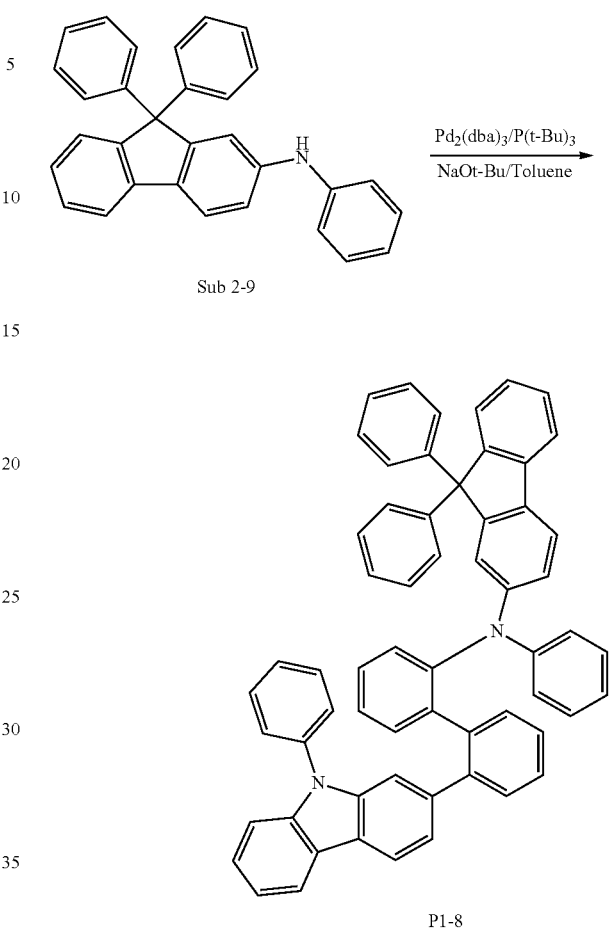

P1-8

The compound P1-8 was synthesized by using Sub 2-9 (10 g, 24.4 mmol), Sub 1-1 (12.7 g, 26.9 mmol), Pd$_2$(dba)$_3$ (1.12 g, 1.22 mmol), P(t-Bu)$_3$ (0.5 g, 2.44 mmol), NaOt-Bu (7.04 g, 73.3 mmol) and toluene (260 ml) in the same manner as described in the synthesis method of the compound Product P1-1 above, whereby a compound P1-8 was obtained in an amount of 15.1 g in 77% yield.

4. Synthesis of Product P1-17

<Reaction Scheme 60>

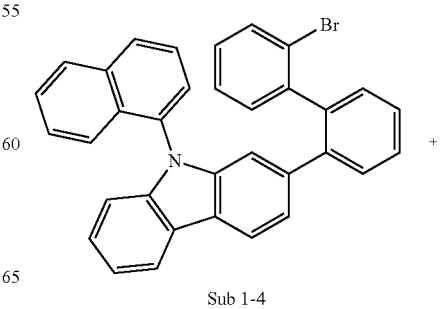

Sub 1-4

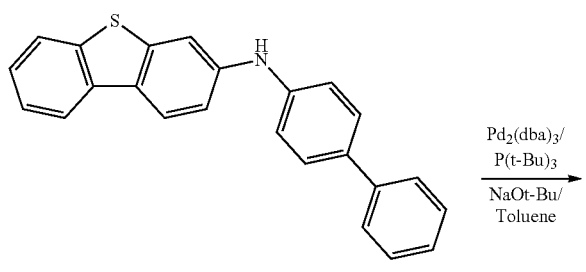

Sub 2-13

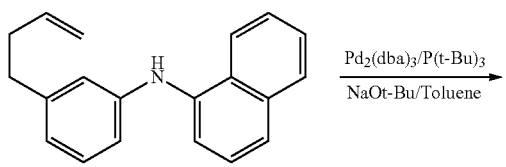

Sub 2-6

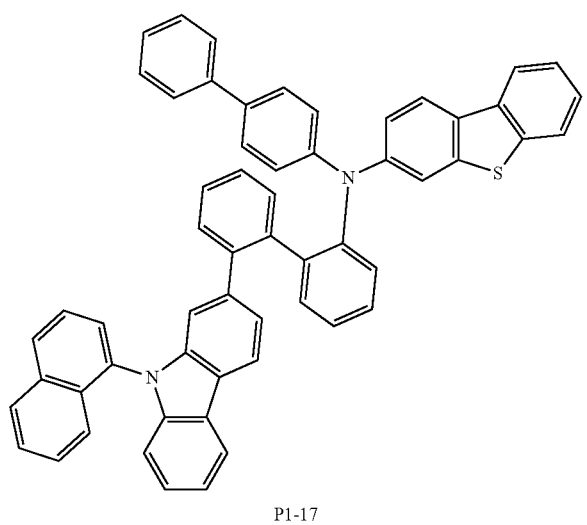

P1-17

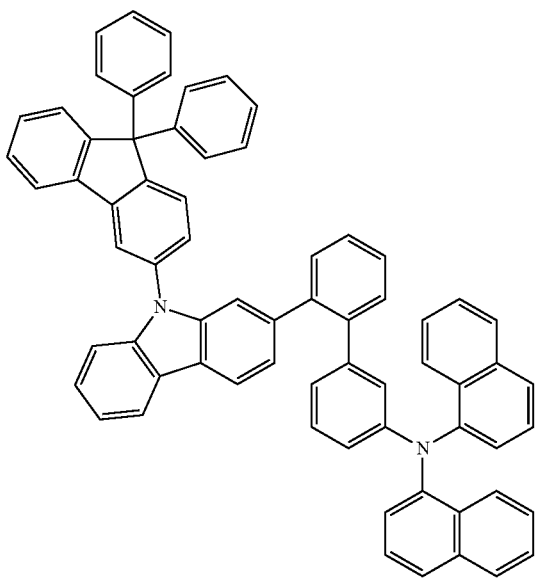

P2-49

The compound P1-17 was synthesized by using Sub 2-13 (10 g, 28.5 mmol), Sub 1-4 (16.4 g, 31.3 mmol), Pd$_2$(dba)$_3$ (1.3 g, 1.42 mmol), P(t-Bu)$_3$ (0.6 g, 2.85 mmol), NaOt-Bu (8.2 g, 85.4 mmol) and toluene (300 ml) in the same manner as described in the synthesis method of the compound Product P1-1 above, whereby a compound P1-17 was obtained in an amount of 16.1 g in 71% yield.

5. Synthesis of Product P2-49

The compound P2-49 was synthesized by using Sub 2-6 (10 g, 37.13 mmol), Sub 1-65 (29.2 g, 40.84 mmol), Pd$_2$(dba)$_3$ (1.7 g, 1.9 mmol), P(t-Bu)$_3$ (0.8 g, 3.7 mmol), NaOt-Bu (10.7 g, 111.4 mmol) and toluene (390 ml) in the same manner as described in the synthesis method of the compound Product P1-1 above, whereby a compound P2-49 was obtained in an amount of 25.1 g in 75% yield.

6. Synthesis of Product P2-77

<Reaction Scheme 61>

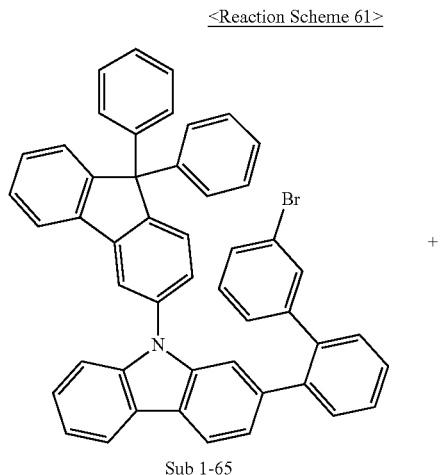

Sub 1-65

+

<Reaction Scheme 62>

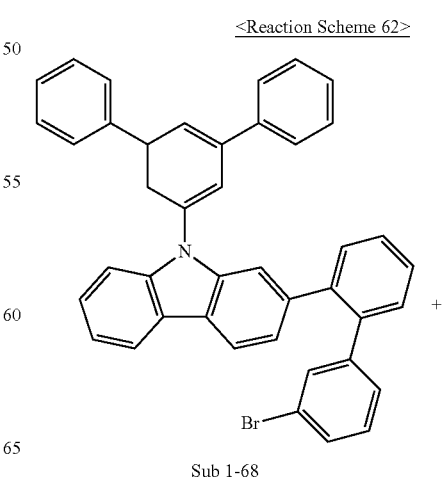

Sub 1-68

+

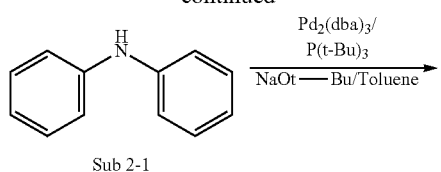

Sub 2-1

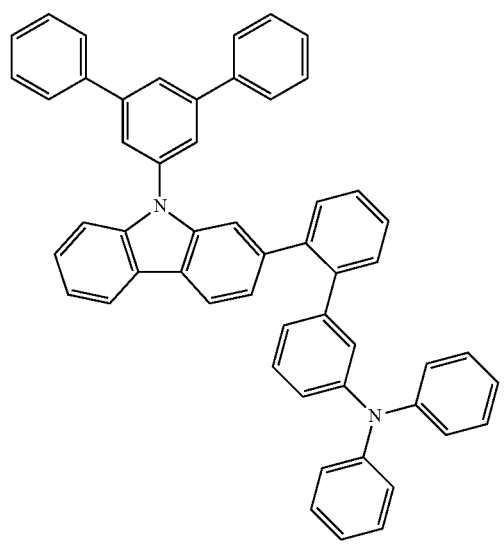

P2-77

The compound P2-77 was synthesized by using Sub 2-1 (8 g, 47.3 mmol), Sub 1-68 (32.6 g, 52 mmol), Pd$_2$(dba)$_3$ (2.2 g, 2.4 mmol), P(t-Bu)$_3$ (1 g, 4.73 mmol), NaOt-Bu (13.6 g, 141.8 mmol) and toluene (500 ml) in the same manner as described in the synthesis method of the compound Product P1-1 above, whereby a compound P2-77 was obtained in an amount of 23.7 g in 70% yield.

7. Synthesis of Product P3-4

<Reaction Scheme 63>

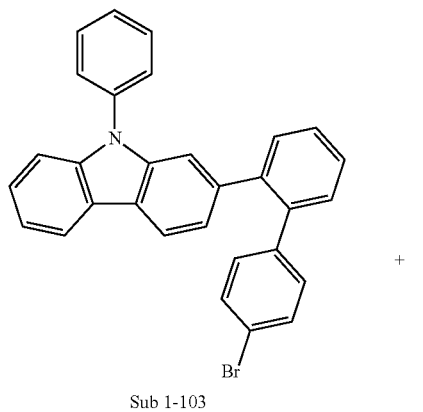

Sub 1-103

+

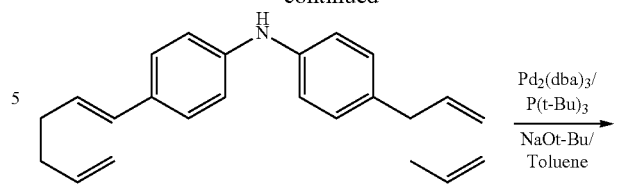

Sub 2-4

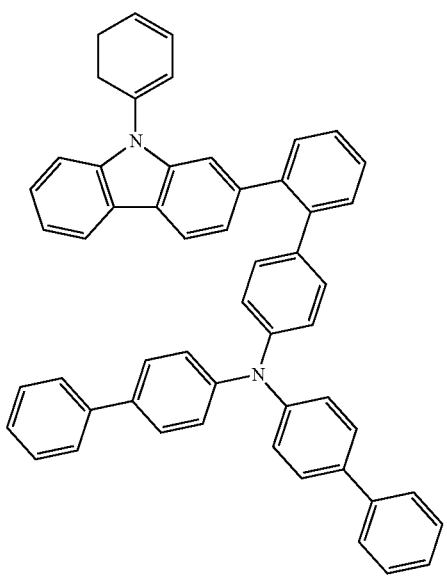

P3-4

The compound P3-4 was synthesized by using Sub 2-4 (8 g, 24.9 mmol), Sub 1-103 (13 g, 27.4 mmol), Pd$_2$(dba)$_3$ (1.14 g, 1.24 mmol), P(t-Bu)$_3$ (0.5 g, 2.49 mmol), NaOt-Bu (7.17 g, 74.7 mmol) and toluene (265 ml) in the same manner as described in the synthesis method of the compound Product P1-1 above, whereby a compound P3-4 was obtained in an amount of 13 g in 73% yield.

8. Synthesis of Product P4-3

<Reaction Scheme 64>

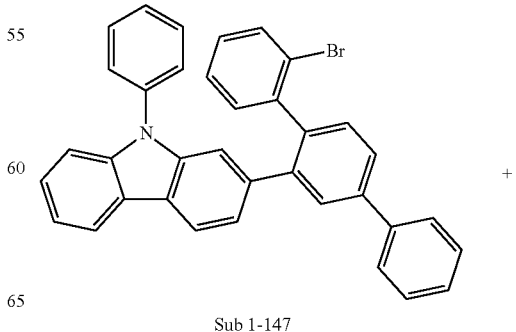

Sub 1-147

+

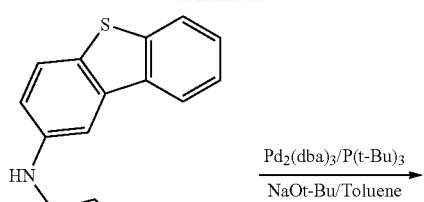

Sub 2-13

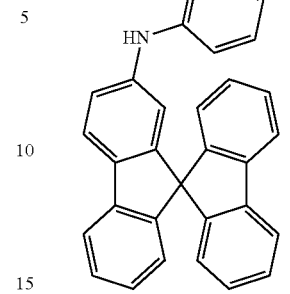

Sub 2-10

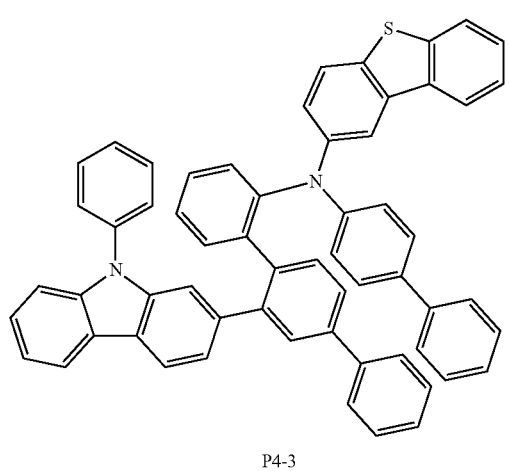

P4-3

The compound P4-3 was synthesized by using Sub 1-147 (26.0 g, 47.3 mmol), Sub 2-13 (18.3 g, 52 mmol), Pd$_2$(dba)$_3$(2.2 g, 2.4 mmol), P(t-Bu)$_3$(1 g, 4.73 mmol), NaOt-Bu (13.6 g, 141.8 mmol) and toluene (500 mL) in the same manner as described in the synthesis method of the compound Product P1-1 above, whereby a compound P4-3 was obtained in an amount of 23.7 g in 61% yield.

9. Synthesis of Product P4-23

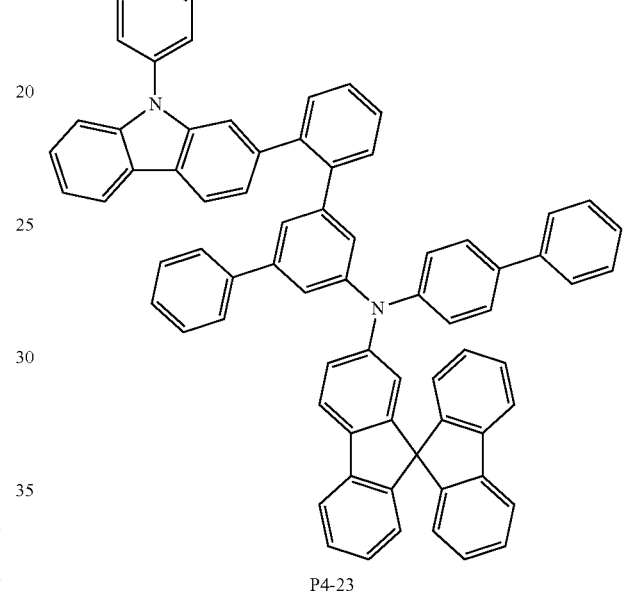

P4-23

The compound P4-23 was synthesized by using Sub 1-155 (26.0 g, 47.3 mmol) 이 Sub 2-10 (25.1 g, 52 mmol), Pd$_2$(dba)$_3$(2.2 g, 2.4 mmol), P(t-Bu)$_3$(1 g, 4.73 mmol), NaOt-Bu (13.6 g, 141.8 mmol) and toluene (500 mL) in the same manner as described in the synthesis method of the compound Product P1-1 above, whereby a compound P4-23 was obtained in an amount of 28.9 g in 64% yield.

10. Synthesis of Product 4-17

<Reaction Scheme 66>

<Reaction Scheme 65>

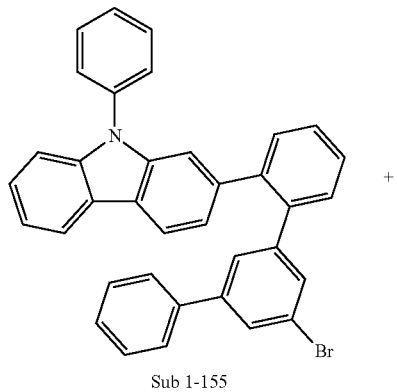

Sub 1-155

+

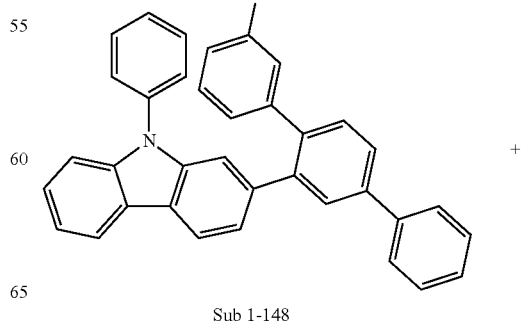

Sub 1-148

+

-continued

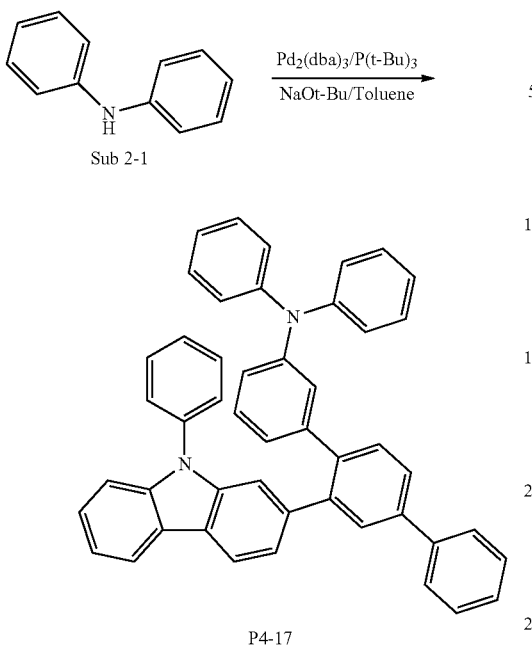

P4-17

The compound 4-17 was synthesized by using Sub 1-148 (26.0 g, 47.3 mmol) 에 Sub 2-1 (8.8 g, 52 mmol), Pd$_2$(dba)$_3$(2.2 g, 2.4 mmol), P(t-Bu)$_3$(1 g, 4.73 mmol), NaOt-Bu (13.6 g, 141.8 mmol) and toluene (500 mL) in the same manner as described in the synthesis method of the compound Product P1-1 above, whereby a compound 4-17 was obtained in an amount of 19.0 g in 63% yield.

11. Synthesis of Product P4-41

-continued

P4-41

The compound P4-41 was synthesized by using Sub 1-156 (28.4 g, 47.3 mmol), Sub 2-1 (8.8 g, 52 mmol), Pd$_2$(dba)$_3$(2.2 g, 2.4 mmol), P(t-Bu)$_3$(1 g, 4.73 mmol), NaOt-Bu (13.6 g, 141.8 mmol) and toluene (500 mL) in the same manner as described in the synthesis method of the compound Product P1-1 above, whereby a compound P4-41 was obtained in an amount of 21.2 g in 65% yield.

12. Synthesis of Product P4-48

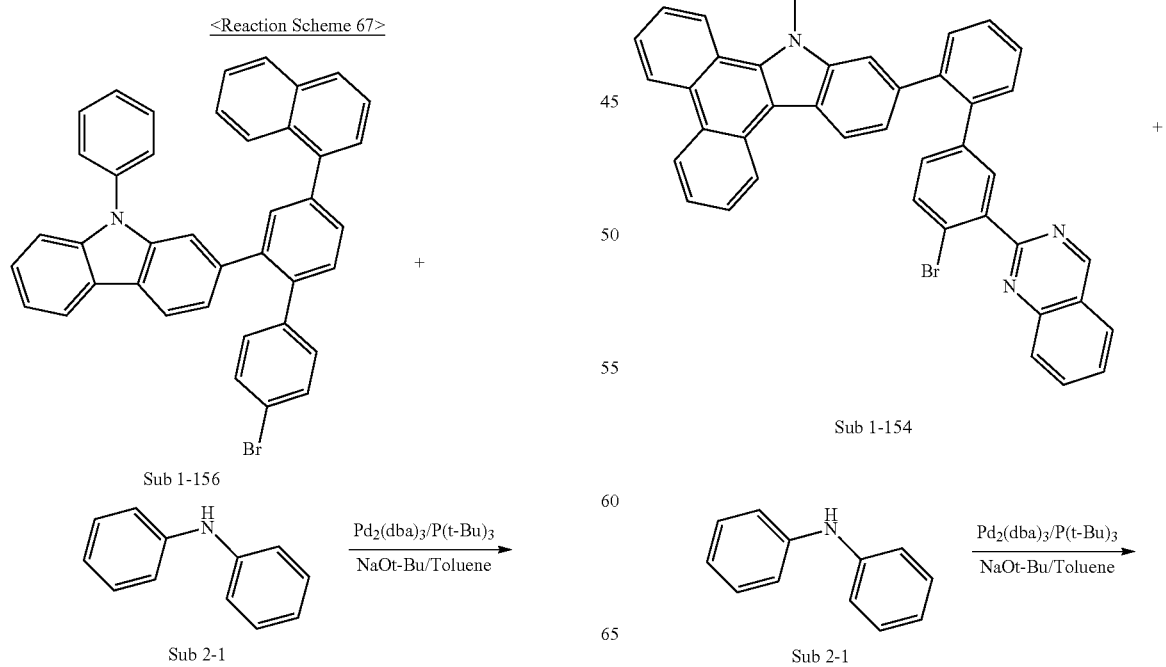

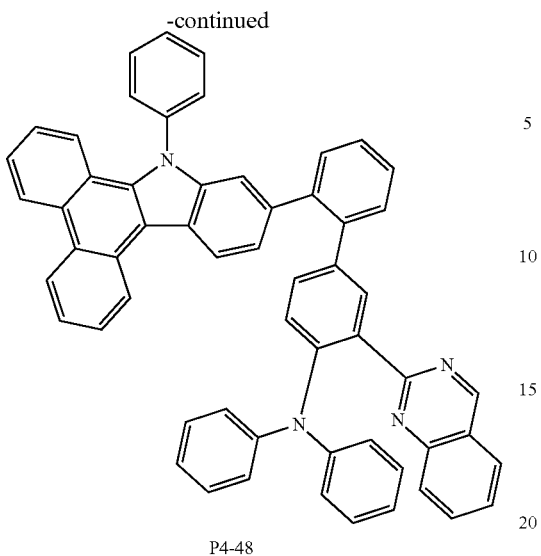

P4-48

The compound P4-48 was synthesized by using Sub 1-154 (33.2 g, 47.3 mmol) 와 Sub 2-1 (8.8 g, 52 mmol), Pd$_2$(dba)$_3$(2.2 g, 2.4 mmol), P(t-Bu)$_3$(1 g, 4.73 mmol), NaOt-Bu (13.6 g, 141.8 mmol) and toluene (500 mL) in the same manner as described in the synthesis method of the compound Product P1-1 above, whereby a compound P4-48 was obtained in an amount of 20.6 g in 55% yield.

FD-MS data of the final products of the inventive compounds P1-1 to P1-112, P2-1 to P2-112, P3-1 to P3-112, and P4-1 to P4-48 according to the above synthesises are given in Table 3 below.

TABLE 3

| Compound | FD-MS | Compound | FD-MS |
|---|---|---|---|
| P1-1 | m/z = 562.24 (C$_{42}$H$_{30}$N$_2$ = 562.70) | P1-2 | m/z = 638.27 (C$_{48}$H$_{34}$N$_2$ = 638.80) |
| P1-3 | m/z = 638.27 (C$_{48}$H$_{34}$N$_2$ = 638.80) | P1-4 | m/z = 714.30 (C$_{48}$H$_{34}$N$_2$ = 714.89) |
| P1-5 | m/z = 662.27 (C$_{50}$H$_{34}$N$_2$ = 662.82) | P1-6 | m/z = 662.27 (C$_{50}$H$_{34}$N$_2$ = 662.82) |
| P1-7 | m/z = 688.29 (C$_{52}$H$_{36}$N$_2$ = 688.86) | P1-8 | m/z = 802.33 (C$_{52}$H$_{36}$N$_2$ = 803.00) |
| P1-9 | m/z = 714.30 (C$_{54}$H$_{38}$N$_2$ = 714.89) | P1-10 | m/z = 876.35 (C$_{67}$H$_{44}$N$_2$ = 877.08) |
| P1-11 | m/z = 612.26 (C$_{46}$H$_{32}$N$_2$ = 612.76) | P1-12 | m/z = 764.32 (C$_{58}$H$_{40}$N$_2$ = 764.95) |
| P1-13 | m/z = 928.38 (C$_{71}$H$_{48}$N$_2$ = 929.15) | P1-14 | m/z = 714.30 (C$_{54}$H$_{38}$N$_2$ = 714.89) |
| P1-15 | m/z = 764.32 (C$_{58}$H$_{40}$N$_2$ = 764.95) | P1-16 | m/z = 738.30 (C$_{56}$H$_{38}$N$_2$ = 738.91) |
| P1-17 | m/z = 794.28 (C$_{58}$H$_{38}$N$_2$S = 795.00) | P1-18 | m/z = 778.30 (C$_{58}$H$_{38}$N$_2$O = 778.94) |
| P1-19 | m/z = 740.29 (C$_{54}$H$_{36}$N$_4$ = 740.89) | P1-20 | m/z = 740.29 (C$_{54}$H$_{36}$N$_4$ = 740.89) |
| P1-21 | m/z = 638.27 (C$_{48}$H$_{34}$N$_2$ = 638.80) | P1-22 | m/z = 638.27 (C$_{48}$H$_{34}$N$_2$ = 638.80) |
| P1-23 | m/z = 856.39 (C$_{62}$H$_{52}$N$_2$S = 857.15) | P1-24 | m/z = 741.29 (C$_{53}$H$_{35}$N$_5$ = 741.88) |
| P1-25 | m/z = 602.27 (C$_{45}$H$_{34}$N$_2$ = 602.76) | P1-26 | m/z = 815.33 (C$_{61}$H$_{41}$N$_3$ = 816.00) |
| P1-27 | m/z = 718.30 (C$_{53}$H$_{38}$N$_2$O = 718.88) | P1-28 | m/z = 866.34 (C$_{64}$H$_{42}$N$_4$ = 867.05) |
| P1-29 | m/z = 802.33 (C$_{61}$H$_{42}$N$_2$ = 803.00) | P1-30 | m/z = 878.37 (C$_{67}$H$_{46}$N$_2$ = 879.10) |
| P1-31 | m/z = 878.37 (C$_{67}$H$_{46}$N$_2$ = 879.10) | P1-32 | m/z = 954.40 (C$_{73}$H$_{50}$N$_2$ = 955.19) |
| P1-33 | m/z = 902.37 (C$_{69}$H$_{46}$N$_2$ = 903.12) | P1-34 | m/z = 902.37 (C$_{69}$H$_{46}$N$_2$ = 903.12) |
| P1-35 | m/z = 928.38 (C$_{71}$H$_{48}$N$_2$ = 929.15) | P1-36 | m/z = 1092.44 (C$_{84}$H$_{56}$N$_2$ = 1093.36) |
| P1-37 | m/z = 954.40 (C$_{73}$H$_{50}$N$_2$ = 955.19) | P1-38 | m/z = 1116.44 (C$_{86}$H$_{56}$N$_2$ = 1117.38) |
| P1-39 | m/z = 852.35 (C$_{65}$H$_{44}$N$_2$ = 853.06) | P1-40 | m/z = 954.40 (C$_{73}$H$_{50}$N$_2$ = 955.19) |
| P1-41 | m/z = 954.40 (C$_{73}$H$_{50}$N$_2$ = 955.19) | P1-42 | m/z = 954.40 (C$_{73}$H$_{50}$N$_2$ = 955.19) |
| P1-43 | m/z = 954.40 (C$_{73}$H$_{50}$N$_2$ = 955.19) | P1-44 | m/z = 954.40 (C$_{73}$H$_{50}$N$_2$ = 955.19) |
| P1-45 | m/z = 802.33 (C$_{61}$H$_{42}$N$_2$ = 803.00) | P1-46 | m/z = 878.37 (C$_{67}$H$_{46}$N$_2$ = 879.10) |
| P1-47 | m/z = 878.37 (C$_{67}$H$_{46}$N$_2$ = 879.10) | P1-48 | m/z = 954.40 (C$_{73}$H$_{50}$N$_2$ = 955.19) |
| P1-49 | m/z = 902.37 (C$_{69}$H$_{46}$N$_2$ = 903.12) | P1-50 | m/z = 902.37 (C$_{69}$H$_{46}$N$_2$ = 903.12) |
| P1-51 | m/z = 928.38 (C$_{71}$H$_{48}$N$_2$ = 929.15) | P1-52 | m/z = 1092.44 (C$_{84}$H$_{56}$N$_2$ = 1093.36) |
| P1-53 | m/z = 954.40 (C$_{73}$H$_{50}$N$_2$ = 955.19) | P1-54 | m/z = 1116.44 (C$_{86}$H$_{56}$N$_2$ = 1117.38) |
| P1-55 | m/z = 852.35 (C$_{65}$H$_{44}$N$_2$ = 853.06) | P1-56 | m/z = 954.40 (C$_{73}$H$_{50}$N$_2$ = 955.19) |
| P1-57 | m/z = 954.40 (C$_{73}$H$_{50}$N$_2$ = 955.19) | P1-58 | m/z = 954.40 (C$_{73}$H$_{50}$N$_2$ = 955.19) |
| P1-59 | m/z = 954.40 (C$_{73}$H$_{50}$N$_2$ = 955.19) | P1-60 | m/z = 954.40 (C$_{73}$H$_{50}$N$_2$ = 955.19) |
| P1-61 | m/z = 802.33 (C$_{61}$H$_{42}$N$_2$ = 803.00) | P1-62 | m/z = 878.37 (C$_{67}$H$_{46}$N$_2$ = 879.10) |
| P1-63 | m/z = 878.37 (C$_{67}$H$_{46}$N$_2$ = 879.10) | P1-64 | m/z = 954.40 (C$_{73}$H$_{50}$N$_2$ = 955.19) |
| P1-65 | m/z = 902.37 (C$_{69}$H$_{46}$N$_2$ = 903.12) | P1-66 | m/z = 902.37 (C$_{69}$H$_{46}$N$_2$ = 903.12) |
| P1-67 | m/z = 928.38 (C$_{71}$H$_{48}$N$_2$ = 929.15) | P1-68 | m/z = 1092.44 (C$_{84}$H$_{56}$N$_2$ = 1093.36) |
| P1-69 | m/z = 954.40 (C$_{73}$H$_{50}$N$_2$ = 955.19) | P1-70 | m/z = 1116.44 (C$_{86}$H$_{56}$N$_2$ = 1117.38) |
| P1-71 | m/z = 852.35 (C$_{65}$H$_{44}$N$_2$ = 853.06) | P1-72 | m/z = 954.40 (C$_{73}$H$_{50}$N$_2$ = 955.19) |
| P1-73 | m/z = 954.40 (C$_{73}$H$_{50}$N$_2$ = 955.19) | P1-74 | m/z = 954.40 (C$_{73}$H$_{50}$N$_2$ = 955.19) |
| P1-75 | m/z = 954.40 (C$_{73}$H$_{50}$N$_2$ = 955.19) | P1-76 | m/z = 954.40 (C$_{73}$H$_{50}$N$_2$ = 955.19) |
| P1-77 | m/z = 714.30 (C$_{54}$H$_{38}$N$_2$ = 714.89) | P1-78 | m/z = 790.33 (C$_{60}$H$_{42}$N$_2$ = 790.99) |
| P1-79 | m/z = 790.33 (C$_{60}$H$_{42}$N$_2$ = 790.99) | P1-80 | m/z = 866.37 (C$_{60}$H$_{42}$N$_2$ = 867.08) |
| P1-81 | m/z = 814.33 (C$_{62}$H$_{42}$N$_2$ = 815.01) | P1-82 | m/z = 814.33 (C$_{62}$H$_{42}$N$_2$ = 815.01) |
| P1-83 | m/z = 840.35 (C$_{64}$H$_{44}$N$_2$ = 841.05) | P1-84 | m/z = 1004.41 (C$_{77}$H$_{52}$N$_2$ = 1005.25) |
| P1-85 | m/z = 866.37 (C$_{66}$H$_{46}$N$_2$ = 867.08) | P1-86 | m/z = 714.30 (C$_{54}$H$_{38}$N$_2$ = 714.89) |
| P1-87 | m/z = 714.30 (C$_{54}$H$_{38}$N$_2$ = 714.89) | P1-88 | m/z = 714.30 (C$_{54}$H$_{38}$N$_2$ = 714.89) |
| P1-89 | m/z = 724.37 (C$_{54}$H$_{28}$D$_{10}$N$_2$ = 724.95) | P1-90 | m/z = 800.40 (C$_{60}$H$_{32}$D$_{10}$N$_2$ = 801.05) |
| P1-91 | m/z = 871.40 (C$_{66}$H$_{41}$D$_5$N$_2$ = 872.12) | P1-92 | m/z = 719.33 (C$_{54}$H$_{33}$D$_5$N$_2$ = 719.92) |
| P1-93 | m/z = 852.35 (C$_{65}$H$_{44}$N$_2$ = 853.06) | P1-94 | m/z = 902.37 (C$_{69}$H$_{46}$N$_2$ = 903.12) |
| P1-95 | m/z = 852.35 (C$_{65}$H$_{44}$N$_2$ = 853.06) | P1-96 | m/z = 902.37 (C$_{69}$H$_{46}$N$_2$ = 903.12) |

TABLE 3-continued

| Compound | FD-MS | Compound | FD-MS |
|---|---|---|---|
| P1-97 | m/z = 930.40 ($C_{71}H_{50}N_2$ = 931.17) | P1-98 | m/z = 912.37 ($C_{67}H_{48}N_2O_2$ = 913.11) |
| P1-99 | m/z = 902.37 ($C_{69}H_{46}N_2$ = 903.12) | P1-100 | m/z = 902.37 ($C_{69}H_{46}N_2$ = 903.12) |
| P1-101 | m/z = 768.26 ($C_{56}H_{36}N_2S$ = 903.12) | P1-102 | m/z = 768.26 ($C_{56}H_{36}N_2S$ = 903.12) |
| P1-103 | m/z = 794.28 ($C_{58}H_{38}N_2S$ = 795.00) | P1-104 | m/z = 958.34 ($C_{71}H_{46}N_2S$ = 959.20) |
| P1-105 | m/z = 752.28 ($C_{56}H_{36}N_2O$ = 752.90) | P1-106 | m/z = 752.28 ($C_{56}H_{36}N_2O$ = 752.90) |
| P1-107 | m/z = 778.30 ($C_{58}H_{38}N_2O$ = 778.94) | P1-108 | m/z = 942.36 ($C_{71}H_{46}N_2O$ = 943.14) |
| P1-109 | m/z = 902.37 ($C_{69}H_{46}N_2$ = 903.12) | P1-110 | m/z = 902.37 ($C_{69}H_{46}N_2$ = 903.12) |
| P1-111 | m/z = 818.28 ($C_{60}H_{38}N_2$ = 819.02) | P1-112 | m/z = 802.30 ($C_{60}H_{38}N_2O$ = 802.96) |
| P2-1 | m/z = 562.24 ($C_{42}H_{30}N_2$ = 562.70) | P2-2 | m/z = 638.27 ($C_{48}H_{34}N_2$ = 638.80) |
| P2-3 | m/z = 638.27 ($C_{48}H_{34}N_2$ = 638.80) | P2-4 | m/z = 714.30 ($C_{48}H_{34}N_2$ = 714.89) |
| P2-5 | m/z = 662.27 ($C_{50}H_{34}N_2$ = 662.82) | P2-6 | m/z = 662.27 ($C_{50}H_{34}N_2$ = 662.82) |
| P2-7 | m/z = 688.29 ($C_{52}H_{36}N_2$ = 688.86) | P2-8 | m/z = 802.33 ($C_{52}H_{36}N_2$ = 803.00) |
| P2-9 | m/z = 714.30 ($C_{54}H_{38}N_2$ = 714.89) | P2-10 | m/z = 876.35 ($C_{67}H_{44}N_2$ = 877.08) |
| P2-11 | m/z = 612.26 ($C_{46}H_{32}N_2$ = 612.76) | P2-12 | m/z = 764.32 ($C_{58}H_{40}N_2$ = 764.95) |
| P2-13 | m/z = 928.38 ($C_{71}H_{48}N_2$ = 929.15) | P2-14 | m/z = 714.30 ($C_{54}H_{38}N_2$ = 714.89) |
| P2-15 | m/z = 764.32 ($C_{58}H_{40}N_2$ = 764.95) | P2-16 | m/z = 738.30 ($C_{56}H_{38}N_2$ = 738.91) |
| P2-17 | m/z = 794.28 ($C_{58}H_{38}N_2S$ = 795.00) | P2-18 | m/z = 778.30 ($C_{58}H_{38}N_2O$ = 778.94) |
| P2-19 | m/z = 740.29 ($C_{54}H_{36}N_4$ = 740.89) | P2-20 | m/z = 740.29 ($C_{54}H_{36}N_4$ = 740.89) |
| P2-21 | m/z = 638.27 ($C_{48}H_{34}N_2$ = 638.80) | P2-22 | m/z = 638.27 ($C_{48}H_{34}N_2$ = 638.80) |
| P2-23 | m/z = 856.39 ($C_{62}H_{52}N_2S$ = 857.15) | P2-24 | m/z = 741.29 ($C_{53}H_{35}N_5$ = 741.88) |
| P2-25 | m/z = 602.27 ($C_{45}H_{34}N_2$ = 602.76) | P2-26 | m/z = 815.33 ($C_{61}H_{41}N_3$ = 816.00) |
| P2-27 | m/z = 718.30 ($C_{53}H_{38}N_2O$ = 718.88) | P2-28 | m/z = 866.34 ($C_{64}H_{42}N_4$ = 867.05) |
| P2-29 | m/z = 802.33 ($C_{61}H_{42}N_2$ = 803.00) | P2-30 | m/z = 878.37 ($C_{67}H_{46}N_2$ = 879.10) |
| P2-31 | m/z = 878.37 ($C_{67}H_{46}N_2$ = 879.10) | P2-32 | m/z = 954.40 ($C_{73}H_{50}N_2$ = 955.19) |
| P2-33 | m/z = 902.37 ($C_{69}H_{46}N_2$ = 903.12) | P2-34 | m/z = 902.37 ($C_{69}H_{46}N_2$ = 903.12) |
| P2-35 | m/z = 928.38 ($C_{71}H_{48}N_2$ = 929.15) | P2-36 | m/z = 1092.44 ($C_{84}H_{56}N_2$ = 1093.36) |
| P2-37 | m/z = 954.40 ($C_{73}H_{50}N_2$ = 955.19) | P2-38 | m/z = 1116.44 ($C_{86}H_{56}N_2$ = 1117.38) |
| P2-39 | m/z = 852.35 ($C_{65}H_{44}N_2$ = 853.06) | P2-40 | m/z = 954.40 ($C_{73}H_{50}N_2$ = 955.19) |
| P2-41 | m/z = 954.40 ($C_{73}H_{50}N_2$ = 955.19) | P2-42 | m/z = 954.40 ($C_{73}H_{50}N_2$ = 955.19) |
| P2-43 | m/z = 954.40 ($C_{73}H_{50}N_2$ = 955.19) | P2-44 | m/z = 954.40 ($C_{73}H_{50}N_2$ = 955.19) |
| P2-45 | m/z = 802.33 ($C_{61}H_{42}N_2$ = 803.00) | P2-46 | m/z = 878.37 ($C_{67}H_{46}N_2$ = 879.10) |
| P2-47 | m/z = 878.37 ($C_{67}H_{46}N_2$ = 879.10) | P2-48 | m/z = 954.40 ($C_{73}H_{50}N_2$ = 955.19) |
| P2-49 | m/z = 902.37 ($C_{69}H_{46}N_2$ = 903.12) | P2-50 | m/z = 902.37 ($C_{69}H_{46}N_2$ = 903.12) |
| P2-51 | m/z = 928.38 ($C_{71}H_{48}N_2$ = 929.15) | P2-52 | m/z = 1092.44 ($C_{84}H_{56}N_2$ = 1093.36) |
| P2-53 | m/z = 954.40 ($C_{73}H_{50}N_2$ = 955.19) | P2-54 | m/z = 1116.44 ($C_{86}H_{56}N_2$ = 1117.38) |
| P2-55 | m/z = 852.35 ($C_{65}H_{44}N_2$ = 853.06) | P2-56 | m/z = 954.40 ($C_{73}H_{50}N_2$ = 955.19) |
| P2-57 | m/z = 954.40 ($C_{73}H_{50}N_2$ = 955.19) | P2-58 | m/z = 954.40 ($C_{73}H_{50}N_2$ = 955.19) |
| P2-59 | m/z = 954.40 ($C_{73}H_{50}N_2$ = 955.19) | P2-60 | m/z = 954.40 ($C_{73}H_{50}N_2$ = 955.19) |
| P2-61 | m/z = 802.33 ($C_{61}H_{42}N_2$ = 803.00) | P2-62 | m/z = 878.37 ($C_{67}H_{46}N_2$ = 879.10) |
| P2-63 | m/z = 878.37 ($C_{67}H_{46}N_2$ = 879.10) | P2-64 | m/z = 954.40 ($C_{73}H_{50}N_2$ = 955.19) |
| P2-65 | m/z = 902.37 ($C_{69}H_{46}N_2$ = 903.12) | P2-66 | m/z = 902.37 ($C_{69}H_{46}N_2$ = 903.12) |
| P2-67 | m/z = 928.38 ($C_{71}H_{48}N_2$ = 929.15) | P2-68 | m/z = 1092.44 ($C_{84}H_{56}N_2$ = 1093.36) |
| P2-69 | m/z = 954.40 ($C_{73}H_{50}N_2$ = 955.19) | P2-70 | m/z = 1116.44 ($C_{86}H_{56}N_2$ = 1117.38) |
| P2-71 | m/z = 852.35 ($C_{65}H_{44}N_2$ = 853.06) | P2-72 | m/z = 954.40 ($C_{73}H_{50}N_2$ = 955.19) |
| P2-73 | m/z = 954.40 ($C_{73}H_{50}N_2$ = 955.19) | P2-74 | m/z = 954.40 ($C_{73}H_{50}N_2$ = 955.19) |
| P2-75 | m/z = 954.40 ($C_{73}H_{50}N_2$ = 955.19) | P2-76 | m/z = 954.40 ($C_{73}H_{50}N_2$ = 955.19) |
| P2-77 | m/z = 714.30 ($C_{54}H_{38}N_2$ = 714.89) | P2-78 | m/z = 790.33 ($C_{60}H_{42}N_2$ = 790.99) |
| P2-79 | m/z = 790.33 ($C_{60}H_{42}N_2$ = 790.99) | P2-80 | m/z = 866.37 ($C_{60}H_{42}N_2$ = 867.08) |
| P2-81 | m/z = 814.33 ($C_{62}H_{42}N_2$ = 815.01) | P2-82 | m/z = 814.33 ($C_{62}H_{42}N_2$ = 815.01) |
| P2-83 | m/z = 840.35 ($C_{64}H_{44}N_2$ = 841.05) | P2-84 | m/z = 1004.41 ($C_{77}H_{52}N_2$ = 1005.25) |
| P2-85 | m/z = 866.37 ($C_{66}H_{46}N_2$ = 867.08) | P2-86 | m/z = 714.30 ($C_{54}H_{38}N_2$ = 714.89) |
| P2-87 | m/z = 714.30 ($C_{54}H_{38}N_2$ = 714.89) | P2-88 | m/z = 714.30 ($C_{54}H_{38}N_2$ = 714.89) |
| P2-89 | m/z = 724.37 ($C_{54}H_{28}D_{10}N_2$ = 724.95) | P2-90 | m/z = 800.40 ($C_{60}H_{32}D_{10}N_2$ = 801.05) |
| P2-91 | m/z = 871.40 ($C_{66}H_{41}D_5N_2$ = 872.12) | P2-92 | m/z = 719.33 ($C_{54}H_{33}D_5N_2$ = 719.92) |
| P2-93 | m/z = 852.35 ($C_{65}H_{44}N_2$ = 853.06) | P2-94 | m/z = 902.37 ($C_{69}H_{46}N_2$ = 903.12) |
| P2-95 | m/z = 852.35 ($C_{65}H_{44}N_2$ = 853.06) | P2-96 | m/z = 902.37 ($C_{69}H_{46}N_2$ = 903.12) |
| P2-97 | m/z = 930.40 ($C_{71}H_{50}N_2$ = 931.17) | P2-98 | m/z = 912.37 ($C_{67}H_{48}N_2O_2$ = 913.11) |
| P2-99 | m/z = 902.37 ($C_{69}H_{46}N_2$ = 903.12) | P2-100 | m/z = 902.37 ($C_{69}H_{46}N_2$ = 903.12) |
| P2-101 | m/z = 768.26 ($C_{56}H_{36}N_2S$ = 903.12) | P2-102 | m/z = 768.26 ($C_{56}H_{36}N_2S$ = 903.12) |
| P2-103 | m/z = 794.28 ($C_{58}H_{38}N_2S$ = 795.00) | P2-104 | m/z = 958.34 ($C_{71}H_{46}N_2S$ = 959.20) |
| P2-105 | m/z = 752.28 ($C_{56}H_{36}N_2O$ = 752.90) | P2-106 | m/z = 752.28 ($C_{56}H_{36}N_2O$ = 752.90) |
| P2-107 | m/z = 778.30 ($C_{58}H_{38}N_2O$ = 778.94) | P2-108 | m/z = 942.36 ($C_{71}H_{46}N_2O$ = 943.14) |
| P2-109 | m/z = 902.37 ($C_{69}H_{46}N_2$ = 903.12) | P2-110 | m/z = 902.37 ($C_{69}H_{46}N_2$ = 903.12) |
| P2-111 | m/z = 818.28 ($C_{60}H_{38}N_2$ = 819.02) | P2-112 | m/z = 802.30 ($C_{60}H_{38}N_2O$ = 802.96) |
| P3-1 | m/z = 562.24 ($C_{42}H_{30}N_2$ = 562.70) | P3-2 | m/z = 638.27 ($C_{48}H_{34}N_2$ = 638.80) |
| P3-3 | m/z = 638.27 ($C_{48}H_{34}N_2$ = 638.80) | P3-4 | m/z = 714.30 ($C_{48}H_{34}N_2$ = 714.89) |
| P3-5 | m/z = 662.27 ($C_{50}H_{34}N_2$ = 662.82) | P3-6 | m/z = 662.27 ($C_{50}H_{34}N_2$ = 662.82) |
| P3-7 | m/z = 688.29 ($C_{52}H_{36}N_2$ = 688.86) | P3-8 | m/z = 802.33 ($C_{52}H_{36}N_2$ = 803.00) |
| P3-9 | m/z = 714.30 ($C_{54}H_{38}N_2$ = 714.89) | P3-10 | m/z = 876.35 ($C_{67}H_{44}N_2$ = 877.08) |
| P3-11 | m/z = 612.26 ($C_{46}H_{32}N_2$ = 612.76) | P3-12 | m/z = 764.32 ($C_{58}H_{40}N_2$ = 764.95) |
| P3-13 | m/z = 928.38 ($C_{71}H_{48}N_2$ = 929.15) | P3-14 | m/z = 714.30 ($C_{54}H_{38}N_2$ = 714.89) |
| P3-15 | m/z = 764.32 ($C_{58}H_{40}N_2$ = 764.95) | P3-16 | m/z = 738.30 ($C_{56}H_{38}N_2$ = 738.91) |
| P3-17 | m/z = 794.28 ($C_{58}H_{38}N_2S$ = 795.00) | P3-18 | m/z = 778.30 ($C_{58}H_{38}N_2O$ = 778.94) |
| P3-19 | m/z = 740.29 ($C_{54}H_{36}N_4$ = 740.89) | P3-20 | m/z = 740.29 ($C_{54}H_{36}N_4$ = 740.89) |
| P3-21 | m/z = 638.27 ($C_{48}H_{34}N_2$ = 638.80) | P3-22 | m/z = 638.27 ($C_{48}H_{34}N_2$ = 638.80) |
| P3-23 | m/z = 856.39 ($C_{62}H_{52}N_2S$ = 857.15) | P3-24 | m/z = 741.29 ($C_{53}H_{35}N_5$ = 741.88) |
| P3-25 | m/z = 602.27 ($C_{45}H_{34}N_2$ = 602.76) | P3-26 | m/z = 815.33 ($C_{61}H_{41}N_3$ = 816.00) |
| P3-27 | m/z = 718.30 ($C_{53}H_{38}N_2O$ = 718.88) | P3-28 | m/z = 866.34 ($C_{64}H_{42}N_4$ = 867.05) |

TABLE 3-continued

| Compound | FD-MS | Compound | FD-MS |
|---|---|---|---|
| P3-29 | m/z = 802.33 ($C_{61}H_{42}N_2$ = 803.00) | P3-30 | m/z = 878.37 ($C_{67}H_{46}N_2$ = 879.10) |
| P3-31 | m/z = 878.37 ($C_{67}H_{46}N_2$ = 879.10) | P3-32 | m/z = 954.40 ($C_{73}H_{50}N_2$ = 955.19) |
| P3-33 | m/z = 902.37 ($C_{69}H_{46}N_2$ = 903.12) | P3-34 | m/z = 902.37 ($C_{69}H_{46}N_2$ = 903.12) |
| P3-35 | m/z = 928.38 ($C_{71}H_{48}N_2$ = 929.15) | P3-36 | m/z = 1092.44 ($C_{84}H_{56}N_2$ = 1093.36) |
| P3-37 | m/z = 954.40 ($C_{73}H_{50}N_2$ = 955.19) | P3-38 | m/z = 1116.44 ($C_{86}H_{56}N_2$ = 1117.38) |
| P3-39 | m/z = 852.35 ($C_{65}H_{44}N_2$ = 853.06) | P3-40 | m/z = 954.40 ($C_{73}H_{50}N_2$ = 955.19) |
| P3-41 | m/z = 954.40 ($C_{73}H_{50}N_2$ = 955.19) | P3-42 | m/z = 954.40 ($C_{73}H_{50}N_2$ = 955.19) |
| P3-43 | m/z = 954.40 ($C_{73}H_{50}N_2$ = 955.19) | P3-44 | m/z = 954.40 ($C_{73}H_{50}N_2$ = 955.19) |
| P3-45 | m/z = 802.33 ($C_{61}H_{42}N_2$ = 803.00) | P3-46 | m/z = 878.37 ($C_{67}H_{46}N_2$ = 879.10) |
| P3-47 | m/z = 878.37 ($C_{67}H_{46}N_2$ = 879.10) | P3-48 | m/z = 954.40 ($C_{73}H_{50}N_2$ = 955.19) |
| P3-49 | m/z = 902.37 ($C_{69}H_{46}N_2$ = 903.12) | P3-50 | m/z = 902.37 ($C_{69}H_{46}N_2$ = 903.12) |
| P3-51 | m/z = 928.38 ($C_{71}H_{48}N_2$ = 929.15) | P3-52 | m/z = 1092.44 ($C_{84}H_{56}N_2$ = 1093.36) |
| P3-53 | m/z = 954.40 ($C_{73}H_{50}N_2$ = 955.19) | P3-54 | m/z = 1116.44 ($C_{86}H_{56}N_2$ = 1117.38) |
| P3-55 | m/z = 852.35 ($C_{65}H_{44}N_2$ = 853.06) | P3-56 | m/z = 954.40 ($C_{73}H_{50}N_2$ = 955.19) |
| P3-57 | m/z = 954.40 ($C_{73}H_{50}N_2$ = 955.19) | P3-58 | m/z = 954.40 ($C_{73}H_{50}N_2$ = 955.19) |
| P3-59 | m/z = 954.40 ($C_{73}H_{50}N_2$ = 955.19) | P3-60 | m/z = 954.40 ($C_{73}H_{50}N_2$ = 955.19) |
| P3-61 | m/z = 802.33 ($C_{61}H_{42}N_2$ = 803.00) | P3-62 | m/z = 878.37 ($C_{67}H_{46}N_2$ = 879.10) |
| P3-63 | m/z = 878.37 ($C_{67}H_{46}N_2$ = 879.10) | P3-64 | m/z = 954.40 ($C_{73}H_{50}N_2$ = 955.19) |
| P3-65 | m/z = 902.37 ($C_{69}H_{46}N_2$ = 903.12) | P3-66 | m/z = 902.37 ($C_{69}H_{46}N_2$ = 903.12) |
| P3-67 | m/z = 928.38 ($C_{71}H_{48}N_2$ = 929.15) | P3-68 | m/z = 1092.44 ($C_{84}H_{56}N_2$ = 1093.36) |
| P3-69 | m/z = 954.40 ($C_{73}H_{50}N_2$ = 955.19) | P3-70 | m/z = 1116.44 ($C_{86}H_{56}N_2$ = 1117.38) |
| P3-71 | m/z = 852.35 ($C_{65}H_{44}N_2$ = 853.06) | P3-72 | m/z = 954.40 ($C_{73}H_{50}N_2$ = 955.19) |
| P3-73 | m/z = 954.40 ($C_{73}H_{50}N_2$ = 955.19) | P3-74 | m/z = 954.40 ($C_{73}H_{50}N_2$ = 955.19) |
| P3-75 | m/z = 954.40 ($C_{73}H_{50}N_2$ = 955.19) | P3-76 | m/z = 954.40 ($C_{73}H_{50}N_2$ = 955.19) |
| P3-77 | m/z = 714.30 ($C_{54}H_{38}N_2$ = 714.89) | P3-78 | m/z = 790.33 ($C_{60}H_{42}N_2$ = 790.99) |
| P3-79 | m/z = 790.33 ($C_{60}H_{42}N_2$ = 790.99) | P3-80 | m/z = 866.37 ($C_{60}H_{42}N_2$ = 867.08) |
| P3-81 | m/z = 814.33 ($C_{62}H_{42}N_2$ = 815.01) | P3-82 | m/z = 814.33 ($C_{62}H_{42}N_2$ = 815.01) |
| P3-83 | m/z = 840.35 ($C_{64}H_{44}N_2$ = 841.05) | P3-84 | m/z = 1004.41 ($C_{77}H_{52}N_2$ = 1005.25) |
| P3-85 | m/z = 866.37 ($C_{66}H_{46}N_2$ = 867.08) | P3-86 | m/z = 714.30 ($C_{54}H_{38}N_2$ = 714.89) |
| P3-87 | m/z = 714.30 ($C_{54}H_{38}N_2$ = 714.89) | P3-88 | m/z = 714.30 ($C_{54}H_{38}N_2$ = 714.89) |
| P3-89 | m/z = 724.37 ($C_{54}H_{28}D_{10}N_2$ = 724.95) | P3-90 | m/z = 800.40 ($C_{60}H_{32}D_{10}N_2$ = 801.05) |
| P3-91 | m/z = 871.40 ($C_{66}H_{41}D_5N_2$ = 872.12) | P3-92 | m/z = 719.33 ($C_{54}H_{33}D_5N_2$ = 719.92) |
| P3-93 | m/z = 852.35 ($C_{65}H_{44}N_2$ = 853.06) | P3-94 | m/z = 902.37 ($C_{69}H_{46}N_2$ = 903.12) |
| P3-95 | m/z = 852.35 ($C_{65}H_{44}N_2$ = 853.06) | P3-96 | m/z = 902.37 ($C_{69}H_{46}N_2$ = 903.12) |
| P3-97 | m/z = 930.40 ($C_{71}H_{50}N_2$ = 931.17) | P3-98 | m/z = 912.37 ($C_{67}H_{48}N_2O_2$ = 913.11) |
| P3-99 | m/z = 902.37 ($C_{69}H_{46}N_2$ = 903.12) | P3-100 | m/z = 902.37 ($C_{69}H_{46}N_2$ = 903.12) |
| P3-101 | m/z = 768.26 ($C_{56}H_{36}N_2S$ = 903.12) | P3-102 | m/z = 768.26 ($C_{56}H_{36}N_2S$ = 903.12) |
| P3-103 | m/z = 794.28 ($C_{58}H_{38}N_2S$ = 795.00) | P3-104 | m/z = 958.34 ($C_{71}H_{46}N_2S$ = 959.20) |
| P3-105 | m/z = 752.28 ($C_{56}H_{36}N_2O$ = 752.90) | P3-106 | m/z = 752.28 ($C_{56}H_{36}N_2O$ = 752.90) |
| P3-107 | m/z = 778.30 ($C_{58}H_{38}N_2O$ = 778.94) | P3-108 | m/z = 942.36 ($C_{71}H_{46}N_2O$ = 943.14) |
| P3-109 | m/z = 902.37 ($C_{69}H_{46}N_2$ = 903.12) | P3-110 | m/z = 902.37 ($C_{69}H_{46}N_2$ = 903.12) |
| P3-111 | m/z = 818.28 ($C_{60}H_{38}N_2$ = 819.02) | P3-112 | m/z = 802.30 ($C_{60}H_{38}N_2O$ = 802.96) |
| P4-1 | m/z = 638.27 ($C_{48}H_{34}N_2$ = 638.80) | P4-2 | m/z = 790.33 ($C_{60}H_{42}N_2$ = 790.99) |
| P4-3 | m/z = 820.29 ($C_{60}H_{40}N_2S$ = 821.04) | P4-4 | m/z = 804.31 ($C_{60}H_{40}N_2O$ = 804.97) |
| P4-5 | m/z = 830.37 ($C_{63}H_{46}N_2$ = 831.05) | P4-6 | m/z = 954.40 ($C_{43}H_{50}N_2$ = 955.19) |
| P4-7 | m/z = 952.38 ($C_{73}H_{48}N_2$ = 953.18) | P4-8 | m/z = 688.29 ($C_{52}H_{36}N_2$ = 688.86) |
| P4-9 | m/z = 688.29 ($C_{52}H_{36}N_2$ = 688.86) | P4-10 | m/z = 840.35 ($C_{64}H_{44}N_2$ = 841.05) |
| P4-11 | m/z = 896.32 ($C_{66}H_{44}N_2S$ = 897.13) | P4-12 | m/z = 880.35 ($C_{66}H_{44}N_2O$ = 881.07) |
| P4-13 | m/z = 956.41 ($C_{73}H_{52}N_2$ = 957.21) | P4-14 | m/z = 1080.44 ($C_{83}H_{56}N_2$ = 1081.35) |
| P4-15 | m/z = 953.38 ($C_{72}H_{47}N_3$ = 954.16) | P4-16 | m/z = 740.29 ($C_{54}H_{36}N_4$ = 740.89) |
| P4-17 | m/z = 638.27 ($C_{48}H_{34}N_2$ = 638.80) | P4-18 | m/z = 790.33 ($C_{60}H_{42}N_2$ = 790.99) |
| P4-19 | m/z = 820.29 ($C_{60}H_{40}N_2S$ = 821.04) | P4-20 | m/z = 804.31 ($C_{60}H_{40}N_2O$ = 804.97) |
| P4-21 | m/z = 830.37 ($C_{63}H_{46}N_2$ = 831.05) | P4-22 | m/z = 954.40 ($C_{43}H_{50}N_2$ = 955.19) |
| P4-23 | m/z = 952.38 ($C_{73}H_{48}N_2$ = 953.18) | P4-24 | m/z = 688.29 ($C_{52}H_{36}N_2$ = 688.86) |
| P4-25 | m/z = 688.29 ($C_{52}H_{36}N_2$ = 688.86) | P4-26 | m/z = 840.35 ($C_{64}H_{44}N_2$ = 841.05) |
| P4-27 | m/z = 896.32 ($C_{66}H_{44}N_2S$ = 897.13) | P4-28 | m/z = 880.35 ($C_{66}H_{44}N_2O$ = 881.07) |
| P4-29 | m/z = 956.41 ($C_{73}H_{52}N_2$ = 957.21) | P4-30 | m/z = 1080.44 ($C_{83}H_{56}N_2$ = 1081.35) |
| P4-31 | m/z = 953.38 ($C_{72}H_{47}N_3$ = 954.16) | P4-32 | m/z = 740.29 ($C_{54}H_{36}N_4$ = 740.89) |
| P4-33 | m/z = 638.27 ($C_{48}H_{34}N_2$ = 638.80) | P4-34 | m/z = 790.33 ($C_{60}H_{42}N_2$ = 790.99) |
| P4-35 | m/z = 820.29 ($C_{60}H_{40}N_2S$ = 821.04) | P4-36 | m/z = 804.31 ($C_{60}H_{40}N_2O$ = 804.97) |
| P4-37 | m/z = 830.37 ($C_{63}H_{46}N_2$ = 831.05) | P4-38 | m/z = 954.40 ($C_{43}H_{50}N_2$ = 955.19) |
| P4-39 | m/z = 952.38 ($C_{73}H_{48}N_2$ = 953.18) | P4-40 | m/z = 688.29 ($C_{52}H_{36}N_2$ = 688.86) |
| P4-41 | m/z = 688.29 ($C_{52}H_{36}N_2$ = 688.86) | P4-42 | m/z = 840.35 ($C_{64}H_{44}N_2$ = 841.05) |
| P4-43 | m/z = 896.32 ($C_{66}H_{44}N_2S$ = 897.13) | P4-44 | m/z = 880.35 ($C_{66}H_{44}N_2O$ = 881.07) |
| P4-45 | m/z = 956.41 ($C_{73}H_{52}N_2$ = 957.21) | P4-46 | m/z = 1080.44 ($C_{83}H_{56}N_2$ = 1081.35) |
| P4-47 | m/z = 953.38 ($C_{72}H_{47}N_3$ = 954.16) | P4-48 | m/z = 790.31 ($C_{58}H_{38}N_4$ = 790.95) |

253
Fabrication and Evaluation of Organic Electronic Element

[Example 1] Green OLED (a Hole Transport Layer)

Organic light emitting diodes (OLEDs) were fabricated according to a conventional method by using a compound of the present invention as a hole transport layer material.

First, an ITO layer (anode) was formed on a glass substrate, and a film of 4,4',4"-Tris[2-naphthyl(phenyl)amino]triphenylamine ("2-TNATA") was vacuum-deposited on the ITO layer to form a hole injection layer with a thickness of 60 nm.

Subsequently, P1-1 of the present invention was vacuum-deposited with a thickness of 60 nm on the hole injection layer to form a hole transport layer.

Subsequently, a light emitting layer with a thickness of 30 nm was deposited on the hole transport layer by doping the hole transport layer with 4,4'-N,N'-dicarbazole-biphenyl ("CBP") as a host material and tris(2-phenylpyridine)-iridium ("Ir(ppy)$_3$") as a dopant material in a weight ratio of 90:10.

Next, a film of ((1,1'-bisphenyl)-4-olato)bis(2-methyl-8-quinolinolato)aluminum ("BAlq") was vacuum-deposited with a thickness of 10 nm on the light emitting layer to form a hole blocking layer, and a film of tris(8-quinolinolato)aluminum ("Alq$_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 348] Green OLED (a Hole Transport Layer)

The OLEDs were manufactured in the same manner as described in Example 1, except that any one of the compounds P1-2 to P1-112, P2-1 to P2-112, P3-1 to P3-112, P4-1 to P4-4, P4-21 to P4-24, P4-37 to P4-40 of the present invention in the Table 4 below was used as the hole transport layer material of the light emitting layer, instead of the inventive compound P1-1.

Comparative Example 1

An OLED was manufactured in the same manner as described in Example 1, except that the following Comparative Compound 1 to Comparative Compound 4 was used as the hole transport layer material, instead of the inventive compound P1-1.

<Comparative compound 1>

254
-continued

<Comparative compound 2>

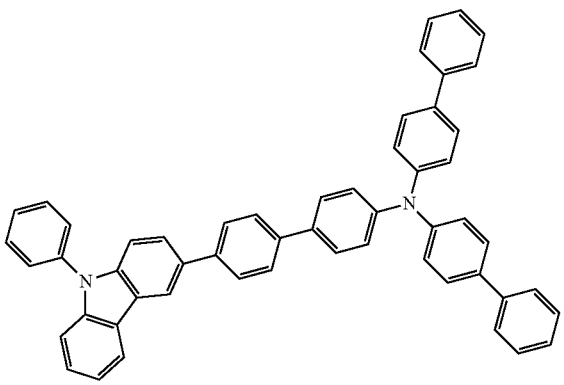

<Comparative compound 3>

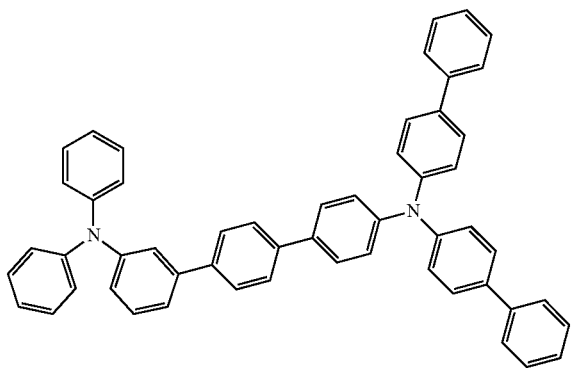

<Comparative compound 4>

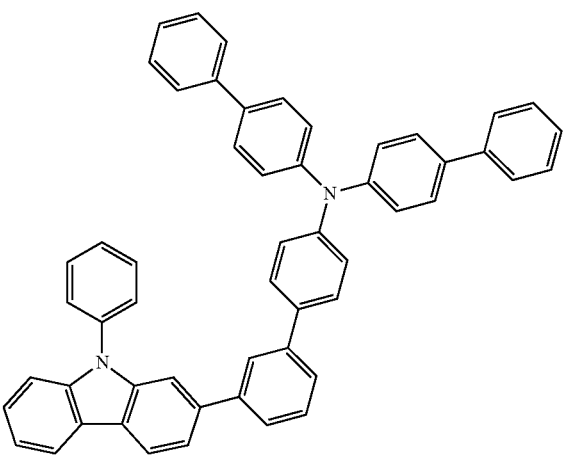

A forward bias DC voltage was applied to each of the OLEDs manufactured through the Examples 1 to 348 and the Comparative Examples 1 to 4, electro-luminescence (EL) characteristics of the OLED were measured by PR-650 (Photoresearch), and T90 life span was measured by life span measuring equipment (Mcscience) at the reference brightness of 5000 cd/m$^2$. Evaluation results are in the Table 4 below.

TABLE 4

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Com. Ex (1) | Com. Com (1) | 5.6 | 17.9 | 5000.0 | 27.9 | 68.2 | 0.33 | 0.62 |
| Com. Ex (2) | Com. Com (2) | 5.3 | 16.0 | 5000.0 | 31.2 | 120.6 | 0.33 | 0.61 |
| Com. Ex (3) | Com. Com (3) | 5.4 | 14.5 | 5000.0 | 34.5 | 109.4 | 0.33 | 0.62 |
| Com. Ex (4) | Com. Com (4) | 5.6 | 13.5 | 5000.0 | 37.0 | 119.1 | 0.33 | 0.62 |
| Ex. (1) | P1-1 | 5.5 | 12.5 | 5000.0 | 40.0 | 130.5 | 0.33 | 0.62 |
| Ex. (2) | P1-2 | 5.5 | 12.7 | 5000.0 | 39.4 | 128.1 | 0.33 | 0.61 |
| Ex. (3) | P1-3 | 5.5 | 13.1 | 5000.0 | 38.1 | 127.8 | 0.33 | 0.61 |
| Ex. (4) | P1-4 | 5.4 | 12.8 | 5000.0 | 39.2 | 122.3 | 0.33 | 0.61 |
| Ex. (5) | P1-5 | 5.5 | 12.7 | 5000.0 | 39.5 | 120.6 | 0.33 | 0.62 |
| Ex. (6) | P1-6 | 5.5 | 13.0 | 5000.0 | 38.6 | 132.7 | 0.33 | 0.62 |
| Ex. (7) | P1-7 | 5.4 | 12.9 | 5000.0 | 38.6 | 130.3 | 0.33 | 0.61 |
| Ex. (8) | P1-8 | 5.5 | 12.7 | 5000.0 | 39.5 | 132.9 | 0.33 | 0.62 |
| Ex. (9) | P1-9 | 5.4 | 12.6 | 5000.0 | 39.6 | 132.4 | 0.33 | 0.61 |
| Ex. (10) | P1-10 | 5.6 | 13.1 | 5000.0 | 38.1 | 123.9 | 0.33 | 0.62 |
| Ex. (11) | P1-11 | 5.6 | 12.9 | 5000.0 | 38.8 | 126.2 | 0.33 | 0.61 |
| Ex. (12) | P1-12 | 5.4 | 12.7 | 5000.0 | 39.4 | 126.9 | 0.33 | 0.61 |
| Ex. (13) | P1-13 | 5.4 | 12.7 | 5000.0 | 39.3 | 124.3 | 0.33 | 0.61 |
| Ex. (14) | P1-14 | 5.4 | 12.9 | 5000.0 | 38.7 | 120.4 | 0.33 | 0.62 |
| Ex. (15) | P1-15 | 5.5 | 12.6 | 5000.0 | 39.7 | 134.6 | 0.33 | 0.61 |
| Ex. (16) | P1-16 | 5.3 | 13.0 | 5000.0 | 38.4 | 120.5 | 0.33 | 0.61 |
| Ex. (17) | P1-17 | 5.4 | 12.6 | 5000.0 | 39.8 | 129.4 | 0.33 | 0.62 |
| Ex. (18) | P1-18 | 5.6 | 13.1 | 5000.0 | 38.3 | 130.3 | 0.33 | 0.61 |
| Ex. (19) | P1-19 | 5.5 | 12.6 | 5000.0 | 39.5 | 130.3 | 0.33 | 0.62 |
| Ex. (20) | P1-20 | 5.3 | 13.0 | 5000.0 | 38.5 | 128.3 | 0.33 | 0.62 |
| Ex. (21) | P1-21 | 5.3 | 12.7 | 5000.0 | 39.2 | 133.1 | 0.33 | 0.61 |
| Ex. (22) | P1-22 | 5.6 | 12.9 | 5000.0 | 38.8 | 126.9 | 0.33 | 0.62 |
| Ex. (23) | P1-23 | 5.4 | 12.8 | 5000.0 | 39.1 | 126.9 | 0.33 | 0.62 |
| Ex. (24) | P1-24 | 5.4 | 12.7 | 5000.0 | 39.5 | 125.8 | 0.33 | 0.62 |
| Ex. (25) | P1-25 | 5.5 | 12.5 | 5000.0 | 40.0 | 126.4 | 0.33 | 0.62 |
| Ex. (26) | P1-26 | 5.6 | 12.6 | 5000.0 | 39.8 | 120.1 | 0.33 | 0.61 |
| Ex. (27) | P1-27 | 5.4 | 12.5 | 5000.0 | 39.9 | 126.0 | 0.33 | 0.61 |
| Ex. (28) | P1-28 | 5.3 | 12.9 | 5000.0 | 38.6 | 122.2 | 0.33 | 0.61 |
| Ex. (29) | P1-29 | 5.5 | 12.8 | 5000.0 | 39.0 | 127.6 | 0.33 | 0.62 |
| Ex. (30) | P1-30 | 5.5 | 13.1 | 5000.0 | 38.2 | 130.8 | 0.33 | 0.62 |
| Ex. (31) | P1-31 | 5.5 | 13.2 | 5000.0 | 38.0 | 135.0 | 0.33 | 0.62 |
| Ex. (32) | P1-32 | 5.4 | 13.1 | 5000.0 | 38.3 | 123.7 | 0.33 | 0.61 |
| Ex. (33) | P1-33 | 5.3 | 12.7 | 5000.0 | 39.4 | 125.0 | 0.33 | 0.61 |
| Ex. (34) | P1-34 | 5.6 | 13.1 | 5000.0 | 38.0 | 134.1 | 0.33 | 0.62 |
| Ex. (35) | P1-35 | 5.3 | 12.9 | 5000.0 | 38.8 | 132.9 | 0.33 | 0.62 |
| Ex. (36) | P1-36 | 5.4 | 12.6 | 5000.0 | 39.6 | 122.7 | 0.33 | 0.61 |
| Ex. (37) | P1-37 | 5.6 | 12.7 | 5000.0 | 39.5 | 131.1 | 0.33 | 0.62 |
| Ex. (38) | P1-38 | 5.5 | 12.6 | 5000.0 | 39.7 | 133.3 | 0.33 | 0.61 |
| Ex. (39) | P1-39 | 5.4 | 12.7 | 5000.0 | 39.3 | 134.8 | 0.33 | 0.62 |
| Ex. (40) | P1-40 | 5.4 | 12.8 | 5000.0 | 39.1 | 120.5 | 0.33 | 0.61 |
| Ex. (41) | P1-41 | 5.3 | 12.8 | 5000.0 | 39.0 | 124.0 | 0.33 | 0.62 |
| Ex. (42) | P1-42 | 5.5 | 12.6 | 5000.0 | 39.6 | 124.2 | 0.33 | 0.61 |
| Ex. (43) | P1-43 | 5.6 | 12.7 | 5000.0 | 39.4 | 134.0 | 0.33 | 0.62 |
| Ex. (44) | P1-44 | 5.3 | 13.1 | 5000.0 | 38.2 | 128.2 | 0.33 | 0.62 |
| Ex. (45) | P1-45 | 5.6 | 12.7 | 5000.0 | 39.4 | 130.8 | 0.33 | 0.62 |
| Ex. (46) | P1-46 | 5.3 | 13.0 | 5000.0 | 38.3 | 131.8 | 0.33 | 0.61 |
| Ex. (47) | P1-47 | 5.3 | 13.0 | 5000.0 | 38.5 | 134.1 | 0.33 | 0.62 |
| Ex. (48) | P1-48 | 5.6 | 13.1 | 5000.0 | 38.1 | 134.3 | 0.33 | 0.61 |
| Ex. (49) | P1-49 | 5.4 | 13.0 | 5000.0 | 38.6 | 121.7 | 0.33 | 0.61 |
| Ex. (50) | P1-50 | 5.6 | 13.1 | 5000.0 | 38.3 | 131.7 | 0.33 | 0.61 |
| Ex. (51) | P1-51 | 5.5 | 13.1 | 5000.0 | 38.3 | 130.1 | 0.33 | 0.61 |
| Ex. (52) | P1-52 | 5.5 | 12.9 | 5000.0 | 38.7 | 128.3 | 0.33 | 0.62 |
| Ex. (53) | P1-53 | 5.3 | 13.1 | 5000.0 | 38.1 | 127.7 | 0.33 | 0.61 |
| Ex. (54) | P1-54 | 5.6 | 12.8 | 5000.0 | 39.2 | 133.2 | 0.33 | 0.62 |
| Ex. (55) | P1-55 | 5.6 | 13.1 | 5000.0 | 38.2 | 121.1 | 0.33 | 0.61 |
| Ex. (56) | P1-56 | 5.4 | 12.7 | 5000.0 | 39.4 | 127.7 | 0.33 | 0.61 |
| Ex. (57) | P1-57 | 5.3 | 12.5 | 5000.0 | 39.9 | 120.9 | 0.33 | 0.62 |
| Ex. (58) | P1-58 | 5.3 | 13.1 | 5000.0 | 38.3 | 134.8 | 0.33 | 0.61 |
| Ex. (59) | P1-59 | 5.4 | 12.6 | 5000.0 | 39.6 | 128.8 | 0.33 | 0.61 |
| Ex. (60) | P1-60 | 5.6 | 12.8 | 5000.0 | 38.9 | 126.1 | 0.33 | 0.61 |
| Ex. (61) | P1-61 | 5.4 | 12.8 | 5000.0 | 39.1 | 133.9 | 0.33 | 0.62 |
| Ex. (62) | P1-62 | 5.5 | 12.8 | 5000.0 | 39.1 | 120.9 | 0.33 | 0.61 |
| Ex. (63) | P1-63 | 5.4 | 12.6 | 5000.0 | 39.7 | 132.2 | 0.33 | 0.62 |
| Ex. (64) | P1-64 | 5.5 | 12.6 | 5000.0 | 39.5 | 129.8 | 0.33 | 0.62 |
| Ex. (65) | P1-65 | 5.4 | 12.9 | 5000.0 | 38.9 | 132.6 | 0.33 | 0.61 |
| Ex. (66) | P1-66 | 5.4 | 12.5 | 5000.0 | 40.0 | 120.3 | 0.33 | 0.62 |
| Ex. (67) | P1-67 | 5.5 | 12.5 | 5000.0 | 40.0 | 129.7 | 0.33 | 0.61 |
| Ex. (68) | P1-68 | 5.5 | 13.0 | 5000.0 | 38.3 | 121.8 | 0.33 | 0.62 |
| Ex. (69) | P1-69 | 5.5 | 13.1 | 5000.0 | 38.1 | 134.3 | 0.33 | 0.62 |
| Ex. (70) | P1-70 | 5.5 | 12.5 | 5000.0 | 39.8 | 134.2 | 0.33 | 0.62 |
| Ex. (71) | P1-71 | 5.5 | 12.9 | 5000.0 | 38.8 | 132.8 | 0.33 | 0.61 |

TABLE 4-continued

|  | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (72) | P1-72 | 5.4 | 12.9 | 5000.0 | 38.8 | 131.0 | 0.33 | 0.62 |
| Ex. (73) | P1-73 | 5.4 | 12.9 | 5000.0 | 38.8 | 134.6 | 0.33 | 0.61 |
| Ex. (74) | P1-74 | 5.5 | 13.1 | 5000.0 | 38.1 | 120.9 | 0.33 | 0.61 |
| Ex. (75) | P1-75 | 5.4 | 13.1 | 5000.0 | 38.2 | 126.7 | 0.33 | 0.61 |
| Ex. (76) | P1-76 | 5.5 | 12.7 | 5000.0 | 39.4 | 127.6 | 0.33 | 0.62 |
| Ex. (77) | P1-77 | 5.4 | 12.8 | 5000.0 | 39.2 | 125.5 | 0.33 | 0.62 |
| Ex. (78) | P1-78 | 5.4 | 12.6 | 5000.0 | 39.8 | 132.1 | 0.33 | 0.61 |
| Ex. (79) | P1-79 | 5.5 | 12.7 | 5000.0 | 39.4 | 128.8 | 0.33 | 0.62 |
| Ex. (80) | P1-80 | 5.3 | 12.6 | 5000.0 | 39.5 | 120.9 | 0.33 | 0.61 |
| Ex. (81) | P1-81 | 5.5 | 12.9 | 5000.0 | 38.8 | 125.6 | 0.33 | 0.61 |
| Ex. (82) | P1-82 | 5.5 | 12.5 | 5000.0 | 40.0 | 122.3 | 0.33 | 0.62 |
| Ex. (83) | P1-83 | 5.4 | 13.0 | 5000.0 | 38.5 | 122.6 | 0.33 | 0.61 |
| Ex. (84) | P1-84 | 5.3 | 13.1 | 5000.0 | 38.2 | 126.6 | 0.33 | 0.61 |
| Ex. (85) | P1-85 | 5.5 | 12.7 | 5000.0 | 39.4 | 134.7 | 0.33 | 0.61 |
| Ex. (86) | P1-86 | 5.6 | 12.8 | 5000.0 | 39.0 | 132.9 | 0.33 | 0.62 |
| Ex. (87) | P1-87 | 5.4 | 12.8 | 5000.0 | 39.1 | 127.1 | 0.33 | 0.61 |
| Ex. (88) | P1-88 | 5.3 | 12.7 | 5000.0 | 39.4 | 120.7 | 0.33 | 0.62 |
| Ex. (89) | P1-89 | 5.6 | 12.8 | 5000.0 | 39.1 | 124.3 | 0.33 | 0.62 |
| Ex. (90) | P1-90 | 5.4 | 13.1 | 5000.0 | 38.2 | 125.0 | 0.33 | 0.61 |
| Ex. (91) | P1-91 | 5.6 | 12.5 | 5000.0 | 39.9 | 131.5 | 0.33 | 0.62 |
| Ex. (92) | P1-92 | 5.4 | 12.6 | 5000.0 | 39.5 | 120.1 | 0.33 | 0.61 |
| Ex. (93) | P1-93 | 5.4 | 12.7 | 5000.0 | 39.4 | 120.7 | 0.33 | 0.62 |
| Ex. (94) | P1-94 | 5.4 | 13.0 | 5000.0 | 38.4 | 132.0 | 0.33 | 0.61 |
| Ex. (95) | P1-95 | 5.5 | 13.1 | 5000.0 | 38.2 | 123.5 | 0.33 | 0.61 |
| Ex. (96) | P1-96 | 5.5 | 12.8 | 5000.0 | 38.9 | 134.6 | 0.33 | 0.62 |
| Ex. (97) | P1-97 | 5.6 | 12.9 | 5000.0 | 38.9 | 131.4 | 0.33 | 0.61 |
| Ex. (98) | P1-98 | 5.3 | 13.1 | 5000.0 | 38.3 | 130.5 | 0.33 | 0.62 |
| Ex. (99) | P1-99 | 5.4 | 13.1 | 5000.0 | 38.1 | 122.7 | 0.33 | 0.62 |
| Ex. (100) | P1-100 | 5.4 | 12.7 | 5000.0 | 39.4 | 125.5 | 0.33 | 0.61 |
| Ex. (101) | P1-101 | 5.5 | 12.8 | 5000.0 | 39.0 | 131.4 | 0.33 | 0.61 |
| Ex. (102) | P1-102 | 5.6 | 12.7 | 5000.0 | 39.5 | 134.7 | 0.33 | 0.61 |
| Ex. (103) | P1-103 | 5.4 | 12.6 | 5000.0 | 39.8 | 121.9 | 0.33 | 0.62 |
| Ex. (104) | P1-104 | 5.6 | 12.5 | 5000.0 | 40.0 | 120.3 | 0.33 | 0.62 |
| Ex. (105) | P1-105 | 5.4 | 12.9 | 5000.0 | 38.9 | 120.2 | 0.33 | 0.62 |
| Ex. (106) | P1-106 | 5.3 | 13.1 | 5000.0 | 38.0 | 127.8 | 0.33 | 0.61 |
| Ex. (107) | P1-107 | 5.4 | 13.0 | 5000.0 | 38.5 | 121.5 | 0.33 | 0.61 |
| Ex. (108) | P1-108 | 5.6 | 13.0 | 5000.0 | 38.6 | 130.2 | 0.33 | 0.62 |
| Ex. (109) | P1-109 | 5.3 | 12.8 | 5000.0 | 38.9 | 133.7 | 0.33 | 0.62 |
| Ex. (110) | P1-110 | 5.4 | 12.7 | 5000.0 | 39.3 | 132.0 | 0.33 | 0.62 |
| Ex. (111) | P1-111 | 5.4 | 12.5 | 5000.0 | 39.9 | 125.8 | 0.33 | 0.61 |
| Ex. (112) | P1-112 | 5.5 | 12.7 | 5000.0 | 39.4 | 122.8 | 0.33 | 0.61 |
| Ex. (113) | P2-1 | 5.5 | 12.1 | 5000.0 | 41.2 | 124.2 | 0.33 | 0.61 |
| Ex. (114) | P2-2 | 5.5 | 12.3 | 5000.0 | 40.7 | 134.3 | 0.33 | 0.61 |
| Ex. (115) | P2-3 | 5.6 | 12.4 | 5000.0 | 40.2 | 126.2 | 0.33 | 0.61 |
| Ex. (116) | P2-4 | 5.5 | 11.8 | 5000.0 | 42.5 | 123.6 | 0.33 | 0.62 |
| Ex. (117) | P2-5 | 5.5 | 12.4 | 5000.0 | 40.3 | 130.9 | 0.33 | 0.61 |
| Ex. (118) | P2-6 | 5.4 | 12.3 | 5000.0 | 40.8 | 132.0 | 0.33 | 0.62 |
| Ex. (119) | P2-7 | 5.6 | 12.3 | 5000.0 | 40.5 | 132.1 | 0.33 | 0.61 |
| Ex. (120) | P2-8 | 5.3 | 12.2 | 5000.0 | 41.1 | 123.6 | 0.33 | 0.62 |
| Ex. (121) | P2-9 | 5.6 | 11.8 | 5000.0 | 42.3 | 127.8 | 0.33 | 0.61 |
| Ex. (122) | P2-10 | 5.5 | 12.3 | 5000.0 | 40.8 | 122.2 | 0.33 | 0.62 |
| Ex. (123) | P2-11 | 5.4 | 11.8 | 5000.0 | 42.5 | 132.8 | 0.33 | 0.61 |
| Ex. (124) | P2-12 | 5.4 | 11.7 | 5000.0 | 42.6 | 125.9 | 0.33 | 0.61 |
| Ex. (125) | P2-13 | 5.5 | 12.5 | 5000.0 | 40.0 | 132.8 | 0.33 | 0.61 |
| Ex. (126) | P2-14 | 5.5 | 11.6 | 5000.0 | 42.9 | 132.1 | 0.33 | 0.62 |
| Ex. (127) | P2-15 | 5.5 | 11.7 | 5000.0 | 42.6 | 120.6 | 0.33 | 0.61 |
| Ex. (128) | P2-16 | 5.5 | 12.4 | 5000.0 | 40.4 | 124.1 | 0.33 | 0.62 |
| Ex. (129) | P2-17 | 5.5 | 12.2 | 5000.0 | 41.1 | 121.0 | 0.33 | 0.62 |
| Ex. (130) | P2-18 | 5.4 | 12.1 | 5000.0 | 41.3 | 133.9 | 0.33 | 0.62 |
| Ex. (131) | P2-19 | 5.5 | 11.9 | 5000.0 | 42.2 | 126.6 | 0.33 | 0.61 |
| Ex. (132) | P2-20 | 5.6 | 11.9 | 5000.0 | 42.1 | 129.3 | 0.33 | 0.62 |
| Ex. (133) | P2-21 | 5.3 | 11.9 | 5000.0 | 41.9 | 121.2 | 0.33 | 0.62 |
| Ex. (134) | P2-22 | 5.6 | 12.0 | 5000.0 | 41.5 | 122.1 | 0.33 | 0.61 |
| Ex. (135) | P2-23 | 5.3 | 12.3 | 5000.0 | 40.8 | 127.4 | 0.33 | 0.62 |
| Ex. (136) | P2-24 | 5.3 | 11.8 | 5000.0 | 42.4 | 132.5 | 0.33 | 0.61 |
| Ex. (137) | P2-25 | 5.4 | 11.6 | 5000.0 | 43.0 | 130.9 | 0.33 | 0.61 |
| Ex. (138) | P2-26 | 5.5 | 12.4 | 5000.0 | 40.3 | 131.6 | 0.33 | 0.61 |
| Ex. (139) | P2-27 | 5.4 | 11.6 | 5000.0 | 42.9 | 129.3 | 0.33 | 0.61 |
| Ex. (140) | P2-28 | 5.4 | 12.3 | 5000.0 | 40.5 | 125.4 | 0.33 | 0.61 |
| Ex. (141) | P2-29 | 5.3 | 11.8 | 5000.0 | 42.4 | 130.7 | 0.33 | 0.62 |
| Ex. (142) | P2-30 | 5.5 | 11.8 | 5000.0 | 42.3 | 132.4 | 0.33 | 0.62 |
| Ex. (143) | P2-31 | 5.5 | 12.5 | 5000.0 | 40.0 | 132.9 | 0.33 | 0.62 |
| Ex. (144) | P2-32 | 5.5 | 12.4 | 5000.0 | 40.3 | 120.1 | 0.33 | 0.61 |
| Ex. (145) | P2-33 | 5.5 | 11.7 | 5000.0 | 42.6 | 132.4 | 0.33 | 0.61 |
| Ex. (146) | P2-34 | 5.4 | 12.2 | 5000.0 | 41.0 | 123.8 | 0.33 | 0.62 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (147) | P2-35 | 5.6 | 11.7 | 5000.0 | 42.8 | 132.2 | 0.33 | 0.62 |
| Ex. (148) | P2-36 | 5.3 | 12.0 | 5000.0 | 41.8 | 132.6 | 0.33 | 0.62 |
| Ex. (149) | P2-37 | 5.5 | 11.8 | 5000.0 | 42.5 | 129.8 | 0.33 | 0.62 |
| Ex. (150) | P2-38 | 5.6 | 12.0 | 5000.0 | 41.8 | 127.6 | 0.33 | 0.62 |
| Ex. (151) | P2-39 | 5.5 | 12.0 | 5000.0 | 41.8 | 132.6 | 0.33 | 0.61 |
| Ex. (152) | P2-40 | 5.5 | 12.1 | 5000.0 | 41.2 | 128.5 | 0.33 | 0.61 |
| Ex. (153) | P2-41 | 5.4 | 12.3 | 5000.0 | 40.8 | 131.8 | 0.33 | 0.62 |
| Ex. (154) | P2-42 | 5.3 | 12.5 | 5000.0 | 40.0 | 128.0 | 0.33 | 0.62 |
| Ex. (155) | P2-43 | 5.6 | 11.8 | 5000.0 | 42.5 | 134.5 | 0.33 | 0.62 |
| Ex. (156) | P2-44 | 5.4 | 11.9 | 5000.0 | 41.9 | 134.5 | 0.33 | 0.61 |
| Ex. (157) | P2-45 | 5.3 | 12.1 | 5000.0 | 41.4 | 130.4 | 0.33 | 0.61 |
| Ex. (158) | P2-46 | 5.4 | 11.8 | 5000.0 | 42.5 | 123.0 | 0.33 | 0.61 |
| Ex. (159) | P2-47 | 5.5 | 12.3 | 5000.0 | 40.6 | 122.5 | 0.33 | 0.61 |
| Ex. (160) | P2-48 | 5.4 | 12.0 | 5000.0 | 41.6 | 130.8 | 0.33 | 0.62 |
| Ex. (161) | P2-49 | 5.5 | 12.0 | 5000.0 | 41.8 | 133.5 | 0.33 | 0.62 |
| Ex. (162) | P2-50 | 5.5 | 12.3 | 5000.0 | 40.7 | 126.6 | 0.33 | 0.62 |
| Ex. (163) | P2-51 | 5.3 | 11.9 | 5000.0 | 42.0 | 130.6 | 0.33 | 0.62 |
| Ex. (164) | P2-52 | 5.3 | 12.2 | 5000.0 | 41.1 | 132.6 | 0.33 | 0.62 |
| Ex. (165) | P2-53 | 5.4 | 12.5 | 5000.0 | 40.1 | 124.8 | 0.33 | 0.62 |
| Ex. (166) | P2-54 | 5.5 | 12.1 | 5000.0 | 41.5 | 131.8 | 0.33 | 0.62 |
| Ex. (167) | P2-55 | 5.3 | 12.3 | 5000.0 | 40.7 | 130.9 | 0.33 | 0.62 |
| Ex. (168) | P2-56 | 5.3 | 12.2 | 5000.0 | 41.1 | 128.0 | 0.33 | 0.61 |
| Ex. (169) | P2-57 | 5.4 | 12.4 | 5000.0 | 40.3 | 132.2 | 0.33 | 0.61 |
| Ex. (170) | P2-58 | 5.5 | 12.0 | 5000.0 | 41.8 | 130.7 | 0.33 | 0.62 |
| Ex. (171) | P2-59 | 5.4 | 12.4 | 5000.0 | 40.3 | 127.7 | 0.33 | 0.61 |
| Ex. (172) | P2-60 | 5.5 | 12.2 | 5000.0 | 41.1 | 124.6 | 0.33 | 0.62 |
| Ex. (173) | P2-61 | 5.5 | 11.8 | 5000.0 | 42.5 | 128.2 | 0.33 | 0.62 |
| Ex. (174) | P2-62 | 5.6 | 12.2 | 5000.0 | 40.9 | 131.8 | 0.33 | 0.61 |
| Ex. (175) | P2-63 | 5.5 | 12.2 | 5000.0 | 41.0 | 124.6 | 0.33 | 0.62 |
| Ex. (176) | P2-64 | 5.5 | 12.0 | 5000.0 | 41.8 | 125.0 | 0.33 | 0.61 |
| Ex. (177) | P2-65 | 5.5 | 12.2 | 5000.0 | 40.9 | 124.5 | 0.33 | 0.61 |
| Ex. (178) | P2-66 | 5.4 | 11.7 | 5000.0 | 42.8 | 128.0 | 0.33 | 0.62 |
| Ex. (179) | P2-67 | 5.4 | 12.0 | 5000.0 | 41.6 | 134.5 | 0.33 | 0.62 |
| Ex. (180) | P2-68 | 5.5 | 12.3 | 5000.0 | 40.7 | 126.7 | 0.33 | 0.61 |
| Ex. (181) | P2-69 | 5.3 | 12.1 | 5000.0 | 41.4 | 134.7 | 0.33 | 0.62 |
| Ex. (182) | P2-70 | 5.4 | 12.0 | 5000.0 | 41.8 | 127.5 | 0.33 | 0.62 |
| Ex. (183) | P2-71 | 5.3 | 11.8 | 5000.0 | 42.3 | 127.1 | 0.33 | 0.61 |
| Ex. (184) | P2-72 | 5.5 | 11.9 | 5000.0 | 41.9 | 127.3 | 0.33 | 0.62 |
| Ex. (185) | P2-73 | 5.4 | 12.4 | 5000.0 | 40.3 | 122.3 | 0.33 | 0.61 |
| Ex. (186) | P2-74 | 5.4 | 12.3 | 5000.0 | 40.6 | 128.2 | 0.33 | 0.62 |
| Ex. (187) | P2-75 | 5.4 | 12.3 | 5000.0 | 40.5 | 131.5 | 0.33 | 0.62 |
| Ex. (188) | P2-76 | 5.6 | 12.1 | 5000.0 | 41.3 | 132.0 | 0.33 | 0.61 |
| Ex. (189) | P2-77 | 5.4 | 11.9 | 5000.0 | 42.2 | 126.4 | 0.33 | 0.61 |
| Ex. (190) | P2-78 | 5.4 | 11.7 | 5000.0 | 42.6 | 131.4 | 0.33 | 0.62 |
| Ex. (191) | P2-79 | 5.6 | 11.7 | 5000.0 | 42.6 | 128.1 | 0.33 | 0.61 |
| Ex. (192) | P2-80 | 5.3 | 11.6 | 5000.0 | 43.0 | 130.3 | 0.33 | 0.61 |
| Ex. (193) | P2-81 | 5.6 | 12.3 | 5000.0 | 40.7 | 120.5 | 0.33 | 0.62 |
| Ex. (194) | P2-82 | 5.4 | 12.2 | 5000.0 | 40.8 | 120.7 | 0.33 | 0.61 |
| Ex. (195) | P2-83 | 5.5 | 12.1 | 5000.0 | 41.4 | 122.5 | 0.33 | 0.61 |
| Ex. (196) | P2-84 | 5.5 | 11.8 | 5000.0 | 42.5 | 120.3 | 0.33 | 0.61 |
| Ex. (197) | P2-85 | 5.4 | 12.5 | 5000.0 | 40.0 | 128.6 | 0.33 | 0.61 |
| Ex. (198) | P2-86 | 5.4 | 11.7 | 5000.0 | 42.9 | 127.2 | 0.33 | 0.62 |
| Ex. (199) | P2-87 | 5.5 | 11.9 | 5000.0 | 41.9 | 123.7 | 0.33 | 0.62 |
| Ex. (200) | P2-88 | 5.4 | 12.5 | 5000.0 | 40.1 | 133.4 | 0.33 | 0.61 |
| Ex. (201) | P2-89 | 5.5 | 11.7 | 5000.0 | 42.6 | 125.5 | 0.33 | 0.61 |
| Ex. (202) | P2-90 | 5.5 | 11.9 | 5000.0 | 42.1 | 131.3 | 0.33 | 0.62 |
| Ex. (203) | P2-91 | 5.6 | 12.5 | 5000.0 | 40.1 | 126.6 | 0.33 | 0.62 |
| Ex. (204) | P2-92 | 5.5 | 11.9 | 5000.0 | 42.1 | 130.5 | 0.33 | 0.62 |
| Ex. (205) | P2-93 | 5.5 | 12.1 | 5000.0 | 41.3 | 121.2 | 0.33 | 0.62 |
| Ex. (206) | P2-94 | 5.3 | 12.1 | 5000.0 | 41.2 | 123.5 | 0.33 | 0.61 |
| Ex. (207) | P2-95 | 5.4 | 11.7 | 5000.0 | 42.6 | 130.3 | 0.33 | 0.61 |
| Ex. (208) | P2-96 | 5.5 | 12.2 | 5000.0 | 41.0 | 130.1 | 0.33 | 0.61 |
| Ex. (209) | P2-97 | 5.4 | 11.8 | 5000.0 | 42.3 | 130.3 | 0.33 | 0.62 |
| Ex. (210) | P2-98 | 5.4 | 12.4 | 5000.0 | 40.3 | 121.8 | 0.33 | 0.62 |
| Ex. (211) | P2-99 | 5.6 | 12.3 | 5000.0 | 40.5 | 130.1 | 0.33 | 0.62 |
| Ex. (212) | P2-100 | 5.6 | 12.2 | 5000.0 | 40.9 | 120.7 | 0.33 | 0.61 |
| Ex. (213) | P2-101 | 5.5 | 11.6 | 5000.0 | 43.0 | 129.4 | 0.33 | 0.61 |
| Ex. (214) | P2-102 | 5.4 | 12.5 | 5000.0 | 40.0 | 122.1 | 0.33 | 0.61 |
| Ex. (215) | P2-103 | 5.5 | 11.7 | 5000.0 | 42.9 | 123.7 | 0.33 | 0.62 |
| Ex. (216) | P2-104 | 5.5 | 12.0 | 5000.0 | 41.5 | 124.9 | 0.33 | 0.61 |
| Ex. (217) | P2-105 | 5.3 | 12.3 | 5000.0 | 40.5 | 122.6 | 0.33 | 0.62 |
| Ex. (218) | P2-106 | 5.5 | 11.7 | 5000.0 | 42.7 | 121.8 | 0.33 | 0.62 |
| Ex. (219) | P2-107 | 5.5 | 11.8 | 5000.0 | 42.5 | 134.3 | 0.33 | 0.61 |
| Ex. (220) | P2-108 | 5.3 | 12.4 | 5000.0 | 40.3 | 130.8 | 0.33 | 0.62 |
| Ex. (221) | P2-109 | 5.5 | 11.9 | 5000.0 | 41.9 | 123.3 | 0.33 | 0.62 |

TABLE 4-continued

|  | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (222) | P2-110 | 5.4 | 12.5 | 5000.0 | 40.0 | 132.1 | 0.33 | 0.61 |
| Ex. (223) | P2-111 | 5.5 | 12.2 | 5000.0 | 41.0 | 124.4 | 0.33 | 0.61 |
| Ex. (224) | P2-112 | 5.4 | 12.3 | 5000.0 | 40.7 | 121.2 | 0.33 | 0.61 |
| Ex. (225) | P3-1 | 5.6 | 12.6 | 5000.0 | 39.6 | 131.9 | 0.33 | 0.62 |
| Ex. (226) | P3-2 | 5.5 | 12.6 | 5000.0 | 39.8 | 132.4 | 0.33 | 0.61 |
| Ex. (227) | P3-3 | 5.6 | 13.0 | 5000.0 | 38.4 | 133.1 | 0.33 | 0.61 |
| Ex. (228) | P3-4 | 5.5 | 13.0 | 5000.0 | 38.5 | 132.0 | 0.33 | 0.61 |
| Ex. (229) | P3-5 | 5.4 | 12.9 | 5000.0 | 38.7 | 121.0 | 0.33 | 0.62 |
| Ex. (230) | P3-6 | 5.4 | 13.2 | 5000.0 | 38.0 | 120.4 | 0.33 | 0.62 |
| Ex. (231) | P3-7 | 5.6 | 12.8 | 5000.0 | 39.2 | 123.5 | 0.33 | 0.61 |
| Ex. (232) | P3-8 | 5.6 | 12.9 | 5000.0 | 38.7 | 127.2 | 0.33 | 0.62 |
| Ex. (233) | P3-9 | 5.3 | 12.8 | 5000.0 | 39.0 | 128.4 | 0.33 | 0.61 |
| Ex. (234) | P3-10 | 5.3 | 12.9 | 5000.0 | 38.9 | 126.3 | 0.33 | 0.62 |
| Ex. (235) | P3-11 | 5.4 | 12.6 | 5000.0 | 39.7 | 134.6 | 0.33 | 0.61 |
| Ex. (236) | P3-12 | 5.5 | 12.8 | 5000.0 | 39.0 | 121.4 | 0.33 | 0.61 |
| Ex. (237) | P3-13 | 5.4 | 12.8 | 5000.0 | 39.1 | 130.5 | 0.33 | 0.61 |
| Ex. (238) | P3-14 | 5.5 | 12.8 | 5000.0 | 39.0 | 122.0 | 0.33 | 0.62 |
| Ex. (239) | P3-15 | 5.3 | 12.8 | 5000.0 | 38.9 | 126.3 | 0.33 | 0.61 |
| Ex. (240) | P3-16 | 5.4 | 12.7 | 5000.0 | 39.4 | 120.2 | 0.33 | 0.61 |
| Ex. (241) | P3-17 | 5.6 | 12.7 | 5000.0 | 39.5 | 122.8 | 0.33 | 0.62 |
| Ex. (242) | P3-18 | 5.5 | 13.0 | 5000.0 | 38.6 | 123.4 | 0.33 | 0.61 |
| Ex. (243) | P3-19 | 5.5 | 13.1 | 5000.0 | 38.3 | 124.3 | 0.33 | 0.62 |
| Ex. (244) | P3-20 | 5.4 | 13.0 | 5000.0 | 38.4 | 124.7 | 0.33 | 0.62 |
| Ex. (245) | P3-21 | 5.5 | 12.8 | 5000.0 | 39.0 | 133.8 | 0.33 | 0.61 |
| Ex. (246) | P3-22 | 5.3 | 12.7 | 5000.0 | 39.5 | 132.2 | 0.33 | 0.62 |
| Ex. (247) | P3-23 | 5.4 | 13.0 | 5000.0 | 38.6 | 120.8 | 0.33 | 0.62 |
| Ex. (248) | P3-24 | 5.6 | 12.6 | 5000.0 | 39.7 | 128.7 | 0.33 | 0.62 |
| Ex. (249) | P3-25 | 5.5 | 12.5 | 5000.0 | 39.9 | 126.2 | 0.33 | 0.62 |
| Ex. (250) | P3-26 | 5.3 | 12.5 | 5000.0 | 39.9 | 130.2 | 0.33 | 0.61 |
| Ex. (251) | P3-27 | 5.4 | 13.1 | 5000.0 | 38.2 | 132.5 | 0.33 | 0.61 |
| Ex. (252) | P3-28 | 5.3 | 13.1 | 5000.0 | 38.2 | 132.6 | 0.33 | 0.61 |
| Ex. (253) | P3-29 | 5.6 | 12.7 | 5000.0 | 39.3 | 124.7 | 0.33 | 0.62 |
| Ex. (254) | P3-30 | 5.4 | 12.9 | 5000.0 | 38.9 | 120.1 | 0.33 | 0.62 |
| Ex. (255) | P3-31 | 5.6 | 12.7 | 5000.0 | 39.2 | 134.7 | 0.33 | 0.62 |
| Ex. (256) | P3-32 | 5.5 | 13.0 | 5000.0 | 38.6 | 130.2 | 0.33 | 0.61 |
| Ex. (257) | P3-33 | 5.5 | 12.7 | 5000.0 | 39.4 | 127.9 | 0.33 | 0.61 |
| Ex. (258) | P3-34 | 5.5 | 13.0 | 5000.0 | 38.5 | 131.3 | 0.33 | 0.62 |
| Ex. (259) | P3-35 | 5.4 | 12.6 | 5000.0 | 39.5 | 134.4 | 0.33 | 0.62 |
| Ex. (260) | P3-36 | 5.4 | 12.7 | 5000.0 | 39.3 | 120.3 | 0.33 | 0.61 |
| Ex. (261) | P3-37 | 5.4 | 12.5 | 5000.0 | 39.9 | 132.7 | 0.33 | 0.62 |
| Ex. (262) | P3-38 | 5.4 | 12.5 | 5000.0 | 40.0 | 128.8 | 0.33 | 0.61 |
| Ex. (263) | P3-39 | 5.3 | 12.8 | 5000.0 | 39.1 | 129.5 | 0.33 | 0.62 |
| Ex. (264) | P3-40 | 5.4 | 12.7 | 5000.0 | 39.5 | 130.4 | 0.33 | 0.61 |
| Ex. (265) | P3-41 | 5.4 | 12.6 | 5000.0 | 39.6 | 121.6 | 0.33 | 0.62 |
| Ex. (266) | P3-42 | 5.4 | 13.1 | 5000.0 | 38.1 | 125.2 | 0.33 | 0.61 |
| Ex. (267) | P3-43 | 5.5 | 12.9 | 5000.0 | 38.6 | 132.3 | 0.33 | 0.62 |
| Ex. (268) | P3-44 | 5.4 | 12.9 | 5000.0 | 38.9 | 122.8 | 0.33 | 0.62 |
| Ex. (269) | P3-45 | 5.5 | 12.9 | 5000.0 | 38.6 | 129.2 | 0.33 | 0.62 |
| Ex. (270) | P3-46 | 5.5 | 12.6 | 5000.0 | 39.7 | 129.9 | 0.33 | 0.61 |
| Ex. (271) | P3-47 | 5.6 | 12.6 | 5000.0 | 39.8 | 131.1 | 0.33 | 0.62 |
| Ex. (272) | P3-48 | 5.5 | 12.7 | 5000.0 | 39.4 | 125.4 | 0.33 | 0.61 |
| Ex. (273) | P3-49 | 5.3 | 13.0 | 5000.0 | 38.3 | 128.8 | 0.33 | 0.61 |
| Ex. (274) | P3-50 | 5.4 | 12.6 | 5000.0 | 39.8 | 120.7 | 0.33 | 0.61 |
| Ex. (275) | P3-51 | 5.3 | 13.1 | 5000.0 | 38.2 | 131.1 | 0.33 | 0.61 |
| Ex. (276) | P3-52 | 5.4 | 12.7 | 5000.0 | 39.4 | 127.5 | 0.33 | 0.62 |
| Ex. (277) | P3-53 | 5.5 | 13.1 | 5000.0 | 38.3 | 128.4 | 0.33 | 0.61 |
| Ex. (278) | P3-54 | 5.3 | 12.6 | 5000.0 | 39.8 | 120.3 | 0.33 | 0.62 |
| Ex. (279) | P3-55 | 5.6 | 13.1 | 5000.0 | 38.1 | 122.7 | 0.33 | 0.61 |
| Ex. (280) | P3-56 | 5.5 | 12.5 | 5000.0 | 39.9 | 121.5 | 0.33 | 0.61 |
| Ex. (281) | P3-57 | 5.4 | 12.9 | 5000.0 | 38.7 | 125.5 | 0.33 | 0.62 |
| Ex. (282) | P3-58 | 5.5 | 13.0 | 5000.0 | 38.4 | 128.1 | 0.33 | 0.61 |
| Ex. (283) | P3-59 | 5.3 | 12.6 | 5000.0 | 39.7 | 129.9 | 0.33 | 0.61 |
| Ex. (284) | P3-60 | 5.4 | 13.0 | 5000.0 | 38.6 | 123.0 | 0.33 | 0.61 |
| Ex. (285) | P3-61 | 5.5 | 13.0 | 5000.0 | 38.4 | 131.0 | 0.33 | 0.62 |
| Ex. (286) | P3-62 | 5.4 | 12.9 | 5000.0 | 38.8 | 126.1 | 0.33 | 0.61 |
| Ex. (287) | P3-63 | 5.3 | 13.0 | 5000.0 | 38.5 | 127.0 | 0.33 | 0.62 |
| Ex. (288) | P3-64 | 5.3 | 13.0 | 5000.0 | 38.5 | 124.7 | 0.33 | 0.62 |
| Ex. (289) | P3-65 | 5.6 | 12.9 | 5000.0 | 38.7 | 129.2 | 0.33 | 0.61 |
| Ex. (290) | P3-66 | 5.5 | 13.0 | 5000.0 | 38.4 | 121.0 | 0.33 | 0.62 |
| Ex. (291) | P3-67 | 5.6 | 12.8 | 5000.0 | 39.2 | 127.0 | 0.33 | 0.61 |
| Ex. (292) | P3-68 | 5.6 | 12.9 | 5000.0 | 38.7 | 126.5 | 0.33 | 0.62 |
| Ex. (293) | P3-69 | 5.4 | 12.7 | 5000.0 | 39.4 | 123.1 | 0.33 | 0.62 |
| Ex. (294) | P3-70 | 5.3 | 12.7 | 5000.0 | 39.5 | 130.5 | 0.33 | 0.62 |
| Ex. (295) | P3-71 | 5.5 | 12.9 | 5000.0 | 38.7 | 123.1 | 0.33 | 0.61 |
| Ex. (296) | P3-72 | 5.6 | 12.8 | 5000.0 | 39.2 | 126.0 | 0.33 | 0.62 |

TABLE 4-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (297) | P3-73 | 5.4 | 13.0 | 5000.0 | 38.4 | 125.6 | 0.33 | 0.61 |
| Ex. (298) | P3-74 | 5.4 | 12.6 | 5000.0 | 39.7 | 121.0 | 0.33 | 0.61 |
| Ex. (299) | P3-75 | 5.5 | 13.1 | 5000.0 | 38.1 | 128.2 | 0.33 | 0.61 |
| Ex. (300) | P3-76 | 5.4 | 12.9 | 5000.0 | 38.9 | 129.3 | 0.33 | 0.62 |
| Ex. (301) | P3-77 | 5.5 | 12.8 | 5000.0 | 39.0 | 123.9 | 0.33 | 0.62 |
| Ex. (302) | P3-78 | 5.6 | 12.6 | 5000.0 | 39.8 | 123.4 | 0.33 | 0.61 |
| Ex. (303) | P3-79 | 5.4 | 13.1 | 5000.0 | 38.3 | 128.1 | 0.33 | 0.62 |
| Ex. (304) | P3-80 | 5.3 | 12.9 | 5000.0 | 38.7 | 134.6 | 0.33 | 0.61 |
| Ex. (305) | P3-81 | 5.4 | 12.7 | 5000.0 | 39.2 | 125.2 | 0.33 | 0.61 |
| Ex. (306) | P3-82 | 5.4 | 12.6 | 5000.0 | 39.6 | 129.9 | 0.33 | 0.62 |
| Ex. (307) | P3-83 | 5.6 | 12.9 | 5000.0 | 38.9 | 128.0 | 0.33 | 0.61 |
| Ex. (308) | P3-84 | 5.4 | 13.1 | 5000.0 | 38.3 | 133.1 | 0.33 | 0.61 |
| Ex. (309) | P3-85 | 5.6 | 13.0 | 5000.0 | 38.3 | 134.9 | 0.33 | 0.61 |
| Ex. (310) | P3-86 | 5.3 | 13.0 | 5000.0 | 38.3 | 132.6 | 0.33 | 0.62 |
| Ex. (311) | P3-87 | 5.4 | 12.8 | 5000.0 | 39.1 | 124.0 | 0.33 | 0.61 |
| Ex. (312) | P3-88 | 5.5 | 12.9 | 5000.0 | 38.8 | 122.1 | 0.33 | 0.62 |
| Ex. (313) | P3-89 | 5.5 | 12.6 | 5000.0 | 39.8 | 124.5 | 0.33 | 0.62 |
| Ex. (314) | P3-90 | 5.5 | 12.9 | 5000.0 | 38.9 | 132.7 | 0.33 | 0.61 |
| Ex. (315) | P3-91 | 5.5 | 13.0 | 5000.0 | 38.4 | 133.9 | 0.33 | 0.62 |
| Ex. (316) | P3-92 | 5.5 | 12.7 | 5000.0 | 39.2 | 127.9 | 0.33 | 0.61 |
| Ex. (317) | P3-93 | 5.3 | 12.9 | 5000.0 | 38.8 | 127.8 | 0.33 | 0.62 |
| Ex. (318) | P3-94 | 5.3 | 12.8 | 5000.0 | 39.2 | 132.6 | 0.33 | 0.61 |
| Ex. (319) | P3-95 | 5.5 | 12.5 | 5000.0 | 40.0 | 134.6 | 0.33 | 0.61 |
| Ex. (320) | P3-96 | 5.5 | 12.7 | 5000.0 | 39.3 | 134.2 | 0.33 | 0.62 |
| Ex. (321) | P3-97 | 5.4 | 13.0 | 5000.0 | 38.4 | 133.8 | 0.33 | 0.61 |
| Ex. (322) | P3-98 | 5.5 | 13.1 | 5000.0 | 38.3 | 124.4 | 0.33 | 0.62 |
| Ex. (323) | P3-99 | 5.4 | 12.6 | 5000.0 | 39.8 | 122.0 | 0.33 | 0.62 |
| Ex. (324) | P3-100 | 5.4 | 12.5 | 5000.0 | 39.9 | 128.7 | 0.33 | 0.61 |
| Ex. (325) | P3-101 | 5.6 | 13.0 | 5000.0 | 38.4 | 121.6 | 0.33 | 0.61 |
| Ex. (326) | P3-102 | 5.4 | 12.8 | 5000.0 | 39.2 | 134.3 | 0.33 | 0.61 |
| Ex. (327) | P3-103 | 5.6 | 13.0 | 5000.0 | 38.4 | 134.3 | 0.33 | 0.62 |
| Ex. (328) | P3-104 | 5.5 | 12.7 | 5000.0 | 39.3 | 128.3 | 0.33 | 0.62 |
| Ex. (329) | P3-105 | 5.3 | 13.1 | 5000.0 | 38.2 | 125.3 | 0.33 | 0.62 |
| Ex. (330) | P3-106 | 5.5 | 12.9 | 5000.0 | 38.9 | 126.3 | 0.33 | 0.61 |
| Ex. (331) | P3-107 | 5.6 | 12.6 | 5000.0 | 39.7 | 121.7 | 0.33 | 0.61 |
| Ex. (332) | P3-108 | 5.4 | 12.9 | 5000.0 | 38.8 | 128.4 | 0.33 | 0.62 |
| Ex. (333) | P3-109 | 5.3 | 12.8 | 5000.0 | 39.0 | 123.0 | 0.33 | 0.62 |
| Ex. (334) | P3-110 | 5.5 | 12.8 | 5000.0 | 39.2 | 123.0 | 0.33 | 0.62 |
| Ex. (335) | P3-111 | 5.4 | 12.7 | 5000.0 | 39.3 | 134.5 | 0.33 | 0.61 |
| Ex. (336) | P3-112 | 5.5 | 12.6 | 5000.0 | 39.6 | 124.5 | 0.33 | 0.61 |
| Ex. (337) | P4-1 | 5.4 | 12.0 | 5000.0 | 41.6 | 90.8 | 0.33 | 0.61 |
| Ex. (338) | P4-2 | 5.4 | 12.3 | 5000.0 | 40.5 | 139.5 | 0.33 | 0.62 |
| Ex. (339) | P4-3 | 5.5 | 12.0 | 5000.0 | 41.5 | 119.6 | 0.33 | 0.62 |
| Ex. (340) | P4-4 | 5.3 | 11.9 | 5000.0 | 42.1 | 96.6 | 0.33 | 0.62 |
| Ex. (341) | P4-21 | 5.3 | 12.1 | 5000.0 | 41.2 | 131.7 | 0.33 | 0.61 |
| Ex. (342) | P4-22 | 5.3 | 11.6 | 5000.0 | 43.3 | 129.8 | 0.33 | 0.62 |
| Ex. (343) | P4-23 | 5.4 | 12.5 | 5000.0 | 40.0 | 124.3 | 0.33 | 0.61 |
| Ex. (344) | P4-24 | 5.3 | 11.9 | 5000.0 | 41.9 | 122.3 | 0.33 | 0.61 |
| Ex. (345) | P4-37 | 5.4 | 12.1 | 5000.0 | 41.3 | 105.6 | 0.33 | 0.61 |
| Ex. (346) | P4-38 | 5.3 | 12.0 | 5000.0 | 41.6 | 146.2 | 0.33 | 0.62 |
| Ex. (347) | P4-39 | 5.3 | 12.0 | 5000.0 | 41.6 | 103.8 | 0.33 | 0.62 |
| Ex. (348) | P4-40 | 5.4 | 12.8 | 5000.0 | 38.9 | 96.2 | 0.33 | 0.61 |

It can be seen from the results in Table 4 above, that the OLEDs employing the inventive compounds as a hole transport layer materials showed predominantly improved efficiency and lifespan, compared to the OLEDs employing comparative compounds 1 to 4 as a hole transport layer materials.

That is, it can be seen that the OLEDs employing the inventive compounds showed predominantly improved efficiency and lifespan, compared to the Comparative Example 1 employing comparative compound 1 of which structure is different from the inventive compound. Further, referring to the Comparative Example 2 to 4 employing comparative compounds 2 to 4 that have carbazole as core as the structure in the present invention, the OLED employing comparative compound 2 where a linker is linked to 3-position of the carbazole moiety ('Com. Ex(2)') showed decreased efficiency yet increased life span, compared to the OLED employing comparative compounds 2 and 3 where a linker is linked to 2-position of the carbazole moiety ('Com. Ex(3) and 'Com. Ex(4)'). The OLED of Com. Ex(4) having a non-linear linker showed increased efficiency, compared to the OLED of Com. Ex(3) having a linear linker to 2-position of the carbazole moiety.

From the result in Table 4, it is seen that the OLED employing as a hole transport layer material, the compound of the present invention that has the carbazole derivative, the biphenyl linker and the amine group, wherein one phenyl of the biphenyl linker is attached to 2-position of the carbazole moiety and the amine groups is attached to the other phenyl of the biphenyl linker, the latter phenyl is bonded on ortho position of the former phenyl attached to the carbazole derivative, and the amine group is bonded on ortho-, meta- or para position of the latter phenyl, (hereinafter each "ortho-ortho type", "ortho-meta type" and "ortho-para type"), showed higher efficiency and increased life span, compared to the OLED of Com. Ex (4) wherein the latter phenyl of the biphenyl linker is bonded on meta position of the former phenyl attached to the carbazole derivative and the amine group is bonded on para position of the latter phenyl (hereinafter "meta-para type").

In addition, the OLED employing compounds of the present invention in P2 type (the compound P2-1 to P2-112; ortho-meta type) as a hole transport layer material showed higher efficiency and longer life span, compared to compounds of the present invention in P2 type (P1-1 to P1-112; ortho-ortho type) and P3 type (P3-1 to P3-112; ortho-para type).

These results are believed to come from that in a compound where the linker is linked on 2-position of the carbazole core, the conjugation length gets shorter than in a compound where the linker is linked on 3-position of the carbazole core, and the band gap gets widened and the HOMO value gets deepen. Further, where the amine group and linker is linked non-linear to the carbazole core, especially on meta position, according to the inventive invention, the bonding angle gets decreased than in a case where the amine group and linker is linked linear to the carbazole core, and the T1 values get higher to improve the electron blocking abilities. Therefore, the OLED employing the inventive compound has a deep HOMO value and the improved electron blocking abilities, and as a result the exciton is more easily produced in the light emitting layer to improve efficiency and lengthen lifespan.

Considering the characteristics (deep HOMO energy level, high T1 value, heat-stability) described above together, it can be seen that the band gap and electrical properties, as well as the surface properties can change much depending on the linking position of the carbazole core and the amine, which can be main factors in improving performance of the organic electric elements.

Furthermore, properties from the hole transport layer should be considered in relation with the light emitting layer (host), and one skilled in the art, even using a similar core compound, would have difficulty in inferring the characteristics shown by the hole transport layer using the compound of the present invention.

[Example 349] An Emission-Auxiliary Layer (Red)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, N,N'-Bis(1-naphthalenyl)-N,N'-bis-phenyl-(1,1'-biphenyl)-4,4'-diamine ("NPD") was vacuum-deposited with a thickness of 60 nm on the hole injection layer to form a hole transport layer.

Subsequently, a film of the compound P1-1 of the present invention was vacuum-deposited on the hole transport layer to form a emission-auxiliary layer with a thickness of 20 nm, and a light emitting layer with a thickness of 30 nm was deposited on the emission-auxiliary layer by using the CBP as a host material and bis-(1-phenylisoquinolyl)iridium (III) acetylacetonate ("(piq)$_2$Ir (acac)") as a dopant material in a weight ratio of 95:5.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Example 350 to [Example 476] an Emission-Auxiliary Layer (Red)

The OLED was manufactured in the same manner as described in Test Example 349, except that any one of the compounds P1-2 to P1-16, P1-63, P1-64, P1-101 to P1-108, P2-1 to P2-20, P2-45 to P2-52, P2-61 to P2-64, P3-17 to P3-20, P3-45 to P3-52, P3-61, P3-62, P3-101 to P3-108, P4-1 to P4-48 of the present invention in the Table below was used as the emission-auxiliary layer material, instead of the inventive compound P1-1.

Comparative Example 5 to [Comparative Example 8]

An OLED was manufactured in the same manner as described in Test Example 349, except that Comparative Compound 2 above in Comparative Example 5, Comparative Compound 3 above in Comparative Example 6, Comparative Compound 4 above in Comparative Example 7, and not forming the emission-auxiliary layer in Comparative Example 8 were used as the emission-auxiliary layer material, instead of the inventive compound P1-1.

A forward bias DC voltage was applied to each of the OLEDs manufactured through Test Examples 349 to 476 and Comparative Example 5 to 8, electro-luminescence (EL) characteristics of the OLED were measured by PR-650 (Photoresearch), and T95 life span was measured by life span measuring equipment (Mcscience) at a reference brightness of 2500 cd/m$^2$. Table 5 below shows evaluation results of OLEDs manufactured Test Examples and Comparative Examples.

TABLE 5

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Com. Ex (5) | Com. Com (2) | 5.9 | 29.0 | 2500.0 | 8.6 | 102.0 | 0.65 | 0.31 |
| Com. Ex (6) | Com. Com (3) | 6.0 | 28.1 | 2500.0 | 8.9 | 111.2 | 0.64 | 0.34 |
| Com. Ex (7) | Com. Com (4) | 6.1 | 27.5 | 2500.0 | 9.1 | 116.0 | 0.66 | 0.33 |
| Com. Ex (8) | — | 5.7 | 34.2 | 2500.0 | 7.3 | 51.5 | 0.64 | 0.31 |
| Ex. (349) | P1-1 | 5.8 | 23.5 | 2500.0 | 10.6 | 138.1 | 0.64 | 0.32 |
| Ex. (350) | P1-2 | 5.8 | 20.0 | 2500.0 | 12.5 | 148.9 | 0.65 | 0.31 |
| Ex. (351) | P1-3 | 6.1 | 18.1 | 2500.0 | 13.8 | 135.3 | 0.66 | 0.32 |
| Ex. (352) | P1-4 | 5.7 | 18.3 | 2500.0 | 13.7 | 147.9 | 0.66 | 0.30 |

TABLE 5-continued

|  | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (353) | P1-5 | 5.8 | 18.2 | 2500.0 | 13.7 | 149.8 | 0.66 | 0.32 |
| Ex. (354) | P1-6 | 6.1 | 17.9 | 2500.0 | 13.9 | 120.2 | 0.64 | 0.30 |
| Ex. (355) | P1-7 | 5.9 | 17.9 | 2500.0 | 13.9 | 142.5 | 0.66 | 0.33 |
| Ex. (356) | P1-8 | 6.1 | 23.9 | 2500.0 | 10.5 | 137.9 | 0.65 | 0.30 |
| Ex. (357) | P1-9 | 5.7 | 23.4 | 2500.0 | 10.7 | 146.0 | 0.65 | 0.31 |
| Ex. (358) | P1-10 | 5.7 | 21.5 | 2500.0 | 11.6 | 128.7 | 0.66 | 0.33 |
| Ex. (359) | P1-11 | 6.0 | 24.7 | 2500.0 | 10.1 | 144.2 | 0.65 | 0.32 |
| Ex. (360) | P1-12 | 5.7 | 20.4 | 2500.0 | 12.3 | 145.1 | 0.65 | 0.30 |
| Ex. (361) | P1-13 | 5.8 | 17.0 | 2500.0 | 14.7 | 137.8 | 0.65 | 0.34 |
| Ex. (362) | P1-14 | 5.7 | 22.4 | 2500.0 | 11.1 | 126.3 | 0.64 | 0.34 |
| Ex. (363) | P1-15 | 6.0 | 19.0 | 2500.0 | 13.1 | 135.8 | 0.64 | 0.31 |
| Ex. (364) | P1-16 | 6.0 | 20.8 | 2500.0 | 12.0 | 142.8 | 0.65 | 0.32 |
| Ex. (365) | P1-63 | 5.8 | 17.5 | 2500.0 | 14.2 | 137.3 | 0.65 | 0.30 |
| Ex. (366) | P1-64 | 6.0 | 23.0 | 2500.0 | 10.9 | 132.2 | 0.66 | 0.32 |
| Ex. (367) | P1-101 | 5.8 | 17.2 | 2500.0 | 14.5 | 146.3 | 0.64 | 0.31 |
| Ex. (368) | P1-102 | 5.9 | 23.9 | 2500.0 | 10.4 | 148.6 | 0.66 | 0.31 |
| Ex. (369) | P1-103 | 5.8 | 17.2 | 2500.0 | 14.5 | 148.0 | 0.65 | 0.30 |
| Ex. (370) | P1-104 | 5.9 | 17.8 | 2500.0 | 14.0 | 130.2 | 0.64 | 0.31 |
| Ex. (371) | P1-105 | 6.0 | 21.3 | 2500.0 | 11.8 | 120.2 | 0.64 | 0.31 |
| Ex. (372) | P1-106 | 5.8 | 21.0 | 2500.0 | 11.9 | 143.1 | 0.65 | 0.33 |
| Ex. (373) | P1-107 | 6.1 | 20.7 | 2500.0 | 12.1 | 140.3 | 0.65 | 0.34 |
| Ex. (374) | P1-108 | 5.9 | 18.6 | 2500.0 | 13.4 | 127.2 | 0.64 | 0.31 |
| Ex. (375) | P2-1 | 5.8 | 14.2 | 2500.0 | 17.6 | 131.5 | 0.65 | 0.31 |
| Ex. (376) | P2-2 | 5.9 | 15.6 | 2500.0 | 16.0 | 133.2 | 0.65 | 0.31 |
| Ex. (377) | P2-3 | 5.7 | 13.0 | 2500.0 | 19.3 | 141.2 | 0.65 | 0.33 |
| Ex. (378) | P2-4 | 5.9 | 15.4 | 2500.0 | 16.2 | 133.7 | 0.66 | 0.31 |
| Ex. (379) | P2-5 | 5.8 | 13.4 | 2500.0 | 18.7 | 130.2 | 0.64 | 0.33 |
| Ex. (380) | P2-6 | 5.9 | 14.3 | 2500.0 | 17.5 | 138.9 | 0.64 | 0.31 |
| Ex. (381) | P2-7 | 6.1 | 12.7 | 2500.0 | 19.7 | 138.8 | 0.64 | 0.31 |
| Ex. (382) | P2-8 | 5.8 | 13.2 | 2500.0 | 18.9 | 145.7 | 0.65 | 0.30 |
| Ex. (383) | P2-9 | 5.9 | 14.4 | 2500.0 | 17.4 | 125.8 | 0.65 | 0.34 |
| Ex. (384) | P2-10 | 6.0 | 14.0 | 2500.0 | 17.8 | 129.3 | 0.66 | 0.33 |
| Ex. (385) | P2-11 | 5.7 | 14.7 | 2500.0 | 17.1 | 131.3 | 0.66 | 0.31 |
| Ex. (386) | P2-12 | 5.9 | 13.7 | 2500.0 | 18.3 | 140.2 | 0.65 | 0.31 |
| Ex. (387) | P2-13 | 6.0 | 14.3 | 2500.0 | 17.5 | 131.3 | 0.66 | 0.32 |
| Ex. (388) | P2-14 | 5.7 | 13.0 | 2500.0 | 19.3 | 125.5 | 0.65 | 0.33 |
| Ex. (389) | P2-15 | 5.8 | 16.2 | 2500.0 | 15.5 | 122.5 | 0.65 | 0.33 |
| Ex. (390) | P2-16 | 6.0 | 14.5 | 2500.0 | 17.3 | 147.1 | 0.65 | 0.32 |
| Ex. (391) | P2-17 | 5.9 | 13.0 | 2500.0 | 19.2 | 124.2 | 0.65 | 0.31 |
| Ex. (392) | P2-18 | 5.7 | 14.2 | 2500.0 | 17.6 | 132.9 | 0.64 | 0.30 |
| Ex. (393) | P2-19 | 5.9 | 15.5 | 2500.0 | 16.2 | 122.3 | 0.65 | 0.33 |
| Ex. (394) | P2-20 | 5.9 | 13.0 | 2500.0 | 19.3 | 132.8 | 0.66 | 0.31 |
| Ex. (395) | P2-45 | 5.8 | 12.7 | 2500.0 | 19.6 | 127.7 | 0.64 | 0.31 |
| Ex. (396) | P2-46 | 5.7 | 14.7 | 2500.0 | 17.0 | 133.4 | 0.66 | 0.30 |
| Ex. (397) | P2-47 | 5.9 | 15.2 | 2500.0 | 16.5 | 128.9 | 0.65 | 0.31 |
| Ex. (398) | P2-48 | 5.9 | 13.2 | 2500.0 | 18.9 | 132.6 | 0.66 | 0.30 |
| Ex. (399) | P2-49 | 5.8 | 12.5 | 2500.0 | 20.0 | 128.4 | 0.65 | 0.33 |
| Ex. (400) | P2-50 | 6.0 | 13.9 | 2500.0 | 17.9 | 144.4 | 0.66 | 0.34 |
| Ex. (401) | P2-51 | 5.8 | 13.1 | 2500.0 | 19.2 | 147.3 | 0.66 | 0.31 |
| Ex. (402) | P2-52 | 5.9 | 13.8 | 2500.0 | 18.1 | 128.9 | 0.65 | 0.34 |
| Ex. (403) | P2-61 | 5.9 | 13.8 | 2500.0 | 18.1 | 131.5 | 0.65 | 0.32 |
| Ex. (404) | P2-62 | 5.7 | 16.5 | 2500.0 | 15.1 | 133.2 | 0.65 | 0.32 |
| Ex. (405) | P2-63 | 6.0 | 15.5 | 2500.0 | 16.2 | 141.2 | 0.64 | 0.30 |
| Ex. (406) | P2-64 | 5.7 | 12.7 | 2500.0 | 19.6 | 133.7 | 0.66 | 0.32 |
| Ex. (407) | P3-17 | 6.1 | 17.4 | 2500.0 | 14.4 | 133.0 | 0.66 | 0.30 |
| Ex. (408) | P3-18 | 5.8 | 21.7 | 2500.0 | 11.5 | 139.7 | 0.64 | 0.31 |
| Ex. (409) | P3-19 | 5.8 | 18.4 | 2500.0 | 13.6 | 132.7 | 0.66 | 0.30 |
| Ex. (410) | P3-20 | 5.7 | 18.4 | 2500.0 | 13.6 | 123.9 | 0.64 | 0.33 |
| Ex. (411) | P3-45 | 5.9 | 24.2 | 2500.0 | 10.3 | 141.4 | 0.66 | 0.33 |
| Ex. (412) | P3-46 | 5.9 | 20.5 | 2500.0 | 12.2 | 133.6 | 0.65 | 0.32 |
| Ex. (413) | P3-47 | 5.9 | 18.4 | 2500.0 | 13.6 | 149.3 | 0.65 | 0.32 |
| Ex. (414) | P3-48 | 5.8 | 19.7 | 2500.0 | 12.7 | 139.8 | 0.64 | 0.31 |
| Ex. (415) | P3-49 | 5.8 | 18.9 | 2500.0 | 13.2 | 123.3 | 0.65 | 0.33 |
| Ex. (416) | P3-50 | 6.0 | 20.0 | 2500.0 | 12.5 | 149.3 | 0.65 | 0.33 |
| Ex. (417) | P3-51 | 5.8 | 16.9 | 2500.0 | 14.8 | 136.3 | 0.66 | 0.32 |
| Ex. (418) | P3-52 | 5.9 | 18.7 | 2500.0 | 13.4 | 147.0 | 0.66 | 0.31 |
| Ex. (419) | P3-61 | 5.9 | 19.7 | 2500.0 | 12.7 | 142.0 | 0.65 | 0.31 |
| Ex. (420) | P3-62 | 5.7 | 22.8 | 2500.0 | 11.0 | 122.5 | 0.64 | 0.32 |
| Ex. (421) | P3-101 | 5.9 | 17.7 | 2500.0 | 14.1 | 141.0 | 0.65 | 0.31 |
| Ex. (422) | P3-102 | 5.7 | 21.4 | 2500.0 | 11.7 | 127.4 | 0.65 | 0.32 |
| Ex. (423) | P3-103 | 6.1 | 22.3 | 2500.0 | 11.2 | 140.9 | 0.65 | 0.31 |
| Ex. (424) | P3-104 | 6.0 | 17.3 | 2500.0 | 14.5 | 121.0 | 0.66 | 0.33 |
| Ex. (425) | P3-105 | 6.0 | 21.1 | 2500.0 | 11.8 | 146.3 | 0.66 | 0.34 |
| Ex. (426) | P3-106 | 5.8 | 21.7 | 2500.0 | 11.5 | 128.1 | 0.66 | 0.31 |
| Ex. (427) | P3-107 | 5.8 | 17.8 | 2500.0 | 14.0 | 131.5 | 0.65 | 0.33 |

TABLE 5-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (428) | P3-108 | 5.8 | 19.0 | 2500.0 | 13.1 | 149.7 | 0.66 | 0.34 |
| Ex. (429) | P4-1 | 5.5 | 14.4 | 2500.0 | 17.4 | 134.8 | 0.64 | 0.32 |
| Ex. (430) | P4-2 | 5.5 | 15.8 | 2500.0 | 15.9 | 132.0 | 0.65 | 0.31 |
| Ex. (431) | P4-3 | 5.5 | 16.5 | 2500.0 | 15.1 | 137.1 | 0.66 | 0.32 |
| Ex. (432) | P4-4 | 5.4 | 12.8 | 2500.0 | 19.5 | 136.7 | 0.66 | 0.30 |
| Ex. (433) | P4-5 | 5.4 | 12.7 | 2500.0 | 19.6 | 141.5 | 0.66 | 0.32 |
| Ex. (434) | P4-6 | 5.4 | 15.3 | 2500.0 | 16.3 | 136.9 | 0.64 | 0.30 |
| Ex. (435) | P4-7 | 5.4 | 12.5 | 2500.0 | 19.9 | 141.6 | 0.66 | 0.33 |
| Ex. (436) | P4-8 | 5.5 | 14.4 | 2500.0 | 17.4 | 147.3 | 0.65 | 0.30 |
| Ex. (437) | P4-9 | 5.4 | 13.3 | 2500.0 | 18.9 | 141.8 | 0.65 | 0.31 |
| Ex. (438) | P4-10 | 5.3 | 13.6 | 2500.0 | 18.4 | 137.9 | 0.66 | 0.33 |
| Ex. (439) | P4-11 | 5.4 | 13.8 | 2500.0 | 18.1 | 142.9 | 0.65 | 0.32 |
| Ex. (440) | P4-12 | 5.4 | 12.8 | 2500.0 | 19.5 | 149.2 | 0.65 | 0.30 |
| Ex. (441) | P4-13 | 5.4 | 16.3 | 2500.0 | 15.4 | 147.3 | 0.65 | 0.34 |
| Ex. (442) | P4-14 | 5.3 | 16.6 | 2500.0 | 15.1 | 135.1 | 0.64 | 0.34 |
| Ex. (443) | P4-15 | 5.3 | 13.9 | 2500.0 | 18.0 | 141.4 | 0.64 | 0.31 |
| Ex. (444) | P4-16 | 5.4 | 14.9 | 2500.0 | 16.8 | 141.2 | 0.65 | 0.32 |
| Ex. (445) | P4-17 | 5.3 | 13.1 | 2500.0 | 19.0 | 148.9 | 0.65 | 0.30 |
| Ex. (446) | P4-18 | 5.4 | 13.7 | 2500.0 | 18.2 | 134.3 | 0.66 | 0.32 |
| Ex. (447) | P4-19 | 5.3 | 14.9 | 2500.0 | 16.8 | 138.9 | 0.64 | 0.31 |
| Ex. (448) | P4-20 | 5.3 | 12.8 | 2500.0 | 19.5 | 145.5 | 0.66 | 0.31 |
| Ex. (449) | P4-21 | 5.4 | 14.5 | 2500.0 | 17.2 | 138.9 | 0.65 | 0.30 |
| Ex. (450) | P4-22 | 5.4 | 15.5 | 2500.0 | 16.1 | 145.4 | 0.64 | 0.31 |
| Ex. (451) | P4-23 | 5.3 | 14.7 | 2500.0 | 17.0 | 130.4 | 0.64 | 0.31 |
| Ex. (452) | P4-24 | 5.4 | 14.5 | 2500.0 | 17.3 | 133.3 | 0.65 | 0.33 |
| Ex. (453) | P4-25 | 5.3 | 15.5 | 2500.0 | 16.1 | 130.8 | 0.65 | 0.34 |
| Ex. (454) | P4-26 | 5.4 | 14.0 | 2500.0 | 17.8 | 140.3 | 0.64 | 0.31 |
| Ex. (455) | P4-27 | 5.5 | 16.4 | 2500.0 | 15.2 | 143.8 | 0.65 | 0.31 |
| Ex. (456) | P4-28 | 5.4 | 16.5 | 2500.0 | 15.1 | 130.3 | 0.65 | 0.31 |
| Ex. (457) | P4-29 | 5.5 | 13.4 | 2500.0 | 18.6 | 140.3 | 0.65 | 0.33 |
| Ex. (458) | P4-30 | 5.4 | 12.7 | 2500.0 | 19.6 | 144.7 | 0.66 | 0.31 |
| Ex. (459) | P4-31 | 5.3 | 13.7 | 2500.0 | 18.3 | 134.9 | 0.64 | 0.33 |
| Ex. (460) | P4-32 | 5.3 | 13.8 | 2500.0 | 18.2 | 146.6 | 0.64 | 0.31 |
| Ex. (461) | P4-33 | 5.3 | 14.3 | 2500.0 | 17.5 | 132.5 | 0.64 | 0.31 |
| Ex. (462) | P4-34 | 5.4 | 15.0 | 2500.0 | 16.6 | 133.9 | 0.65 | 0.30 |
| Ex. (463) | P4-35 | 5.4 | 15.7 | 2500.0 | 15.9 | 146.8 | 0.65 | 0.34 |
| Ex. (464) | P4-36 | 5.4 | 16.2 | 2500.0 | 15.4 | 137.2 | 0.66 | 0.33 |
| Ex. (465) | P4-37 | 5.4 | 14.4 | 2500.0 | 17.3 | 135.6 | 0.66 | 0.31 |
| Ex. (466) | P4-38 | 5.4 | 13.9 | 2500.0 | 18.0 | 149.9 | 0.65 | 0.31 |
| Ex. (467) | P4-39 | 5.4 | 16.6 | 2500.0 | 15.0 | 139.2 | 0.66 | 0.32 |
| Ex. (468) | P4-40 | 5.4 | 15.8 | 2500.0 | 15.8 | 137.4 | 0.65 | 0.33 |
| Ex. (469) | P4-41 | 5.4 | 12.7 | 2500.0 | 19.6 | 143.9 | 0.65 | 0.33 |
| Ex. (470) | P4-42 | 5.5 | 13.6 | 2500.0 | 18.4 | 141.9 | 0.65 | 0.32 |
| Ex. (471) | P4-43 | 5.5 | 13.5 | 2500.0 | 18.5 | 147.7 | 0.65 | 0.31 |
| Ex. (472) | P4-44 | 5.5 | 15.1 | 2500.0 | 16.6 | 137.9 | 0.64 | 0.30 |
| Ex. (473) | P4-45 | 5.3 | 13.3 | 2500.0 | 18.8 | 140.9 | 0.65 | 0.33 |
| Ex. (474) | P4-46 | 5.4 | 13.1 | 2500.0 | 19.1 | 136.2 | 0.66 | 0.31 |
| Ex. (475) | P4-47 | 5.3 | 14.2 | 2500.0 | 17.6 | 145.1 | 0.64 | 0.31 |
| Ex. (476) | P4-48 | 5.4 | 12.8 | 2500.0 | 19.5 | 138.4 | 0.66 | 0.30 |

[Example 477] Green OLED (an Emission-Auxiliary Layer)

Organic light emitting diodes (OLEDs) were fabricated according to a conventional method by using a compound of the present invention as an emission-auxiliary layer material First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer.

Subsequently, a film of the compound P1-21 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and Ir(ppy)$_3$ as a dopant material in a weight ratio of 95:5.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Example 478 to [Example 516] Green OLED (an Emission-Auxiliary Layer)

The OLED was manufactured in the same manner as described in Test Example 477, except that any one of the compounds P1-22 to P1-30, P2-31 to P2-38, P3-39 to P3-44, and P3-77 to P3-92 of the present invention in the Table 6 below was used as the emission-auxiliary layer material, instead of the inventive compound P1-21.

Comparative Example 9 to [Comparative Example 12] Green OLED (an Emission-Auxiliary Layer)

An OLED was manufactured in the same manner as described in Test Example 477, except that Comparative compound 2 in comparative example 9, Comparative Compound 3 in comparative example 10, and Comparative Compound 4 in comparative example 11 were used as the emission-auxiliary layer material, instead of the inventive compound P1-21, and except that the emission-auxiliary layer in Comparative Example 12 was not formed.

A forward bias DC voltage was applied to each of the OLEDs manufactured through Test Examples 477 to 516 and Comparative Example 9 to 12, electro-luminescence (EL) characteristics of the OLED were measured by PR-650 (Photoresearch), and T95 life span was measured by life span measuring equipment (Mcscience) at a reference brightness of 5000 cd/m². Table 6 below shows evaluation results of OLEDs manufactured Test Examples and Comparative Examples.

and longer lifespan, compared to the OLEDs employing comparative compounds 2 to 4 as the auxiliary emission layer material and the OLEDs not having the auxiliary emission layer. That is, the OLEDs employing the inventive compounds showed improved efficiency and lifespan, compared to the OLEDs of Comparative Examples 5 to 7 and Comparative Examples 9 to 11 employing comparative compounds 2 to 4. Especially, the OLEDs employing the present invention compounds showed predominantly improved efficiency and long life span, compared to the OLEDs not forming the auxiliary emission layer (Com. Ex (8) and Com. Ex (12)).

Further, significant difference in life span was shown between the compounds having a linker equally linked to the same 2-position of the carbazole cores yet the substituent amine group is linked on a different position of the linker. This is believed because different bonding angle occurs depending on to which position of the linker the amine group is linked, so does the different T1 values, which causes different electron blocking abilities.

TABLE 6

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Com. Ex (9) | Com. Com (2) | 5.6 | 13.6 | 5000 | 36.8 | 116.9 | 0.33 | 0.61 |
| Com. Ex (10) | Com. Com (3) | 5.8 | 12.3 | 5000 | 40.5 | 118.7 | 0.33 | 0.61 |
| Com. Ex (11) | Com. Com (4) | 6.1 | 11.6 | 5000 | 43.2 | 124.5 | 0.33 | 0.61 |
| Com. Ex (12) | — | 5.6 | 21.7 | 5000 | 23.0 | 65.7 | 0.33 | 0.61 |
| Ex. (477) | P1-21 | 5.7 | 10.8 | 5000.0 | 46.4 | 143.2 | 0.33 | 0.62 |
| Ex. (478) | P1-22 | 5.9 | 10.4 | 5000.0 | 48.0 | 139.4 | 0.33 | 0.62 |
| Ex. (479) | P1-23 | 5.9 | 11.0 | 5000.0 | 45.4 | 131.1 | 0.33 | 0.61 |
| Ex. (480) | P1-24 | 5.7 | 11.1 | 5000.0 | 45.2 | 146.6 | 0.33 | 0.61 |
| Ex. (481) | P1-25 | 5.9 | 11.0 | 5000.0 | 45.5 | 138.3 | 0.33 | 0.62 |
| Ex. (482) | P1-26 | 5.9 | 10.5 | 5000.0 | 47.6 | 145.8 | 0.33 | 0.61 |
| Ex. (483) | P1-27 | 5.8 | 10.7 | 5000.0 | 46.7 | 130.1 | 0.33 | 0.62 |
| Ex. (484) | P1-28 | 5.7 | 11.0 | 5000.0 | 45.5 | 136.1 | 0.33 | 0.62 |
| Ex. (485) | P1-29 | 5.8 | 10.6 | 5000.0 | 47.0 | 144.8 | 0.33 | 0.62 |
| Ex. (486) | P1-30 | 5.6 | 10.7 | 5000.0 | 46.8 | 137.0 | 0.33 | 0.61 |
| Ex. (487) | P2-31 | 5.8 | 9.5 | 5000.0 | 52.6 | 137.7 | 0.33 | 0.62 |
| Ex. (488) | P2-32 | 5.8 | 9.9 | 5000.0 | 50.7 | 145.9 | 0.33 | 0.61 |
| Ex. (489) | P2-33 | 5.7 | 9.5 | 5000.0 | 52.8 | 140.5 | 0.33 | 0.62 |
| Ex. (490) | P2-34 | 5.8 | 9.5 | 5000.0 | 52.5 | 149.4 | 0.33 | 0.61 |
| Ex. (491) | P2-35 | 5.9 | 10.1 | 5000.0 | 49.7 | 144.3 | 0.33 | 0.61 |
| Ex. (492) | P2-36 | 5.9 | 9.7 | 5000.0 | 51.7 | 133.7 | 0.33 | 0.62 |
| Ex. (493) | P2-37 | 5.9 | 10.1 | 5000.0 | 49.3 | 149.7 | 0.33 | 0.61 |
| Ex. (494) | P2-38 | 5.7 | 9.9 | 5000.0 | 50.5 | 141.0 | 0.33 | 0.61 |
| Ex. (495) | P3-39 | 6.0 | 10.5 | 5000.0 | 47.6 | 132.8 | 0.33 | 0.62 |
| Ex. (496) | P3-40 | 5.6 | 10.8 | 5000.0 | 46.4 | 141.7 | 0.33 | 0.61 |
| Ex. (497) | P3-41 | 5.8 | 10.8 | 5000.0 | 46.5 | 142.7 | 0.33 | 0.61 |
| Ex. (498) | P3-42 | 5.8 | 11.0 | 5000.0 | 45.3 | 141.3 | 0.33 | 0.62 |
| Ex. (499) | P3-43 | 5.7 | 11.1 | 5000.0 | 45.0 | 141.2 | 0.33 | 0.61 |
| Ex. (500) | P3-44 | 5.9 | 10.8 | 5000.0 | 46.5 | 130.3 | 0.33 | 0.62 |
| Ex. (501) | P3-77 | 5.7 | 11.1 | 5000.0 | 45.2 | 139.9 | 0.33 | 0.62 |
| Ex. (502) | P3-78 | 5.9 | 11.0 | 5000.0 | 45.3 | 134.6 | 0.33 | 0.61 |
| Ex. (503) | P3-79 | 5.9 | 10.6 | 5000.0 | 47.2 | 132.9 | 0.33 | 0.61 |
| Ex. (504) | P3-80 | 5.9 | 10.7 | 5000.0 | 46.6 | 149.2 | 0.33 | 0.61 |
| Ex. (505) | P3-81 | 5.8 | 11.1 | 5000.0 | 45.2 | 142.9 | 0.33 | 0.62 |
| Ex. (506) | P3-82 | 5.8 | 11.0 | 5000.0 | 45.5 | 143.5 | 0.33 | 0.62 |
| Ex. (507) | P3-83 | 5.7 | 10.6 | 5000.0 | 47.2 | 135.9 | 0.33 | 0.61 |
| Ex. (508) | P3-84 | 5.9 | 10.5 | 5000.0 | 47.7 | 140.3 | 0.33 | 0.62 |
| Ex. (509) | P3-85 | 5.9 | 10.8 | 5000.0 | 46.3 | 143.4 | 0.33 | 0.61 |
| Ex. (510) | P3-86 | 5.8 | 11.0 | 5000.0 | 45.4 | 131.0 | 0.33 | 0.61 |
| Ex. (511) | P3-87 | 5.8 | 10.7 | 5000.0 | 46.7 | 148.2 | 0.33 | 0.61 |
| Ex. (512) | P3-88 | 5.8 | 10.9 | 5000.0 | 46.0 | 143.8 | 0.33 | 0.62 |
| Ex. (513) | P3-89 | 5.7 | 10.6 | 5000.0 | 47.4 | 146.7 | 0.33 | 0.62 |
| Ex. (514) | P3-90 | 6.0 | 10.5 | 5000.0 | 47.5 | 137.4 | 0.33 | 0.61 |
| Ex. (515) | P3-91 | 5.8 | 10.6 | 5000.0 | 47.2 | 138.4 | 0.33 | 0.61 |
| Ex. (516) | P3-92 | 5.8 | 11.0 | 5000.0 | 45.6 | 145.0 | 0.33 | 0.61 |

It can be seen from the results in Tables 5 and 6 above, that the OLEDs employing the inventive compounds as the auxiliary emission layer material showed higher efficiency Especially, referring to the result in Table 5, it can be seen that although efficiency is similar, but driving voltage and life span are improved where the compounds (P4-1 to P4-48) of the present invention having $R^3$ or $R^4$ substituted with a substituent other than hydrogen is employing as a red auxiliary emission layer, compared to the compounds having $R^3$ or $R^4$ substituted with hydrogen.

As described above, it was shown that linking position between the carbazole core, the linker and the amine group is important factor because the performance ability of the organic elements in an auxiliary emission layer as well as a hole transfer layer changes depending on the compounds having different linking position between the carbazole core and the linker, and between the linker and the amine group substituted thereto.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

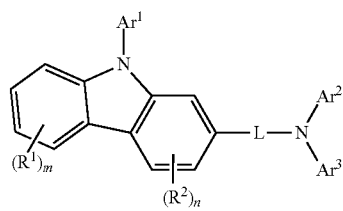

[Formula 1]

wherein,

Ar¹ to Ar³ are each independently selected form the group consisting of a $C_6$-$C_{18}$ aryl group; a fluorenyl group; and a $C_2$-$C_{16}$ heterocyclic group containing at least one heteroatom selected from the group consisting of O, N and S, L is

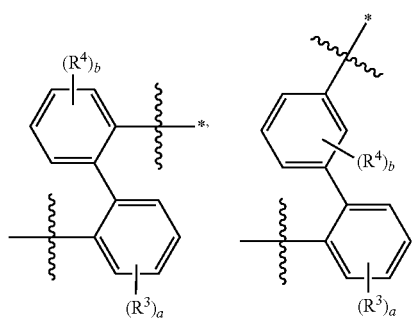

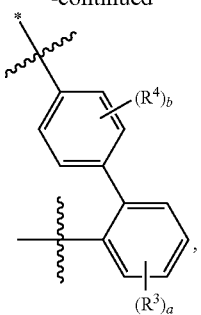

wherein * indicates the position to which the nitrogen atom(N) of the amine group in Formula 1 is linked, a, b and m are each an integer of 0 to 4, and n is an integer of 0 to 3, $R^1$ to $R^4$ are each independently selected from the group consisting of deuterium; a $C_6$-$C_{18}$ aryl group; a fluorenyl group; a $C_2$-$C_{14}$ heterocyclic group containing at least one heteroatom selected from the group consisting of O, N and S; and a $C_2$-$C_{20}$ alkenyl group; or adjacent groups of $R^1$s to $R^4$s may be linked to form benzene ring, and the group(s) not forming the ring is(are) the same as defined in the above, and each of the above aryl group, fluorenyl group, heterocyclic group, alkenyl group, may be substituted with one or more substituents selected from the group consisting of deuterium; halogen; a silane group; a siloxane group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N and S, a $C_3$-$C_{20}$ cycloalkyl group; a $C_7$-$C_{20}$ arylalkyl group; and a $C_8$-$C_{20}$ arylalkenyl group.

2. The compound of claim 1, wherein a and b are each 0 (zero), or $R^3$ and $R^4$ are each independently selected from the following structures:

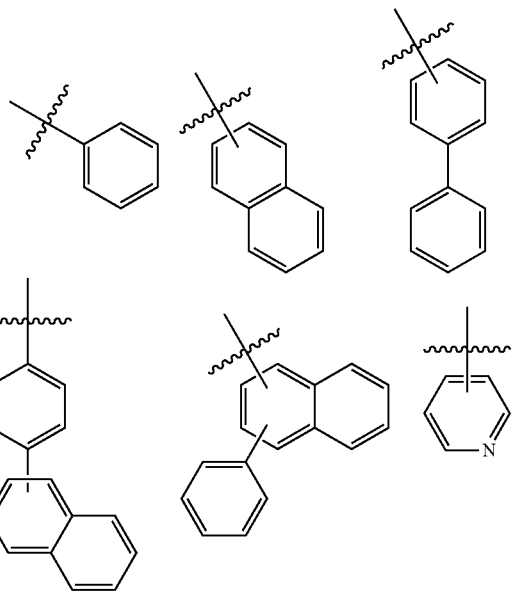

-continued

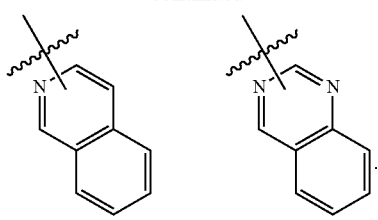

3. The compound of claim 1, wherein at least one of $R^1$s or $R^2$s is linked to form benzene ring between adjacent groups.

4. The compound of claim 3 represented by one of Formulas below:

[Formula 2]

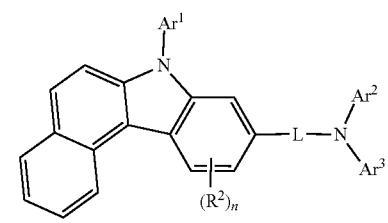

[Formula 3]

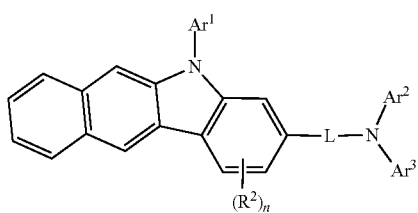

[Formula 4]

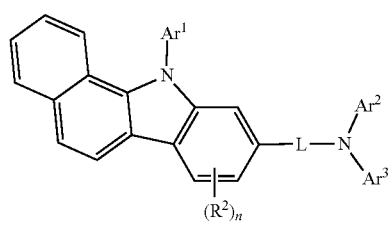

[Formula 5]

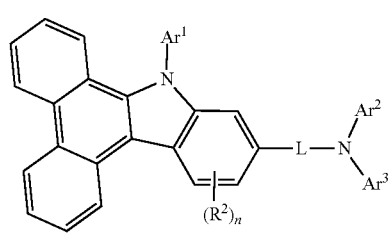

-continued

[Formula 6]

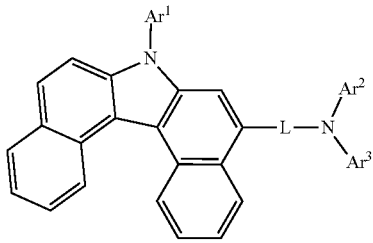

[Formula 7]

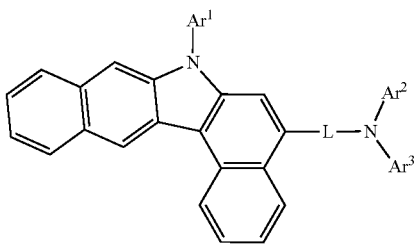

[Formula 8]

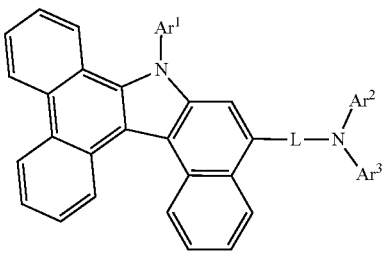

[Formula 9]

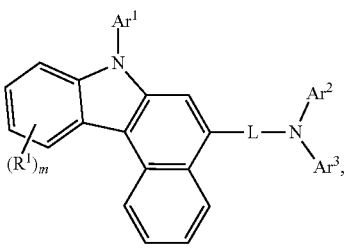

[Formula 10]

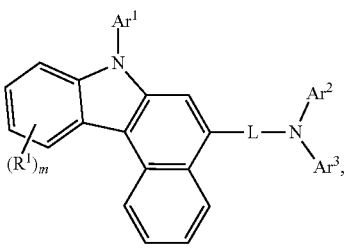

wherein, $Ar^1$ to $Ar^3$, L, $R^1$, $R^2$, m and n are the same as defined in claim 1.

5. The compound of claim 1, wherein $Ar^1$ is selected from the following structures:

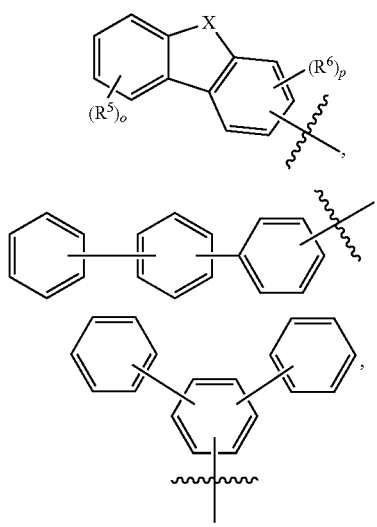

wherein X is O, S or C(R')(R"),

R' and R" are each independently selected from the group consisting of a $C_6$-$C_{20}$ aryl group; and a $C_1$-$C_{20}$ alkyl group, or R' and R" may be linked together to form a spiro compound with the carbon to which they are attached, o is an integer of 0 to 4, and p is an integer of 0 to 3, $R^5$ and $R^6$ are each independently selected from the group consisting of deuterium; a $C_6$-$C_{20}$ aryl group; a fluorenyl group; a $C_2$-$C_{20}$ heterocyclic group containing at least one heteroatom selected from the group consisting of O, N and S, a $C_1$-$C_{20}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, or adjacent groups of $R^5$s and $R^6$s may be linked to form benzene ring, and the group(s) not forming the ring is(are) the same as defined in the above.

6. The compound of claim 5,
wherein $Ar^1$ is

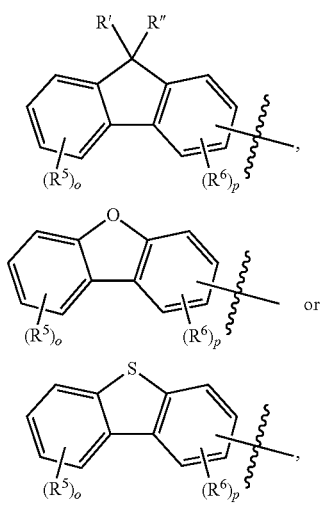

and

Formula 1 is represented by one of Formulas 11 to 20 below:

[Formula 11]

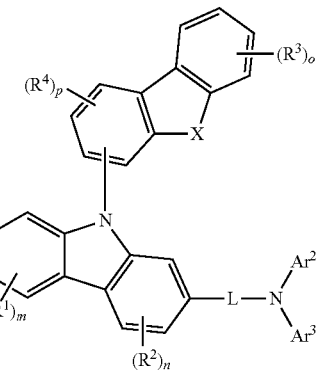

[Formula 12]

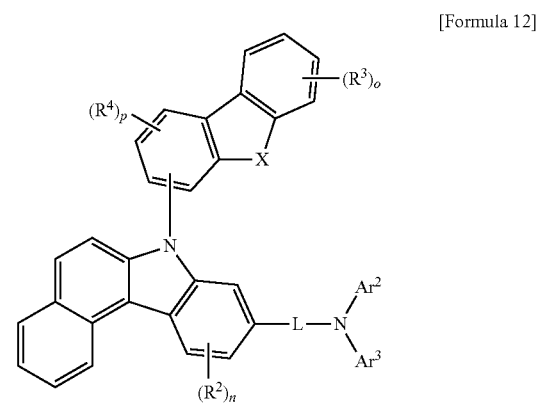

[Formula 13]

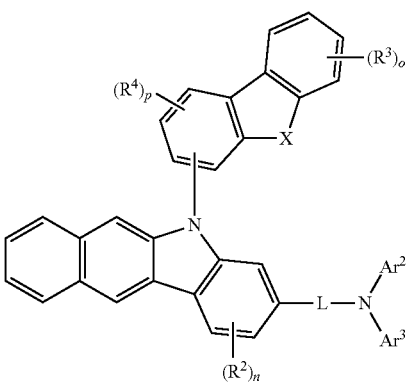

[Formula 14]

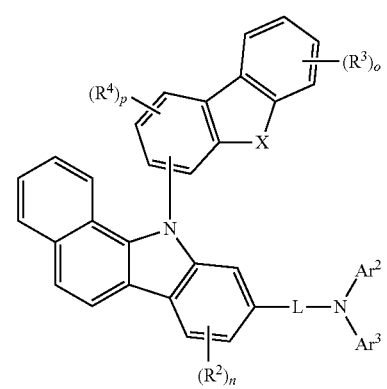

[Formula 15]
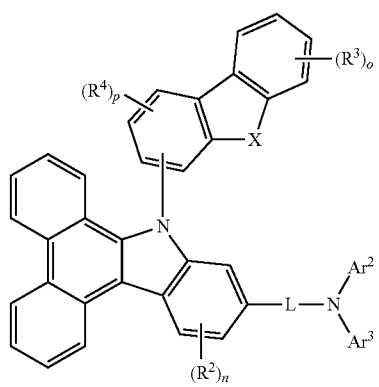
[Formula 16]
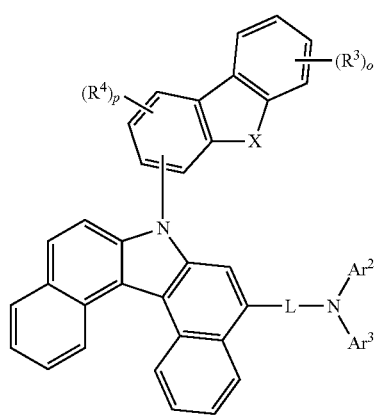
[Formula 17]
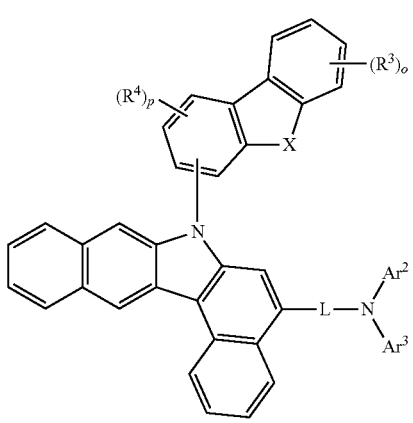
[Formula 18]
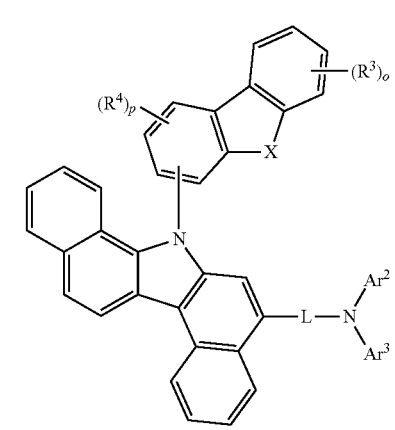
[Formula 19]
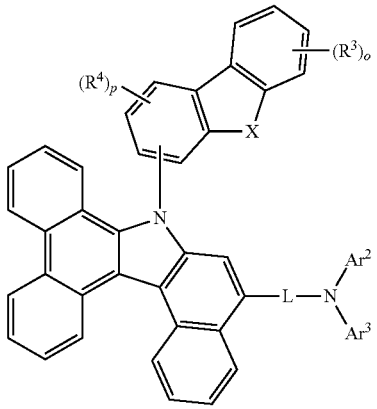
[Formula 20]
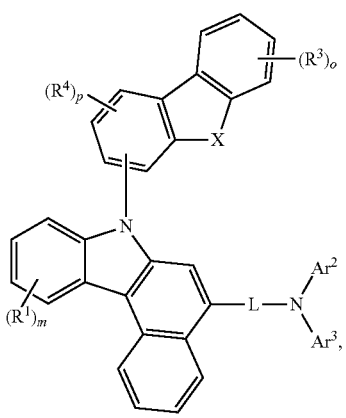
in Formulas 11 to 20, $Ar^2$, $Ar^3$, L, $R^1$, $R^2$, m and n are the same as defined in claim 1, and X, $R^5$, $R^6$, o and p are the same as defined in claim 5.
7. The compound of claim 1, wherein $Ar^2$ and $Ar^3$ are each independently selected from the following structures:
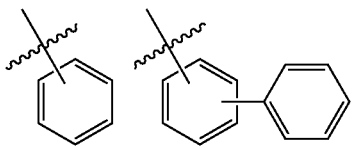
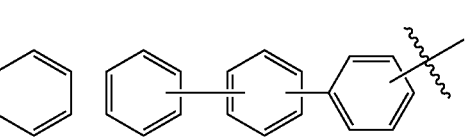
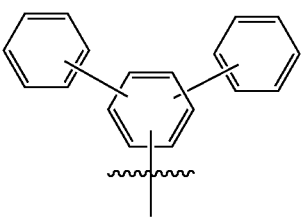

-continued
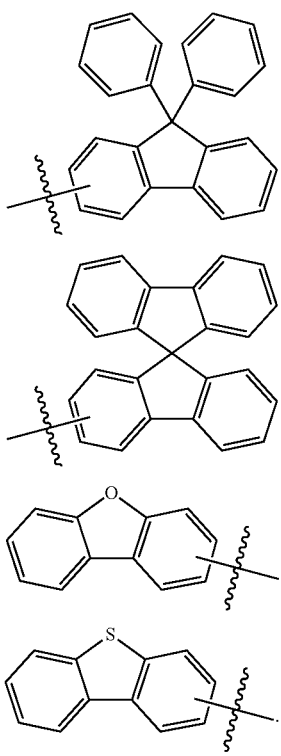
8. The compound of claim 1, wherein Formula 1 is any one of the compounds below:
-continued
P1-3
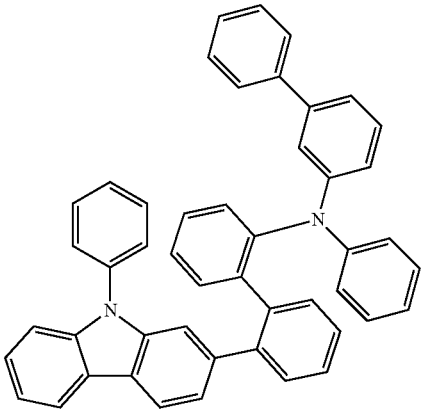
P1-4
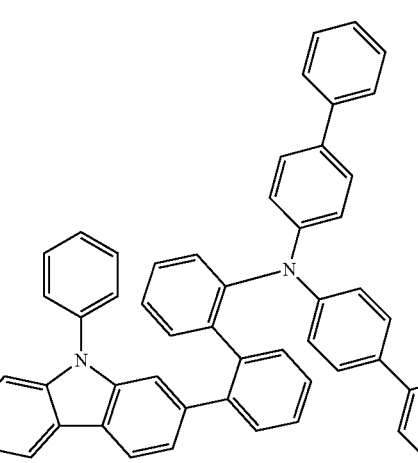
P1-5
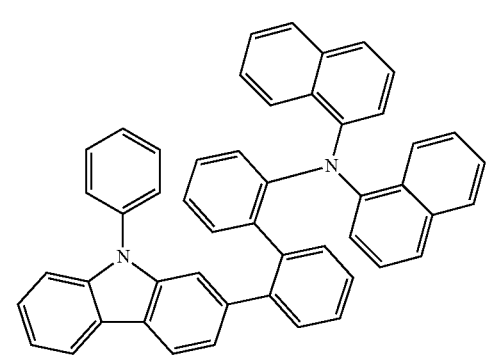
P1-6
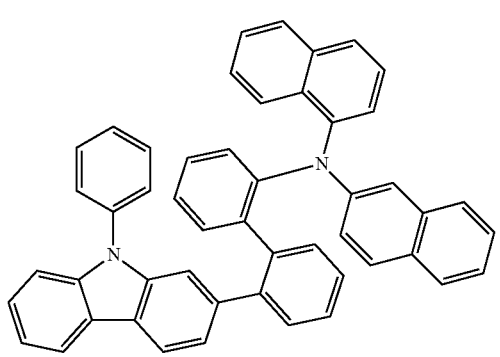
P1-1
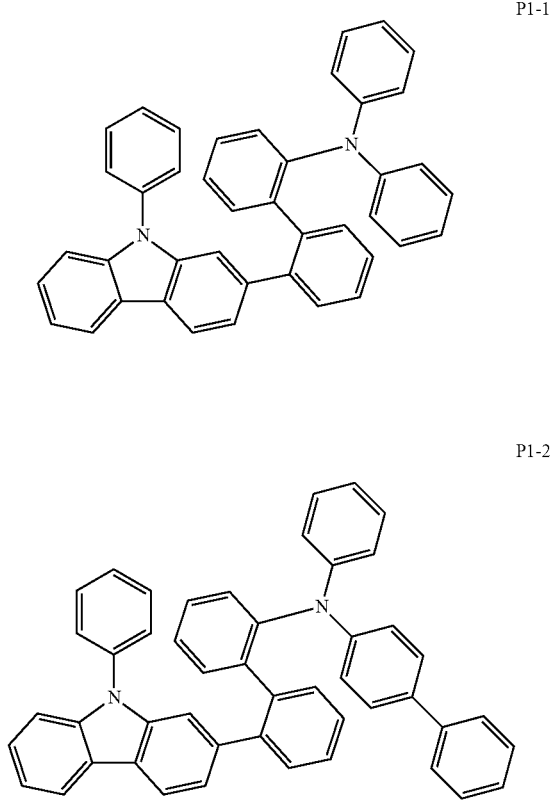
P1-2

-continued
P1-7
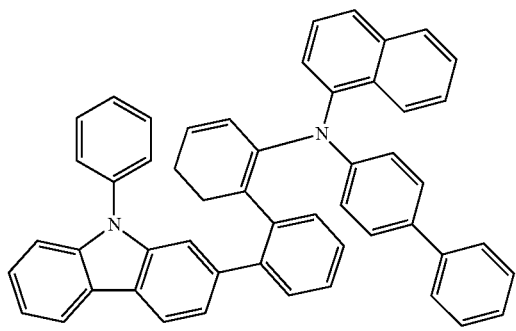
P1-8
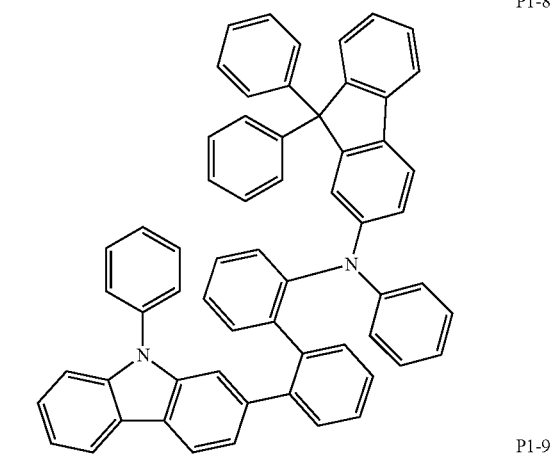
P1-9
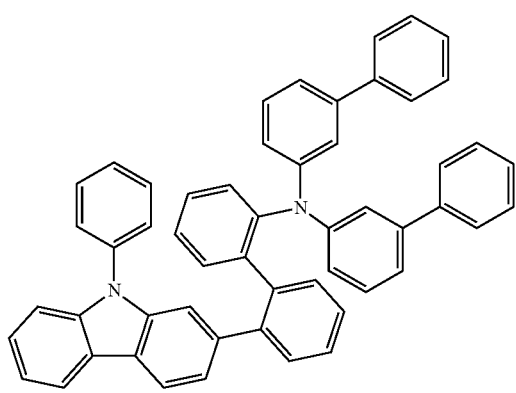
P1-10
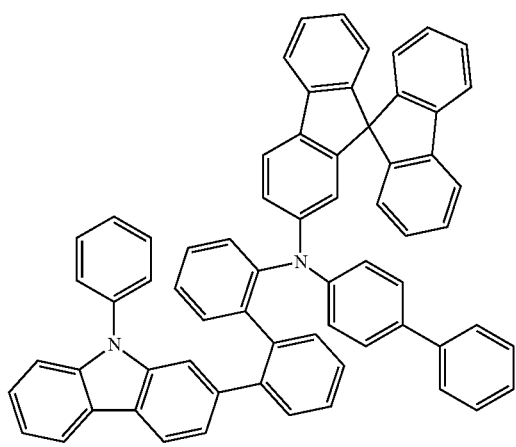
-continued
P1-11
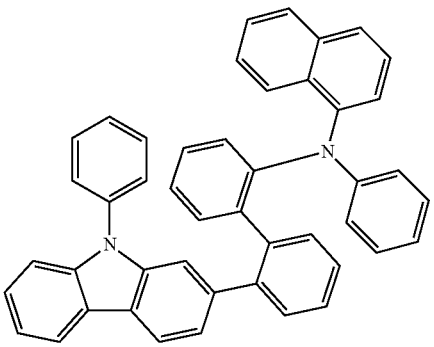
P1-12
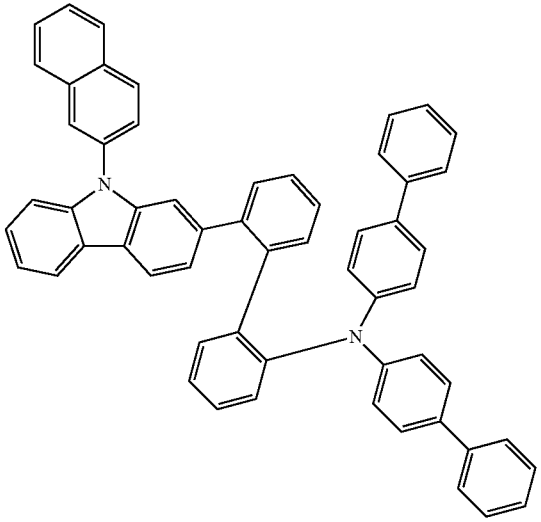
P1-13
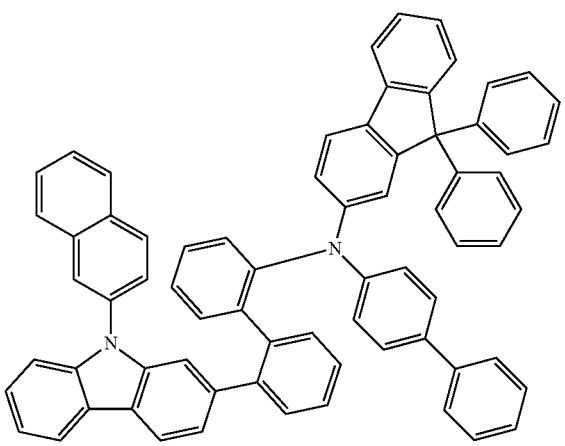

-continued
P1-14
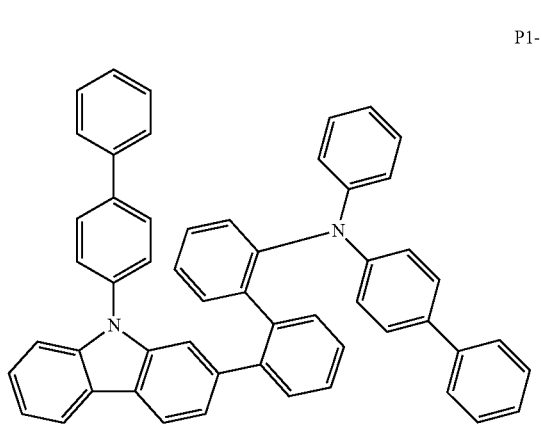
P1-15
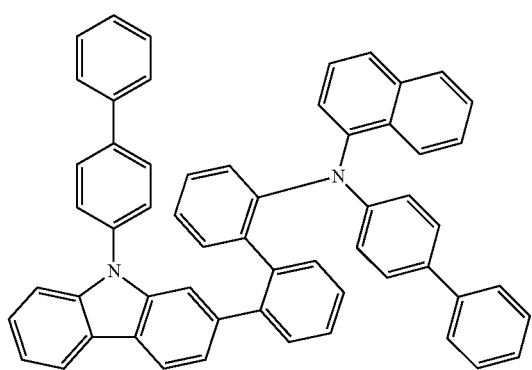
P1-16
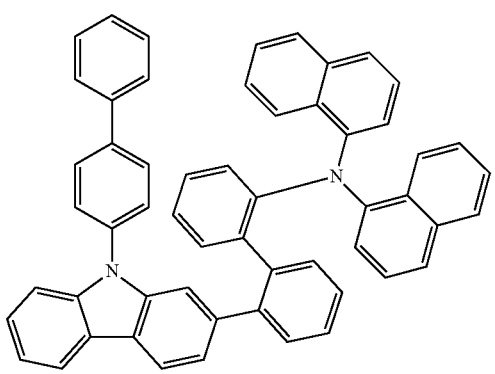
-continued
P1-17
P1-18
P1-19
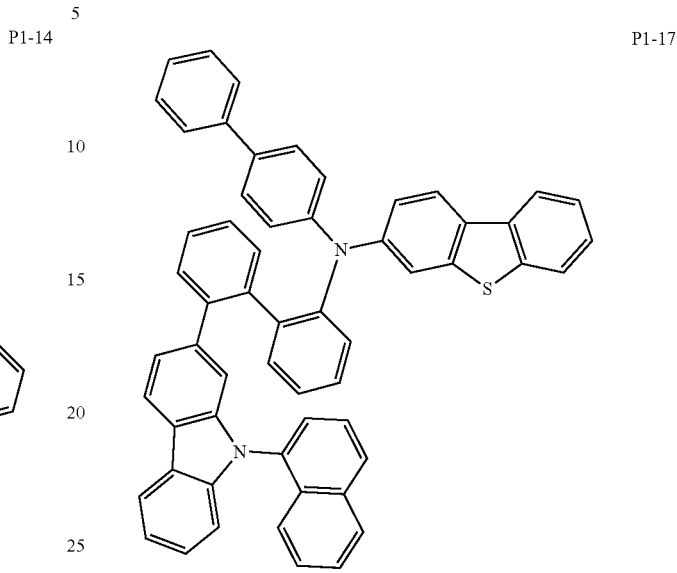
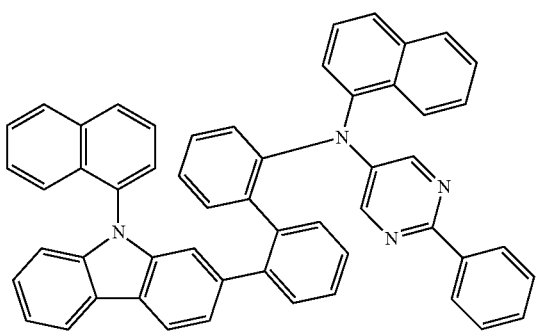

P1-20
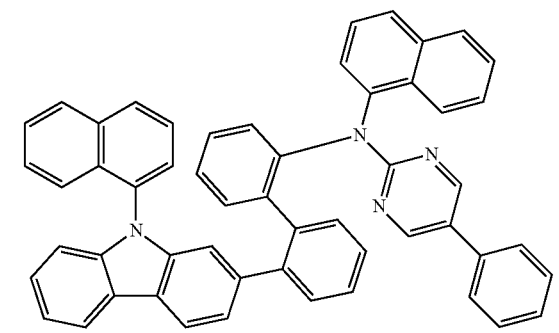
P1-21
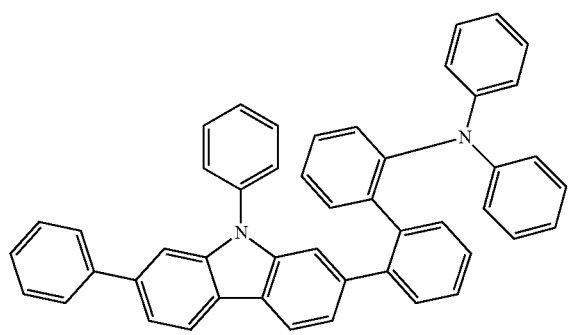
P1-22
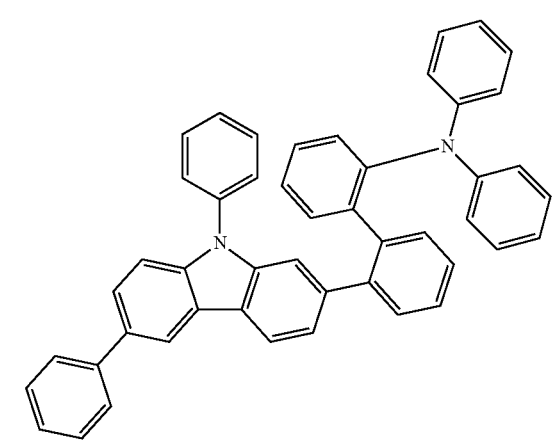
P1-23
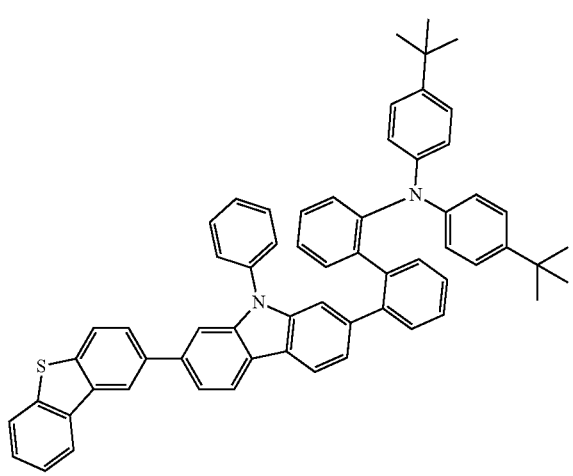
P1-24
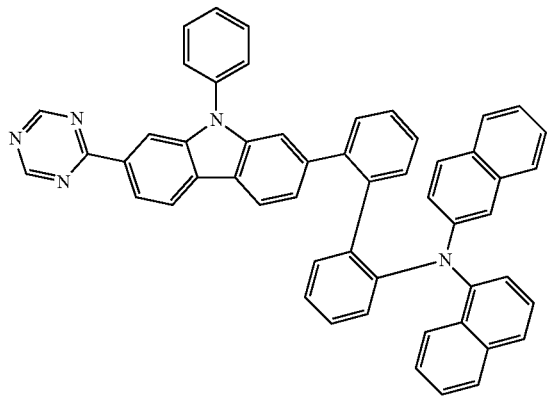
P1-25
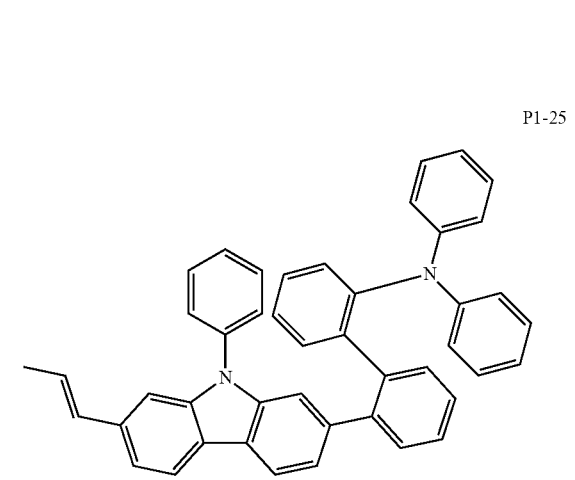
P1-26
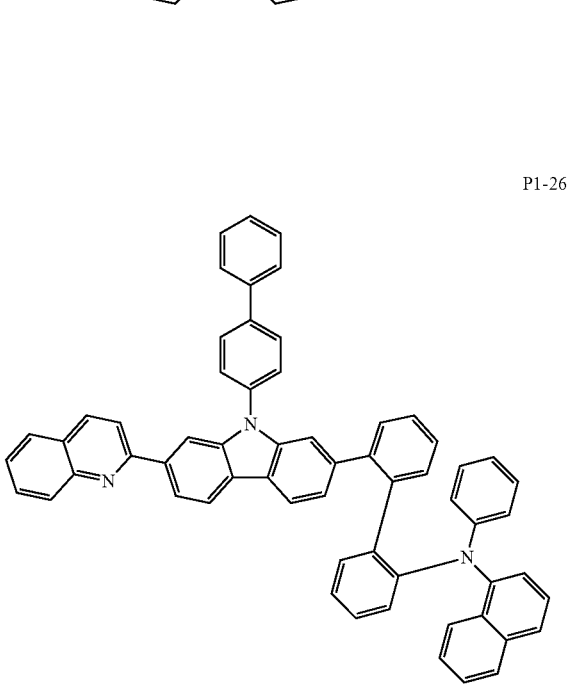

P1-27
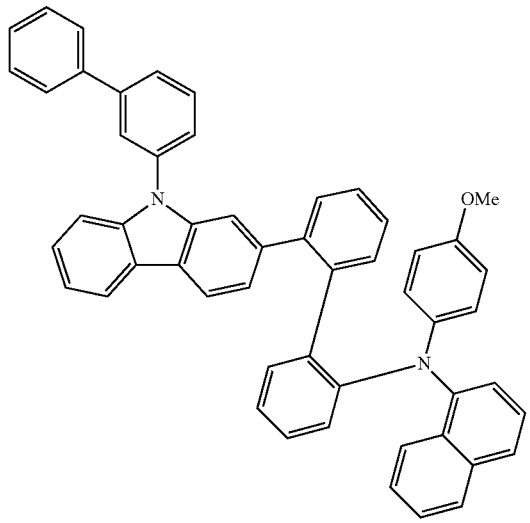
P1-28
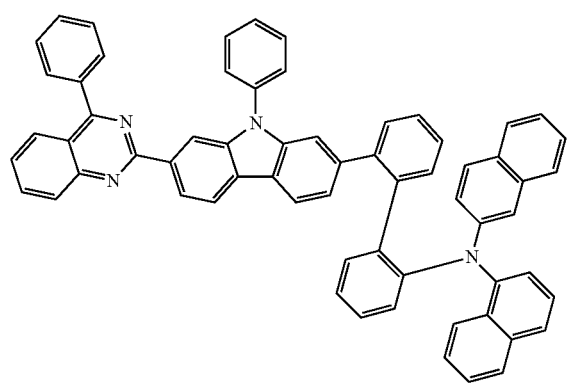
P1-29
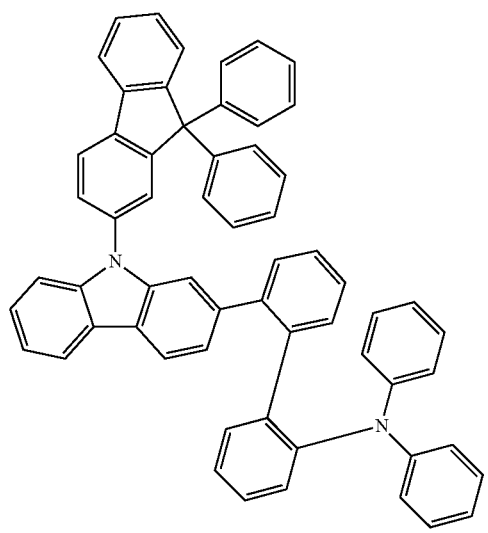
P1-30
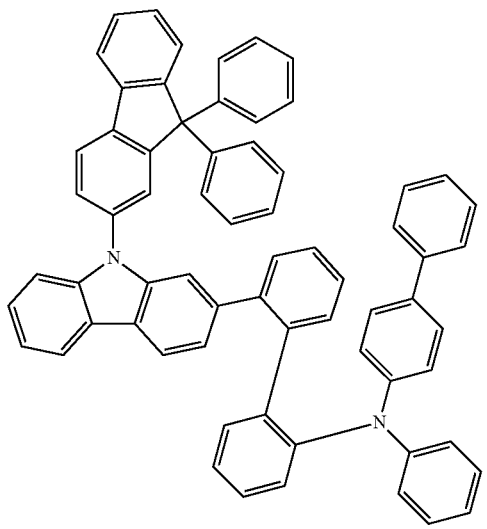
P1-31
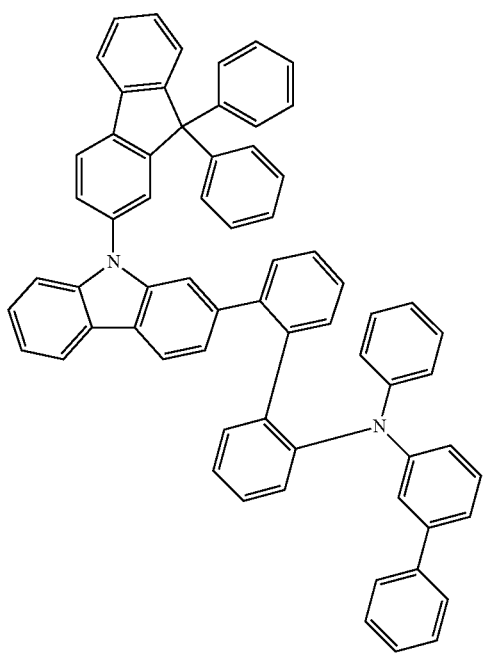
P1-32
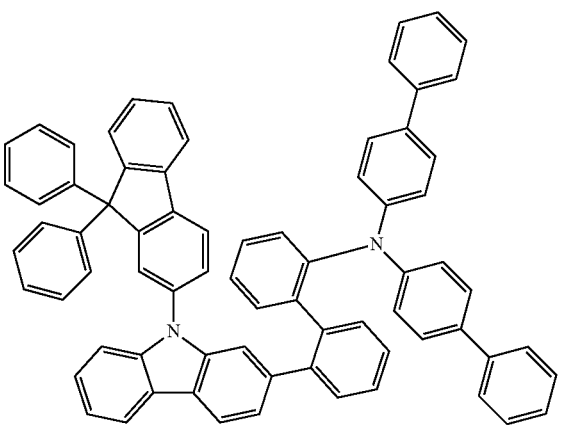

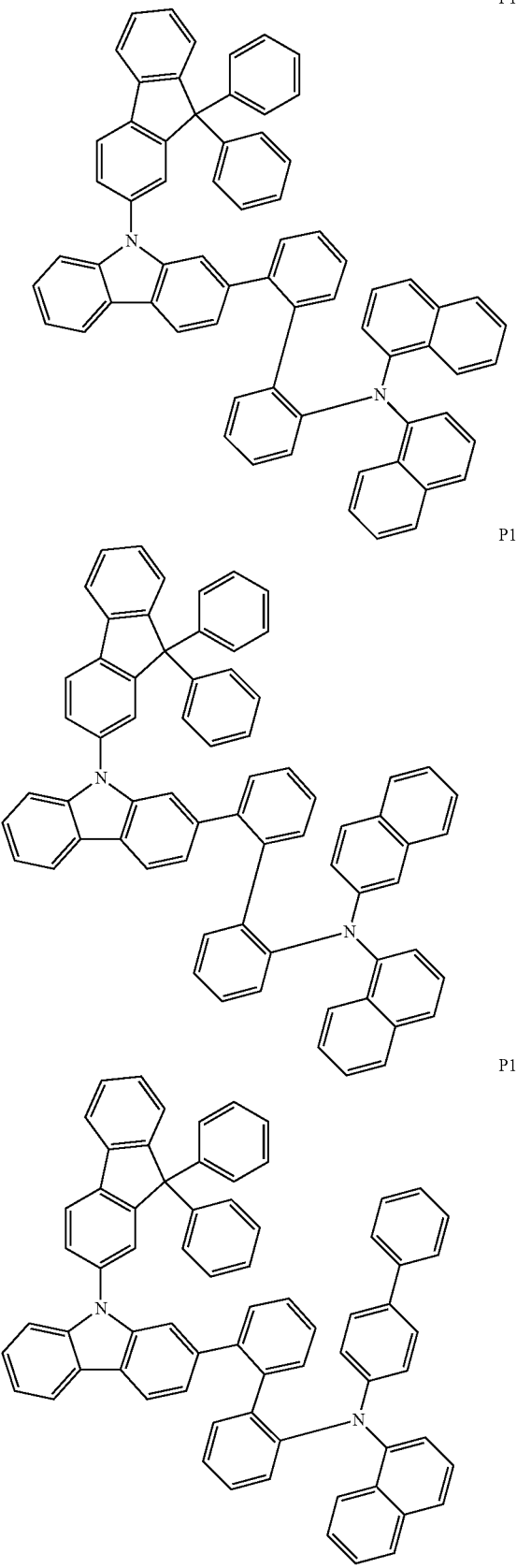
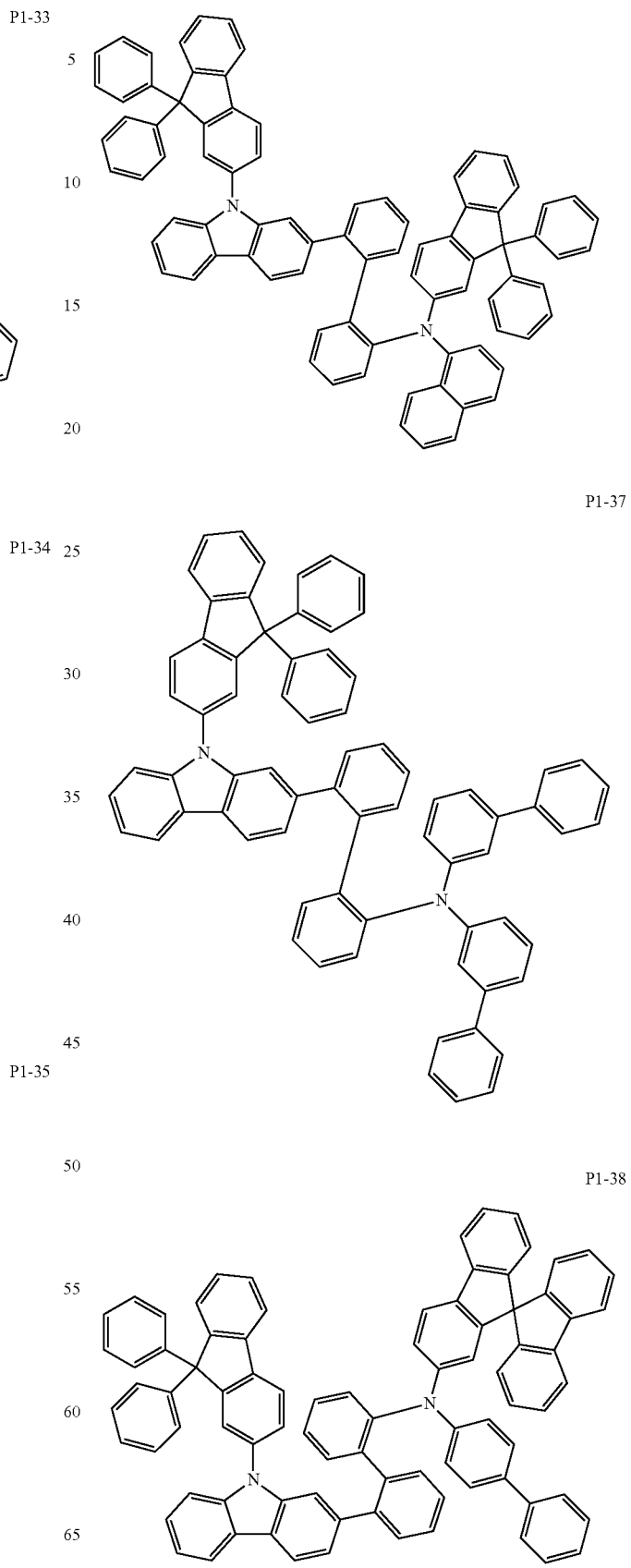

P1-39
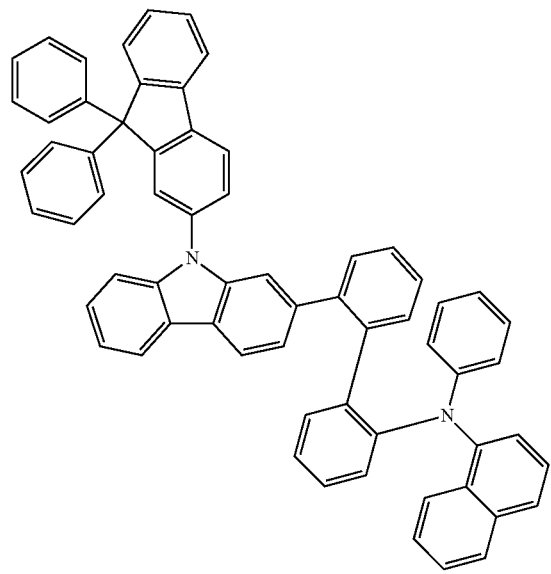
P1-40
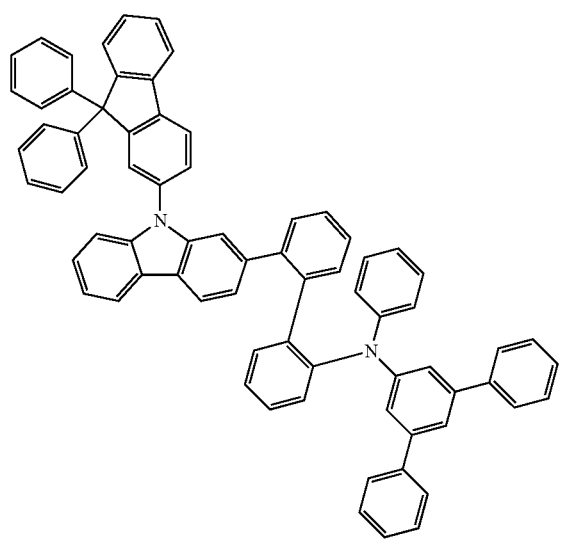
P1-41
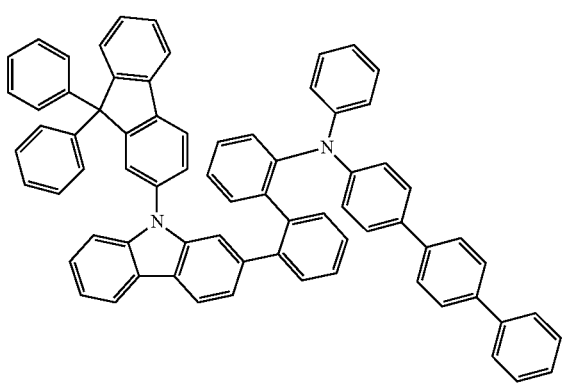
P1-42
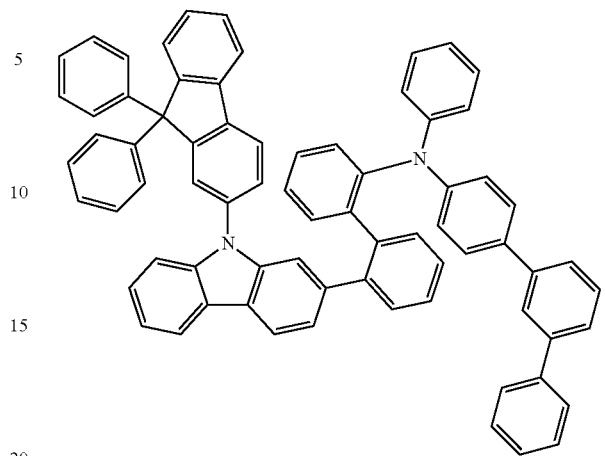
P1-43
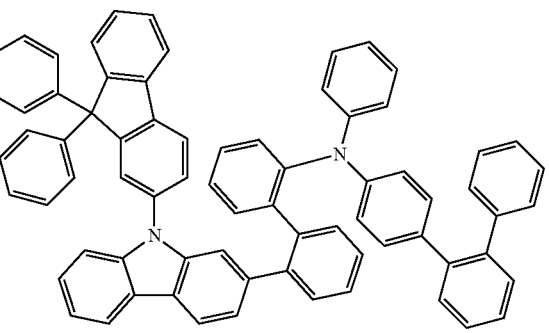
P1-44
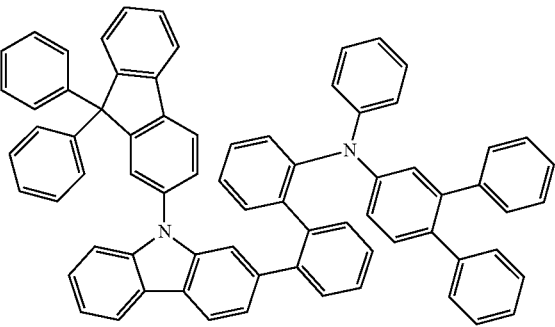
P1-45
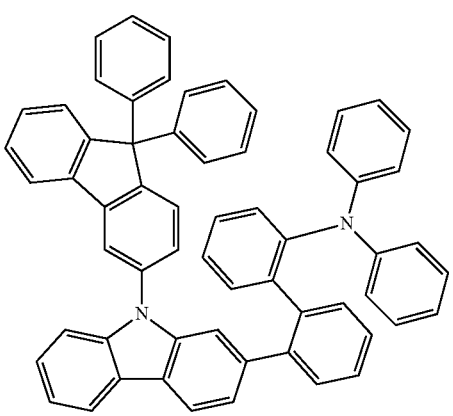

P1-46
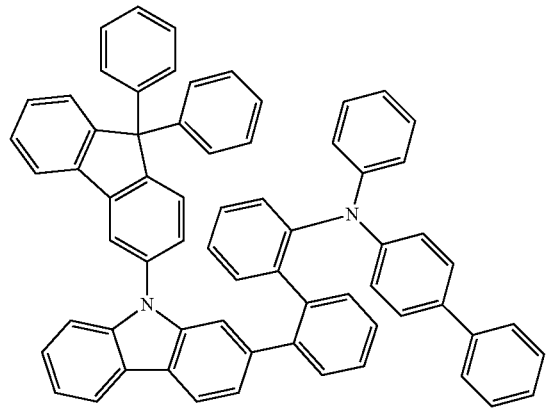
P1-47
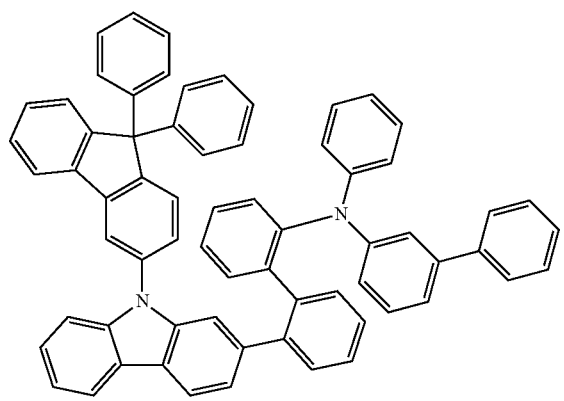
P1-48
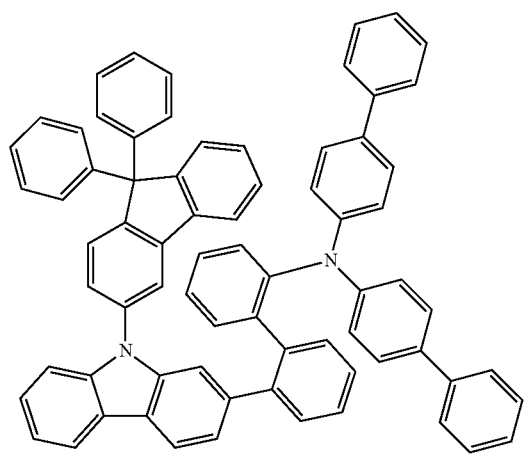
P1-49
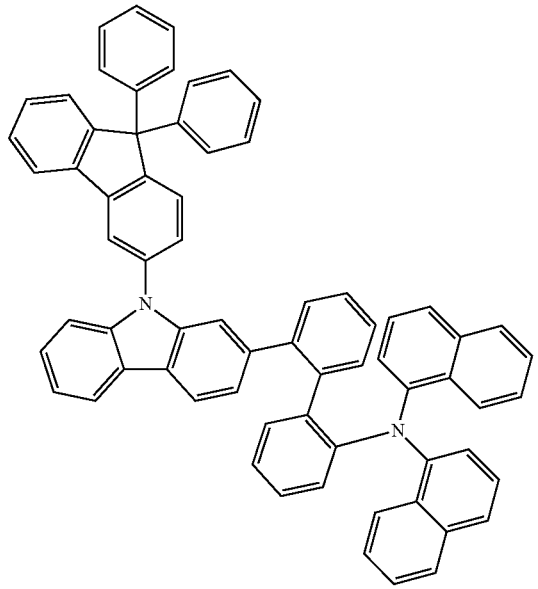
P1-50
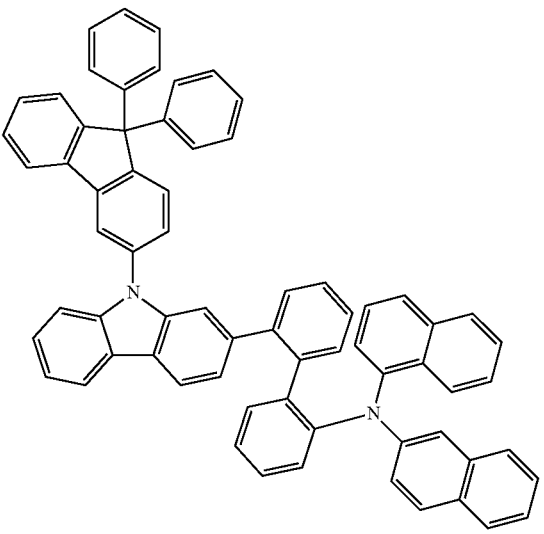
P1-51
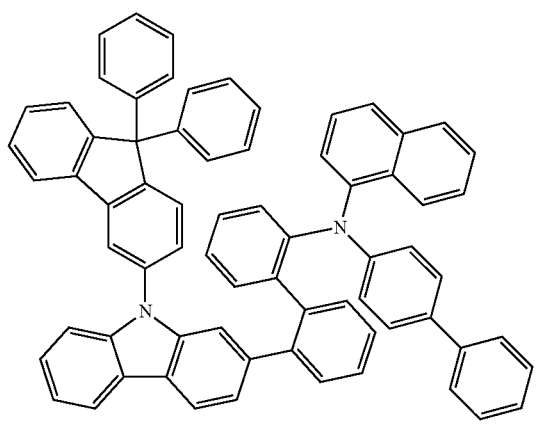

-continued
P1-52
P1-53
P1-54
-continued
P1-55
P1-56
P1-57
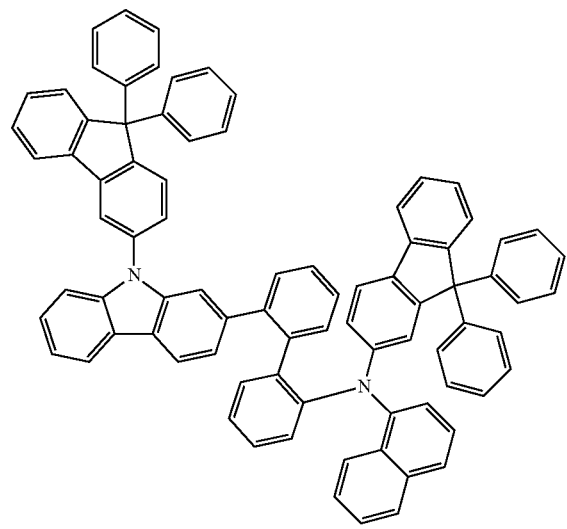
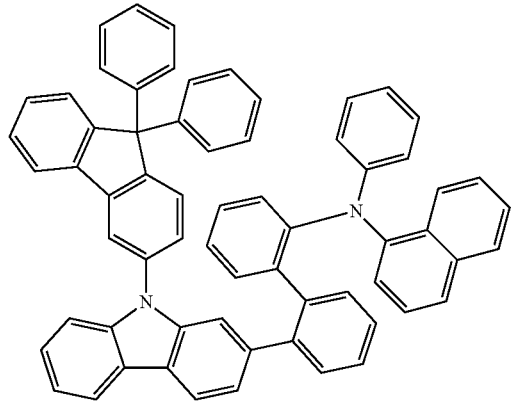

P1-58
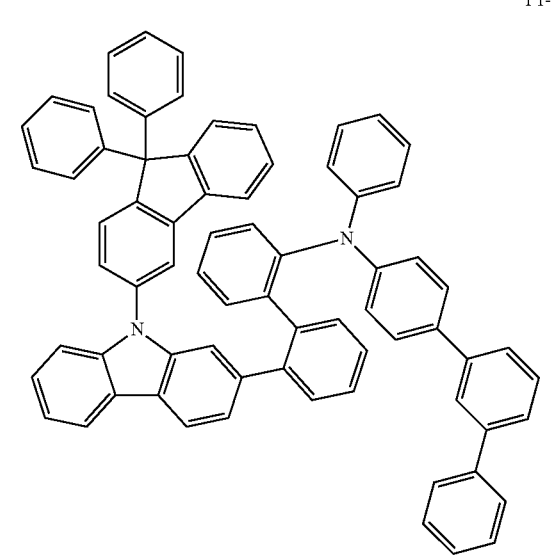
P1-59
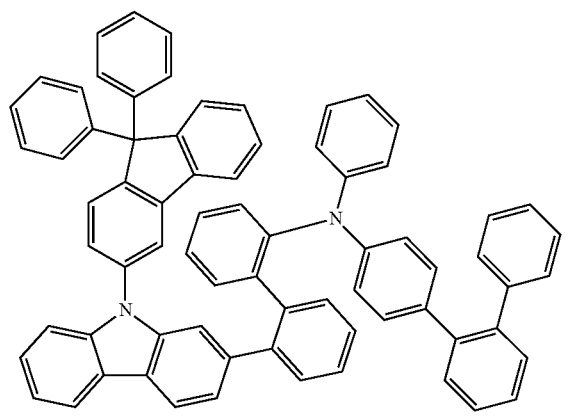
P1-60
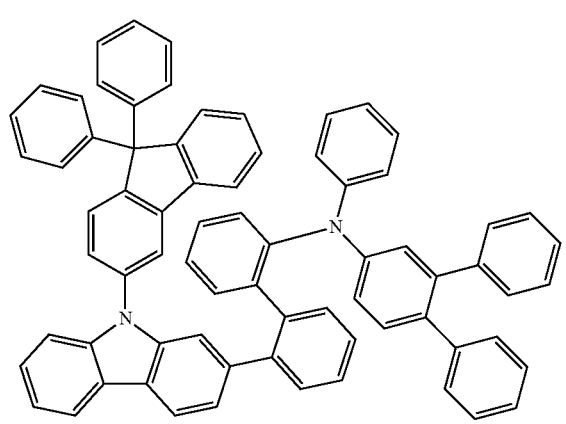
P1-61
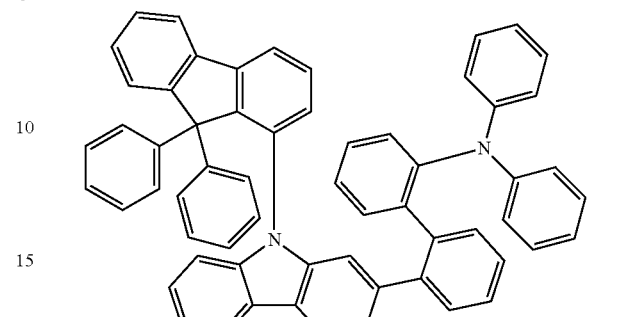
P1-62
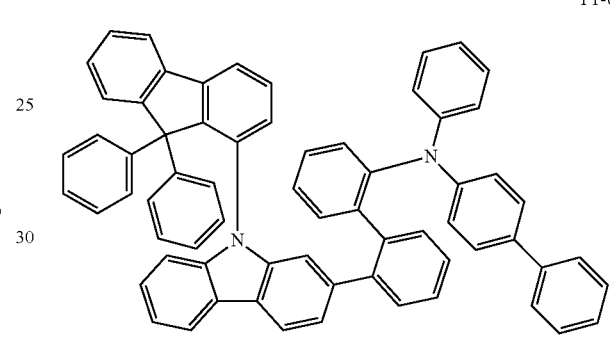
P1-63
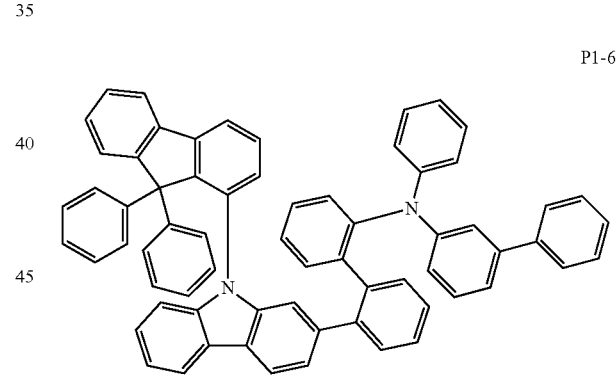
P1-64
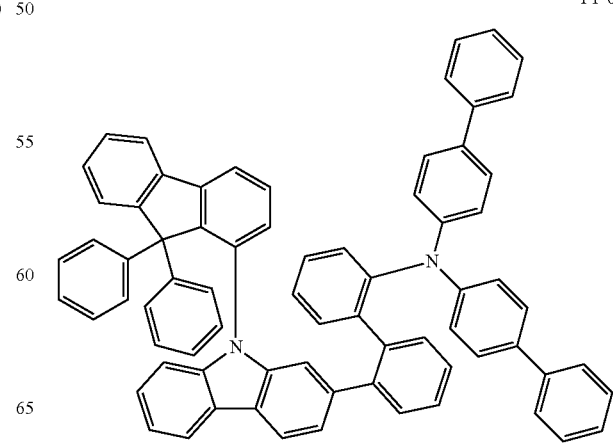

P1-65
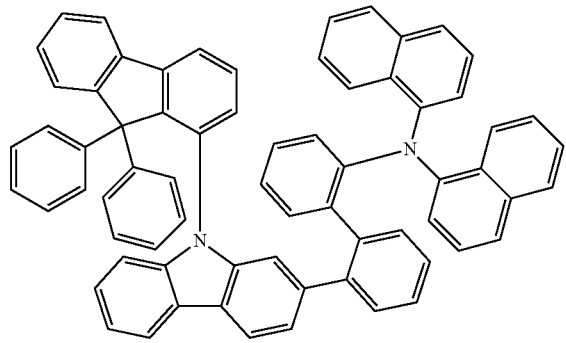
P1-66
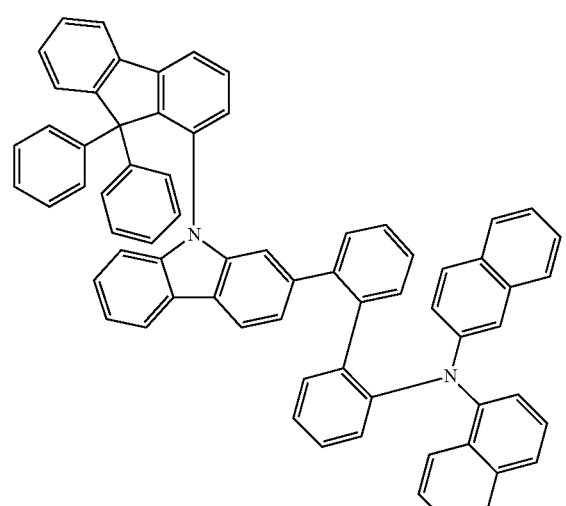
P1-67
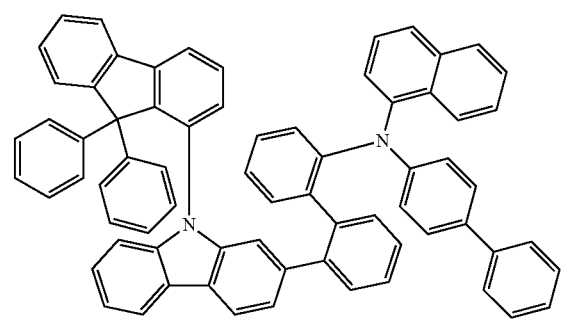
P1-68
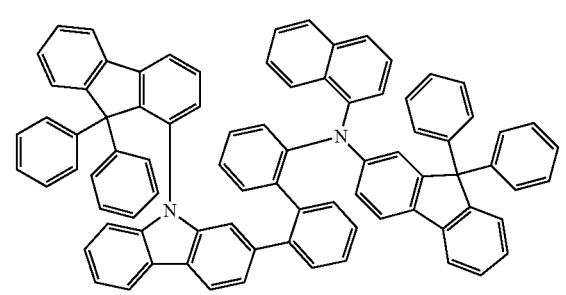
P1-69
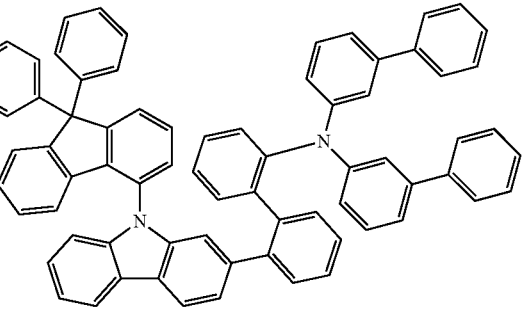
P1-70
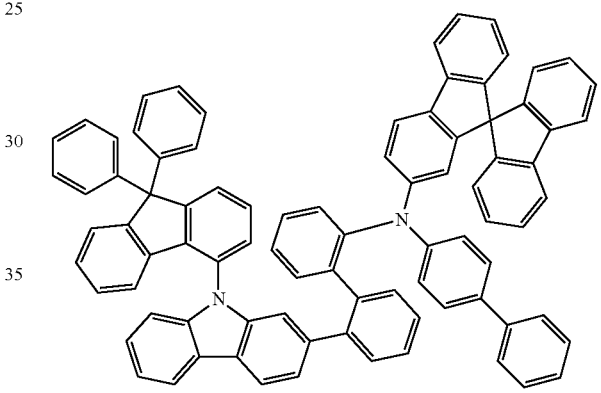
P1-71
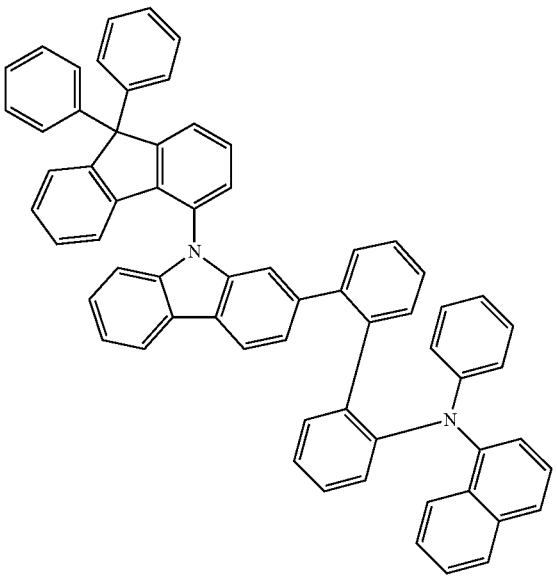

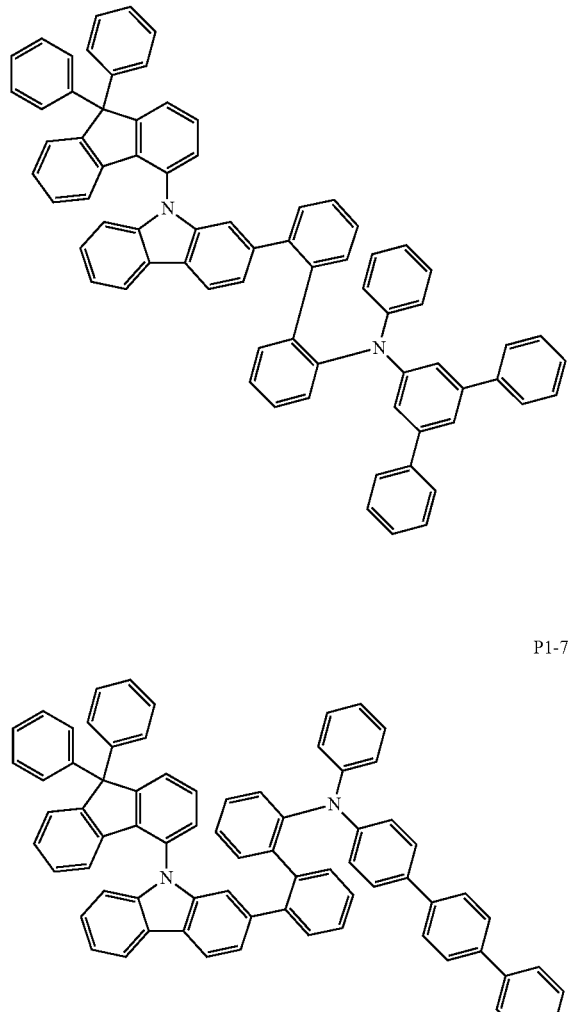
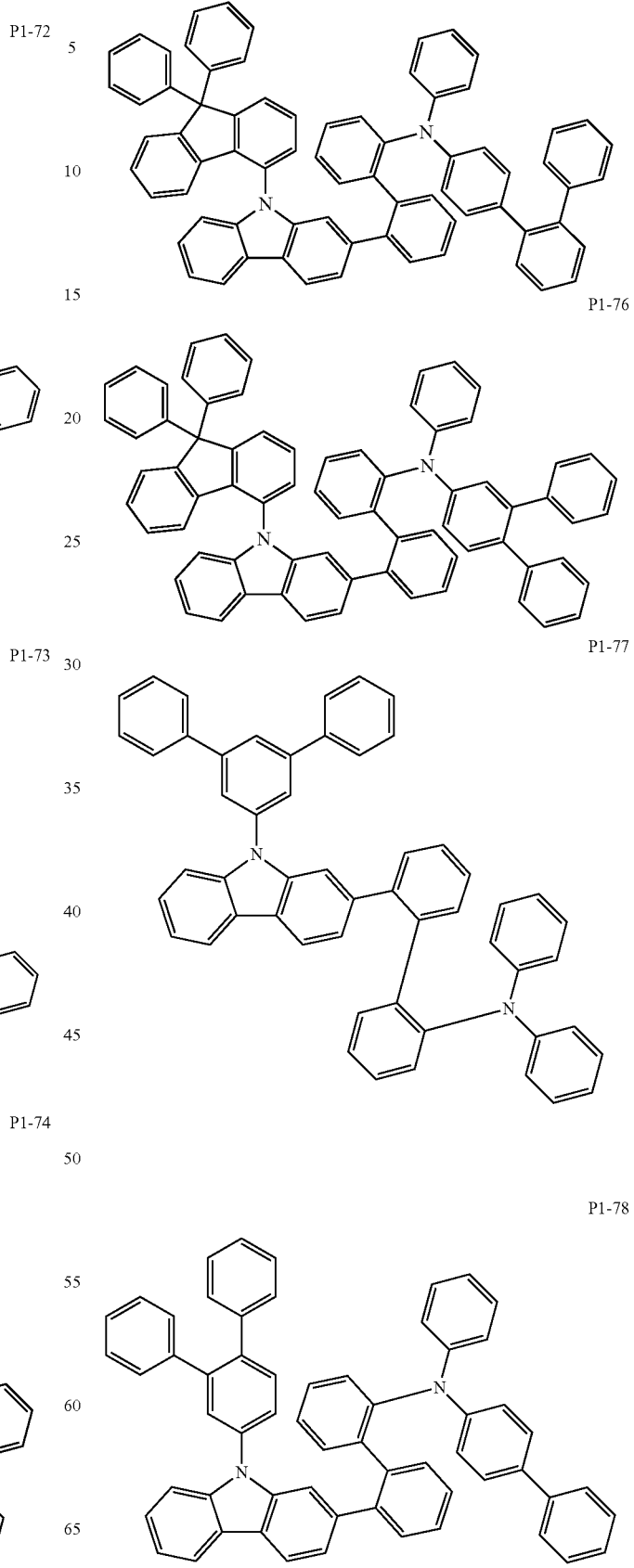

P1-79
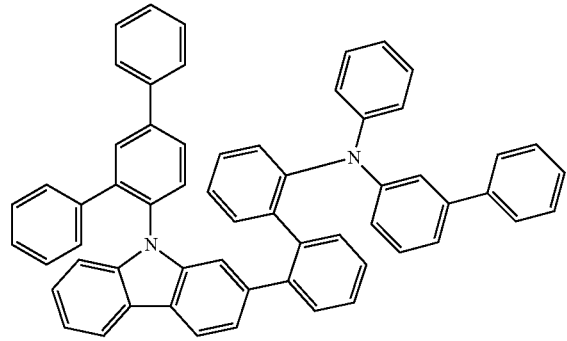
P1-80
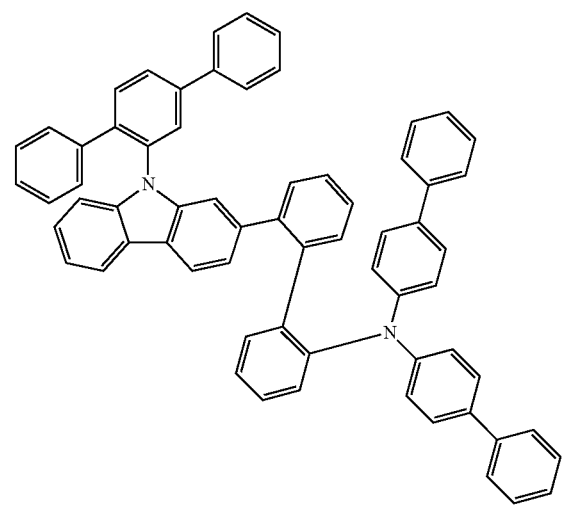
P1-81
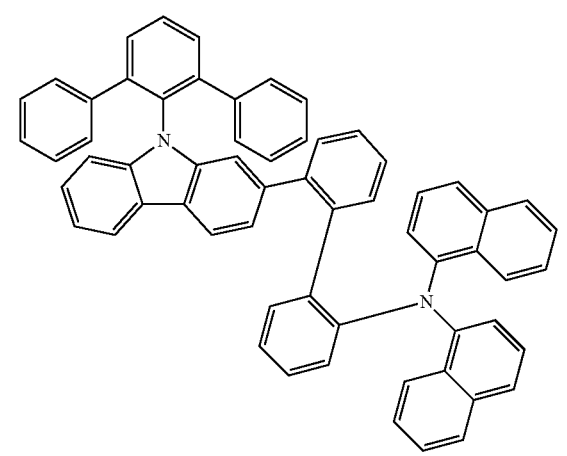
P1-82
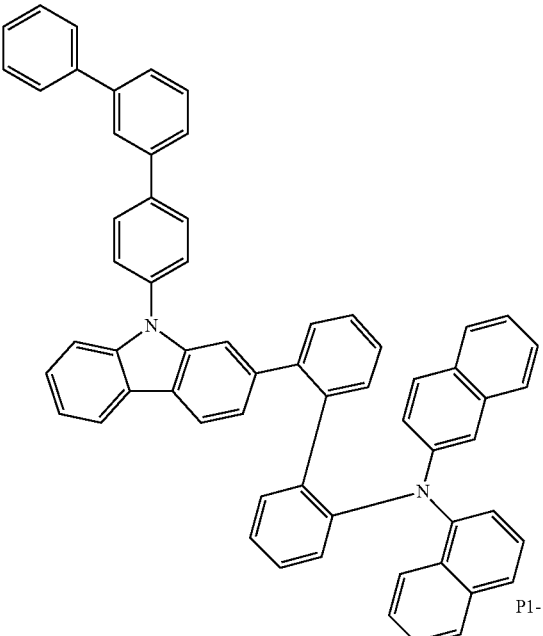
P1-83
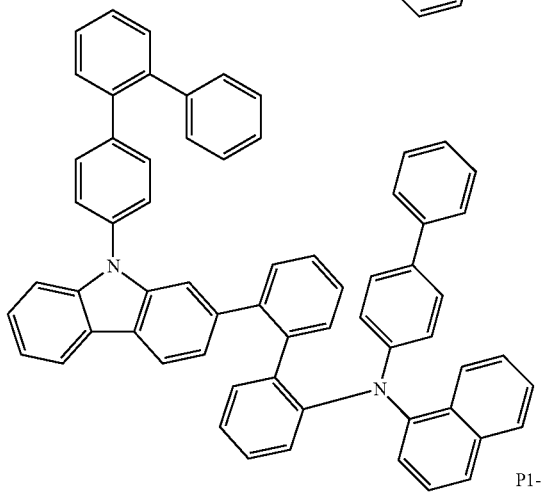
P1-84
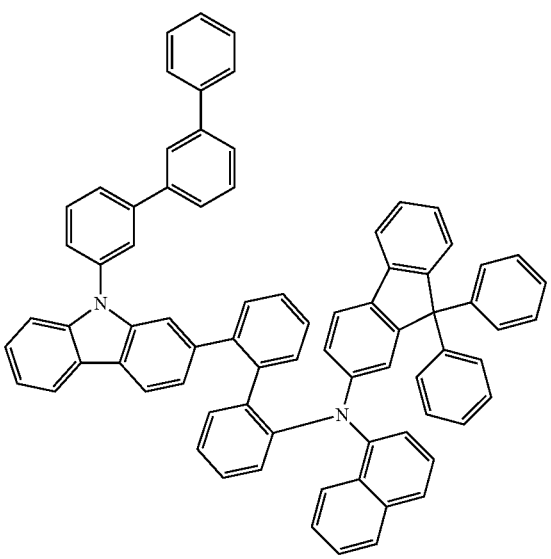

P1-85
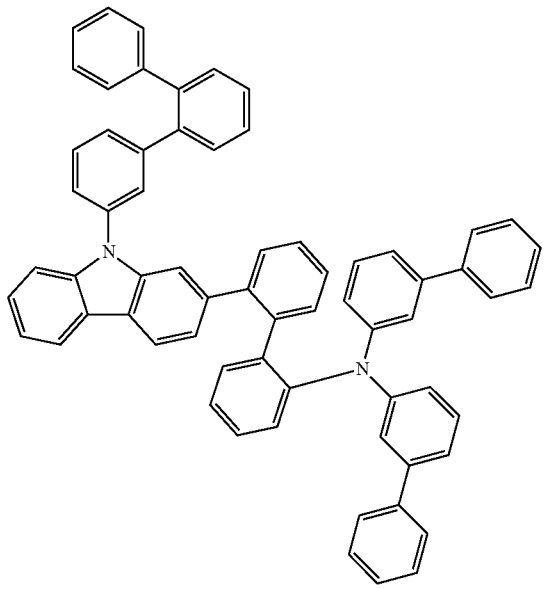
P1-86
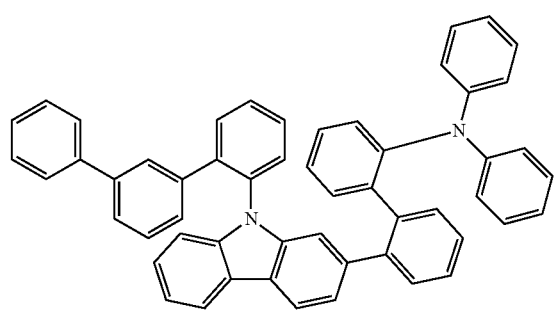
P1-87
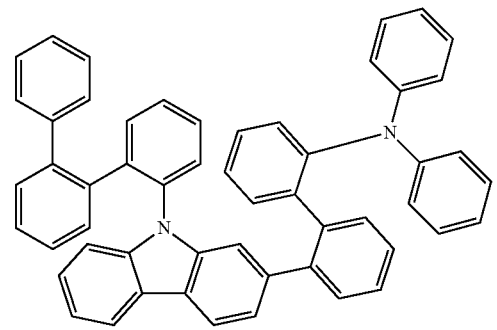
P1-88
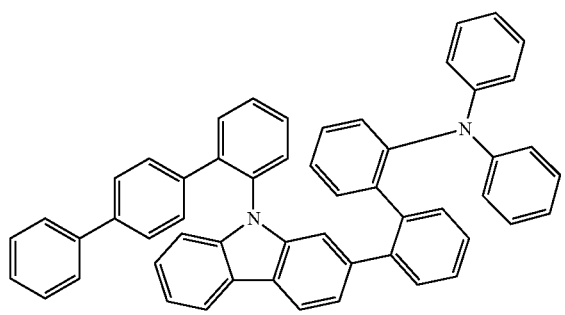
P1-89
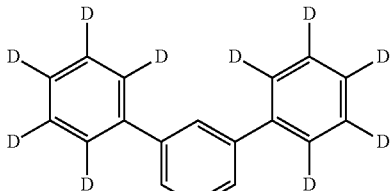
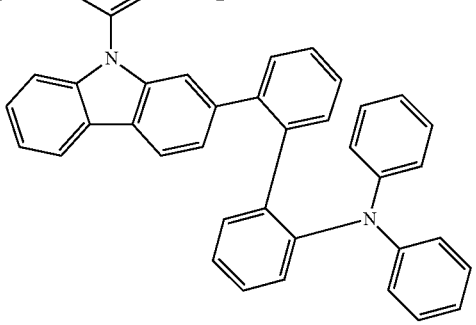
P1-90
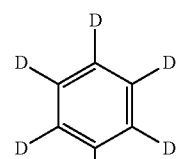
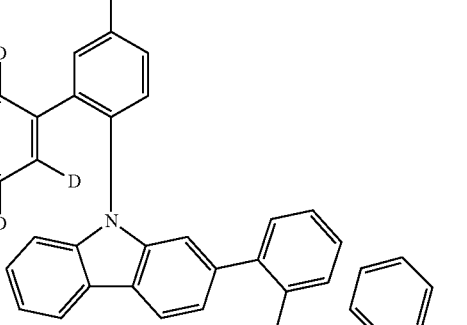
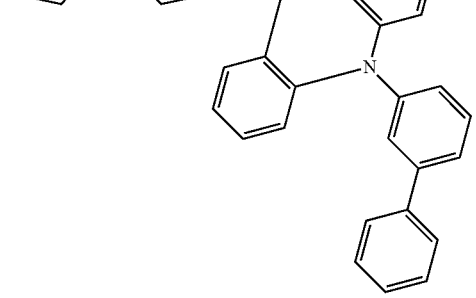

P1-91
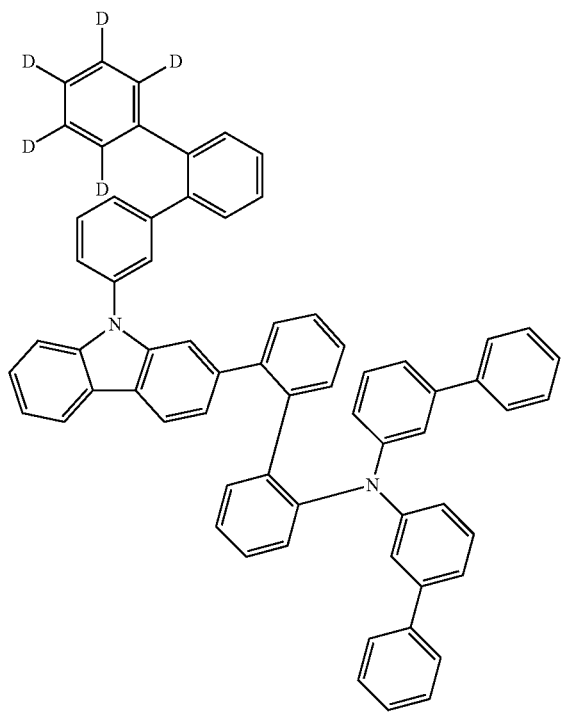
P1-92
P1-93
P1-94
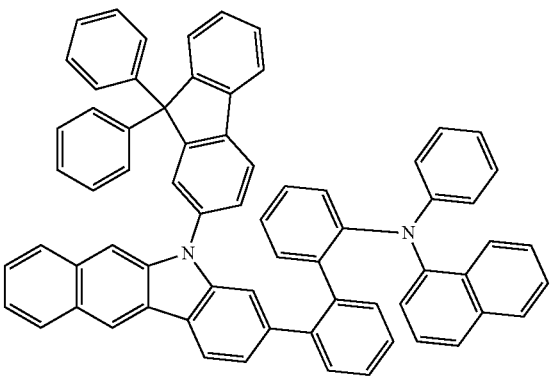
P1-95
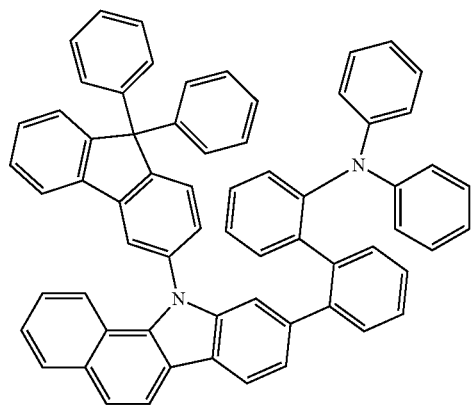
P1-96
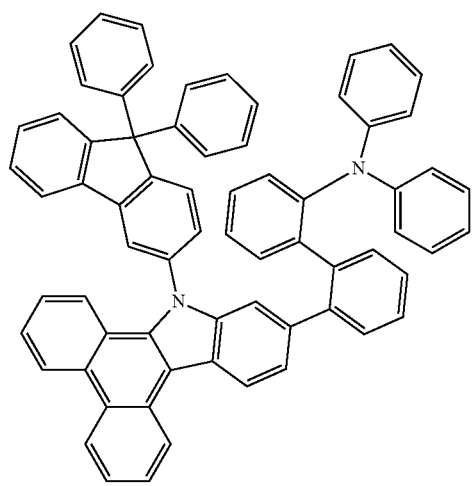

P1-97
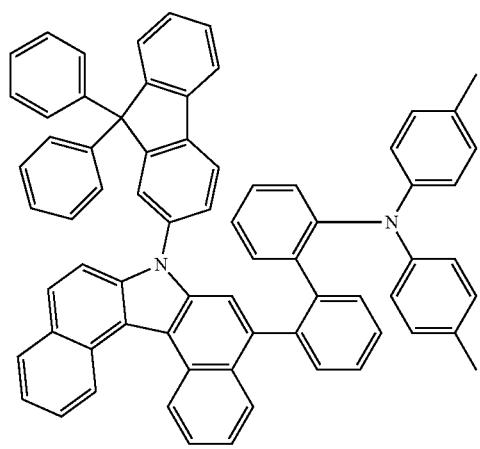
P1-98
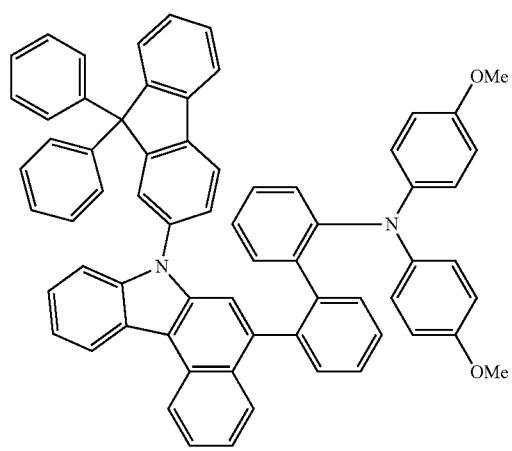
P1-99
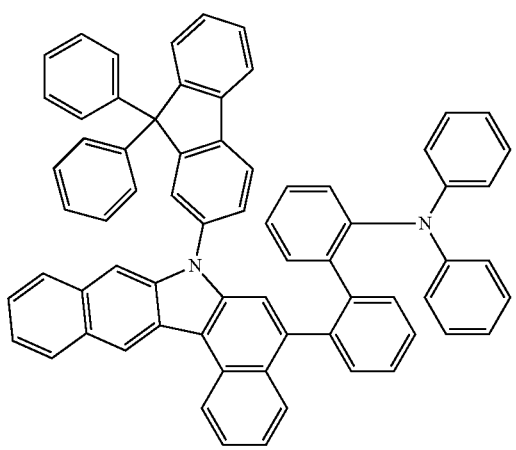
P1-100
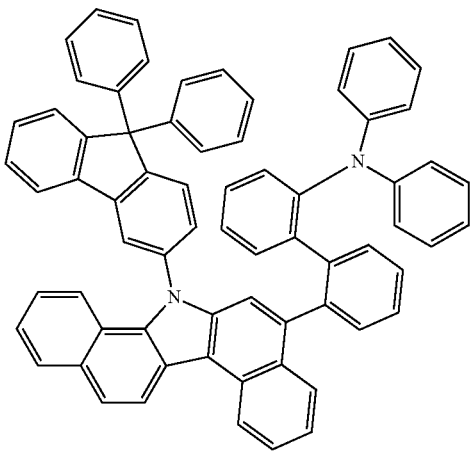
P1-101
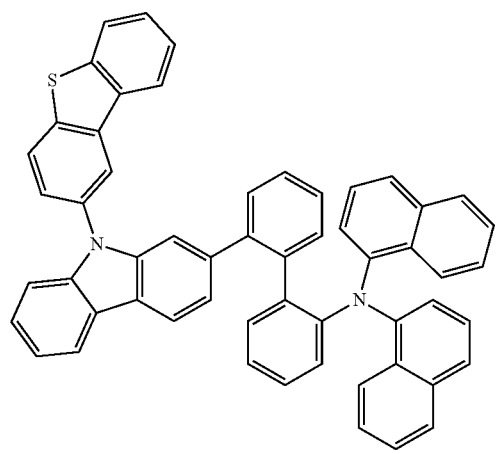
P1-102
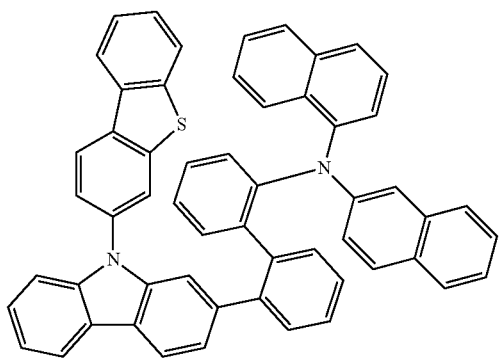

-continued
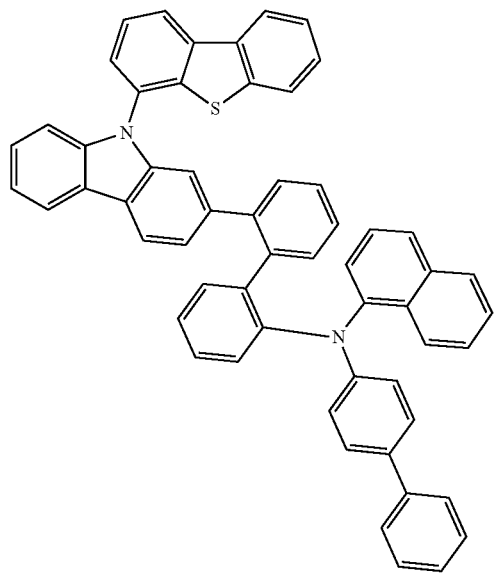
P1-103
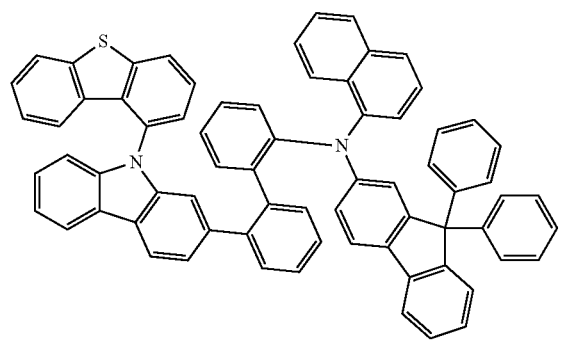
P1-104
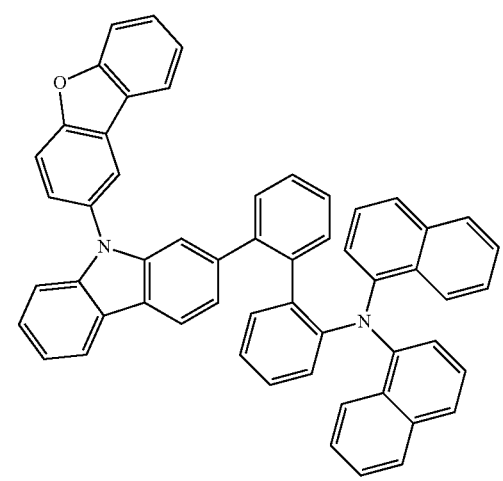
P1-105
-continued
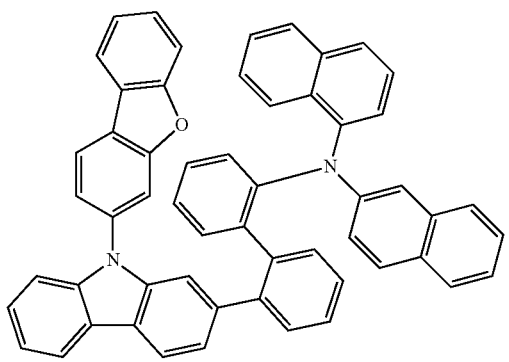
P1-106
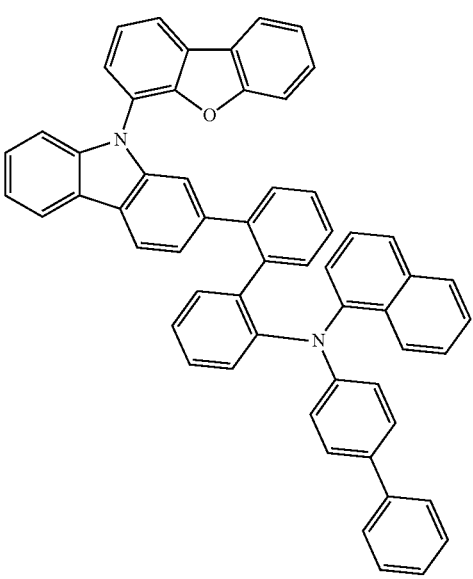
P1-107
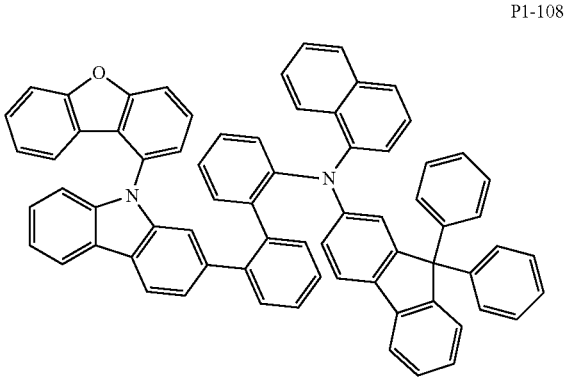
P1-108

P1-109
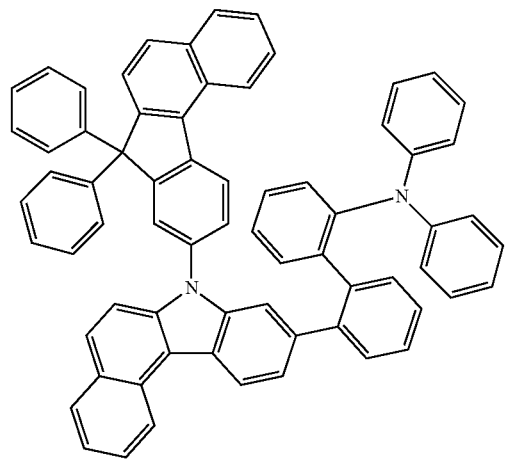
P1-110
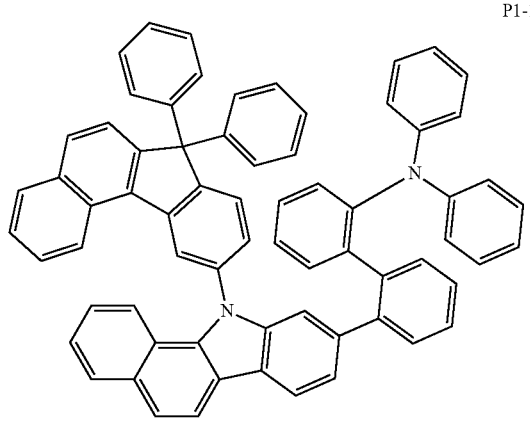
P1-111
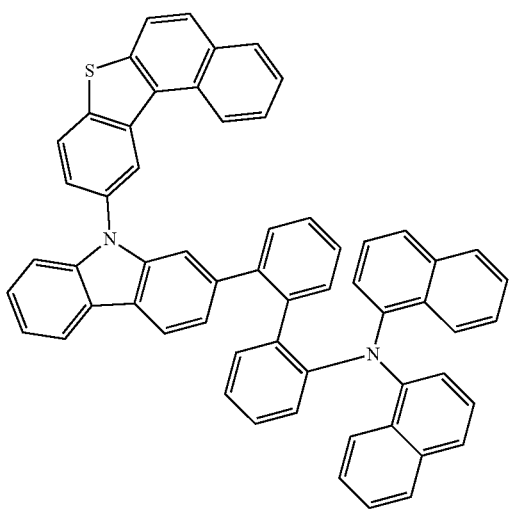
P1-112
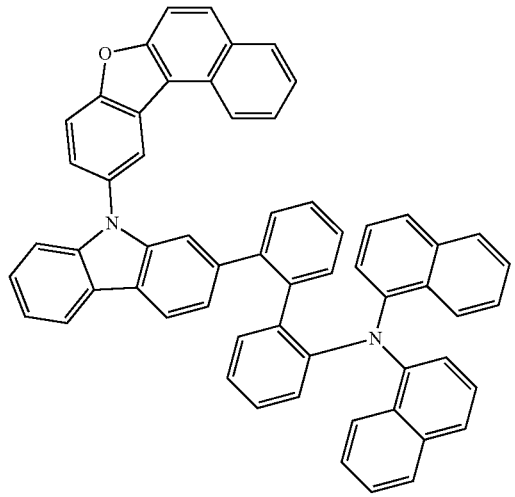
P2-1
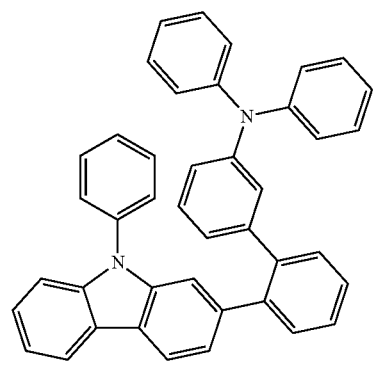
P2-2
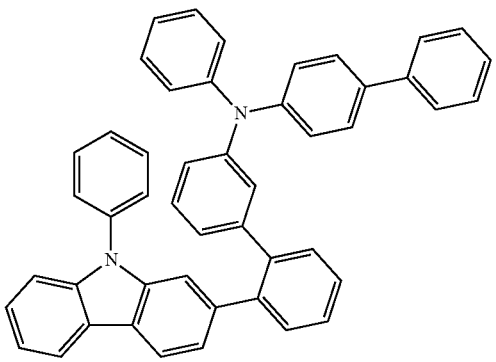
P2-3
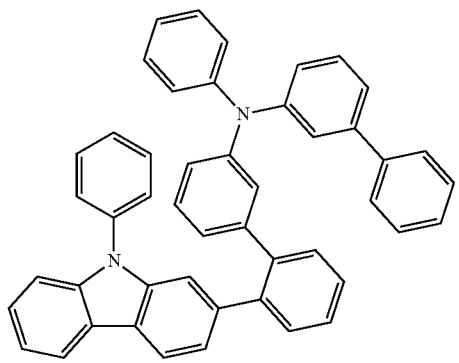

P2-4
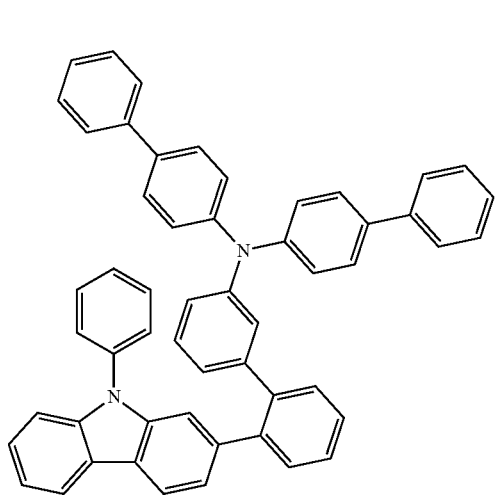
P2-5
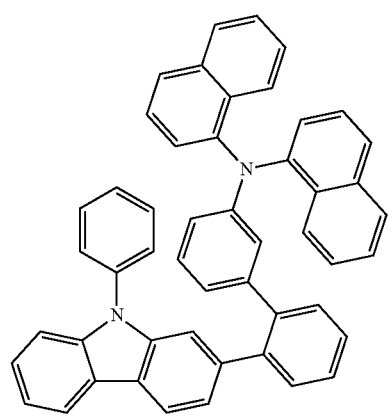
P2-6
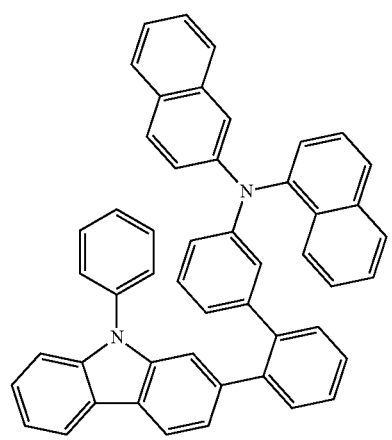
P2-7
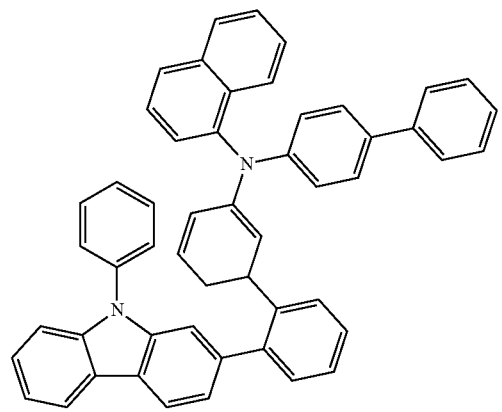
P2-8
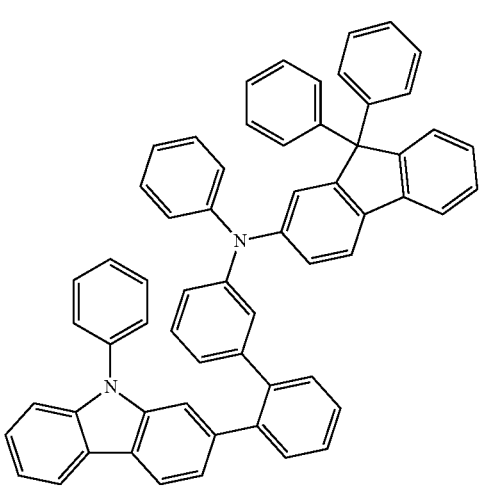
P2-9
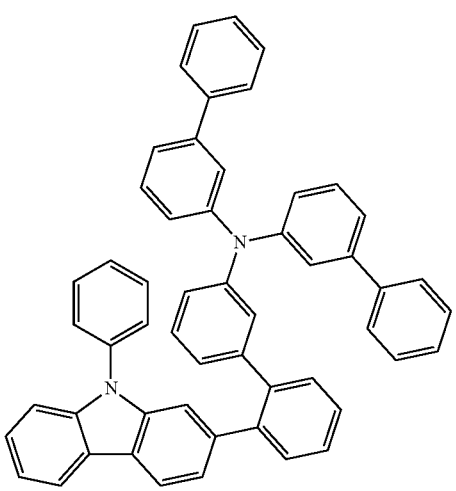

P2-10
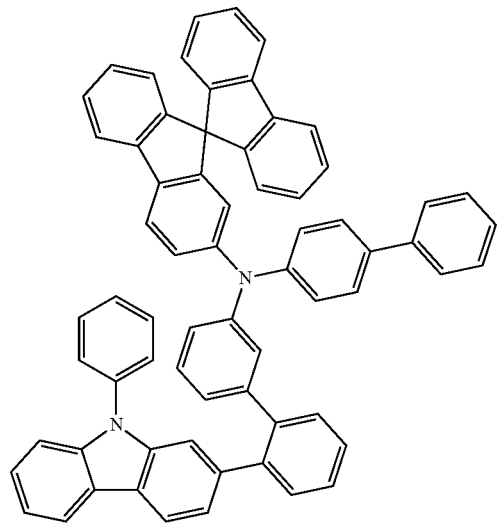
P2-11
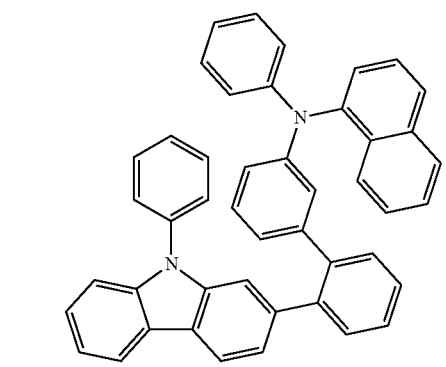
P2-12
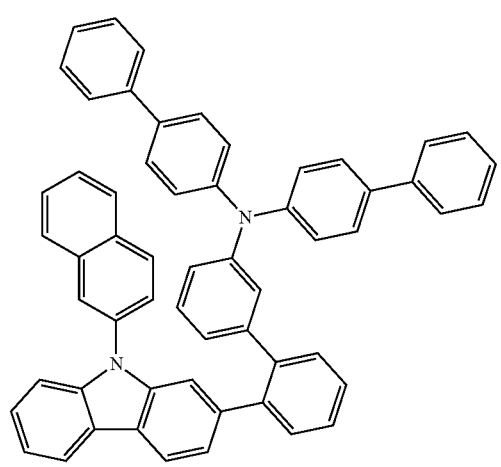
P2-13
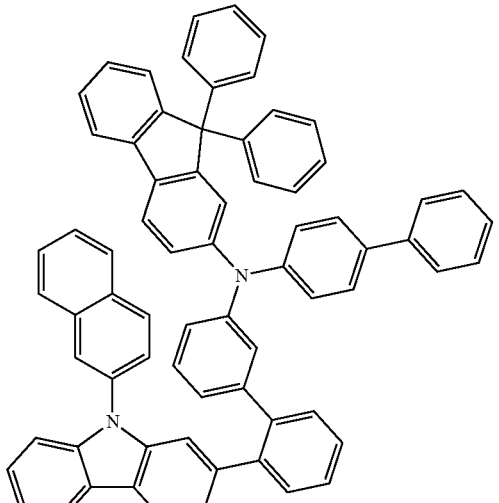
P2-14
P2-15
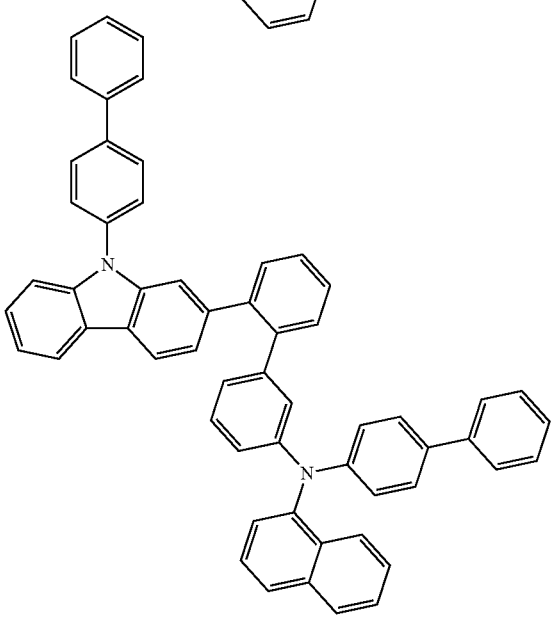

-continued
P2-16
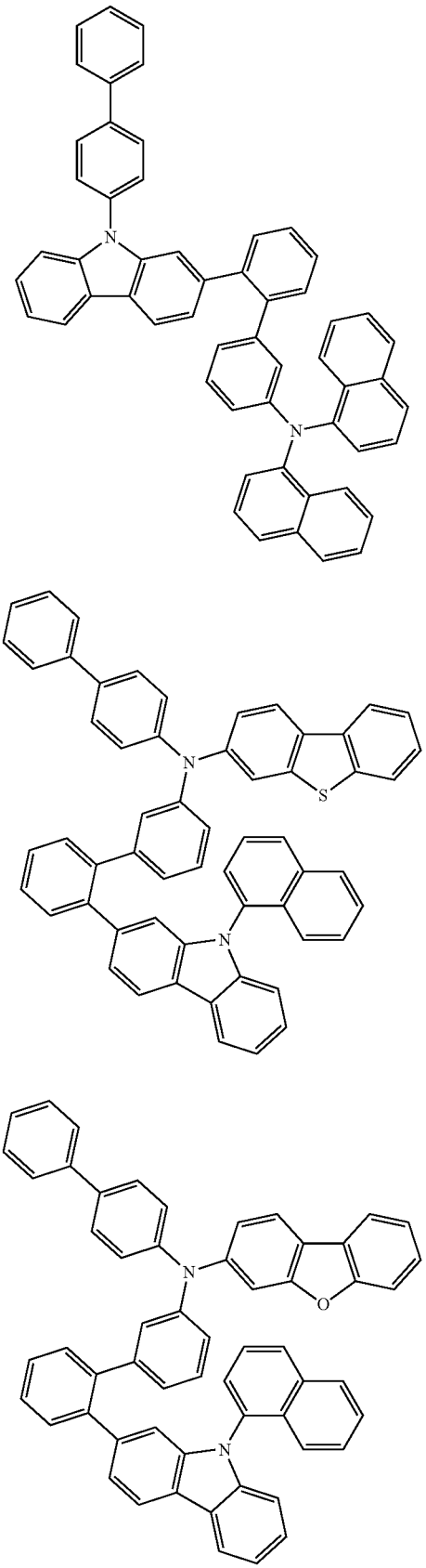
P2-17
P2-18
-continued
P2-19
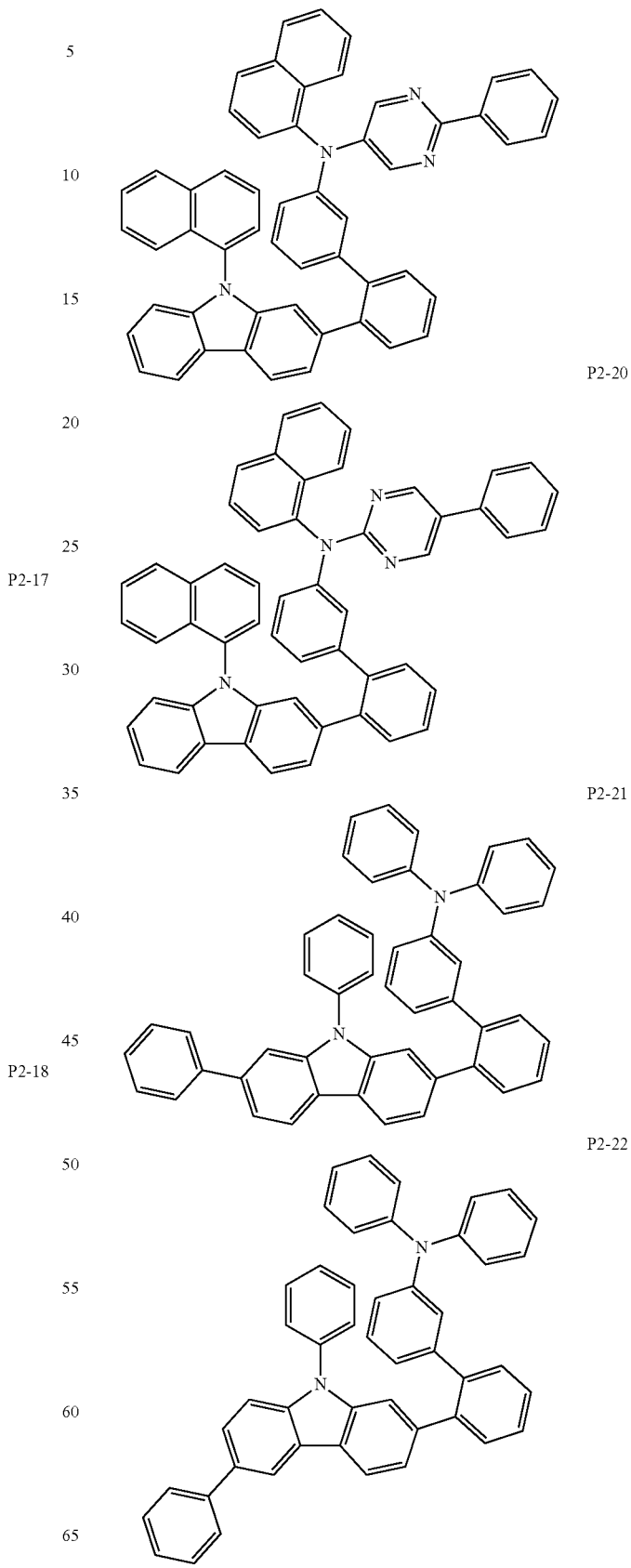
P2-20
P2-21
P2-22

P2-23
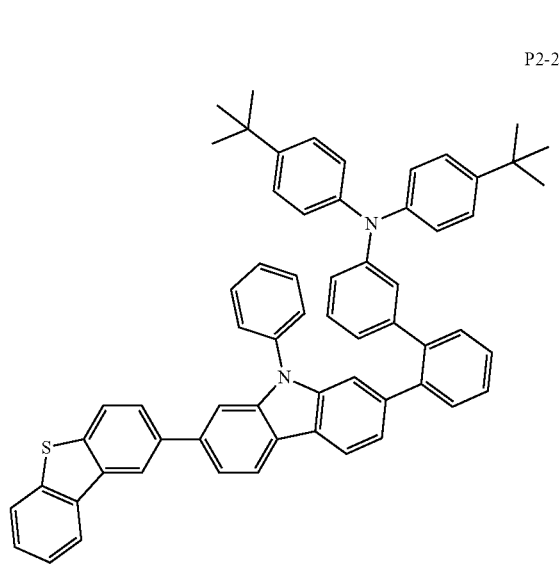
P2-24
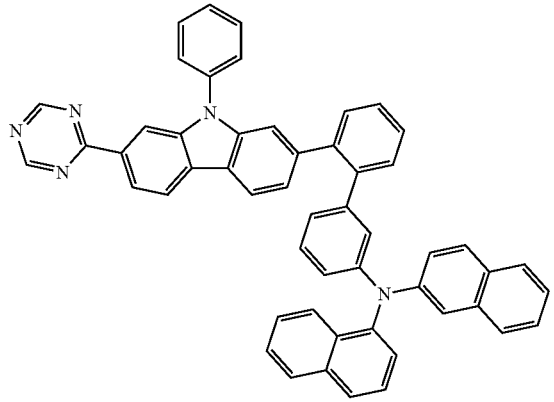
P2-25
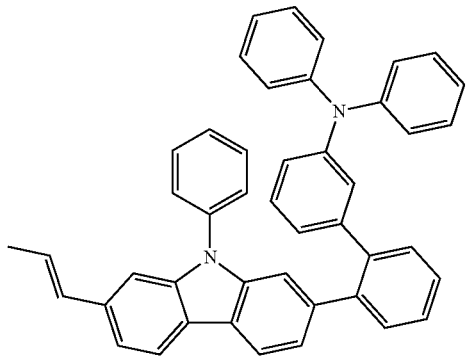
P2-26
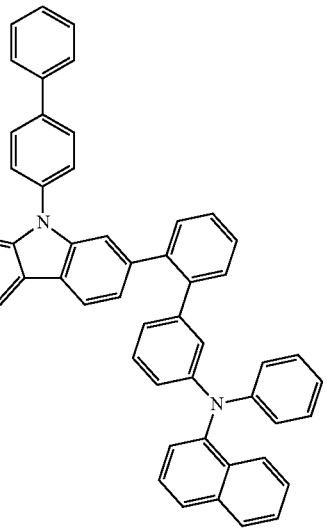
P2-27
P2-28
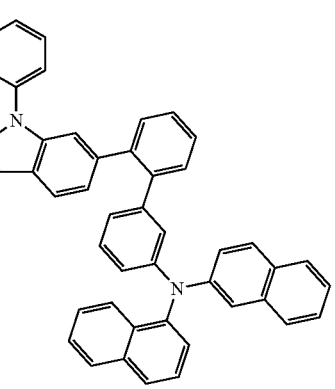

-continued
P2-29
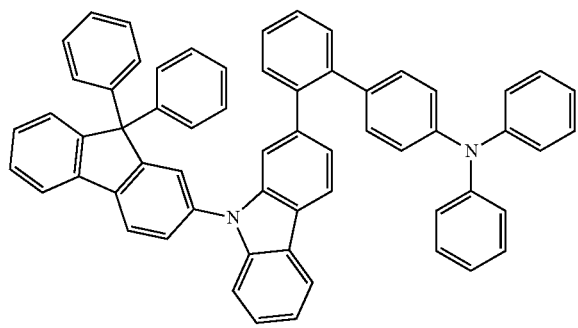
P2-30
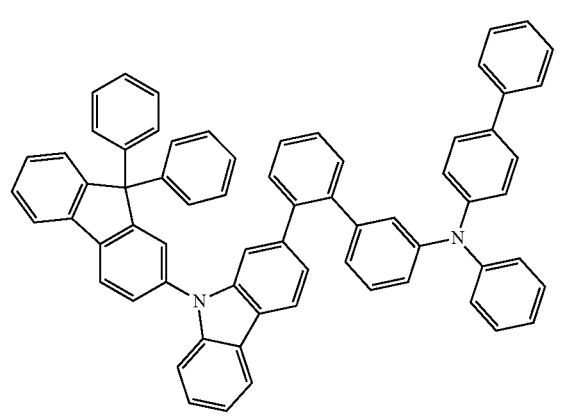
P2-31
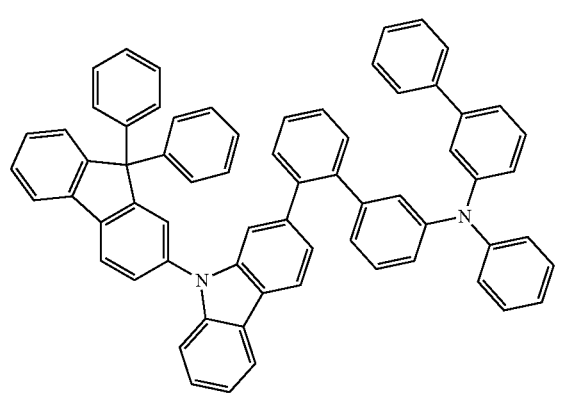
P2-32
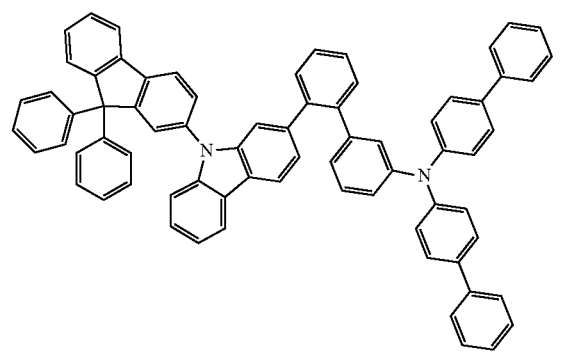
-continued
P2-33
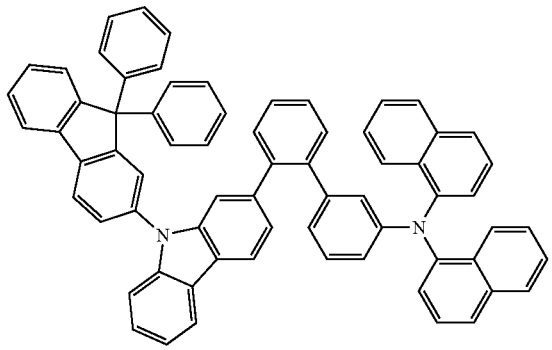
P2-34
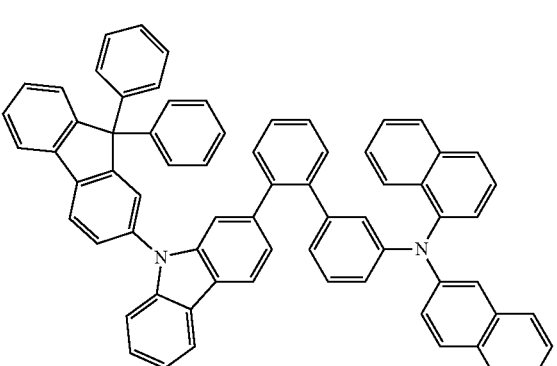
P2-35
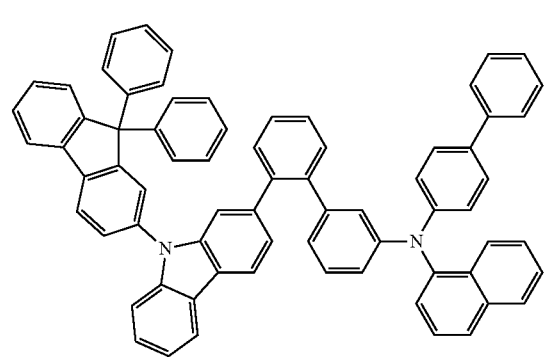
P2-36
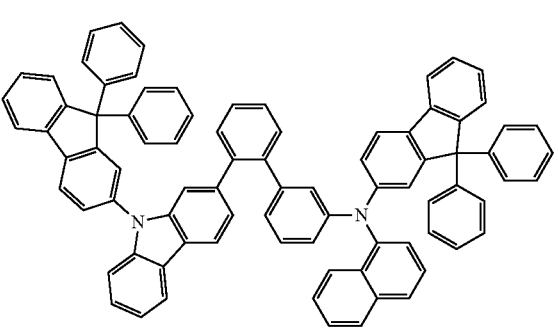

P2-37
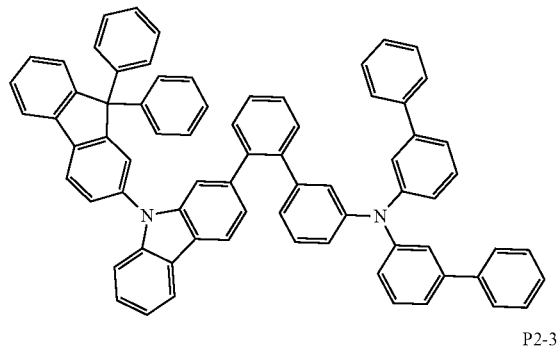
P2-38
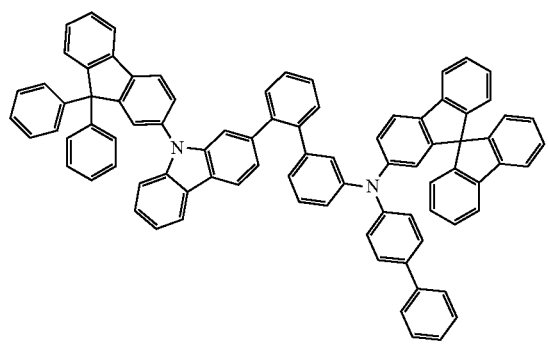
P2-39
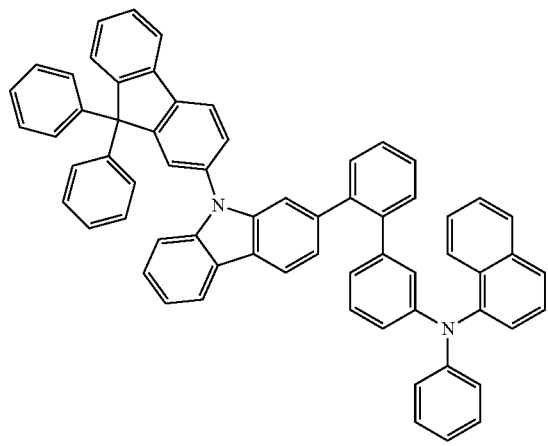
P2-40
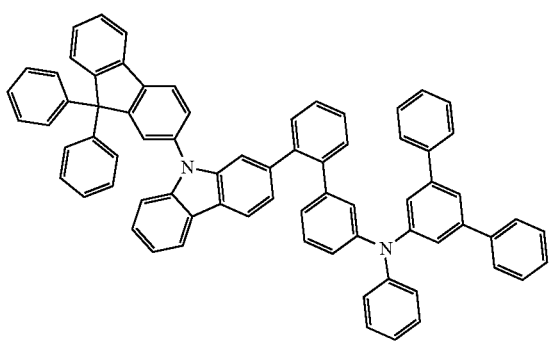
P2-41
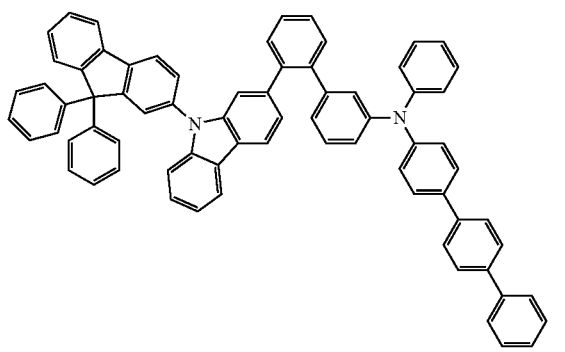
P2-42
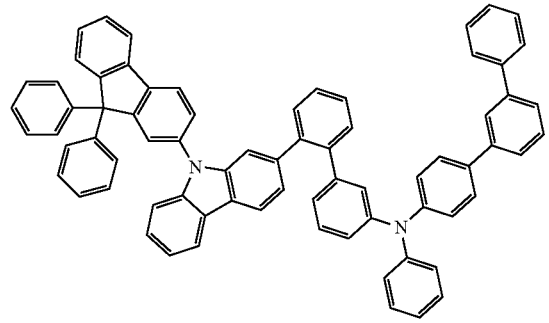
P2-43
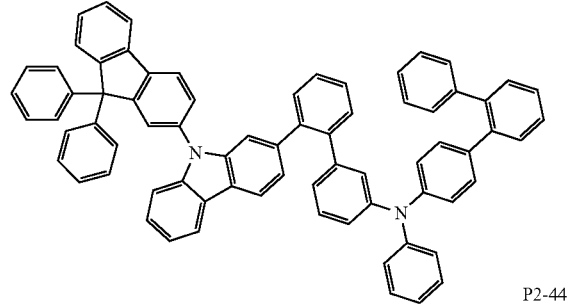
P2-44
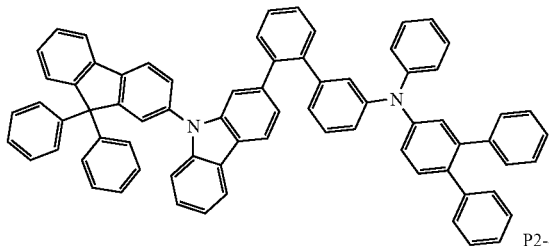
P2-45
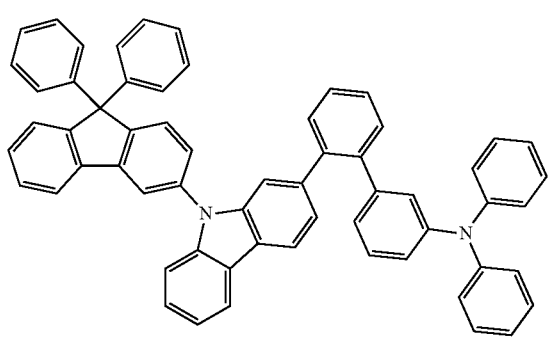

P2-46
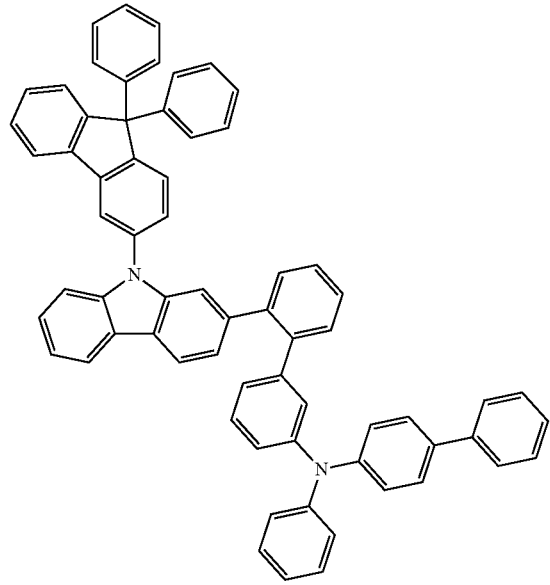
P2-47
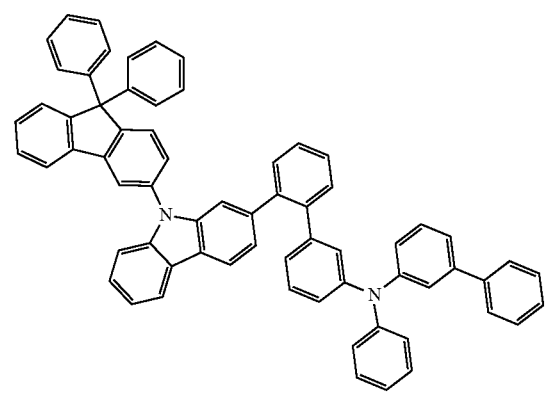
P2-48
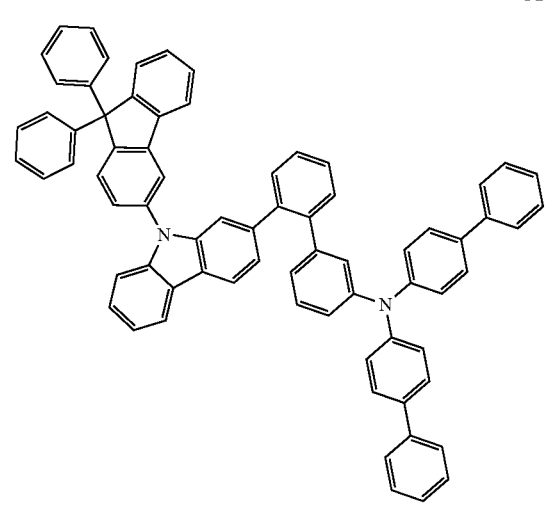
P2-49
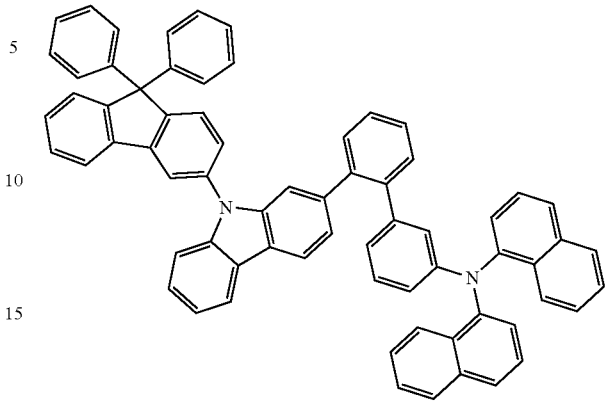
P2-50
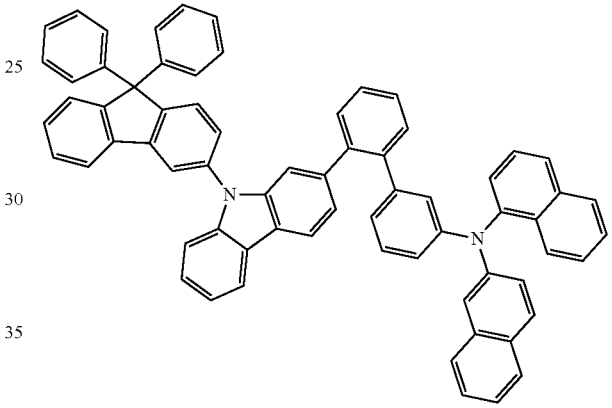
P2-51
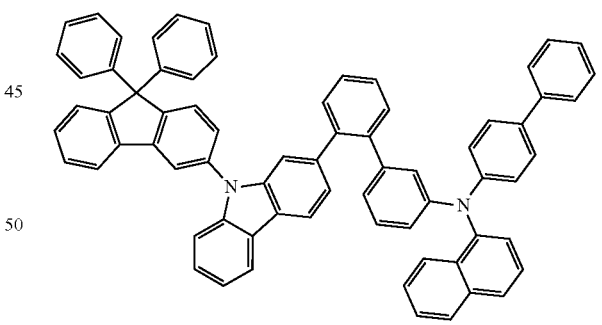
P2-52
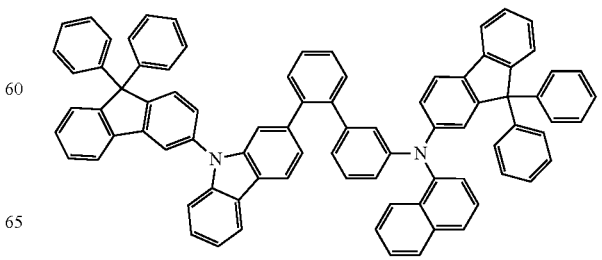

P2-53
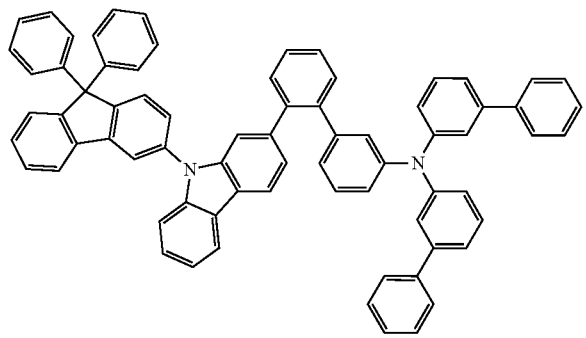
P2-54
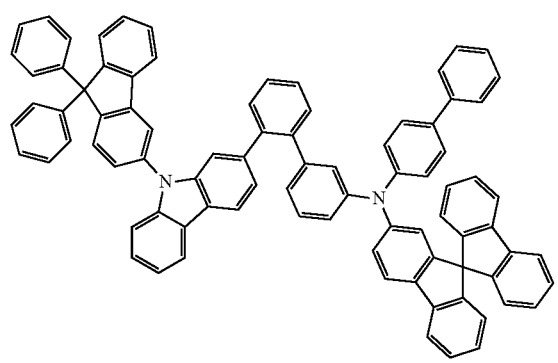
P2-55
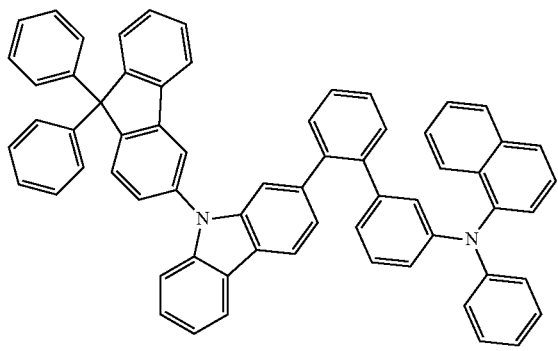
P2-56
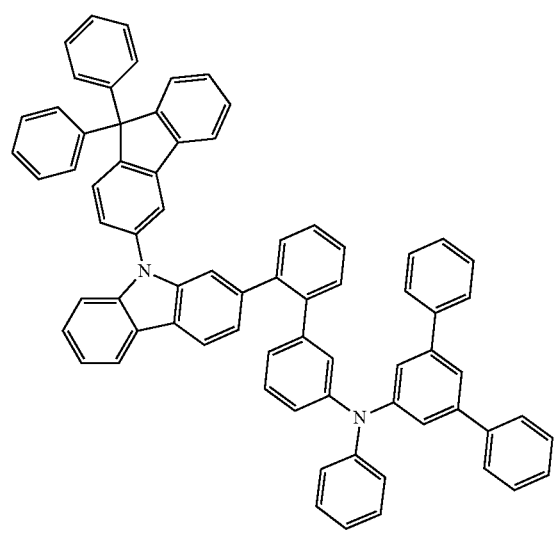
P2-57
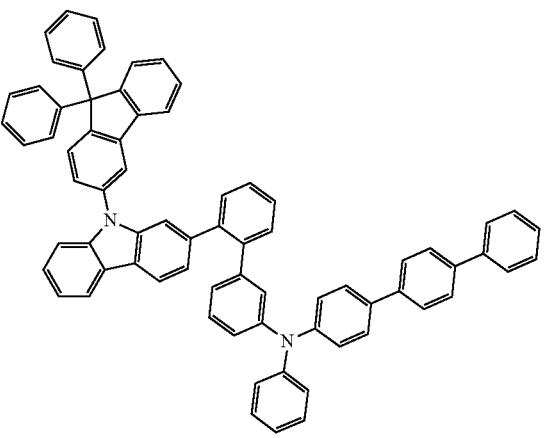
P2-58
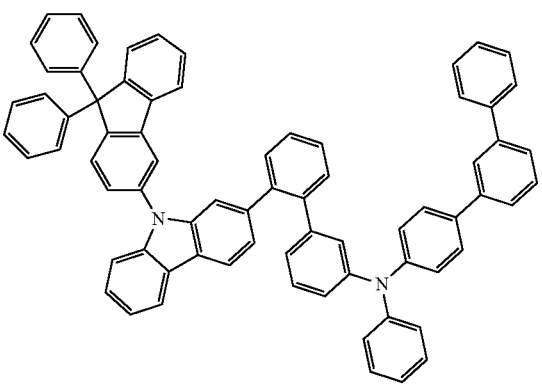
P2-59
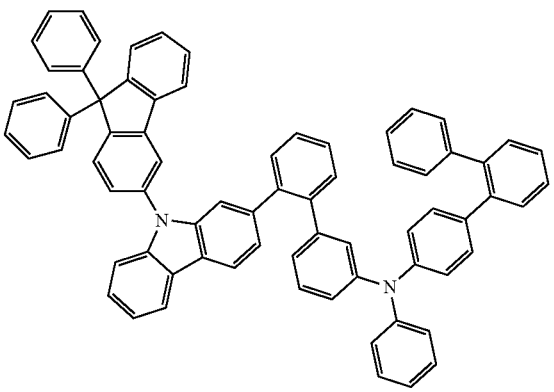
P2-60
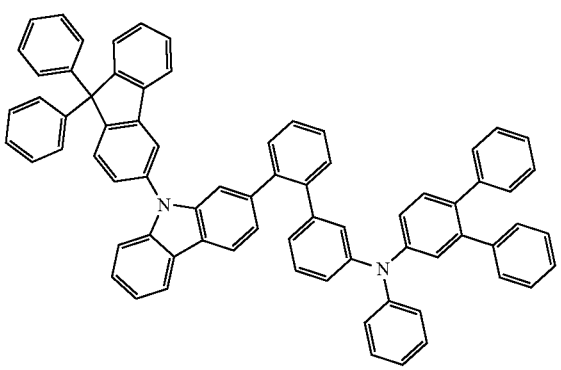

P2-61
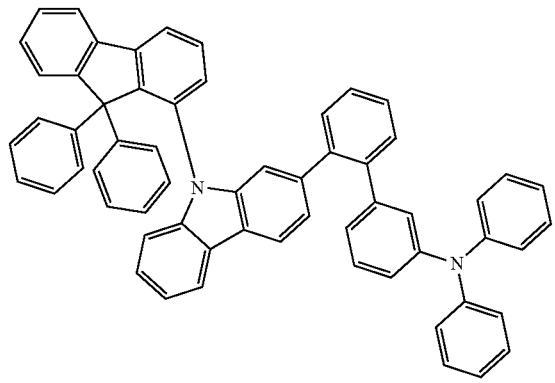
P2-62
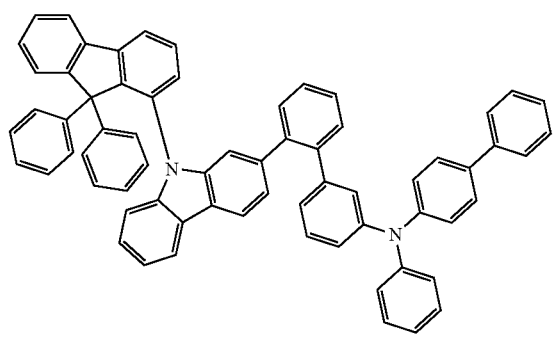
P2-63
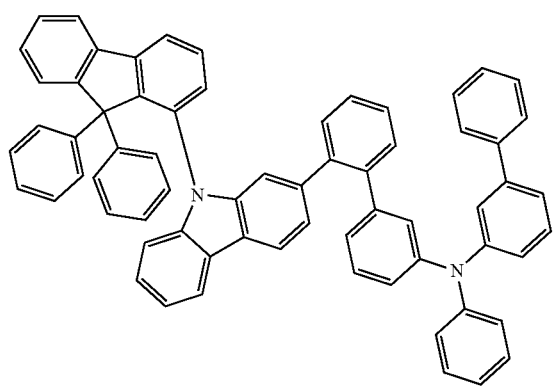
P2-64
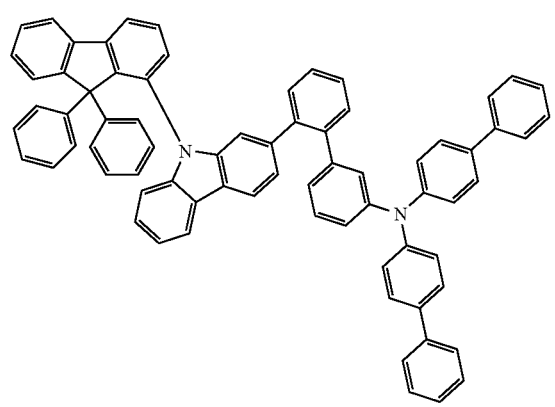
P2-65
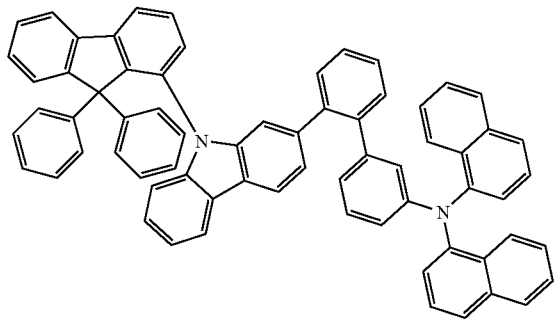
P2-66
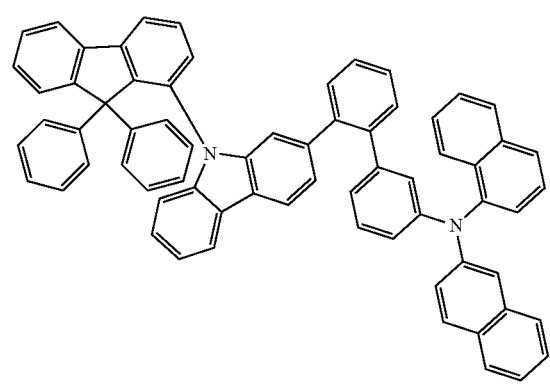
P2-67
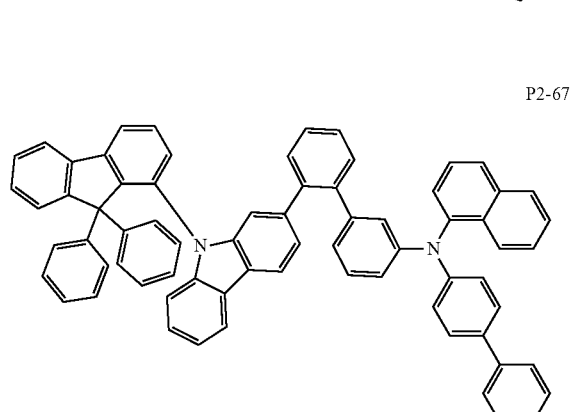
P2-68
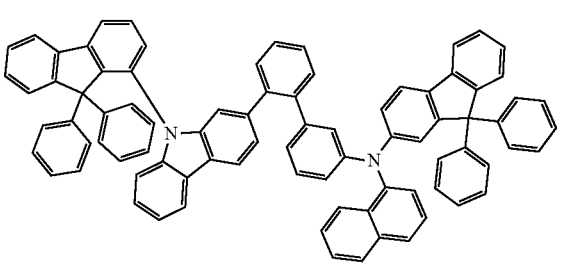

-continued
P2-69
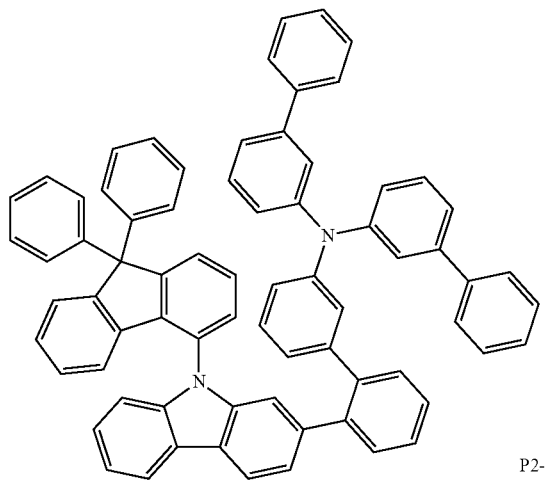
P2-70
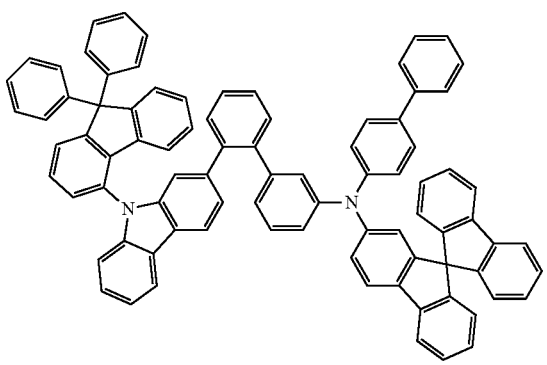
P2-71
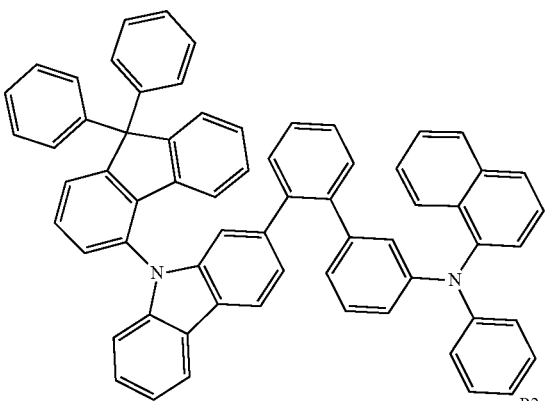
P2-72
-continued
P2-73
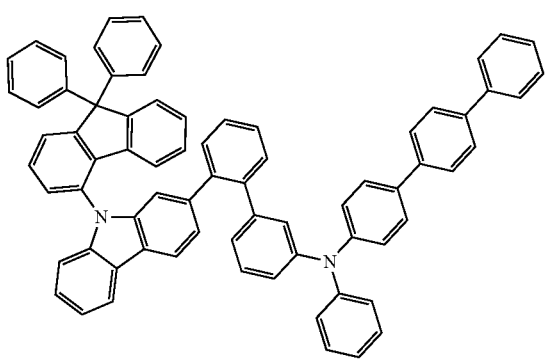
P2-74
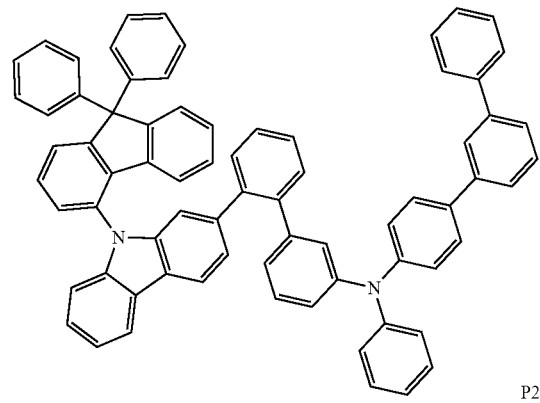
P2-75
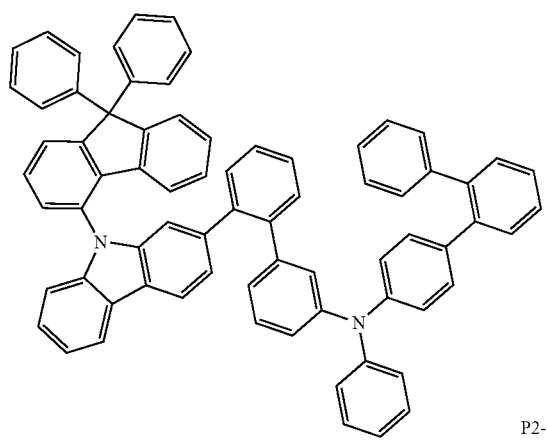
P2-76
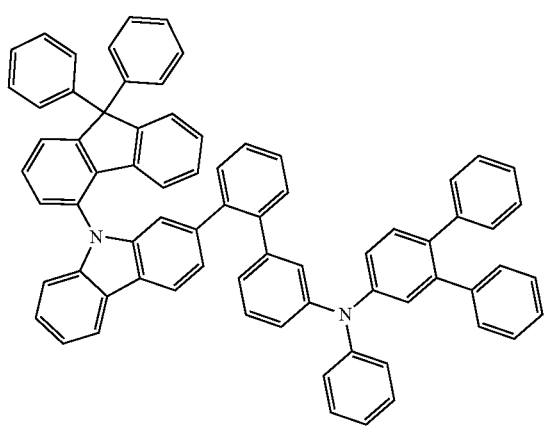

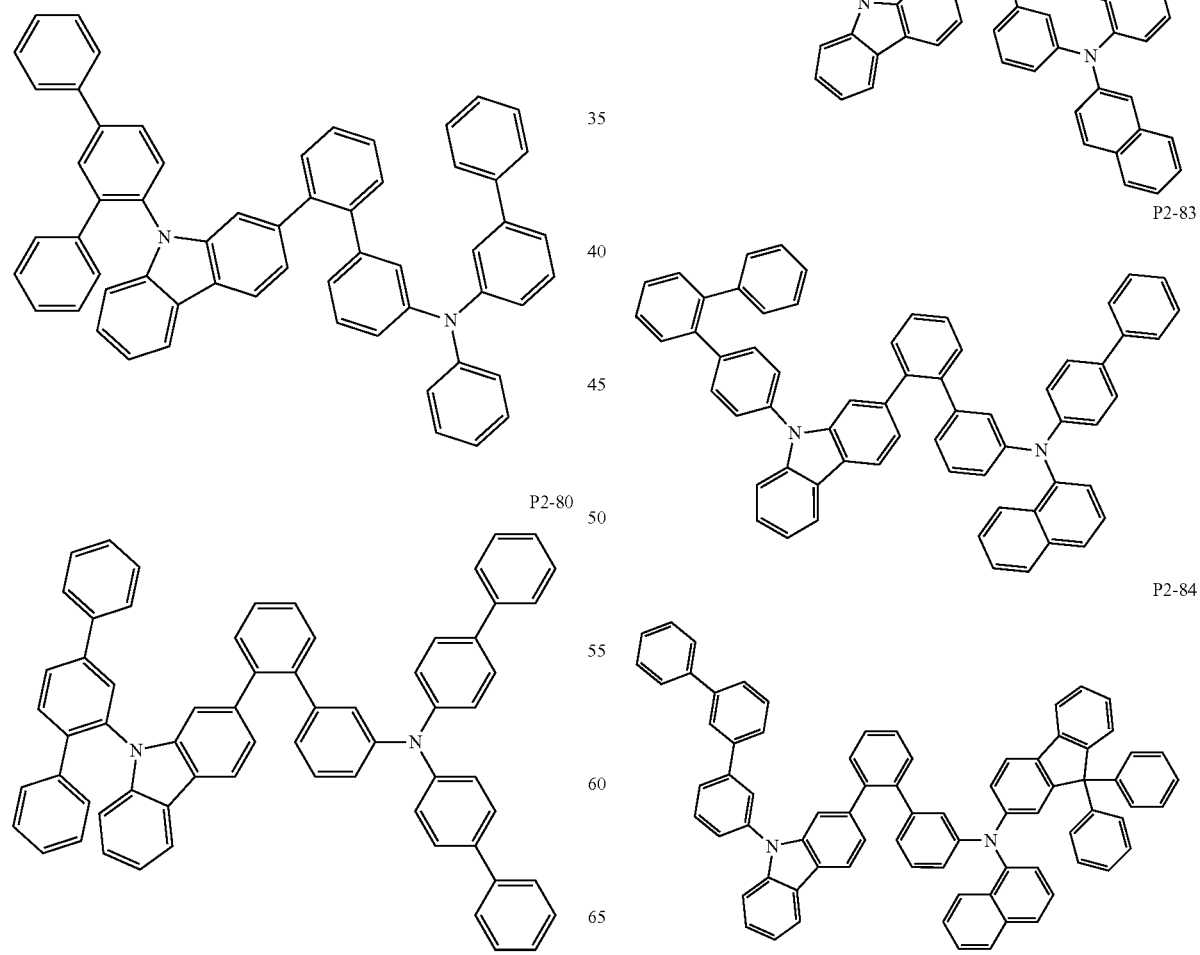

P2-85
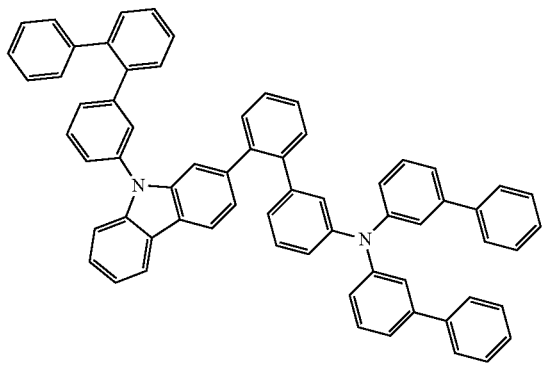
P2-86
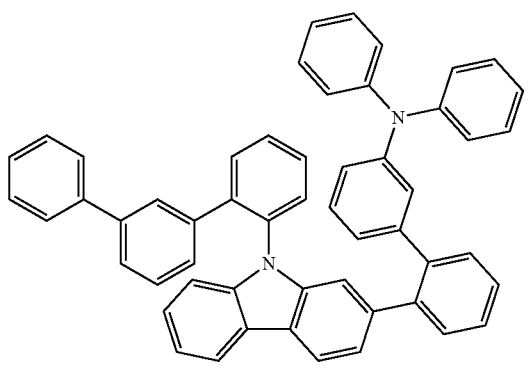
P2-87
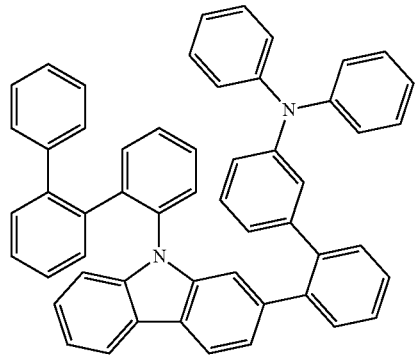
P2-88
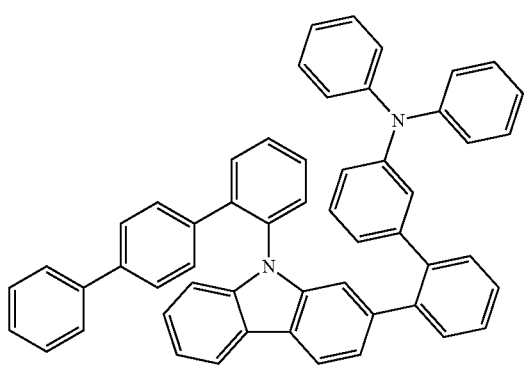
P2-89
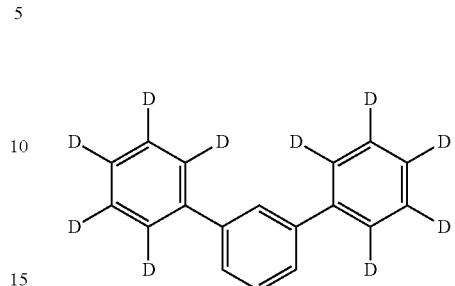
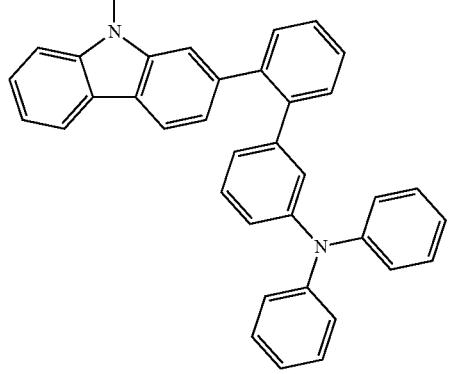
P2-90
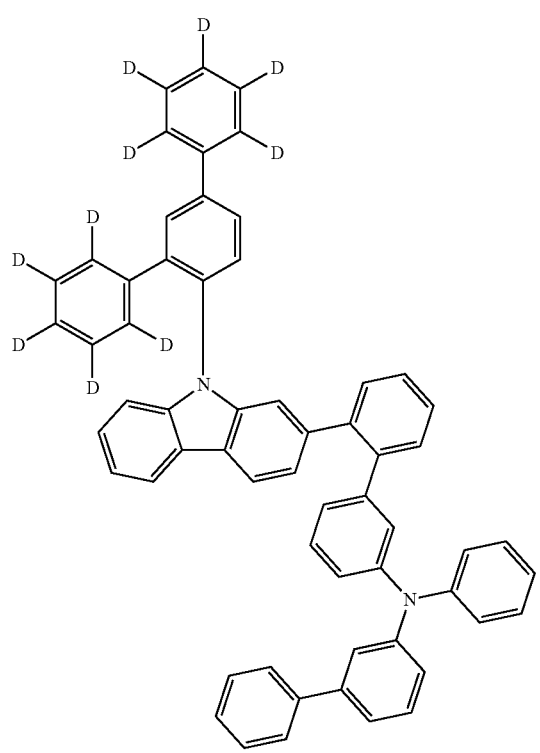

-continued
P2-91
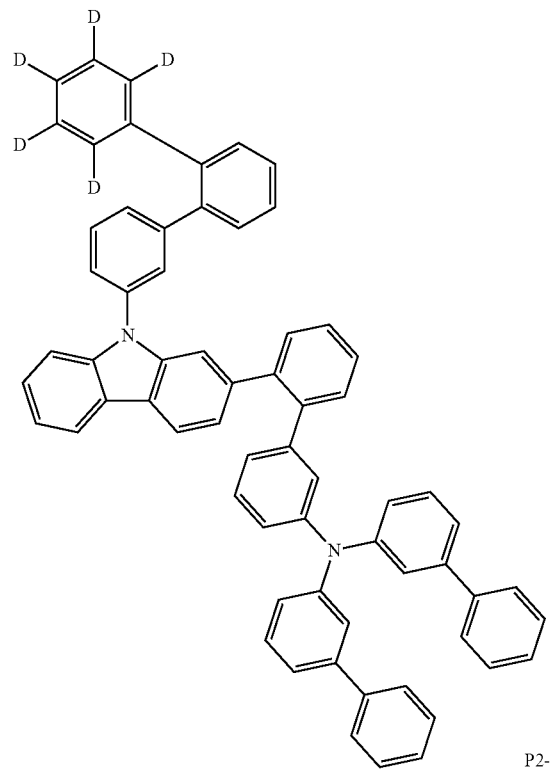
P2-92
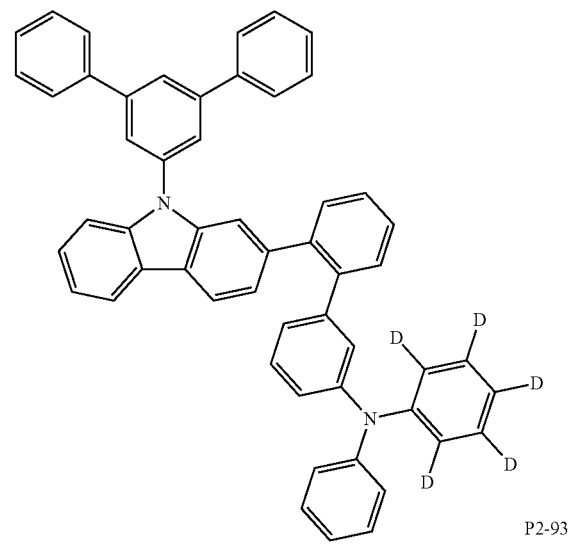
P2-93
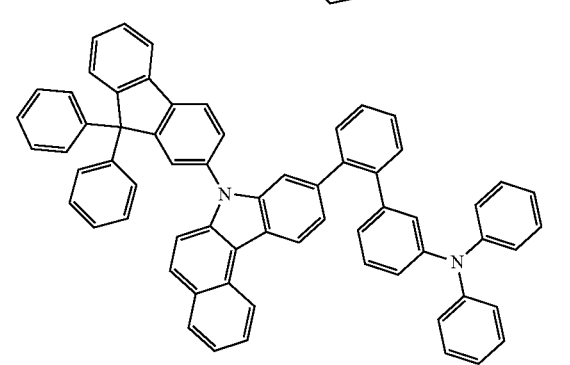
-continued
P2-94
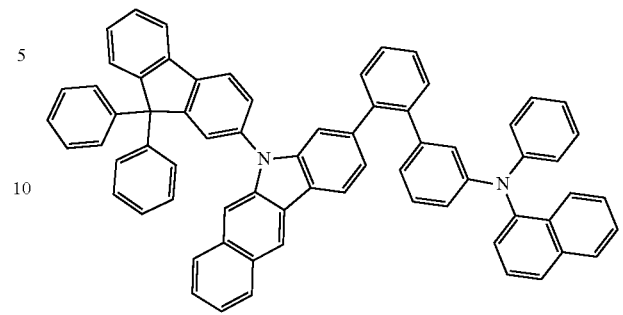
P2-95
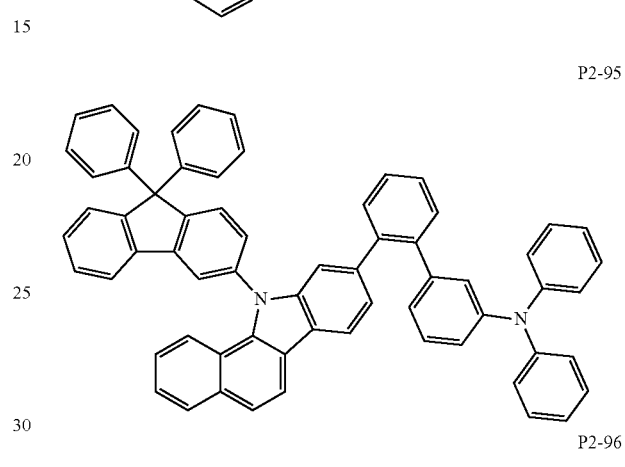
P2-96
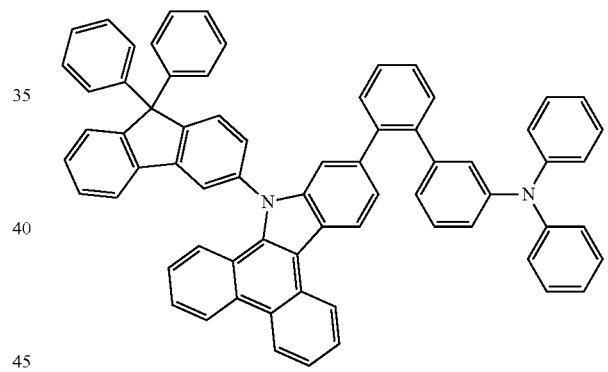
P2-97
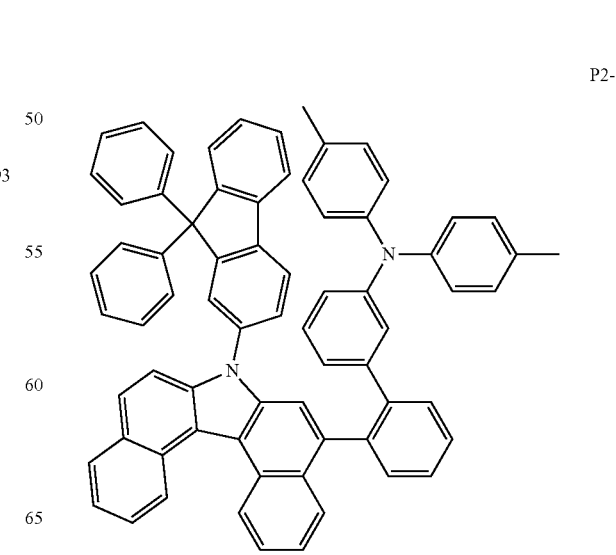

-continued
P2-98
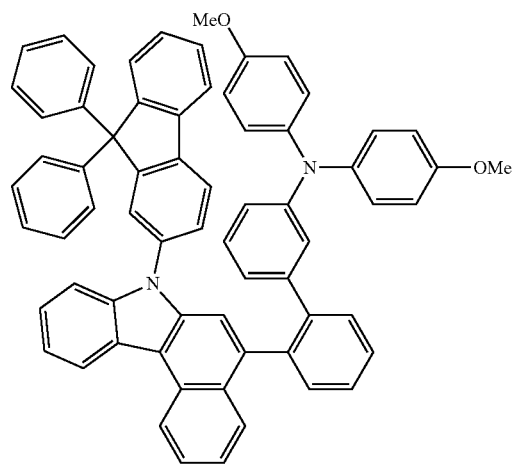
P2-99
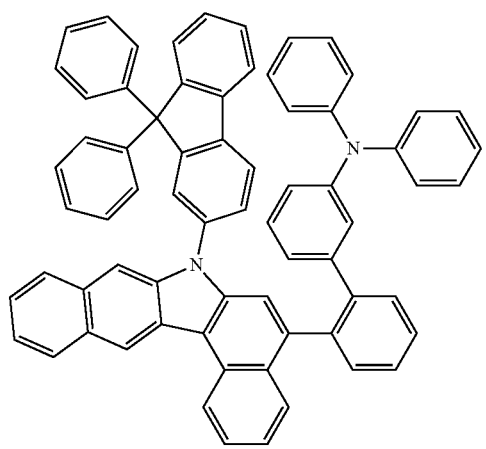
P2-100
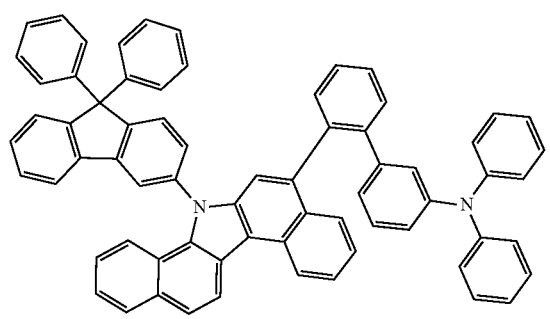
P2-101
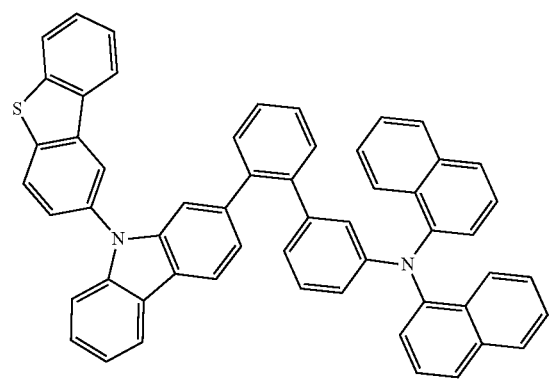
-continued
P2-102
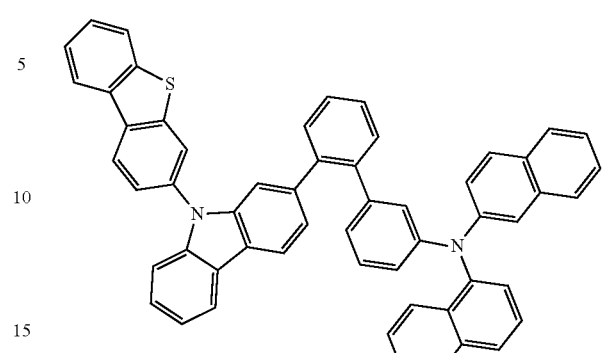
P2-103
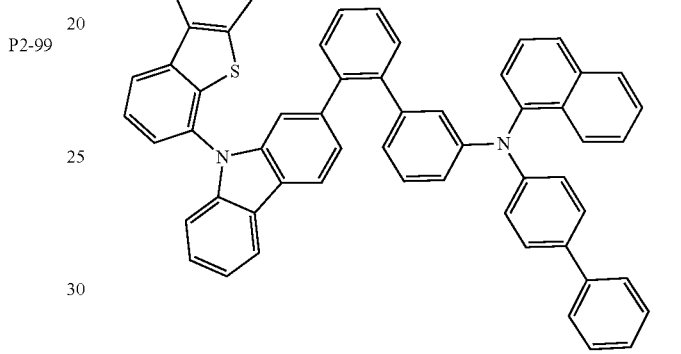
P2-104
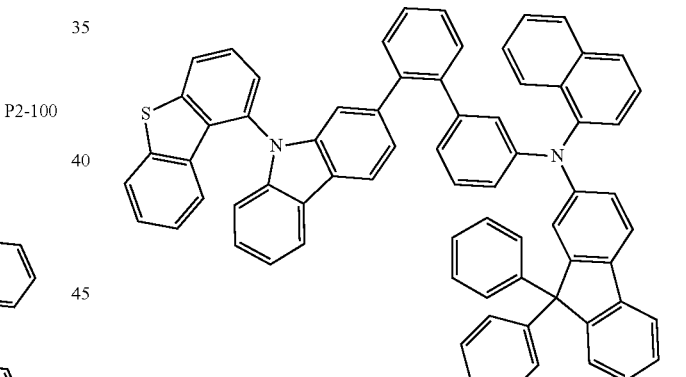
P2-105
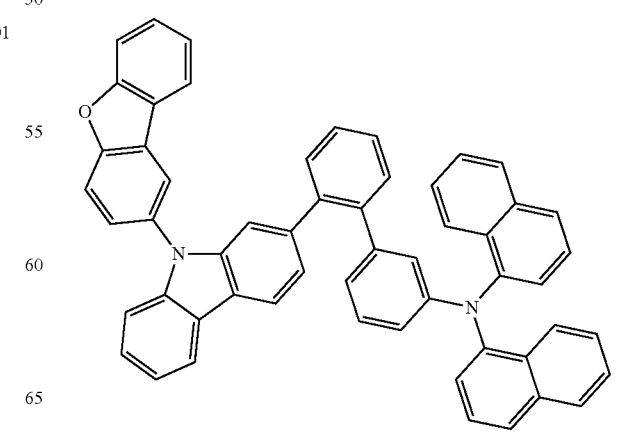

P2-106
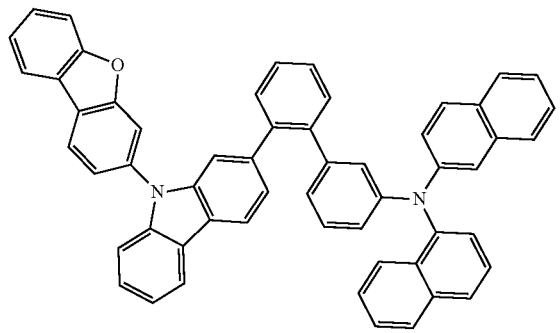
P2-107
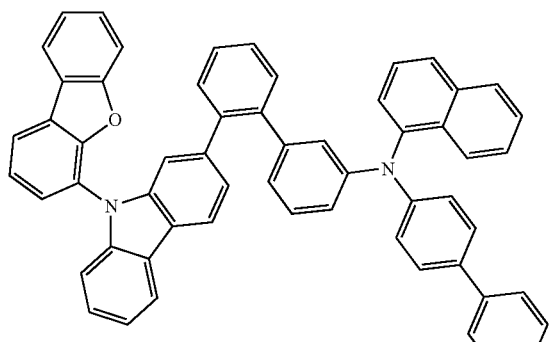
P2-108
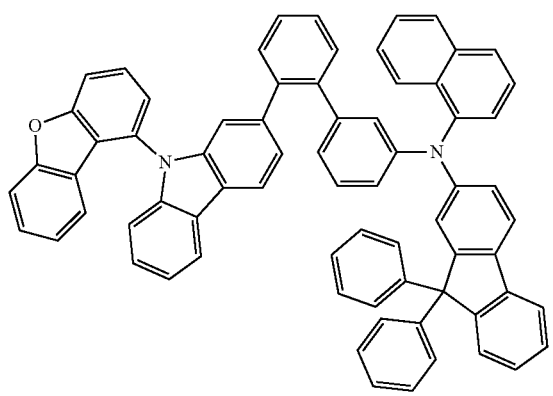
P2-109
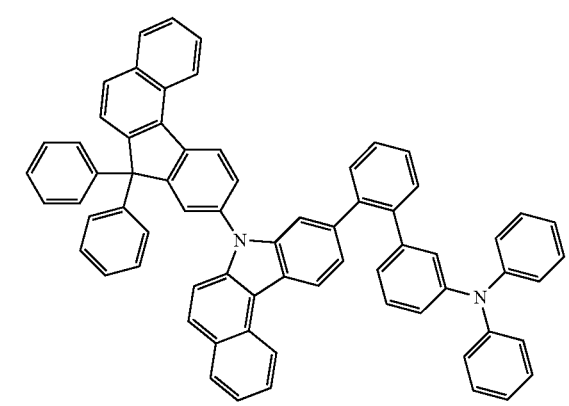
P2-110
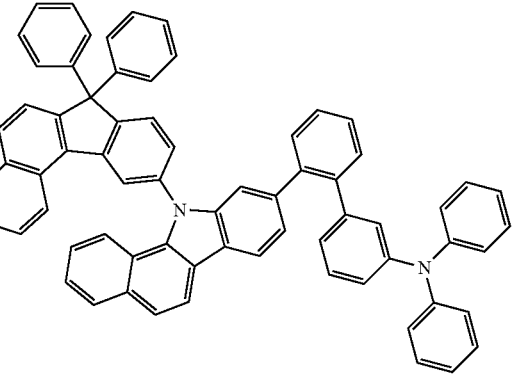
P2-111
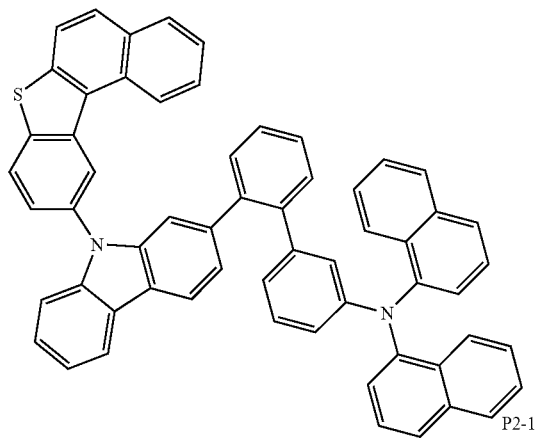
P2-112
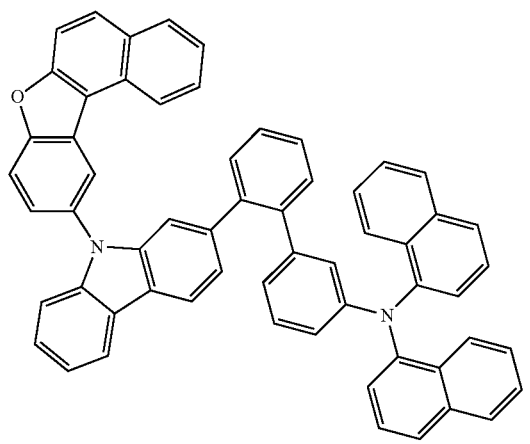
P3-1
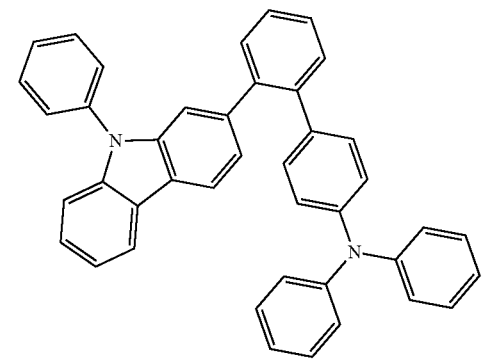

P3-2
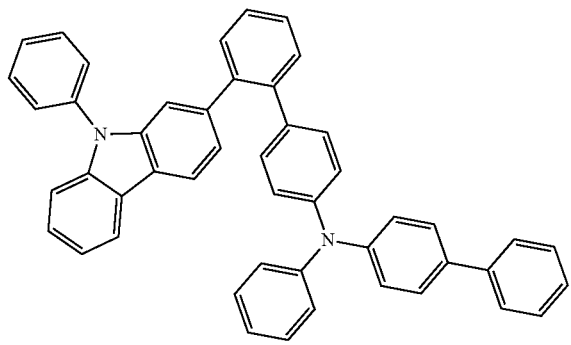
P3-3
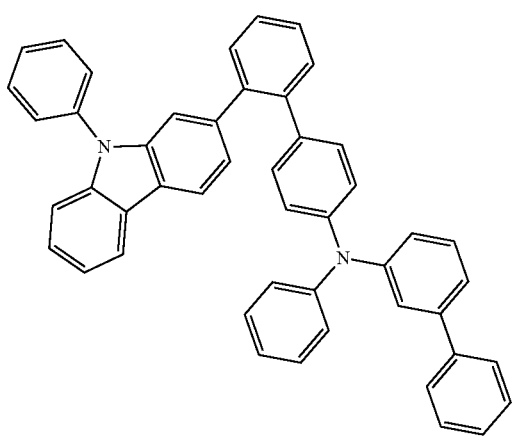
P3-4
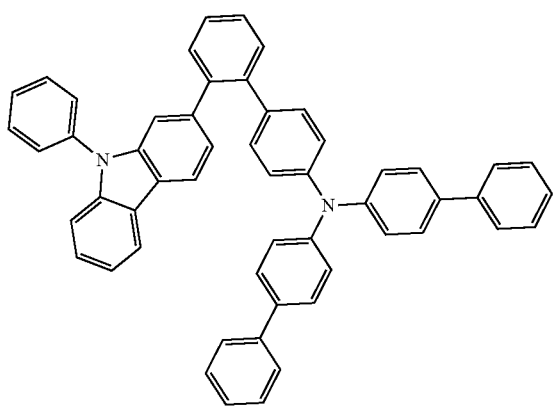
P3-5
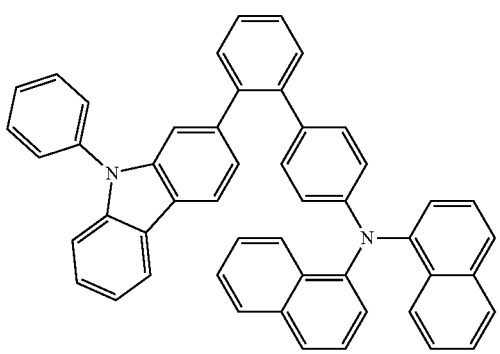
P3-6
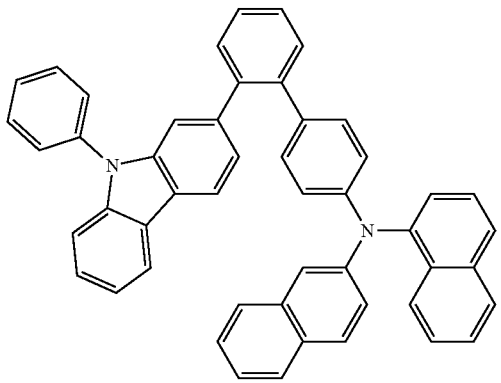
P3-7
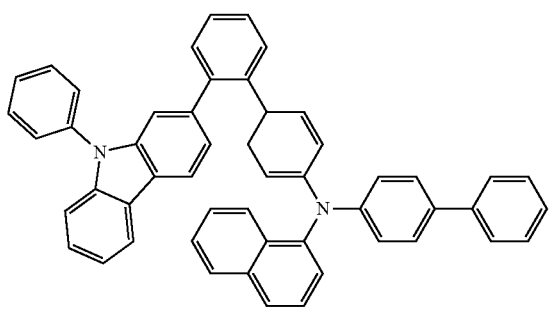
P3-8
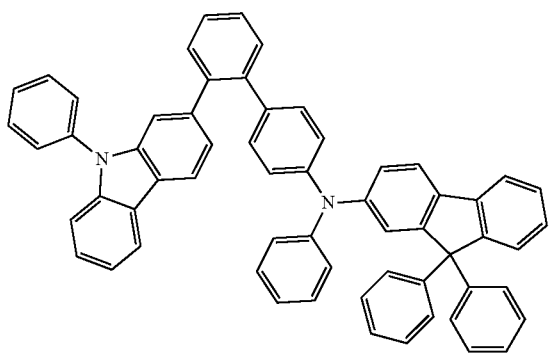
P3-9
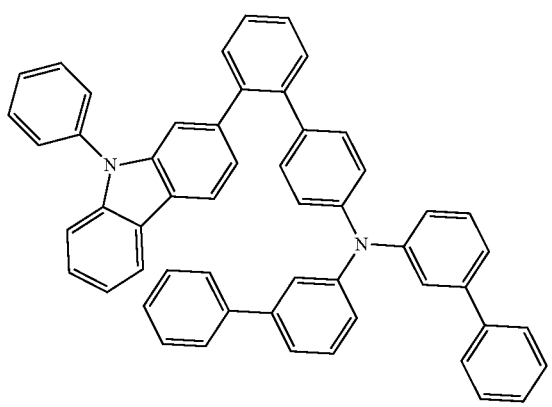

P3-10
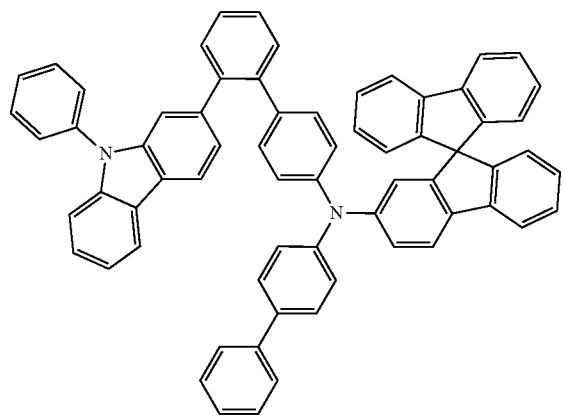
P3-11
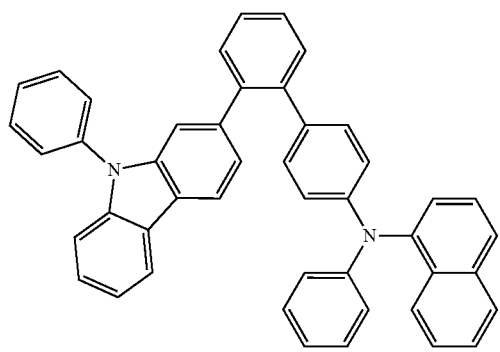
P3-12
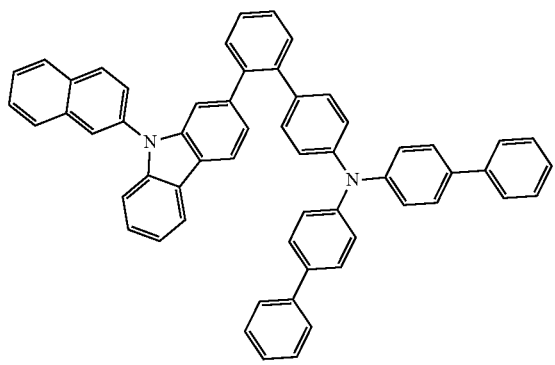
P3-13
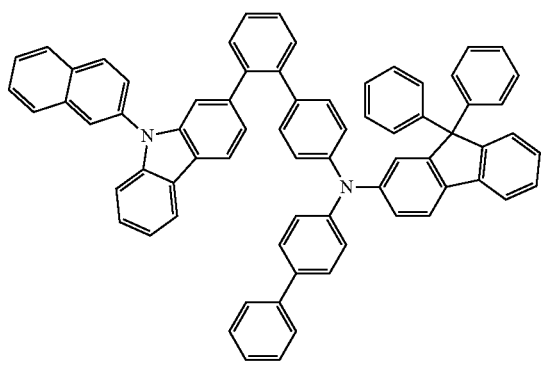
P3-14
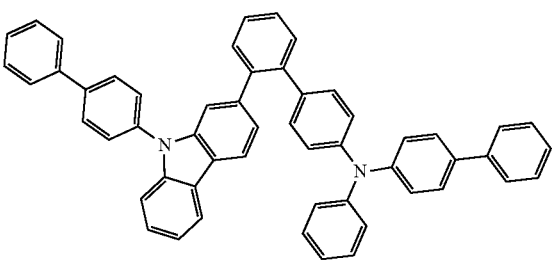
P3-15
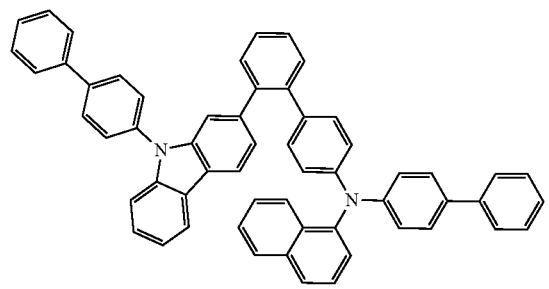
P3-16
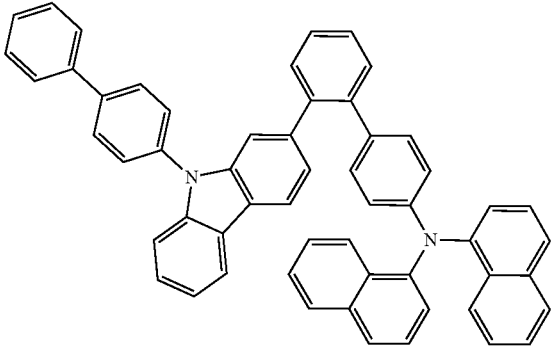
P3-17
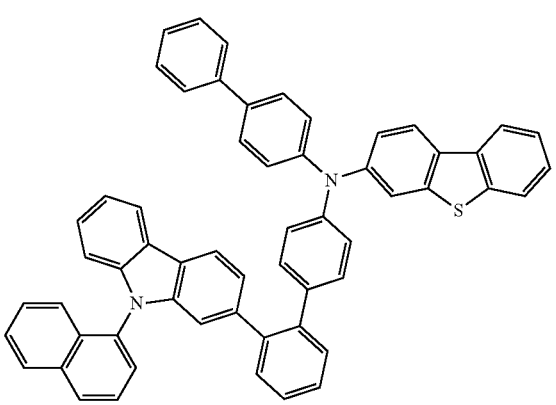

-continued
P3-18
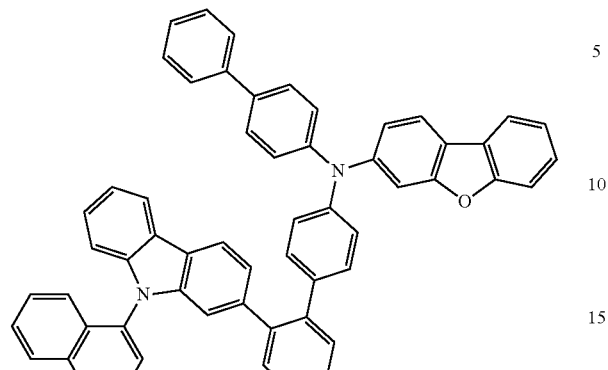
P3-19
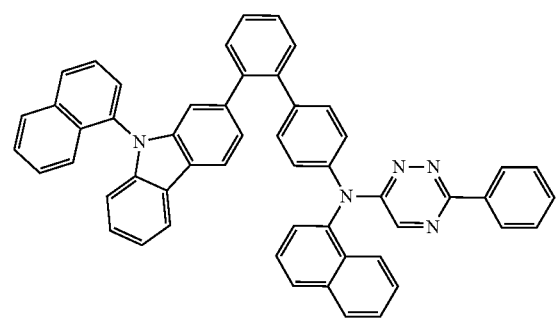
P3-20
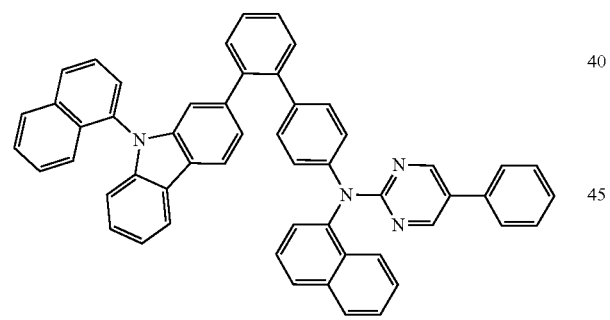
P3-21
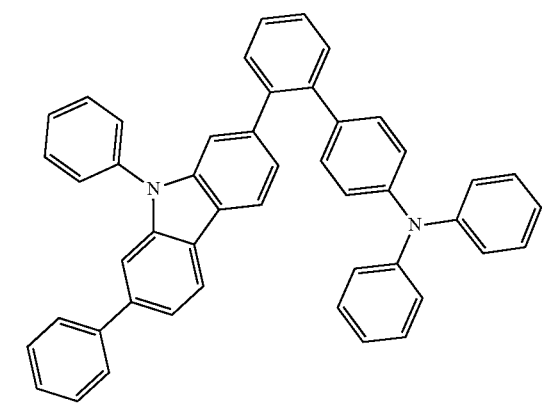
-continued
P3-22
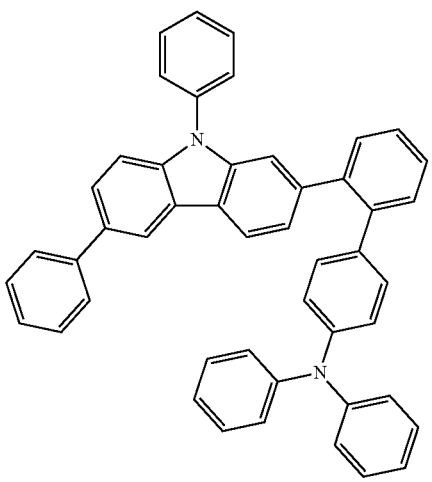
P3-23
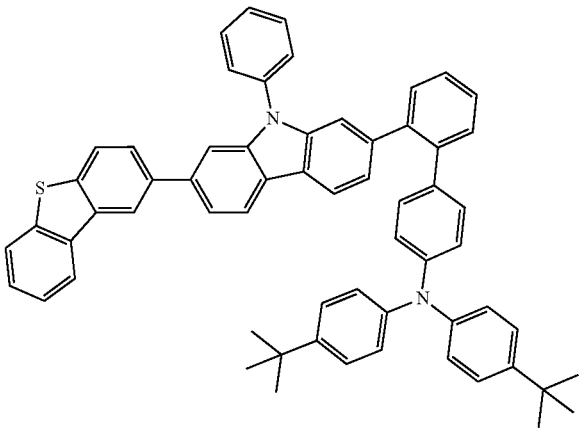
P3-24
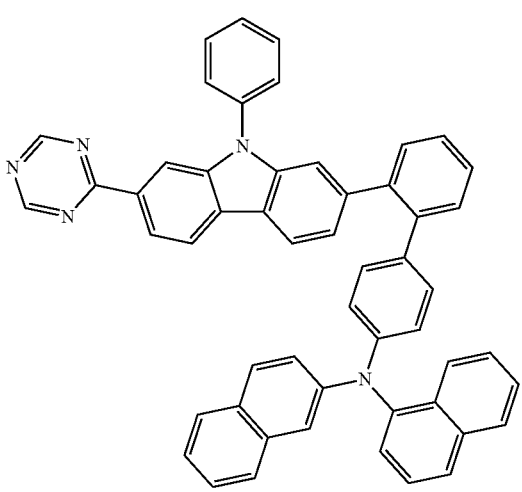

P3-25
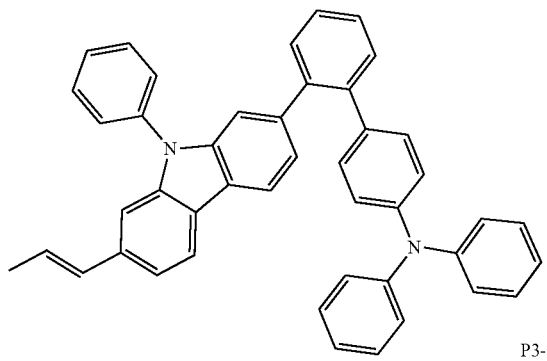
P3-26
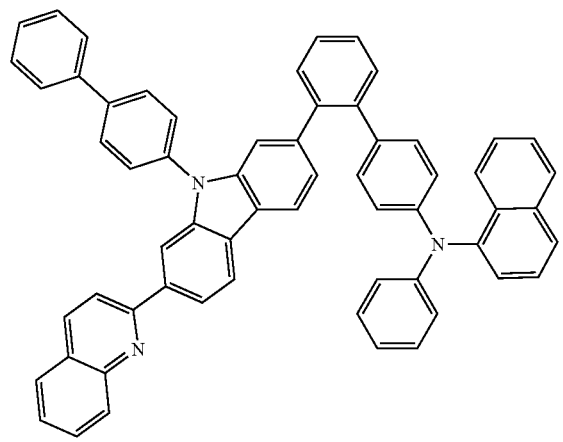
P3-27
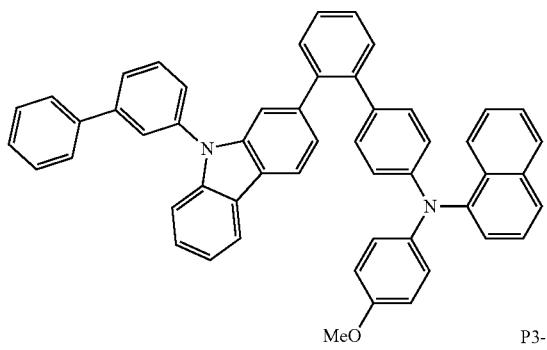
P3-28
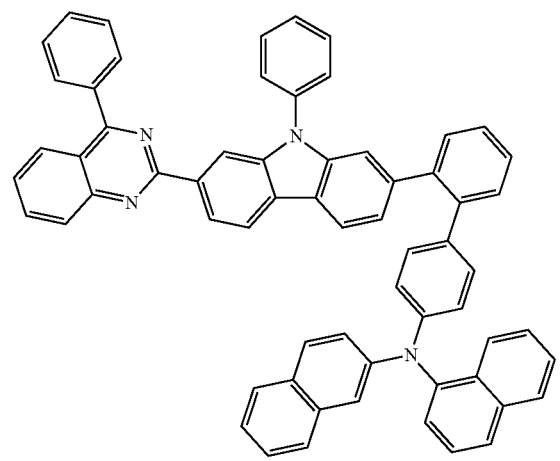
P3-29
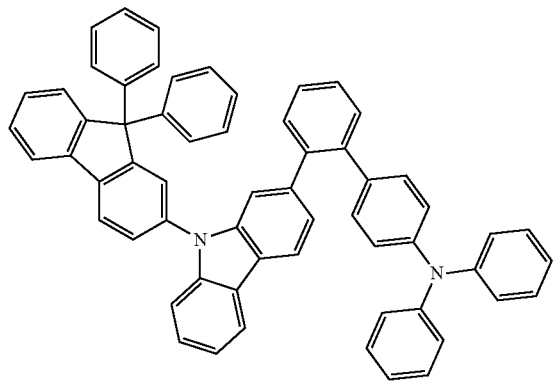
P3-30
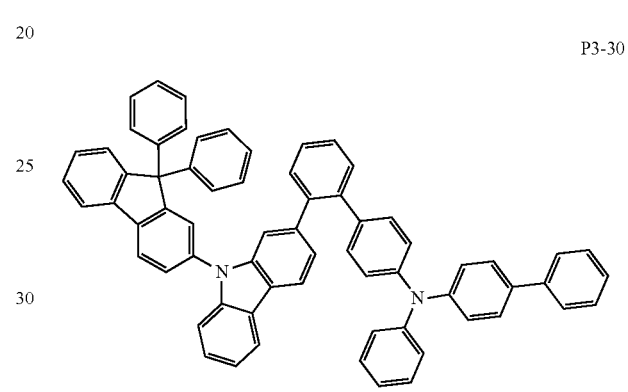
P3-31
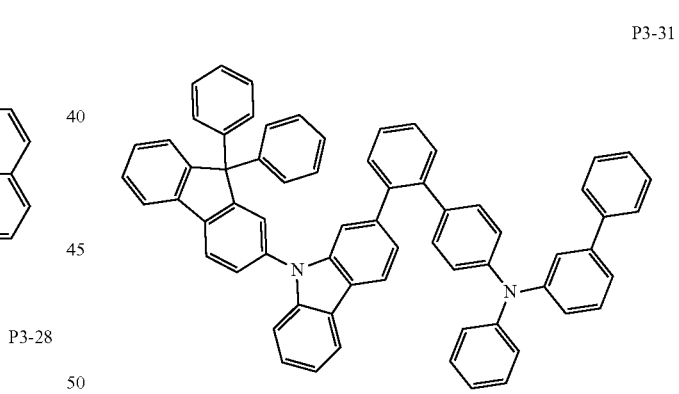
P3-32
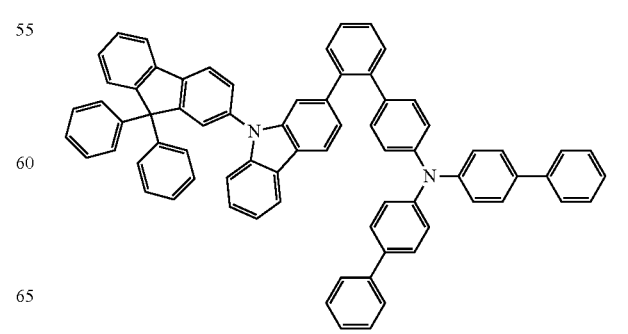

P3-33
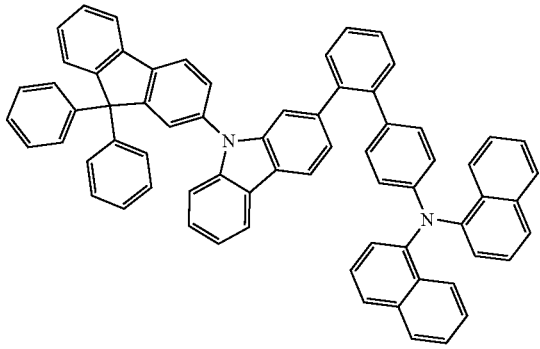
P3-34
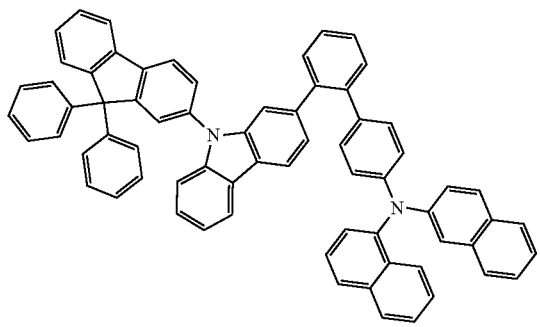
P3-35
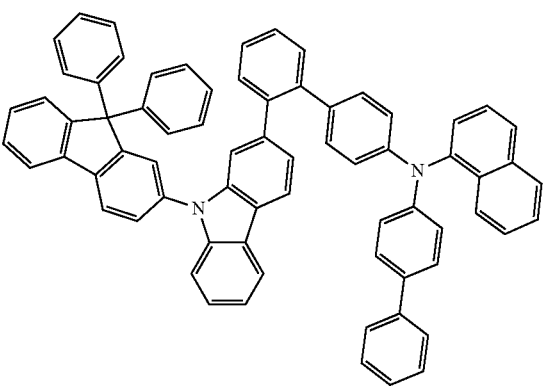
P3-36
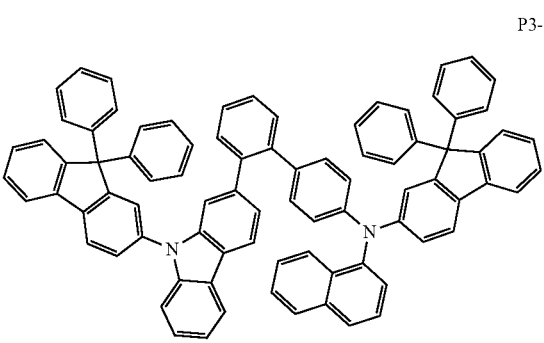
P3-37
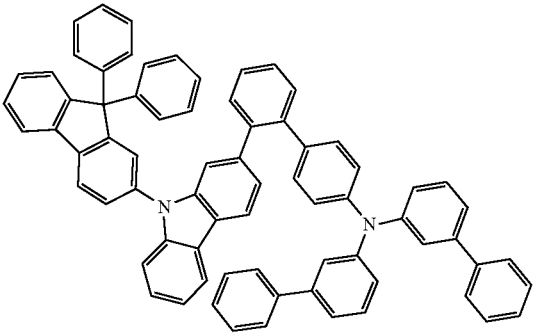
P3-38
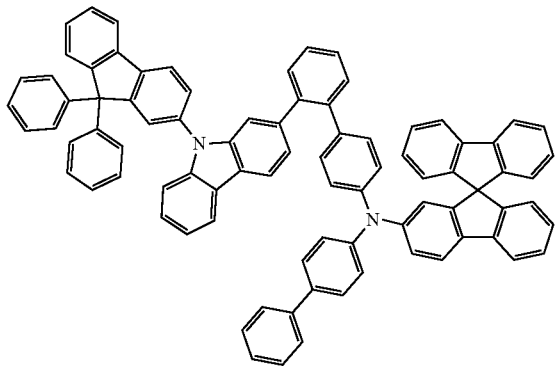
P3-39
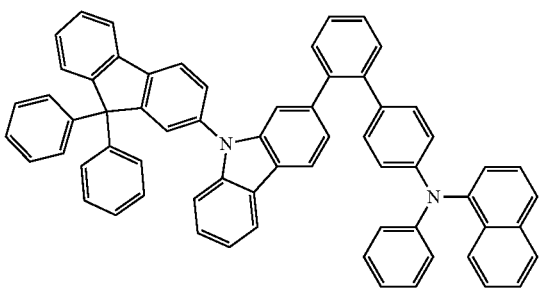
P3-40
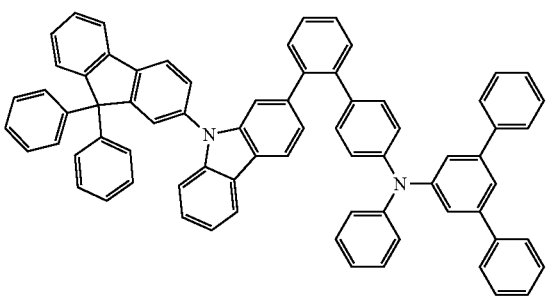

P3-41
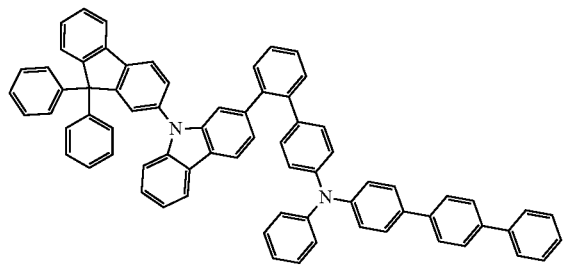
P3-42
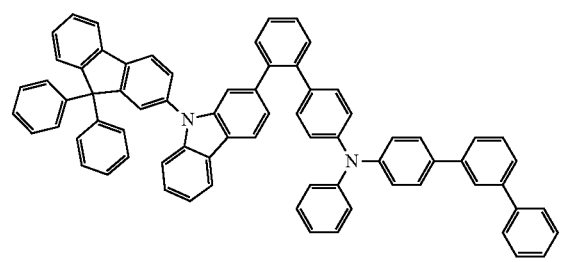
P3-43
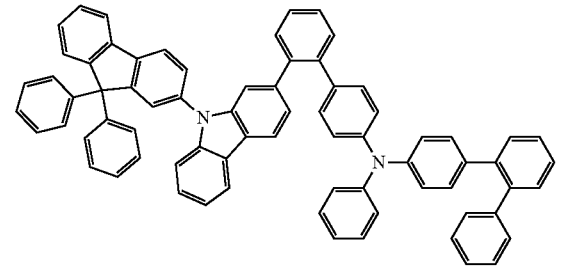
P3-44
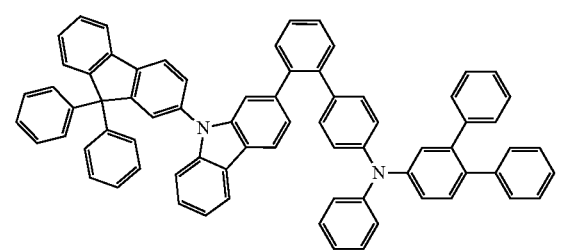
P3-45
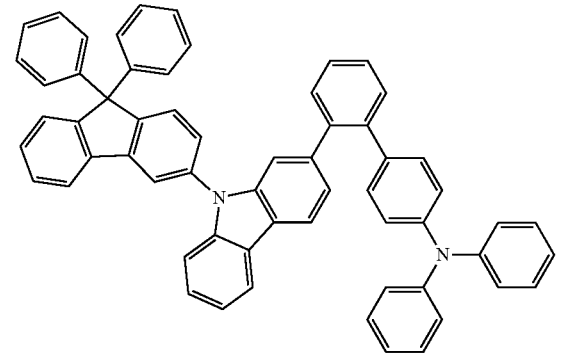
P3-46
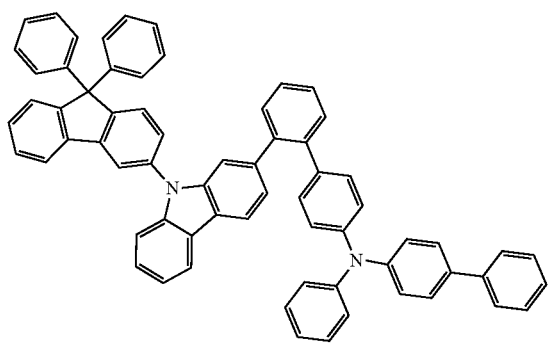
P3-47
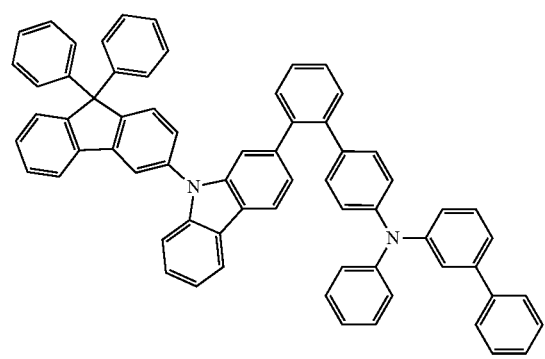
P3-48
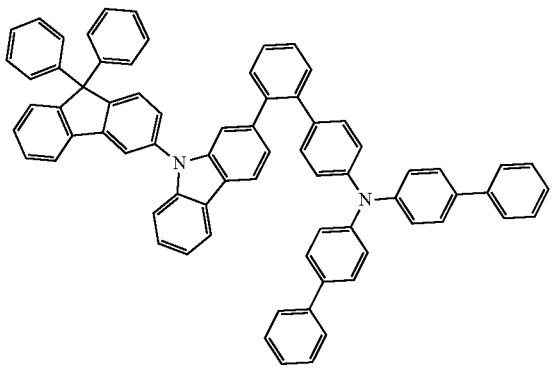
P3-49
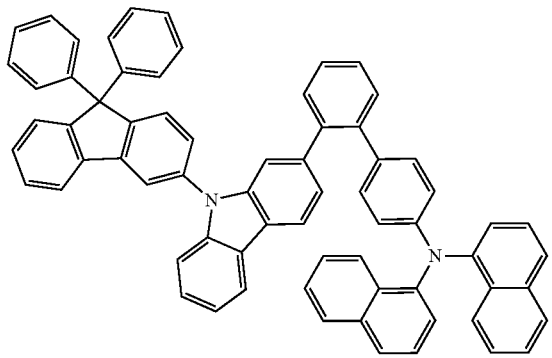

P3-50
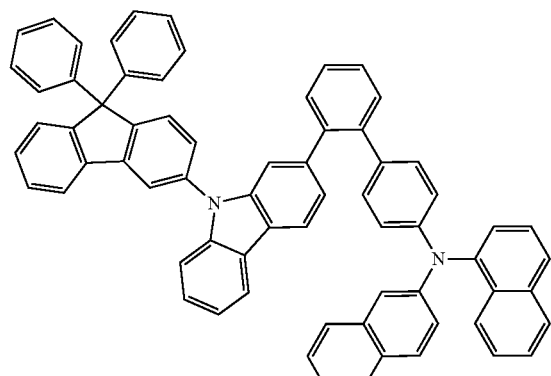
P3-51
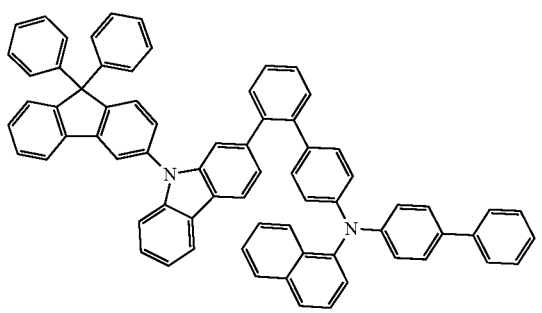
P3-52
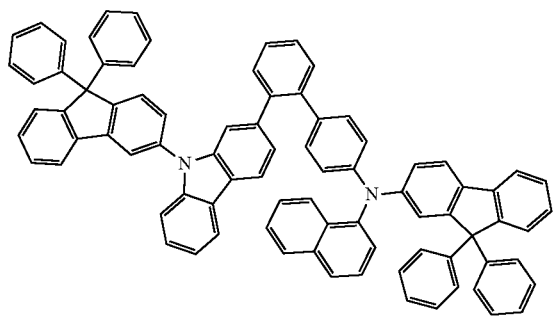
P3-53
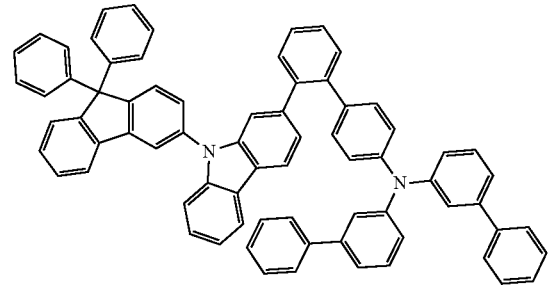
P3-54
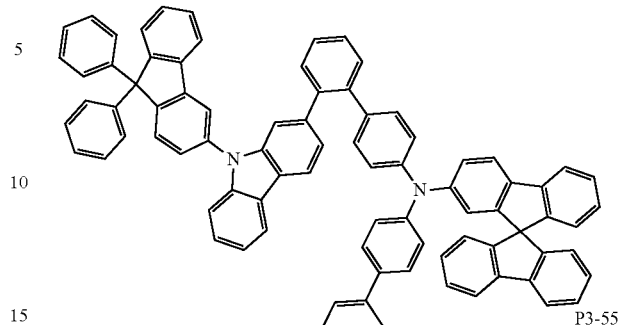
P3-55
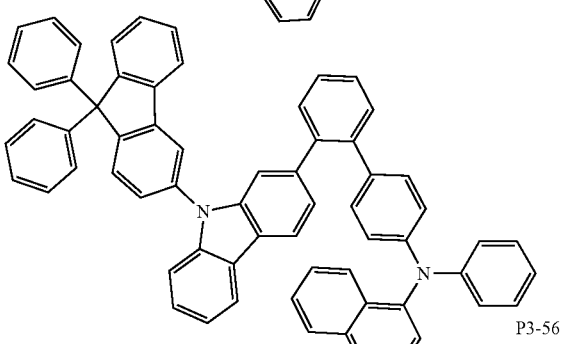
P3-56
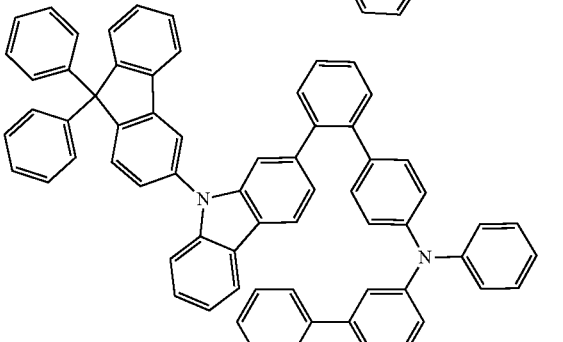
P3-57
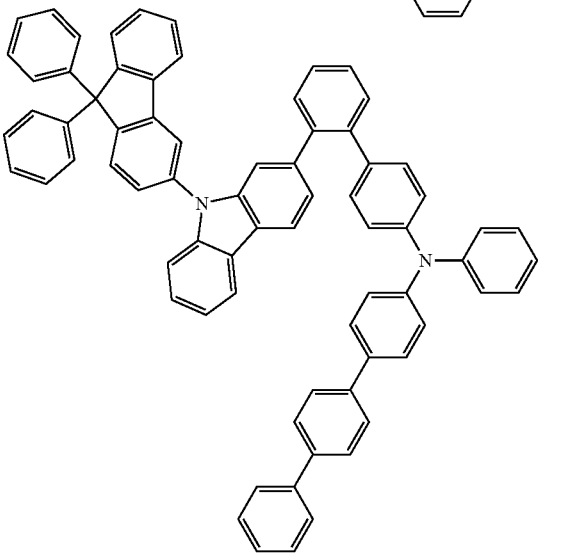

P3-58
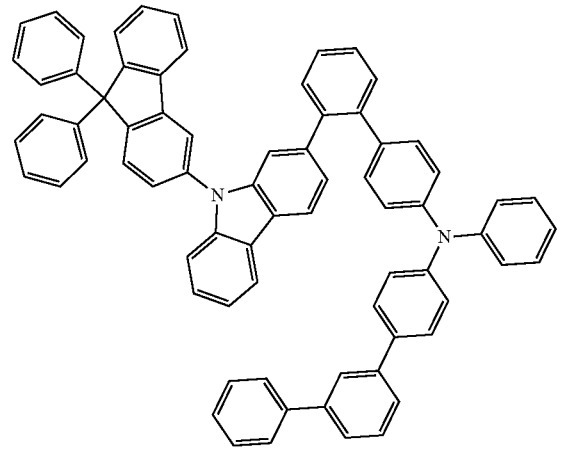
P3-59
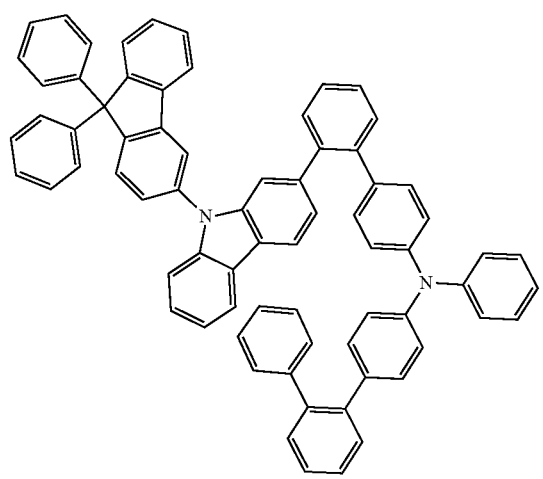
P3-60
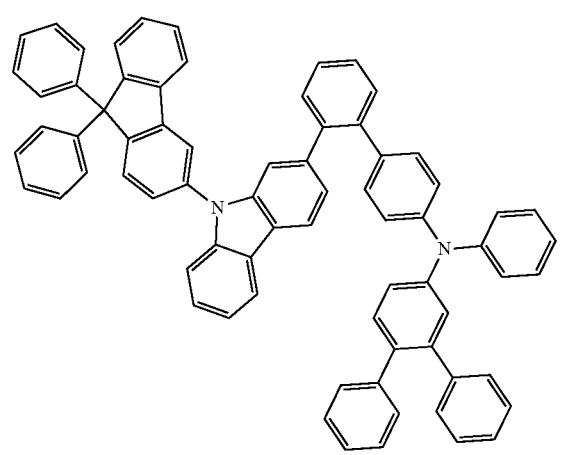
P3-61
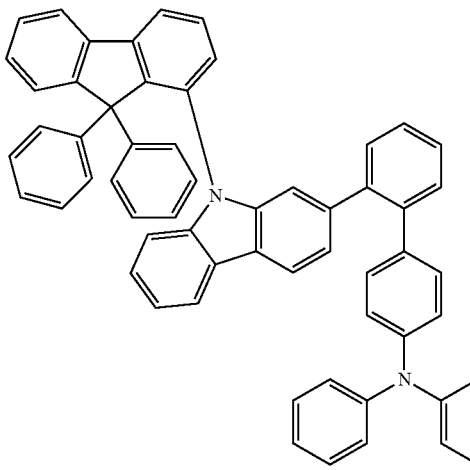
P3-62
P3-63
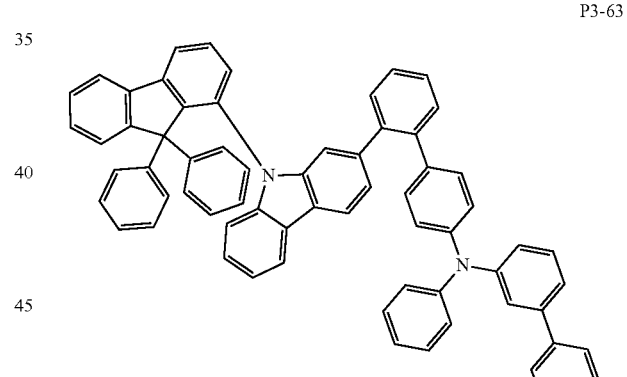
P3-64
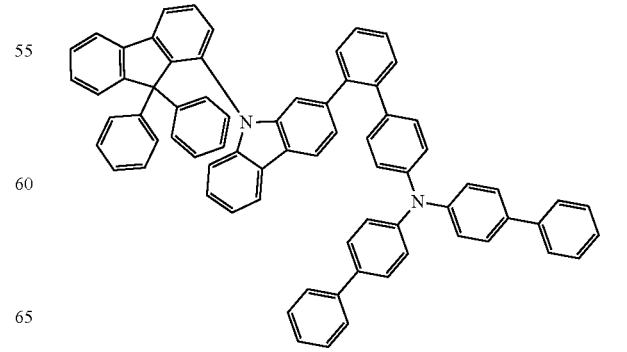

P3-65
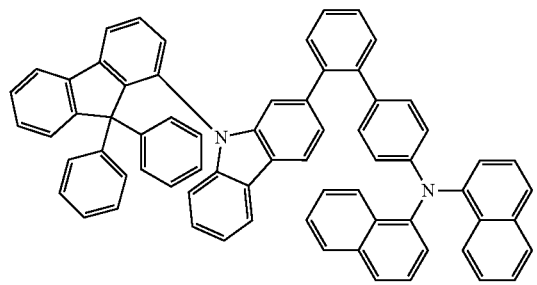
P3-66
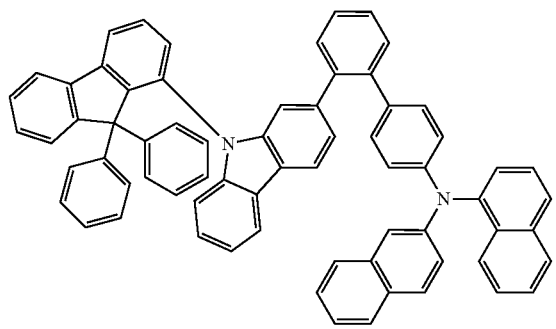
P3-67
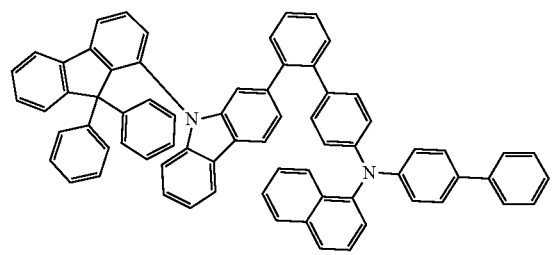
P3-68
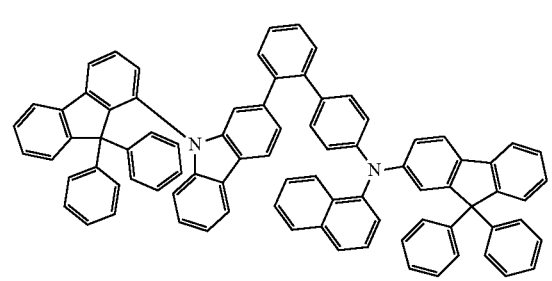
P3-69
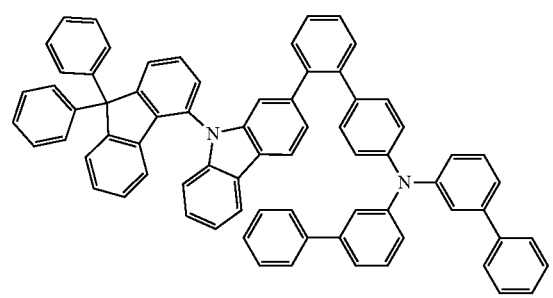
P3-70
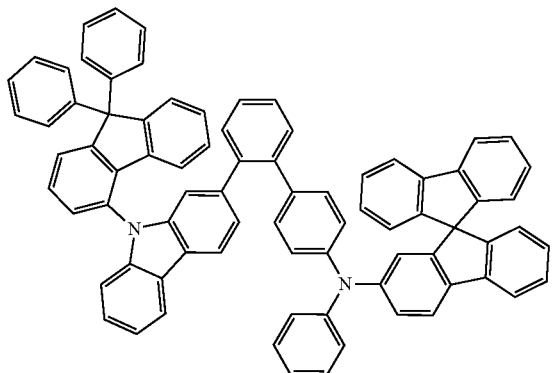
P3-71
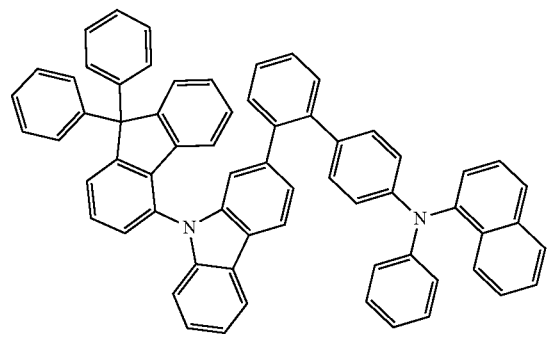
P3-72
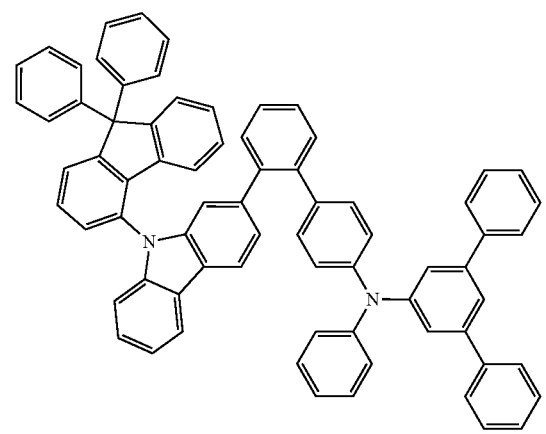
P3-73
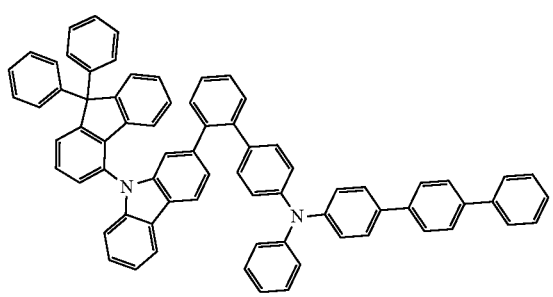

P3-74
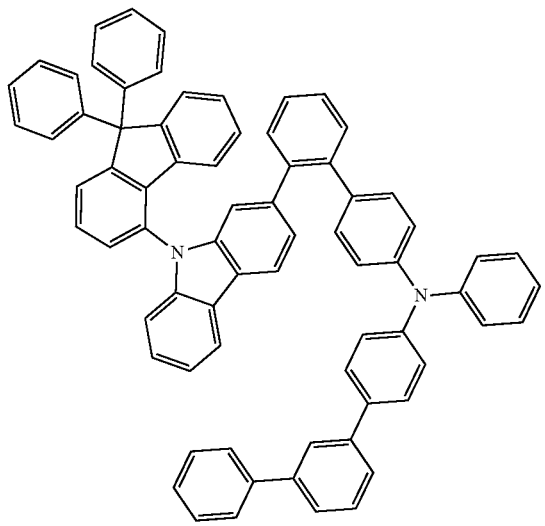
P3-75
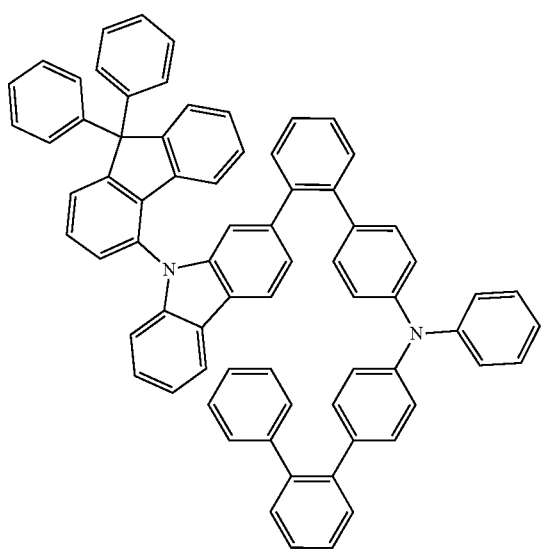
P3-76
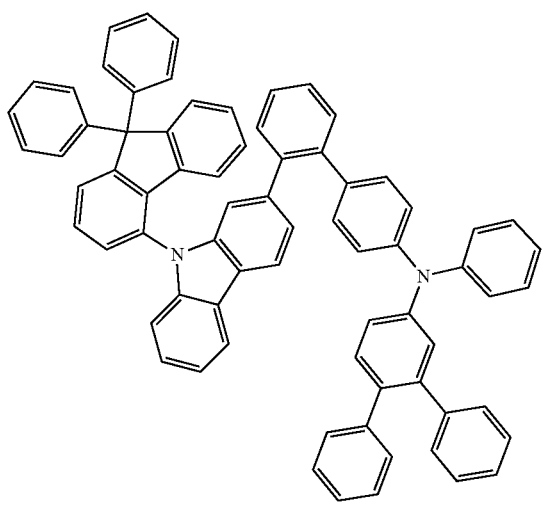
P3-77
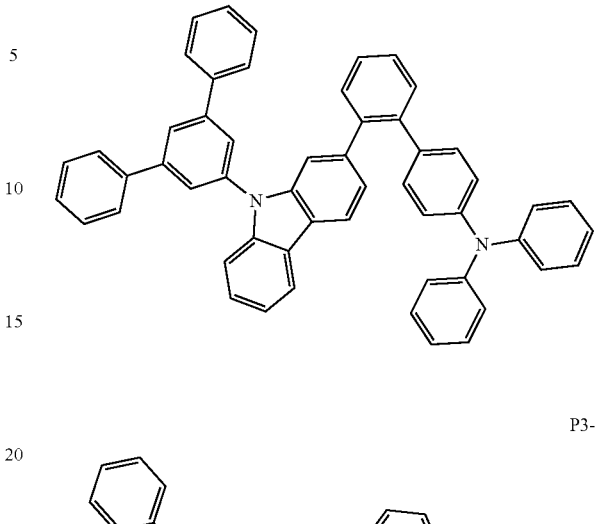
P3-78
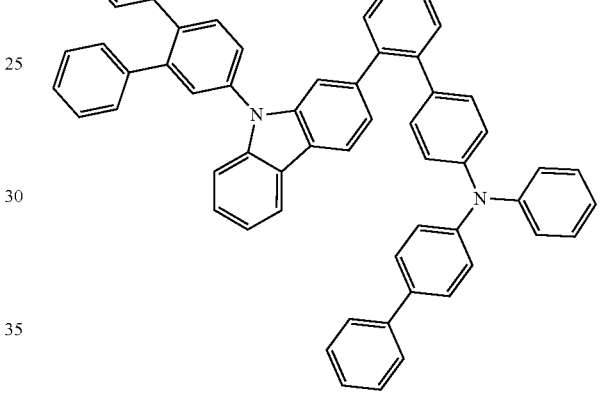
P3-79
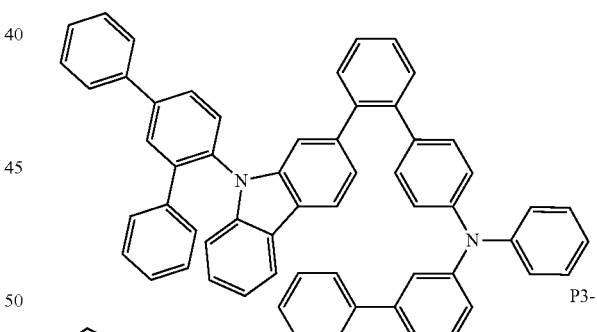
P3-80
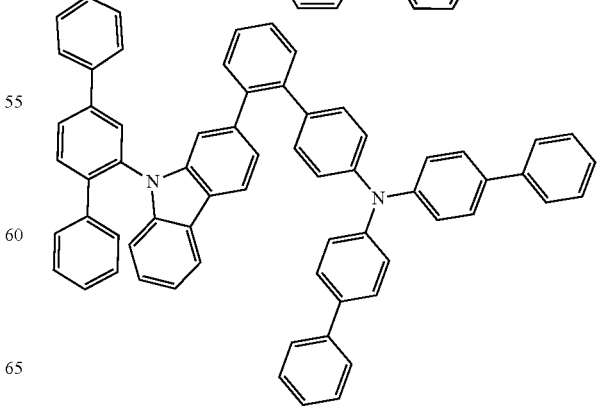

P3-81
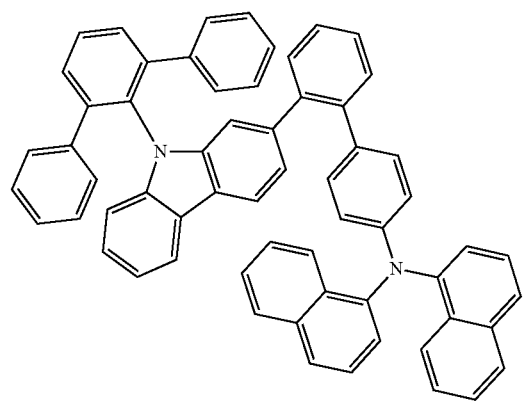
P3-82
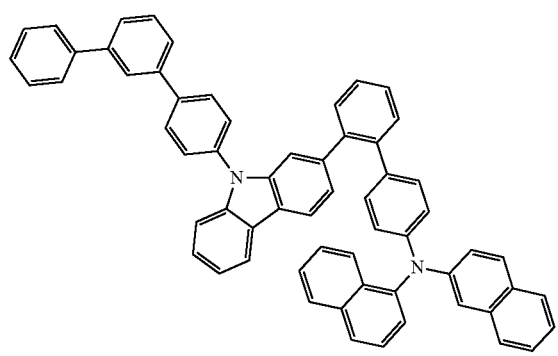
P3-83
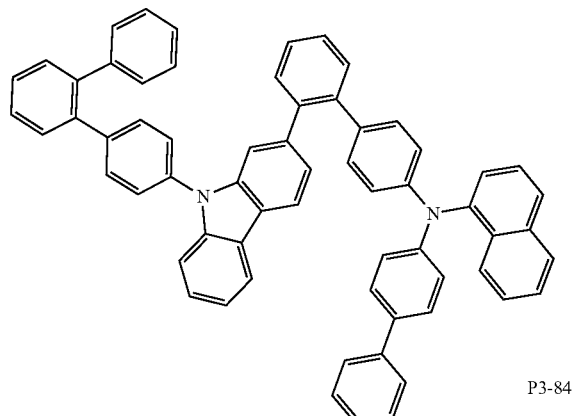
P3-84
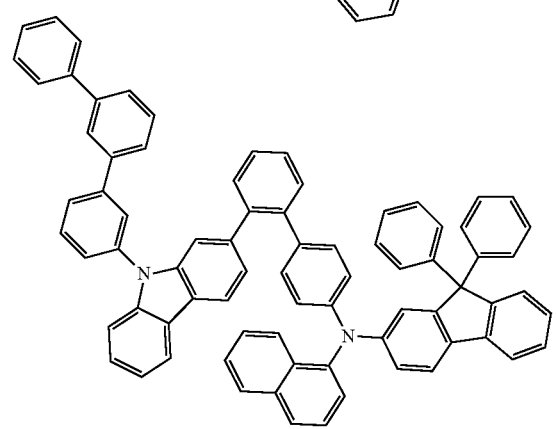
P3-85
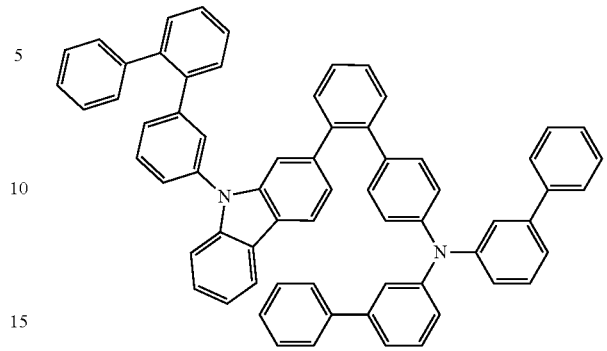
P3-86
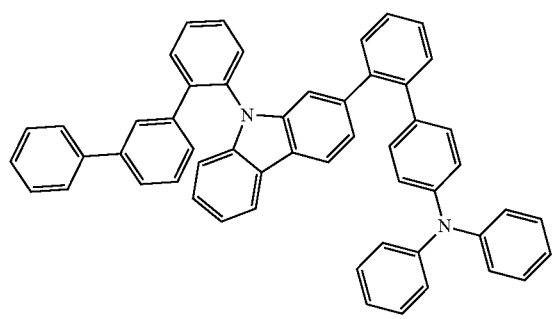
P3-87
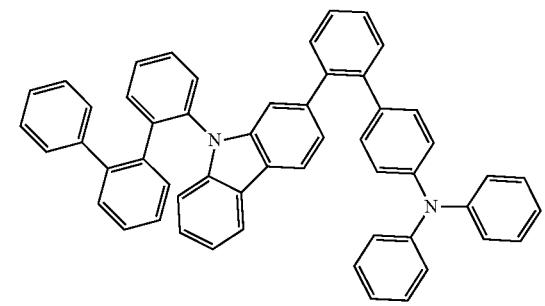
P3-88
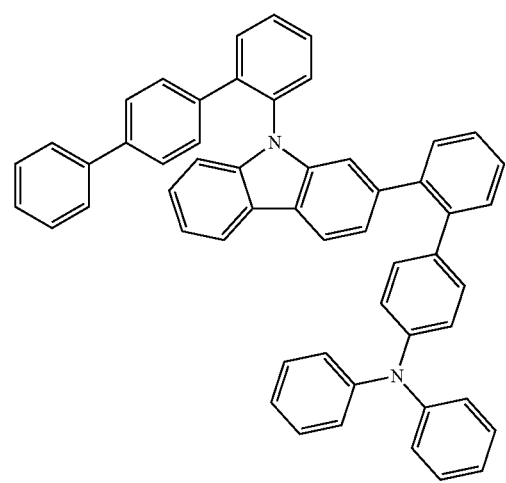

P3-89
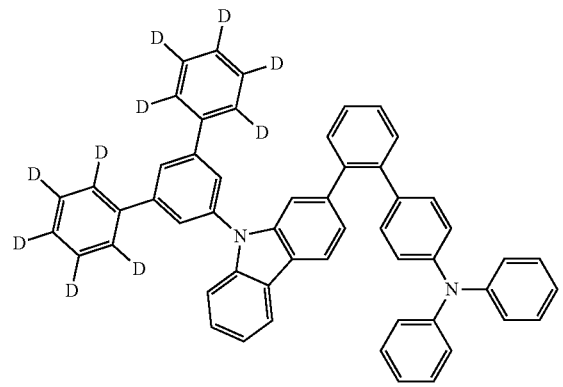
P3-90
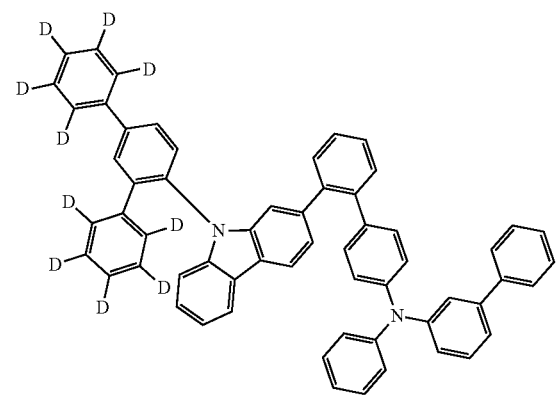
P3-91
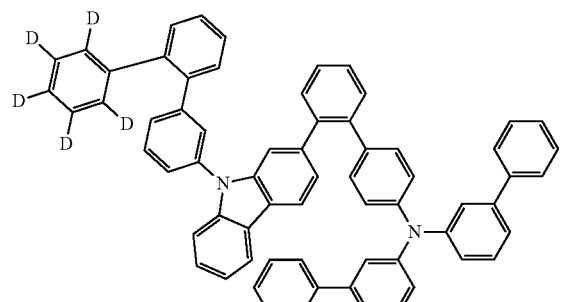
P3-92
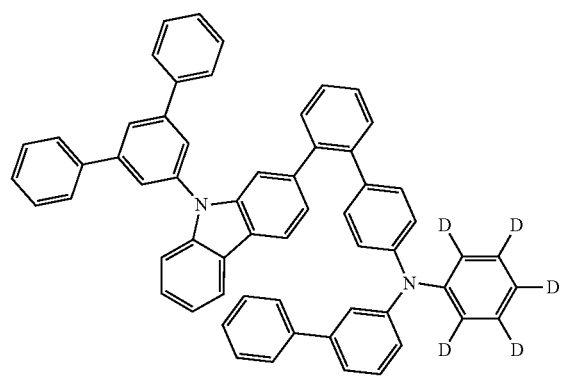
P3-93
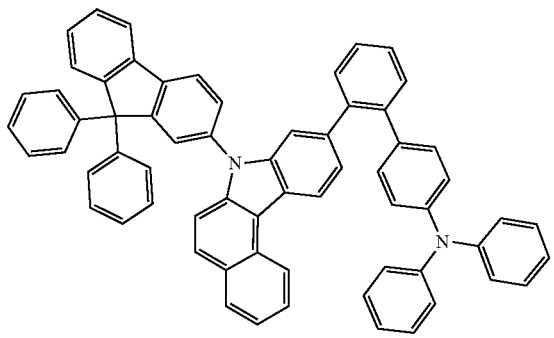
P3-94
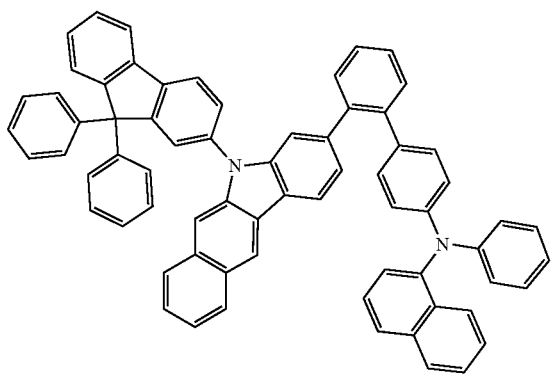
P3-95
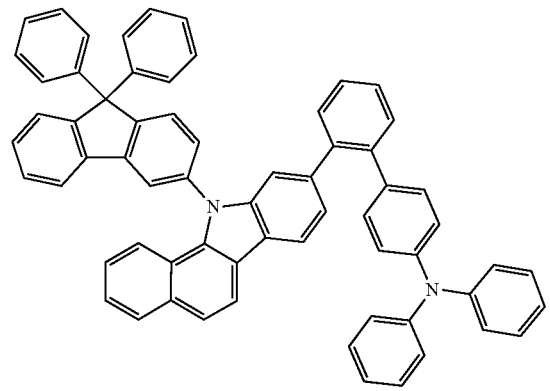
P3-96
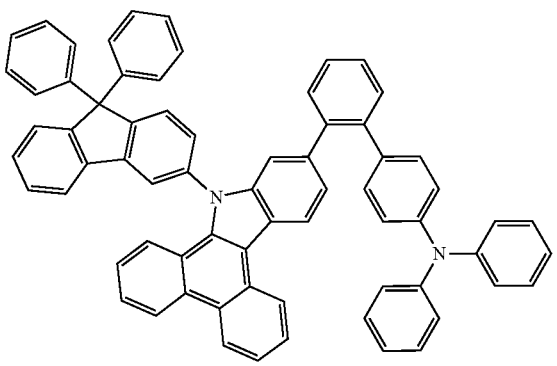

P3-97
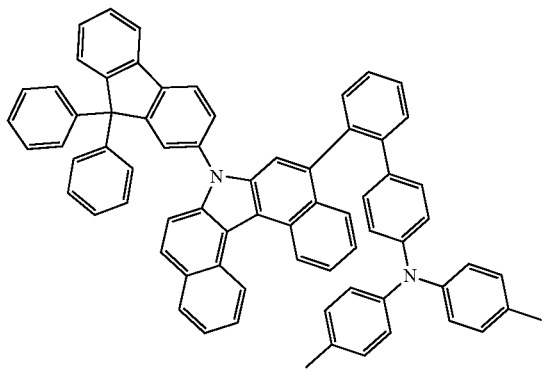
P3-98
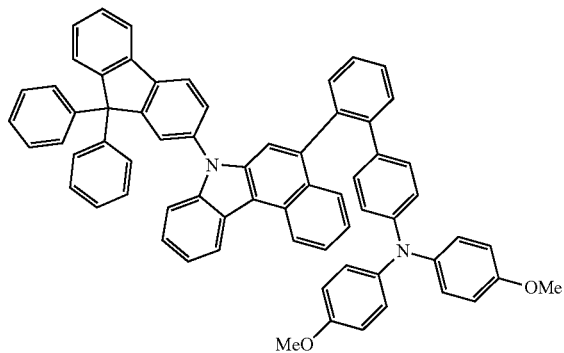
P3-99
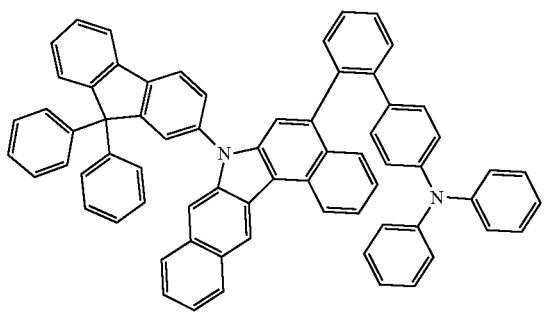
P3-100
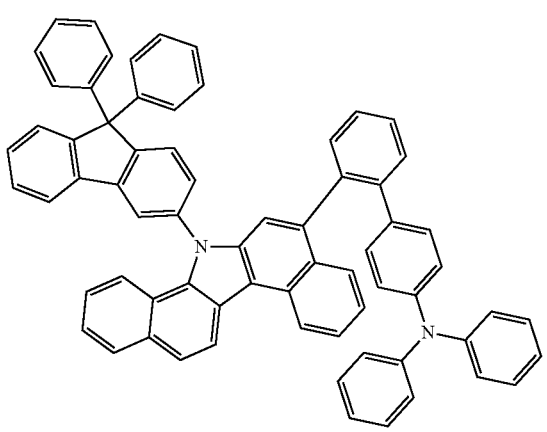
P3-101
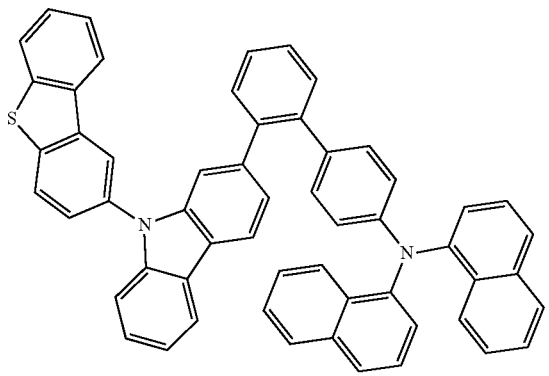
P3-102
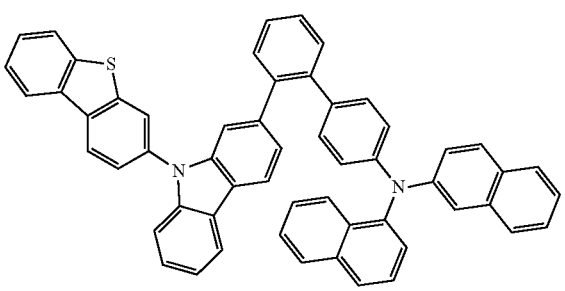
P3-103
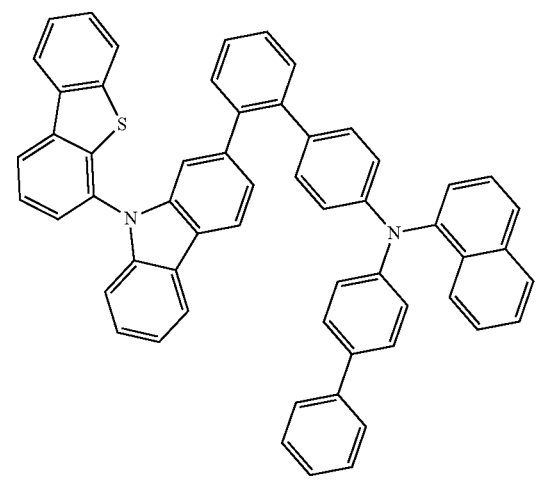
P3-104
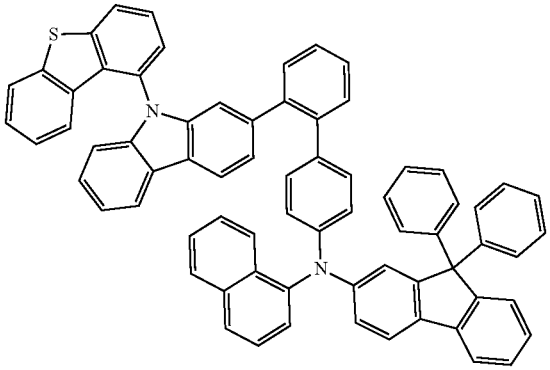

P3-105
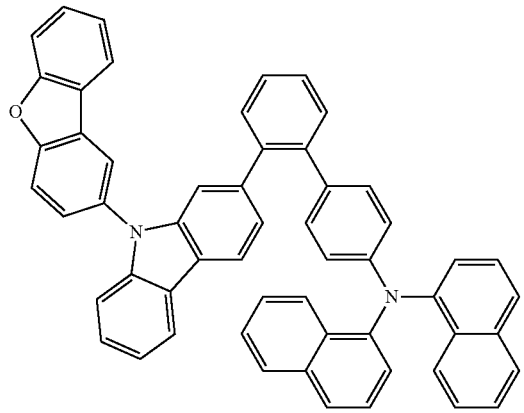
P3-106
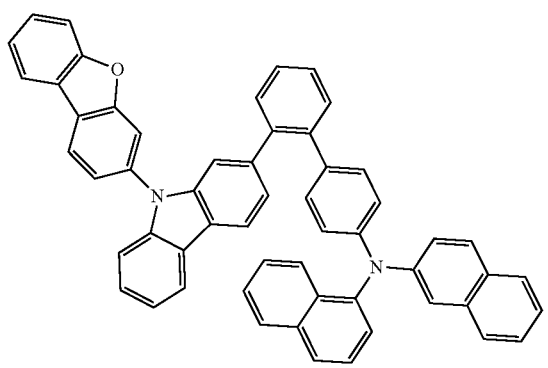
P3-107
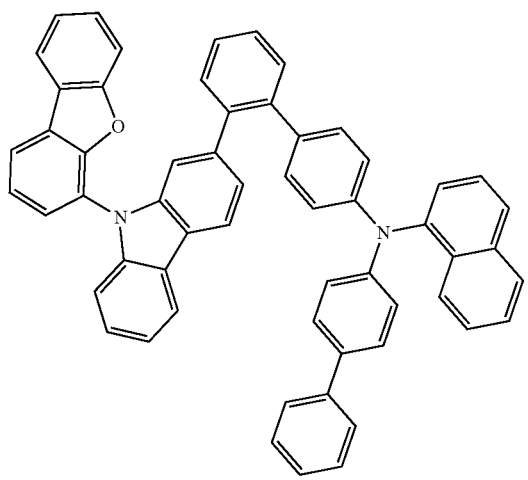
P3-108
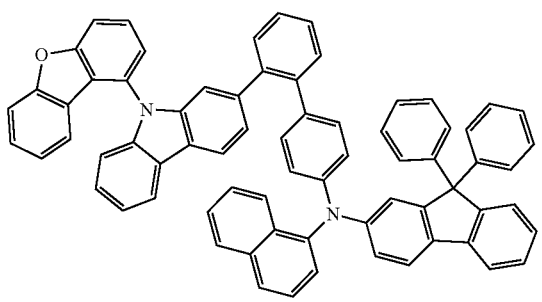
P3-109
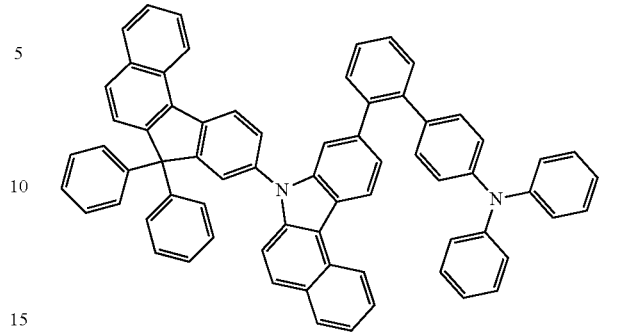
P3-110
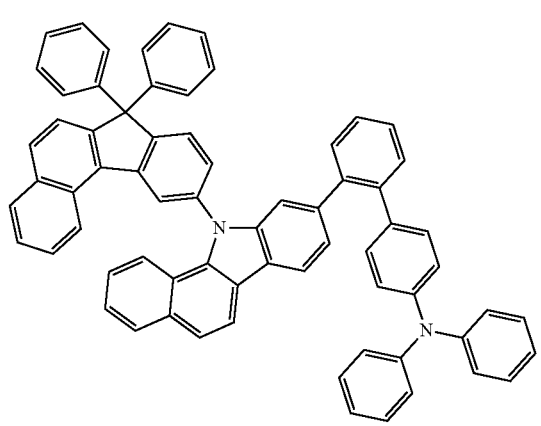
P3-111
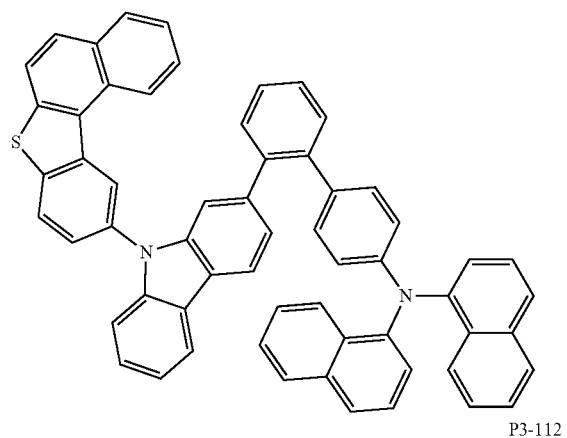
P3-112
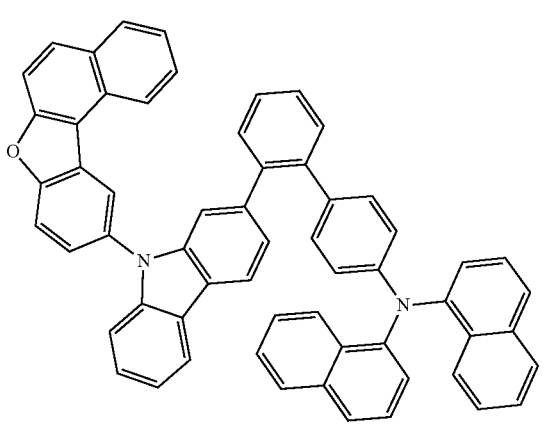

P4-1
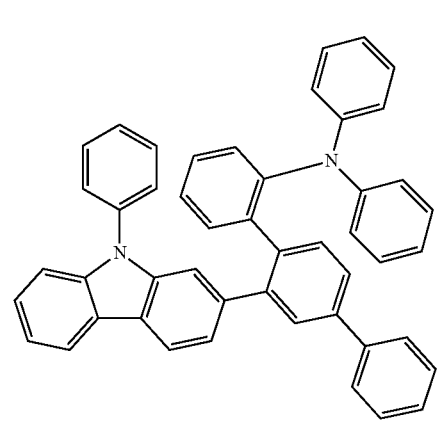
P4-4
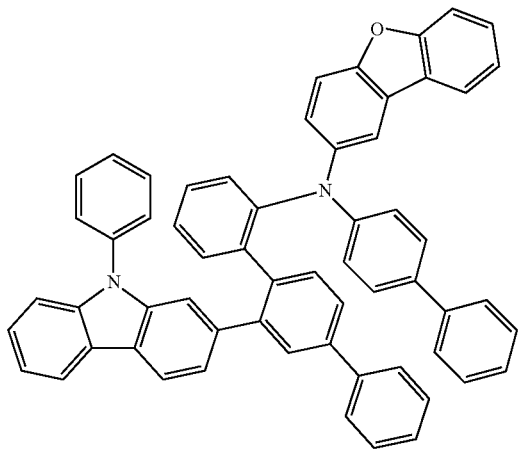
P4-2
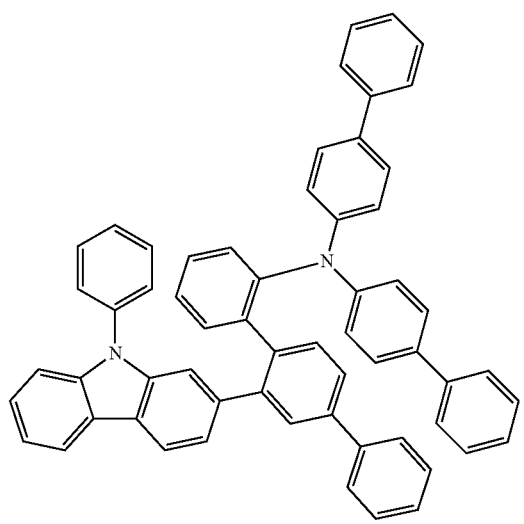
P4-5
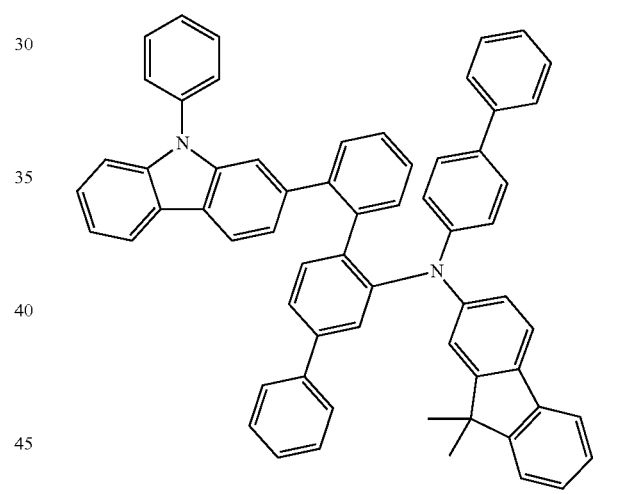
P4-3
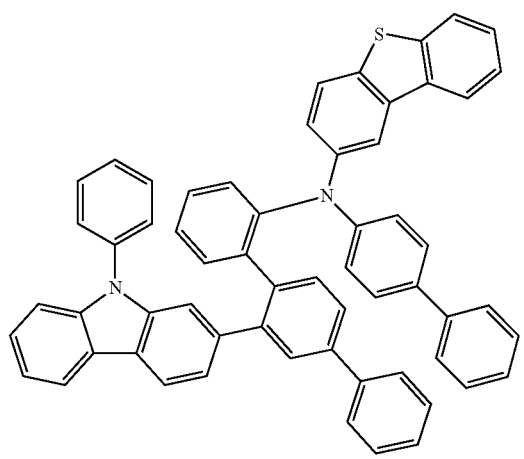
P4-6
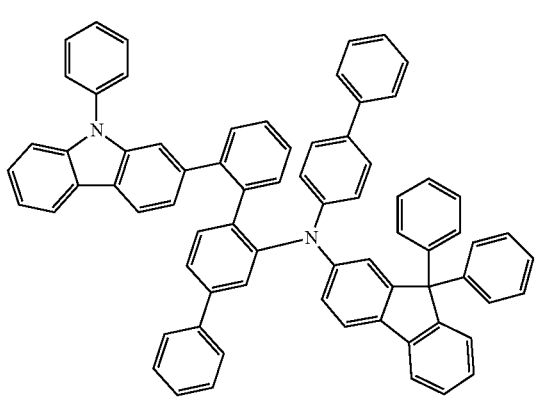

P4-7
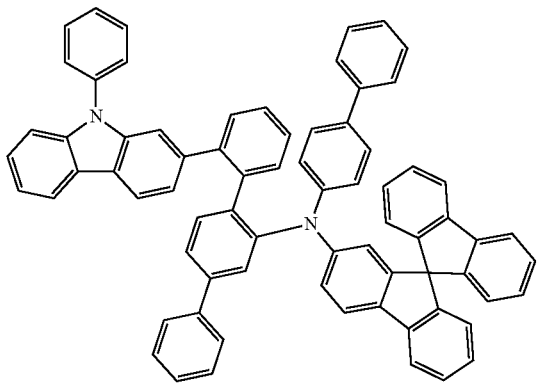
P4-8
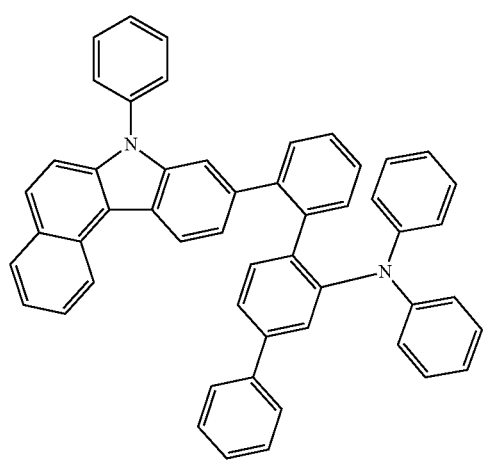
P4-9
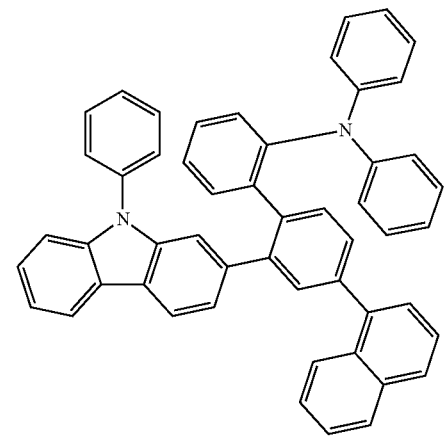
P4-10
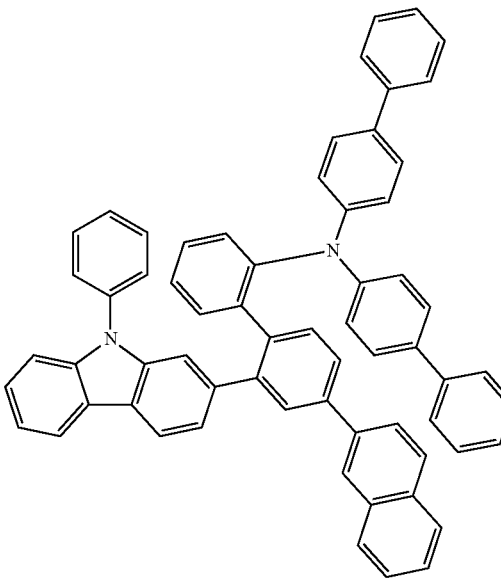
P4-11
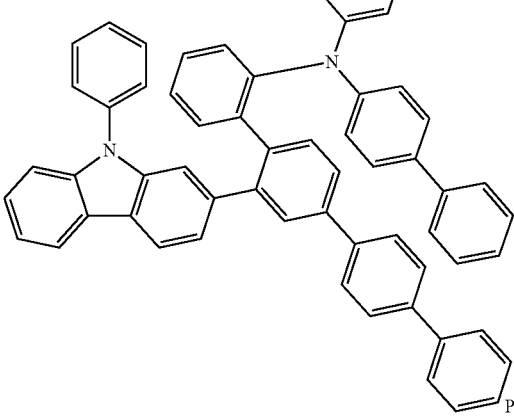
P4-12
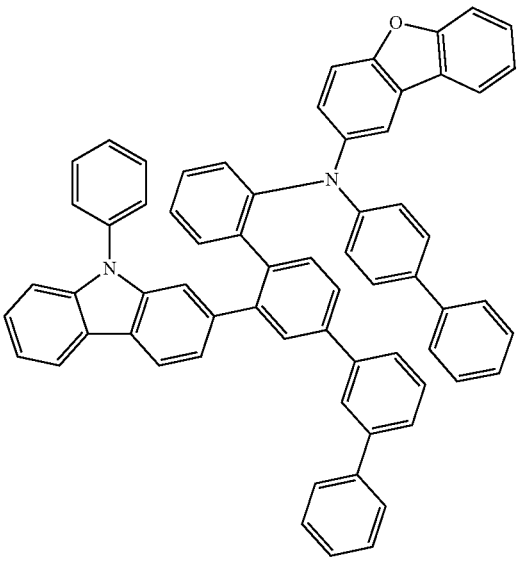

P4-13
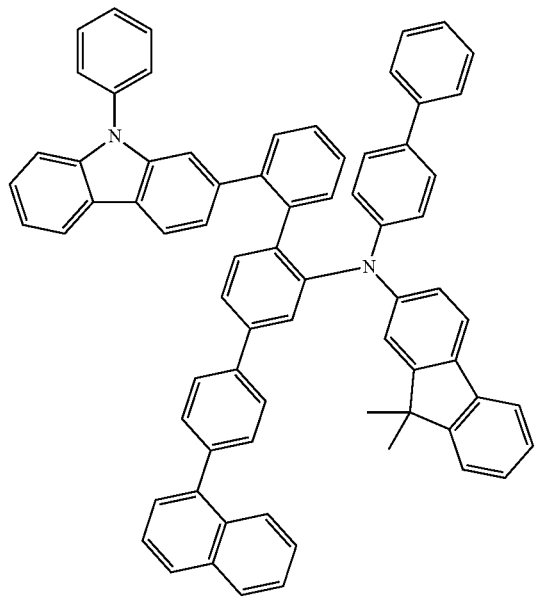
P4-14
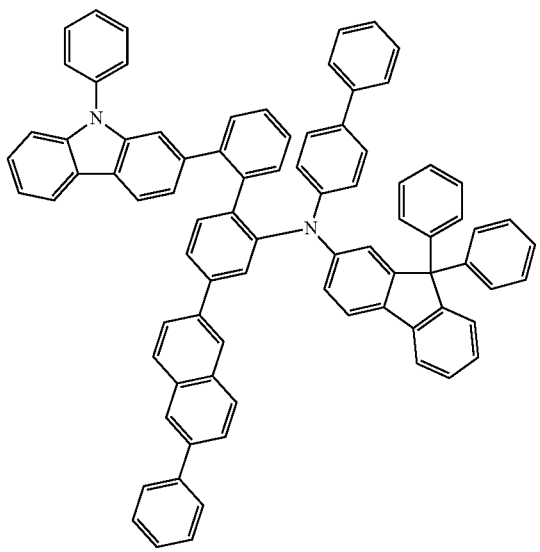
P4-15
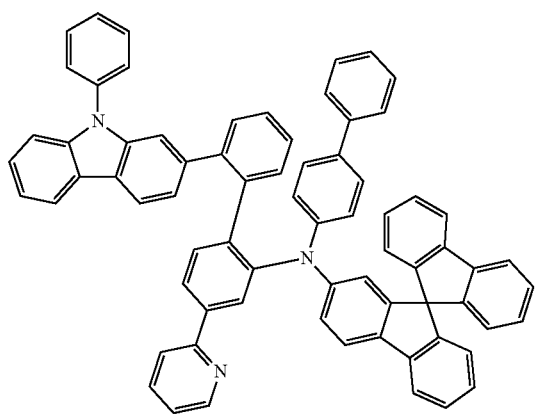
P4-16
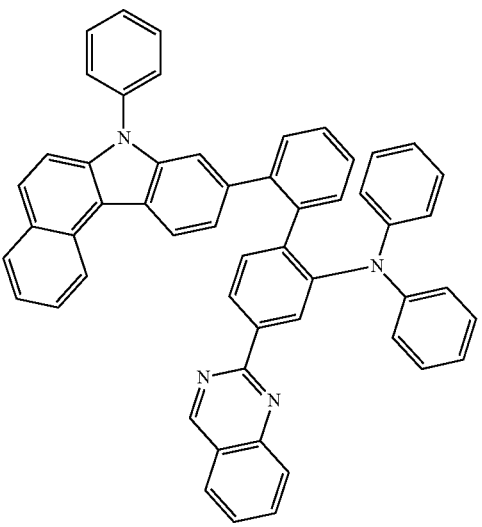
P4-17
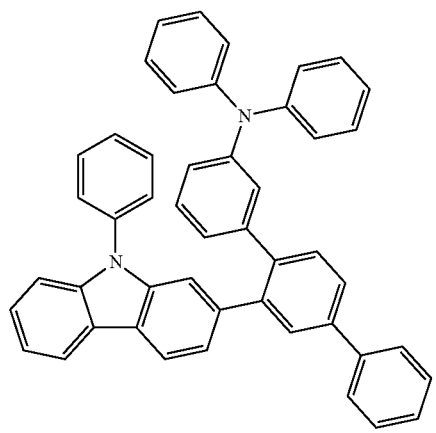
P4-18
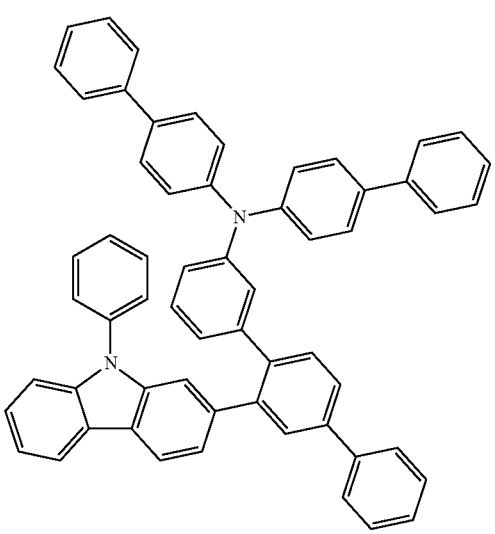

-continued
P4-19
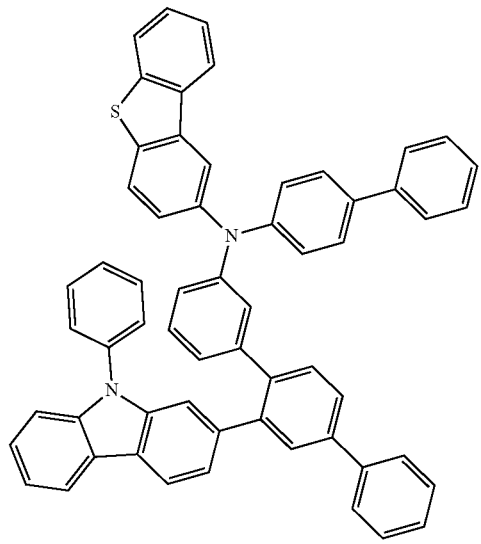
P4-20
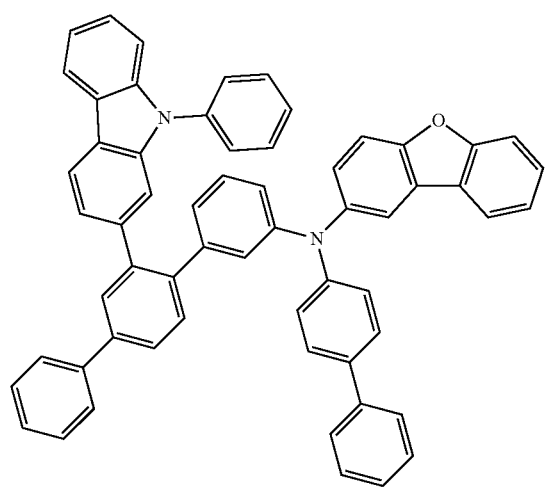
P4-21
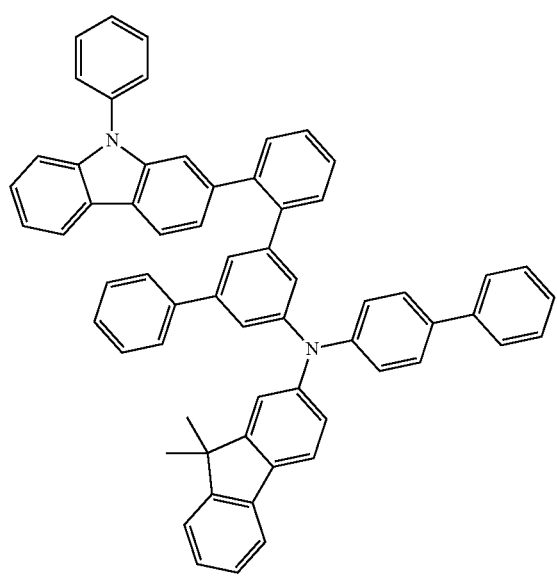
-continued
P4-22
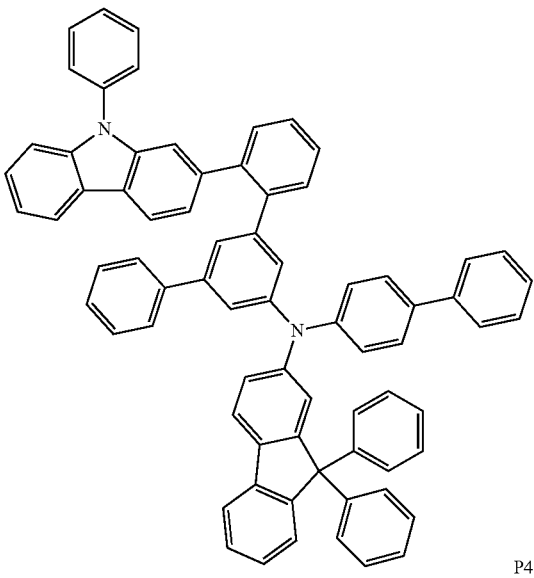
P4-23
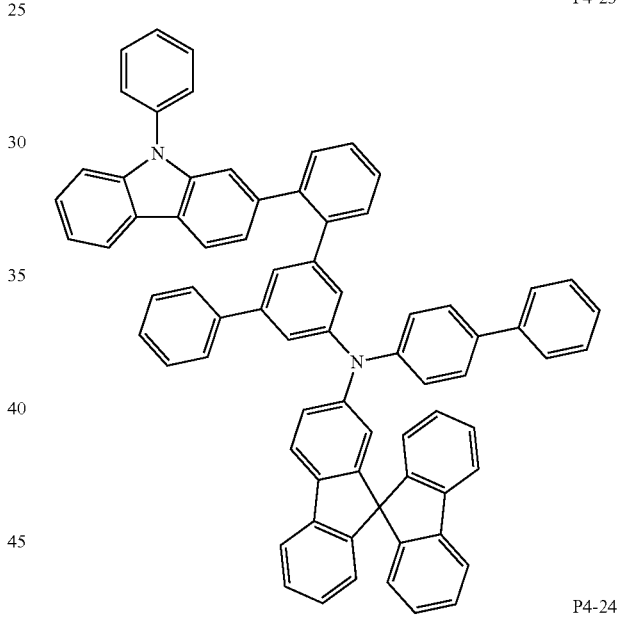
P4-24
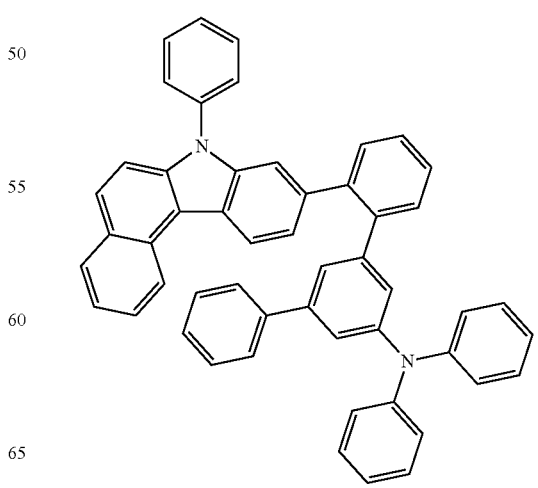

P4-25
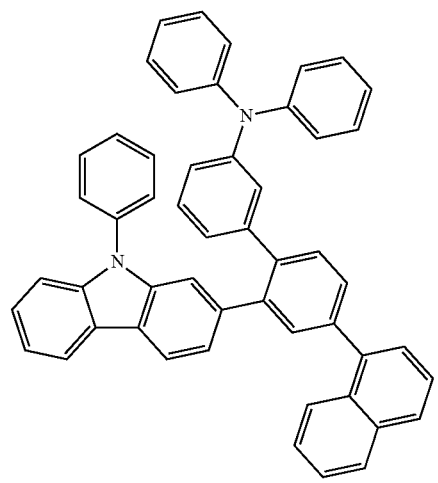
P4-26
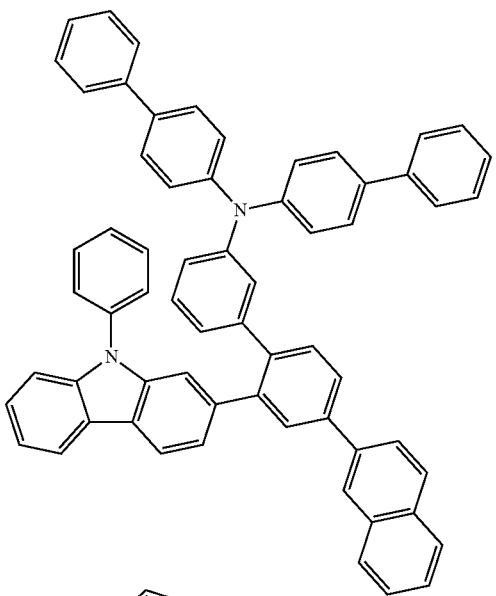
P4-27
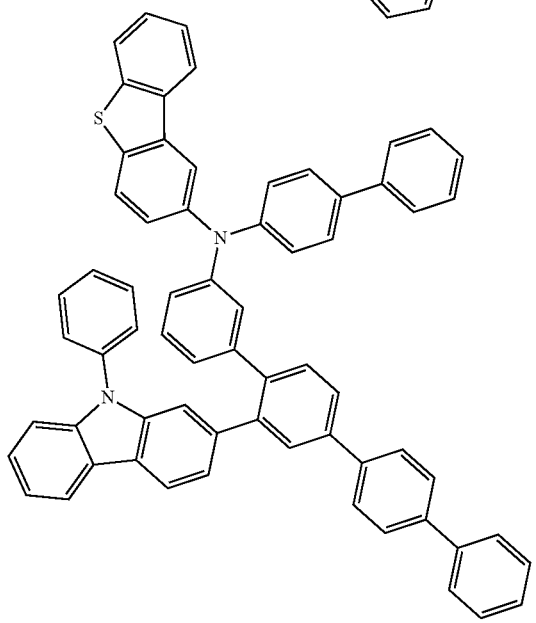
P4-28
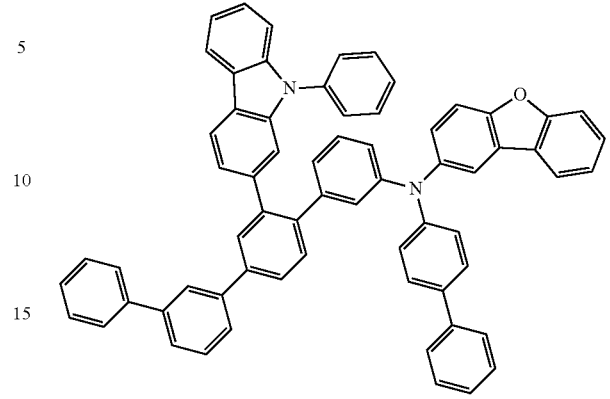
P4-29
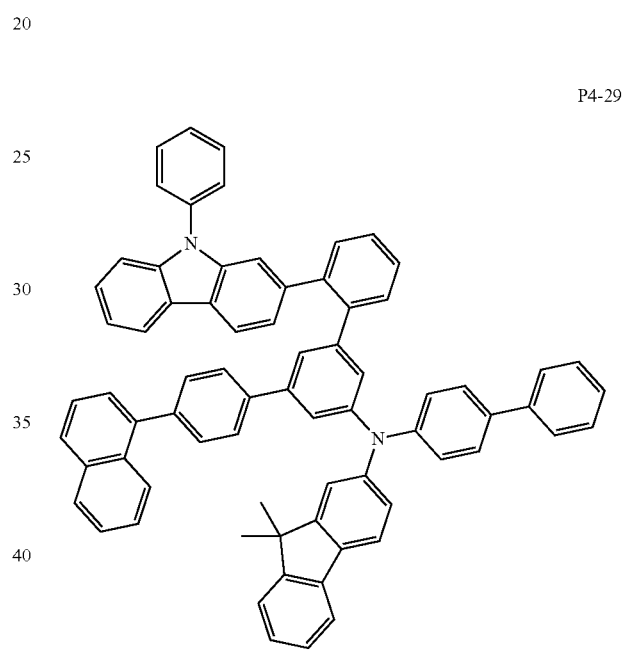
P4-30
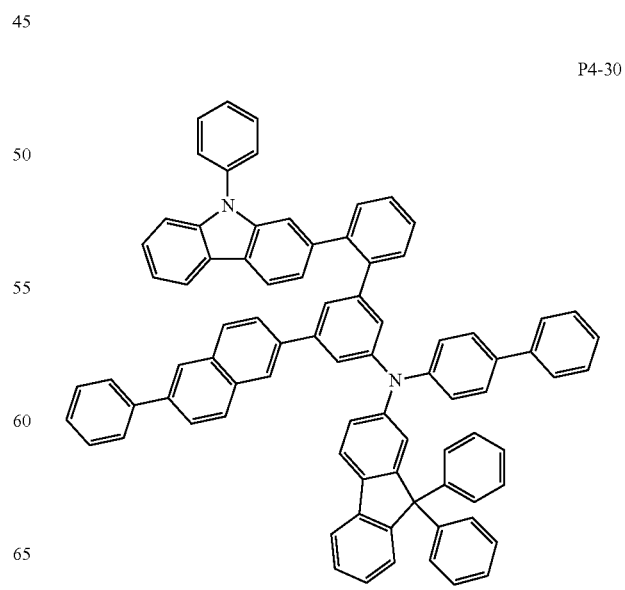

P4-31
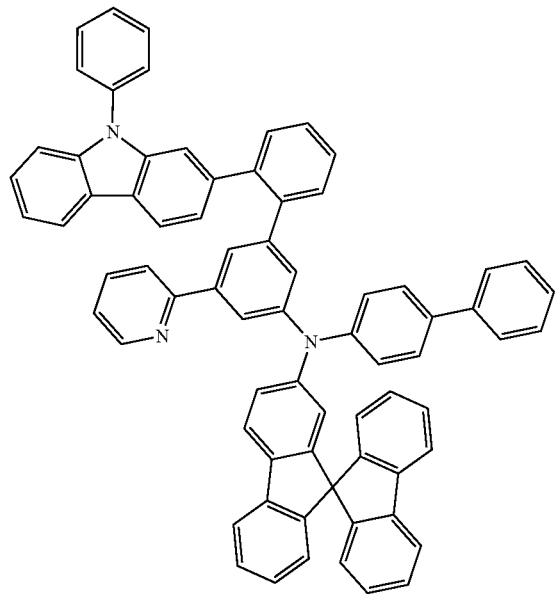
P4-32
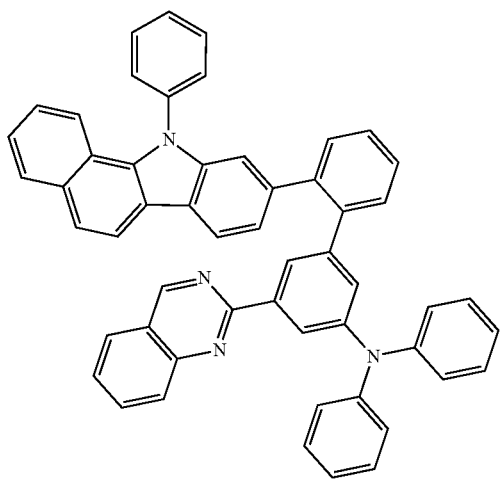
P4-33
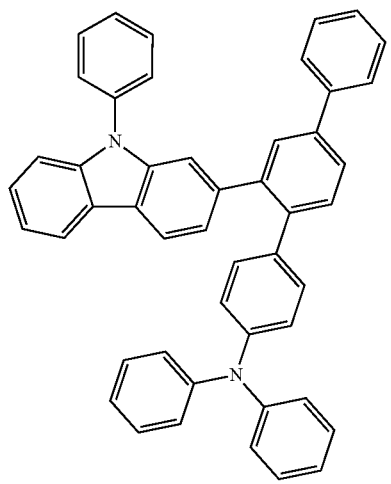
P4-34
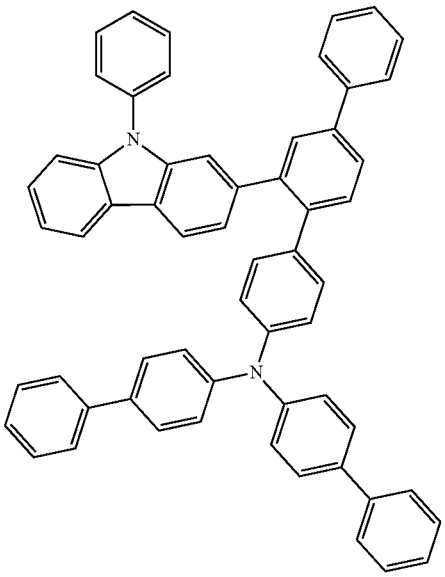
P4-35
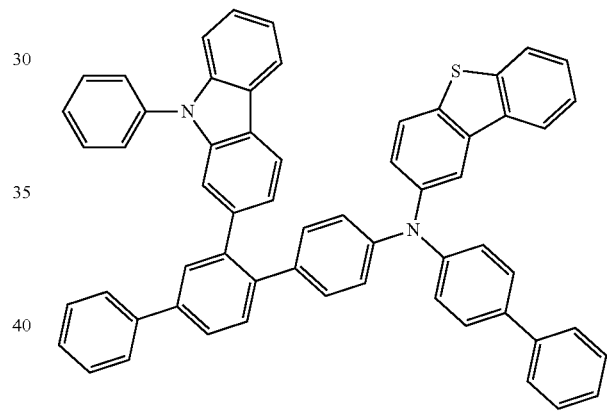
P4-36
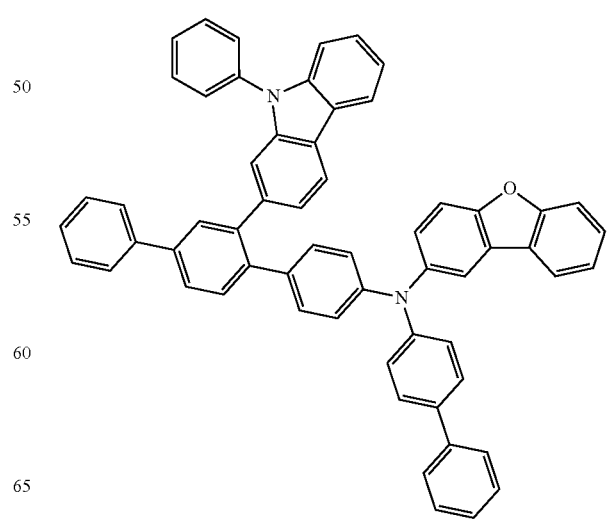

-continued
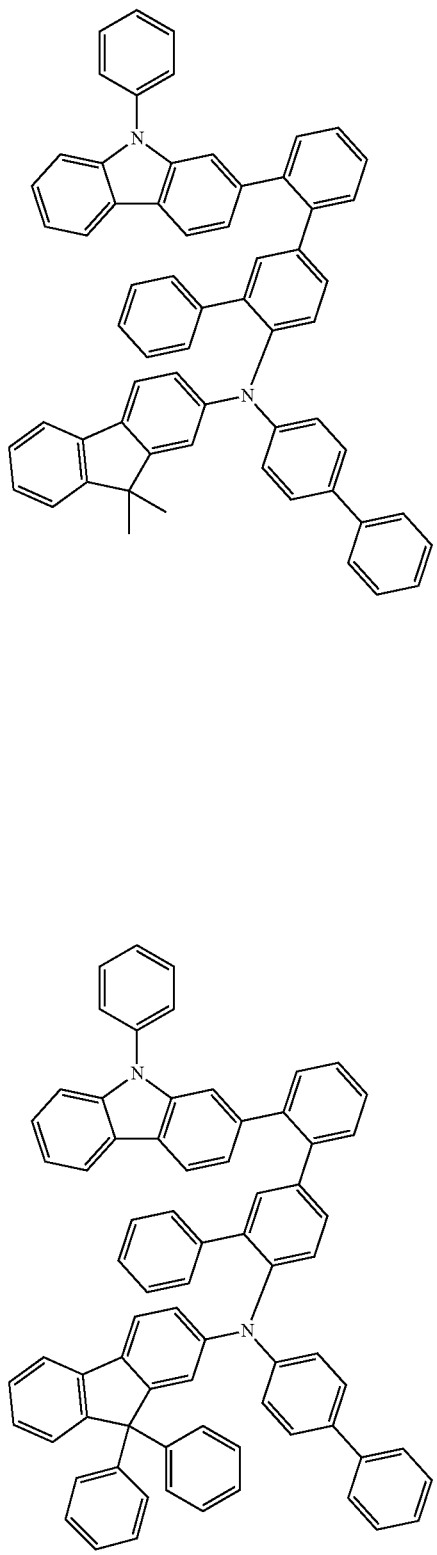
P4-37
P4-38
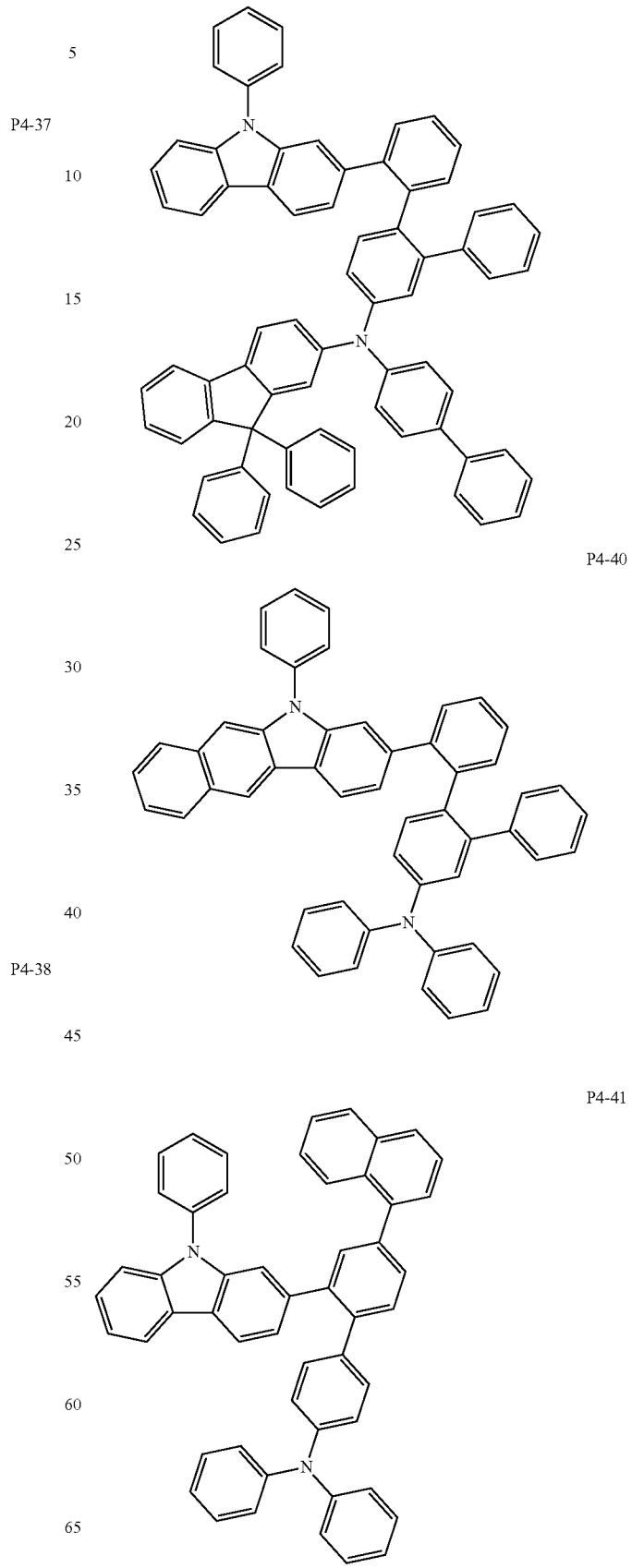
P4-39
P4-40
P4-41

P4-42
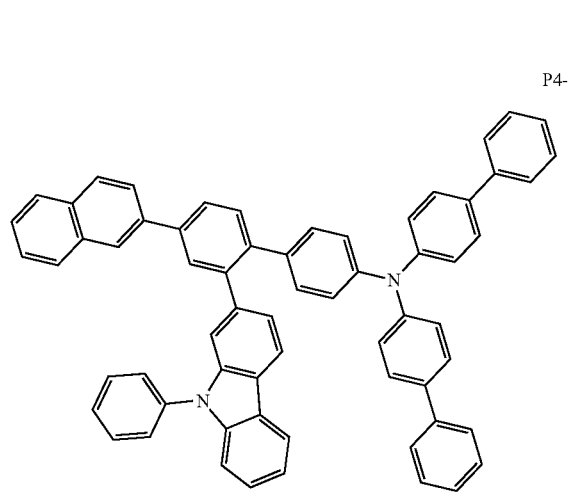
P4-43
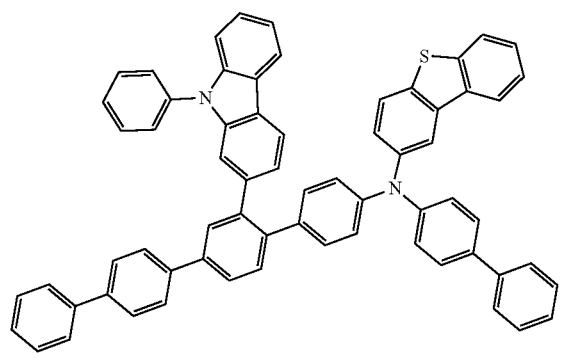
P4-44
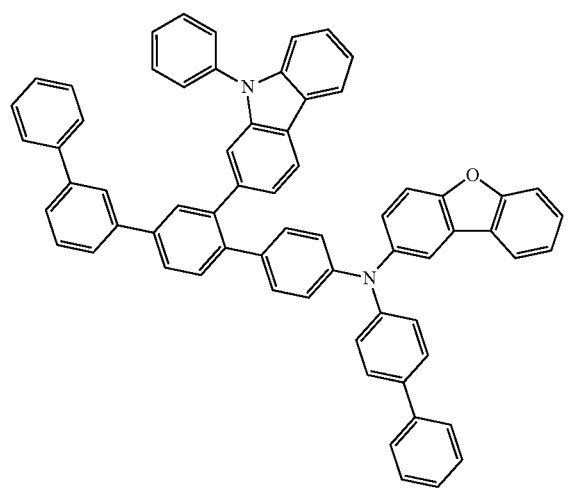
P4-45
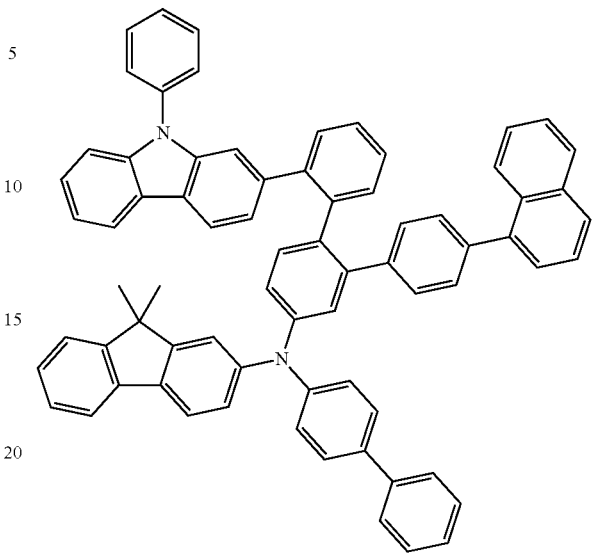
P4-46
P4-47
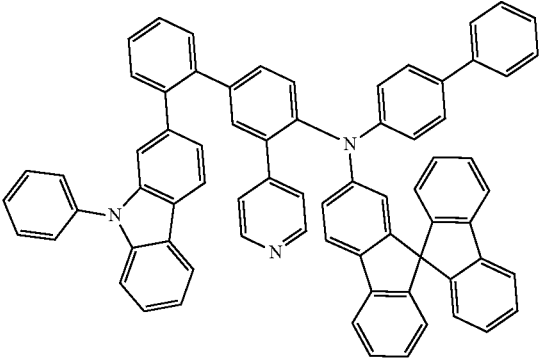

-continued

P4-48

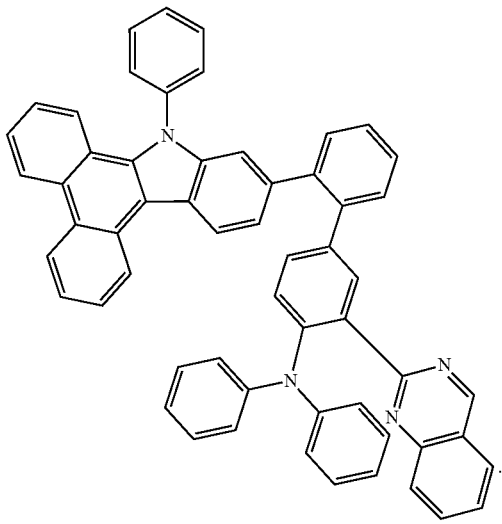

9. An organic electric element comprising a first electrode, a second electrode, and an organic material layer disposed between the first electrode and the second electrode, wherein the organic material layer comprises the compound of claim 1.

10. The organic electric element of claim 9, wherein the organic material layer comprises one or more of a hole injection layer, a hole transport layer, an emission-auxiliary layer and an emitting layer, the one or more layer(s) comprising the compound.

11. The organic electric element of claim 9, wherein the organic electric element further comprises an additional layer(s) formed on at least one of the sides of the first and second electrodes opposite to the organic material layer.

12. The organic electric element of claim 9, wherein the organic material layer is formed by any one of the processes of spin coating, nozzle printing, inkjet printing, slot coating, dip coating and roll-to-roll.

13. An electronic device comprising a display device, which comprises the organic electric element of claim 9, and a control unit for driving the display device.

14. The electronic device of claim 13, wherein the organic electric element comprises at least one of an organic light emitting diode, an organic solar cell, an organic photo conductor, an organic transistor, and an element for monochromatic or white illumination.

\* \* \* \* \*